US008188113B2

(12) United States Patent
Flynn et al.

(10) Patent No.: US 8,188,113 B2
(45) Date of Patent: May 29, 2012

(54) DIHYDROPYRIDOPYRIMIDINYL, DIHYDRONAPHTHYIDINYL AND RELATED COMPOUNDS USEFUL AS KINASE INHIBITORS FOR THE TREATMENT OF PROLIFERATIVE DISEASES

(75) Inventors: Daniel L. Flynn, Lawrence, KS (US); Peter A. Petillo, Lawrence, KS (US); Michael D. Kaufman, Lawrence, KS (US); William C. Patt, Lawrence, KS (US)

(73) Assignee: Deciphera Pharmaceuticals, Inc., Lawrence, KS (US)

( * ) Notice: Subject to any disclaimer, the term of this patent is extended or adjusted under 35 U.S.C. 154(b) by 1049 days.

(21) Appl. No.: 11/854,354

(22) Filed: Sep. 12, 2007

(65) Prior Publication Data
US 2008/0114006 A1    May 15, 2008

Related U.S. Application Data

(60) Provisional application No. 60/844,552, filed on Sep. 14, 2006.

(51) Int. Cl.
C07D 471/04    (2006.01)
A61K 31/4375    (2006.01)
A61P 35/00    (2006.01)
A61P 29/00    (2006.01)
A61P 19/00    (2006.01)
A61P 11/00    (2006.01)
A61P 9/00    (2006.01)
A61P 37/00    (2006.01)

(52) U.S. Cl. ........................ 514/300; 546/122
(58) Field of Classification Search .................. 544/279; 514/264.1
See application file for complete search history.

(56) References Cited

U.S. PATENT DOCUMENTS

| | | |
|---|---|---|
| 3,528,980 A | 9/1970 | Islip |
| 3,818,024 A | 6/1974 | Krenzer |
| 3,939,122 A | 2/1976 | Merten et al. |
| 3,949,002 A | 4/1976 | Feasey et al. |
| 4,093,624 A | 6/1978 | Revankar et al. |
| 4,296,237 A | 10/1981 | Cragoe, Jr. et al. |
| 4,366,189 A | 12/1982 | Burdeska et al. |
| 4,432,992 A | 2/1984 | Cragoe, Jr. et al. |
| 4,525,450 A | 6/1985 | Itoh et al. |
| 4,816,454 A | 3/1989 | Zoller et al. |
| 5,103,014 A | 4/1992 | Musser et al. |
| 5,162,360 A | 11/1992 | Creswell et al. |
| 5,189,045 A | 2/1993 | Peglion et al. |
| 5,319,099 A | 6/1994 | Kamata et al. |
| 5,494,925 A | 2/1996 | Court et al. |
| 5,621,010 A | 4/1997 | Sueda et al. |
| 5,721,231 A | 2/1998 | Moriwaki et al. |
| 5,811,456 A | 9/1998 | Seman et al. |
| 6,020,357 A | 2/2000 | Pinto et al. |
| 6,080,763 A | 6/2000 | Regan et al. |
| 6,197,599 B1 | 3/2001 | Chin et al. |
| 6,235,786 B1 | 5/2001 | Dai et al. |
| 6,294,573 B1 | 9/2001 | Curtin et al. |
| 6,319,921 B1 | 11/2001 | Cirillo et al. |
| 6,410,254 B1 | 6/2002 | Finer et al. |
| 6,500,628 B1 | 12/2002 | Robison |
| 6,525,046 B1 | 2/2003 | Cirillo et al. |
| 6,645,990 B2 | 11/2003 | Askew et al. |
| 6,916,924 B2 | 7/2005 | Tan et al. |
| 7,030,128 B2 | 4/2006 | Blackaby et al. |
| 7,071,199 B1 | 7/2006 | Hirst et al. |
| 7,135,550 B2 | 11/2006 | Come et al. |
| 7,144,911 B2 | 12/2006 | Flynn et al. |
| 7,202,257 B2 | 4/2007 | Flynn et al. |
| 7,211,575 B2 | 5/2007 | Moss et al |
| 7,342,037 B2 | 3/2008 | Flynn et al. |
| 7,531,566 B2 | 5/2009 | Flynn et al. |
| 2002/0058678 A1 | 5/2002 | Cirillo et al. |
| 2002/0077486 A1 | 6/2002 | Scarborough et al. |
| 2003/0060455 A1 | 3/2003 | Moss et al. |
| 2003/0207870 A1 | 11/2003 | Dumas et al. |
| 2003/0232865 A1 | 12/2003 | Cirillo et al. |
| 2004/0043388 A1 | 3/2004 | Come et al. |
| 2004/0157827 A1 | 8/2004 | Pevarello et al. |

(Continued)

FOREIGN PATENT DOCUMENTS
DE    4343831    6/1995
(Continued)

OTHER PUBLICATIONS

Lorenzi et al, "Amino Acid Ester Prodrugs of 2-Bromo-5,6-dichloro-1-(β-D-ribofuranosyl)benzimidazole Enhance Metabolic Stability in Vitro and In Vivo," *J. Pharm. Exp. Therpeutics* (2005) 314 (2): 883-890.
Chan et al, "Copper promoted C-N and C-O bond dross-coupling with phenyl and pyridylboronates," *Tetrahedron Lett.* (2003) 44: 3863-3865.
Chan et al, "New N- and O-Arylations with Phenylboronic Acids and Cupric Acetate," *Tetrahedron Lett.* (1998) 39: 2933-2936.

(Continued)

*Primary Examiner* — James O Wilson
*Assistant Examiner* — Cecilia M Jaisle
(74) *Attorney, Agent, or Firm* — Cooley LLP

(57) ABSTRACT

The present invention relates to novel dihydropyridopyrimidinyl, dihydronaphthyridinyl, and related compounds which are kinase inhibitors and modulator useful for the treatment of various diseases. More particularly, the invention is concerned with such compounds, kinase/compound adducts, methods of treating diseases, and methods of synthesis of the compounds. Preferably, the compounds are useful for the modulation of kinase activity of Raf kinases and disease polymorphs thereof. Compounds of the present invention find utility in the treatment of mammalian cancers and especially human cancers including but not limited to malignant melanoma, colorectal cancer, ovarian cancer, papillary thyroid carcinoma, non small cell lung cancer, and mesothelioma. Compounds of the present invention also find utility in the treatment of rheumatoid arthritis and retinopathies including diabetic retinal neuropathy and macular degeneration.

19 Claims, No Drawings

U.S. PATENT DOCUMENTS

| | | | |
|---|---|---|---|
| 2004/0167224 A1 | 8/2004 | Ozaki et al. | |
| 2004/0171075 A1 | 9/2004 | Flynn et al. | |
| 2004/0180906 A1 | 9/2004 | Flynn et al. | |
| 2004/0229937 A1 | 11/2004 | Dumas et al. | |
| 2005/0014753 A1 | 1/2005 | Ding et al. | |
| 2005/0165024 A1 | 7/2005 | Milanov et al. | |
| 2005/0165031 A1 | 7/2005 | Grotzfeld et al. | |
| 2005/0192314 A1 | 9/2005 | Mehta et al. | |
| 2005/0197371 A1 | 9/2005 | Milanov et al. | |
| 2005/0256174 A1 | 11/2005 | Wood et al. | |
| 2005/0267182 A1 | 12/2005 | Milanov et al. | |
| 2005/0288286 A1 | 12/2005 | Flynn et al. | |
| 2007/0037794 A1 | 2/2007 | Ungashe et al. | |
| 2007/0078121 A1 | 4/2007 | Flynn et al. | |
| 2007/0155764 A1 | 7/2007 | Lang et al. | |
| 2007/0191336 A1 | 8/2007 | Flynn et al. | |
| 2008/0045531 A1 | 2/2008 | Flynn et al. | |
| 2008/0045706 A1 | 2/2008 | Flynn et al. | |
| 2008/0090856 A1 | 4/2008 | Flynn et al. | |
| 2008/0113967 A1 | 5/2008 | Flynn et al. | |
| 2008/0132506 A1 | 6/2008 | Flynn et al. | |
| 2008/0187978 A1 | 8/2008 | Flynn et al. | |
| 2008/0220497 A1 | 9/2008 | Flynn et al. | |
| 2008/0248487 A1 | 10/2008 | Flynn et al. | |
| 2008/0248548 A1 | 10/2008 | Flynn et al. | |
| 2009/0069310 A1 | 3/2009 | Flynn et al. | |
| 2009/0075986 A1 | 3/2009 | Flynn et al. | |
| 2009/0099190 A1* | 4/2009 | Flynn et al. | 514/249 |
| 2009/0105230 A1 | 4/2009 | Flynn et al. | |
| 2009/0137021 A1 | 5/2009 | Flynn et al. | |
| 2009/0312349 A1 | 12/2009 | Flynn et al. | |
| 2010/0209420 A1* | 8/2010 | Lamb et al. | 424/133.1 |

FOREIGN PATENT DOCUMENTS

| | | |
|---|---|---|
| EP | 0021228 | 1/1981 |
| EP | 0025232 | 3/1981 |
| EP | 0661276 | 7/1995 |
| EP | 0692483 | 1/1996 |
| EP | 0739884 | 10/1996 |
| EP | 0867435 | 9/1998 |
| EP | 0927555 | 7/1999 |
| EP | 928790 | 7/1999 |
| EP | 0956855 | 11/1999 |
| EP | 1281399 | 2/2003 |
| FR | 2337554 | 8/1977 |
| FR | 2396549 | 2/1979 |
| GB | 971307 | 9/1964 |
| GB | 1410279 | 10/1975 |
| GB | 2220206 | 1/1990 |
| JP | 59-15247 | 1/1984 |
| JP | 59-177557 | 10/1984 |
| JP | 9-221476 | 8/1997 |
| JP | 2000-275886 | 10/2000 |
| JP | 2001-2687 | 7/2002 |
| WO | WO 91/19708 | 12/1991 |
| WO | WO 92/08693 | 5/1992 |
| WO | WO 94/18176 | 8/1994 |
| WO | WO 94/21617 | 9/1994 |
| WO | WO 94/24095 | 10/1994 |
| WO | WO 95/15954 | 6/1995 |
| WO | WO 95/29902 | 11/1995 |
| WO | WO 95/34540 | 12/1995 |
| WO | WO 96/16046 | 5/1996 |
| WO | WO 96/19477 | 6/1996 |
| WO | WO 97/34900 | 9/1997 |
| WO | WO 97/40028 | 10/1997 |
| WO | WO 98/22103 | 5/1998 |
| WO | WO 98/52558 | 11/1998 |
| WO | WO 99/15164 | 4/1999 |
| WO | WO 99/23091 | 5/1999 |
| WO | WO 99/23093 | 5/1999 |
| WO | WO 99/32106 | 7/1999 |
| WO | WO 99/32110 | 7/1999 |
| WO | WO 99/32111 | 7/1999 |
| WO | WO 99/32455 | 7/1999 |
| WO | WO 99/37622 | 7/1999 |
| WO | WO 99/59959 | 11/1999 |
| WO | WO 00/06550 | 2/2000 |
| WO | WO 00/07980 | 2/2000 |
| WO | WO 00/18738 | 4/2000 |
| WO | WO 00/21927 | 4/2000 |
| WO | WO 00/41698 | 7/2000 |
| WO | WO 00/42012 | 7/2000 |
| WO | WO 00/43384 | 7/2000 |
| WO | WO 00/55139 | 9/2000 |
| WO | WO 00/59506 | 10/2000 |
| WO | WO 01/12621 | 2/2001 |
| WO | WO 01/14372 | 3/2001 |
| WO | WO 01/74771 | 10/2001 |
| WO | WO 01/96298 | 12/2001 |
| WO | WO 02/14291 | 2/2002 |
| WO | WO 02/14311 | 2/2002 |
| WO | WO 02/28835 | 4/2002 |
| WO | WO 02/34727 | 5/2002 |
| WO | WO 02/060869 | 8/2002 |
| WO | WO 02/060876 | 8/2002 |
| WO | WO 02/062763 | 8/2002 |
| WO | WO 03/068223 | 8/2002 |
| WO | WO 02/070662 | 9/2002 |
| WO | WO 03/005999 | 1/2003 |
| WO | WO 03/053368 | 7/2003 |
| WO | WO 03/059373 | 7/2003 |
| WO | WO 03/068229 | 8/2003 |
| WO | WO 03/072577 | 9/2003 |
| WO | WO 03/084539 | 10/2003 |
| WO | WO 2004/004720 | 1/2004 |
| WO | WO 2004/056783 | 7/2004 |
| WO | WO 2004/060306 | 7/2004 |
| WO | WO 2004/061084 | 7/2004 |
| WO | WO 2004/078128 | 9/2004 |
| WO | WO 2004/113352 | 12/2004 |
| WO | WO 2005/002673 | 1/2005 |
| WO | WO 2005/034869 | 4/2005 |
| WO | WO 2005/110994 | 11/2005 |
| WO | WO 2006/014290 | 2/2006 |
| WO | WO 2006/046552 | 5/2006 |
| WO | WO 2006/071940 | 7/2006 |
| WO | WO 2006071940 | * 7/2006 |
| WO | WO 2006/081034 | 8/2006 |
| WO | WO 2006081034 | * 8/2006 |
| WO | WO 2007/008917 | 1/2007 |
| WO | WO 2007/076473 | 7/2007 |
| WO | WO 2008/033999 | 3/2008 |
| WO | WO 2008/046003 | 4/2008 |
| WO | WO 2008/051757 | 5/2008 |
| WO | WO 2008/131276 | 10/2008 |

OTHER PUBLICATIONS

Chan, D. M. T., "Promotion of Reaction of N-H Bonds with Triarylbismuth and Cuprie Acetate," *Tetrahedron Lett.* (1996) 37 (50): 9013-9016.

Seto, et al, "2-Substituted-4-aryl-6,7,8,9-tetrahydro-5*H*-pyrimido [4,5-*b*][1,5]oxazocin-5-one as a structurally new $NK_1$ antagonist," *Biorg. Med. Chem. Lett.* (2005) 15: 1485-1488.

Pierrat et al, "Solid Phase Synthesis of Pyridine-Based Derivatives from a 2-Chloro-5-Bromopyridine Scaffold," *J. Comb. Chem.* (2005) 7 (6): 879-886.

Schlosser et al., "Regiochemically Flexible Substitutions of Di-, Tri-, and Tetrahalopyridines: The Trialkylsily Trick," *J. Org. Chem.* (2005) 70: 2494-2502.

Kuse et al., "Synthesis of azide-fluoro-dehydrocoelenterazine analog as a photoaffinity-labeling probe and photolysis of azide-fluoro-coelenterazine," *Tetrahedron Lett.* (2005) 61: 5754-5762.

Schindler, et al, "Structural Mechanism for STI-571 Inhibition of Abelson Tyrosine Kinase," *Science* (Sep. 2000) 289: 1938-1942.

Peyssonnaux, C. et al, "The Raf/MEK/ERK pathway: new concepts of activation," *Biol. Cell* (2001) 93: 53-62.

Bolton et al., "Chapter 17. *Ras* Oncogene Directed Approaches in Cancer Chemotherapy," *Ann. Rep. Med. Chem.* (1994) 29: 165-174.

Avruch, J. et al., "Ras Activation of the Raf Kinase: Tyrosine Kinase Recruitment of the MAP Kinase Cascade," *Recent Prog. Horm. Res.* (2001) 56: 127-155.

Kolch, W., "Meaningful relationships: the regulation of the Ras/Raf/MEK/ERK pathway by protein interactions," *Biochem. J.* (2000) 351: 289-305.

Davies, H. et al, "Mutations of the BRAF gene in human cancer," *Nature* (Jun. 2002) 417: 949-954.

Lowinger et al, "Design and Discovery of Small Molecules Targeting Raf-1 Kinase," *Current Pharmaceutical Design* (2002) 8: 2269-2278.

Dumas, J. et al, "Recent developments in the discovery of protein kinase inhibitors from the urea class," *Current Opinion in Drug Discovery & Development* (2004) 7 (5): 600-616.

Wan, P.T.C. et al, "Mechanism of Activation of the RAF-ERK Signaling Pathway by Oncogenic Mutations of B-RAF," *Cell* (Mar. 2004) 116: 855-867.

Huse, M. et al, "The Conformational Plasticity of Protein Kinases," *Cell* (May 2002) 109: 275-282.

Ettmayer et al, "Lessons Learned from Marketed and Investigational Prodrugs," *J. Med. Chem* (May 2004) 47 (10): 2393-2404.

Magnuson et al, "The Raf-1 serine/threonine protein kinase," *Seminars in Cancer Biology*. (1994) 5: 247-253.

Ranatunge et al, "Synthesis and Selective Cyclooxygenase-2 Inhibitory Activity of a Series of Novel, Nitric Oxide Donor-Containing Pyrazoles," *J. Med Chem*. (2004) 47: 2180-2193.

Barvian et al, "Pyrido[2,3-*d*]pyrimidin-7-one Inhibitors of Cyclin-Dependent Kinases," *J. Med Chem*. (2000) 43: 4606-4616.

U.S. Appl. No. 12/268,997, filed Nov. 11, 2008, Flynn et al.

"Additions and Corrections", Journal of Medicinal Chemistry, 32(12):2583 (1989).

Aklilu, et al., "Increased PTHRP Production by a Tyrosine Kinase Oncogene, Tpr-Met: Rose of the Ras Signaling Pathway", American Journal of Physiology—Endocrinology and Metabolism, 271(2) pp. E277-E283 (1996).

Albericio, et al., "Synthesis of a Sulfaydantion Library", J. Comb. Chem., 3:290-300 (2001).

Almerico, et al., "On the Preparation of 1-aryl-2-heteroaryl- and 2-aryl-1-heteroaryl-pyrroles as Useful Building Blocks for Biologically Interesting Heterocycles", ARKIVOC (vi), Rudy Abramovitch Issue, pp. 129-142 (2001).

Anzai, et al., "Alkyl- and Arylthiation of Uracil and Indole", J. Heterocyclic Chem., 16:567-569 (1979).

Askew, et al., "Molecular Recognition with Convergent Functional Groups: 6. Synthetic and Structural Studies with a Model Receptor for Nucleic Acid Components", J. Am. Chem., 111:1082-1090 (1989).

Bais, et al., "Inhibition of Endogenous Wxalate Production: Biochemical Consideration of the Roles of Glycollate Oxidase and Lactate Dehydrogenase", Clinical Science, 76:303-309 (1989).

Baker, et al., "Irreversible Enzyme Inhibitors. 188. Inhibition of Mammalian Thymidine Phosphorylase", Journal of Medicinal Chemistry, 14:812-816 (1971).

Barker, et al., "Characterization of pp60c-src Tyrosine Kinase Activities Using a Continuous Assay: Autoactivation of the Enzyme is an Intermolecular Autophosphorylation Process", Biochemistry, 35:14843-14851 (1995).

Bausch, et al., "Proton-Transfer Chemistry of Urazoles and Related Imides, and Diacyl Hydrazides", J. Org. Chem., 56:5643-5651 (1991).

Benvenuti, et al., "Crystallization of Soluble Proteins in Vapor Diffusion for X-Ray Crystallography", Nature Protocols, 2(7):1633-1651 (2007).

Bosca, et al., "Circular Dichroism Analysis of Ligand-Induced Conformational Changes in Protein Kinase C", Biochem J., 290:827-832 (1993).

Boschelli, et al., "4-Anilino-3-quinolinecarbonitriles: An Emerging Class of Kinase Inhibitors", Current Topics in Medicinal Chemistry, 2:1051-1063 (2002).

Bourdonnec, et al., "Synthesis and Pharmacological Evaluation of New Pyrazolidine-3,5-diones as AT1 Angiotensin II Receptor Antagonists", J. Med. Chem., 43:2685-2697 (2000).

Boyer, "Small Molecule Inhibitors of KDR (VEGFR-2) Kinase: An Overview of Structure Activity Relationships", Current Topics in Medicinal Chemisty, 2:973-1000 (2002).

Brady, et al., "Fast Prediction and Visualization of Protein Binding Pockets with PASS". Journal of Computer-Aided Molecular Design, 14:383-401 (2000).

Brasher, et al., "C-Abul has High Intrinsic Tyrosine Kinase Activity that is Stimulated by Mutation of the Src Homology 3 Domain and by Autophosphorylation at Two Distinct Regulatory Tyrosines", Journal of Biological Chemistry, 275:35631-35637 (2000).

Bullock, et al., "Prospects for Kinase Activity Modulators in the Treatment of Diabetes and Diabetic Complications", Current Topics in Medicinal Chemistry, 2:915-938 (2002).

Byron, et al., "The Synthesis of some Substituted Biphenyl-4-carboxylic Acids, 4-Biphenylylacetic Acids, and 4-Aminobiphenyls", J. Chem. Soc. (C), Organic, pp. 840-845 (1966).

Cardillo, et al., "Sulle 1,2-difenil-3.5-dichetopirazolidine", Gazz. Chim., Ital., 9:973-985 (1966)—Italian Language—English Summary.

Charmm "NHLBI LBC Computational Biophysics Section", CHARMM Documentation Index, http://www.lobos.nih.gov/Charmm/chmdoc.html, printed Mar. 4, 2005 (1 page).

Chen, et al., "Biochemical Evidence for the Autophosphorylation and Transphosphorylation of Transforming Growth Factor b Receptor Kinases", Proc. Natl. Acad. Sci. USA, 92:1565-1569 (1995).

Cheng, et al., "Novel Solution Phase Strategy for the Synthesis of Chemical Libraries Containing Small Organic Molecules", J. Am. Chem. Soc., 118:2567-2573 (1996).

Cheng, et al., "Synthesis and SAR of Heteroaryl-phenyl-substituted Pyrazole Derivatives as Highly Selective and Potent Canine COX-2 Inhibitors", Bioorganic & Medicinal Chemistry Letters, 16:2076-2080 (2006).

Chu, et al., "Using Affinity Capillary Electrophoresis to Determine Binding Stoichiometries of Protein-Ligand Interactions", Biochemistry, 33:10616-10621 (1994).

Cirillo, et al. "The Non-Diaryl Heterocycle Classes of p38 MAP Kinase Inhibitors", Current Topics in Medicinal Chemistry, 2:1021-1035 (2002).

Closier, et al., "Nitrofuryl Heterocyclics. 1", Journal of Medicinal Chemistry, 13(4):638-640 (1970).

Cockerill, et al., "Small Molecule Inhibitors of the Class 1 Receptor Tyrosine Kinase Family", Current Topics in Medicinal Chemistry, 2:1001-1010 (2002).

Colton, et al., "Affinity Capillary Electrophoresis: A Physical-Organic Tool for Studying Interactions in Biomolecular Recognition", Electrophoresis, 19:367-382 (1998).

Cortes, et al., "Results of Imatinib Mesylate Therapy in Patients with Refractory or Recurrent Acute Myeloid Leukemia, High-Risk Myelodysplastic Syndrime, and Myeloproliferative Disorders", Cancer, 97(11):2760-2766 (2003).

Cross, et al., "Inhibition of Glycogen Synthase Kinase-3 by Insulin Mediated by Protein Kinase B", Nature, 378:785-789 (1995).

Dajani, et al., "Crystal Structure of Glycogen Synthase Kinas 3b: Structural Basis for Phosphate-Primed Substrate Specificity and Autoinhibition", Cell, 105:721-732 (2001).

Dajani, et al., "Structural Basis for Recruitment of Glycogen Synthase Kinase 3b to the Axin-APC Scaffold Complex", EMBO J., 22(3):494-501 (2003).

Daley, et al., "Induction of Chronic Myelogenous Leukemia in Mice by the P210bcr/abl Gene of the Philadelphia Chromosome", Science, 247:824-830 (1990) (8 pgs).

Davis, et al., "Iterative Size-Exclusion Chromatography Coupled with Liquid Chromatographic Mass Spectrometry to Enrich and Identify Tight-Binding Ligands from Complex Mixtures", Tetrahedron, 55:11653-11667 (1999).

de Boer, et al., "Synthesis and Characterization of Conjugated Mono- and Dithiol Oligomers and Characterization of Their Self-Assembled Monolayers", Langmuir, 19:4272-4284 (2003).

de Silva, et al., "Gastrointestinal Stromal Tumors (GIST): C-kin Mutations, CD117 Expression, Differential Diagnosis and Targeted Cancer Therapy with Imatinib", Pathology Oncology Research, 9(1):13-19 (2003).

Deng, et al., "Expression, Characterization, and Crystallization of the Pyrophosphate-Dependent Phosphofructo-1-Kinase of Borrelia Burgdorferi", Archives of Biochemistry and Biophysics, 371(2):326-331 (1999).

Dess, et al., "A Useful 12-I-5 Triacetoxyperiodiane (the Dess-Martin Periodiane) for Selective Oxidation of Primary or Secondary Alcohols and a Variety of Related 12-I-5 Species", J. Am. Chem., Soc., 113:7277-7287 (1991).

Dumas, "Preface", Current Topics in Medicinal Chemistry 2(9):i (2002) (1 Page).

Dumas, "Protein Kinase Inhibitors: Emerging Pharmacophores", Exp. Opin. Ther. Patents, 11(3):405-429 (2001).

Dumas, et al., "Discovery of a New Class of p38 Kinase Inhibitors", Bioorganic & Medicinal Chemistry Letters, 10:2047-2050 (2000).

Ewing, "Critical Evaluation of Search Algorithms for Automated Molecular Docking and Database Screening", Journal of Computational Chemistry, 18(9):1175-1189 (1997).

Farooqui, et al., "Interactions Between Neural Membrane Glycerophospholipid and Sphingolipid Mediators: A Recipe for Neural Cell Survival or Suicide", Journal of Neuroscience Research, 85:1834-1850 (2007).

Fathalla, "Synthesis of New Pyrazolo[1,5-a]pyrimidine Derivative Using 5-Aminouracil and Ketene Dithiacetal", Arch Pharm Res, 22(6):571-574 (1999).

Fathalla, et al., "Synthesis of New Uracil-5-Sulfonamide Derivatives and Immuno-Stimulatory Effect of a Chemically Modified Hemolymph of Biomphalaria Alexandrina on Schistosoma Manosi Infected Mice", Arch Pharm Res., 26(5):358-366 (2003).

Fathalla, et al., "Synthesis of New Uracil-5-Sulphonamide-p-Phenyl Derivatives and Their Effect on Biomphalaria alexandrina Snail's Nucleoproteins", Arch. Pharm. Res., 23(2):128-138 (2000).

Flatt, et al., "Synthesis of Thiol Substituted Oligoanilines for Molecular Device Candidates", Tetrahedron Letters, 44:6699-6702 (2003).

Fletcher, et al., "Diagnosis of Gastrointestinal Stromal Tumors: A Consensus Approach", Human Pathology 33(5):459-465 (2002).

Frame, et al., "A Common Phosphate Binding Site Explains the Unique Substrate Specificity of GSK3 and Its Inactivation by Phosphorylation", Molecular Cell, 7:1321-1327 (2001).

Furuya, et al., "Addition of 4-Ethoxyimidazoles to Dimethyl Acetylenedicarboxylate and Transformation of the Adducts to Pyrimidian-5-yl Acetates", Chem. Pharm. Bull., 36(5):1669-1675 (1988).

Garcia-Tellado, et al., "Molecular Recognition in the Solid Waste State: Controlled Assembly of Hydrogen-Bonded Molecular Sheets", J. Am. Chem. Soc., 113:9265-9269 (1991).

Gishizky, et al., "Efficient Transplantation of BCR-ABL-Induced Chronic Myelogenous Leukemia-Like Syndrome in Mice", Proceedings of the National Academy of Sciences of the United States of America, 90(8):3755-3759 (1993) (6 pages).

Greene, et al., "Chapter 7: Protection for the Amino Group", in Protective Groups in Organic Synthesis, Third Edition, John Wiley: New York, pp. 494-653 (1999).

Griffith, et al., "TPAP: Tetra-n-propylammonium Perruthenate, A Mild and Convenient Oxidant for Alcohols", Aldrichimica Acta, 23(1):13-19 (1990).

Guzel, "Investigation of the Relationship Between the Inhibitory Activity of Glycolic Acid Oxidase (GAO) and its Chemical Structure: Electron-Topological Approach", Journal of Molecular Structure, 366:131-137 (1996).

Haar, et al., "Structure of GSK3b Reveals a Primed Phosphorylation Mechanism", Nature Structural Biology, 8(7):593-596 (2001).

Haesslein, et al., "Recent Advances in Cyclin-Dependent Kinase Inhibition. Purine-Based Derivatives as Anti-Cancer Agents. Roles and Perspectives for the Future", Current Topics in Medicinal Chemistry, 2:1037-1050 (2002).

Heegaard, et al., "Affinity Capillary Electrophoresis: Important Application Areas and Some Recent Developments", Journal of Chromatography B, 715:29-54 (1998).

Honda, et al., "Determination of the Association Constant of Monovalent Mode Protein-Sugar Interaction by Capillary Zone Electrophoresis", Journal of Chromatography, 597:377-382 (1992).

Hu, et al., "Capillary Electrophoresis for the Analysis of Biopolymers", Anal., Chem., 74:2833-2850 (2002).

Huang, et al., "Inhibition of Nucleoside Transport by Protein Kinase Inhibitors", The Journal of Pharmacology and Experimental Therapeutics, 304(2):753-760 (2003).

Hubbard, "Crystal Structure of the Activated Insulin Receptor Tyrosine Kinase in Complex with Peptide Substrate and ATP Analog", EMBO J., 16(18):5573-5581 (1997).

Hubbard, et al., "Crystal Structure of the Tyrosine Kinase Domain of the Human Insulin Receptor", Nature, 372:746-754 (1994).

Hughes, et al., "Modulation of the Glycogen Synthase Kinase-3 Family by Tyrosine Phosphorylation", EMBO J., 12(2):803-808 (1993).

Huse, et al., "The TGFb Receptor Activation Process: An Inhibitor- to Substrate-Binding Switch", Molecular Cell, 8:671-682 (2001).

Igarashi, et al., "Antimicrobial Activities of 2-arylthio-N-alkylmaleimides", Journal of Industrial Microbiology, 9:91-96 (1992).

International Human Genome Sequencing Consortium, "Initial Sequencing and Analysis of the Human Genome", Nature, 409:860-921 (2001).

Ishida, et al., "Molecular Arrangement and Electrical Conduction of Self-Assembled Monolayers Made from Terphenyl Thiols", Surface Science, 514:187-193 (2002).

Islip, et al., "Nitrofuryl Heterocyclics 3", Journal of Medicinal Chemistry, 16(11):1308-1310 (1973).

Jackson, et al., "N-Terminal Mutations Activate the Leukemogenic Potential of the Myristoylated form of c-abl", EMBO, 8(2):449-456 (1989).

Jackson, et al., "Pyridinylimidazole Based p38 MAP Kinase Inhibitors", Current Topics in Medicinal Chemistry, 2:1011-1020 (2002).

Jiang, et al., ""Soft Docking": Matching of Molecular Surface Cubes", J. Mol. Biol., 219:79-102 (1991).

Jiang, et al., "Synthesis and SAR Investigations for Novel Melanin-Concentrating Hormone 1 Receptor (MCH1) Antagonists Part 1. The Discovery of Arylacetamides as Viable Replacements for the Dihydropyrimidione Moiety of an HTS Hit",J. Med. Chem.,50:3870-82, 2007.

Johnson, "Circular Dichroism Spectroscopy and The Vacuum Ultraviolet Region", Ann. Rev. Phys. Chem., 29:93-114 (1978).

Johnson, "Protein Secondary Structure and Circular Dichroism: A Practical Guide", Proteins: Structure, Function, and Genetics, 7:205-214 (1990).

Johnson, et al., "An Evaluation of the Effect of Light Stabilisers on the Exterior Durability of Polyester Powder Coatings for the Architectural Market", Surface Coatings International, 3:134-141 (1999).

Johnson, et al., "The Stereochemistry of Oxidation at Sulfur Oxidation of 2-Thiabicyclo[2.2.1]Hpetane", Tetrahedron, 25:5649-5653 (1969).

Kallander, et al., "4-Aryl-1,2,3-triazole: A Novel Template for a Reversible Methionine Aminopeptidase 2 Inhibitor, Optimized to Inhibit Angiogenesis in Vivo", J Med Chem 48: 5644-5647 (2005).

Katritzky, et al., "Novel Chromophoric Heterocycles Based on Maleimide and Naphthoquinone", J. Heterocyclic Chem., 26:885-892 (1989).

Kern, et al., "Synthese von Makromolekeln einheitlicher Brobe. II Mitt: Syntheses neuer Diol-oligo-urethane nach dem Duplikationsverfahren", Makromolekulara Chemie, 16:89-107 (1955)—German—English Summary (20 pages).

Kim, et al., "Solid Phase Synthesis of Benzamidine and Butylamine-Derived Hydantoin Libraries", Molecular Diversity, 3:129-132 (1998).

Klayman, et al., "The Reaction of S-Methiodide Derivatives of Activated Thioureas with Hydroxylic Compounds. A Novel Synthesis of Mercaptans", J. Org. Chem., 37(10):1532-1537 (1972).

Kleywegt, et al., "Detection, Delineation, Measurement and Display of Cavities in Macromolecular Structures", Acta Cryst, D50:178-185 (1994).

Koch, et al., "QSAR and Molecular Modelling for a Series of Isomeric X-Sulfanilamido-1-phenylpyrazoles", Quant. Struct. Act. Relat., 12:373-382 (1993).

Krasovitskii, et al., "Synthesis and Spectral-Luminescence Properties of Hetarylethylene Derivatives of 2,5-Diphenyloxazole and 2,5-Diphenyl-1,3,4-Oxadiazole", Khimiya Geterotsiklicheskikh Soedinenii, 5:617-621 (1982)—English Translation (10 pages).

Kuhn, et al., "The Genesis of High-Throughput Structure-Based Drug Discovery using Protein Crystallography", Analytical Techniques, Current Opinion in Chemical Biology, 6:704-710 (2002).

Kumar, et al., "P38 Map Kinases: Key Signalling Molecules as Therapeutic Targets for Inflammatory Diseases", Nature Reviews Drug Discovery, 2:717-726 (2003).

Kundrot, "Which Strategy for a Protein Crystallization Project", CMLS, Cell. Mol. Life Sci., 61:525-536 (2004).

Kundu, et al., "Depropargylation Under Palladium-Copper Catalysis: Synthesis of Diaryl Sulfides", Tetrahedron, 57:5885-5895 (2001).

Kurogi, et al., "Discovery of Novel Mesangial Cell Proliferation Inhibitors Using a Three-Dimensional Database Searching Method", J. Med. Chem., 44:2304-2307 (2001).

Kwong, et al., "A General, Efficient, and Inexpensive Catalyst System for the Coupling Aryl Iodides and Thiols", Organic Letters, 4(20):3517-3520 (2002).

Laskowski, "Surfnet: A Program for Visualizing Molecular Surfaces, Cavities, and Intermolecular Interactions", Journal of Molecular Graphics, 13:323-330 (1995).

Leca, et al., "A New Practical One-Pot Access to Sulfonimidates", Organic Letters, 4(23):4093-4095 (2002).

Lefevre, et al., "Roles of Stem Cell Factor/c-Kit and Effects of Glivecâ/STI571 in Human Uveal Melanoma Cell Tumorigenesis", Journal of Biological Chemistry, 279(30):31769-31779 (2004).

Lesort, et al., "Insulin Transiently Increases Tau Phosphorylation: Involvement of Glycogen Synthase Kinase-3b and Fyn Tyrosine Kinase", Journal of Neurochemistry, 72(2):576-584 (1999).

Leung, et al., "The Difluoromethylensulfonic Acid Groups as a Monoanionic Phosphate Surrogate for Obtaining PTP1B Inhibitors", Bioorganic & Medicinal Chemistry, 10:2309-2323 (2002).

Li, et al., "Targeting Serine/Threonine Protein Kinase B/Akt and Cell-cycle Checkpoint Kinases for Treating Cancer", Current Topics in Medicinal Chemistry, 2:939-971 (2002).

Li, et al., "The P190, P210, and P230 Forms of the BCR/ABL Oncogene Induce a Similar Chronic Myeloid Leukemia-like Syndrome in Mice but Have Different Lymphoid Leukemogenic Activity", J. Exp. Med., 189(9):1399-1412 (1999).

Link, et al., "Synthesis of 8-Substituted 5-Deazaflavins", J. Heterocyclic Chem, 22:841-848 (1985).

Lipinski, et al., "Experimental and Computational Approaches to Estimate Solubility and Permeability in Drug Discovery and Development Settings", Advanced Drug Delivery Reviews, 23:3-25 (1997).

Lohse, et al., The Palladium Catalyzed Suzuki Coupling of 2- and 4-Chloropyridines, Synlett 1: 45-48 (1999).

Loren, et al., "NH-1,2,3-Triazoles from Azidomethyl Pivalate and Carbamates: Base-Labile N-Protecting Groups", SYNLETT, 18:2847-2850 (2005).

Ma, et al., "c-MET Mutational Analysis in Small Cell Lung Cancer: Novel Juxtamembrane Domain Mutations Regulating Cytoskeletal Functions", Cancer Research, 63:6272-6281 (2003).

Ma, et al., "c-MET: Structure, Functions and Potential for Therapeutic Inhibition", Cancer and Metastasis Reviews, 22:309-325 (2003).

Mallakpour, et al., "Uncatalyzed Polymerization of Bistriazolinediones with Electron-Rich Aromatic Compounds via Electrophilic Aromatic Substitution", Journal of Polymer Science: Part A: Polymer Chemistry, 27:217-235 (1989).

Mamaev, et al., "Synthesis of 2,5'-Bipyrimidines from Substituted 5-Cyanopyrimidines", Khimiya Geterotsiklicheskikh Soedinenni, 24(3):371-375—(1988) English Translation.

Smith, et al., "Classification of Reactions by Type of Compound Synthesized", March's Advanced Organic Chemistry: Reactions, Mechanisms, and Structure, Fifth Edition, Smith and March Editors, Wiley-Interscience Publication (2001) pp. 1654-1655.

Smith, et al., "Tautomerism", from March's Advanced Organic Chemistry, Fifth Edition, Smith and March Editors, Wiley-Interscience Publication (2001) pp. 69-74.

Martinez, et al., "First Non-ATP Competitive Glycogen Synthase Kinase 3b (GSK-3b) Inhibitors: Thiadizolidinones (TDZD) as Potential Drugs for the Treatment of Alzheimers Disease", J. Med. Chem., 45(2002)1292-1299 (2002).

Mattsson, et al., "Six X-Linked Agammaglobulinemia-Causing Missense Mutations in the Src Homology 2 Domain of Bruton's Tyrosine Kinase: Phosphotyrosine-Binding and Circular Dichroism Analysis", Journal of Immunology, 64: 4170-4177 (2000).

McPherson, "Current Approaches to Macromolecular Crystallization", Eur. J. Biochem, 189:1-23 (1990).

Medebielle, et al., "A Convenient Synthesis of Perfluoroalkylated and Fluorinated-Aryl Nitrogen Bases by Electrochemically Induced SRN1 Substitution", J. Org. Chem., 61:1331-1340 (1996).

Medebielle, et al., "A New Convenient Synthesis of 5-Aryl Uracils Using SRN1 Aromatic Nucleophilic Substitution", Tetrahedron Letters, 34(21):3409-3412 (1993).

Mikhaleva, et al., "Relative Reactivities of the Chlorine Atoms of 2,2',4-Trichloro-4',5-Dipyrimidinyl in its Reaction with Piperidine", Khimiya Geterotsiklicheskikh Soedinenii, 6:821-826 (1979)—English Translation (12 pages).

Morris, et al., "Automated Docking of Flexible Ligands to Macromolecules", AutoDock Website, www.scripps.edu/mb/olson/doc/autodock/, printed Mar. 3, 2005 (3 pages).

Morris, et al., "Automated Docking Using a Lamarckian Genetic Algorithm and an Empirical Binding Free Energy Function", Journal of Computational Chemistry, 19(14):1639-1662 (1998).

Morstyn, et al., "Stem Cell Factor Is a Potent Synergistic Factor in Hematopoiesis", Oncology, 51:205-214 (1994).

Moss, et al., "Basic Terminology of Stereochemistry", Pure & Appl. Chem., 68(12):2193-2222 (1996).

Muller, "Glossary of Terms Used in Physical Organic Chemistry", Pure & Appl. Chem., 66(5):1077-1184 (1994).

Muller, et al., "A General Synthesis of 4-Substituted 1,1-Dioxo-1,2,5-thiadiazolidin-3-ones Derived from a-Amino Acids", J. Org. Chem., 54:4471-4473 (1989).

Murayama, et al., "JNK (c-Jun NH2 Terminal Kinase) and p38 During Ischemia Reperfusion Injury in the Small Intestine" Transplantation, 81(9):1325-1330 (2006).

Mutlib, et al., "Disposition of 1-[3-(Aminomethyl)phenyl]-N-[3-fluoro-2'-(methylsulfonyl)-[1,1'-biphenyl]-4-yl]-3(trifluomethyl)-1H-pyrazole-5-carboxamide (DPC 423) by Novel Metabolic Pathways. Characterization of Unusual Metabolites by Liquid Chromatography/Mass Spectrometry and NMR", Chem. Res. Toxicol., 15:48-62 (2002).

Mutlib, et al., "P450-Mediated Metabolism of 1-[3-(Aminomethyl)phenyl]-N-[3-fluoro-2'-(methylsulfonyl)-[1,1'-biphenyl]-4-yl]-3(trifluomethyl)-1H-pyrazole-5-carboxamide (DCP 423) and Its Analogues to Aldoximes. Characterization of Glutathione Conjugates of Postulated Intermediates Derived from Aloximes", Chem. Res. Toxicol., 15:63-75 (2002).

Nagano, M. et al. "Studies on Organic Sulfur Compounds. XIV. The Reaction of N-alkoxy-carbonyl-N'-(2-thiazolyl)thioureas with some oxidants." Chemical and Pharmaceutical Bulletin. vol. 21, No. 11, pp. 2408-2416. Nov. 1973.

Nagar, et al., "Crystal Structures of the Kinase Domain of c-Abl in Complex with the Small Molecule Inhibitors PD173955 and Imatinib (STI-571)", Cancer Research, 62:4236-4243 (2002).

Nagar, et al., "Structural Basis for the Autoinhibition of c-Abl Tyrosine Kinase", Cell, 112:859-871 (2003).

Nakopoulou, et al., "c-Met Tyrosine Kinase Receptor Expression is Associated with Abnormal b-catenin Expression and Favourable Prognostic Factors in Invasive Breast Carcinoma", Histopathology, 36:313-325 (2000).

Nantka-Namirski, et al., "Condensation Reaction of Ethyl (4-Uracil)-Acetate with Ethyl Orthoformate", ACTA Polon. Pharm XXVII(5):455-463 (1971).

National Academy of Sciences, "Abstracts of Papers Presented at the Autumn Meeting, Nov. 14-16, 1960", Science, 132:1488-1501 (1960) (15 pages).

Nicolaou, et al.,"Molecular Design and Chemical Synthesis of a Highly Potent Epothilone", ChemMedChem, 1:41-44 (2006).

Nikolaev, et al., "Solubility Polytherm in the System HNO3-H20-(C4H9O)PO(C4H9)2", Doklady Akademii Nauk SSSR, 160(4):841-844 (1965)—English Translation.

Nofal, et al., "Synthesis of Novel Uracil-5-Sulphonamide Derivatives of Possible Biological Activity", Egypt J. Chem., 33(4):375-380 (1990).

O'Dell, et al., "Treatment of Rheumatoid Arthritis with Methotrexate Alone, Sulfasalazine and Hydroxychloroquine, or a Combination of All Three Medications", New England J. Med., 334(20):1287-1291(1996).

O'Neill, "Targeting Signal Transduction as a Strategy to Treat Inflammatory Diseases", Nature Review Drug Discovery, Published Online Jun. 9, 2006, www.nature.com/reviews/drugdisc (15 pages).

Okano, et al., "o-Bromophenylzinc Compound: A Readily Available and Efficient Synthetic Equivalent of o-Phenylene 1-Anion 2-Cation", Tetrahedron Letters 39:3001-3004 (1998).

Okishio, et al., "Differential Ligand Recognition by the Src and Phosphatidylinositol 3-Kinase Src Homology 3 Domains: Circular Dichroism and Ultraviolet Resonance Raman Studies", Biochemistry, 42:208-216 (2003).

Okishio, et al., "Identification of Tyrosine Residues Involved in Ligand Recognition by the Phosphatidylinositol 3-Kinase Src Homology 3 Domain: Circular Dichroism and UV Resonance Raman Studies", Biochemistry, 40:15797-15804 (2001).

Okishio, et al., "Role of the Conserved Acidic Residue Asp21 in the Structure of Phosphatidylinositol 3-Kinase Src Homolgy 3 Domain: Circular Dichroism and Nuclear Magnetic Resonance Studies", Biochemistry 40:119-129 (2001).

Parang, et al., "Mechanism-based Design of a Protein Kinase Inhibitor", Nature Structural Biology, 8(1):37-41 (2001).

Pargellis, et al., "Inhibition of p38 MAP Kinase by Utilizing a Novel Allosteric Binding Site", Nature Structural Biology, 9(4):268-272 (2002).

Park, et al., "Mechanism of met Oncogene Activation", Cell, 45:895-904 (1986).

Pearlman, et al., "Assisted Model Building with Energy Refinement", Amber Home Page, amber.scripts.edu (9 pages), 2005.

Pedersen, "The Preparation of Some N-Methyl-1,2,3-Triazoles", Acta Chimica Scandinavica, 13(5):888-892 (1959).

Peng, et al., "Identification of Novel Inhibitors of BCR-ABL Tyrosine Kinase via Virtual Screening", Bioorganic & Medicinal Chemistry Letters, 13:3693-3699 (2003).

Pereira, et al., "The Role of c-kit and Imatinib Mesylate in Uveal Melonoma", Journal of Carcinogenesis, 4:19 (2005) (8 pages).

Picard, et al., "Inhibitors of Acyl-CoA: Cholesterol O-Acyltrasferase. 17. Structure-Activity Relationships of Several Series of Compounds Derived from N-Chlorosulfonyl Isocyanate", J. Med. Chem., 39:1243-1252 (1996).

Pluk, et al., "Autoinhibition of c-Abl", Cell, 108:247-259 (2002).

Ponzetto, et al., "A Novel Recognition Motif for Phosphatidylinositol 3-Kinase Binding Mediates Its Association with the Hepatocyte Growth Factor/Scatter Factor Receptor", Molecular and Cellular Biology, 13(8):4600-4608 (1993).

Raimbault, et al., "Effects of pH and KCl on the Conformations of Creatine Kinase from Rabbit Muscle", Eur. J. Biochem., 234:570-578 (1995).

Rebek, et al. "Convergent Functional Groups: Synthetic and Structural Studies", J. Am. Chem. Soc., 107:7476-7481 (1985).

Rebek, et al., "Convergent Functional Groups. 2. Structure and Selectivity in Olefin Epoxidation with Peracids", J. Org. Chem., 51:1649-1653 (1986).

Reed, et al., "Circular Dichroic Evidence for an Ordered Sequence Ligand/Binding Site Interactions in the Catalytic Reaction of the cAMP-Dependent Protein Kinase", Biochemistry, 24:2967-2973 (1985).

Regan, et al., "Pyrazole Urea-Based Inhibitors of p38 MAP Kinase: From Lead Compound to Clinical Candidate", J. Med. Chem., 45:2994-3008 (2002).

Regan, et al., "Structure-Activity Relationships of the p38a MAP Kinase Inhibitor 1-)5-tert-Butyl-2-p-tolyl-2H-pyrazol-3-yl)-3-[4-(2-morpholin-4-yl-ethoxy)naph-thalen-1-yl]urea (BIRB 796)", J. Med. Chem., 46:4676-4686 (2003).

Rooney, et al., "Inhibitors of Gylcolic Acid Oxidase. 4-Substituted 3-Hydroxy-1H-pyrrole-2,5-dione Derivatives", J. Med. Chem., 26(5):700-714 (1983).

Roux, et al., "ERK and p38 MAPK-Activated Protein Kinases: a Family of Protein Kinases with Diverse Biological Functions", Microbiology and Molecular Biology Reviews, 68(2):320-344 (2004).

Rowley, "A New Consistent Chromosomal Abnormality in Chronic Myelogenous Leukaemia Identified by Quinacrine Fluorescence and Giemsa Staining", Nature, 243:290-293 (1973).

Russell, et al., "3-[3-(Piperdin-1-yl)propyl]indoles as Highly Selective h5-HT1D Receptor", J. Med. Chem., 42:4981-5001 (1999).

Saiga, et al., "Consecutive Cross-Coupling of o-Phenylenedizinc Compound with Acyl and/or Aryl Halides in the Presence of Pd(0)-tris(2,4,6-trimethoxyphenyl)phosphine", Tetrahedron Letters, 41:4629-4632 (2000).

Sakamoto, et al., "Condensed Heteroaromatic Ring Systems. XIX. Synthesis and Reactions of 5-(Tributylstannyl)Isoxazoles", Tetrahedron, 47(28):5111-5118 (1991).

Sakuma, et al., "c-kit Gene Mutations in Intracranial Germinomas", Cancer Sci, 95(9):716-720 (2004).

Satsangi, et al., "1-(4-Substituted-thiazol-2-yl)hydatoins as Anti-inflammatory and CNS-Active Agents", Pharmazie, 38:341-342 (1983).

Schiering, et al, "Crystal Structure of the Tyrosine Kinase Domain of the Hepatocyte Growth Factor Receptor c-Met and its Complex with the Microbial Alkaloid K-252a", Proc. Nat'l Acad. Sci 100(22): 12654-12659 (2003).

Schmidt, et al., "Germline and Somatic Mutations in the Tyrosine Kinase Domain of the MET proto-oncogene in Papillary Renal Carcinomas", Nature Genetics, 16:68-73 (1997).

Schmidt, et al., "Novel Mutations of the MET Proto-oncogene in Papillary Renal Carcinomas", Oncogene, 18:2343-2350 (1999).

Seimiya, et al., "Telomere Shortening and Growth Inhibition of Human Cancer Cells by Novel Synthetic Telomerase Inhibitors MST-312, MST-295, and MST-199", Molecular Cancer Therapeutics, 1:657-665 (2002).

Seminario, et al., "Theoretical Study of a Molecular Resonant Tunneling Diode", J. Am. Chem. Soc., 122:3015-3020 (2000).

Shah, et al., "Circular Dichroic Studies of Protein Kinase C and its Interactions with Calcium and Lipid Vesicles", Biochimica et Biophysica Acta, 1119:19-26 (1992).

Shi, et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate", Bull. Chem. Soc. Jpn., 65:3315-3321 (1992).

Shinkai, et al., "Coenzyme Models, Part 45. Synthesis of Atropisomeric Flavins and their Novel Redox-induced Racernisation", J. Chem. Soc. Perkin Trans., pp. 313-319 (1988).

Shiozaki, et al., "Impaired Differentiation of Endocrine and Exocrine Cells of the Pancreas in Transgenic Mouse Expressing the Truncated Type II Activin Receptor", Biochimica et Biophysica Acta, 1450:1-11 (1999).

Stout, et al., "High-Throughput Structural Biology in Drug Discovery: Protein Kinases", Current Pharmaceutical Design, 10:1069-1082 (2004).

Sugden, et al., ""Stress-Responsive" Mitogen-Activated Protein Kinases (c-Jun N-Terminal Kinases and p38 Mitogen-Activated Protein Kinases) in the Myocardium", Circulation Research—Journal of the American Heart Association, 83:345-352 (1998).

Tanis, et al., "Two Distinct Phosphorylation Pathways Have Additive Effects on Abl Family Kinase Activation", Molecular and Cellular Biology, 23(11):3884-3896 (2003).

Teague, "Implications of Protein Flexibility for Drug Discovery", Nature Reviews Drug Discovery, 2:527-541 (2003).

Tominaga, et al., "General model for Estimation of the Inhibition of Protein Kinases Using Monte Carlo Simulations", J. Med. Chem., 47:2534-2549 (2004).

Tremblay, et al., "Efficient Solid-Phase Synthesis of Sulfahydantoins", J. Comb. Chem., 4:429-435 (2002).

"Trilateral Project WM4 -Comparative Studies in New Technologies: Report on Comparative Study on Protein 3-Dimensional Structure Related Claims—ANNEX 3: Comments of the USPTO", Vienna, Austria, Nov. 4-8, pp. 58-79 (2002).

Tsuzuki, et al., "Synthesis and Structure-Activity Relationships of Novel 7-Substituted 1,4-Dihydro-4-oxo-1-(2-thiazolyl)-1,8-napthyridine-3-carboxylic Acids as Antitumor Agents. Part 2", J. Med. Chem., 47:2097-2109 (2004).

Van Etten, "Cycling, Stressed-Out and Nervous: Cellular Functions of c-Abl", Trends in Cell Biology, 9:179-186 (1999).

Venter, et al., "The Sequence of the Human Genome", Science, 291:1304-1351, Feb. 16, 2001; Erratum, Jun. 8, 2001 (49 pages).

Waetzig, et al., "Review Article: Mitogen-Activated Protein Kinases in Chronic Intestinal Inflammation—Targeting Ancient Pathways to Treat Modern Diseases", Aliment Pharmacol Ther, 18:17-32 (2003).

Welker, et al., "Glucocorticoid-Induced Modulation of Cytokine Secretion from Normal and Leukemic Human Myelomonocytic Cells", Int. Arch. Allergy Immunol, 109:110-115 (1996).

Wentland, et al., "3-Quinolinecarboxamides. A Series of Novel Orally-Active Antiherpetic Agents", J. Med. Chem., 36:1580-1596 (1993).

Wilson, et al., "The Structural Basis for the Specificity of Pyridinylimidazole Inhibitors of p38 MAP Kinase", Chemistry & Biology, 4(6):423-431 (1997).

Wilson, et el., "Laser-Jet Delayed Trapping: Electron-Transfer Trapping of the Photoenol from 2-Methylbenzophenone", J. Am. Chem. Soc., 109:4743-4745 (1987).

Wolter, et al., "Copper-Catalyzed Coupling of Aryl Iodides with Aliphatic Alcohols", Organic Letters, 4(6):973-976 (2002).

Wrana, et al., "Mechanism of Activation of the TGF-b Receptor", Nature, 370:341-347 (1994).

Wu, et al., "Discovery of a Novel Family of CDK Inhibitors with the Program LIDAEUS: Structual Basis for Ligand-Induced Disordering of the Acivation Loop", Structure, 11:399-410 (2003).

Yang, et al., "Molecular Mechanism for the Regulation of Protein Kinase B/Akt by Hydrophobic Motif Phosphorylation", Molecular Cell, 9:1227-1240 (2002).

Yang, et al., "Palladium-Catalyzed Amination of Any Halides and Sulfonates", Journal of Organometallic Chemistry, 576:125-146 (1999).

Yarden, et al., "Human Proto-oncogene c-kit: a New Cell Surface Receptor Tyrosine Kinase for an Unidentified Ligand", The EMBO Journal, 6(11):3341-3351 (1987).

Yoneda, et al., "A New Synthesis of Purines", J.C.S. Chem. Comm., p. 551 (1974).

Yonezawa, et al., "Synthesis of Sequentially Controlled Isomeric, Wholly aromatic Polyketones Composed of 2-trifluoromethylbiphenylene and 2,2'-dimethoxybiphenylene Units", Reactive & Functional Polymers, 52:19-30 (2002).

Yoshimoto, et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Reductase, Malate Dehydrogenase, Glutamate Dehydrogenase, Lactate Dehydrogenase, and Glyceraldehyde-phosphate Dehydrogenase", Journal of Medicinal Chemistry, 19(1):71-98 (1976).

Yoshino, et al., "Organic Phosphorous Compounds. 2. Synthesis and Coronary Vasodilator Activity of (Benzothiazolybenzyl) Phosphonate Derivatives", J. Med. Chem., 32:1528-1532 (1989).

Yu, et al., "Frequency of TPR-MET Rearrangement in Patients with Gastric Carcinoma and in First-Degree Relatives", Cancer, 88(8):1801-1806 (2000).

Zaidi, et al., "New Anti-Mycobacterial Hydantoins", Pharmazie, 35:755-756 (1980).

Zhen, et al., "Structural and Functional Domains Critical for Constitutive Activation of the HGF-Receptor (Met)", Oncogene, 9(6):1691-1697 (1994).

Zvilichovsky, et al., "Aminolysis and Polymerization of 3-(p-Toluenesulfonoxy) Hydantoin", Israel Journal of Chemistry, 7:547-554 (1969).

International Preliminary Report on Patentability for PCT/US2007/078408, mailed Apr. 11, 2008 (8 pages).

Extended European Search Report for Ep 07 84 2438, mailed Sep. 1, 2010 (4 pages).

* cited by examiner

DIHYDROPYRIDOPYRIMIDINYL, DIHYDRONAPHTHYIDINYL AND RELATED COMPOUNDS USEFUL AS KINASE INHIBITORS FOR THE TREATMENT OF PROLIFERATIVE DISEASES

CROSS-REFERENCE TO RELATED APPLICATIONS

This application claims the benefit of Provisional Application 60/844,552 filed Sep. 14, 2006. This application is incorporated by reference herein.

FIELD OF THE INVENTION

The present invention relates to novel kinase inhibitors and modulator compounds useful for the treatment of various diseases. More particularly, the invention is concerned with such compounds, kinase/compound adducts, methods of treating diseases, and methods of synthesis of the compounds. Preferably, the compounds are useful for the modulation of kinase activity of Raf kinases and disease polymorphs thereof.

BACKGROUND OF THE INVENTION

Several members of the protein kinase family have been clearly implicated in the pathogenesis of various proliferative diseases and thus represent important targets for treatment of these diseases. Some of the proliferative diseases relevant to this invention include cancer, rheumatoid arthritis, atherosclerosis, and retinopathies. Important examples of kinases which have been shown to cause or contribute to the pathogensis of these diseases including, but not limited to, BRaf, CRaf, Abl, KDR(VEGF), EGFR/HER1, HER2, HER3, cMET, FLT-3, PDGFR-a, PDGFR-b, p38, cKIT, JAK2.

A major signaling pathway downstream of cell surface growth factor receptor activation is the Ras-RAF-MEK-ERK-MAP kinase pathway (Peyssonnaux, C. et al, Biol. Cell (2001)93: 53-62, Cancers arise when mutations occur in one or more of the proteins involved in this signaling cascade. Cell proliferation and differentiation become dysregulated and cell survival mechanisms are activated which allow unregulated cancer cells to override protective programmed cell death surveillance. Mutations in the p21-Ras protein have been shown to be a major cause of dysregulation of this signaling pathway, leading to the development of human cancers. P21-Ras mutations have been identified in approximately 30% of human cancers (Bolton et al, *Ann. Rep. Med. Chem.* (1994)29: 165-174). Cancer-causing mutations in the P21-Ras protein lead to a constitutively active signaling cascade, causing unregulated activation of the downstream components of the RAF-MEK-ERK-MAP kinase pathway (Magnuson et al, *Semin. Cancer Biol.* (1994)5: 247-253). The three RAF kinases which participate in this signaling cascade are known as ARAF, BRAF, and CRAF (Peyssonnaux, C. et al, *Biol. Cell* (2001)93: 53-62; Avruch, J., *Recent Prog. Horm. Res.* (2001)56: 127-155; Kolch, W., *Biochem. J.* (2000)351: 289-305). These RAF kinase isoforms are all activated by Ras, and thus are activated in cancers that result from mutated and upregulated p21-Ras protein activity. In addition to activation of this signaling cascade at the initial p21-Ras protein level, mutations have also been found in BRAF kinase which results in activation of the cascade downstream from p21-Ras (Davies, H., et al, *Nature* (2002)417: 949-954). A dominant single site mutation at position 600 in the BRAF kinase was shown to be particularly aggressive and linked to approximately 80% of the observed human malignant melanomas. This mutation substitutes the negatively charged amino acid glutamic acid for the normally occurring neutral amino acid valine. This single site mutation is sufficient to render the mutated BRAF kinase constitutively active, resulting in signaling pathway dysregulation and human cancer. Hence small molecule inhibitors of BRAF kinase are a rational approach to the treatment of human malignancy, whether the signaling mutation is at the level of the upstream p21-Ras protein or at the level of BRAF kinase.

The majority of small molecule kinase inhibitors that have been reported have been shown to bind in one of three ways. Most of the reported inhibitors interact with the ATP binding domain of the active site and exert their effects by competing with ATP for occupancy. Other inhibitors have been shown to bind to a separate hydrophobic region of tire protein known as the "DFG-in-conformation" pocket, and still others have been shown to bind to both the ATP domain and the "DFG-in-conformation" pocket. Examples specific to inhibitors of RAF kinases can be found in Lowinger et al, *Current Pharmaceutical Design* (2002)8: 2269-2278; Dumas, J. et al, *Current Opinion in Drug Discovery & Development* (2004)7: 600-616; Dumas, J. et al, WO 2003068223 A1 (2003); Dumas, J., et al, WO 9932455 A1 (1999), and Wan, P. T. C., et al, *Cell* (2004)116: 855-867.

Physiologically, kinases are regulated by a common activation/deactivation mechanism wherein a specific activation loop sequence of the kinase protein binds into a specific pocket on the same protein which is referred to as the switch control pocket (see WO 200380110049 for further details). Such binding occurs when specific amino acid residues of the activation loop are modified for example by phosphorylation, oxidation, or nitrosylation. The binding of the activation loop into the switch pocket results in a conformational change of the protein into its active form (Huse, M. and Kuriyan, *J. Cell* (109)275-282.).

SUMMARY OF THE INVENTION

Compounds of the present invention find utility in the treatment of mammalian cancers and especially human cancers including but not limited to malignant melanoma, colorectal cancer, ovarian cancer, papillary thyroid carcinoma, lung cancers, kidney cancers, pancreatic cancer, glioblastomas, myeloproliferative diseases, and mesothelioma. Compounds of the present invention also find utility in the treatment of inflammatory diseases including rheumatoid arthritis, retinopathies including diabetic retinal neuropathy and macular degeneration, cardiovascular disease and metabolic diseases.

DESCRIPTION OF THE PREFERRED EMBODIMENTS

The following descriptions refer to various compounds and moieties thereof.

Carbocyclyl refers to carbon rings taken from cyclopropyl, cyclobutyl, cyclopentyl, cyclohexyl, cycloheptanyl, cyclooctanyl, norboranyl, norborenyl, bicyclo[2.2.2]octanyl, and bicyclo[2.2.2]octenyl;

Halogen refers to fluorine, chlorine, bromine and iodine;

Aryl refers to monocyclic or fused bicyclic ring systems characterized by delocalized π electrons (aromaticity) shared among the ring carbon atoms of at least one carbocyclic ring; preferred aryl rings are taken from phenyl, naphthyl, tetrahydronaphthyl, indenyl, and indanyl;

Heteroaryl refers to monocyclic or fused bicyclic ring systems characterized by delocalized % electrons (aromaticity) shared among the ring carbon or heteroatoms including nitrogen, oxygen, or sulfur of at least one carbocyclic or heterocyclic ring; heteroaryl rings are taken from, but not limited to, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyridinyl, pyrimidinyl, pyrazinyl, pyridazinyl, triazinyl, indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl, thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyridiminyl, thiazolonopyrimidinyl, oxazolopyridiminyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, or benzoxazepinyl;

Heterocyclyl refers to monocyclic rings containing carbon and heteroatoms taken from oxygen, nitrogen, or sulfur and wherein there is not delocalized π electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

Poly-aryl refers to two or more monocyclic or fused aryl bicyclic ring systems characterized by delocalized π electrons (aromaticity) shared among the ring carbon atoms of at least one carbocyclic ring wherein the rings contained therein are optionally linked together;

Poly-heteroaryl refers to two or more monocyclic or fused bicyclic systems characterized by delocalized π electrons (aromaticity) shared among the ring carbon or heteroatoms including nitrogen, oxygen, or sulfur of at least one carbocyclic or heterocyclic ring wherein the rings contained therein are optionally linked together, wherein at least one of the monocyclic or fused bicyclic rings of the poly-heteroaryl system is taken from heteroaryl as defined broadly above and the other rings are taken from either aryl, heteroaryl, or heterocyclyl as defined broadly above;

Poly-heterocyclyl refers to two or more monocyclic or fused bicyclic ring systems containing carbon and heteroatoms taken from oxygen, nitrogen, or sulfur and wherein there is not delocalized π electrons (aromaticity) shared among the ring carbon or heteroatoms wherein the rings contained therein are optionally linked, wherein at least one of the monocyclic or fused bicyclic rings of the poly-heteroaryl system is taken from heterocyclyl as defined broadly above and the other rings are taken from either aryl, heteroaryl, or heterocyclyl as defined broadly above;

Lower alkyl refers to straight or branched chain C1-C6alkyls;

Substituted in connection with a moiety refers to the fact that a further substituent may be attached to the moiety to any acceptable location on the moiety.

The term salts embraces pharmaceutically acceptable salts commonly used to form alkali metal salts of free acids and to form addition salts of free bases. The nature of the salt is not critical, provided that it is pharmaceutically-acceptable. Suitable pharmaceutically-acceptable acid addition salts may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, and heterocyclyl containing carboxylic acids and sulfonic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, 2-hydroxyethanesulfonic benzenesulfonic, pantothenic, toluenesulfonic, 2-hydroxyethanesulfonic, sulfanilic, cyclohexylaminosulfonic, algenic, 3-hydroxybutyric, galactaric and galacturonic acid. Suitable pharmaceutically-acceptable salts of free acid-containing compounds of the invention include metallic salts and organic salts. More preferred metallic salts include, but are not limited to appropriate alkali metal (group Ia) salts, alkaline earth metal (group IIa) salts and other physiological acceptable metals. Such salts can be made from aluminum, calcium, lithium, magnesium, potassium, sodium and zinc. Preferred organic salts can be made from primary amines, secondary amines, tertiary amines and quaternary ammonium salts, including in part, tromethamine, diethylamine, tetra-N-methylammonium, N,N'-dibenzylethylenediamine, chloroprocaine, choline, diethanolamine, ethylenediamine, meglumine (N-methylglucamine) and procaine.

The term prodrug refers to derivatives of active compounds which revert in vivo into the active form. For example, a carboxylic acid form of an active drug may be esterified to create a prodrug, and the ester is subsequently converted in vivo to revert to the carboxylic acid form. See Ettmayer et. al, *J. Med. Chem.*, 2004, 47(10), 2393-2404 and Lorenzi et. al, *J. Pharm. Exp. Therpeutics,* 2005, 883-8900 for reviews.

1. First Aspect of The Invention-Compounds, Preparations and Methods

In the first aspect of the invention, compounds are of the formula Ia

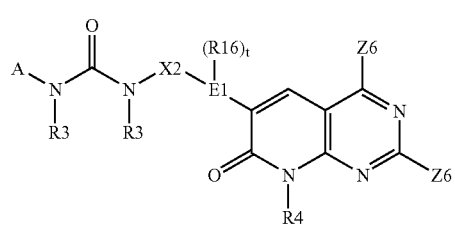

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein A is selected from the group consisting of phenyl, naphthyl, C3-C8carbocyclyl, indanyl, tetralinyl, indenyl, G1, G2, G3, G4 and —CHR4R8;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

G2 is a fused bicyclic heteroaryl taken from the group consisting of indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl, thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyridiminyl, thiazolonopyrimidinyl, oxazolopyridiminyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, benzisothiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, and benzoxazepinyl;

G3 is a non-fused bicyclic heteroaryl taken from the group consisting of pyridylpyridiminyl pyrimidinylpyrimidinyl, oxazolylpyrimidinyl, thiazolylpyrimidinyl, imidazolylpyrimidinyl, isoxazolylpyrimidinyl, isothiazolylpyrimidinyl, pyrazolylpyrimidinyl, triazolylpyrimidinyl, oxadiazoylpyrimidinyl, thiadiazoylpyrimidinyl, morpholinylpyrimidinyl, dioxothiomorpholinylpyrimidinyl, and thiomorpholinylpyrimidinyl;

G4 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

the A ring may be optionally substituted with one or more —X1-A1 moieties;

X1 is selected from the group consisting of —(CH$_2$)$_n$—(O)$_r$—(CH$_2$)$_n$—, —(CH$_2$)$_n$—(NR3)$_r$-(CH$_2$)$_n$—, —(CH$_2$)$_n$—(S)$_r$—(CH$_2$)$_n$—, —(CH$_2$)$_n$—(C=O)$_r$—(CH$_2$)$_n$—, —(CH$_2$)$_u$—(C(=O)—NR3)$_r$-(CH$_2$)$_n$—, and —(CH$_2$)$_n$—(SO$_2$—NR3)$_r$-(CH$_2$)$_n$—, wherein any of the alkylenes may be straight or branched chain;

X2 is selected from the group consisting of C1-C6alkyl, branched C2-C6alkyl, and a direct bond wherein E1 is directly linked to the NR3 group of formula Ia;

A1 is selected from the group consisting of hydrogen, aryl, G1, G2, G3, G4, C1-C6 alkyl, branched C3-C8alkyl, R19 substituted C3-C8-carbocyclyl, fluoroC1-C6alkyl wherein the alkyl is fully or partially fluorinated, halogen, cyano, hydroxyl, —N(R4)$_2$, —R5, —C(O)N(R4)$_2$, C(O)R5, C1-C6alkoxy, and fluoroC1-C6alkoxy wherein the alkyl group is fully or partially fluorinated;

When A and A1 have one or more substitutable sp2-hybridized carbon atom, each respective sp2 hybridized carbon atom may be optionally substituted with a Z1 or Z3 substituent;

when A and A1 have one or more substitutable sp3-hybridized carbon atom, each respective sp3 hybridized carbon atom may be optionally substituted with a Z2 or R3 substituent;

when A and A1 have one or more substitutable nitrogen atom, each respective nitrogen atom may be optionally substituted with a Z4 substituent;

each Z1 is independently and individually selected from the group consisting of hydrogen, hydroxyC1-C6alkyl, C1-C6alkoxy, C1-C6alkoxyC1-C6alkyl, (R4)$_2$NC1-C6alkyl, (R4)$_2$NC2-C6alkylN(R4)-(CH$_2$)$_n$—, (R4)$_2$NC2-C6alkylO—(CH$_2$)$_n$—, (R3)$_2$N—C(=O)—, (R4)$_2$N—C(=O)—, (R4)$_2$N—CO—C1-C6alkyl-, C1-C6alkoxycarbonyl-, -carboxyC1-C6alkyl, C1-C6alkoxycarbonylC1-C6alkyl, (R3)$_2$NSO$_2$—, —SOR3, (R4)$_2$NSO$_2$—, —SO$_2$R3, —SOR4, —C(=O)R6, —C(=NOH)R6, —C(=NOR3)R6, —(CH$_2$)$_n$N(R4)C(O)R8, —(CH$_2$)$_n$-G1, —(CH$_2$)$_n$-G4, phenoxy, —(CH$_2$)$_n$—O—(CH$_2$)$_n$-G1, —(CH$_2$)$_n$—O—(CH$_2$)$_n$-G4, —(CH$_2$)$_n$—NR3-(CH$_2$)$_n$-aryl, —(CH$_2$)$_n$—NR3-(CH$_2$)$_n$-G1, —(CH$_2$)$_n$—NR3-(CH$_2$)$_n$-G4, —S(O)$_2$R5, —N=S(O)R6R8, —S(O)(=NR3)R6, —(CH$_2$)$_n$NHC(O)NHS(O)$_2$R8, —(CH$_2$)$_n$NHS(O)$_2$NHC(O)R8, —C(O)NHS(O)$_2$R8, —S(O)$_2$NHC(O)R8, —(CH$_2$)$_n$NHC(O)(CH$_2$)$_n$R5, —(CH$_2$)$_n$NHS(O)$_2$(CH$_2$)$_n$R5, —(CH$_2$)$_n$C(O)NH(CH$_2$)$_q$R5, —(CH$_2$)$_n$C(O)R5, —(CH$_2$)$_n$OC(O)$_n$R5, —(CH$_2$)$_n$S(O)$_2$NH(CH$_2$)$_q$R5, —CH(OH)(CH$_2$)$_p$R5, —CH(OH)CH(OH)R4, —(CH$_2$)$_n$N(R4)$_2$, —(CH$_2$)$_n$R5, —C(=NH)R5, —C(=NH)N(R4)$_2$, —C(=NOR3)R5, —C(=NOR3)N(R4)$_2$, and —NHC(=NH)R8;

in the event that Z1 contains an alkyl or alkylene moiety, such moieties may be further substituted with one or more C1-C6alkyls;

each Z2 is independently and individually selected from the group consisting of hydrogen, aryl, C1-C6alkyl, C3-C8-carbocyclyl, hydroxyl, hydroxyC1-C6alkyl-, cyano, (R3)$_2$N—, (R4)$_2$N—, (R4)$_2$NC1-C6alkyl-, (R4)$_2$NC2-C6alkylN(R4)-(CH$_2$)$_n$—, (R4)$_2$NC2-C6alkylO—(CH$_2$)$_n$—, (R3)$_2$N—C(=O)—, (R4)$_2$N—C(=O)—, (R4)$_2$N—CO—C1-C6alkyl-, carboxyl, carboxyC1-C6alkyl, C1-C6alkoxycarbonyl, C1-C6alkoxycarbonylC1-C6alkyl, (R3)$_2$NSO$_2$—, (R4)$_2$NSO$_2$—, —SO$_2$R5, —SO$_2$R8, —(CH$_2$)$_n$N(R4)C(O)R8, —C(O)R8, =O, =NOH, =N(OR6), —(CH$_2$)$_n$-G1, —(CH$_2$)$_n$-G4, —(CH$_2$)$_n$—O—(CH$_2$)$_n$-G1, —(CH$_2$)$_n$—O—(CH$_2$)$_n$-G4, —(CH$_2$)$_n$—NR3-(CH$_2$)$_n$-aryl, —(CH$_2$)$_n$—NR3-(CH$_2$)$_n$-G1, —(CH$_2$)$_n$—NR3-(CH$_2$)$_n$-G4, —(CH$_2$)$_n$NHC(O)NHS(O)$_2$R8, —(CH$_2$)$_n$NHS(O)$_2$NHC(O)R8, —C(O)NHS(O)$_2$R8, (CH$_2$)NHC(O)(CH$_2$)$_n$R5, —(CH$_2$)$_n$NHS(O)$_2$R5, —(CH$_2$)$_n$C(O)NH(CH$_2$)$_q$R5, —(CH$_2$)$_n$C(O)R5, —(CH$_2$)$_n$OC(O)R5, and —(CH$_2$)$_n$R5;

in the event that Z2 contains an alkyl or alkylene moiety, such moieties may be further substituted with one or more C1-C6alkyls;

each Z3 is independently and individually selected from the group consisting of H, C1-C6alkyl, branched C3-C7alkyl, C3-C8-carbocyclyl, halogen, fluoroalkyl wherein the alkyl moiety can be partially or fully fluorinated, cyano, hydroxyl, methoxy, oxo, (R3)$_2$N—C(=O)—, (R4)$_2$N—C(=O)—, —N(R4)-C(=O)R8, (R3)$_2$NSO$_2$—, (R4)$_2$NSO$_2$—, —N(R4)SO$_2$R5, —N(R4)SO$_2$R8, —(CH$_2$)$_n$—N(R3)$_2$, —(CH$_2$)$_n$—N(R4)$_2$, —O—(CH$_2$)$_q$—N(R4)$_2$, —O—(CH$_2$)$_q$—O-alkyl, —N(R3)-(CH$_2$)$_q$—O-alkyl, —N(R3)-(CH$_2$)$_q$—N(R4)$_2$, —O—(CH$_2$)$_q$—R5, —N(R3)-(CH$_2$)$_q$—R5, —C(=O)R5, —C(=O)R8, and nitro;

in the event that Z3 contains an alkyl or alkylene moiety, such moieties may be further substituted with one or more C1-C6alkyls;

each Z4 is independently and individually selected from the group consisting of H, C1-C6alkyl, hydroxyC2-C6alkyl, C1-C6alkoxyC2-C6alkyl, $(R4)_2$N—C2-C6alkyl, $(R4)_2$N—C2-C6alkylN(R4)-C2-C6alkyl, $(R4)_2$N—C2-C6alkyl-O—C2-C6alkyl, $(R4)_2$NCO—C1-C6alkyl, carboxyC1-C6alkyl, C1-C6alkoxycarbonylC1-C6alkyl, —C2-C6alkylN(R4)C(O)R8, R8-C(=NR3)-, —SO$_2$R8, —COR8, —(CH$_2$)$_n$-G1, —(CH$_2$)$_n$-G4, —(CH$_2$)$_q$—O—(CH$_2$)$_n$-G1, —(CH$_2$VO—(CH$_2$)$_n$-G4, —(CH$_2$)$_q$—NR3-(CH$_2$)$_n$-G1, —(CH$_2$)$_q$—NR3-(CH$_2$)$_n$-G4, —(CH$_2$)$_q$NHC(O)(CH$_2$)$_n$R5, —(CH$_2$)$_q$C(O)NH(CH$_2$)$_q$R5, —(CH$_2$)$_q$C(O)R5, —(CH$_2$)$_q$OC(O)R5, —(CH$_2$)$_q$R5, —(CH$_2$)$_q$NR4(CH$_2$)$_q$R5, and —(CH$_2$)$_q$—O—(CH$_2$)$_q$R5;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, C1-C6alkoxy, —OR4, C1-C6alkylthio, $(R3)_2$N—, $(R4)_2$N—, —R5, —N(R3)COR8, —N(R4)COR8, —N(R3)SO$_2$R5-, —CON(R3)$_2$, —CON(R4)$_2$, —COR5, —SO$_2$N(R4)$_2$, halogen, fluoroC1-C6alkyl wherein the alkyl is fully or partially fluorinated, cyano, fluoroC1-C6alkoxy wherein the alkyl is fully or partially fluorinated, —O—(CH$_2$)$_q$—N(R4)$_2$, —N(R3)-(CH$_2$)$_q$—N(R4)$_2$, —O—(CH$_2$)$_q$—O-alkyl, —N(R3)-(CH$_2$)$_q$—O-alkyl, —O—(CH$_2$)$_q$—R5, —N(R3)-(CH$_2$)$_q$—R5, —(NR3)$_r$-(CH$_2$)$_n$—R17, —(O)$_r$—R17, —(S)$_r$R17, and (CH$_2$)$_r$—R17;

in the event that Z6 contains an alkyl or alkylene moiety, such moieties may be further substituted with one or more C1-C6alkyls;

wherein each R3 is independently and individually selected from the group consisting of H, C1-C6alkyl, branched C3-C7alkyl, C3-C8-carbocyclyl, and Z3-substituted phenyl;

each R4 is independently and individually selected from the group consisting of H, C1-C6alkyl, hydroxyC1-C6alkyl, dihydroxyC1-C6alkyl, C1-C6alkoxyC1-C6alkyl, branched C3-C7alkyl, branched hydroxyC1-C6alkyl, branched C1-C6alkoxyC1-C6alkyl, branched dihydroxyC1-C6alkyl, —(CH$_2$)$_p$—N(R7)$_2$, —(CH$_2$)$_p$—R5, —(CH$_2$)$_p$—C(O)N(R7)$_2$, —(CH$_2$)$_n$C(O)R5, —(CH$_2$)$_n$C(O)OR3, C3-C8-carbocyclyl, hydroxyl substituted C3-C8-carbocyclyl, alkoxy substituted C3-C8carbocyclyl, dihydroxy substituted C3-C8-carbocyclyl, and —(CH$_2$)$_n$—R17;

each R5 is independently and individually selected from the group consistig of

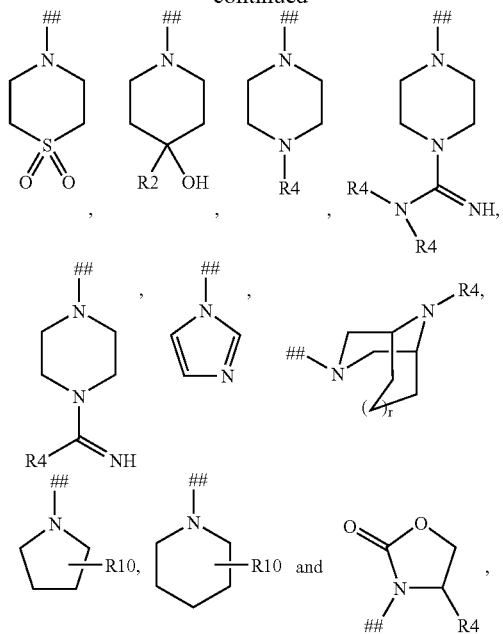

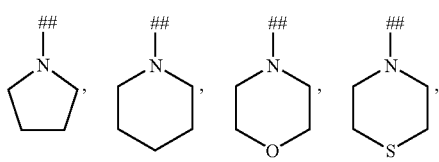

and wherein the symbol (##) is the point of attachment of the R5 moiety;

each R6 is independently and individually selected from the group consisting of C1-C6alkyl, branched C3-C7alkyl, C3-C8-carbocyclyl, phenyl, G1, and G4;

each R7 is independently and individually selected from the group consisting of H, C1-C6alkyl, hydroxyC2-C6alkyl, dihydroxyC2-C6alkyl, C1-C6alkoxyC2-C6alkyl, branched C3-C7alkyl, branched hydroxyC2-C6 alkyl, branched C1-C6alkoxyC2-C6alkyl, branched dihydroxyC2-C8alkyl, —(CH$_2$)$_q$—R5, —(CH$_2$)$_n$—C(O)R5, —(CH$_2$)$_n$—C(O)OR3, C3-C8-carbocyclyl, hydroxyl substituted C3-C8-carbocyclyl, alkoxy substituted C3-C8-carbocyclyl, dihydroxy substituted C3-C8-carbocyclyl, and —(CH$_2$)$_n$—R17;

each R8 is independently and individually selected from the group consisting of C1-C6alkyl, branched C3-C7alkyl, fluoroalkyl wherein the alkyl moiety is partially or fully fluorinated, C3-C8-carbocyclyl, Z3-substituted phenyl, Z3-substituted phenyl C1-C6alkyl, Z3-substituted G1, Z3-substituted G1-C1-C6alkyl, Z2-substituted G4, Z2-substituted G4-C1-C6alkyl, OH, C1-C6alkoxy, N$(R3)_2$, N$(R4)_2$, and R5;

each R10 is independently and individually selected from the group consisting of CO$_2$H, CO$_2$C1-C6alkyl, CO—N(R4)$_2$, OH, C1-C6alkoxy, and —N(R4)$_2$;

R16 is independently and individually selected from the group consisting of hydrogen, C1-C6alkyl, branched C3-C7alkyl, C3-C8-carbocyclyl, halogen, fluoroalkyl wherein the alkyl moiety can be partially or fully fluorinated, cyano, hydroxyl, C1-C6alkoxy, C1-C6-fluoroalkoxy wherein the alkyl moiety can be partially or fully fluorinated, —N(R3)$_2$, —N(R4)$_2$, C2-C3alkynyl, and nitro;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, azepinyl, oxepinyl, diazepinyl, pyrrolidinyl, and piperidinyl;

wherein R17 can be further substituted with one or more Z2, Z3 or Z4 moieties;

R19 is H or C1-C6alkyl;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

and k is 1 or 2; n is 0-6; p is 1-4; q is 2-6; r is 0 or 1; t is 1-3.

1.1 Compounds of Formula Ia which Exemplify Preferred E1-X2 Moieties

In an embodiment of section 1, preferred compounds have the structures of formula Ib

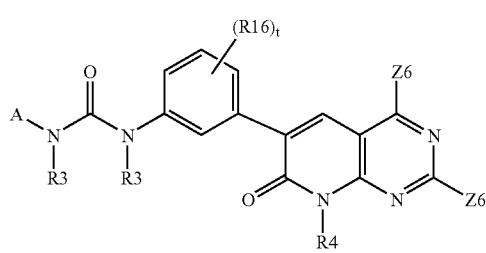

Ib

1.2 Compounds of Formula Ia which Exemplify Preferred A Moieties

In an embodiment of section 1.1, preferred compounds have the structures of formula Ic

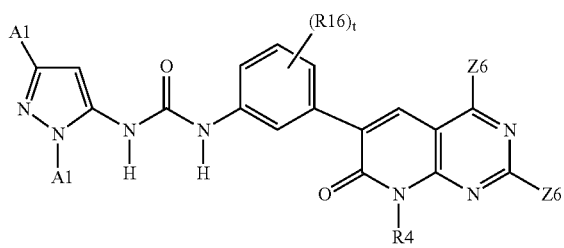

Ic

1.3 Compounds of Formula Ia which Exemplify Preferred A1 Moieties

In an embodiment of section 1.2, preferred compounds have the structures of formula Id

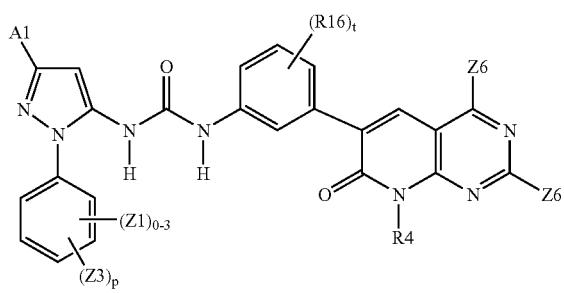

Id wherein A1 is selected from the group consisting of branched C3-C8alkyl, R19 substituted C3-C8-carbocyclyl, C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.3a Compounds of Formula Id which Exemplify More Preferred X2-E1 Moieties

In an embodiment of section 1.3, preferred compounds have the structures of formula Ie

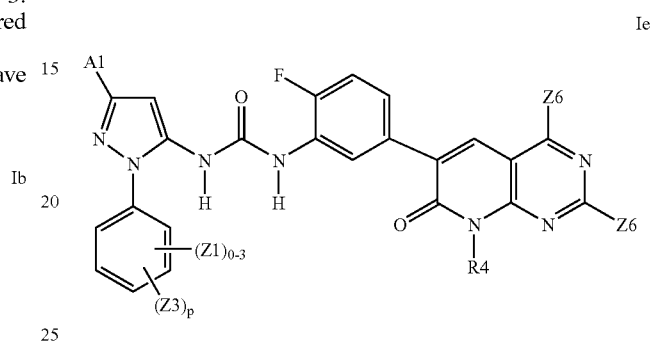

Ie

1.3b Additional Compounds of Formula Id which Exemplify More Preferred X2-E1 Moieties In another embodiment of section 1.3, preferred compounds have the structures of formula If

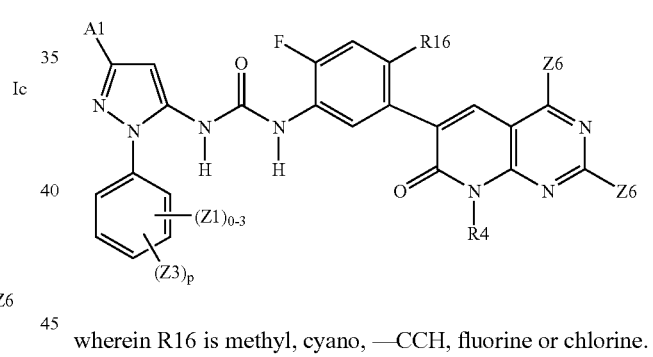

If wherein R16 is methyl, cyano, —CCH, fluorine or chlorine.

1.4 Compounds of Formula Ia which Exemplify Additional Preferred A1 Moieties In a different embodiment of section 1.2, additional preferred compounds have the structures of formula Ig

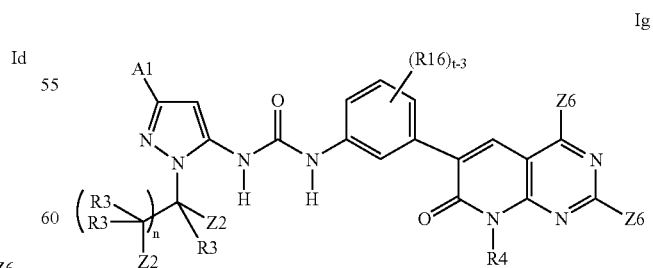

Ig wherein A1 is selected from the group consisting of branched C3-C8alkyl, R19 substituted C3-C8carbocyclyl, C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.4a Additional Compounds of Formula Ig which Exemplify More Preferred X2-E1 Moieties In an embodiment of section 1.4, preferred compounds have the structures of formula Ih 1.5a Additional Compounds of Formula Ij which Exemplify More Preferred X2-E1 Moieties In an embodiment of section 1.5, preferred compounds have the structures of formula Ik

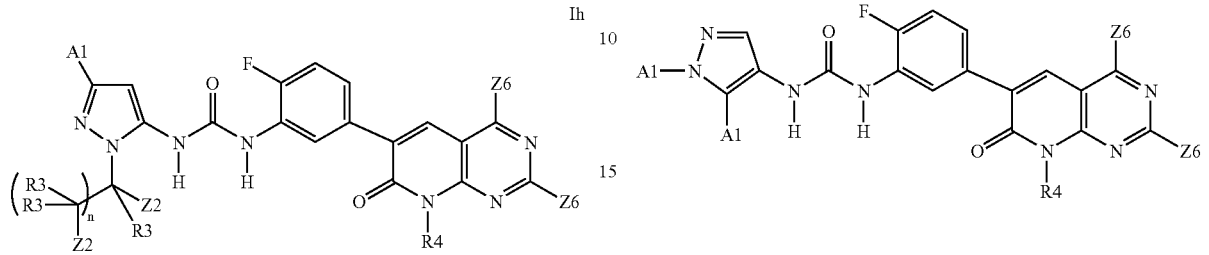

1.4b Additional Compounds of Formula Ig which Exemplify More Preferred X2-E1 Moieties In another embodiment of section 1.4, preferred compounds have the structures of formula Ii 1.5b Additional Compounds of Formula Ij which Exemplify More Preferred X2-E1 Moieties In another embodiment of section 1.5, preferred compounds have the structures of formula Il

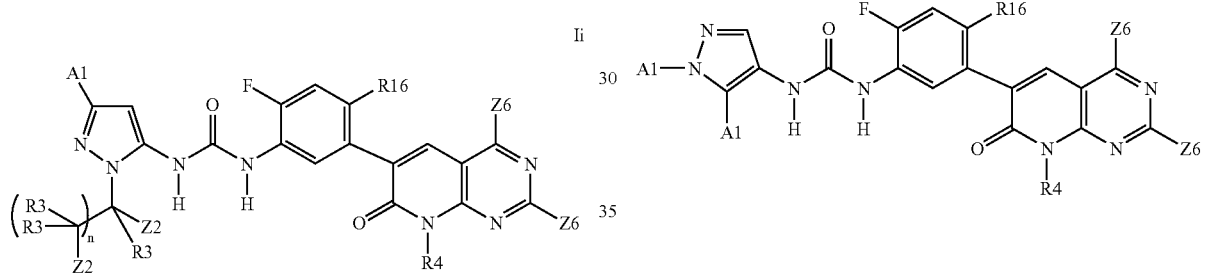

wherein R16 is C1-C6alkyl, cyano, —CCH, fluorine or chlorine.

1.5. Compounds of Formula Ia which Exemplify Additionally Preferred A Moieties

In a different embodiment of section 1.1, additional preferred compounds have the structures of formula Ij wherein R16 is C1-C6alkyl, cyano, —CCH, fluorine or chlorine.

1.6 Compounds of Formula Ia which Exemplify Additionally Preferred A Moieties

In a different embodiment of section 1.1, additional preferred compounds have the structures of formula Im

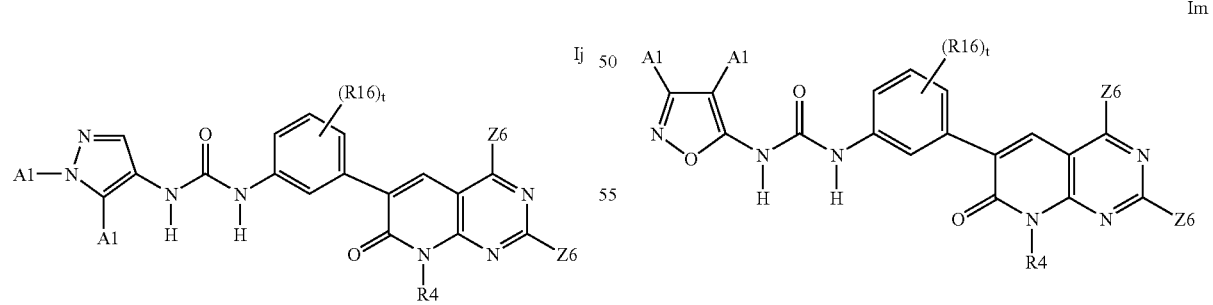

wherein A1 is selected from the group consisting of branched Z2-substituted C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

wherein A1 is selected from the group consisting of hydrogen, Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.6a Additional Compounds of Formula Im which Exemplify More Preferred X2-E1 Moieties In an embodiment of section 1.6, preferred compounds have the structures of formula In

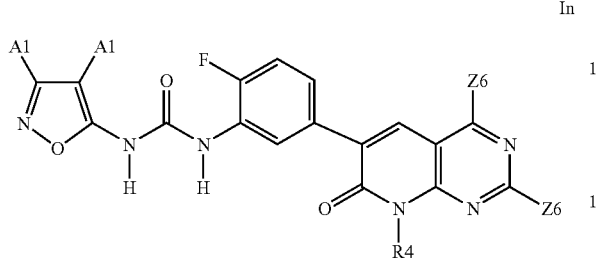

In 1.6b Additional Compounds of Formula Im which Exemplify More Preferred X2-E1 Moieties In another embodiment of section 1.6, preferred compounds have the structures of formula Io

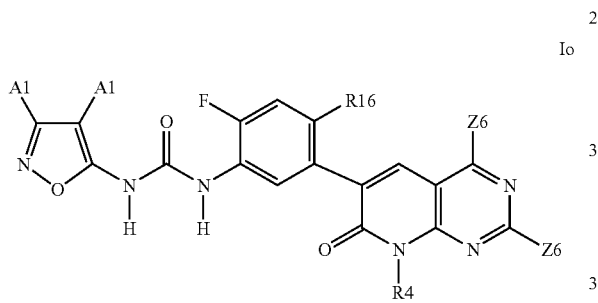

Io wherein R16 is C1-C6alkyl, cyano, —CCH, fluorine or chlorine.

1.7 Compounds of Formula Ia which Exemplify Additionally Preferred a Moieties

In a different embodiment of section 1.1, additional preferred compounds have the structures of formula Ip

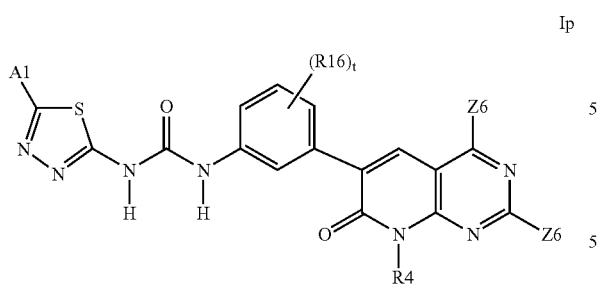

Ip wherein A1 is selected from the group consisting of Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.7a Additional Compounds of Formula Ip which Exemplify More Preferred X2-E1 Moieties In an embodiment of section 1.7, preferred compounds have the structures of formula Iq

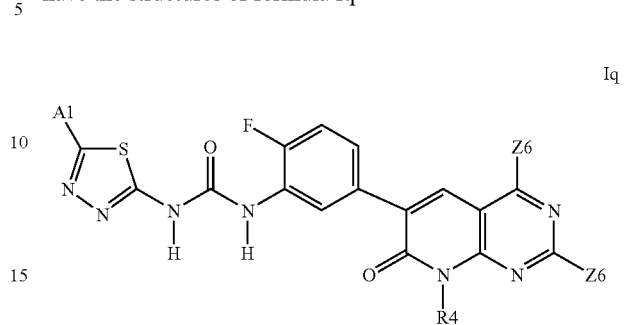

Iq 1.7b Additional Compounds of Formula Ip which Exemplify More Preferred X2-E1 Moieties In another embodiment of section 1.7, preferred compounds have the structures of formula Ir

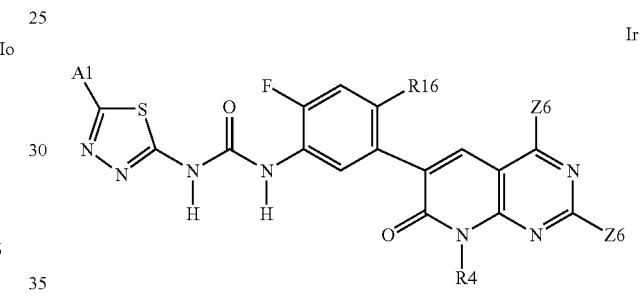

Ir and wherein R16 is C1-C6alkyl, cyano, —CCH, fluorine or chlorine.

1.8 Compounds of Formula Ia which Exemplify Additionally Preferred A Moieties

In a different embodiment of section 1.1, additional preferred compounds have the structures of formula Is

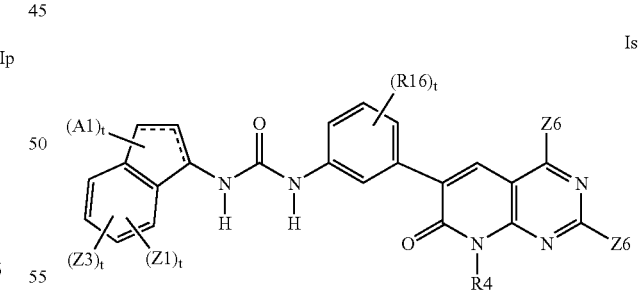

Is wherein the hashed bond is a saturated or unsaturated bond;

and wherein A1 is selected from the group consisting of hydrogen, Z2-substituted branched C3-C8alkyl, R19 substituted C3-C8-carbocyclyl, Z2-substituted C1-C6alkyl, halogen, cyano, C1-C6alkoxy, fluoroC1-C6alkoxy, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.8a Additional Compounds of Formula Is which Exemplify More Preferred X2-E1 Moieties In an embodiment of section 1.8, preferred compounds have the structures of formula It

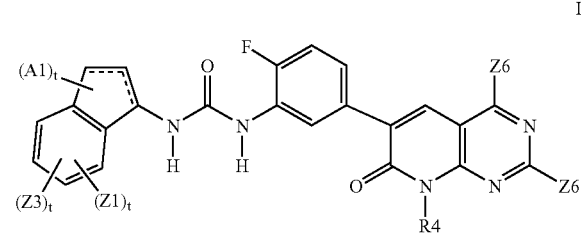

It 1.8b Additional Compounds of Formula Is which Exemplify More Preferred X2-E1 Moieties In another embodiment of section 1.8, preferred compounds have the structures of formula Iu

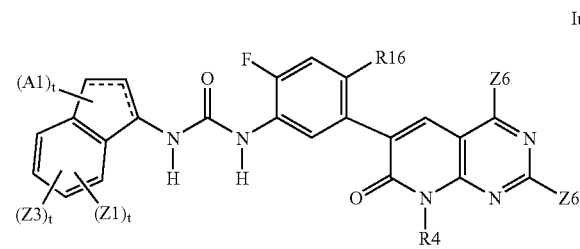

Iu wherein R16 is C1-C6alkyl, cyano, —CCH, fluorine or chlorine.

1.9 Compounds of Formula Ia which Exemplify Additionally Preferred A Moieties

In a different embodiment of section 1.1, additional preferred compounds have the structures of formula Iv

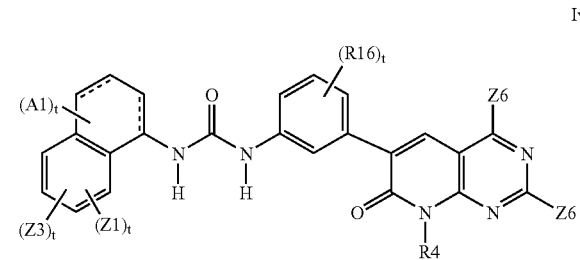

Iv wherein the hashed bond is a saturated or unsaturated bond; and wherein A1 is selected from the group consisting of hydrogen, Z2-substituted branched C3-C8alkyl, R19 substituted C3-C8-carbocyclyl, Z2-substituted C1-C6alkyl, halogen, cyano, C1-C6alkoxy, fluoroC1-C6alkoxy, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.9a Additional Compounds of Formula Iv which Exemplify More Preferred X2-E1 Moieties In an embodiment of section 1.9, preferred compounds have the structures of formula Iw

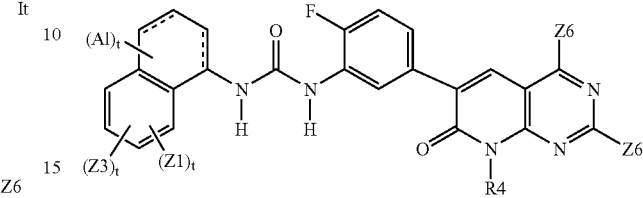

Iw 1.9b Additional Compounds of Formula Iv which Exemplify More Preferred X2-E1 Moieties In another embodiment of section 1.9, preferred compounds have the structures of formula Ix

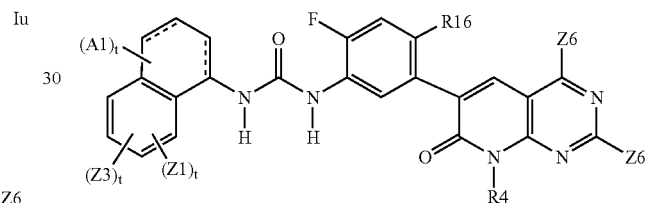

Ix and wherein R16 is C1-C6alkyl, cyano, —CCH, fluorine or chlorine.

1.10 Compounds of Formula Ia which Exemplify Additionally Preferred A Moieties

In a different embodiment of section 1.1, additional preferred compounds have the structures of formula Iy

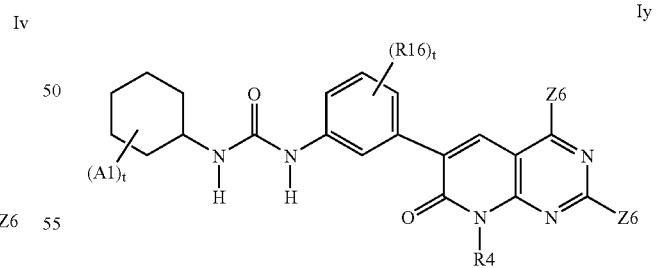

Iy wherein A1 is selected from the group consisting of Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.10a Additional Compounds of Formula Iy which Exemplify More Preferred X2-E1 Moieties In an embodiment of section 1.10, preferred compounds have the structures of formula Iz

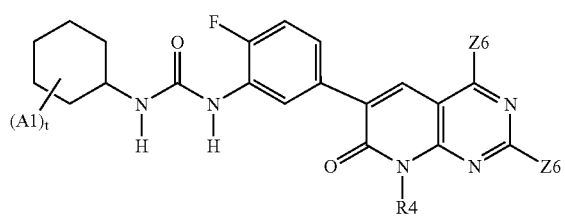
Iz

1.10b Additional Compounds of Formula Iy which Exemplify More Preferred X2-E1 Moieties In another embodiment of section 1.10, preferred compounds have the structures of formula Iaa

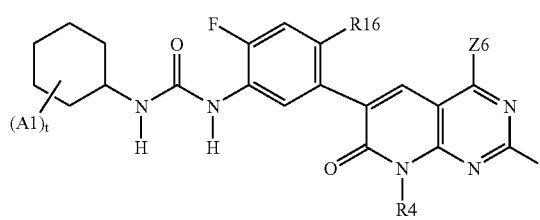
Iaa wherein R16 is C1-C6alkyl, cyano, —CCH, fluorine or chlorine.

1.11 Compounds of Formula Ia which Exemplify Additionally Preferred A Moieties In a different embodiment of section 1.1, additional preferred compounds have the structures of formula Ibb

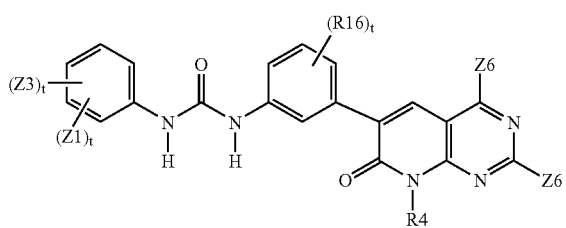
Ibb wherein R16 is C1-C6alkyl, cyano, —CCH, or halogen.

1.11a Additional Compounds of Formula Ibb which Exemplify More Preferred X2-E1 Moieties In an embodiment of section 1.11, preferred compounds have the structures of formula Icc

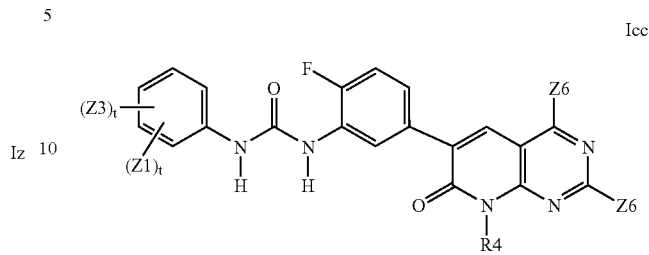
Icc

1.11b Additional Compounds of Formula Ibb which Exemplify More Preferred X2-E1 Moieties In another embodiment of section 1.11, preferred compounds have the structures of formula Idd

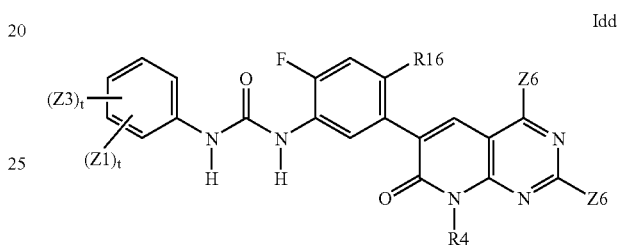
Idd wherein R16 is C1-C6alkyl, cyano, —CCH, fluorine or chlorine.

1.12 Compounds of Formula Ia which Exemplify Additionally Preferred A Moieties In a different embodiment of section 1.1, additional preferred compounds have the structures of formula Iee

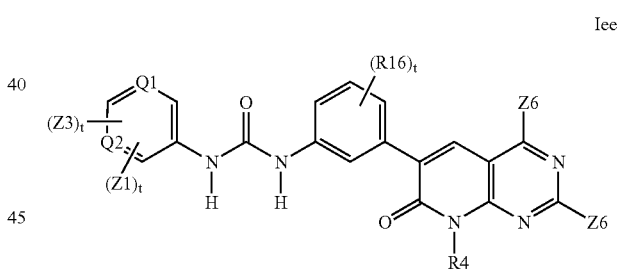
Iee wherein Q1 and Q2 are individually and independently taken from the group consisting of N and CH;
and wherein R16 is C1-C6alkyl, cyano, —CCH, or halogen.

1.12a Additional Compounds of Formula Iee which Exemplify More Preferred X2-E1 Moieties In an embodiment of section 1.12 preferred compounds have the structures of formula Iff

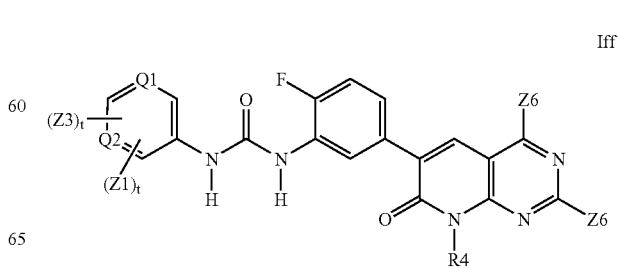
Iff

1.12b Additional Compounds of Formula Lee which Exemplify More Preferred X2-E1 Moieties In another embodiment of section 1.12, preferred compounds have the structures of formula Igg

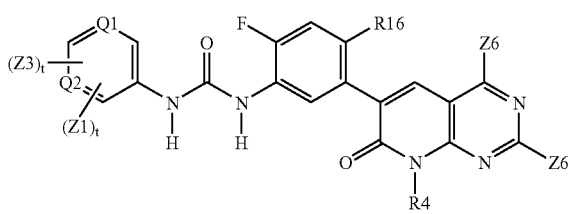

wherein R16 is C1-C6alkyl, cyano, —CCH, fluorine or chlorine.

1.13 Compounds of Formula Ia which Exemplify Additionally Preferred A Moieties In a different embodiment of section 1.1, additional preferred compounds have the structures of formula Ihh

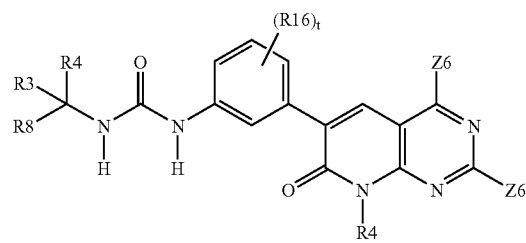

and wherein R16 is C1-C6alkyl, cyano, —CCH or halogen.

1.13a Additional Compounds of Formula Ihh which Exemplify More Preferred X2-E1 Moieties In an embodiment of section 1.13, preferred compounds have the structures of formula Iii

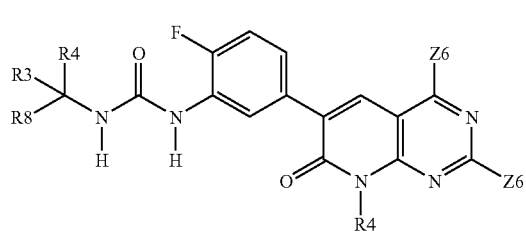

1.13b Additional Compounds of Formula Ihh which Exemplify More Preferred X2-E1 Moieties In another embodiment of section 1.13, preferred compounds have the structures of formula Ijj

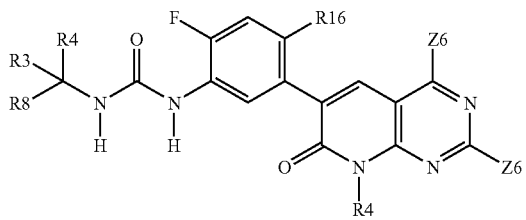

and wherein R16 is methyl, cyano, —CCH, fluorine or chlorine.

1.14 Compounds of Formula Ia which Exemplify Additionally Preferred A Moieties In a different embodiment of section 1.1, additional preferred compounds have the structures of formula Ikk

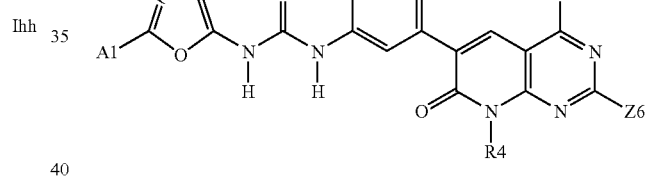

wherein Q6 is N or C-A1;

wherein A1 is selected from the group consisting of hydrogen, Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.14a Additional Compounds of Formula Ikk which Exemplify More Preferred X2-E1 Moieties In an embodiment of section 1.14, preferred compounds have the structures of formula Ill

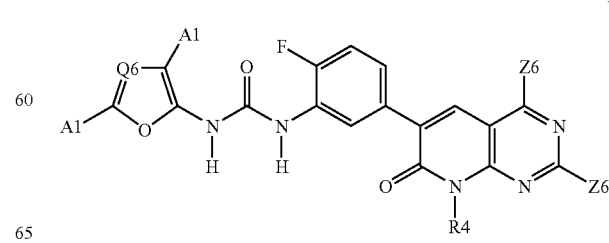

1.14b Additional Compounds of Formula Ikk which Exemplify More Preferred X2-E1 Moieties In another embodiment of section 1.14, preferred compounds have the structures of formula Imm

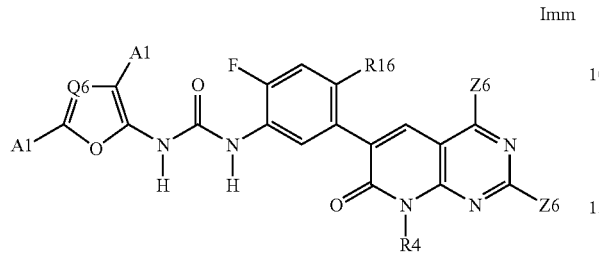

Imm wherein R16 is C1-C6alkyl, cyano, —CCH, fluorine or chlorine.

1.15 Compounds of Formula Ia which Exemplify Additionally Preferred A Moieties

In a different embodiment of section 1.1, additional preferred compounds have the structures of formula Inn

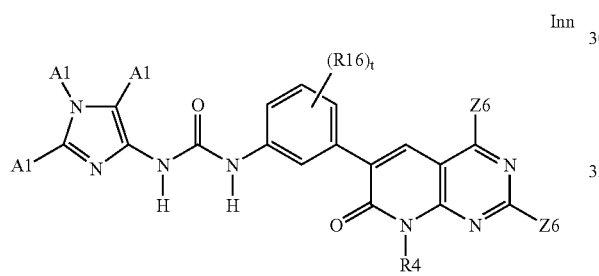

Inn wherein A1 is selected from the group consisting of hydrogen, Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

1.15a Additional Compounds of Formula Inn which Exemplify More Preferred X2-E1 Moieties In an embodiment of section 1.15, preferred compounds have the structures of formula Ioo

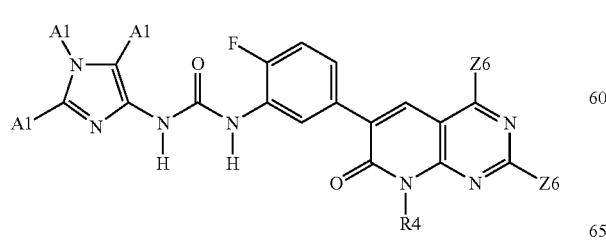

Ioo 1.15b Additional Compounds of Formula Inn which Exemplify More Preferred X2-E1 Moieties In another embodiment of section 1.15, preferred compounds have the structures of formula Ipp

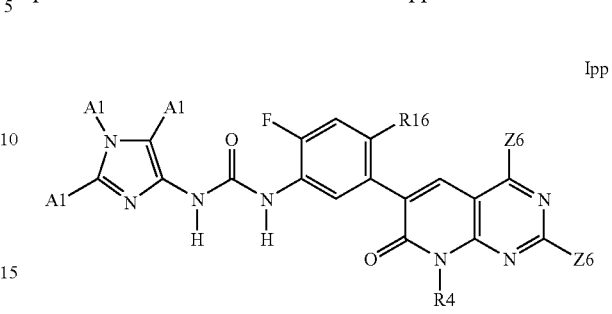

Ipp wherein R16 is C1-C6alkyl, cyano, —CCH, fluorine or chlorine.

1.16 Compounds of Formula Ia which Exemplify Additionally Preferred A Moieties

In a different embodiment of section 1.1, additional preferred compounds have the structures of formula Iqq

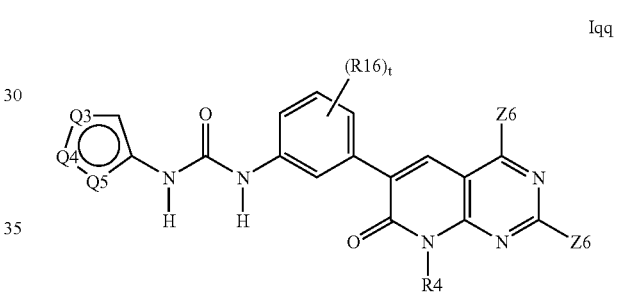

Iqq wherein Q3, Q4 and Q5 are selected from the group consisting of N-A1 and C-A1, and only one of Q3, Q4, or Q5 is N-A1;

wherein A1 is selected from the group consisting of hydrogen, Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

wherein R16 is C1-C6alkyl, cyano, —CCH, or halogen.

1.16a Additional Compounds of Formula Iqq which Exemplify More Preferred X2-E1 Moieties In an embodiment of section 1.16, preferred compounds have the structures of formula Irr

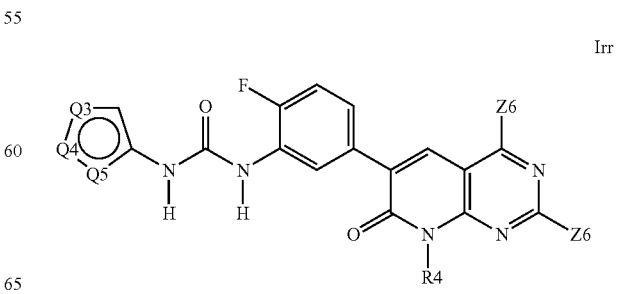

Irr 1.16b Additional Compounds of Formula Iqq which Exemplify More Preferred X2-E1 Moieties In another embodiment of section 1.16, preferred compounds have the structures of formula Iss

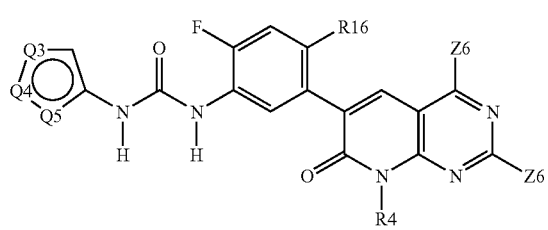

Iss wherein R16 is C1-C6alkyl, cyano, —CCH, fluorine or chlorine.

1.17 Methods
1.17a Methods of Protein Modulation

The invention includes methods of modulating kinase activity of RAF kinases and other kinases in the RAS-RAF-MEK-ERK-MAP kinase pathway including, but not limited to, A-Raf, B-Raf, and C-Raf. The kinases may be wildtype kinases, oncogenic forms thereof, aberrant fusion proteins thereof or polymorphs of any of the foregoing. The method comprises the step of contacting the kinase species with compounds of the invention and especially those set forth in sections 1.1-1.16. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

1.17b Treatment Methods

The methods of the invention, especially those of sections 1.1-1.16, also include treating individuals suffering from a condition selected from the group consisting of chronic myelogenous leukemia, acute lymphocytic leukemia, gastrointestinal stromal tumors, hypereosinophillic syndrome, glioblastomas, ovarian cancer, pancreatic cancer, prostate cancer, lung cancers, breast cancers, kidney cancers, cervical carcinomas, metastasis of primary solid tumor secondary sites, ocular diseases characterized by hyperproliferation leading to blindness including various retinopathies including diabetic retinopathy and age-related macular degeneration, rheumatoid arthritis, melanomas, colon cancer, thyroid cancer, a disease caused by a mutation in the RAS-RAF-MEK-ERK-MAP kinase pathway, human inflammation, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic obstructive pulmonary disease, bone resorptive diseases, graft-versus-host reaction, Citron's disease, ulcerative colitis, inflammatory bowel disease, pyresis, and combinations thereof,

1.18 Pharmaceutical Preparations

The compounds of the invention, especially those of sections 1.1-1.16, may form a part of a pharmaceutical composition by combining one or more such compounds with a pharmaceutically acceptable carrier. Additionally, the compositions may include an additive selected from the group consisting of adjuvants, excipients, diluents, and stabilizers.

2. Second Aspect of The Invention-Compounds, Methods, Preparations and Adducts Compounds of the Formula IIa

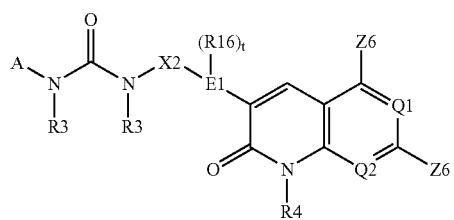

IIa wherein one of Q1 and Q2 is N and the other is CR3;

wherein E1 is selected from the group consisting cyclopropyl, cyclobutyl, cyclopentyl, cyclohexyl, pyrrolidinyl piperidinyl, phenyl, thienyl, oxazolyl, thiazolyl, isoxazolyl, isothiazolyl, pyrrolyl, pyrazolyl, oxadiazolyl, thiadiazolyl, furyl, imidazolyl, pyridyl, pyrimidinyl and naphthyl;

wherein A is selected from the group consisting of phenyl, naphthyl, C3-C8-carbocyclyl, indanyl, tetralinyl, indenyl, G1, G2, G3, G4 and —CHR4R8;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

G2 is a fused bicyclic heteroaryl taken from the group consisting of indolyl, indolinyl, isoindolyl, isoindolinyl, indazolyl, benzofuranyl, benzothienyl, benzothiazolyl, benzothiazolonyl, benzoxazolyl, benzoxazolonyl, benzisoxazolyl, benzisothiazolyl, benzimidazolyl, benzimidazolonyl, benztriazolyl, imidazopyridinyl, pyrazolopyridinyl, imidazolonopyridinyl, thiazolopyridinyl, thiazolonopyridinyl, oxazolopyridinyl, oxazolonopyridinyl, isoxazolopyridinyl, isothiazolopyridinyl, triazolopyridinyl, imidazopyrimidinyl, pyrazolopyrimidinyl, imidazolonopyrimidinyl, thiazolopyridiminyl, thiazolonopyrimidinyl, oxazolopyridiminyl, oxazolonopyrimidinyl, isoxazolopyrimidinyl, isothiazolopyrimidinyl, triazolopyrimidinyl, dihydropurinonyl, pyrrolopyrimidinyl, purinyl, pyrazolopyrimidinyl, phthalimidyl, phthalimidinyl, pyrazinylpyridinyl, pyridinopyrimidinyl, pyrimidinopyrimidinyl, cinnolinyl, quinoxalinyl, quinazolinyl, quinolinyl, isoquinolinyl, phthalazinyl, benzodioxyl, benzisomiazoline-1,1,3-trionyl, dihydroquinolinyl, tetrahydroquinolinyl, dihydroisoquinolyl, tetrahydroisoquinolinyl, benzoazepinyl, benzodiazepinyl, benzoxapinyl, and benzoxazepinyl;

G3 is a non-fused bicyclic heteroaryl taken from the group consisting of pyridylpyridiminyl pyrimidinylpyrimidinyl, oxazolylpyrimidinyl, thiazolylpyrimidinyl, imidazolylpyrimidinyl, isoxazolylpyrimidinyl, isothiazolylpyrimidinyl, pyrazolylpyrimidinyl, triazolylpyrimidinyl, oxadiazoylpyrimidinyl, thiadiazoylpyrimidinyl, morpholinylpyrimidinyl, dioxothiomorpholinylpyrimidinyl, and thiomorpholinylpyrimidinyl;

G4 is a heterocyclyl taken from the group consisting of oxetanyl, azetadinyl, tetrahydrofuranyl, pyrrolidinyl, oxazolinyl, oxazolidinyl, imidazolonyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;

the A ring may be optionally substituted with one or more —X1-A1 moieties;

X1 is selected from the group consisting of —(CH$_2$)$_n$—(O)$_r$—(CH$_2$)$_n$—, —(CH$_2$)$_n$—(NR3)$_r$-(CH$_2$)$_n$—, —(CH$_2$)$_n$—(S)$_r$—(CH$_2$)$_n$—, —(CH$_2$)$_n$—(C=O)$_r$—(CH$_2$)$_n$—, —(CH$_2$)$_n$—(C(=O)—NR3)$_r$-(CH$_2$)$_n$—, and —(CH$_2$)$_n$—(SO$_2$—NR3)$_r$-(CH$_2$)$_n$—, wherein any of the alkylenes may be straight or branched chain;

X2 is selected from the group consisting of C1-C6alkyl, branched C2-C6alkyl, and a direct bond wherein E1 is directly linked to the NR3 group of formula Ia;

A1 is selected from the group consisting of hydrogen, aryl, G1, G2, G3, G4, C1-C6 alkyl, branched C3-C8alkyl, R19 substituted C3-C8-carbocyclyl, fluoroC1-C6alkyl wherein the alkyl is fully or partially fluorinated, halogen, cyano, hydroxyl, —N(R4)$_2$, —R5, —C(O)N(R4)$_2$, C(O)R5, C1-C6alkoxy, and fluoroC1-C6alkoxy wherein the alkyl group is fully or partially fluorinated;

When A and A1 have one or more substitutable sp2-hybridized carbon atom, each respective sp2 hybridized carbon atom may be optionally substituted with a Z1 or Z3 substituent;

when A and A1 have one or more substitutable sp3-hybridized carbon atom, each respective sp3 hybridized carbon atom may be optionally substituted with a Z2 or R3 substituent;

when A and A1 have one or more substitutable nitrogen atom, each respective nitrogen atom may be optionally substituted with a Z4 substituent;

each Z1 is independently and individually selected from the group consisting of hydrogen, hydroxyC1-C6alkyl, C1-C6alkoxy, C1-C6alkoxyC1-C6alkyl, (R4)$_2$NC1-C6alkyl, (R4)$_2$NC2-C6alkylN(R4)-(CH$_2$)$_n$—, (R4)$_2$NC2-C6alkylO—(CH$_2$)$_n$—, (R3)$_2$N—C(=O)—, (R4)$_2$N—C(=O)—, (R4)$_2$N—CO—C1-C6alkyl-, C1-C6alkoxycarbonyl-, -carboxyC1-C6alkyl, C1-C6alkoxycarbonylC1-C6alkyl, (R3)$_2$NSO$_2$—, —SOR3, (R4)$_2$NSO$_2$—, —SO$_2$R3, —SOR4, —C(=O)R6, —C(=NOH)R6, —C(=NOR3)R6, —(CH$_2$)$_n$N(R4)C(O)R8, —(CH$_2$)$_n$-G1, —(CH$_2$)$_n$-G4, phenoxy, —(CH$_2$)$_n$—O—(CH$_2$)$_n$-G1, —(CH$_2$)$_n$—O—(CH$_2$)$_n$-G4, —(CH$_2$)$_n$NR3-(CH$_2$)$_n$-aryl, —(CH$_2$)$_n$—NR3-(CH$_2$)$_n$-G1, —(CH$_2$)$_n$—NR3-(CH$_2$)$_n$-G4, —S(O)$_2$R5, —N=S(O)R6R8, —S(O)(=NR3)R6, —(CH$_2$)$_n$NHC(O)NHS(O)$_2$R8, (CH$_2$)$_n$NHS(O)$_2$NHC(O)R8, —C(O)NHS(O)$_2$R8, —S(O)$_2$NHC(O)R8, —(CH$_2$)$_n$NHC(O)(CH$_2$)$_n$R5, —(CH$_2$)$_n$NHS(O)$_2$(CH$_2$)$_n$R5, —(CH$_2$)$_n$C(O)NH(CH$_2$)$_q$R5, —(CH$_2$)$_n$C(O)R5, —(CH$_2$)$_n$OC(O)R5, —(CH$_2$)$_n$S(O)$_2$NH(CH$_2$)$_q$R5, —CH(OH)(CH$_2$)$_p$R5, —CH(OH)CH(OH)R4, —(CH$_2$)$_n$N(R4)$_2$, —(CH$_2$)$_n$R5, —C(=NH)R5, —C(=NH)N(R4)$_2$, —C(=NOR3)R5, —C(=NOR3)N(R4)$_2$, and —NHC(=NH)R8;

in the event that Z1 contains an alkyl or alkylene moiety, such moieties may be further substituted with one or more C1-C6alkyls;

each Z2 is independently and individually selected from the group consisting of hydrogen, aryl, C1-C6alkyl, C3-C8-carbocyclyl, hydroxyl, hydroxyC1-C6alkyl-, cyano, (R3)$_2$N—, (R4)$_2$N—, (R4)$_2$NC1-C6alkyl-, (R4)$_2$NC2-C6alkylN(R4)-(CH$_2$)$_n$—, (R4)$_2$NC2-C6alkylO—(CH$_2$)$_n$—, (R3)$_2$N—C(=O)—, (R4)$_2$N—C(=O)—, (R4)$_2$N—CO—C1-C6alkyl-, carboxyl, carboxyC1-C6alkyl, C1-C6alkoxycarbonyl, C1-C6alkoxycarbonylC1-C6alkyl, (R3)$_2$NSO$_2$—, (R4)$_2$NSO$_2$—, —SO$_2$R5, —SO$_2$R8, —(CH$_2$)$_n$N(R4)C(O)R8, —C(O)R8, =O, =NOH, =N(OR6), —(CH$_2$)$_n$-G1, —(CH$_2$)$_n$-G4, —(CH$_2$)$_n$—O—(CH$_2$)$_n$-G1, —(CH$_2$)$_n$—O—(CH$_2$)$_n$-G4, —(CH$_2$)$_n$—NR3-(CH$_2$)$_n$-aryl, —(CH$_2$)$_n$—NR3-(CH$_2$)$_n$-G1, —(CH$_2$)$_n$—NR3-(CH$_2$)$_n$-G4, —(CH$_2$)$_n$NHC(O)NHS(O)2R8, —(CH$_2$)$_n$NHS(O)2NHC(O)R8, —C(O)NHS(O)2R8, —(CH$_2$)$_n$NHC(O)(CH$_2$)$_n$R5, —(CH$_2$)$_n$NHS(O)2R5, —(CH$_2$)$_n$C(O)NH(CH$_2$)$_q$R5, —(CH$_2$)$_n$C(O)R5, —(CH$_2$)$_n$OC(O)R5, and —(CH$_2$)$_n$R5;

in the event that Z2 contains an alkyl or alkylene moiety, such moieties may be further substituted with one or more C1-C6alkyls;

each Z3 is independently and individually selected from the group consisting of H, C1-C6alkyl, branched C3-C7alkyl, C3-C8-carbocyclyl, halogen, fluoroalkyl wherein the alkyl moiety can be partially or folly fluorinated, cyano, hydroxyl, methoxy, oxo, (R3)$_2$N—C(=O)—, (R4)$_2$N—C(=O)—, —N(R4)-C(=O)R8, (R3)$_2$NSO$_2$—, (R4)$_2$NSO$_2$—, —N(R4)SO$_2$R5, —N(R4)SO$_2$R8, —(CH$_2$)$_n$—N(R3)$_2$, —(CH$_2$)$_n$—N(R4)$_2$, —O—(CH$_2$)$_q$—N(R4)$_2$, —O—(CH$_2$)$_q$—O-alkyl, —N(R3)-(CH$_2$)$_q$—O-alkyl, —N(R3)-(CH$_2$)$_q$—N(R4)$_2$, —O—(CH$_2$)$_q$—R5, —N(R3)-(CH$_2$)$_q$—R5, —C(=O)R5, —C(=O)R8, and nitro;

in the event that Z3 contains an alkyl or alkylene moiety, such moieties may be further substituted with one or more C1-C6alkyls;

each Z4 is independently and individually selected from the group consisting of H, C1-C6alkyl, hydroxyC2-C6alkyl, C1-C6alkoxyC2-C6alkyl, (R4)$_2$N—C2-C6alkyl, (R4)$_2$N—C2-C6alkylN(R4)-C2-C6alkyl, (R4)$_2$N—C2-C6alkyl-O—C2-C6alkyl, (R4)$_2$N—CO—C1-C6alkyl, carboxyC1-C6alkyl, C1-C6alkoxycarbonylC1-C6alkyl, —C2-C6alkylN(R4)C(O)R8, R8-C(=NR3)-, —SO$_2$R8, —C(O)R8, —(CH$_2$)$_n$-G1, —(CH$_2$)$_n$-G4, —(CH$_2$)$_q$—O—(CH$_2$)$_n$-G1, —(CH$_2$)$_q$—O—(CH$_2$)$_n$-G4, —(CH$_2$)$_q$—NR3-(CH$_2$)$_n$-G1, —(CH$_2$)$_q$—NR3-(CH$_2$)$_n$-G4, —(CH$_2$)$_q$NHC(O)(CH$_2$)$_n$R5, —(CH$_2$)$_q$C(O)NH(CH$_2$)$_q$R5, —(CH$_2$)$_q$C(O)R5, —(CH$_2$)$_q$OC(O)R5, —(CH$_2$)$_q$R5, —(CH$_2$)$_q$NR4(CH$_2$)$_q$R5, and —(CH$_2$)$_q$O(CH$_2$)$_q$R5;

in the event that Z4 contains an alkyl or alkylene moiety, such moieties may be further substituted with one or more C1-C6alkyls;

each Z6 is independently and individually selected from the group consisting of H, C1-C6alkyl, branched C3-C7alkyl, hydroxyl, C1-C6alkoxy, —OR4, C1-C6alkylthio, (R3)$_2$N—, (R4)$_2$N—, —R5, —N(R3)COR8, —N(R4)COR8, —N(R3)SO$_2$R6-, —CON(R3)$_2$, —CON(R4)$_2$, —COR5, —SO$_2$N(R4)$_2$, halogen, fluoroC1-C6alkyl wherein the alkyl is fully or partially fluorinated, cyano, fluoroC1-C6alkoxy wherein the alkyl is fully or partially fluorinated, —O—(CH$_2$)$_q$—N(R4)$_2$, —N(R3)-(CH$_2$)$_q$—N(R4)$_2$, —O—(CH$_2$)$_q$—O-alkyl, —N(R3)-(CH$_2$)$_q$—O-alkyl, —O(CH$_2$)$_q$—R5, —N(R3)-(CH$_2$)$_q$—R5, —(NR3)$_r$-(CH$_2$)$_n$—R17, —(O)$_r$R17, (S)$_r$—R17, and —(CH$_2$)$_r$—R17;

in the event that Z6 contains an alkyl or alkylene moiety, such moieties may be further substituted with one or more C1-C6alkyls;

wherein each R3 is independently and individually selected from the group consisting of H, C1-C6alkyl, branched C3-C7alkyl, C3-C8-carbocyclyl, and Z3-substituted phenyl;

each R4 is independently and individually selected from the group consisting of H, C1-C6alkyl, hydroxyC1-C6alkyl, dihydroxyC1-C6alkyl, C1-C6alkoxyC1-C6alkyl, branched C3-C7alkyl, branched hydroxyC1-C6alkyl, branched C1-C6alkoxyC1-C6alkyl, branched dihydroxyC1-C6alkyl, —(CH$_2$)$_p$—N(R7)2, —(CH$_2$)$_p$—R5, —(CH$_2$)$_p$—C(O)N(R7)2, —(CH$_2$)$_n$C(O)R5, —(CH$_2$)$_n$—C(O)OR3, C3-C8-carbocyclyl, hydroxyl substituted C3-C8-carbocyclyl, alkoxy substituted C3-C8-carbocyclyl, dihydroxy substituted C3-C8-carbocyclyl, and —(CH$_2$)$_n$—R17;

each R5 is independently and individually selected from the group consisting of

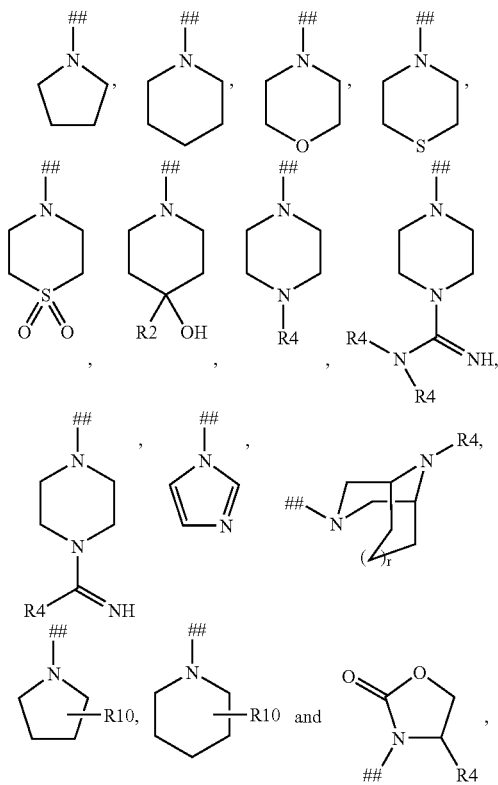

and wherein the symbol (##) is the point of attachment of the R5 moiety;

each R6 is independently and individually selected from the group consisting of C1-C6alkyl, branched C3-C7alkyl, C3-C8-carbocyclyl, phenyl, G1, and G4;

each R7 is independently and individually selected from the group consisting of H, C1-C6alkyl, hydroxyC2-C6alkyl, dihydroxyC2-C6alkyl, C1-C6alkoxyC2-C6alkyl, branched C3-C7alkyl, branched hydroxyC2-C6 alkyl, branched C1-C6alkoxyC2-C6alkyl, branched dihydroxyC2-C6alkyl, (CH$_2$)$_q$—R5, —(CH$_2$)$_n$—C(O)R5, —(CH$_2$)$_n$—C(O)OR3, C3-C8-carbocyclyl, hydroxyl substituted C3-C8-carbocyclyl, alkoxy substituted C3-C8-carbocyclyl, dihydroxy substituted C3-C8carbocyclyl, and —(CH$_2$)$_n$—R17;

each R8 is independently and individually selected from the group consisting of C1-C6alkyl, branched C3-C7alkyl, fluoroalkyl wherein the alkyl moiety is partially or fully fluorinated, C3-C8-carbocyclyl, Z3-substituted phenyl, Z3-substituted phenyl C1-C6alkyl, Z3-substituted G1, Z3-substituted G1-C1-C6alkyl, Z2-substituted G4, Z2-substituted G4-C1-C6alkyl, OH, C1-C6alkoxy, N(R3)$_2$, N(R4)$_2$, and R5;

each R10 is independently and individually selected from the group consisting of CO$_2$H, CO$_2$C1-C6alkyl, CO—N(R4)$_2$, OH, C1-C6alkoxy, and —N(R4)$_2$;

R16 is independently and individually selected from the group consisting of hydrogen, C1-C6alkyl, branched C3-C7alkyl, C3-C8-carbocyclyl, halogen, fluoroalkyl wherein the alkyl moiety can be partially or fully fluorinated, cyano, hydroxyl, C1-C6alkoxy, C1-C6-fluoroalkoxy wherein the alkyl moiety can be partially or fully fluorinated, —N(R3)$_2$, —N(R4)$_2$, C2-C3alkynyl, and nitro;

each R17 is taken from the group comprising phenyl, naphthyl, pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, azepinyl, oxepinyl, diazepinyl, pyrrolidinyl, and piperidinyl;

wherein R17 can be further substituted with one or more Z2, Z3 or Z4 moieties;

R19 is H or C1-C6alkyl;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

and k is 1 or 2; n is 0-6; p is 1-4; q is 2-6; r is 0 or 1; t is 1-3.

2.1 Compounds of Formula IIa which Exemplify Preferred E1-X2 Moieties

In an embodiment of section 2, prefrred compounds have the structures of formula IIb

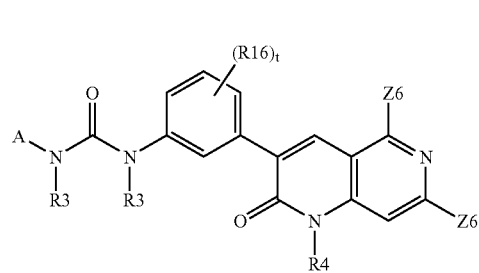

2.2 Compounds of Formula IIa which Exemplify Preferred A Moieties

In an embodiment of section 2.1, preferred compounds have the structures of formula IIe

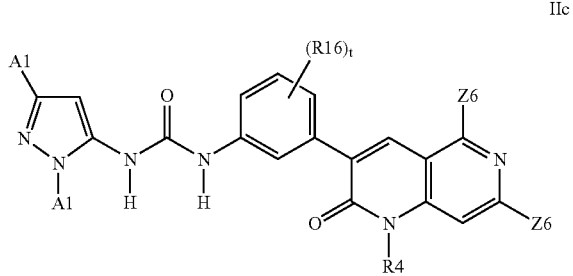

2.3 Compounds of Formula IIa which Exemplify Preferred A1 Moieties

In an embodiment of section 2.2, preferred compounds have the structures of formula IId

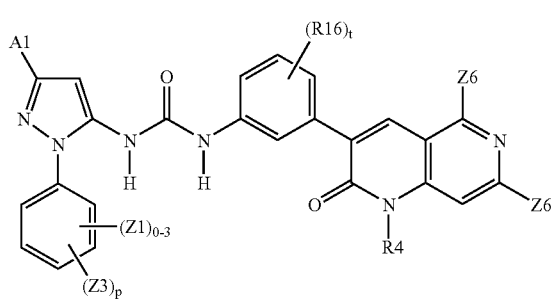

IId wherein A1 is selected from the group consisting of branched C3-C8alkyl, R19 substituted C3-C8-carbocyclyl, C1-C6alkyl, fluoroC1-C6alkyl wherein the alkyl is fully or partially fluorinated, Z3-substituted phenyl, and Z3-substituted G1;

and wherein R16 is C1-C6alkyl, —CCH, cyano, halogen.

2.3a Compounds of Formula IId which Exemplify More Preferred X2-E1 Moieties

In an embodiment of section 2.3, preferred compounds have the structures of formula IIe

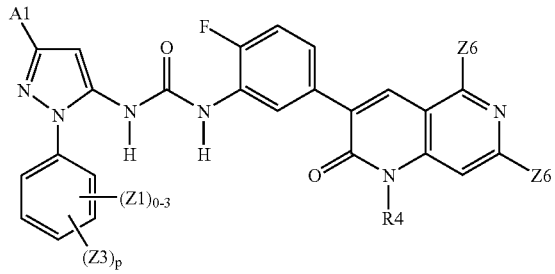

IIe

2.3b Additional Compounds of Formula IId which Exemplify More Preferred X2-E1 Moieties In another embodiment of section 2.3, preferred compounds have the structures of formula IIf

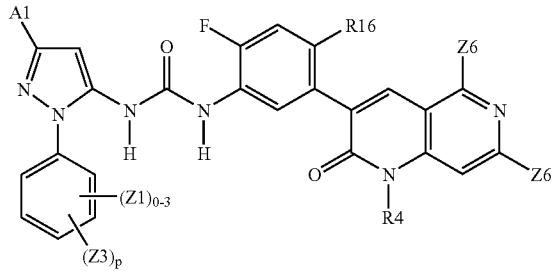

IIf wherein R16 is methyl, cyano, —CCH, fluorine or chlorine.

2.4 Compounds of Formula IIa which Exemplify Additional Preferred A1 Moieties In a different embodiment of section 2.2, additional preferred compounds have the structures of formula IIg

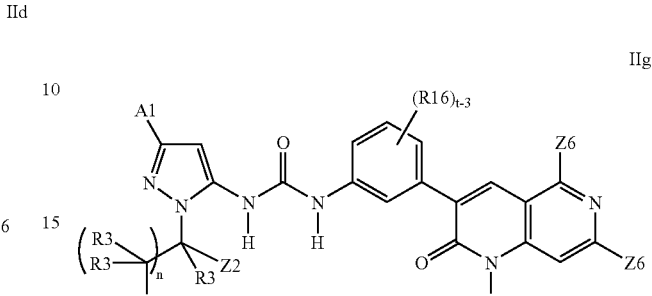

IIg wherein A1 is selected from the group consisting of branched C3-C8alkyl, R19 substituted C3-C8-carbocyclyl, C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.4a Additional Compounds of Formula IIg which Exemplify More Preferred X2-E1 Moieties In an embodiment of section 2.4, preferred compounds have the structures of formula IIh

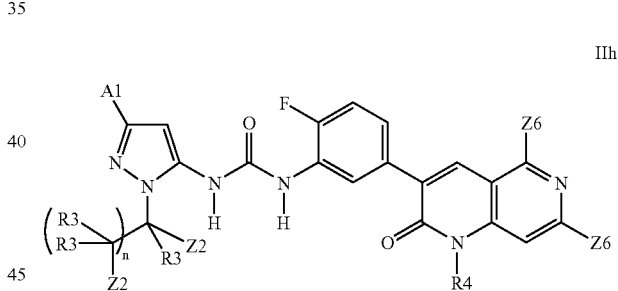

IIh

2.4b Additional Compounds of Formula IIg which Exemplify More Preferred X2-E1 Moieties In another embodiment of section 2.4, preferred compounds have the structures of formula IIi

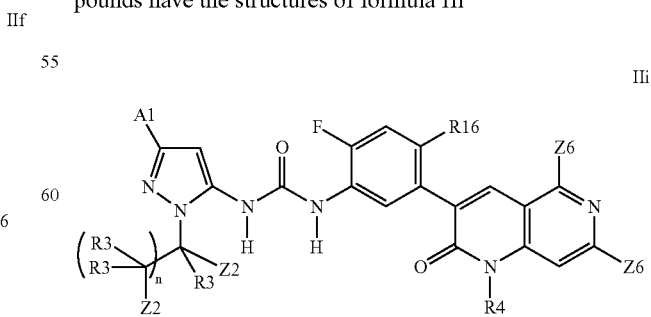

IIi wherein R16 is methyl, cyano, —CCH, fluorine or chlorine.

2.5 Compounds of Formula IIa which Exemplify Additionally Preferred A Moieties In a different embodiment of section 2.1, additional preferred compounds have the structures of formula IIj

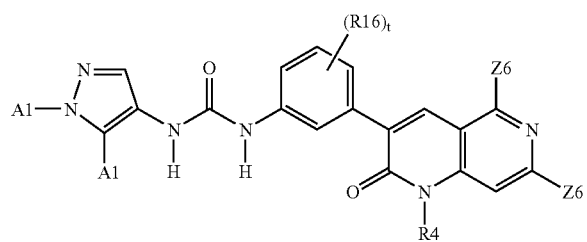

IIj wherein A1 is selected from the group consisting of branched Z2-substituted C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.5a Additional Compounds of Formula IIj which Exemplify More Preferred X2-E1 Moieties In an embodiment of section 2.5, preferred compounds have the structures of formula IIk

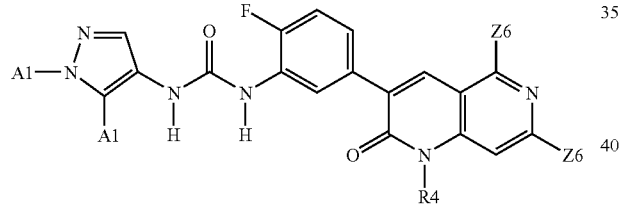

IIk

2.5b Additional Compounds of Formula IIj which Exemplify More Preferred X2-E1 Moieties In another embodiment of section 2.5, preferred compounds have the structures of formula III

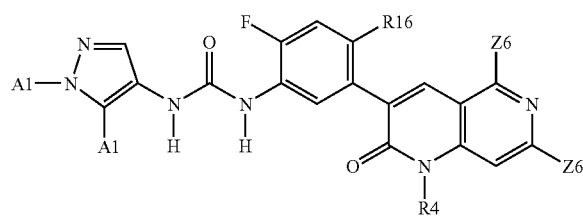

III wherein R16 is methyl, cyano, —CCH, fluorine or chlorine.

2.6 Compounds of Formula IIa which Exemplify Additionally Preferred A Moieties In a different embodiment of section 2.1, additional preferred compounds have the structures of formula IIm

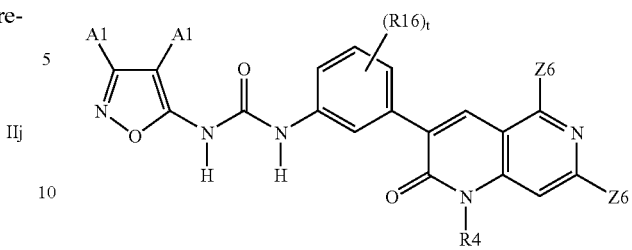

IIm wherein A1 is selected from the group consisting of hydrogen, Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.6a Additional Compounds of Formula IIm which Exemplify More Preferred X2-E1 Moieties In an embodiment of section 2.6, preferred compounds have the structures of formula IIn

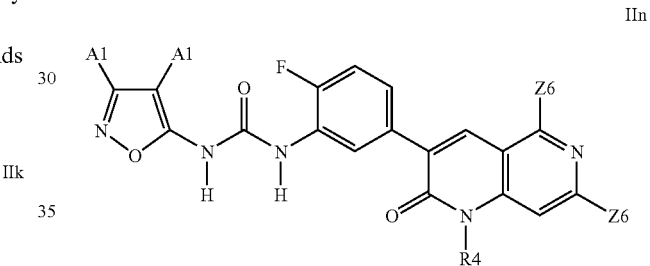

IIn

2.6b Additional Compounds of Formula IIm which Exemplify More Preferred X2-E1 Moieties In another embodiment of section 2.6, preferred compounds have the structures of formula IIo

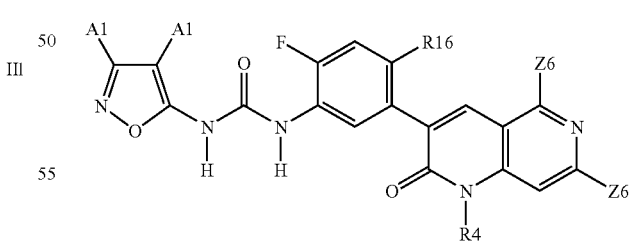

IIo wherein R16 is C1-C6alkyl, cyano, —CCH, fluorine or chlorine.

2.7 Compounds of Formula IIa which Exemplify Additionally Preferred A Moieties In a different embodiment of section 2.7, additional preferred compounds have the structures of formula IIp

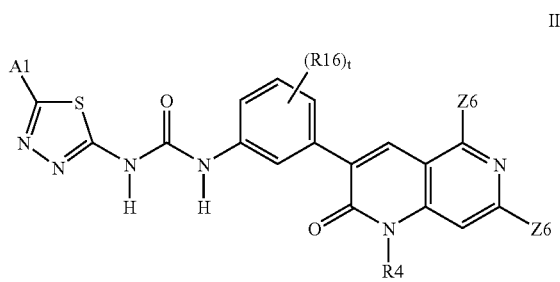

IIp

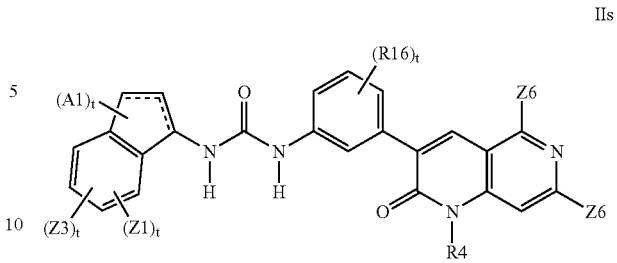

IIs wherein A1 is selected from the group consisting of Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.7a Additional Compounds of Formula IIp which Exemplify More Preferred X2-EI Moieties In an embodiment of section 2.7, preferred compounds have the structures of formula IIq wherein the hashed bond is a saturated or unsaturated bond; and wherein A1 is selected from the group consisting of hydrogen, Z2-substituted branched C3-C8alkyl, R19 substituted C3-C8-carbocyclyl, Z2-substituted C1-C6alkyl, halogen, cyano, C1-C6alkoxy, fluoroC1-C6alkoxy, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.8a Additional Compounds of Formula IIs which Exemplify More Preferred X2-E1 Moieties In an embodiment of section 2.8, preferred compounds have the structures of formula IIt

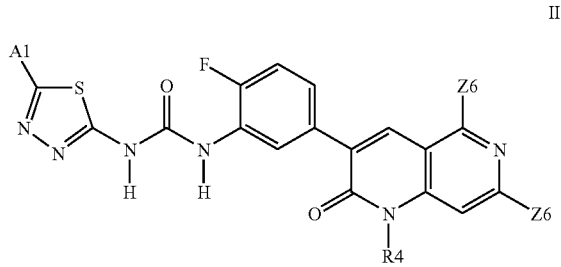

IIq

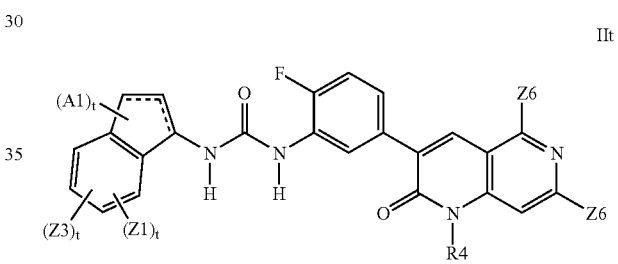

IIt 2.7b Additional Compounds of Formula IIp which Exemplify More Preferred X2-E1 Moieties In another embodiment of section 2.7, preferred compounds have the structures of formula IIr 2.8b Additional Compounds of Formula IIs which Exemplify More Preferred X2-E1 Moieties In another embodiment of section 2.8, preferred compounds have the structures of formula IIu

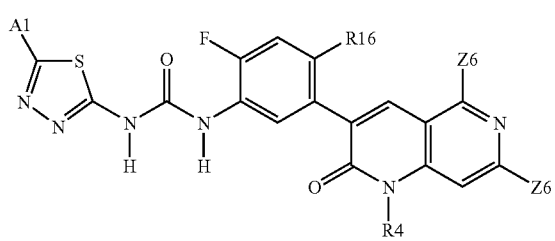

IIr

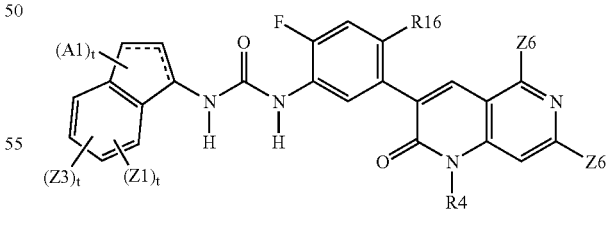

IIu and wherein R16 is methyl, cyano, —CCH, fluorine or chlorine.

2.8 Compounds of Formula IIa which Exemplify Additionally Preferred A Moieties

In a different embodiment of section 2.1, additional preferred compounds have the structures of formula IIs and wherein R16 is C1-C6alkyl, cyano, —CCH, fluorine or chlorine.

2.9 Compounds of Formula IIa which Exemplify Additionally Preferred A Moieties

In a different embodiment of section 2.1, additional preferred compounds have the structures of formula IIv

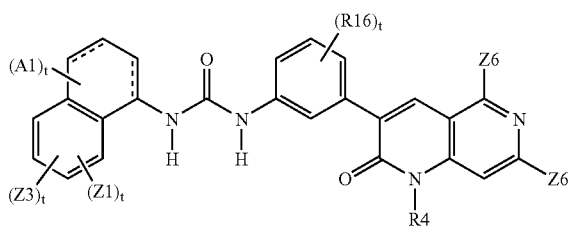

IIv

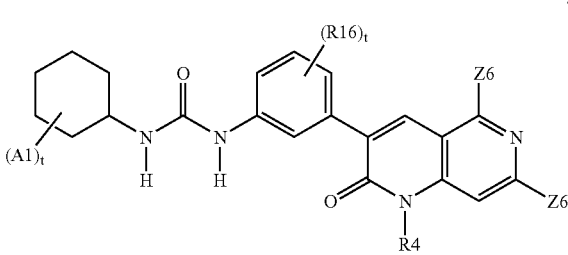

IIy wherein the hashed bond is a saturated or unsaturated bond;
and wherein A1 is selected from the group consisting of hydrogen, Z2-substituted branched C3-C8alkyl, R19 substituted C3-C8-carbocyclyl, Z2-substituted C1-C6alkyl, halogen, cyano, C1-C6alkoxy, fluoroC1-C6alkoxy, fluoroC1-C6 alkyl wherein the alkyl is fully or partially fluorinated, Z3-substituted phenyl, and Z3-substituted G1;

and wherein R16 is C1-C6alkyl, cyano, —CCH, or halogen.

2.9a Additional Compounds of Formula IIv which Exemplify More Preferred X2-E1 Moieties In an embodiment of section 2.9, preferred compounds have the structures of formula IIw wherein A1 is selected from the group consisting of Z2-substituted branched C3-C8alkyl, R19 substituted C3-C8-carbocyclyl, Z2-substituted C1-C6alkyl, fluoroC-C6alkyl wherein the alkyl is fully or partially fluorinated, Z3-substituted phenyl, and Z3-substituted G1;

and wherein R16 is C1-C6alkyl, cyano, —CCH, or halogen.

2.10a Additional Compounds of Formula IIy which Exemplify More Preferred X2-E1 Moieties In an embodiment of section 2.10, preferred compounds have the structures of formula IIz

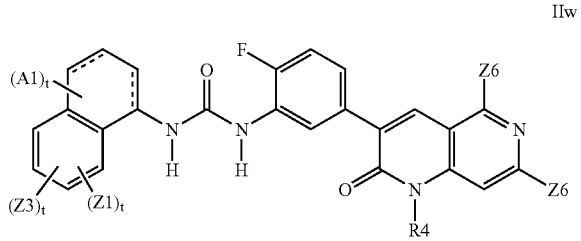

IIw

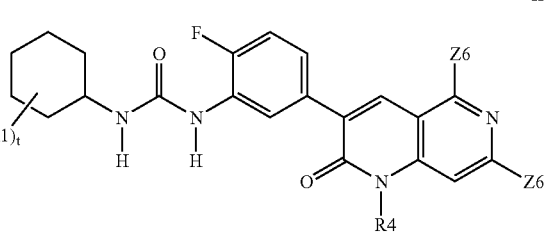

IIz 2.9b Additional Compounds of Formula IIv which Exemplify More Preferred X2-E1 Moieties In another embodiment of section 2.9, preferred compounds have the structures of formula IIx 2.10b Additional Compounds of Formula IIy which Exemplify More Preferred X2-E1 Moieties In another embodiment of section 2.10, prefered compounds have the structures of formula IIaa

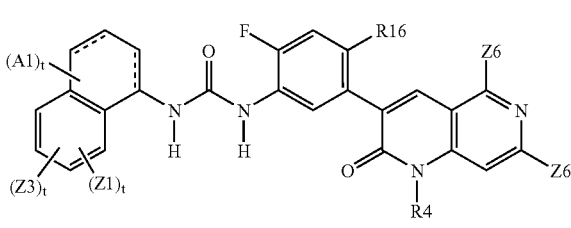

IIx

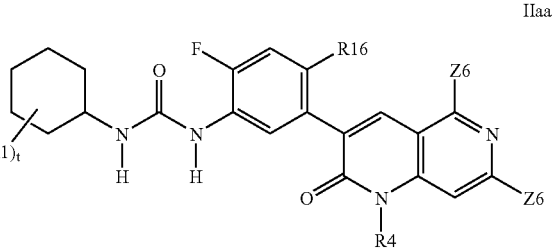

IIaa and wherein R16 is C1-C6alkyl, cyano, —CCH, fluorine or chlorine.

2.10 Compounds of Formula IIa which Exemplify Additionally Preferred A Moieties

In a different embodiment of section 2.1, additional preferred compounds have the structures of formula IIy wherein R16 is methyl, cyano, —CCH, fluorine or chlorine.

2.11 Compounds of Formula IIa which Exemplify Additionally Preferred A Moieties

In a different embodiment of section 2.1, additional preferred compounds have the structures of formula IIbb IIbb

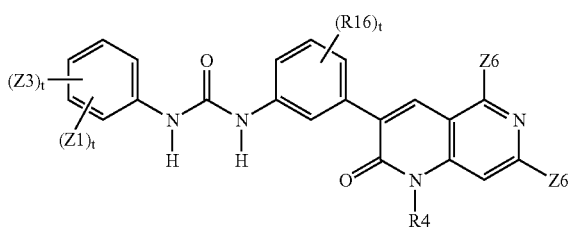

wherein R16 is C1-C6alkyl, cyano, —CCH, or halogen.

2.11a Additional Compounds of Formula IIbb which Exemplify More Preferred X2-E1 Moieties In an embodiment of section 2.11, preferred compounds have the structures of formula IIcc IIcc

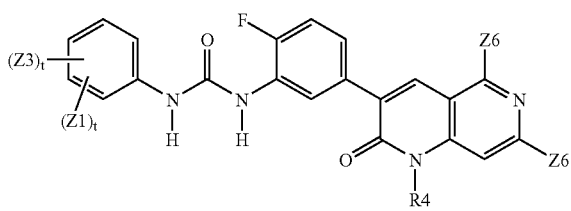

2.11b Additional Compounds of Formula IIbb which Exemplify More Preferred X2-E1 Moieties In another embodiment of section 2.11, preferred compounds have the structures of formula IIdd IIdd

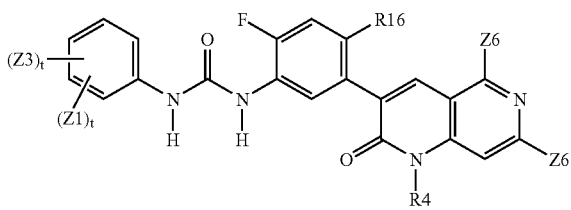

wherein R16 is C1-C6alkyl, cyano, —CCH, fluorine or chlorine.

2.12 Compounds of Formula IIa which Exemplify Additionally Preferred A Moieties

In a different embodiment of section 2.1, additional preferred compounds have the structures of formula IIee IIee

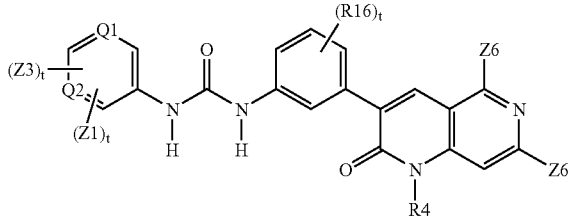

wherein Q1 and Q2 are individually and independently taken from the group consisting of N and CH;
and wherein R16 is C1-C6alkyl, cyano, —CCH, or halogen.

2.12a Additional Compounds of Formula IIee which Exemplify More Preferred X2-E1 Moieties In an embodiment of section 2.12 preferred compounds have the structures of formula IIff IIff

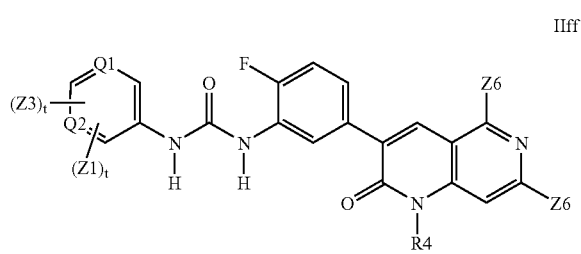

2.12b Additional Compounds of Formula Iee which Exemplify More Preferred X2-E1 Moieties In another embodiment of section 2.12, preferred compounds have the structures of formula IIgg IIgg

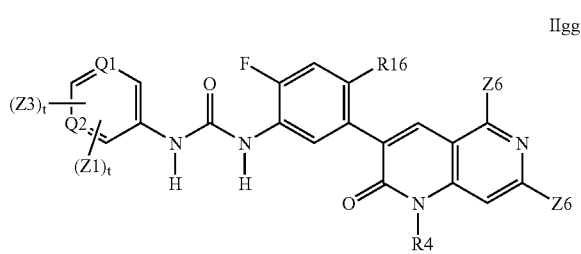

wherein R16 is C1-C6alkyl, cyano, —CCH, fluorine or chlorine.

2.13 Compounds of Formula IIa which Exemplify Additionally Preferred A Moieties

In a different embodiment of section 2.1, additional preferred compounds have the structures of formula IIhh IIhh

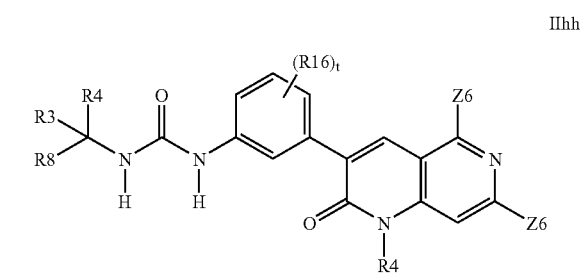

and wherein R16 is C1-C6alkyl, cyano, —CCH, or halogen.

2.13a Additional Compounds of Formula IIhh which Exemplify More Preferred X2-E1 Moieties In an embodiment of section 2.13, preferred compounds have the structures of formula IIii

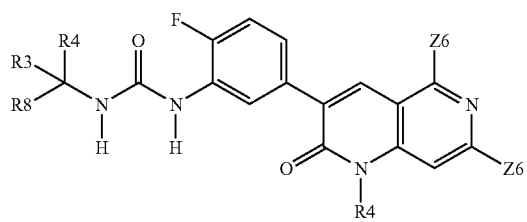

IIii

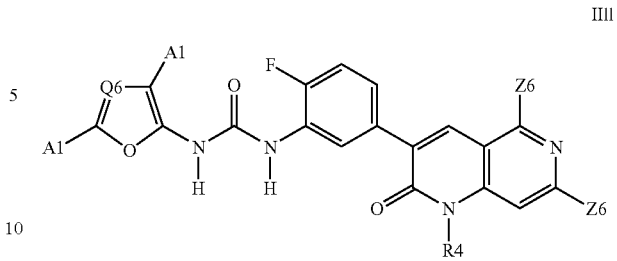

IIll 2.13b Additional Compounds of Formula IIhh which Exemplify More Preferred X2-E1 Moieties In another embodiment of section 2.13, preferred compounds have the structures of formula IIjj 2.14b Additional Compounds of Formula IIkk which Exemplify More Preferred X2-E1 Moieties In another embodiment of section 2.14, preferred compounds have the structures of formula

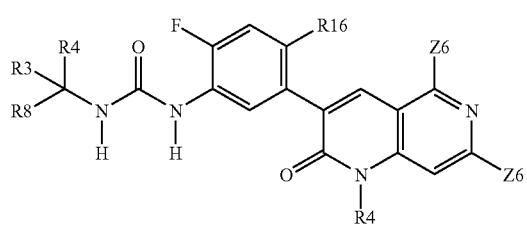

IIjj

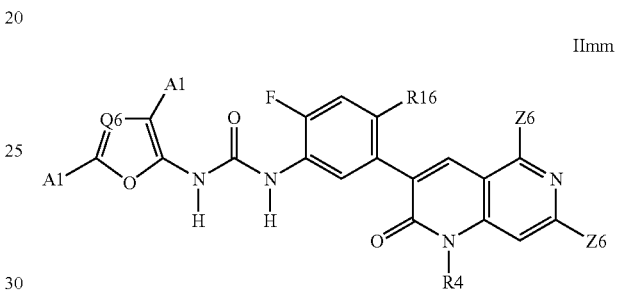

IImm and wherein R16 is methyl, cyano, —CCH, fluorine or chlorine.

2.14 Compounds of Formula IIa which Exemplify Additionally Preferred A Moieties

In a different embodiment of section 2.1, additional preferred compounds have the structures of formula IIkk wherein R16 is C1-C6alkyl, cyano, —CCH, fluorine or chlorine.

2.15 Compounds of Formula IIa which Exemplify Additionally Preferred A Moieties

In a different embodiment of section 2.1, additional preferred compounds have the structures of formula IInn

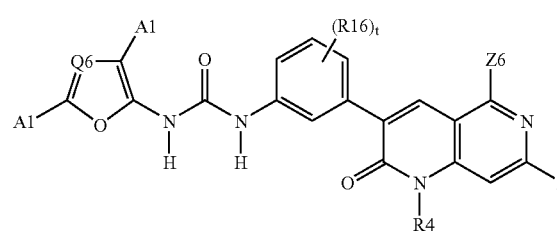

Ikk

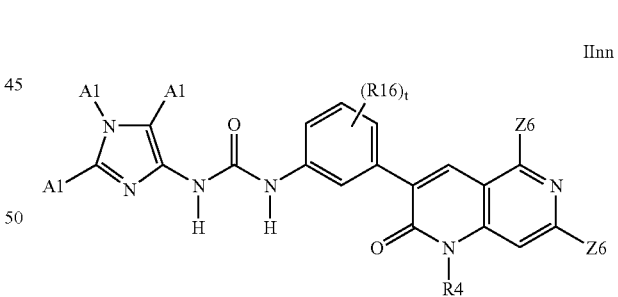

IInn wherein Q6 is N or C-A1;

wherein A1 is selected from the group consisting of hydrogen, Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.14a Additional Compounds of Formula IIkk which Exemplify More Preferred X2-E1 Moieties In an embodiment of section 2.14, preferred compounds have the structures of formula OII wherein A1 is selected from the group consisting of hydrogen, Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.15a Additional Compounds of Formula IInn which Exemplify More Preferred X2-E1 Moieties In an embodiment of section 2.15, preferred compounds have the structures of formula IIoo

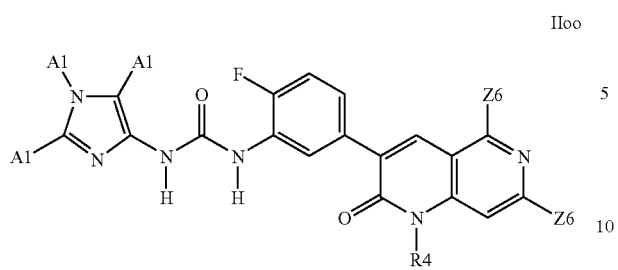

IIoo

2.15b Additional Compounds of Formula IInn which Exemplify More Preferred X2-E1 Moieties In another embodiment of section 2.15, preferred compounds have the structures of formula IIpp

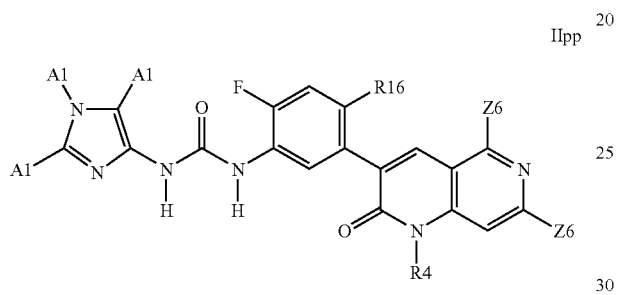

IIpp wherein R16 is C1-C6alkyl, cyano, —CCH, fluorine or chlorine.

2.16 Compounds of Formula IIa which Exemplify Additionally Preferred A Moieties In a different embodiment of section 2.1, additional preferred compounds have the structures of formula IIqq

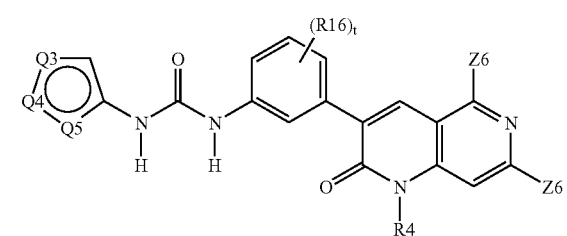

IIqq wherein Q3, Q4 and Q5 are selected from the group consisting of N-A1 and C-A1, and only one of Q3, Q4, or Q5 is N-A1;

wherein A1 is selected from the group consisting of hydrogen, Z2-substituted branched C3-C8alkyl, R19 substituted C3-C8-carbocyclyl, Z2-substituted C1-C6alkyl, fluoroC1-C6alkyl wherein the alkyl is fully or partially fluorinated, Z3-substituted phenyl, and Z3-substituted G1;

and wherein R16 is C1-C6alkyl, cyano, —CCH, or halogen.

2.16a Additional Compounds of Formula IIqq which Exemplify More Preferred X2-E1 Moieties In an embodiment of section 2.16, preferred compounds have the structures of formula IIrr

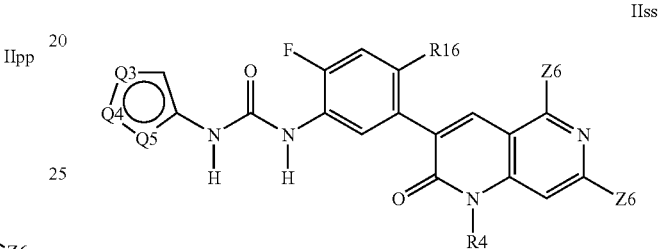

IIrr

2.16b Additional Compounds of Formula IIqq which Exemplify More Preferred X2-E1 Moieties In another embodiment of section 2.16, preferred compounds have the structures of formula IIss IIss wherein R16 is C1-C6alkyl, cyano, —CCH, fluorine or chlorine.

2.17 Methods

2.17a Methods of Protein Modulation

The invention includes methods of modulating kinase activity of RAF kinases and other kinases in the RAS-RAF-MEK-ERK-MAP kinase pathway including, but not limited to, A-Raf, B-Raf, and C-Raf. The kinases may be wildtype kinases, oncogenic forms thereof, aberrant fusion proteins thereof or polymorphs of any of the foregoing. The method comprises the step of contacting the kinase species with compounds of the invention and especially those set forth in sections 2.1-2.16. The kinase species may be activated or unactivated, and the species may be modulated by phosphorylations, sulfation, fatty acid acylations glycosylations, nitrosylation, cystinylation (i.e. proximal cysteine residues in the kinase react with each other to form a disulfide bond) or oxidation. The kinase activity may be selected from the group consisting of catalysis of phospho transfer reactions, kinase cellular localization, and recruitment of other proteins into signaling complexes through modulation of kinase conformation.

2.17b Treatment Methods

The methods of the invention, especially those of sections 2.1-2.16, also include treating individuals suffering from a condition selected from the group consisting of chronic myelogenous leukemia, acute lymphocytic leukemia, gastrointestinal stromal tumors, hypereosinophillic syndrome, glioblastomas, ovarian cancer, pancreatic cancer, prostate cancer, lung cancers, breast cancers, kidney cancers, cervical carcinomas, metastasis of primary solid tumor secondary sites, ocular diseases characterized by hyperproliferation leading to blindness including various retinopathies including diabetic retinopathy and age-related macular degeneration, rheumatoid arthritis, melanomas, colon cancer, thyroid cancer, a disease caused by a mutation in the RAS-RAF-MEK-ERK-MAP kinase pathway, human inflammation, rheumatoid spondylitis, ostero-arthritis, asthma, gouty arthritis, sepsis, septic shock, endotoxic shock, Gram-negative sepsis, toxic shock syndrome, adult respiratory distress syndrome, stroke, reperfusion injury, neural trauma, neural ischemia, psoriasis, restenosis, chronic obstructive pulmonary disease, bone resorptive diseases, graft-versus-host reaction, Chron's disease, ulcerative colitis, inflammatory bowel disease, pyresis, and combinations thereof, 2.18 Pharmaceutical Preparations The compounds of the invention, especially those of sections 2.1-2.16, may form a part of a pharmaceutical composition by combining one or more such compounds with a pharmaceutically acceptable carrier. Additionally, the compositions may include an additive selected from the group consisting of adjuvants, excipients, diluents, and stablilizers.

3. Synthesis of Compounds of the Present Invention

The compounds of Formulae Ia and IIa are prepared by the general synthetic methods illustrated in the Schemes below and the accompanying examples.

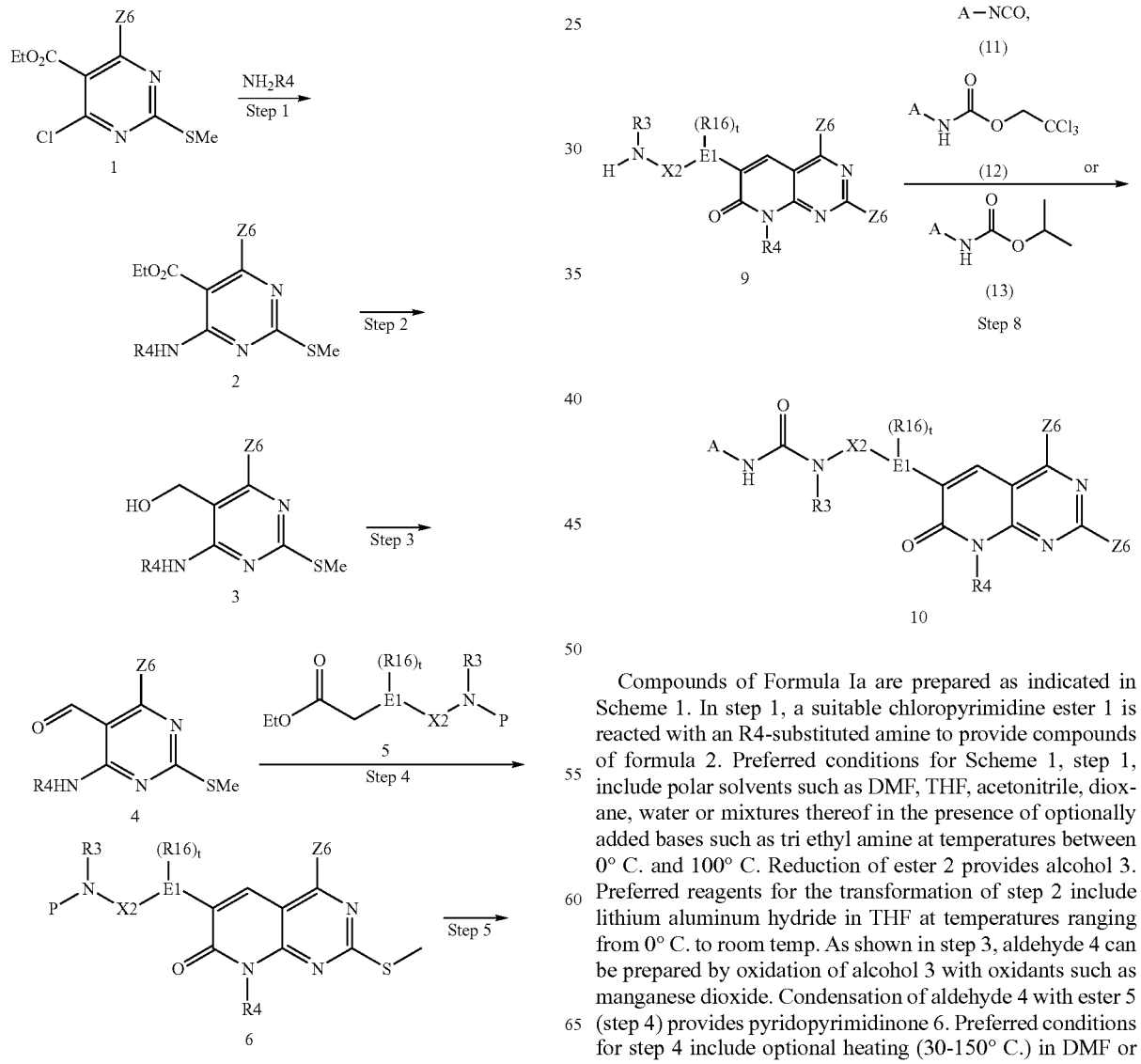

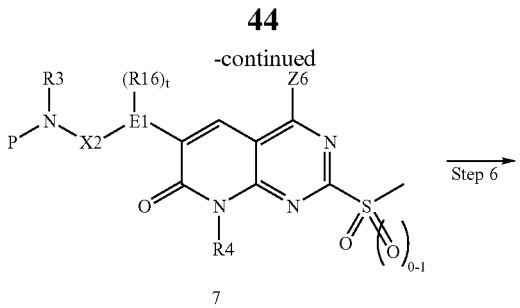

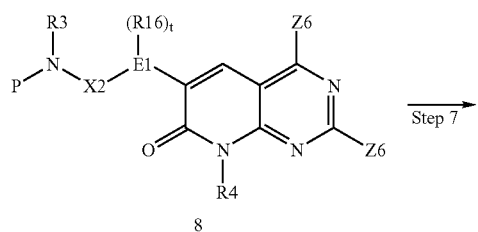

Compounds of Formula Ia are prepared as indicated in Scheme 1. In step 1, a suitable chloropyrimidine ester 1 is reacted with an R4-substituted amine to provide compounds of formula 2. Preferred conditions for Scheme 1, step 1, include polar solvents such as DMF, THF, acetonitrile, dioxane, water or mixtures thereof in the presence of optionally added bases such as tri ethyl amine at temperatures between 0° C. and 100° C. Reduction of ester 2 provides alcohol 3. Preferred reagents for the transformation of step 2 include lithium aluminum hydride in THF at temperatures ranging from 0° C. to room temp. As shown in step 3, aldehyde 4 can be prepared by oxidation of alcohol 3 with oxidants such as manganese dioxide. Condensation of aldehyde 4 with ester 5 (step 4) provides pyridopyrimidinone 6. Preferred conditions for step 4 include optional heating (30-150° C.) in DMF or DMAc in the presence of potassium carbonate or cesium carbonate for a period of time ranging from 1 h to 4 days. Other preferred conditions for Scheme 1, step 4 include combining aldehyde 4, ester 5 and alumina-supported potassium fluoride in DMAc with stirring and optional sonication and/or optional heating (30-150° C.) for a period of 30 min to 48 h. The group "P" in formula 5-8 represents a hydrogen atom or an optional amine protecting group, such as tert-butyl carbamate (Boc), benzyl carbamate (Cbz), acetamide or the like. It is understood by those skilled in the art that the moiety R3-N—P—X2 in formulae 5-8 might also represent an amino surrogate such as nitro or cyano that can be converted to an amino group or aminomethyl group in step 7 by reduction under suitable conditions.

In Scheme 1, step 5, the thiomethyl moiety of 6 can be oxidized to a sulfoxide or sulfone to provide 7. Preferred reagents for such transformations include peroxybenzoic acids, oxone, oxaziridines, or other oxidants that will be recognized as standard oxidants of sulfur atoms by those skilled in the art. In practice, mixtures of sulfoxides and sulfones can be used in step 6 without prior separation. In step 6, the sulfone or sulfoxide moiety of 7 can be converted to a Z6 moiety that is linked to the pyridopyrimidinone through a heteroatom to provide 8 by the contacting of 7 with moieties of Z6-H [for example $NH(R4)_2$, HOR4 or HSR4] optionally in the presence of a base such as potassium tert-butoxide, sodium hydride or the like or, alternatively, in the presence of a strong acid such as hydrochloric acid. Preferred solvents for such transformations include dioxane, DMF, THF, alcoholic solvents or neat Z6-H at temperatures ranging from 0° C. to 200° C. Those skilled in the art will recognize that in certain instances, compounds of formula 8 can be prepared directly from compounds of formula 6 using the conditions of step 6. In the instance that Z6 is hydrogen, preferred methods include exposure of compounds of formula 6 or 7 to hydrogen gas in the presence of a suitable hydrogenation catalyst, for example Raney Nickel® or Pd on carbon in a suitable solvent such as ethanol, methanol, ethyl acetate or THF.

In Scheme 1, step 7, the optional protecting group P of formula 8 can be removed, if necessary, by appropriate deprotection conditions (for example, acidic hydrolysis for a Boc or hydrogenation for a Cbz) to provide compounds of formula 9. Step 7 may also encompass the conversion of amine surrogates (such as nitro) into amines by appropriate chemistries (for example, reduction of a nitro group with Zn/ammonium chloride or by hydrogenation with a Pd catalyst). Finally, the conversion of compounds of formula 9 to compounds of formula 10, an aspect of formula Ia. can be accomplished in step 8 by reaction with isocyanates of formula A-NCO, 11. It will be understood that the isocyantes 11 may be either introduced into the reaction directly or may be prepared in situ, for example, by the decomposition of acyl azides (Curtius rearrangement) in the presence of 9. It will be further understood by those skilled in the art that certain carbamates, for example trichloroethyl carbamates (12) and isopropenyl carbamates (13) also function as isocyanate equivalents and will find use in step 8.

An alternative preparation of intermediate 6 is shown in Scheme 2. Treatment of aldehyde 4 from Scheme 1 with ethyl (triphenylphosphoranylidene)acetate provides compounds of formula 14. Bromination of 14 with N-bromosuccinimide (step 2) provides bromide 15. In step 3, Suzuki-type couplings of 15 with boronic acids 16 in the presence of palladium catalysts provide compounds of formula 6, useful for the preparation of compounds of formula 10 as illustrated in Scheme 1.

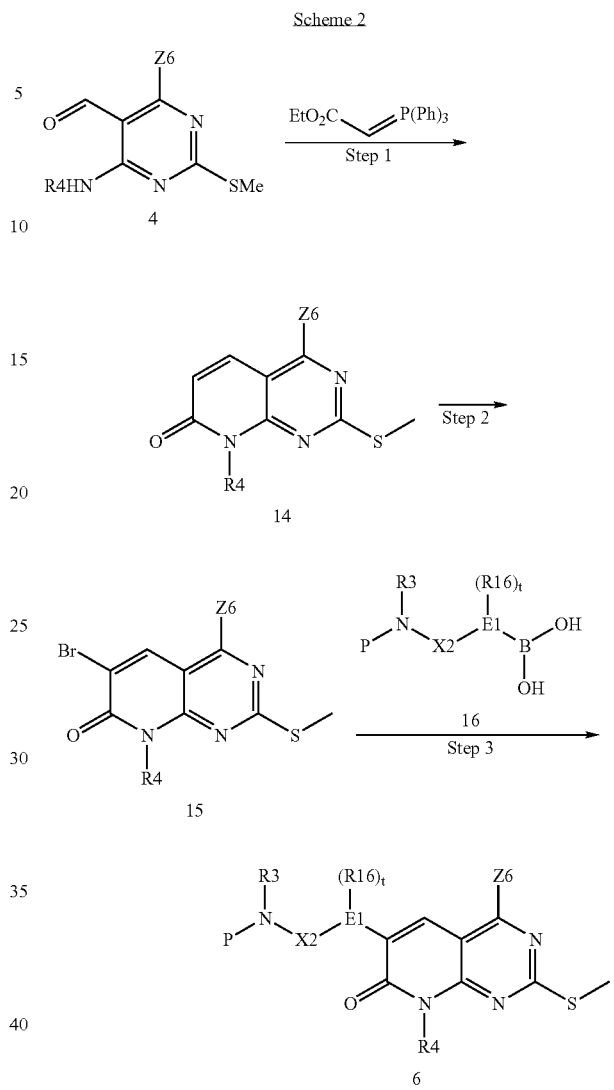

Non-commercially available pyrimidines 1 can be readily prepared from known intermediate 17 [See Seto, et al. *Biorg, Med, Chem. Lett.* 2005, 75, 1485]. (Scheme 3) Thus, lithiation of 17 with LDA followed by $CO_2$ quench provides acid 18. Conversion of acid 18 to ester 19 provides a scaffold to introduce Z6 groups of the invention. When the Z6 moiety is attached to the pyrrolidine ring through a Z6 nitrogen atom, a Z6 oxygen atom or a Z6 sulfur atom, compounds of formula 1 can be prepared by contacting the amine Z6-H, the alcohol Z6-H or the thiol Z6-H with compound 19, either neat (Z6-H as solvent) or in a suitable solvent such as DMF, DMSO or an alcoholic solvent at temperatures ranging from −78° C. to 200° C. in the presence of suitable base such as triethylamine, potassium carbonate, or potassium tert-butoxide. When the Z6 moiety is attached to the pyrimidine through a Z6 carbon atom, preferred methods include contacting compound 19 with a species of formula Z6-M in the presence of a palladium catalyst, wherein M is a species that participates in transition-metal catalyzed cross-coupling reactions. Examples of suitable M groups include but are not limited to, boronic acids and boronic esters, zinc, copper, tin, silicon, magnesium, lithium, and aluminum.

Scheme 3

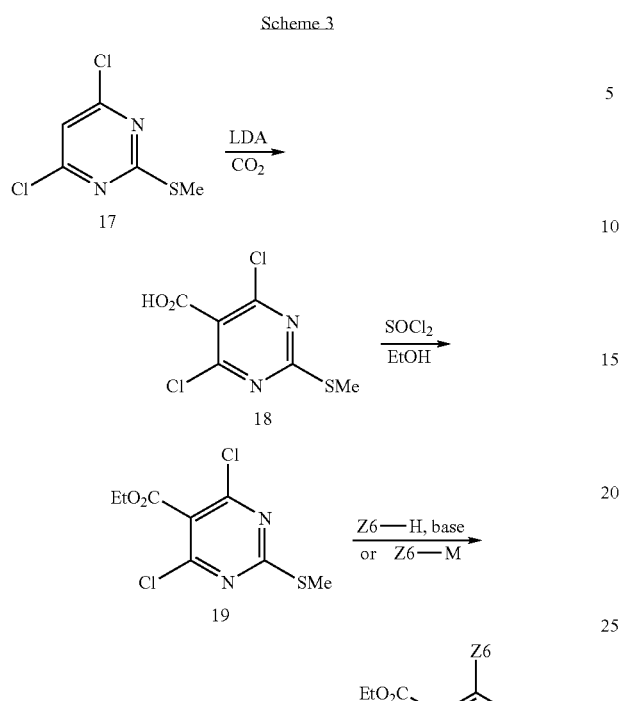

Compounds of both Formulae Ia and IIa can be prepared by the additional methods in Scheme 4, below. As shown in step 1, reaction of R4-substituted amines with 5-bromo-2,6-dichloropyrimidine (22, commercially available), 3-bromo-2,6-dichloropyridine (21, available by the procedure of Pierrat et al. *J. Comb. Chem.* 2005, 7, 879-886) or 5-bromo-2,4-dichloropyridine 20, available by the procedure of Schlosser et al, *J. Org. Chem.* 2004, 70, 2494-2502) provides compounds 23-25 respectively. In step 2, treatment of bromides 23-25 with tributylvinyltin in the presence of a palladium catalyst provides compounds of formula 26-28. In step 3, oxidative cleavage of the olefin moiety provides aldehydes of formula 29-31.

Scheme 4

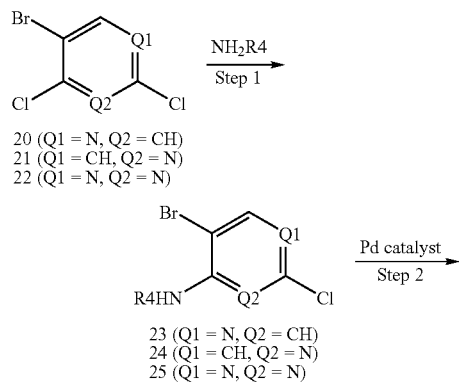

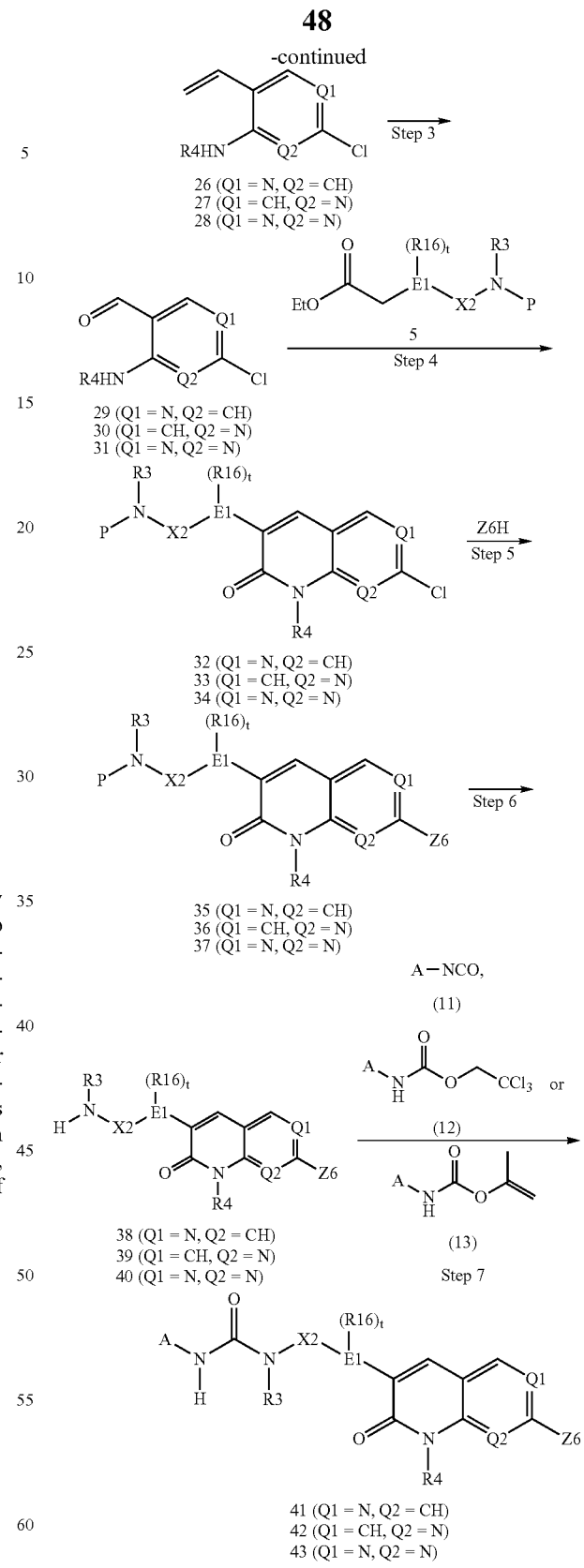

In Scheme 4, step 4, condensation of 29-31 with ester 5 provides 32-34. Preferred conditions for step 4 include optional heating (30-150° C.) in DMF or DMAc in the presence of potassium carbonate or cesium carbonate for a period of time ranging from 1 h to 4 days. Other preferred conditions for Scheme 4, step 4 include combining aldehyde 29-31, ester 5 and alumina-supported potassium fluoride in DMAc with stirring and optional sonication and/or optional heating (30-150° C.) for a period of 30 min to 48 h. As described in Scheme 1, the group "P" present in formulas 32-37 represents a hydrogen atom or an optional amine protecting group, such as tert-butyl carbamate (Boc), benzyl carbamate (Cbz), acetamide or the like. It is understood by those skilled in the art that the moiety R3-N—P—X2 in formula 32-37 might also represent an amino surrogate such as nitro or cyano that can be converted to an amino group or an aminomethyl group in step 6 by reduction under suitable conditions.

As shown in Scheme 4, step 5, compounds of formula 32-34 can be converted to compounds of formula 35-37 by replacement of the chloride moiety of 32-34 with a Z6 moiety. There are several methods through which this can be accomplished, depending on the nature of the Z6. When the Z6 moiety is attached to the Q1-containing ring through a Z6 nitrogen atom, preferred methods include heating compounds of formula 32-34 with an excess of the amine Z6-H either neat or in a solvent such as N-methylpyrrolidinone, DMF, DMSO or an alcoholic solvent at temperatures ranging from room temp to 200° C. For the case of aryl and heteroaryl amines Z6-H, additional preferred methods include the heating of compounds 32-34 with an excess of the amine Z6-H and an acid catalyst (for example, TsOH, HCl, HOAc or the like) in a suitable solvent such as DMF, DMSO or an alcoholic solvent. Additional preferred methods for aryl and heteroaryl amines Z6-H include heating with compounds 32-34 in the presence of a transition metal catalyst such as a palladium catalyst in a suitable solvent like 1,4-dioxane or DMF. When the Z6 moiety is attached to the Q-containing ring through a Z6 oxygen or sulfur atom, preferred methods include heating 32-34 with alcohol or thiol Z6-H in the presence of a strong base (for example, NaH or potassium tert-butoxide) either neat using Z6-H as the solvent, or in a polar solvent such as DMF or DMSO at temperatures ranging from room temp to 200° C. When the Z6 moiety is attached to the pyridopyrimidine through a Z6 carbon atom, preferred methods include contacting compounds 32-34 with a species of formula Z6-M in the presence of a palladium catalyst, wherein M is a species that participates in transition-metal catalyzed cross-coupling reactions. Examples of suitable M groups include but are not limited to, boronic acids and boronic esters, zinc, trialkyltin, silicon, magnesium, lithium, and aluminum. In the instance that Z6 is hydrogen, preferred methods include exposure of compounds of formula 32-34 to hydrogen gas in the presence of a suitable hydrogenation catalyst, for example Raney Nickel® or Pd on carbon in a suitable solvent such as ethanol, ethyl acetate or THF.

As shown in Scheme 4, step 6, removal of the optional protecting group P provides compounds of formula 38-40, which can be further converted (step 7) to compounds of formula 41-43, examples of Formula Ia and IIa, by the methods described in Scheme 1.

Scheme 5 illustrates an alternate, preferred method for the preparation of chloropyridine aldehydes 29, useful for the preparation of amines 32 and compounds of general formula IIa. Thus, by analogy to Scheme 1, ethyl 4,6-dichloronicotinate (44) is reacted with an R4-substituted amine to provide a compound of formula 45. Preferred conditions for Scheme 5, step 1, include polar solvents such as DMF, THF, acetonitrile, dioxane, water or mixtures thereof in the presence of optionally added bases such as triethylamine at temperatures between 0° C. and 100° C. Reduction of ester 45 provides alcohol 46. Preferred reagents for the transformation of step 2 include lithium aluminum hydride in THF at temperatures ranging from 0° C. to room temp. As shown in step 3, aldehyde 29 can be prepared by oxidation of alcohol 46 with oxidants such as manganese dioxide. Condensation of aldehyde 29 with ester 5 according to Scheme 4 provides 32, useful for the preparation of compounds of Formula IIa.

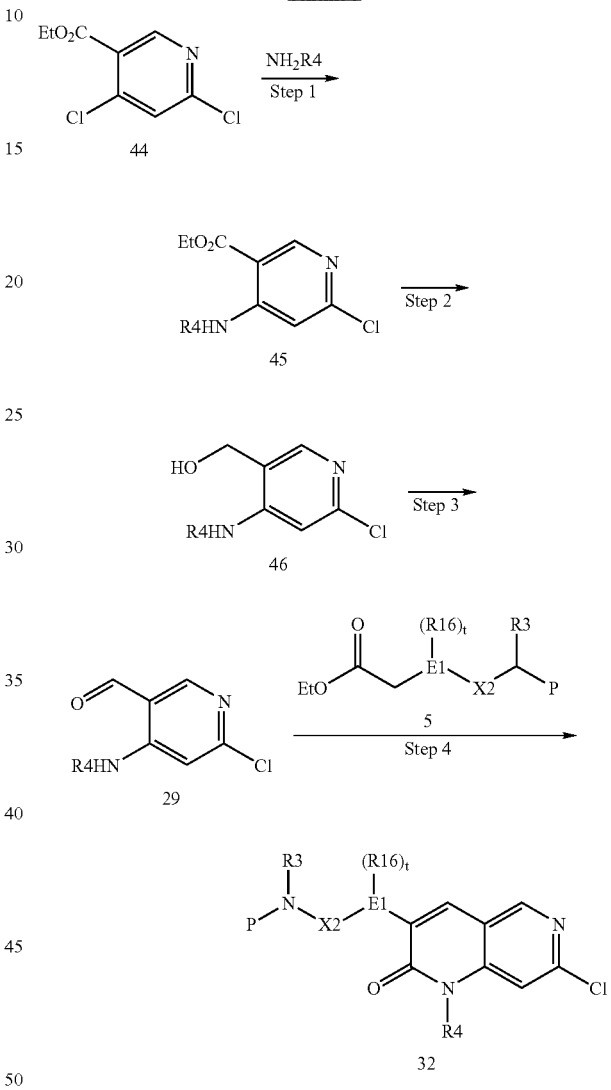

It will be recognized in the above Schemes and the accompanying examples that some Z6 moieties may be introduced with protecting groups that will require additional de-protection steps. For example, Scheme 6 shows a preferred route to preparing pyridopyridines of formula 48 wherein Z6 is NHMe. In Scheme 6, step 1, chloropyridine 32 is reacted with (4-methoxybenzyl)methylamine to provide 47. Step 1 may be performed in neat (4-methoxybenzyl)methylamine at temperatures between 150° C. and 200° C. Or more preferably, step 1 can be conducted using only a slight excess of (4-methoxybenzyl)methylamine and DBU (1,8-diazabicyclo[5.4.0]undec-7-ene) in N-methylpyrrolidinone at temperatures between 150° C. and 200° C. In step 2, removal of the 4-methoxybenzyl protecting group from 47 with trifluoroacetic acid provides amine 48.

Scheme 6

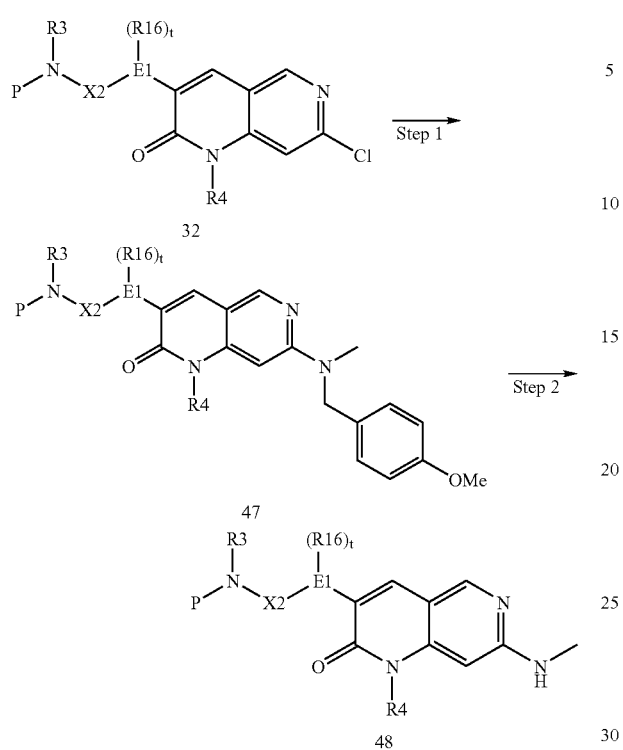

In addition to the methods of urea formation described in Schemes 1 and 4 above, ureas of formulae Ia and IIa may also be prepared as shown in Scheme 7. In Scheme 7, step 1, amines of formulae 49-51 are reacted with isopropenyl chloroformate to afford the corresponding isopropenyl carbamates 52-54. In step 2, carbamates 52-54 are reacted with amines of formula A-NHR3 (55) to provide ureas of formula 56-58. In the event that R3 is not H, the mono-substituted ureas 56-58 can be optionally further transformed into bis-R3-substituted ureas 59-61. Thus, in step 3, exposure of the NH-ureas 56-58 to alkyl halides in the presence of a base, for example potassium carbonate, NaH, potassium t-butoxide or BEMP, in a suitable solvent such as DMF provides ureas 59-61 wherein the newly incorporated R3 group is alkyl.

Alternatively, exposure of ureas 56-58 to copper(II) acetate and phenylboronic acids [See: Chan et. al, *Tetrahedron Lett.* 2003, 44, 3863-3865; Chan et. al, *Tetrahedron Lett.* 1998, 39, 2933-2936; Chan, D. M. T. *Tetrahedron Lett.* 1996, 37, 9013-9016] provides the analogous compounds 59-61 wherein the newly incorporated R3 is phenyl.

Scheme 7

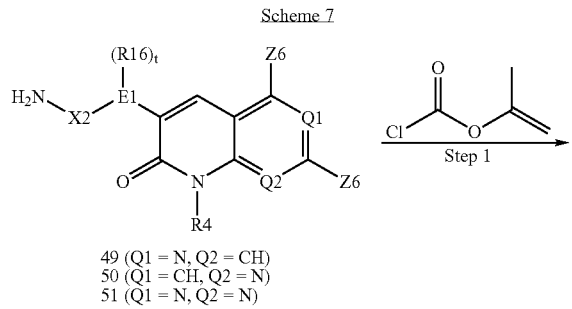

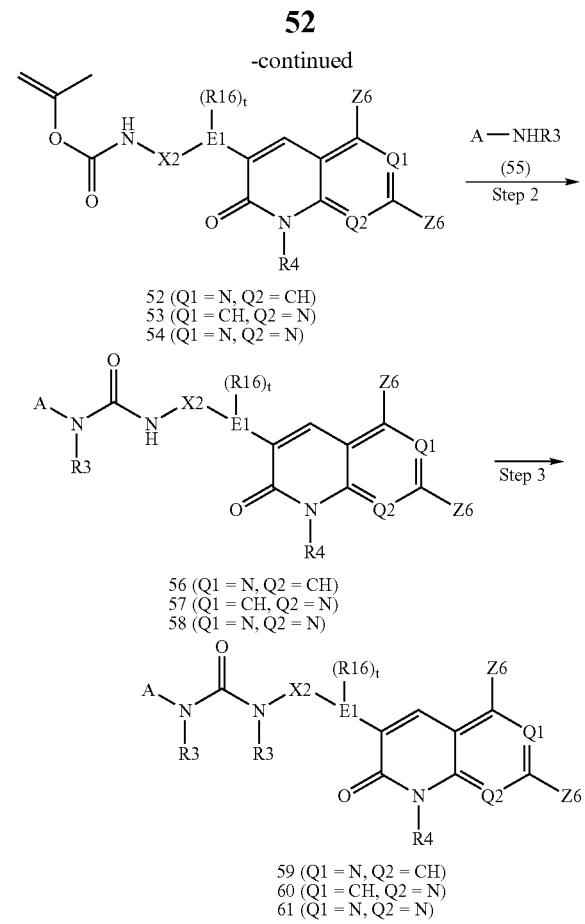

General method A: To a solution of the starting pyrazole amine (1 eq) in EtOAc were added 2,2,2-trichloroethylchloroformate (1.1 eq) and saturated NaHCO$_3$ (2-3 eq) at 0° C. After stirring for 3 h at RT, the layers were separated and the aqueous layer extracted with EtOAc. The combined organic extracts were washed with brine, dried (Na$_2$SO$_4$) and concentrated in vacuo to yield the crude TROC carbamate of the pyrazole amine. To the carbamate (1 eq) in DMSO were added thisopropylethylamine (2 eq), the appropriate amine (2 eq) and the mixture was stirred at 60° C. for 16 h or until all the starting carbamate was consumed. Water was added to the mixture and the product was extracted with EtOAc (2×25 mL). The combined organic extracts were washed with brine solution, dried (Na$_2$SO$_4$) and concentrated in vacuo to yield crude product, which was purified by column chromatography to yield the target compound.

General method B: To a suspension of the amine (usually 0.67 mmol) in EtOAc (2 mL) was added aqueous 1N NaOH. The reaction mixture was cooled to 0° C. and treated with isopropenyl chloroformate (0.1 mL, 0.94 mmol) over 30 sec. The reaction mixture was stirred 15 min at 0° C. and 1 h at RT. The reaction was poured into THF-EtOAc (1:1; 40 mL) and washed with H$_2$O (2×10 mL) and brine (2×10 mL). The organics were dried (Na$_2$SO$_4$), concentrated in vacuo and the residue purified via column chromatography to provide the target (prop-1-en-2-yl)carbamate. To the carbamate (usually 0.26 mmol) was added the appropriate amine (usually 0.26 mmol) in THF (2 mL) and 1-methylpyrrolidine (Catalytic amount) at 60° C. for 18 h. The mixture was diluted with CH$_2$Cl$_2$ (2 mL) and hexane (0.5 mL) solution, and stirred for 10 min. The resultant solid was filtered and dried and the resulting solid converted to the amine hydrochloride salt by treatment with 0.1 N HCl solution and lyophilization.

General Method C: To a stirring solution of amine (2 mmol, 1.00 eq) and pyridine (4 mmol, 2.00 eq) in $CH_2Cl_2$ (18 ml) at RT was added Troc-Cl (1.87 mmol, 1.05 eq). After 4 hours the reaction was washed with 3M HCl (1×), satd. $NaHCO_3$ (1×), dried ($Na_2SO_4$), filtered and evaporated to afford the target 2,2,2-trichloroethyl carbamate. The material was used as is in the next reaction.

The 2,2,2-trichloroethyl carbamate (0.7 mmol, 1.00 eq), the appropriate (0.7 mmol, 1.00 eq) and $iPr_2NEt$ (1.54 mmol, 2.20 eq) were combined in DMSO (3 ml) and stirred with heating at 70° C. After 18 h, the completed reaction was diluted with brine (30 ml) and extracted with EtOAc (3×). The combined organics were washed with brine (2×), dried ($MgSO_4$), filtered and evaporated to give the crude product which was purified via flash column chromatography.

General Method D: To a stirring solution of carboxylic acid (0.50 mmol, 1.00 eq) and DPPA (0.75 mmol, 1.50 eq) in 1,4-dioxane (5.0 ml) at RT was added $Et_3N$ (1.5 mmol, 3.00 eq). After stirring for 30 min at RT, the appropriate amine (0.76 mmol, 1.50 eq) was added and the mixture was heated at 100° C. After 2 h, the completed reaction was cooled to RT, diluted with brine and extracted with EtOAc (2×). The combined organics were washed with 3M HCl (1×), satd. $NaHCO_3$ (2×), and brine (1×), dried ($MgSO_4$), filtered and evaporated to give the crude product which was purified by flash column chromatography to afford the target urea.

General Method E: To a solution of aryl sulfone and/or aryl sulfoxide (0.4 mmol) in THF added the appropriate amine (2 mmol, 5 eq) and the reaction was stirred for 2 h at RT. The mixture was diluted with EtOAc (3 mL) and resultant solid filtered, washed and dried to provide the desired product aryl amine.

General Method F: To a stirring suspension of isocyanate (0.51 mmol, 1.00 eq) and pyridine (0.0418 ml, 0.51 mmol, 1.00 eq) in $CH_2Cl_2$ (5 ml) at RT was added the appropriate amine (0.51 mmol, 1.00 eq). A thick suspension gradually formed. After 3.5 h, the solids were collected by filtration, rinsed well with $CH_2Cl_2$ and dried on the filter to afford the desired urea.

General Method G: To a solution of amine (11 mmol) in THF (100 mL) was added LiHMDS (22 mmol) at −78° C. under Ar. After 20 min, prop-1-en-2-yl carbonochloridate (11 mmol) was added and the reaction was stirred for 30 min. The mixture was quenched with 2N HCl (15 mL) at −78° C. and warmed to RT. It was diluted with brine (50 mL) and EtOAc (50 mL), the organic layer was separated and washed with brine, dried ($Na_2SO_4$) and concentrated in vacuo. Purification by silica gel chromatography or recrystallization provided the appropriate prop-1-en-2-yl carbamate.

To the carbamate (usually 0.26 mmol) was added the appropriate amine (usually 0.26 mmol) in THF (2 mL) and 1-methylpyrrolidine (Catalytic amount) at 60° C. for 18 h. The mixture was diluted with $CH_2Cl_2$ (2 mL) and hexane (0.5 mL) solution, and stirred for 10 min. The resultant solid was filtered and dried and the resulting solid converted to the amine hydrochloride salt by treatment with 0.1 N HCl solution and lyophilization.

EXAMPLE A1

To a solution of Example A3 (6.0 g, 19 mmol) in $CH_2Cl_2$ (50 mL) was added m-chloroperoxybenzoic acid (mCPBA, 6.5 g, 38 mmol) in one portion. After stirring for 2 h at RT, sat. aq $NaHCO_3$ and aq $NaHSO_3$ solution were added and stirring was continued for a few minutes. The combined organic layer was washed with brine, dried and concentrated in vacuo. The residue was dissolved in DMSO (5 mL) and ammonia in dioxane (2 M, 200 mL, 400 mmol) was added. The resultant reaction mixture was stirred overnight at RT. The solvent was removed under reduced pressure and the residue was purified by reverse phase prep-HPLC to provide 2-amino-6-(3-amino-4-fluorophenyl)-8-methylpyrido[2,3-d]pyrimidin-7(8H)-one (1.9 g, 35% yield). $^1$H NMR (300 MHz, DMSO-$d_6$), δ 8.63 (s, 1 H), 7.80 (s, 1 H), 7.39 (br s, 2 H), 7.12 (d, J=6.0 Hz, 1 H), 7.03 (t, J=12.0 Hz, 1 H), 6.80 (m, 1 H), 3.53 (s, 3 H); MS (ESI) m/z: 286.2 (M+H$^+$).

EXAMPLE A2

Using a procedure analogous to Example A1, Example A9 (3.50 g, 10.6 mmol) was oxidized with mCPBA (2.87 g, 11.7 mmol, 70% wt) to afford the intermediate 6-(3-amino-4-fluorophenyl)-8-ethyl-2-(methylsulfinyl)pyrido[2,3-d]pyrimidin-7(8H)-one (2.35 g, 61% yield). The intermediate (1.40 g, 3.86 mmol) and 0.5 M ammonia in dioxane (15.5 mL, 2 eq) were combined and purified by silica gel column chromatography to obtain 2-amino-6-(3-amino-4-fluorophenyl)-8-ethylpyrido[2,3-d]pyrimidin-7(8H)-one (0.65 g, 56% yield). $^1$H NMR (400 MHz, DMSO-$d_6$): δ 8.63 (s, 1H), 7.79 (s, 1H), 7.27 (s, 1H), 7.10 (dd, J=2.4, 8.8 Hz, 1H), 7.00 (dd, J=8.8, 11.6 Hz, 1H), 6.75 (m, 1H), 5.14 (s, 2H), 4.31 (q, J=6.8 Hz, 2H), 1.18 (t, J=6.8 Hz, 3H); LC-MS (EI) m/z: 300.0 (M+H$^+$).

EXAMPLE A3

A mixture of Example C1 (15 g, 82 mmol), ethyl 2-(3-amino-4-fluorophenyl)acetate (19.4 g, 98 mmol; prepared by the method of Kuse et al. *Tetrahedron* (2005), 61, 5754-5762) and $K_2CO_3$ (34.0 g, 246 mmol) in DMF (100 mL) was heated at 110° C. overnight. The mixture was poured into water and product was extracted with ethyl acetate (3×200 mL). The combined organics were washed with brine, dried ($Na_2SO_4$) and concentrated in vacuo. Purification by silica gel chromatography provided 6-(3-amino-4-fluorophenyl)-8-methyl-2-(methylthio)pyrido[2,3-d]pyrimidin-7(8H)-one (13.0 g, 50% yield). $^1$H NMR (300 MHz, DMSO-$d_6$), ε 8.91 (s, 1 H), 7.99 (s, 1 H), 7.15 (dd, J=8.7, 2.1 Hz, 1 H), 7.04 (dd, J=11.4, 8.4, 1 H), 6.80 (m, 1 H), 5.21 (br s, 2 H), 3.65 (s, 3 H), 2.60 (s, 3 H); MS (ESI) m/z: 317.2 (M+H$^+$).

EXAMPLE A4

Using general method E, 6-(3-amino-4-fluorophenyl)-8-ethyl-2-(methylsulfinyl)pyrido[2,3-d]pyrimidin-7(8H)-one from Example 2 (0.94 g, 2.73 mmol) and 2.0M methylamine/THF (2.73 mL, 5.5 mmol) were stirred overnight at RT. Water (50 mL) was added and the product was extracted with EtOAc (2×30 mL). The combined organic layers were washed with brine, dried ($Na_2SO_4$) and concentrated to afford crude product. This crude product was stirred with 60% $CH_2Cl_2$/hexane solution (10 mL) for 10 min. The resultant solid was filtered and washed with 60% $CH_2Cl_2$/hexane solution and dried to afford 6-(3-amino-4-fluorophenyl)-8-ethyl-2-(methylamino) pyrido[2,3-d]pyrimidin-7(8H)-one (0.32 g, 37% yield) as a solid. $^1$H NMR (400 MHz, DMSO-$d_6$): δ 8.62 (s, 1H), 7.82-7.77 (m, 2H), 7.11 (dd, J=8.8 Hz, 1.6 Hz, 1H), 7.00 (dd, J=11.2 Hz, 8.0 Hz, 1H), 6.78-6.74 (m, 1H), 5.14 (s, 2H), 4.39-4.35 (m, 2H), 2.89 (d, J=4.4 Hz, 3H), 1.26-1.22 (m, 3H); MS (ESI) m/z: 314.3 (M+H$^+$).

EXAMPLE A5

Using a two-step procedure analogous to Example A27, Example A55 (1.3 g, 3.2 mmol) and 4-Methoxybenzylamine (10 mL) were converted to 7-amino-3-(3-amino-4-fluorophenyl)-1-methyl-1,6-naphthyridin-2(1H)-one (0.55 g, 54%, yield, two steps). $^1$H NMR (400 MHz, DMSO-d$_6$): δ8.34 (s, 1H), 7.77 (s, 1 H), 7.07 (dd, J=9.2, 2.4 Hz, 1 H), 6.97 (m, 1H), 6.75 (m, 1 H), 6.50 (s, 2 H), 6.24 (s, 1H), 5.10 (s, 2H), 3.47 (s, 3 H), MS (ESI) m/z (M+H$^+$): 285.3.

EXAMPLE A6

Using a procedure analogous to Example A1, Example A10 (0.200 g, 0.605 mmol) and N,N-dimethylethylenediamine (0.334 ml, 3.03 mmol) were combined to afford 6-(5-amino-4-fluoro-2-methylphenyl)-2-(2-(dimethylamino)ethylamino)-8-methylpyrido[2,3-d]pyrimidin-7(8H)-one (0.095 g, 42% yield) as a yellow foam. $^1$H NMR (400 MHz, CDCl$_3$) δ 8.40 (s, 1H), 7.36 (s, 1H), 6.85 (d, J=11.6 Hz, 1H), 6.62 (d, J=9.2 Hz, 1H), 6.11 (s, 1H), 3.79 (s, 3H), 3.57 (q, J=5.6 Hz, 2H), 2.56 (t, J=6.0 Hz, 2H), 2.29 (s, 6H), 2.07 (s, 3H); MS (ESI) m/z: 371.2 (M+H$^+$).

EXAMPLE A7

The mixture of Example A11 (0.050 g, 0.16 mmol) and N,N-dimethylethane-1,2-diamine (2.0 mL, 18 mmol) was heated at 175° C. under N2 overnight. The reaction was cooled down to RT and solvent was removed under reduced pressure. The residue was quenched with satd. NaHCO$_3$ (6 mL) and extracted with EtOAc (2×10 mL). The combined organic layers were washed with brine (6 mL), dried (MgSO$_4$) and concentrated to afford 3-(5-amino-4-fluoro-2-methylphenyl)-7-(2-(dimethylamino)ethylamino)-1-methyl-1,6-naphthyridin-2(1H)-one (0.050 g, 86% yield) as a light yellow foam. $^1$H NMR (400 MHz, CDCl$_3$), δ 8.28 (s, 1H), 7.43 (s, 1H), 6.86 (d, J=12.0 Hz, 1H), 6.64 (d, J=9.2 Hz, 1H), 6.06 (s, 1H), 5.58 (m, 1H), 3.60 (s, 3H), 3.40 (q, J=5.2 Hz, 2H), 2.60 (t, J=6.0 Hz, 2H), 2.28 (s, 6H), 2.09 (s, 3H); MS (ESI) m/z: 370.2 (M+H$^+$).

EXAMPLE A8

Using procedures analogous to Example C2 and Example A2, ethyl 4-chloro-2-(methylthio)pyrimidine-5-carboxylate, cyclopropyl amine, ethyl 2-(3-amino-4-fluorophenyl)acetate (prepared by the method of Kuse et al. *Tetrahedron* (2005), 67, 5754-5762) and 0.5 M ammonia in dioxane (2 ml) were combined to afford 2-amino-6-(3-amino-4-fluorophenyl)-8-cyclopropylpyrido[2,3-d]pyrimidin-7(8H)-one as an off-white solid (67 mg). $^1$H NMR (400 MHz, DMSO-d$_6$): δ 8.57 (s, 1H), 7.73 (s, 1H), 7.15 (brs, 1H), 7.06 (dd, J=9.2 Hz, 2.4 Hz, 1H), 6.99 (dd, J=11.2 Hz, 11.6 Hz, 1H), 6.75-6.71 (m, 1H), 2.88-2.82 (m, 1H), 1.18-1.13 (m, 2H), 0.83-0.78 (m, 2H); MS (ESI) m/z: 312.0 (M+H$^+$).

EXAMPLE A9

Method 1: To a solution of Example C2 (8.0 g, 0.041 mol) and ethyl 2-(3-amino-4-fluorophenyl)acetate (8.0 g, 0.041 mol) in DMAc (200 mL) was added KF on Al$_2$O$_3$ (40 wt %, 40 g, 0.275 mol) and the mixture was stirred at RT for 1 h. The reaction mixture was filtered and the filtrate was concentrated to dryness. The residue was washed with ethyl ether to provide 6-(3-amino-4-fluorophenyl)-8-ethyl-2-(methylthio)pyrido[2,3-d]pyrimidin-7(8 H)-one (10.9 g, 81% yield). $^1$H NMR (400 MHz, DMSO-d$_6$): δ 8.88 (s, 1 H), 7.96 (s, 1 H), 7.10 (dd, J=9.2, 2.4 Hz, 1 H), 7.00 (dd, J=11.4, 8.6 Hz, 1 H), 6.76 (m, 1 H), 5.17 (s, 2 H), 4.36 (q, J=6.8 Hz, 2 H), 2.57 (s, 3 H), 1.22 (t, J=6.8 Hz, 3 H); MS (ESI) m/z: 331.1 [M+H]$^+$.

Method 2: The compound from Example C2 (2.08 g, 10.5 mmol), ethyl 2-(3-amino-4-fluorophenyl)acetate (2.29 g, 11.6 mmol) and powdered K$_2$CO$_3$ (4.37 g, 31.6 mmol) were combined in DMF (15 mL) and vigorously stirred with heating at 110° C. under a N$_2$ atmosphere. The completed reaction was cooled partially and diluted with H$_2$O (60 mL) to precipitate product. The suspension was chilled thoroughly in ice. The solid was filtered and washed with water (100 mL) to obtain the crude product, 6-(3-amino-4-fluorophenyl)-8-ethyl-2-(methylthio)pyrido[2,3-d]pyrimidin-7(8H)-one (3.50 g, 100% yield).

EXAMPLE A10

Nitrogen was bubbled though a solution of Example D4 (2 g, 8.0 mmol), 6-bromo-8-methyl-2-(methylthio)pyrido[2,3-d]pyrimidin-7(8H)-one (2.5 g, 8.8 mmol) and potassium carbonate (3.3 g, 23.9 mmol) in DMF (10 mL) for 20 min, then tetrakis(triphenyl phosphine) palladium (460 mg, 0.4 mmol) was added and the nitrogen was continued for 30 min. The resulting mixture was heated at 80° C. for 16 h. The excess DMF was removed under reduced pressure and the residue was partitioned between water and EtOAc. The organic layer was washed with brine, dried, filtered concentrated and purified by silica gel column chromatography to give 6-(5-amino-4-fluoro-2-methylphenyl)-8-methyl-2-(methylthio)pyrido[2,3-d]pyrimidin-7(8H)-one (1.1 g, 42.3% yield). $^1$H NMR (400 MHz, DMSO-d$_6$): δ 8.86 (s, 1 H), 7.80 (s, 1 H), 6.87 (d, J=12.0 Hz, 1 H), 6.58 (d, J=8.0 Hz, 1 H), 4.96 (br s, 2 H), 3.62 (s, 3 H), 2.59 (s, 3 H), 1.95 (s, 3 H). MS (ESI) m/z: 331.2 (M+H$^+$).

Method 2: Example C1 (3 g, 16.4 mmol) and Example D1 (3.46 g, 16.4 mmol) were combined in DMAc (30 mL). KF/Al$_2$O$_3$ (40 wt %, 19 g. 130 mmol) was added and resulting slurry was stirred vigorously at RT for 30 min. The solids were removed by filtration and the filter cake was washed with DMAc. The combined organics were concentrated in vacuo to give a residue which was slurried with water and filtered to provide 6-(5-amino-4-fluoro-2-methylphenyl)-8-methyl-2-(methylthio)pyrido[2,3-d]pyrimidin-7(8H)-one (700 mg, 13% yield).

Method 3: Cs$_2$CO$_3$ (40.0 g, 123 mmol) was added to a solution of Example D1 (10.00 g, 47 mmol, 1 eq) and Example C1 (8.0 g, 44 mmol, 0.92 eq) in DMF (100 mL). The reaction mixture was stirred at RT for 15 hours. Water (800 mL) was added with stirring. The precipitate was filtered and washed with water to provide the crude product. The crude product was slurried in methanol with heating to 50° C. for 20 minutes. The hot suspension was filtered and the collected solids were dried in vacuo to provide 6-(5-amino-4-fluoro-2-methylphenyl)-8-methyl-2-(methylthio)pyrido[2,3-d]pyrimidin-7(8H)-one (11.4 g, 73% yield).

EXAMPLE A11

To a solution of Example C3 (2 g, 11.8 mmol) in DMAc (40 mL) was added Example D1 (2.5 g, 11.8 mmol), followed by KF/Al$_2$O$_3$ (40 wt %, 10 g, 68 mmol). The reaction mixture was stirred at RT for 2 hours. The reaction mixture was filtered and the filtrate was poured into water and the precipitate was collected by filtration and dried to give 3-(5-amino-4-fluoro-2-methylphenyl)-7-chloro-1-methyl-1,6-naphthyridin-2(1H)-one (2.5 g, 69% yield). $^1$H NMR (300 MHz, DMSO-d$_6$): δ 8.72 (s, 1 H), 7.90 (s, 1 H), 7.62 (s, 1 H), 6.88 (d, J=12.3 Hz, 1H), 6.60 (d, 7-6 Hz, 1 H), 4.95 (s, 2 H), 3.60 (s, 3 H), 1.95 (s, 3 H); MS (ESI) m/z: 318.0 [M+H]$^+$.

EXAMPLE A12

Using a procedure analogous to Example A1, Example A3 (4.0 g, 12.6 mmol), mCPBA (3.43 g, 13.9 mmol) and methylamine hydrochloride (1.73 g, 25.3 mmol) were combined to afford 6-(3-amino-4-fluorophenyl)-8-methyl-2-(methylamino)pyrido[2,3-d]pyrimidin-7(8H)-one as a yellow solid (3.00 g, 79% yield). $^1$H NMR (400 MHz, DMSO-d$_6$) δ 8.70 and 8.62 (br s, 1 H), 7.81 (s, 1 H), 7.78 (m, 1 H), 7.11 (dd, J=8.8, 2.0 Hz, 1 H), 7.00 (dd, J=11.6, 8.0 Hz, 1H), 6.77 (m, 1 H), 5.13 (s, 2 H), 3.59 and 3.54 (s, 3 H), 2.91 (d, J=4.4 Hz, 3 H); MS (ESI) m/z: 300.3 [M+H]$^+$.

EXAMPLE A13

A solution of Example A3 (2.5 g, 7.9 mmol) in EtOH (30 ml) was treated with Raney Nickel® (50% slurry in water, 10 g, 85 mmol) and the mixture was refluxed for 3 h. The cooled reaction was filtered and the filtrate was concentrated to give the crude product, which was washed with cold MeOH (2 mL) to give 6-(3-amino-4-fluoro-phenyl)-8-methyl-8H-pyrido[2,3-d]pyrimidin-7-one (1.0 g, 47% yield). $^1$HNMR (300 MHz, DMSO-d$_6$)δ 9.10 (s, H), 9.07 (s, 1 H), 8.06 (s, 1 H), 7.14 (dd, J=8.7, 2.1 Hz, 1 H), 7.05 (dd, J=11.4, 8.4 Hz, 1 H), 6.82 (m, 1 H), 5.22 (s, 2 H), 3.68 (s, 3 H); MS (ESI) m/z: 271.3 (M+H$^+$).

EXAMPLE A14

A solution of Example A10 (500 mg, 1.5 mmol) in dioxane (1 mL) and NH$_3$.H$_2$O (5 mL) was heated to 180° C. in a steel bomb for 3 h. The solvent was removed under reduced pressure, and the residue was purified by silica gel column chromatography to afford 2-amino-6-(5-amino-4-fluoro-2-methylphenyl)-8-methylpyrido[2,3-d]pyrimidin-7(8H)-one (110 mg, 24% yield). $^1$H NMR (300 Hz, DMSO-d$_6$): δ 8.58 (s, 1 H), 7.59 (s, 1 H), 7.25 (s, 2 H), 6.85 (d, J=12.6 Hz, 1 H), 6.57 (d, J=9.3 Hz, 1 H), 4.88 (s, 2 H), 3.53 (s, 3 H), 1.95 (s, 3 H); MS (ESI) m/z: 300.3 [M+H]$^+$.

EXAMPLE A15

By analogy to Example A3,4-amino-2-(methylthio)pyrimidine-5-carbaldehyde (1 g, 5.9 mmol, prepared according to Barvian et. al. J. Med. Chem. (2000), 43, 4606-4616), K$_2$CO$_3$ (2.4 g, 17.4 mmol) and (3-amino-4-fluoro-phenyl)-acid ethyl ester (1.4 g, 7.1 mmol) were combined to provide 6-(3-amino-4-fluorophenyl)-2-(methylthio)pyrido[2,3-d]pyrimidin-7(8H)-one (1.1 g, 56%, yield). $^1$H NMR (300 MHz, DMSO-d$_6$), δ 12.51 (br s, 1 H), 8.87 (s, 1 H), 7.95 (s, 1 H), 7.12 (dd, J=9.0, 2.1 Hz, 1 H), 7.02 (dd, J=11.4, 8.4 Hz, 1 H), 6.80 (m, 1 H), 5.19 (s, 2H), 2.55 (s, 3 H); MS (ESI) m/z: 303.2 [M+H]$^+$.

EXAMPLE A16

A mixture of Example C1 (2.4 g, 13 mmol), Example D2 (2.8 g, 13 mmol) and KF/Al$_2$O$_3$ (40 wt %, 10 g, 69 mmol) in DMAc was stirred at RT for 10 min. The reaction mixture was poured into water and the mixture was extracted with EtOAc (3×). The combined organic extracts were washed with brine, dried (Na$_2$SO$_4$), concentrated in vacuo and chromatographed to give 6-(5-amino-2,4-difluorophenyl)-8-methyl-2-(methylthio)pyrido[2,3-d]pyrimidin-7(8H)-one (2.5 g, 58% yield). $^1$H NMR (300 MHz, DMSO-d$_6$): δ 8.91 (s, 1 H), 7.98 (s, 1 H), 7.13-7.06 (t, J=10.8 Hz, 1 H), 6.86-6.80 (t, J=7.8 Hz, 1 H), 5.10 (s, 2 H), 3.62 (s, 3 H), 2.59 (s, 3 H); MS (ESI) m/z: 335.0 [M+H]$^+$.

EXAMPLE A17

To a solution of Example D3 (3 g, 13 mmol) and Example C1 (2.4 g, 13 mmol) in DMAc (50 mL) was added KF/Al$_2$O$_3$ (40 wt %, 10 g, 69 mmol). The resultant mixture was stirred at RT for 1 hour. The reaction was filtered and the filtrate was concentrated in vacuo and poured into water. The precipitate was collected by filtration and washed with Et$_2$O to provide 6-(5-amino-2-chloro-4-fluoro-phenyl)-8-methyl-2-methyl-sulfanyl-8H-pyrido[2,3-d]pyrimidin-7-one (2.9 g, 64% yield). $^1$H NMR (400 MHz, CDCl$_3$): δ 8.59 (s, 1 H), 7.58 (s, 1 H), 7.09 (d, J=10.4 Hz, 1 H), 6.73 (d, J=9.2 Hz, 1 H), 3.75 (s, 3 H), 3.72 (br s, 2 H), 2.62 (s, 3 H); MS (ESI) m/z: 351.2 [M+H]$^+$.

EXAMPLE A18

A solution of Example C2 (2.0 g, 10.2 mmol), Example D3 (2.3 g, 10.2 mmol) and KF/Al$_2$O$_3$ (40 wt %, 4 g, 27 mmol) in anhydrous DMAc (50 mL) was stirred at RT for 10 min. The reaction mixture was poured into water and extracted with EtOAc (3×100 mL). The combined organic layers were washed with brine, dried (Na$_2$SO$_4$), concentrated in vacuo and purified by silica gel chromatography to give 6-(5-amino-2-chloro-4-fluorophenyl)-8-ethyl-2-(methylamino)pyrido[2,3-d]pyrimidin-7(8H)-one (2.5 g, 67.6% yield). $^1$H NMR (300 MHz, DMSO-d$_6$), δ 8.89 (s, 1 H), 7.91 (s, 1 H), 7.23 (d, J=11.1 Hz, 1 H), 6.75 (d, J=9.3 Hz, 1 H), 5.40 (s, 2 H), 4.35 (q, J=6.6 Hz, 2 H), 2.59 (s, 3 H), 1.22 (t, J=6.6 Hz, 3 H); MS (ESI) m/z: 365.2 [M+H]$^+$.

EXAMPLE A19

Example C4 (1 g, 4.2 mmol) in DMAc (10 mL), ethyl (3-amino-4-fluoro-phenyl)-acetate (0.83 g, 4.2 mmol) and KF/Al$_2$O$_3$ (40 wt %, 2 g, 34 mmol) in DMAc (10 mL) were combined by the procedure of Example A17 to provide 6(3-amino-4-fluorophenyl)-8-cyclopentyl-2-(methylthio)pyrido[2,3-d]pyrimidin-7(8H)-one (1 g, 64% yield). $^1$H NMR (400 MHz, CDCl$_3$): δ 8.63 (s, 1 H), 7.60 (s, 1 H), 7.13 (dd, J=8.4, 2.0 Hz, 1 H), 7.03 (dd, J=10.8, 8.4 Hz, 1 H), 6.92 (m, 1 H), 6.05 (m, 1 H), 2.64 (s, 3 H), 2.41-2.32 (m, 2 H), 2.13-2.05 (m, 2 H), 1.95-1.87 (m, 2 H), 1.72-1.65 (m, 2 H); MS (ESI) m/z: 371.0 [M+H]$^+$.

EXAMPLE A20

To a solution of Example A10 (1.30 g, 3.93 mmol) in ethanol (20 mL) was placed Raney Nickel® (50% slurry in water, 5.08 g, 43.3 mmol). The reaction mixture was refluxed overnight. The mixture was filtered through Celite and washed with EtOH. The combined filtrates were evaporated. The residue was treated with EtOAc and the solid was filtered to obtain 6-(5-amino-4-fluoro-2-methylphenyl)-8-methylpyrido[2,3-d]pyrimidin-7(8H)-one (0.65 g, 58% yield). $^1$H NMR (400 MHz, DMSO-d$_6$): δ 9.10 (s, 1H), 9.08 (s, 1H), 7.91 (s, 1H), 6.90 (d, J=12.8 Hz, 1H), 6.61 (d, J=9.2 Hz, 1H), 4.00 (bis, 2H), 3.67 (s, 3H), 1.97 (s, 3H); MS (ESI) m/z: 285.0 (M+H$^+$).

EXAMPLE A21

Example C4 (2 g, 8.4 mmol) and Example D1 (1.78 g, 8.4 mmol) were combined by the procedure of Example A19 to give 6-(5-amino-4-fluoro-2-methylphenyl)-8-cyclopentyl-2-(methylthio)pyrido[2,3-d]pyrimidin-7(8H)-one (0.9 g, 27% yield). $^1$H NMR (400 MHz, CDCl$_3$): δ 8.53 (s, 1 H), 7.39 (s, 1 H), 6.82 (d, J=11.6 Hz, 1 H), 6.59 (d, J=8.8 Hz, 1 H), 5.98 (m, 1 H), 2.57 (s, 3 H), 2.26 (m, 2 H), 2.03-1.97 (m, 5 H), 1.85-1.83 (m, 2 H), 1.62-1.60 (m, 2 H); MS (ESI) m/z: 385.0 [M+H]$^+$.

EXAMPLE A22

Example A25 (2.0 g, 6.3 mmol) in methanol (50 mL) was hydrogenated (45 psi) overnight at 50° C. in the presence of 10% Pd(OH)$_2$ (Pearlman's catalyst, 0.5 g, 0.35 mmol). The reaction mixture was filtered, concentrated under reduced pressure and purified by silica gel column chromatography to provide 3-(3-amino-4-fluorophenyl)-1-ethyl-1,6-naphthyridin-2(1H)-one (0.81 g, 45% yield). $^1$H NMR (400 MHz, DMSO-d$_6$): δ 8.91 (s, 1 H), 8.54 (d, J=6.0 Hz, 1H), 8.06 (s, 1 H), 7.51 (d, J=6.4 Hz, 1 H), 7.14 (dd, J=8.8, 2.0 Hz, 1 H), 7.02 (dd, J=11.6, 8.4 Hz, 1 H), 6.81 (m, 1 H), 5.18 (s, 2 H), 4.27 (q, 7.2 Hz, 2 H), 1.21 (t, J=7.2 Hz, 3 H), MS (ESI) m/z (M+H$^+$): 284.2.

EXAMPLE A23

A steel bomb was charged with Example A25 (2.5 g, 7.8 mmol) and 4-methoxy-benzylamine (20 mL). The bomb was sealed and the mixture was heated to 180° C. for 6 hours. The cooled reaction mixture was poured into a solution of AcOH (15 mL) in ice-water (100 mL) and then extracted with EtOAc (3×100 mL). The combined extracts were washed with brine (3×50 mL), dried (MgSO$_4$) and concentrated in vacuo. The crude product was purified by silica gel column chromatography to provide 7-(4-methoxybenzylamino)-3-(3-amino-4-fluorophenyl)-1-ethyl-1,6-naphthyridin-2(1H)-one (2.8 g, 85% yield). $^1$H NMR (400 MHz, DMSO-d$_6$): δ 8.39 (s, 1 H), 7.76 (s, J=6.0 Hz, 1 H), 7.45 (br s, 1 H), 7.28 (d, J=7.6 Hz, 2 H), 7.07 (d, J=8.0 Hz, 1H), 6.96 (m, 1 H), 6.86 (d, J=8.4 Hz, 2 H), 6.74 (m, 1 H), 6.27 (s, 1 H), 5.08 (s, 2 H), 4.46 (d, J= 5.6 Hz, 2 H), 4.08 (q, J=1.2, 14.0 Hz, 2 H), 3.69 (s, 3 H), 1.12 (t, J=7.2 Hz, 3 H), MS (ESI) m/z 419.3 (M+H$^+$).

To a solution of TFA in CH$_2$Cl$_2$ (10%, 50 mL) was added 3-(3-amino-4-fluoro-phenyl)-1-ethyl-7-(4-methoxy-benzylamino)-1H-[1,6]naphthyridin-2-one (2.0 g, 4.78 mmol). The resulting mixture was stirred at 50° C. overnight. The reaction mixture was poured saturated aq NaHCO$_3$ solution (100 mL), and was extracted with CH$_2$Cl$_2$ (3×75 mL). The combined organic layer was dried (MgSO$_4$) and concentrated in vacuo. The residue was purified by silica gel column chromatography to give 7-amino-3-(3-amino-4-fluorophenyl)-1-ethyl-1,6-naphthyridin-2(1H)-one (0.45 g, 32% yield). $^1$H NMR (300 MHz, DMSO-d$_6$): δ 8.35 (s, 1 H), 7.76 (s, 1 H), 7.09 (dd, J=9.0, 2.1 Hz, 1 H), 6.97 (dd, J=11.4, 8.4 Hz, 1 H), 6.75 (m, 1 H), 6.44 (s, 2 H), 6.31 (s, 1 H), 5.09 (s, 2 H), 4.08 (q, J=7.2 Hz, 2 H), 1.20 (t, J=7.2 Hz, 3 H), MS (ESI) m/z (M+H$^+$): 299.3.

EXAMPLE A24

Using the 2-step procedure of Example A23, Example A25 (0.85 g, 2.7 mmol) and 4-methoxybenzylmethylamine (10 mL) were combined to provide 3-(3-amino-4-fluorophenyl)-1-ethyl-7-(methylamino)-1,6-naphthyridin-2(1H)-one (0.45 g, 32% yield, 2 steps). $^1$H NMR (300 MHz, DMSO-d$_6$): δ8.40 (s, 1 H), 7.77 (s, 1 H), 7.11 (d, J=9.0 Hz, 1 H), 6.95 (m, 2 H), 6.76 (m, 1 H), 6.19 (s, 1 H), 5.09 (s, 2 H), 4.14 (m, 2 H), 2.85 (br s, 3 H), 1.20 (t, J=6.0, 3 H); MS (ESI) m/z (M+H$^+$): 313.3.

EXAMPLE A25

A solution of Example C5 (6.0 g, 0.033 mol), ethyl 2-(3-amino-4-fluorophenyl)acetate (6.4 g, 0.033 mol) and K$_2$CO$_3$ (9.17 g, 0.066 mol) in DMF (100 mL) was heated to 80° C. overnight. The reaction mixture was poured into the water and extracted with EtOAc (3×200 mL). The combined extracts were washed with saturated brine (3×100 mL), dried (MgSO$_4$), concentrated in vacuo and purified by chromatography to provide 3-(3-amino-4-fluorophenyl)-7-chloro-1-ethyl-1,6-naphthyridin-2(1H)-one (7.0 g, 67.9% yield). $^1$H NMR (400 MHz, DMSO-d$_6$): δ 8.75 (s, 1 H), 8.07 (s, 1 H), 7.67 (s, 1 H), 7.13 (dd, J=8.8, 2.0 Hz, 1 H), 7.02 (dd, J=11.6, 8.4 Hz, 1 H), 6.80 (m, 1 H), 5.20 (s, 2 H), 4.25 (q, J=6.8 Hz, 2 H), 1.19 (t, J=6.8 Hz, 3 H; MS (ESI) m/z: 318.2 [M+H]$^+$.

EXAMPLE A26

Example A11 (1.36 g, 4.28 mmol, 1.00 eq), 4-methoxy-N-methylbenzylamine (0.971 g, 6.42 mmol, 1.50 eq) and DBU (0.960 ml, 6.42 mmol, 1.50 eq) were combined in NMP (20 ml) and stirred with heating at 180° C. under Ar overnight. The completed reaction was cooled to RT and poured onto H$_2$O (200 ml). Solids immediately separated which were collected by filtration and rinsed very well with H$_2$O. The solids were dried on the filter to dampness and then dissolved in EtOAc. The solution was dried (MgSO$_4$), filtered and evaporated to afford 7-((4-methoxybenzyl)(methyl)amino)-3-(5-amino-4-fluoro-2-methylphenyl)-1-methyl-1,6-naphthyridin-2(1H)-one (1.86 g, 100% yield) as a brittle brown foam which was used as is in the next reaction. $^1$H NMR (400 MHz, DMSO-d$_6$): δ 8.45 (s, 1H), 7.63 (s, 1H), 7.16 (d, J=8.8 Hz, 2H), 6.85 (d, J=8.8 Hz, 2H), 6.86-6.82 (m, 1H), 6.57 (d, J=9.6 Hz, 1H), 6.29 (s, 1H), 4.88 (brs, 2H), 4.85 (s, 2H), 3.69 (s, 3H), 3.52 (s, 3H), 3.07 (s, 3H), 1.94 (s, 3H); MS (ESI) m/z: 433.3 (M+H$^+$).

7-((4-methoxybenzyl)(methyl)amino)-3-(5-amino-4-fluoro-2-methylphenyl)-1-methyl-1, 6-naphthyridin-2(1H)-one (1.86 g, 4.3 mmol, 1.0 eq) and CF$_3$CO$_2$H (9.5 ml, 13.8 g, 121 mmol, 28 eq) were combined and stirred at RT overnight. The completed reaction was treated slowly with 2M Na$_2$CO$_3$ until the mixture was just faintly basic. The resulting suspension was stirred at RT for 1 h. The solids were collected by filtration, washed thoroughly with H$_2$O, dried partially in the air and then under high vacuum at 65° C. The crude product was purified by flash column chromatography (100% EtOAc to 25% THF/EtOAc) to afford 3-(5-amino-4-fluoro-2-methylphenyl)-1-methyl-7-(methylamino)-1,6-naphthyridin-2 (1H)-one (0.86 g, 64% yield) as an off-white solid. $^1$H NMR (400 MHz, DMSO-d$_6$): δ 8.35 (s, 1H), 7.58 (s, 1H), 6.99 (q, J=4.8 Hz, 1H), 6.56 (d, J=12.0 Hz, 1H), 6.56 (d, J=9.2 Hz, 1H), 6.15 (s, 1H), 4.87 (brs, 2H), 3.48 (s, 3H), 2.84 (d, J=5.2 Hz, 3H), 1.94 (s, 3H); MS (ESI) m/z: 313.2 (M+H$^+$).

EXAMPLE A27

A solution of Example A11 (2.2 g, 6.9 mmol) in 4-methoxybenzylamine (30 ml) was refluxed at 140° C. for two hours. After cooling to RT, the reaction mixture was poured into 20% aq. solution of acetic acid and stirred for 30 min. The mixture was filtered to provide 7-(4-methoxybenzylamino)-3-(5-amino-4-fluoro-2-methylphenyl)-1-methyl-1,6-naphthyridin-2(1H)-one (2.3 g, 79% yield). $^1$H NMR (300 MHz, DMSO-d$_6$): δ 8.81 (s, 1 H), 7.99 (s, 1 H), 7.81-7.78 (d, J=9 Hz, 2 H), 7.35-7.32 (d, J=9 Hz, 2 H), 7.26 (d, J=12 Hz, 1 H), 7.14 (d, J=9 Hz, 1 H), 6.79 (s, 1 H), 5.05-5.02 (d, J=9 Hz, 2 H), 4.86 (m, 1H), 4.20 (s, 3 H), 3.85 (s, 3 H), 2.52 (s, 3H); MS (ESI) m/z: 419.1[M+H]$^+$.

Trifluoroacetic acid (2 mL, 26.9 mmol) was added to a solution of 7-(4-methoxybenzylamino)-3-(5-amino-4-fluoro-2-methylphenyl)-1-methyl-1,6-naphthyridin-2(1H)-one (0.8 g, 1.9 mmol) in DCM (10 mL) and the reaction mixture was refluxed at 50° C. for 2 hour. After cooling to RT, the reaction mixture was washed with water and the combined aqueous layers were neutralized with saturated aq NaHCO$_3$ to pH 7-8. Then the aqueous layer was extracted with EtOAc (3×50 mL), the extracts were dried (Na$_2$SO$_4$) and concentrated to give 7-amino-3-(5-amino-4-fluoro-2-methylphenyl)-1-methyl-1,6-naphthyridin-2(1H)-one (0.3 g, 53% yield). $^1$H NMR (300 MHz, DMSO-d$_6$): δ 8.29 (s, 1H), 7.57 (s, 1 H), 6.83 (d, J=12.4 Hz, 1 H), 6.56 (d, J=9.6 Hz, 1 H), 6.48 (s, 2 H), 6.24 (s, 1 H), 4.87 (s, 2 H), 3.45 (s, 3 H), 1.94 (s, 3 H); MS (ESI) m/z: 299.0 [M+H]$^+$.

EXAMPLE A28

Example D3 (3 g, 12.9 mmol), Example C3 (2.2 g, 12.9 mmol) and KF/Al$_2$O$_3$ (40%, 6 g, 41 mmol) were combined in DMAc (40 mL) and the resultant mixture was stirred at RT for about 1 hour. The reaction mixture was filtered and the filtrate was concentrated in vacuo. The residue was washed with Et$_2$O to give 3-(5-amino-2-chloro-4-fluorophenyl)-7-chloro-1-methyl-1,6-naphthyridin-2(1H)-one (2.6 g, 59.6% yield). $^1$H NMR (300 MHz, DMSO-d$_6$): δ 8.74 (s, 1 H), 8.00 (s, 1 H), 7.63 (s, 1 H), 7.23 (d, J=11.2 Hz, 1 H), 6.75 (d, J=9.2 Hz, 1H), 5.40 (s, 2 H), 3.60 (s, 3 H); MS (ESI) m/z: 338.1 [M+H]$^+$.

A mixture of 3-(5-amino-2-chloro-4-fluorophenyl)-7-chloro-1-methyl-1,6-naphthyridin-2(1H)-one (2.5 g, 7.4 mmol) and 4-methoxy-N-methylbenzylamine (4 mL) was heated to 180° C. under N$_2$ for about 3 hour. After cooling, the reaction mixture was diluted with Et$_2$O. The precipitate was filtered, washed with water, and dried to give 7-((4-methoxybenzyl)(methyl)amino)-3-(5-amino-2-chloro-4-fluorophenyl)-1-methyl-1,6-naphthyridin-2(1H)-one (3 g, 89% yield). $^1$H NMR (400 MHz, DMSO-d$_6$): δ 8.47 (s, 1 H), 7.77 (s, 1 H) 7.22 (m, 2 H), 7.17 (d, J=8.0 Hz, 2 H), 6.86 (d, J=8.4 Hz, 2 H), 5.86 (d, J=9.6 Hz, 1H), 6.30 (s, 1 H), 5.32 (s, 2 H) 4.87 (s, 1 H), 3.72 (s, 3 H), 3.52 (s, 3 H), 3.09 (s, 3 H); MS (ESI) m/z: 453.2[M+H]$^+$.

A solution of 7-((4-methoxybenzyl)(methyl)amino)-3-(5-amino-2-chloro-4-fluorophenyl)-1-methyl-1,6-naphthyridin-2(1H)-one (3 g, 6.6 mmol) in CH$_2$Cl$_2$ (50 mL) was treated with TFA (20 mL) and the mixture was heated to reflux overnight. The mixture was concentrated under reduced pressure, the residue was dissolved in 10% aq. of HCl (50 mL) and the aqueous layer was washed with EtOAc. The aqueous layer was neutralized with NaHCO$_3$ aq. solution to pH 8, and then extracted with EtOAc (3×50 mL). The combined organics were washed with brine, dried (Na$_2$SO$_4$) and concentrated in vacuo to give 3-(5-amino-2-chloro-4-fluorophenyl)-1-methyl-7-(methylamino)-1,6-naphthyridin-2(1H)-one (1.6 g, 72% yield) $^1$H NMR (300 MHz, DMSO-d$_6$): δ 8.36 (s, 1 H), 7.66 (s, 1 H), 7.17 (d, J=10.8 Hz, 1 H), 7.05 (m, 1H), 6.71 (d, J=9.6 Hz, 1 H), 6.15 (s, 1 H), 5.30 (s, 2 H), 3.47 (s, 3 H), 3.42 (s, 1 H), 2.84 (d, J=4.4 Hz, 3 H); MS (ESI) m/z: 333.1 [M+H]$^+$

EXAMPLE A29

Example C3 (2 g, 9.3 mmol), Example D2 (1.6 g, 9.3 mmol) and KF/Al$_2$O$_3$ (40%, 5 g, 34.4 mmol) were combined in DMAc and stirred for 10 min. The reaction mixture was poured into water and extracted with ethyl acetate. The combined organic layers were washed with brine, dried (Na$_2$SO$_4$) and concentrated in vacuo. The residue was purified by chromatography to give 3-(5-amino-2,4-difluorophenyl)-7-chloro-1-methyl-1,6-naphthyridin-2(1H)-one (2 g, 68% yield). $^1$H NMR (300 MHz, DMSO-d$_6$): δ 8.41 (s, 1 H), 7.73 (s, 1 H), 7.06-7.03 (m, 1 H), 6.81-6.75 (m, 1 H), 6.15 (s, 1 H), 4.98 (s, 2 H), 3.48 (s, 3 H); MS (ESI) m/z: 322.7 [M+H]$^+$.

3-(5-Amino-2,4-difluorophenyl)-7-chloro-1-methyl-1,6-naphthyridin-2(1H)-one (2.4 g, 7.5 mmol) and 4-methoxy-N-methylbenzyl amine (10 mL) were combined in a sealed vessel and heated to 200° C. overnight. The volatiles were removed in vacuo and the residue was purified by column chromatography to give 7-((4-methoxybenzyl)(methyl)amino)-3-(5-amino-2,4-difluorophenyl)-1-methyl-1,6-naphthyridin-2(1H)-one (3 g, 91% yield), which was used in the next step without further purification.

To a solution of 7-((4-methoxybenzyl)(methyl)amino)-3-(5-amino-2,4-difluorophenyl)-1-methyl-1,6-naphthyridin-2 (1H)-one (3 g, 6.8 mmol) in DCM (100 mL) was added CF$_3$COOH (20 mL) and the resulting mixture was stirred at 25° C. for 6 h. Water was added and the mixture was extracted with water. The combined aqueous layers were neutralized with NH$_3$H$_2$O to pH 7. The precipitate was collected by filtration and dried to give 3-(5-amino-2,4-difluorophenyl)-1-methyl-7-(methylamino)-1,6-naphthyridin-2(1H)-one (661 mg, 30% yield). $^1$H NMR (300 MHz, DMSO-d$_6$): δ 8.39 (s, 1 H), 7.78 (s, 1 H), 7.08-6.93 (m, 2 H), 6.80 (dd, J=10.2, 8.1 Hz, 1H), 6.16 (s, 1 H), 5.00 (s, 2 H), 3.50 (s, 3 H), 2.84 (d, J=4.8 Hz, 3 H); MS (ESI) m/z: 317.0[M+H]$^+$.

EXAMPLE A30

In a manner analogous to that described for the preparation of Example A26, Example A34 (1.61 g, 4.85 mmol) was converted to 3-(5-amino-4-fluoro-2-methylphenyl)-1-ethyl-7-(methylamino)-1,6-naphthyridin-2(1H)-one (1.16 g, 73% yield for two steps). $^1$H NMR (400 MHz, DMSO-d$_4$): δ 8.36 (s, 1H), 7.58 (s, 1H), 6.94-6.92 (bun, 1H), 6.83 (d, J=12.0 Hz, 1H), 6.57 (d, J=9.6 Hz, 1H), 4.87 (brs, 2H), 4.12 (q, J=6.8 Hz, 2H), 2.84 (d, J=4.8 Hz, 3H), 1.94 (s, 3H), 1.185 (t, J=7.2 Hz, 3H); MS (ESI) m/z: 327.2(M+H).

EXAMPLE A31

Example A34 (2.5 g, 7.5 mmol) and 4-methoxybenzylamine (30 ml) were combined by the 2-step procedure of Example A27 to provide 7-amino-3-(5-amino-4-fluoro-2-methylphenyl)-1-ethyl-1,6-naphthyridin-2(1H)-one (0.9 g, 46% yield, 2 steps).

$^1$H-NMR (300 MHz, DMSO-d$_6$): δ 8.30 (s, 1H), 7.56 (s, 1 H), 6.83 (d, 0.7=12.3 Hz, 1 H), 6.57 (d, J=9.6 Hz, 1 H), 6.40 (s, 2 H), 6.32 (s, 1 H), 4.85 (s, 2 H), 4.07 (q, J=6.9 Hz, 2 H), 1.94 (s, 3H), 1.19 (t, J=6.9 Hz, 3 H); MS (ESI) m/z: 313.3 [M+H]$^+$.

EXAMPLE A32

Example C5 (3.5 g, 19 mmol), Example D3 (4.4 g, 19 mmol) and KF/Al$_2$O$_3$ (40 wt %, 10 g, 69 mmol) were combined by the procedure of Example A17 to give 3-(5-amino-2-chloro-4-fluorophenyl)-7-chloro-1-ethyl-1,6-naphthyridin-2(1H)-one (4 g, 60% yield). $^1$H NMR (400 MHz, DMSO-d$_6$): δ 8.75 (s, 1 H), 8.01 (s, 1 H), 7.72 (s, 1 H), 7.24 (d, J=10.8

Hz, 1 H), 6.76 (d, J=9.2 Hz, 1 H), 5.40 (s, 2 H), 4.26-4.24 (m, 2 H), 1.18 (t, J=6.8 Hz, 3 H); MS (ESI) m/z: 352.1 [M+H]+.

EXAMPLE A33

Using the procedure of Example A28, steps 2 and 3, Example A32 (3 g, 8.5 mmol) was converted to 3-(5-amino-2-chloro-4-fluorophenyl)-1-ethyl-7-(methylamino)-1,6-naphthyridin-2(1H)-one (1 g, 32% yield over two steps). ¹HNMR (400 MHz, DMSO-$d_6$): δ 8.46 (s, 1 H), 7.75 (s, 1 H), 7.1 (d, J=11.2 Hz, 1 H), 6.73 (d, J=9.6 Hz, 1 H), 6.43 (s, 1 H), 4.95 (br s, 1 H), 4.14 (m, 2 H), 2.92 (s, 3 H), 1.14 (t, J=6.8 Hz, 3 H); MS (ESI) m/z: 347.2 [M+H]+.

EXAMPLE A34

Example D1 (1.32 g, 6.25 mmol, 1.00 eq), Example C5 (1.15 g, 6.25 mmol, 1.00 eq) and KF/$Al_2O_3$ (40.00 wt %, 9.08 g, 62.5 mmol, 10.00 eq) were combined in DMAc (35 ml) and sonicated for 2 h. The completed reaction was filtered through Celite, rinsing forward with EtOAc (3×35 ml). The combined filtrates were washed with $H_2O$ (3×50-75 ml). The combined aqueous layers were extracted with EtOAc (1×). The combined organics were washed with brine (2×), dried ($MgSO_4$), filtered and evaporated. The crude product was purified by flash column chromatography (5% EtOAc/hexanes to 100% EtOAc) to afford 3-(5-amino-4-fluoro-2-methylphenyl)-7-chloro-1-ethyl-1,6-naphthyridin-2(1H)-one (1.61 g, 78% yield) as a brittle foam. MS (ESI) m/z: 332.0 (M+H), 334.0 (M+2+H)+.

EXAMPLE A35

A solution of ethyl 4,6-dichloronicotinate (16 g, 73 mmol), aniline (8.2 g, 88 mmol) and conc. HCl (0.5 mL) in EtOH (100 mL) was heated at reflux overnight. The solvent was removed under reduced pressure. Water was added and the solution was basified to pH 8 and extracted with EtOAc. The combined extracts were washed with brine, dried ($MgSO_4$), and concentrated in vacuo. The residue was purified by chromatography to give ethyl 6-chloro-4-(phenylamino)nicotinate (10 g, 50% yield). ¹H NMR (40 MHz, DMSO-$d_6$): δ 9.73 (s, 1 H), 8.67 (s, 1 H), 7.50-7.46 (m, 2 H), 7.36-7.31 (m, 3 H), 6.78 (s, 1 H), 4.37 (q, J=7.2 Hz, 2 H), 1.35 (t, J=7.2 Hz, 3 H).

A solution of ethyl 6-chloro-4-(phenylamino)nicotinate (19 g, 89 mmol) in anhydrous THF (40 mL) was added dropwise to a 0° C. suspension of $LiAlH_4$ (8.5 g, 223 mmol) in anhydrous THF (80 mL). After complete addition, the reaction mixture was stirred at RT for 3 h. The mixture was quenched by the addition of 10% aq NaOH (8.5 mL) and water (8.5 mL). The solids were removed by filtration and the organic phase was concentrated in vacuo to provide (6-chloro-4-(phenylamino)pyridin-3-yl)methanol (12 g, 80% yield). ¹H NMR (400 MHz, DMSO-$d_6$): δ 8.09 (s, 1 H), 8.08 (s, 1 H), 7.39-7.10 (m, 5 H), 6.73 (s, 1 H), 5.37 (s, 1 H), 4.52 (s, 2 H).

$MnO_2$ (39 g, 448 mmol) was added to a solution of (6-chloro-4-phenylamino-pyridin-3-yl)-methanol (13 g, 56 mmol) in $CH_2Cl_2$ (100 ml) and the mixture was stirred at RT overnight. The solids was removed by filtration and the filtrate was concentrated to give 6-chloro-4-(phenylamino) nicotinaldehyde (11 g, 86% yield). ¹H-NMR (400 MHz, DMSO-$d_6$): δ 10.18 (s, 1H), 9.99 (s, 1 H), 8.62 (s, 1 H), 7.49-7.31 (m, 5 H), 6.80 (s, 1 H).

A mixture of 6-Chloro-4-(phenylamino)nicotinaldehyde (3 g, 13 mmol), ethyl 2-(3-amino-4-fluorophenyl)acetate (2.6 g, 13 mmol), and KF/$Al_2O_3$ (40 wt %, 10 g, 69 mmol) in DMAc (30 mL) was stirred at RT for 2 hours. The solids were removed by filtration and the filtrate was concentrated in vacuo. Recrystallization (EtOAc) provided 3-(3-amino-4-fluorophenyl)-7-chloro-1-phenyl-1,6-naphthyridin-2(1H)-one (2.6 g, 55% yield). ¹H NMR (400 MHz, DMSO-$d_6$): δ 8.81 (s, 1 H), 8.20 (s, 1 H), 7.62-7.56 (m, 3 H), 7.40 (d, J=7.2 Hz, 2 H), 7.13 (d, J=7.6 Hz, 1 H), 7.02 (t, J=10.0 Hz, 1 H), 6.82 (m, 1 H), 6.26 (s, 1 H), 5.19 (s, 2 H); MS (ESI) m/z: 366.2 [M+H]+.

EXAMPLE A36

A suspension of Example A35 (2.5 g, 7 mmol) in 4-methoxybenzylmethylamine (5 mL) was heated at 160° C. for 3 h. The reaction mixture was cooled to RT and diluted with ether. The resultant white precipitate was collected by filtration and dried to obtained 7-((4-methoxybenzyl)(methyl)amino)3-(3-amino-4-fluorophenyl)-1-phenyl-1,6-naphthyridin-2(1H)-one (3 g, 77%), which was used in the next step without further purification. A suspension of 7-((4-methoxybenzyl) (methyl)amino)-3-(3-amino-4-fluorophenyl)-1-phenyl-1,6-naphthyridin-2(1H)-one (3.0 g, 6 mmol) in mixture of $CF_3CO_2H$ and $CH_2Cl_2$ (3:7, 30 mL) was heated at reflux overnight. Then the solvent was removed under reduced pressure and the residue was recrystallized (EtOAc-petroleum ether) to give 3-(3-amino-4-fluorophenyl)-7-(methylamino)-1-phenyl-1,6-naphthyridin-2(1H)-one (1 g, 45% yield). ¹H NMR (400 MHz, DMSO-$d_6$): δ 8.43 (s, 1 H), 7.88 (s, 1 h), 7.60-7.50 (m, 3 H), 7.31-7.29 (m, 2 H), 7.10-6.75 (m, 4H), 5.26 (s, 1 H), 5.08 (s, 2 H), 2.63 (br s, 3 H); MS (ESI) m/z: 361.3 [M+H]+.

EXAMPLE A37

A mixture of Example A60 (1.1 g, 3.7 mmol) and 28% ammonium hydroxide (6.0 mL) in a sealed-vessel was heated at 160° C. for 2 h. After cooling to RT, the reaction mixture was filtered and the solid was washed with cold EtOAc to provide 2-amino-6-(3-aminophenyl)-8-methylpyrido[2,3-d] pyrimidin-7(8H)-one (440 mg, 45% yield). ¹H NMR (300 MHz, DMSO-$d_4$): 8.61 (s, 1 H), 7.77 (s, 1 H), 7.24 (br s, 2 H), 7.02 (t, J=8.0 Hz, 1 H), 6.84 (s, 1 H), 6.73 (d, J=7.8 Hz, 1 H), 6.51 (d, 8.0 Hz, 1 H), 5.05 (br s, 2 H), 3.54 (s, 3 H). MS (ESI) m/z: 268.1 (M+H+).

EXAMPLE A38

Using a procedure analogous to Example A28, Example A55 was converted to 3-(3-amino-4-fluorophenyl)-1-methyl-7-(methylamino)-1,6-naphthyridin-2(1H)-one (1.6 g, 59% yield). ¹HNMR (300 MHz, DMSO-$d_6$): δ 8.39 (s, 1 H), 7.78 (s, 1 H), 7.07 (d, J=8.7 Hz, 1 H), 7.05-6.93 (m, 2 H), 6.75 (m, 1 H), 6.13 (s, 1 H), 5.10 (s, 2 H), 3.50 (s, 3 H), 2.84 (d, J=4.8 Hz, 3 H); MS (ESI) m/z: 299.2(M+H+).

EXAMPLE A39

Using a procedure analogous to Example A1, Example A10 (1.500 g, 4.54 mmol, 1.0 eq), 3-chloroperbenzoic acid (70 wt %, 269 mg, 1.090 mmol, 1.20 eq) and 2.0M $MeNH_2$ in THF (11.400 ml, 22.80 mmol, 5.00 eq) were combined to afford crude 6-(5-amino-4-fluoro-2-methylphenyl)-8-methyl-2-(methylamino)pyrido[2,3-d]pyrimidin-7(8H)-one (1.56 g, 105% yield) as an orange foam which was used as is. MS (ESI) m/z: 314.3 (M+H).

EXAMPLE A40

In dimethylacetamide (30 mL) was placed 4-aminonicotinaldehyde (1.50 g, 12.3 mmol) and ethyl 2-(3-amino-4-fluorophenyl)acetate (2.42 g, 12.3 mmol). To this was added 40% KF/alumina (8.92 g, 61.4 mmol) and the mixture was stirred at RT for 48 hrs. The mixture was filtered through a Celite pad and the pad was washed with ethyl acetate (2×30 mL). The filtrate was diluted with water (100 mL) and the biphasic mixture was set aside to precipitate. The solid was collected by filtration, washed with water (2×25 mL) and dried on high vac line at 65° C. for 3 hrs in the abderhalden and identified as 3-(3-amino-4-fluorophenyl)-1,6-naphthyridin-2(1H)-one (1.55 g, 49% yield). Used as is. MS (ESI) m/z: 256.0 (M+H$^+$).

EXAMPLE A41

Example C2 (5.0 g, 25 mmol), Example D1 (5.8 g, 27 mmol) and $Cs_2CO_3$ (22.7 g, 70 mmol) were combined DMF (150 mL) and stirred at 60° C. overnight. The resulting mixture was concentrated under reduced pressure and the residue was washed with ethyl ether to give 6-(5-amino-4-fluoro-2-methylphenyl)-8-ethyl-2-(methylthio)pyrido[2,3-d]pyrimidin-7(8H)-one (3.59 g, 42% yield). $^1$H NMR (400 MHz, DMSO-$d_6$): δ 8.88 (s, 1 H), 7.82 (s, 1 H), 6.89 (d, J=12.4 Hz, 1 H), 6.61 (d, J=9.6 Hz, 1 H), 4.96 (s, 2 H), 4.38 (q, J=6.8 Hz, 2 H), 2.61 (s, 3 H), 1.96 (s, 3 H), 1.24 (t, J=6.8 Hz, 3 H); MS (ESI) m/z: 345.2 [M+H]$^+$.

EXAMPLE A42

Example C6 (4.2 g, 19.9 mmol), Example D1 (4.2 g, 20 mmol), and $Cs_2CO_3$ (16.86 g, 51.74 mmol) were combined in DMF (80 mL) and heated at reflux overnight. The reaction mixture was poured into water and the mixture was extracted with ethyl acetate. The combined extracts were washed with brine, dried ($Na_2SO_4$), and concentrated in vacuo. Purification by chromatography on silica gel gave 6-(5-amino-4-fluoro-2-methylphenyl)-8-isopropyl-2-(methylthio)pyrido[2,3-d]pyrimidin-7(8H)-one (1.47 g, 20% yield). $^1$H NMR (400 MHz, DMSO-$d_6$): δ 8.83 (s, 1 H), 7.75 (s, 1 H), 6.86 (d, J=12.4 Hz, 1 H), 6.58 (d, J=9.2 Hz, 1H), 5.71 (m, 1 H), 4.92 (s, 2 H), 2.58 (s, 3 H), 1.93 (s, 3 H), 1.53 (d, J=7.2 Hz, 6 H); MS (ESI) m/z: 359.0 [M+H]$^+$.

EXAMPLE A43

Using a procedure analogous to Example A1, Example A10 (0.200 g, 0.605 mmol) and N',N'-dimethylpropane-1,3-diamine (0.378 ml, 3.03 mmol) were combined to afford 6-(5-amino-4-fluoro-2-methylphenyl)-2-(3-(dimethylamino)propylamino)-8-methylpyrido[2,3-d]pyrimidin-7(8H)-one (0.076 g, 33% yield) as yellow solid. MS (ESI) m/z: 385.2 (M+H$^+$)

EXAMPLE A44

In methylene chloride (50 mL) was placed 2-methyl-5-nitrobenzoic acid (3.00 g, 16.6 mmol) and 1 microdrop of dimethylformamide. The solution was cooled to 0° C. and to this was added oxalyl chloride (3.15 g, 24.8 mmol). After 15 minutes the mixture was allowed to warm to RT and stirred a further 2 hours. The mixture evaporated at reduced pressure. This residue was dissolved in THF (60 mL) and cooled to 0° C. To this was added the 2.00N TMS-diazomethane (18.6 mL, 37.3 mmol) and the mixture stirred at 0° C. for 5 hrs. The solution was evaporated at reduced pressure and the new residue was treated with benzyl alcohol (15 mL) and 2,4,6-collidine (10 mL) and warmed to 180° C. for 15 min. After cooling to RT and diluting with ethyl acetate (100 mL), the resulting solution was washed successively with water (2×100 mL), 5% citric acid (100 mL, till pH of aqueous phase is acidic), water (100 mL) and brine (100 mL). The solvent was removed at reduced pressure and the resultant oil was dried on the high vacuum line at 65° C. to remove most excess benzyl alcohol. The oil was purified by chromatography (Biotage Si-40 column, 10-40% ethyl acetate/Hex—1398 mL) to give benzyl 2-(2-methyl-5-nitrophenyl)acetate as an oil (2.465 g, 52% yield) which was used as is.

In a solution of THF:ethanol (1:1, 100 mL) was placed the crude benzyl 2-(2-methyl-5-nitrophenyl)acetate (2.46 g, 8.62 mmol) and ammonium chloride (4.61 g, 86.2 mmol). To this was added zinc dust (5.64 g, 86.2 mmol) and the resulting slurry was stirred at RT for 4 hrs. The slurry was filtered through Celite and washed with ethanol (2×50 mL). The combined filtrates were evaporated at reduced pressure to give an oily mass. This was dissolved in a mixture of ethyl acetate (75 mL) and brine (75 mL). The organic phase dried ($Na_2SO_4$) and evaporated at reduced pressure to give benzyl 2-(5-amino-2-methylphenyl)acetate as an oil, which appears to be 6:4 mix of product:non-homologated compound. Used as is.

In dimethylacetamide (35 mL) was placed Example C1 (1.31 g, 7.13 mmol) and the crude benzyl 2-(5-amino-2-methylphenyl)acetate (2.00 g, 5.09 mmol). To this was added KF/Alumina (11.1 g, 76.4 mmol) and the mixture sonicated at RT for 1.5 hrs. The reaction mixture was diluted with $CH_2Cl_2$ (100 mL) and filtered free of insolubles. The filtrate was washed with water (100 mL) and brine (100 mL), dried ($Na_2SO_4$) and concentrated in vacuo to remove dimethylacetamide to give an oil. The oil was treated with ethyl acetate (30 mL), forming a precipitate overnight. The solid was collected by filtration, washed with ethyl acetate (2×10 mL) and then dried in vacuo. The isolated solid was warmed to reflux in methanol (15 mL), filtered and dried on high vacuum line to give 6-(5-amino-2-methylphenyl)-8-methyl-2-(methylthio)pyrido[2,3-d]pyrimidin-7(8H)-one (879 mg, 55% yield). $^1$H NMR (300. MHz, DMSO-$d_6$): δ 1.93 (s, 3 H), 2.48 (s, 3 H), 2.60 (s, 3 H), 4.89 (br. s, 1 H), 6.39 (s, 1 H), 6.48-6.50 (m, 1 H), 6.86-6.88 (m, 1 H), 7.79 (s, 1 H), 8.87 (s, 2 H); MS (ESI) m/z: 313.0 (M+H$^+$).

EXAMPLE A45

Following the procedure of Example A60, Example C2 (0.42 g, 2.1 mmol), ethyl 2-(3-aminophenyl)acetate (0.38 g, 2.1 mmol), and $K_2CO_3$ (0.44 g, 3.2 mmol) were combined to give 6-(3-aminophenyl)-8-ethyl-2-(methylthio)pyrido[2,3-d]pyrimidin-7(8H)-one (0.44 g, 66% yield). $^1$H NMR (400 MHz, DMSO-$d_6$): δ 8.93 (s, 1 H), 7.99 (s, 1 H), 7.08 (t, J=8.0 Hz, 1 H), 6.91 (t, J=2.0 Hz, 1 H), 6.78 (dt, J=7.6, 1.2 Hz, 1 H), 6.60 (m, 1 H), 5.14 (s, 2 H), 4.04 (q, J=7.2 Hz, 2 H), 2.62 (s, 3 H), 1.26 (t, J=3 H); MS (ESI) m/z: 313.2 [M+H]$^+$.

EXAMPLE A46

To stirring fuming $HNO_3$ (15 mL) at −15° C. was added 2-bromo-4-fluorophenylacetic acid (10 g, 43 mmol) in portions such that the internal temperature remained below −10° C. After completing the addition the reaction was stirred with warming to +5° C. over 15 min. The mixture was poured onto ice (500 g). Product separated as a slightly sticky solid which on manipulation with a spatula became powdery. The suspension was stirred vigorously until the ice had completely melted. While still very cold, the solids were collected by filtration, rinsed very well with $H_2O$ (1 L). The solid was dried under vacuum to afford 2-(2-bromo-4-fluoro-5-nitrophenyl)

acetic acid (6.04 g, 51% yield) as a pale yellow solid which was used as is in the next reaction.

2-(2-bromo-4-fluoro-5-nitrophenyl)acetic acid (6.04 g, 21.7 mmol) and conc. $H_2SO_4$ (1.2 mL) were combined in EtOH (100 mL) and stirred with heating at 85° C. After 1.5 h, the completed reaction was cooled to RT and concentrated as completely as possible. The residue was dissolved in MTBE (50 mL) and washed with $H_2O$ (2×), and brine (2×), dried ($MgSO_4$), filtered and evaporated to afford a dark orange oil. The crude was purified by silica gel column chromatography to obtain ethyl 2-(2-bromo-4-fluoro-5-nitrophenyl)acetate (5.8 g, 87% yield).

Ethyl 2-(2-bromo-4-fluoro-5-nitrophenyl)acetate (1.00 g, 3.27 mmol), $PdCl_2(PPh_3)2$ (115 mg, 0.16 mmol), CuI (44 mg, 0.23 mmol), and trimethylsilylacetylene (0.7 mL, 4.9 mmol) were dissolved in $Et_3N$ (5 mL). The mixture was immediately degassed by vacuum, and the flask was charged with N2. The mixture was heated overnight at 50° C. Water was added and then the solution was extracted with EtOAc (3×). The organic was washed with $NH_4Cl$, brine and dried ($MgSO_4$). The solvent was removed and then the residue was purified by silica gel column chromatography to obtain ethyl 2-(4-fluoro-5-nitro-2-(2-(trimethylsilyl)ethynyl)phenyl)acetate (0.66 g, 62% yield).

To a stirring suspension of ethyl 2-(4-fluoro-5-nitro-2-(2-(trimethylsilyl)ethynyl)phenyl)acetate (0.66 g, 2.04 mmol) in MeOH/THF (1:1, 20 mL) was added $NH_4Cl$ (1.09 g, 20.4 mmol), followed by Zn dust (1.33 g, 20.4 mmol). After stirring 1.5 h, the mixture was filtered through C elite, and rinsed forward with MeOH. The combined filtrates were concentrated, diluted with brine and extracted with THF (2×). The combined organic layers were washed with brine (1×), dried ($MgSO_4$), filtered and concentrated to afford ethyl 2-(5-amino-4-fluoro-2-(2-(trimethylsilyl)ethynyl)phenyl)acetate (0.54 g, 90% yield). $^1$H NMR (400 MHz, DMSO-$d_6$): δ 6.86 (d, J=12.0 Hz, 1H), 6.47 (d, J=8.8 Hz, 1H), 5.47 (brs, 2H), 3.88 (d, J= 6.8 Hz, 2H), 3.43 (s, 2H), 1.00 (d, J=6.8 Hz, 3H), 0.00 (s, 9H); MS (ESI) m/z: 294.0 (M+H$^+$).

To a solution of ethyl 2-(5-amino-4-fluoro-2-(2(trimethylsilyl)ethynyl)phenyl)acetate (0.30 g, 1.02 mmol) and Example C1 (0.19 g, 1.02 mmol) in 4 mL of DMF was added cesium carbonate (0.87 g, 2.66 mmol) and then the reaction mixture was stirred overnight at RT. The mixture was diluted with water (50 ml) stirred, filtered and washed with water to provide the crude product. The crude was filtered and dried under vacuum to provide 6-(5-amino-2-ethynyl-4-fluorophenyl)-8-methyl-2-(methylthio)pyrido[2,3-d]pyrimidin-7 (8H)-one (300 mg, 71% yield) which was used for the next reaction. $^1$H NMR (400 MHz, DMSO-$d_6$): δ 8.87 (s, 1H), 7.90 (s, 1H), 7.15 (d, y=12.0 Hz, 1H), 6.69 (d, J=9.2 Hz, 1H), 5.65 (s, 2H), 3.77 (s, 1H), 3.60 (s, 3H), 2.57 (s, 3H); MS (ESI) m/z: 341.0 (M+H$^+$).

Using a procedure analogous to Example A1, 6-(5-amino-2-ethynyl-4-fluorophenyl)-8-methyl-2-(methylamino)pyrido[2,3-d]pyrimidin-7(8H)-one (0.250 g, 0.734 mmol), MCPBA (0.217 g, 0.881 mmol) and 2 M methylamine (1.5 mL, 2.95 mmol) were combined to obtain 6-(5-amino-2-ethynyl-4-fluorophenyl)-8-methyl-2-(methylamino)pyrido [2,3-d]pyrimidin-7(8H)-one (140 mg, 59% yield). $^1$H NMR (400 MHz, DMSO-$d_6$): δ 8.59 (s, 1H), 7.82 (m, 1H), 7.73 (s, 1H), 7.15 (d, J=12.0 Hz, 1H), 6.71 (d, J=9.2 Hz, 1H), 5.61 (s, 2H), 3.78 (s, 1H), 3.58 (s, 3H), 2.90 (d, J=4.4 Hz, 1H); MS (ESI) m/z: 324.2 (M+H$^+$).

EXAMPLE A47

Ethyl 2-(4-fluoro-5-nitro-2-(2-(trimethylsilyl)ethynyl) phenyl)acetate (0.85 g, 2.6 mmol) and $K_2CO_3$ (3.6 g) were dissolved in THF/MeOH (5:1, 30 mL) and the mixture was stirred overnight at RT. The reaction mixture was diluted with $Et_2O$ and washed with sat'd $NH_4Cl$ solution. The organic layer was dried ($MgSO_4$), filtered, and concentrated. The residue was purified by silica gel column chromatography to obtain ethyl 2-(2-ethynyl-4-fluoro-5-nitrophenyl)acetic acid.

Ethyl 2-(2-ethynyl-4-fluoro-5-nitrophenyl)acetic acid and conc. $H_2SO_4$ were combined in EtOH (5 mL) and stirred with heating at 85° C. After 4 h, the completed reaction was cooled to RT and concentrated as completely as possible. The residue was dissolved in MTBE (50 mL) and washed with $H_2O$ (2×), and brine (2×), dried ($MgSO_4$), filtered and evaporated to afford desired product as a dark orange oil. The crude was purified by silica gel column chromatography to obtain ethyl 2-(2-ethynyl-4-fluoro-5-nitrophenyl)acetate (160 mg, 21% yield). MS (ESI) m/z: 252.0 (M+H$^+$).

Ethyl 2-(2-ethynyl-4-fluoro-5-nitrophenyl)acetate (160 mg, 0.64 mmol) was dissolved in MeOH (5 mL) and EtOAc (5 mL) and then Pd—C (20 mg) was added. The reaction mixture was shaken in a Parr hydrogenator (46 psi) overnight at RT. The reaction mixture was filtered, washed with methanol, and concentrated to obtain ethyl 2-(5-amino-2-ethyl-4-fluorophenyl)acetate (135 mg, 93% yield). MS (ESI) m/z: 226.2 (M+H$^+$).

To a solution of ethyl 2-(5-amino-2-ethyl-4-fluorophenyl) acetate (135 mg, 0.6 mmol) and Example C1 (110 mg, 0.6 mmol) in DMF (2 mL) was added cesium carbonate (500 mg, 1.5 mmol) and stirred overnight at RT. The reaction mixture was diluted with water (50 mL) stirred, filtered and washed to provide the crude product. The crude product was stirred in EtOH overnight at RT. The solid was filtered, washed and dried to provide 6-(5-amino-2-ethyl-4-fluorophenyl)-8-methyl-2-(methylthio)pyrido[2,3-d]pyrimidin-7(8H)-one (100 mg, 48% yield). $^1$H NMR (400 MHz, DMSO-$d_6$, major isomers): δ 8.87 (s, 1H), 7.81 (s, 1H), 6.91 (d, J=12.8 Hz, 1H), 6.54 (d, J=9.2 Hz, 1H), 4.98 (s, 2H), 3.63 (s, 3H), 2.60 (s, 3H), 2.26 (q, J=7.2 Hz, 2H), 0.97 (t, J=7.2 Hz, 3H), MS (ESI) m/z: 345.0 (M+H$^+$).

EXAMPLE A48

Ethyl 2-(2-bromo-4-fluoro-5-nitrophenyl)acetate (1.0 g, 3.27 mmol) and zinc cyanide (0.77 g, 6.54 mmol) were combined in DMF (8 mL), de-gassed under vacuum and backfilled with argon (4×). Palladium tetrakis(triphenylphosphine) (380 mg, 0.32 mmol) was added and the reaction was heated at 160° C. under microwave for 30 min. The solution was diluted with EtOAc and then the solid was filtered. The filtrate was washed with brine (3×) and dried ($Na_2SO_4$), concentrated in vacuo and the residue was purified by silica gel column chromatography to obtain ethyl 2-(2-cyano-4-fluoro-5-nitrophenyl)acetate (0.3 g, 37% yield).

To a solution of ethyl 2-(2-cyano-4-fluoro-5-nitrophenyl) acetate in methanol and EtOAc (1:1, 10 mL) was added 10% Pd/C. The solution was stirred under $H_2$ (1 arm) at RT for 3 days. The solution was filtered and evaporated to obtain ethyl 2-(5-amino-2-cyano-4-fluorophenyl)acetate (0.21 g, 81% yield).

To a solution of ethyl 2-(5-amino-2-cyano-4-fluorophenyl) acetate (0.21 g, 0.95 mmol) and Example C1 (0.17 g, 0.95 mmol) in 4 mL of DMF was added cesium carbonate (0.80 g, 2.46 mmol) and then the reaction mixture was stirred overnight at RT. The reaction mixture was diluted with water (50 ml) stirred, filtered and washed with water to provide the crude product. The crude was filtered and dried under vacuum to provide 4-amino-5-fluoro-2-(8-methyl-2-(methylthio)-7-oxo-7,8-dihydropyrido[2,3-d]pyrimidin-6-yl)benzonitrile (125 mg, 39% yield). ¹H NMR (400 MHz, DMSO-$d_6$): δ 8.94 (s, 1H), 8.07 (s, 1H), 7.61 (d, J=11.6 Hz, 1H), 6.82 (d, J=8.8 Hz, 1H), 6.35 (s, 2H), 3.65 (s, 3H), 2.62 (s, 3H); MS (ESI) m/z: 342.0 (M+H$^+$).

EXAMPLE A49

Using a procedure analogous to Example A1, Example A59 (0.18 g, 0.52 mmol), MCPBA (0.1 g, 0.57 mmol) and 2 M Methylamine in THF (1 ml) were combined to afford 6-(3-amino-4-fluorophenyl)-8-isopropyl-2-(methylamino) pyrido[2,3-d]pyrimidin-7(8H)-one as a light yellow solid (105 mg, 61% yield). ¹H NMR (400 MHz, DMSO-$d_6$): δ 8.57 (s, 1H), 7.72 (s, 1H), 7.06 (dd, J=8.8 Hz, 2.0 Hz, 1H), 6.97 (dd, J=11.2 Hz, 8.4 Hz, 1H), 6.72-6.68 (m, 1H), 5.77-5.74 (m, 1H), 5.11 (brs, 2H), 2.88 (d, J=4.8 Hz, 3H), 1.57-1.51 (m, 6H); MS (ESI) m/z: 328.3 (M+H$^+$).

EXAMPLE A50

Using a procedure analogous to Example A1, Example A41 (0.6 g, 1.7 mmol) and 2M methylamine in THF (3 eq) were combined to afford 6-(5-amino-4-fluoro-2-methylphenyl)-8-ethyl-2-(methylamino)pyrido[2,3-d]pyrimidin-7 (8H)-one as a white solid (0.31, 54% yield). ¹H NMR (400 MHz, Acetone-4): δ 8.53 (s, 1H), 7.55 (s, 1H), 6.85-6.82 (m, 2H), 6.70 (d, J=9.6 Hz, 1H), 4.46-4.43 (m, 2H), 3.05 (d, J=4.8 Hz, 3H), 1.31-1.27 (m, 3H); MS (ESI) m/z: 328.0 (M+H$^+$).

EXAMPLE A51

Using a procedure analogous to Example A1, Example A42 (0.5, 1.4 mmol), MCPBA (0.26 g, 1.5 mmol) and 2 M methylamine in THF (3 eq) were combined to provide 6-(5-amino-4-fluoro-2-methylphenyl)-8-isopropyl-2-(methylamino)pyrido[2,3-d]pyrimidin-7(8H)-one as a foam (0.33 g, 69% yield). ¹H NMR (400 MHz, DMSO-$d_6$): δ 8.62-8.54 (m, 1H), 7.72-7.69 (m, 1H), 7.54 (s, 1H), 6.84 (d, J=12.0 Hz, 1H), 6.57 (d, J=9.6 Hz, 1H), 5.74 (brs, 2H), 4.90 (brs, 2H), 2.88 (d, J=4.4 Hz, 1H), 1.94 (s, 3H), 1.56-1.50 (m, 6H); MS (ESI) m/z: 342.0 (M+H$^+$).

EXAMPLE A52

To a degassed solution of 6-bromo-8-isopropyl-2-(methylthio)pyrido[2,3-d]pyrimidin-7(8H)one (0.78 g, 2 mmol; J. Med. Chem., 48, 2371, 2005) in DME (10 ml) was added Pd(PPh$_3$)4 (0.1 g, 5% mol), 4-fluoro-3-nitrophenylboronic acid (0.5 g, 3 mmol) and 2M Na$_2$CO$_3$ solution (3 ml, 6 mmol) and the mixture was heated to 80° C. for 16 h. The mixture was poured into water (40 mL), and product was extracted with EtOAc (3×25 mL). The combined organics were washed with brine, dried (Na$_2$SO$_4$) and concentrated in vacuo afforded crude product. Purification by silica gel chromatography provided 6-(4-fluoro-3-nitrophenyl)-8-isopropyl-2-(methylthio)pyrido[2,3-d]pyrimidin-7(8H)-one as off-white solid (0.82 g, 88% yield). ¹H NMR (400 MHz, DMSO-$d_6$): δ 8.94 (s, 1H), 8.52 (dd, J=7.2 Hz, 2.4 Hz, 1H), 8.28 (s, 1H), 8.15-8.12 (m, 1H), 7.70 (dd, J=11.6 Hz, 8.8 Hz, 1H), 5.81-5.78 (m, 1H), 2.63 (s, 3H), 1.60 (d, J=6.8 Hz, 6H); MS (ESI) m/z: 375.0 (M+H$^+$).

Using a procedure analogous to Example A1, 6-(4-fluoro-3-nitrophenyl)-8-isopropyl-2-(methylthio)pyrido[2,3-d]pyrimidin-7(8H)-one (0.82 g, 2.2 mmol), MCPBA (0.38 g, 2.2 mmol) and 0.5 M ammonia in dioxane (8 mL) were combined to afford 2-amino-6-(4-fluoro-3-nitrophenyl)-8-isopropylpyrido[2,3-d]pyrimidin-7(8H)-one as a yellow solid (0.52 g, 69% yield). ¹H NMR (400 MHz, MeOH-$d_4$): δ 8.61 (s, 1H), 8.44 (dd, J=7.6 Hz, 2.4 Hz, 1H), 8.03-8.00 (m, 1H), 7.95 (s, 1H), 7.48 (dd, J=10.8 Hz, 7.6 Hz, 1H), 5.96-5.92 (m, 1H), 2.63 (s, 3H), 1.64 (d, J= 6.4 Hz, 6H); MS (ESI) m/z: 344.3 (M+H$^+$).

To a solution of 2-amino-6-(4-fluoro-3-nitrophenyl)-8-isopropylpyrido[2,3-d]pyrimidin-7(8H)-one (0.52 g, 1.5 mmol) in EtOAc and methanol (5:1, 30 mL) was added palladium on carbon (50 mg of 10% mol) and mixture was stirred under a hydrogen atmosphere at RT for 16 h. The mixture was filtered over a Celite pad and the pad was washed with EtOAc (2×10 mL). The combined filtrate was concentrated in vacuo to provide crude product. Purification by silica gel chromatography afforded 2-amino-6-(3-ammo-4-fluorophenyl)-8-isopropylpyrido[2,3-d]pyrimidin-7(8H)-one as an off-white solid (0.34 g, 72% yield). ¹H NMR (400 MHz, DMSO-$d_6$): δ 8.60 (s, 1H), 7.73 (s, 1H), 7.22 (s, 2H), 7.08 (dd, J=9.2 Hz, 1.2 Hz, 1H), 6.99 (dd, J=10.8 Hz, 8.4 Hz, 1H), 6.74-6.70 (m, 1H), 5.78-5.76 (m, 1H), 5.13 (s, 2H), 1.53 (d, J=6.8 Hz, 6H); MS (ESI) m/z: 314.0 (M+H$^+$).

EXAMPLE A53

Using a procedure analogous to Example A7, N,N-dimethylpropane-1,3-diamine (3.27 g, 32 mmol) and Example A11 (100 mg, 0.32 mmol) were combined to provide 3-(5-amino-4-fluoro-2-methylphenyl)-7-(3-(dimethylamino)propylamino)-1-methyl-1,6-naphthyridin-2(1H)-one (93 mg, 77% yield). MS (ESI) m/z: 384.2 (M+H$^+$).

EXAMPLE A54

A solution of Example A11 (0.200 g, 0.629 mmol), KOAc (0.093 g, 0.944 mmol) and 10% Pd/C (0.33 g, 0.031 mmol) in THF/MeOH (2:1, 15 mL) was stirred at RT under a H$_2$ atmosphere overnight. The mixture was filtered on Celite and rinsed forward with MeOH. The combined filtrates were concentrated, diluted with satd. NaHCO$_3$ and extracted with EtOAc (2×). The combined organic layers were washed with brine (1×), dried (MgSO$_4$), filtered and concentrated to afford 3-(5-amino-4-fluoro-2-methylphenyl)-1-methyl-1,6-naphthyridin-2(1H)-one (0.161 g, 90%) as a yellow solid. MS (ESI) m/z: 284.0 (M+H$^+$).

EXAMPLE A55

A mixture of ethyl (3-amino-4-fluorophenyl)acetate (3.5 g, 17.6 mmol) and K$_2$CO$_3$ (6.1 g, 44.1 mmol) in DMF (20 mL) was stirred at RT for 30 min. Example C3 (2.5 g, 14.7 mmol) was added to the above mixture and the resulting mixture was stirred at 80° C. for 10 h. The DMF was removed under reduced pressure and the crude residue was suspended in H$_2$O and extracted with EtOAc (3×20 mL). The organics were washed with brine, dried (MgSO$_4$) and concentrated to give 3-(3-amino-4-fluorophenyl)-7-chloro-1-methyl-1,6-naphthyridin-2(1H)-one (4 g, 90% yield). ¹H NMR (300 MHz, DMSO-$d_6$): δ 8.75 (s, 1 H), 8.07 (s, 1 H), 7.61 (s, 1H), 7.13-7.00 (m, 2 H), 6.80 (m, 1 H), 5.21 (s, 2 H), 3.61 (s, 3 H). MS (ESI) m/z: 304.2 (M+H$^+$).

EXAMPLE A56

Using a procedure analogous to Example A7, N,N-dimethylethane-1,2-diamine (6.0 mL, 55 mmol) and Example A55 (150 mg, 0.49 mmol) were combined to afford 3-(3-amino-4-fluorophenyl)-7-(2-(dimethylamino)ethylamino)-1-methyl-1,6-naphthyridin-2(1H)-one (151 mg, 86% yield) as a yellow solid. MS (ESI) m/z: 356.3 (M+H$^+$).

EXAMPLE A57

A mixture of Example A60 (1.1 g, 3.7 mmol) and 25% CH$_3$NH$_2$/EtOH solution (10 mL) was heated at 160° C. in a steel bomb for 2 h. The cooled reaction mixture was filtered and the solid was recrystallized (EtOH) to give 6-(3-amino-phenyl)-8-methyl-2-methylamino-8H-pyrido[2,3-d]pyrimidin-7-one (610 mg, 59% yield). $^1$H NMR (300 MHz, DMSO-d$_6$): 8.69 and 8.61 (s, 1 H), 7.78 (m, 2 H), 7.01 (t, J=7.8 Hz, 1 H), 6.85 (br s, 1 H), 6.73 (d, J=7.8 Hz, 1H), 6.51 (d, J=7.8 Hz, 1 H), 5.05 (br s, 2 H), 3.56 and 3.52 (s, 3 H), 2.88 (m, 3 H). MS (ESI) m/z: 282.2 (M+H$^+$).

EXAMPLE A58

KF/Al$_2$O$_3$ (40 wt %, 10 g, 69 mmol) was added to a solution of Example C7 (6 g, 30 mmol) and ethyl (3-amino-4-fluorophenyl)acetate (6 g, 30 mmol) in DMAc (80 mL). The reaction mixture was stirred at RT for 1 hour. The mixture was filtered and the filtrate was concentrated under vacuum. The residue was poured into water, and the precipitate was collected by filtration, washed with ethyl ether, and dried in vacuo to give 3-(3-amino-4-fluorophenyl)-7-chloro-1-isopropyl-1,6-naphthyridin-2(1H)-one (7 g, 70% yield). $^1$H NMR (400 Hz, DMSO-d$_6$): δ 8.71 (s, 1 H), 8.00 (s, 1 H), 7.76 (s, 1 H), 7.11 (dd, J=9.2, 2.4 Hz, 1 H), 7.05 (dd, J=11.6, 8.4 Hz, 1 H), 6.76 (m, 1 H), 5.18 (s, 2 H), 5.15 (m, 1 H), 1.52 (d, J=7.2 Hz, 1H); MS (ESI) m/z: 332.0 [M+H]$^+$.

A mixture of 3-(3-amino-4-fluorophenyl)-7-chloro-1-isopropyl-1,6-naphthyridin-2(1H)-one (4 g, 12.1 mmol) and (4-methoxybenzyl)methylamine (15 mL) was degassed under reduced pressure and heated to 180° C. under N2 for 4 h. After cooling, the reaction mixture was diluted with Et$_2$O. The precipitate was filtered, washed with ether and dried in vacuo to give 3-(3-amino-4-fluoro-phenyl)-1-isopropyl-7-[(4-methoxybenzyl)-methyl-amino]-1H-[1,6]naphthyridin-2-one (5.3 g) as a solid contaminated with (4-methoxybenzyl)methylamine HCl salt.

The above prepared 3-(3-amino-4-fluoro-phenyl)-1-isopropyl-7-[(4-methoxy-benzyl)-methyl-amino]-1H-[1,6] naphthyridin-2-one (5.3 g) was combined in DCM (150 mL) with TFA (50 mL) and the resultant mixture was heated at reflux overnight. The volatiles were removed under reduced pressure, and the residue was dissolved in 10% HCl aqueous solution. The aqueous layer was washed with EtOAc (3×100 mL) and the aqueous layer was basified to pH 11, and extracted with EtOAc. The combined extracts were dried (Na$_2$SO$_4$) and concentrated to give 3-(3-amino-4-fluoro-phenyl)-1-isopropyl-7-methylamino-1H-[1,6]naphthyridin-2-one (1.26 g, 32% yield for two steps). $^1$H NMR (400 MHz, DMSO-d$_6$): δ 8.36 (s, 1 H), 7.70 (s, 1 H), 7.06 (dd, J=8.4, 2.0 Hz, 1 H), 6.94 (dd, J=11.6, 8.4 Hz, 1 H), 6.88 (m, 1 H), 6.72 (m, 1 H), 6.39 (s, 1 H), 5.07 (m, 1 H), 5.06 (s, 2 H), 2.83 (d, J=4.8 Hz, 1 H), 1.51 (d, J=6.8 Hz, 6 H); MS (ESI) m/z: 327.1 [M+H]$^+$.

EXAMPLE A59

Method 1: To a solution of Example A15 (0.5 g, 1.7 mmol) in DMF (5 mL) was added NaH (0.048 g, 2.0 mmol) at RT. After stirring for 30 min, 2-iodopropane (0.56 g, 3.3 mmol) was added and the mixture was stirred for 3 h at RT. Sat. NH$_4$Cl solution was added, and the product was extracted with ethylacetate (2×35 mL). The combined organics were washed with brine solution, dried (Na$_2$SO$_4$) and concentrated in vacuo to provide crude residue. Purification by silica gel chromatography provided 6-(3-amino-4-fluorophenyl)-8-isopropyl-2-(methylthio)pyrido[2,3-d]pyrimidin-7(8H)-one as a light orange solid (0.18 g, 32% yield). $^1$H NMR (400 MHz, DMSO-d$_6$): δ 8.88 (s, 1H), 7.93 (s, 1H), 7.10 (dd, J=8.8 Hz, 2.0 Hz, 1H), 7.02 (dd, J=11.2 Hz, 8.4 Hz, 1H), 6.77-6.73 (m, 1H), 5.78-5.74 (m, 1H), 5.19 (br s, 2H), 2.60 (s, 3H), 1.56 (d, J=7.2 Hz, 6H); MS (ESI) m/z: 345.2 (M+H$^+$).

Method 2: Example C6 (3.0 g, 14.2 mmol), ethyl 2-(3-amino-4-fluorophenyl)acetate (2.8 g, 14.2 mmol), and KF/Al$_2$O$_3$ (40 wt %, 9 g, 62 mmol) were combined in DMAc (30 mL) and stirred at RT for 12 hours. The reaction mixture was filtered and the filtrate was concentrated under reduced pressure, washed with ethyl ether and dried in vacuo to give 6-(3-amino-4-fluorophenyl)-8-isopropyl-2-(methylthio)pyrido[2,3-d]pyrimidin-7(8H)-one (2.1 g, 42.9% yield).

EXAMPLE A60

Chlorotrimethylsilane (13.3 g, 122 mmol was added to a solution of 2-(3-nitrophenyl)acetonitrile (10 g, 61.2 mmol) in EtOH (100 mL) and the mixture was refluxed overnight. The reaction mixture was concentrated under reduced pressure. Water was added and the mixture was neutralized to pH=7 with saturated aq Na$_2$CO$_3$ solution and extracted with EtOAc (3×70 mL). The combined organics were washed with brine, dried (MgSO$_4$) and concentrated to give ethyl 2-(3-nitrophenyl)acetate (12 g, 94% yield). $^1$H NMR (400 MHz, DMSO-d$_6$): δ 8.15 (s, 1H), 8.10 (d, J=8.4 Hz, 1 H), 7.71 (d, J=7.6 Hz, 1 H), 7.61 (t, J=8.0 Hz, 1 H), 4.06 (q, J=7.2 Hz, 2 H), 3.85 (s, 2 H), 1.15 (t, J=7.2 Hz, 3 H).

A mixture of ethyl 2-(3-nitrophenyl)acetate (12 g, 57.4 mmol) and Pd/C (1.2 g, 10%) in methanol (100 mL) was hydrogenated (45 psi) at RT for 12 h. The mixture was filtered and the filtrate was concentrated to afford ethyl 2-(3-aminophenyl)acetate (10 g, 97% yield). $^1$H NMR (400 MHz, DMSO-d$_6$): δ 6.91 (t, J=1.6 Hz, 1 H), 6.42-6.40 (m, 2 H), 6.35 (d, J=7.6 Hz, 1 H), 5.00 (s, 2 H), 4.03 (q, J=7.2 Hz, 2 H), 3.41 (s, 2 H), 1.15 (t, J=7.2 Hz, 3 H).

Example C1 (5.1 g, 27.9 mmol), ethyl 2-(3-aminophenyl)acetate (5.0 g, 29.3 mmol), and K$_2$CO$_3$ (7.7 g, 55.8 mmol) were combined in DMF (60 mL) and the resulting mixture was stirred at 100° C. for 10 hours. The reaction mixture was concentrated under reduced pressure, diluted with water (100 mL), and the aqueous layer was extracted with EtOAc (3×70 mL). The combined organic layers were washed with brine, dried (MgSO$_4$) and concentrated in vacuo. The residue was purified by column chromatography on silica gel to give 6-(3-aminophenyl)-8-methyl-2-(methylthio)pyrido[2,3-d] pyrimidin-7(8H)-one (5.2 g, 62.7% yield). $^1$H NMR (400 MHz, DMSO-d$_6$): δ 8.89 (s, 1 H), 7.97 (s, 1 H), 7.05 (t, J=8.0 Hz, 1 H), 6.87 (s, 1 H), 7.76 (d, J= 7.6 Hz, 1 H), 6.57 (d, J=8.4 Hz, 1 H), 5.11 (s, 2 H), 3.64 (s, 3 H), 2.59 (s, 3 H); MS (ESI) m/z: 299.2 [M+H]$^+$.

EXAMPLE A61

Example C3 (3.2 g, 18.8 mmol), Example D6 (4.0 g, 18.8 mmol) and Cs$_2$CO$_3$ (12.3 g, 37.6 mmol) were combined in DMF (80 mL) and heated to 80° C. with stirring for 4 h. The reaction mixture was poured into water (600 mL) and precipitate was collected by filtration and dried under reduced pressure to give 3-(5-amino-2-chlorophenyl)-7-chloro-1-methyl-1,6-naphthyridin-2(1H)-one (5.0 g, 83% yield). $^1$H-NMR (400 MHz, DMSO-d$_6$): δ 8.74 (s, 1 H), 7.97 (s, 1 H), 7.63 (s, 1H), 7.09 (d, J=8.4 Hz, 1 H), 6.57 (dd, J=8.4 Hz, 2.8 Hz, 1 H), 6.52 (s, 1H), 5.31 (s, 2 H), 3.60 (s, 3 H).

A mixture of 3-(5-amino-2-chlorophenyl)-7-chloro-1-methyl-1,6-naphthyridin-2(1H)-one (5 g, 15.67 mmol), 4-Methoxybenzylmethylamine (3.6 g, 23.5 mmol) and DBU (3.7 g, 23.5 mmol) in NMP (80 mL) was heated at 180° C. under N2 for 4 h. The reaction was cooled to room temperature and poured into water (600 mL). The precipitate was collected by filtration and dried in vacuo to give 7-((4-methoxybenzyl)(methyl)amino)-3-(5-amino-2-chlorophenyl)-1-methyl-1,6-naphthyridin-2(1H)-one (6.5 g, 95% yield). $^1$H NMR (400 MHz, DMSO-$d_6$): δ 8.46 (s, 1 H), 7.68 (s, 1 H), 7.16 (d, J=8.8 Hz, 2 H), 7.06 (d, J=8.4 Hz, 1 H), 6.85 (d, J=8.8 Hz, 2H), 6.54-6.51 (m, 2 H), 6.29 (s, 1 H), 5.23 (s, 2 H), 4.85 (s, 2 H), 3.69 (s, 3 H), 3.51 (s, 3 H), 3.07 (s, 3 H).

Trifluoroacetic acid (10 mL, 134 mmol) was added to a solution of 7-((4-methoxybenzyl)(methyl)amino)-3-(5-amino-2-chlorophenyl)-1-methyl-1,6-naphthyridin-2(1H)-one (4 g, 9.2 mmol) in CH$_2$Cl$_2$ (50 mL). The mixture was heated to reflux for 3 hrs. The reaction mixture was concentrated under reduced pressure, dissolved in aq HCl solution and washed with EtOAc (3×50 mL). The aqueous layer was neutralized with saturated Na$_2$CO$_3$ solution to pH 8, and was extracted with EtOAc (3×50 mL). The combined extracts were washed with brine, dried over Na$_2$SO$_4$ and concentrated under reduced pressure. The residue was purified by chromatography to give 3-(5-amino-2-chlorophenyl)-1-methyl-7-(methylamino)-1,6-naphthyridin-2(1H)-one (1.7 g, 58% yield). $^1$H NMR (400 MHz, DMSO-$d_6$): δ 8.36 (s, 1 H), 7.63 (s, 1 H), 7.06-7.00 (m, 2 H), 6.54-6.50 (m, 2 H), 6.14 (s, 1 H), 5.21 (s, 2 H), 3.48 (s, 3 H), 2.84 (d, J=4.8 Hz, 3 H); MS (ESI) m/z: 314.9 [M+H]$^+$.

EXAMPLE A62

Using the three-step procedure of Example 61, Example C5 (3.5 g, 18.8 mmol), Example D6 (4.0 g, 18.8 mmol), Cs$_2$CO$_3$ (12.3 g, 37.6 mmol), 4-methoxybenzylmethylamine (3.6 g, 23.5 mmol) and trifluoroacetic acid (10 mL, 134 mmol) were combined to provide 3-(5-amino-2-chlorophenyl)-1-ethyl-7-(methylamino)-1,6-naphthyridin-2(1H)-one (1.68 g, 27% yield over 3 steps). $^1$H NMR (400 MHz, DMSO-$d_6$): δ 8.36 (s, 1 H), 7.62 (s, 1 H), 7.05 (dd, J=7.2, 2.0 Hz, 1 H), 6.96 (q, J=4.8 Hz, 1 H), 6.54-6.50 (m, 2 H), 6.21 (s, 1 H), 5.21 (s, 2 H), 4.11 (q, J=7.2 Hz, 2 H), 2.84 (d, J=4.8 Hz, 3 H), 1.18 (t, J=7.2 Hz, 3 H); MS (ESI) m/z: 329.2 [M+H]$^+$.

EXAMPLE A63

Using a procedure analogous to Example A1, Example A18 (1.01 g, 2.77 mmol) and 2M Methylamine in THF (6 mLl) were combined and purified by silica gel chromatography to afford 6-(5-amino-2-chloro-4-fluorophenyl)-8-ethyl-2-(methylamino)pyrido[2,3-d]pyrimidin-7(8H)-one as orange colored solid (0.55 g, 57% yield). $^1$H NMR (400 MHz, DMSO-$d_6$): δ 8.59 (s, 1H), 7.84-7.81 (m, 1H), 7.67 (s, 1H), 6.20 (d, J=11.2 Hz, 1H), 6.72 (A, J=9.6 Hz, 1H), 5.33 (s, 2H), 4.35-4.30 (m, 2H), 2.89 (d, J=6.0 Hz, 3H), 1.21 (t, J=6.8 Hz, 3H); MS (ESI) m/z: 348.0 (M+H$^+$).

EXAMPLE A64

Example D6 (1.0 g, 4.68 mmol), Example C1 (0.858 g, 4.68 mmol) and Cs$_2$CO3 (3.96 g, 12.2 mmol) were combined in DMF (18 mL) by the procedure of Example A10, method 3, to provide 6-(5-amino-2-chlorophenyl)-8-methyl-2-(methylthio)pyrido[2,3-d]pyrimidin-7(8H)-one (1.37 g, 88% yield). $^1$H NMR (400 MHz, DMSO-$d_6$): δ 8.90 (s, 1H), 7.90 (s, 1H), 7.10 (d, J=8.0 Hz, 1H), 6.58 (dd, J=8.8, 2.4 Hz, 1H), 6.53 (d, 0.7= 2.4 Hz, 1H), 5.33 (s, 2H), 3.64 (s, 3H), 2.61 (s, 3H); MS (ESI) m/z: 330.0 (M+H$^+$).

6-(5-amino-2-chlorophenyl)-8-methyl-2-(methylthio)pyrido[2,3-d]pyrimidin-7(8H)-one (0.500 g, 1.5 mmol), mCPBA (0.481 g, 1.953 mmol) and methylamine (0.76 mL. 2.0 M in THF, 1.52 mmol) were combined by analogy to Example A1 to provide 6-(5-amino-2-chlorophenyl)-8-methyl-2-(methylamino)pyrido[2,3-d]pyrimidin-7(8H)-one (0.378 g, 80% yield). MS (ESI) m/z: 316.0 (M+H$^+$).

EXAMPLE A65

Example C5 (1.8 g, 10 mmol) and ethyl 2-(5-amino-2-methylphenyl)acetate (1.9 g, 10 mmol, and KF/Al$_2$O$_3$ (40%, 5.4 g, 37 mmol) were combined in DMAc (40 mL) by the procedure of Example A11 to give 3-(5-amino-2-methylphenyl)7-chloro-1-ethyl-1,6-naphthyridin-2(1H)-one (1.9 g, 61% yield). $^1$H NMR (400 MHz, DMSO-$d_6$): δ 8.73 (s, 1 H), 7.88 (s, 1 H), 7.68 (s, 1 H), 6.87 (d, J=8.4 Hz, 1 H), 6.49 (d, J=8.4 Hz, 1 H), 6.41 (m, 1 H), 4.89 (s, 2 H), 4.24 (q, J=7.2 Hz, 2 H), 1.92 (s, 3 H), 1.16 (t, J=7.2 Hz, 3 H).

Using a procedure analogous to Example A26, 3-(5-amino-2-methylphenyl)-7-chloro-1-ethyl-1,6-naphthyridin-2(1H)-one (1.9 g, 6.4 mmol), 4-methoxybenzylmethylamine (1.5 g, 9.6 mmol), DBU (1.6 g, 9.6 mmol), and trifluoroacetic acid (10 mL, 134 mmol) were combined to give 3-(5-amino-2-methylphenyl)-1-ethyl-7-(methylamino)-1,6-naphthyridin-2(1H)-one (0.84 g, 43% yield, 2 steps). $^1$H NMR (300 MHz, DMSO-$d_6$): δ 8.36 (s, 1 H), 7.56 (s, 1 H), 6.91-6.82 (m, 2 H), 6.47-6.39 (m, 2 H), 6.22 (s, 1 H), 4.80 (s, 2 H), 4.13 (q, J=6.9 Hz, 2 H), 2.84 (d, J=4.8 Hz, 3 H), 1.92 (s, 3 H), 1.19 (t, J=6.9 Hz, 3 H); MS (ESI) m/z: 308.9 [M+H]$^+$.

EXAMPLE B1

Phenyl hydrazine and 4,4-dimethyl-3-oxopentanenitrile were combined according to literature procedures to yield 3-tert-butyl-1-phenyl-1H-pyrazol-5-amine. See WO 2006/071940.

EXAMPLE B2

Methyl hydrazine and 4,4-dimethyl-3-oxopentanenitrile were combined according to literature procedures to yield 3-tert-butyl-1-methyl-1H-pyrazol-5-amine. See WO 2006/071940.

EXAMPLE B3

3-(2-amino-2-oxoethyl)phenyl hydrazine and 4,4-dimethyl-3-oxopentanenitrile were combined according to literature procedures to yield 2-(3-(5-amino-3-tert-butyl-1H-pyrazol-1-yl)phenyl)acetamide. See WO 2006/071940.

EXAMPLE B4

A mixture of 5-nitro-1H-indazole (25 g, 0.153 mmol) and 10% Pd/C (2.0 g) in MeOH was stirred under H$_2$ (1 atm) overnight. After filtration, the filtrate was concentrated to yield 1H-indazol-5-ylamine (20 g, 97% yield) as a yellow solid. $^1$H NMR (300 MHz, DMSO-$d_6$): δ 12.50 (brs, 1H), 7.70 (s, 1H), 7.21 (d, J=8.7 Hz, 1H), 6.77 (d, J=8.7 Hz, 1H), 6.74 (s, 1H), 4.71 (brs, 1H), 3.15 (d, J=4.8 Hz, 2H); MS (ESI) m/z: 134 (M+H$^+$).

To a solution of 1H-indazol-5-ylamine (20 g, 153 mmol) in conc. HCl (50 mL) was added an aqueous solution (50 mL) of NaNO$_2$ (19 g, 158 mmol) at 0° C. and the resulting mixture was stirred for 1 h. A solution of SnCl$_2$.2H$_2$O (90 g, 306 mmol) in conc. HCl (70 mL), pre-cooled to 0° C., was then added. The reaction solution was stirred for 2 h at RT. The precipitate was filtered and washed with ether to yield (1H-indazol-5-yl)-hydrazine hydrochloride as a yellow solid, which was used for the next reaction without further purification.

A mixture of (1H-indazol-5-yl)-hydrazine hydrochloride and 4,4-dimethyl-3-oxo-pentanenitrile (19 g, 1.05 eq) in EtOH (200 mL) was heated at reflux overnight. The reaction was concentrated and the residue purified by column chromatography to yield 3-t-butyl-1-(1H-indazol-5-yl)-1H-pyrazol-5-amine (23 g, 60% for two steps). $^1$H NMR (300 MHz, DMSO-d$_6$): δ 8.24 (s, 1 H), 8.06 (s, 1 H), 7.75 (d, J=9.0 Hz, 1 H), 7.45 (dd, J=9.0 Hz, 1.8 Hz, 1 H), 5.7 (s, 1H), 1.31 (s, 9 H); MS (ESI) m/z: 256 (M+H$^+$).

To a solution of 3-t-butyl-1-(1H-indazol-5-yl)-1H-pyrazol-5-amine (14 g, 48 mmol) in dioxane (100 mL) was added 10% NaOH (50 mL) at RT and the mixture stirred for 0.5 h. Boc anhydride (12 g, 1.2 eq) was added to the mixture and the solution stirred for 3 h. The mixture was extracted with CH$_2$Cl$_2$ (3×100 mL). The combined organic extracts were concentrated and purified by column chromatography to yield t-butyl 5-(5-amino-3-t-butyl-1H-pyrazol-1-yl)1H-indazole-1-carboxylate (7.8 g, 46%). $^1$H NMR (300 MHz, DMSO-d$_6$): 8.44 (s, 1 H), 8.10 (d, J=9.0 Hz, 1H), 8.00 (s, 1 H), 7.82 (d, J=9.0 Hz, 1 H), 5.39 (s, 1 H), 5.24 (br s, 2 H), 1.65 (s, 9 H), 1.21 (s, 9H); MS (ESI) m/z: 356 (M+H$^+$).

EXAMPLE B5

Phenyl hydrazine and 3-oxo-3-(thiophen-2-yl)propanenitrile were combined according to literature procedures to yield 1-phenyl-3-(thiophen-2-yl)-1H-pyrazol-5-amine. See WO 2006/071940.

EXAMPLE B6

Methyl hydrazine (0.35 g, 7.6 mmol) and 2-thionyl acetonitrile (1.1 g, 7.6 mmol) were heated to 80° C. in ethanol in the presence of conc. HCl (1 drop) for 18 h. Solvents were removed; sat. NaHCO$_3$ solution (35 ml) was added and the product was extracted with ethyl acetate (2×30 ml). The combined organic layers were washed with brine, dried (Na$_2$SO$_4$) and concentrated to afford 1-methyl-3-(thiophen-2-yl)-1H-pyrazol-5-amine (1.25 g, 92% yield) as a solid. $^1$H NMR (400 MHz, DMSO-d$_6$): δ 7.34 (dd, J=4.8 Hz, 1.2 Hz, 1H), 7.19 (dd, J=3.6 Hz, 1.2 Hz, 1H), 7.00 (dd, J=4.8 Hz, 3.6 Hz, 1H), 5.80 (s, 1H), 5.29 (s, 2H), 3.51 (s, 3H); MS (ESI) m/z: 180.0 (M+H$^+$).

EXAMPLE B7

3-Fluorophenylboronic acid (0.70 g, 5.0 mmol), ethyl 3-tert-butyl-1H-pyrazole-5-carboxylate (0.981 g, 5.0 mmol), Cu(OAc)$_2$ (0.908 g, 5.0 mmol), pyridine (2.45 ml, 30 mmol) and 4A MS (1.9 g) were combined in CH$_2$Cl$_2$ (48 ml) and stirred open to air at RT for 4 d. The reaction mixture was diluted with EtOAc (150 mL), washed with 3M HCl (2×50 mL), H$_2$O (50 mL) and brine (50 mL), dried (MgSO$_4$) and concentrated in vacuo. The crude product was purified by chromatography to afford ethyl 3-tert-butyl-1-(3-fluorophenyl)-1H-pyrazole-5-carboxylate (0.786 g, 54% yield) as colorless oil. MS (ESI) m/z: 291 (M+H$^+$).

To a stirring solution of ethyl 3-tert-butyl-1-(3-fluorophenyl)-1H-pyrazole-5-carboxylate (0.786 g, 2.71 mmol) in 1:1:1 THF/EtOH/H$_2$O (36 ml) at RT was added LiOH.H$_2$O (0.568 g, 13.5 mmol). After stirring at RT overnight, the reaction mixture was diluted with 3M HCl (30 mL) and extracted with EtOAc (3×50 mL). The combined organic layers were washed with brine (2×30 mL), dried (MgSO$_4$) and concentrated to afford 3-tert-butyl-1-(3-fluorophenyl)-1H-pyrazole-5-carboxylic acid (0.602 g, 85% yield) as white solid. MS (ESI) m/z: 263 (M+H$^+$).

To a stirring solution of 3-tert-butyl-1-(3-fluorophenyl)-1H-pyrazole-5-carboxylic acid (0.26 g, 0.60 mmol) and TEA (0.13 ml, 0.90 mmol) in 1,4-dioxane (9 ml) was added DPPA (0.16 ml, 0.75 mmol), After stirring for 30 min at RT, 2,2,2-trichloroethanol (0.58 ml, 6.0 mmol) was added and the reaction was heated at 100° C. for 2 h. The reaction mixture was diluted with brine (10 ml) and extracted with EtOAc (3×20 ml). The combined organic phases were washed with 5% citric acid (10 ml), satd. NaHCO$_3$ (10 ml), dried (MgSO$_4$), filtered and evaporated. The crude product was purified by chromatography to afforded 2,2,2-trichloroethyl 3-tert-butyl-1-(3-fluorophenyl)-1H-pyrazol-5-ylcarbamate (0.180 g, 73% yield) as colorless oil. MS (ESI) m/z: 410(M+H$^+$).

EXAMPLE B8

Method 1: To a solution of quinolin-6-ylamine (5 g, 35 mmol) in conc. HCl (12 mL) was added dropwise an aqueous solution (4 mL) of NaNO$_2$ (2.42 g, 35 mmol) at 0° C. The resulting mixture was stirred for 1 h and then treated dropwise with a solution of SnCl$_2$.2H$_2$O (15.8 g, 70 mmol) in conc. HCl (15 mL) at 0° C. The reaction mixture was stirred for 2 h at RT. The precipitate was collected and washed with EtOH and Et$_2$O to yield 1-(quinolin-6-yl)hydrazine hydrochloride (4.3 g, 77% yield) as a yellow powder, which was used for the next reaction without further purification.

A mixture of 1-(quinolin-6-yl)hydrazine hydrochloride (4.0 g, 20.5 mmol) and 4,4-dimethyl-3-oxo-pentanenitrile (3.6 g, 30 mol) in EtOH (50 mL) and conc. HCl (5 mL) was heated at reflux overnight. After removal of the solvent, the residue was purified by column chromatography to yield 3-t-butyl-1-(quinolin-6-yl)-1H-pyrazol-5-amine (2.8 g, 51% yield). $^1$H NMR (300 MHz, DMSO-d$_6$): δ 8.84 (d, J=4.2 Hz, 1H), 8.37 (d, J=7.5 Hz, 1H), 8.09 (s, 1H), 8.04 (s, 2H), 7.52 (m, 1H), 5.46 (s, 1H), 5.40 (brs, 2H), 1.29 (s, 9H). MS (ESI) m/z (M+H$^+$): 267.2.

Method 2: A solution of triflic anhydride (42.8 g, 0.15 mol) in methylene chloride (100 mL) was added dropwise to a 0° C. solution of 6-hydroxyquinoline (20.00 g, 0.138 mol) and pyridine (23 g, 0.277 mol) in methylene chloride (500 mL). The cooling bath was removed and the resulting solution was stirred at RT for 4 h. The reaction mixture was washed with water (3×300 mL) and the organics were dried (MgSO$_4$) and concentrated under vacuum to afford crude quinolin-6-yl trifluoromethanesulfonate (40 g, >100% yield) as an oil. $^1$H-NMR (400 MHz, DMSO-d$_6$): δ 9.00 (d, 1 H, J=2.8 Hz), 8.50 (d, 1H, J=8.0 Hz), 8.21 (d, J=2.8 Hz, 1H), 8.18 (d, J=9.2 Hz, 1H), 7.80 (m, 1 H), 7.64 (m, 1 H); MS (ESI) m/z: 277.9 (M+H$^+$).

To a suspension of quinolin-6-yl trifluoromethanesulfonate (40 g, 0.14 mol), benzophenone hydrazone (35.6 g, 0.18 mol), cesium carbonate (74 g, 0.23 mol) and 1,1'-bis(diphenylphosphino)ferrocene (2.5 g, 4.5 mmol) in degassed toluene (1 L) was added palladium acetate (0.013 g, 0.058 mmol). The resultant mixture was heated to 90° C. under a nitrogen atmosphere. After 16 h, the mixture was concentrated in vacuo and the residue was purified through silica gel column chromatography (20-30% EtOAc in pet ether) to provide 1-(diphenylmethylene)-2-(quinolin-6-yl)hydrazine (32 g, 68.6% yield). $^1$H-NMR (300 MHz, DMSO-d$_6$): δ 9.22 (s, 1 H), 8.58 (t, J=1.8 Hz, 1 H), 8.13 (d, J=3.6 Hz, 1 H), 7.80 (d, J=3.6 Hz, 1 H), 7.61 (d, J=3.9 Hz, 1 H), 7.59-7.51 (m, 4 H), 7.50 (d, J=3.6 Hz, 2 H), 7.33-7.39 (m, 6H); MS (ESI) m/z: 324 (M+H$^+$).

A solution of 1-(diphenylmethylene)-2-(quinolin-6-yl)hydrazine (32 g, 99 mmol) and 4,4-dimethyl-3-oxo-pentanenitrile (26 g, 0.15 mol) in ethanol (500 mL) was treated with conc HCl (80 ml, 12 N, 0.96 mol) and the mixture was heated to reflux overnight. The cooled reaction mixture was concentrated under vacuum and the residue was washed with Et$_2$O to remove the diphenylketone. The crude product was dissolved in EtOAc and neutralized (pH 8) with saturated Na$_2$CO$_3$ solution. The organic layer was dried (Na$_2$SO$_4$) and concentrated in vacuo. The residue was further purified by silica gel chromatography to give 3-t-butyl-1-(quinolin-6-yl)-1H-pyrazol-5-amine (23 g, 87% yield). $^1$H-NMR (300 MHz, DMSO-d$_4$): δ 8.86 (m, 1 H), 8.39 (d, J=5.7 Hz, 1 H), 8.11-8.02 (m, 3H), 7.54 (m, 1 H), 5.46 (s, 1 H), 5.42 (br s, 2H), 1.23 (s, 9 H); MS (ESI) m/z (M+H$^+$): 267.2.

EXAMPLE B9

Methyl hydrazine (0.46, 10 mmol) and 2-fluorophenyl acetonitrile (1.63 g, 10 mmol) were heated to 80° C. in presence of conc. HCl (1 drop) in ethanol (30 mL) for 18 h. Solvents were removed; sat. NaHCO$_3$ solution (35 ml) was added and the product was extracted with ethyl acetate (2×30 mL). The combined organic layers were washed with brine, dried (Na$_2$SO$_4$) and concentrated to afford crude product which was purified by chromatography (methanol/CH$_2$Cl$_2$) to afford 3-(2-fluorophenyl)-1-methyl-1H-pyrazol-5-amine (1.25 g, 65% yield) as a thick residue. $^1$H NMR (400 MHz, DMSO-d$_6$): δ 7.86 (td, J=8.8 Hz, 2.4 Hz, 1H), 7.28-7.15 (m, 3H), 5.71 (d, J=4.4 Hz, 1H), 5.28 (brs, 2H), 3.58 (s, 3H); MS (ESI) m/z: 192.0 (M+H$^+$).

To a biphasic solution of 3-(2-fluorophenyl)-1-methyl-1H-pyrazol-5-amine (1.19 g, 6.22 mmol) in ethyl acetate (30 mL) and NaHCO$_3$ solution (30 mL) was added isopropenylchloroformate (1.28 g, 10.6 mmol) and mixture was stirred at RT for 24 h. Both layers were separated; the aqueous layer was extracted with ethyl acetate (1×30 mL) and the combined organic layers were washed with brine, dried (Na$_2$SO$_4$) and concentrated to afford crude product which was purified by chromatography (ethyl acetate/hexane) to afford prop-1-en-2-yl 3-(2-fluorophenyl)-1-methyl-1H-pyrazol-5-ylcarbamate (1.15 g, 82% yield) as a pasty mass. $^1$H NMR (400 MHz, DMSO-d$_6$): δ 10.09 (brs, 1H), 7.90 (td, J=8.0 Hz, 1.6 Hz, 1H), 7.38-7.22 (m, 3H), 6.54 (d, J=3.6 Hz, 1H), 4.79-4.77 (m, 2H), 3.76 (s, 3H), 1.96 (s, 3H); MS (ESI) m/z: 276.0 (M+H$^+$).

EXAMPLE B10

A mixture of 5-hydrazinyl-2-methylpyridine hydrochloride from Example B27 (5.0 g, 31.4 mmol) and 4,4-dimethyl-3-oxopentanenitrile (8.3 g, 66.3 mmol) in EtOH (50 mL) was heated at reflux overnight. The reaction was concentrated and the residue was dissolved in EtOAc and neutralized with saturated Na$_2$CO$_3$ solution. The organic layer was dried (Na$_2$SO$_4$), concentrated in vacuo and purified by column chromatography to yield 3-tert-butyl-1-(6-methylpyridin-3-yl)-1H-pyrazol-5-amine (5.2 g, 71% yield). $^1$HNMR (400 MHz, CDCl$_3$) δ 8.72 (s, 1 H), 7.81 (dd, J=8.0, 2.4 Hz, 1 H), 7.23 (d, J=8.4 Hz, 1 H), 5.54 (s, 1 H), 3.71 (br s, 1 H), 2.58 (s, 3 H), 1.29 (s, 9 H); MS (ESI) m/z: 231.2 (M+H$^+$).

EXAMPLE B11

To a stirring solution of Example B35, 0.240 g, 0.86 mmol) in dry THF (8.0 mL) at RT was added LiAlH$_4$ (1.0 M in THF, 2.6 mL, 2.6 mmol) and the resulting mixture was stirred at RT for 1 h. The reaction was carefully quenched by the addition of H$_2$O (0.10 mL), 3M NaOH (0.10 mL) and H$_2$O (0.20 mL), and the mixture was stirred at RT overnight. The suspension was filtered through Celite and rinsed with EtOAc (20 mL). The filtrate was dried (MgSO$_4$) and concentrated to afford 2-(5-amino-1-phenyl-1H-pyrazol-3-yl)-2-methylpropan-1-ol (0.208, 105% yield) as a yellow oil. MS (ESI) m/z: 232.2 (M+H$^+$).

To a solution of 2-(5-amino-1-phenyl-1H-pyrazol-3-yl)-2-methylpropan-1-ol (0.208 g, 0.85 mmol) in DMF (2.0 mL) was added imidazole (0.32 g, 4.7 mmol) and TBSCl (0.39 g, 2.6 mmol). The resulting mixture was stirred at RT for 5 h. Solvent was removed under reduced pressure. The residue was diluted with H$_2$O (10 mL) and extracted with EtOAc (2×20 mL). The combined organic layers were dried (MgSO$_4$) and concentrated. The crude product was purified by chromatography to afford 3-(1-(tert-butyldimethylsilyloxy)-2-methylpropan-2-yl)-1-phenyl-1H-pyrazol-5-amine (0.125 g, 42% yield) as a light yellow oil. MS (ESI) m/z: 346.3 (M+H$^+$).

EXAMPLE B12

Using a procedure analogous to Example B11, Example B36 was converted to 3-(1-(tert-butyldimethylsilyloxy)-2-methylpropan-2-yl)-1-methyl-1H-pyrazol-5-amine in 42% yield. $^1$H NMR (400 MHz, CDCl$_3$): δ 5.59 (s, 1H), 3.69 (s, 3H), 3.55 (s, 2H), 1.26 (s, 6H), 0.89 (s, 9H), 0.00 (s, 6H); MS (ESI) m/z: 284.2 (M+H$^+$).

EXAMPLE B13

Potassium t-butoxide (0.51 g, 4.5 mmol) was dissolved in DMSO (10 mL) and to this solution was added ethyl 3-(thiophen-2-yl)-1H-pyrazole-5-carboxylate (1.01 g, 4.5 mmol) in small portions and stirred under Ar for 15 min. To this solution was added 2-iodopropane (1.2 g, 6.8 mmol) slowly and stirred for 1 h at RT. Sat. NH$_4$Cl solution was added, the product was extracted with EtOAc (2×40 mL). The combined organics were washed with brine, dried (Na$_2$SO$_4$) and concentrated in vacuo. Purification by silica gel chromatography provided ethyl 1-isopropyl-3-(thiophen-2-yl)-1H-pyrazole-5-carboxylate as a pasty mass (0.88 g, 73% yield). $^1$H NMR (400 MHz, Acetone-d$_6$): δ 7.47 (dd, J=3.2 Hz, 1.2 Hz, 1H), 7.42 (dd, J=4.8 Hz, 1.2 Hz, 1H), 7.12-7.09 (m, 2H), 5.57-5.51 (m, 1H), 4.37 (q, J=7.2 Hz, 2H), 1.50 (d, J=6.8 Hz, 6H), 1.38 (t, J=7.2 Hz, 3H); MS (ESI) m/z: 265.0 (M+H$^+$).

To a solution of ethyl 1-isopropyl-3-(thiophen-2-yl)-1H-pyrazole-5-carboxylate (0.88 g, 3.3 mmol) in THF (10 mL) was added aq. LiOH solution (0.42 g, 10 mmol, 5 mL) and the mixture was stirred for 16 h at RT. Solvents were removed and the thick liquid was diluted with water (5 mL) and acidified with 3M HCl solution to pH 4-5. The product precipitated and was filtered, washed with water and dried to afford 1-isopropyl-3-(thiophen-2-yl)-1H-pyrazole-5-carboxylic acid as a white solid (0.69 g, 88% yield).

To a solution of 1-isopropyl-3-(thiophen-2-yl)-1H-pyrazole-5-carboxylic acid (0.68 g, 2.9 mmol) in dioxane (10 mL) was added with triethylamine (0.44 g, 4.3 mmol), diphenylphosphorylazide (0.95 g, 3.5 mmol) and trichloroethanol (0.86 g, 5.8 mmol) and the mixture was heated to 90° C. for 4 h. The mixture was poured into 3 M HCl (40 mL) solution and the product was extracted with EtOAc (2×40 mL). The combined organics were washed with brine, dried ($Na_2SO_4$) and concentrated in vacuo. Purification by silica gel chromatography provided 2,2,2-trichloroethyl 1-isopropyl-3-(thiophen-2-yl)-1H-pyrazol-5-ylcarbamate (0.88 g, 80% yield) as a white solid. $^1$H NMR (400 MHz, Acetone-$d_6$): δ 7.36-7.34 (m, 3H), 7.07 (dd, J=5.6 Hz, 4.0 Hz, 1H), 6.52 (s, 1H), 5.83 (t, J=7.2 Hz, 3H), 4.95 (s, 2H), 4.66-4.62 (m, 1H), 1.45 (d, J=6.8 Hz, 6H); MS (ESI) m/z: 382.0 (M+H$^+$).

EXAMPLE B14

In a procedure analogous to Example B8 (method 1), 2-methylquinoline-6-amine (1.00 g, 6.32 mmol) and 4,4-dimethyl-3-oxopentanenitrile (1.03 g, 8.22 mmol) were combined to provide 3-tert-butyl-1-(2-methylquinolin-6-yl)-1H-pyrazol-5-amine (428 mg, 24% yield) as a solid. $^1$H NMR (300 MHz, DMSO-$d_6$), δ 1.24 (s, 9 H), 2.66 (s, 3 H), 5.37 (s, 2 H), 5.43 (s, 1H), 7.44 (d, J=8.4, 1 H), 7.97 (s, 2 H), 8.05 (s, 1 H), 8.28 (d, J=8.4, 1 H); MS (ESI) m/z: 281.2 (M+H$^+$).

EXAMPLE B15

To a suspension of KCN (1.90 g, 29.1 mmol) in MeOH (35 mL) was added dropwisely 3-bromo-1,1,1-trifluoropropan-2-one oxime (5.00 g, 24.3 mmol) in MeOH (72 mL) at RT. The reaction mixture was stirred at RT for 3 hours. The solution was evaporated and then the residue was dissolved in EtOAc and stirred at RT. The solid was filtered and the filtrate was evaporated to obtain the crude product. The crude product was purified by silica gel column chromatography (Biotage: 25M, 10% to 60% EtOAc/hexane: 550 mL) to obtain 3-(trifluoromethyl)isoxazol-5-amine (1.38 g, 37% yield). MS (ESI) m/z: 153.0 (M+H$^+$).

Using general method G, 3-(trifluoromethyl)isoxazol-5-amine (1.38 g, 9.1 mmol) and isopropenyl chloroformate (1.1 g, 9.1 mmol) in presence of LiHMDS (1.0M, 18 mL, 18.2 mmol) were combined to afford prop-1-en-2-yl 3-(trifluoromethyl)isoxazol-5-ylcarbamate (0.82 g, 38% yield.). $^1$H NMR (400 MHz, DMSO-$d_6$): δ 12.3 (s, 1H), 6.48 (s, 1H), 4.83 (m, 1H), 4.80 (m, 1H), 1.93 (s, 3H); MS (ESI) m/z: 237.0 (M+H$^+$).

EXAMPLE B16

Potassium t-butoxide (0.29 g, 2.5 mmol) was dissolved in DMSO (5 mL) and to this solution was added Example B37 (0.50 g, 2.5 mmol) in small portions under argon atmosphere. After 15 minutes, 2-iodoethane (0.31 mL, 3.8 mmol) was added slowly. After stirring for 1.5 hours, LC-MS showed disappearance of starting material and formation of product. Sat. $NH_4Cl$ solution was added, product was extracted with ethyl acetate (2×40 ml), the combined organic layers were washed with brine, dried ($Na_2SO_4$) and concentrated to afford crude product. The crude product was purified by silica gel column chromatography (Biotage: 25M, 5% to 35% EtOAc/hexane: 340 mL, 35% to 100% EtOAc/hexane: 300 mL) to afford ethyl 3-tert-butyl-1-ethyl-1H-pyrazole-5-carboxylate (0.35 g, 61% yield). MS (ESI) m/z; 225.3 (M+H$^+$).

To a solution of ethyl 3-tert-butyl-1-ethyl-1H-pyrazole-5-carboxylate (0.35 g, 1.6 mmol) in a mixture of ethanol:dioxane:water (1:1:1, 6 mL) was added lithium hydroxide (0.15 g, 6.2 mmol). The reaction mixture was stirred overnight at RT. The solution diluted with EtOAc (50 mL) and 5% citric acid (50 mL). The organic phase separated, washed with brine (20 mL), dried ($Na_2SO_4$) and evaporated under reduced pressure to afford 3-tert-butyl-1-ethyl-1H-pyrazole-5-carboxylic acid (0.30 g, 98% yield) as a yellow solid. $^1$H NMR (400 MHz, DMSO-$d_6$): δ 6.64 (s, 1H), 4.40 (q, J=7.2 Hz, 2H), 1.27 (t, J=7.2 Hz, 3H), 1.22 (s, 9H); MS (ESI) m/z: 197.3 (M+H$^+$).

EXAMPLE B17

Potassium t-butoxide (2.6 g, 23 mmol) was dissolved in DMSO (10 mL) and to this solution was added Example B37 (4.5 g, 23 mmol) in small portions and stirred under Ar for 15 min. To this solution was added t-butyl-bromoacetate (5.4 g, 28 mmol) slowly at 0° C. with stirring for 45 min at RT. Sat. $NH_4Cl$ solution was added and product was extracted with ethylacetate (3×50 mL). The combined organic layers were washed with brine, dried ($Na_2SO_4$) and concentrated to afford (7.0 g) coupled product as a pasty mass. The above pasty mass was dissolved in TFA (10 mL) and stirred for 3 h at RT. Solvents were removed, to the residue water (100 mL) was added and product was extracted with DCM (3×50 ml). The combined organic extracts were washed with brine solution, dried ($Na_2SO_4$) and concentrated to yield 2-(3-tert-butyl-5-(ethoxycarbonyl)-1H-pyrazol-1-yl)acetic acid (5.8 gm, 100%) as a pasty mass. $^1$H NMR (400 MHz, Acetone-4): δ 6.78 (s, 1H), 5.25 (s, 2H), 4.30 (q, J=7.2 Hz, 2H), 1.35-1.30 (m, 12H); MS (ESI) m/z: 255.2 (M+H$^+$).

To a solution of acid (0.41 g, 1.6 mmol) in DMF (5 mL) was added PyBop (0.84 g, 1.6 mmol), DIEA (0.42 g, 3.2 mmol) and dimethylamine hydrochloride (0.26 g, 3.2 mmol). After stirring the mixture for 1 h at RT, water (50 mL) was added, and the product was extracted with ethylacetate (2×30 ml). The combined organic layers were washed with 3M HCl solution (1×30 mL), dried ($Na_2SO_4$) and concentrated to afford crude product which was purified by chromatography (EtOAc/DCM) to afford ethyl 3-tert-butyl-1-(2-(dimethylamino)-2-oxoethyl)-1H-pyrazole-5-carboxylate (0.25 g, 55%) as a thick paste. $^1$H NMR (400 MHz, Acetone-$d_6$): δ 6.73 (s, 1H), 5.35 (s, 2H), 4.27 (q, J=7.2 Hz, 2H), 3.15 (s, 3H), 2.90 (s, 3H), 1.33-1.28 (m, 12H); MS (ESI) m/z: 282.3 (M+H$^+$).

To a solution of ethyl 3-tert-butyl-1-(2-(dimethylamino)-2-oxoethyl)-1H-pyrazole-5-carboxylate (1.16 g, 4 mmol) in THF (10 mL) was added 1M borane/THF (12 ml, 12 mmol) at 0° C. under Ar and stirring continued for 12 h at 60° C. The mixture was cooled to 0° C., quenched with 3M HCl solution and heated to 60° C. for 30 min. The mixture was basified with solid $NaHCO_3$ to pH around 8 and the product was extracted with $CHCl_3$ (2×30 ml). The combined organics were washed with brine, dried ($Na_2SO_4$) and concentrated in vacuo provided crude product. Purification by silica gel chromatography provided ethyl 3-tert-butyl-1-(2-(dimethylamino)ethyl)-1H-pyrazole-5-carboxylate as a pasty mass (0.47 g, 43% yield). $^1$H NMR (400 MHz, MeOH-$d_4$): δ 6.73 (s, 1H), 4.66 (t, J 6.8 Hz, 2H), 4.35 (q, J=7.2 Hz, 2H), 2.80 (t, J= 7.2 Hz, 2H), 2.34 (s, 6H), 1.38 (t, J=7.2 Hz, 3H), 1.31 (s, 9H); MS (ESI) m/z: 268.2 (M+H$^+$).

To a solution of ethyl 3-tert-butyl-1-(2-(dimethylamino)ethyl)-1H-pyrazole-5-carboxylate (0.47 g, 1.8 mmol) in THF (10 mL) was added aqueous LiOH (0.22 g, 5.3 mmol, 5 mL) and mixture was stirred for 16 h at RT. Solvents were removed, the thick liquid was diluted with water (5 mL) and acidified with 50% aq. acetic acid solution to pH 5-6. The product was extracted with EtOAc (2×50 ml) and the combined organics were washed with brine, dried ($Na_2SO_4$) and concentrated in vacuo to afford 3-tert-butyl-1-(2-(dimethylamino)ethyl)-1H-pyrazole-5-carboxylic acid as a pasty mass (0.12 g, 29% yield). $^1$H NMR (400 MHz, DMSO-$d_6$): δ 6.56 (s, 1H), 4.66 (t, J=6.0 Hz, 2H), 3.17 (t, J=6.0 Hz, 2H), 2.53 (s, 6H), 1.17 (s, 9H); MS (ESI) m/z: 240.3 (M+H$^+$).

EXAMPLE B18

3-t-butylisoxazol-5-amine was prepared according to the method disclosed in WO 99/32111, 0.250.

EXAMPLE B19

A mixture of 1,1,3,3-tetramethoxypropane (37 g, 226 mmol), tert-butyl-hydrazine hydrochloride (28 g, 226 mmol) and conc HCl (60 mL, 720 mmol) in EtOH (300 mL) was heated at reflux overnight. The mixture was poured into water and the resulting mixture was extracted with ether. The combined organics were washed with brine, dried (MgSO$_4$) and concentrated in vacuo to give 1-tert-butyl-1H-pyrazole (25 g, 89% yield). $^1$H NMR (400 MHz, DMSO-$d_6$): δ7.73 (s, 1 H), 7.38 (s, 1 H), 6.17 (s, 1 H), 1.47 (s, 9 H); MS (ESI) m/z: 125.1[M+H]$^+$.

HNO$_3$ (11.7 g, 185 mmol) was added dropwise to a mixture of 1-tert-butyl-1H-pyrazole (23 g, 185 mmol) in conc. H$_2$SO$_4$ (30 mL) at 0° C. The resulting mixture was stirred at 0° C. for 30 min and was poured onto crashed ice. The aqueous mixture was extracted with EtOAc. The combined organics were washed with brine, dried (MgSO$_4$) and concentrated in vacuo to give 1-tert-butyl-4-nitro-1H-pyrazole (20 g, 64% yield). $^1$H NMR (400 MHz, DMSO-$d_6$): δ8.85 (s, 1H), 8.23 (s, 1 H), 1.52 (s, 9 H).

A mixture of 1-tert-butyl-4-nitro-1H-pyrazole (20 g, 118 mmol) and Pd/C (10%, 2 g, 1.9 mmol) in MeOH (100 mL) was hydrogenated under 1 atmosphere of hydrogen at RT for 16 h. The reaction mixture was filtered and the filtrate was concentrated in vacuo to give 1-tert-butyl-1H-pyrazol-4-ylamine (15 g, 93%). $^1$H NMR (400 MHz, DMSO-$d_6$): δ 7.08 (s, 1 H), 6.90 (s, 1H), 3.70 (s, 2 H), 1.41 (s, 9 H); MS (ESI) m/z: 140.1 [M+H]$^+$.

EXAMPLE B20

Prepared according to the method disclosed in WO 99/32111.

EXAMPLE B21

4,4,4-Trifluoro-3-oxo-butyronitrile and phenylhydrazine were combined by the procedure of Example B22 to provide 1-phenyl-3-(trifluoromethyl)-1H-pyrazol-5-amine.
$^1$H-NMR (400 MHz, DMSO-$d_6$) δ 7.59-7.50 (m, 4 H), 7.42 (m, 1 H), 5.78 (s, 1 H), 5.73 (br s, 2 H).

EXAMPLE B22

A solution of ethyl trifluoroacetate (14.2 g, 0.1 mol) and anhydrous acetonitrile (5.0 g, 0.12 mol) in THF (100 mL) was added dropwise to a suspension of NaH (60%, 6.0 g, 0.15 mol) in THF (100 mL) at 80° C. The resulting mixture was heated to reflux overnight, and then cooled to RT. The reaction mixture was concentrated in vacuo and the residue was diluted with EtOAc and 10% aq HCl. The organic layer was washed with water and brine, dried (MgSO$_4$) and concentrated in vacuo to yield crude 4,4,4-Trifluoro-3-oxo-butyronitrile (15 g), which was used without further purification.

A solution of methylhydrazine (5.0 g, 60 mmol) and 4,4,4-trifluoro-3-oxo-butyronitrile (9.8 g, 71 mmol) in EtOH (50 mL) was treated with conc. HCl (5 mL) and the resultant mixture was heated to reflux overnight. The solvent was removed in vacuo and the crude product was dissolved in EtOAc washed with saturated aq. Na$_2$CO$_3$ solution until the washings were pH 8. The organics were concentrated and purified by pre-HPLC to provide 2-methyl-5-trifluoromethyl-2H-pyrazol-3-ylamine (2.07 g, 21% yield). $^1$HNMR (300 MHz, DMSO-$d_6$), δ 5.57 (s, 1 H), 5.54 (br s, 2 H), 3.55 (s, 3 H); MS (ESI) m/z: 166.1 (M+H$^+$).

EXAMPLE B23

Example B37 (3.3 g, 17 mmol) was added to a solution of potassium t-butoxide (1.9 g, 17 mmol) in DMSO (40 mL) and the reaction was stirred under argon for 15 min. 2-Bromopropane (2.9 g, 24 mmol) was added and the reaction was stirred 2 h at RT. Water was then added and the solution was extracted with EtOAc (3×50 mL). The organics were washed with water and brine, dried (MgSO$_4$) and concentrated under reduced pressure. Chromatography provided ethyl 3-tert-butyl-1-isopropyl-1H-pyrazole-5-carboxylate (1.65 g, 41% yield). $^1$H NMR (400 MHz, DMSO-$d_6$): 6.64 (s, 1 H), 5.31 (m, 1 H), 4.22 (q, J=7.2 Hz, 2H), 1.37 (d, J=6.4 Hz, 6 H), 1.24 (t, J=7.2 Hz, 3 H), 1.14 (s, 9 H). MS (ESI) m/z: (M+H$^+$) 239.2.

A solution comprised of LiOH (2.3 g, 9 mmol) in water (12 mL) was added to a solution of ethyl 3-tert-butyl-1-isopropyl-1H-pyrazole-5-carboxylate (2.3 g, 9 mmol) in THF (24 mL) and the reaction mixture was heated to 50° C. overnight. The reaction was concentrated under reduced pressure and diluted with water. The solution pH was adjusted to pH 5 and the solution was extracted with EtOAc. The organics were washed with water and brine, dried (MgSO$_4$) and concentrated under reduced pressure to give 3-tert-butyl-1-isopropyl-1H-pyrazole-5-carboxylic acid (1.85 g, 93% yield). $^1$H NMR (300 MHz, DMSO-$d_6$): 6.62 (s, 1 H), 5.37 (m, 1 H), 1.35 (d, J=6.6 Hz, 6 H), 1.22 (s, 9 H). MS (ESI) m/z: (M+H$^+$) 211.2

To a stirring solution of 3-tert-butyl-1-isopropyl-1H-pyrazole-5-carboxylic acid (7.92 g, 38 mmol) and triethylamine (5.7 g, 56 mmol) in 1,4-dioxane (80 mL) was added diphenylphosphoryl azide (12 g, 44 mmol). The resultant reaction mixture was stirred 30 min at RT. 2,2,2-Trichloroethanol (78 g, 527 mmol) was added and the reaction was heated to 100° C. After 4 h, the completed reaction was diluted with brine and extracted with EtOAc. The organic layer was washed with water, dried (MgSO$_4$), and concentrated in vacuo. Purification of the residue by chromatography provided 2,2,2-trichloroethyl 3-tert-butyl-isopropyl-1H-pyrazol-5-ylcarbamate (4.0 g, 31% yield). $^1$H-NMR (400 MHz, DMSO-$d_6$): 9.85 (s, 1 H), 5.94 (s, 1 H), 4.90 (s, 2 H), 4.37 (m, 1 H), 1.27 (d, J=7.2 Hz, 6 H), 1.18 (s, 9 H). MS (ESI) m/z: 356.1 (M+H$^+$).

EXAMPLE B24

4-Fluorophenylboronic acid (1.0 g, 7.15 mmol) was reacted with Example B38 (1.56 g, 10.7 mmol) in presence of copper (II) acetate (1.95 g, 10.7 mmol) at 80° C. for 3 hours in pyridine (15 mL) to provide the product, ethyl 1-(4-fluorophenyl)-3-isopropyl-1H-pyrazole-5-carboxylate (0.95 g, 48% yield). $^1$HNMR (400 MHz, DMSO-$d_6$): δ 7.45 (m, 2H), 7.30 (m, 2H), 6.9 (s, 1H), 4.17 (q, J=6 Hz, 2H), 2.9 (m, 1H), 1.25 (d, J=6 Hz, 6H), 1.18 (d, J=6 Hz, 3H); MS (ESI) m/z: 277.0 (M+H$^+$). The ethyl ester (0.9 g, 3.3 mmol) was hydrolyzed with lithium hydroxide monohydrate (0.67 g, 16.0 mmol) in a THF/ethanol/water mixture to provide 1-(4-fluorophenyl)-3-isopropyl-1H-pyrazole-5-carboxylic acid (0.71 g, 88% yield). $^1$H NMR (400 MHz, DMSO-$d_6$): δ 7.47 (m, 2H), 7.30 (m, 2H), 6.89 (s, 1H), 2.97 (m, 1H), 1.25 (d, J=6 Hz, 6H), 1.17 (t, J=6 Hz, 3H); MS (ESI) m/z: 249.0 (M+H$^+$).

EXAMPLE B25

3-Cyanophenylboronic acid (0.4 g, 2.74 mmol), was reacted with Example B38 (0.5 g, 2.74 mmol) in the presence of copper (II) acetate (0.5 g, 2.74 mmol) at 80° C. for 3 hours in pyridine (3.5 ml) to provide ethyl 1-(3-cyanophenyl)-3-isopropyl-1H-pyrazole-5-carboxylate (0.18 g, 24% yield). $^1$H NMR (400 MHz, DMSO-d$_6$): δ 8.06 (m, 1H), 7.92 (m, 1H), 7.83 (m, 1H), 7.69 (m, 1H), 7.02 (s, 1H), 4.20 (q, J=6 Hz, 1H), 3.00 (m, 1H), 1.26 (d, J=6 Hz, 6H), 1.20 (t, J=6 Hz, 3H); MS (ESI) m/z: 284.2 (M+H$^+$). Hydrolysis of the ester with lithium hydroxide monohydrate provided 1-(3-cyanophenyl)-3-isopropyl-1H-pyrazole-5-carboxylic acid in 94% yield. $^1$H NMR (400 MHz, DMSO-d$_6$): δ 8.02 (m, 1H), 7.89 (m, 1H), 7.83 (m, 1H), 7.67 (m, 1H), 6.97 (s, 1H), 3.00 (m, 1H), 1.26 (q, J=6 Hz, 6H); MS (ESI) m/z: 256.0 (M+H$^+$).

EXAMPLE B26

6-(2-(Diphenylmethylene)hydrazinyl)quinoline (4.0 g, 12.3 mmol) and 4-methyl-3-oxo-pentanenitrile (1.5 g, 13.5 mmol) were combined by the procedure of Example B8 (method 2) to give 5-isopropyl-2-quinolin-6-yl-2H-pyrazol-3-ylamine (1.1 g, 35.5% yield). $^1$H NMR (400 MHz, CDCl$_3$) δ 8.93 (dd, J=4.4, 1.6 Hz, 1 H), 8.21-8.18 (m, 2 H), 8.05-8.02 (m, 2H), 7.44 (dd, J=8.4, 4.4 Hz, 1 H), 5.56 (s, 1 H), 3.85 (br s, 2 H), 2.97 (m, 1 H), 1.31 (d, J=6.8 Hz, 6 H); MS (ESI) m/z: 253.2 (M+H$^+$).

EXAMPLE B27

To a 0° C. solution of 6-methylpyridin-3-amine (12 g, 0.11 mol) in cone HCl (40 mL) was added a solution of NaNO$_2$ (7.7 g, 110 mmol) in water (30 mL) and the resulting mixture was stirred at 0° C. for 1 h. A solution of SnCl$_2$ (50 g, 0.22 mol) in cone HCl (60 mL) was added at 0° C. The reaction solution was warmed to RT and stirred for 2 hours. The precipitate was collected by filtration to provide 5-hydrazinyl-2-methylpyridine hydrochloride (10 g, 57% yield) which was used without further purification.

A mixture of 5-hydrazinyl-2-methylpyridine hydrochloride (5.0 g, 31 mmol) and 4,4,4-trifluoro-3-oxo-butyronitrile (9.0 g, 65 mmol) in ethanol (50 mL) was treated with cone HCl (5.0 mL, 60 mmol) and the resultant mixture was heated to reflux overnight. The solvent was removed in vacuo and the residue was dissolved in EtOAc and neutralized with saturated Na$_2$CO$_3$ solution. The organic layer was dried (Na$_2$SO$_4$), concentrated in vacuo and purified by pre-HPLC to give 2-(6-methyl-pyridin-3-yl)-5-trifluoromethyl-2H-pyrazol-3-ylamine (1.3 g, 10% yield over 2 steps). $^1$HNMR (400 MHz, CDCl$_3$) δ 9.17 (d, J=1.6 Hz, 1 H), 8.40 (dd, J=8.4, 2.4 Hz, 1 H), 7.62 (d, J=8.4 Hz, 1 H), 5.97 (s, 1 H), 2.80 (s, 3 H); MS (ESI) m/z: 243.2 (M+H$^+$).

EXAMPLE B28

A solution of ethyl cyclopentanecarboxylate (prepared by esterification of commercially available cyclopentantecarboxylic acid, 30 g, 0.21 mol) and acetonitrile (10.1 g, 0.25 mol) in dry THF (80 mL) was added dropwise to a suspension of NaH (12.5 g, 0.31 mol) in dry THF (80 mL) and the resulting mixture was refluxed overnight. The reaction mixture was concentrated under reduced pressure and partitioned between water and EtOAc. The aqueous layer was separated, adjusted to pH 8 and extracted with EtOAc. The combined extracts were washed with brine, dried (MgSO$_4$), and concentrated to give 3-cyclopentyl-3-oxopropanenitrile (26 g, 90% yield), which was used in the next step without further purification. $^1$H NMR (400 MHz, DMSO-d$_6$): δ4.06 (s, 2 H), 2.92 (m, 1 H), 1.41-1.77 (m, 8 H).

Hydroxylamine hydrochloride (6 g, 86 mmol) and 3-cyclopentyl-3-oxopropanenitrile (10 g, 73 mmol) were added to a solution of NaOH (9 g, 225 mmol) in water (100 mL) and the resulting mixture was heated at 50° C. overnight. The precipitate was collected by filtration, washed with water, and dried to give 3-cyclopentylisoxazol-5-amine (6.7 g, 61% yield). $^1$H NMR (400 MHz, DMSO-d$_6$): δ 6A3 (s, 2 H), 4.77 (s, 1 H), 2.84 (m, 1 H), 1.87-1.51(m, 8 H); MS (ESI) m/z: 153.1 (M+H$^+$).

EXAMPLE B29

A solution of nBuLi in hexanes (242 mL, 387 mmol) was added to a −78° C. solution of thisopropylamine (39.1 g, 387 mmol) in anhydrous THF (300 mL) and the resultant mixture was stirred for 30 min at −78° C. A solution of ethyl cyclopentanecarboxylate (50 g, 352 mmol) in anhydrous THF (150 mL) was added dropwise into the mixture and the reaction mixture was stirred at −78° C. for 1 h. Iodomethane (79.2 g, 558 mmol) was added dropwise and the resulting mixture was warmed to RT and stirred overnight The mixture was poured into water and extracted with ethyl ether. The combined extracts were washed with brine, dried (MgSO$_4$) and concentrated in vacuo to give ethyl 1-methylcyclopentanecarboxylate (47 g, 85%). $^1$H NMR (300 MHz, DMSO-d$_6$): δ 4.03 (q, J=7.2 Hz, 2 H), 1.37-2.03 (m, 8 H), 1.15-1.12 (m, 6H).

Ethyl 1-methylcyclopentanecarboxylate (47 g, 301 mmol), acetonitrile (14.5 g, 363 mmol), NaH (18 g, 450 mmol), NaOH (6.8 g, 170 mmol) and hydroxylamine hydrochloride (4 g, 57 mmol) were sequentially combined by a procedure analogous to Example B28 to provide 3-(1-methylcyclopentyl)isoxazol-5-amine (7 g, 70% yield over 2 steps). $^1$H NMR (400 MHz, DMSO-d$_6$): δ 6.41 (s, 2 H), 4.81 (s, 1 H), 1.91-1.86 (m, 2 H), 1.67-1.48 (m, 6 H), 1.19 (s, 3H); MS (ESI) m/z: 167.1 (M+H$^+$).

EXAMPLE B30

To a suspension of Na$_2$CO$_3$ (36 g, 339 mmol) in CH$_2$Cl$_2$ (300 mL) was added 1-t-butyl-1H-pyrazole from Example B19 (21 g, 170 mmol) and Br$_2$ (9 mL), and the resulting mixture was stirred at RT overnight. The solid was removed by filtration and the filter cake was washed with CH$_2$Cl$_2$. The filtrates were washed with water and brine, dried (MgSO$_4$), and concentrated to give crude 4-bromo-1-J-butyl-1H-pyrazole (29 g, 85%), used without further purification. $^1$H NMR (300 MHz, CDCl$_3$): δ 7.49 (s, 1 H), 7.45 (s, 1 H), 1.53 (s, 9 H); MS (ESI) m/z: 203 [M+H]$^+$.

To a −78° C. solution of 4-bromo-1-t-butyl-1H-pyrazole (15 g, 74.3 mmol) in anhydrous THF (100 mL) was added n-BuLi (2.5 M in hexane, 53 mL, 132 mmol) under N$^2$, and the resulting mixture was stirred at −78° C. for 30 min. Excess dry ice was added at −78° C., and the mixture was warmed slowly to RT and stirred overnight. The reaction was concentrated in vacuo, water was added and the pH was adjusted to pH 3 by the addition of 2N aq HCl. The aqueous solution was extracted with EtOAc. The extracts were washed with brine, dried (MgSO$_4$) and concentrated in vacuo. The residue was recrystallized (EtOAc-pet. ether) to give 1-t-butyl-1H-pyrazole-4-carboxylic acid (8.0 g, 67% yield). $^1$H NMR (300 MHz, CDCl$_3$): δ 8.10 (s, 1 H), 8.03 (s, 1 H), 1.64 (s, 9 H); MS (ESI) m/z: 168.9 [M+H]$^+$.

EXAMPLE B31

Cyclopentyl-3-oxopropanenitrile (8 g, 0.058 mol), methylhydrazine (40% aqueous, 32.5 g, 0.29 mol) and conc. HCl (40 mL, 0.48 mol) were combined in EtOH (200 mL) and the reaction mixture was heated at reflux overnight. The mixture was concentrated in vacuo, poured into water and washed with EtOAc (3×100 mL). The aqueous portion was basified to pH 8 with aq NaHCO$_3$ and the mixture was extracted with EtOAc (3×100 mL). The extracts were washed with brine, dried (Na$_2$SO$_4$) and concentrated in vacuo. Crystallization from EtOAc afforded 5-cyclopentyl-2-methyl-2H-pyrazol-3-ylamine (2.1 g, 22% yield). $^1$HNMR (400 MHz, DMSO-d$_6$): δ 5.05 (s, 1 H), 4.95 (s, 2 H), 3.39 (s, 3 H), 2.75 (m, 1 H), 1.78 (m, 2 H), 1.62-1.50 (m, 6 H); MS (ESI) m/z: 166.2 [M+H]$^+$.

EXAMPLE B32

In a mixture of saturated sodium bicarbonate:toluene:ethanol (1:2:1) (20 mL) was dissolved methyl 2-tert-butyl-4-chloropyrimidine-5-carboxylate (2.71 g, 11.85 mmol), phenylboronic acid (2.88 g, 23.7 mmol) and to this was added tetrakis-(triphenylphosphine)palladium(0) (300 mg). The reaction stirred at 75° C., under Ar, overnight. After dilution with ethyl acetate (75 mL) and water (75 mL), the mixture was filtered through Celite and the organic phase separated. The organic phase was washed with 5% citric acid (75 mL), brine (75 mL), dried (Na$_2$SO$_4$) and evaporated at reduced pressure to give a semi solid/oil. The solid was purified by chromatography (Biotage Si-40 column, 5-30% ethyl acetate/Hex—900 mL) to give a clear thick oil, which solidified to a white solid identified as methyl 2-tert-butyl-4-phenylpyrimidine-5-carboxylate (2.58 g, 81% yield). $^1$H NMR (300 MHz, DMSO-d$_6$), δ 1.39 (s, 9 H), 3.70 (s, 3 H), 7.49-7.52 (m, 3 H), 7.61-7.63 (m, 2 H), 9.04 (s, 1 H); MS (ESI) m/z: 271.3 (M+H$^+$).

In a 1:1:1 mix of methanol:dioxane:water (15 mL) was placed methyl 2-tert-butyl-4-phenylpyrimidine-5-carboxylate (2.58 g, 9.54 mmol) and lithium hydroxide hydrate (1.20 g, 28.6 mmol). The solution was stirred at RT overnight. The mix was diluted with ethyl acetate (70 mL) and washed with 5% citric acid (100 mL). The organic phase washed with brine, dried (Na$_2$SO$_4$) and evaporated at reduced pressure to give a white solid, identified as 2-tert-butyl-4-phenylpyrimidine-5-carboxylic acid (2.31 g, 94% yield). $^1$H NMR (300 MHz, DMSO-d$_6$), δ 1.38 (s, 9 H), 7.48-7.50 (m, 3 H), 7.64-7.67 (m, 2 H), 9.01 (s, 1 H), 12.75 (s, 1 H); MS (ESI) m/z: 257.3 (M+H$^+$).

EXAMPLE B33

In ethanol (25 mL) was placed pivalamidine hydrochloride (1.138 g, 8.33 mmol). This was treated with 21% sodium ethoxide in ethanol (2.70 g, 8.33 mmol) and stirred at RT for 15 min. To this was added ethyl 2-(ethoxymethylene)-4,4,4-trifluoro-3-oxobutanoate (2.00 g, 8.33 mmol) in ethanol (10 mL) and stirred at RT overnight. Tire mix was warmed to reflux for 1 hr, cooled to RT and evaporated at reduced pressure to give a slurry. The slurry was dissolved in a mix of ethyl acetate (75 mL) and 5% citric acid (75 mL). The organic phase was washed with brine, dried (Na$_2$SO$_4$) and evaporated at reduced pressure to give a thick oil identified as ethyl 2-tert-butyl-4-(trifluoromethyl)pyrimidine-5-carboxylate (1.67 g, 72% yield). MS (ESI) m/z: 277.0 (M+H$^+$).

EXAMPLE B34

Using a procedure analogous to Example B32, methyl 2-tert-butyl-4-chloropyrimidine-5-carboxylate (0.849 g, 3.71 mmol), N-methylindole-5-boronic acid (1.30 g, 7.43 mmol) and tetrakis-(triphenylphosphine)palladium(0) (86 mg) were combined to give methyl 2-tert-butyl-4-(1-methyl-1 H-indol-5-yl)pyrimidine-5-carboxylate (898 mg, 74% yield). $^1$H NMR (300 MHz, DMSO-d$_6$): δ 1.40 (s, 9 H), 3.70 (s, 3 H), 3.82 (s, 3 H), 6.57 (s, 1 H), 7.41-7.44 (m, 2 H), 7.53 (d, J=8.6 Hz, 1 H), 7.92 (s, 1 H), 8.94 (s, 1 H); MS (ESI) m/z: 324.0 (M+H$^+$).

Using a procedure analogous to Example B32, methyl 2-tert-butyl-4-(1-methyl-1 H-indol-5-yl)pyrimidine-5-carboxylate (898 mg, 2.78 mmol) and lithium hydroxide hydrate (466 mg, 11.11 mmol) were combined to give 2-tert-butyl-4-(1-methyl-1 H-indol-5-yl)pyrimidine-5-carboxylic acid (833 mg, 97% yield). $^1$H NMR (300 MHz, DMSO-d$_6$): δ 1.39 (s, 9 H), 3.82 (s, 3H), 6.54 (s, 1 H), 7.40 (s, 1 H), 7.52 (m, 2 H), 7.94 (s, 1 H), 8.91 (s, 1 H), 12.70 (s, 1 H); MS (ESI) m/z: 310.0 (M+H$^+$).

EXAMPLE B35

A solution of anhydrous acetonitrile (2.3 g, 56 mmol) in THF (100 mL) was added dropwise at 80° C. to a mixture of NaH (60%, 2.8 g, 70 mmol) and methyl 2-cyano-2-methyl-propanoate (6 g, 47 mmol) in THF (100 mL). The resultant reaction mixture was heated at reflux for 8 hours. The solvent was removed in vacuo and the residue was diluted with EtOAc and washed with 10% HCl, water and brine. The organics were dried (MgSO$_4$) and concentrated in vacuo to obtain crude 2,2-dimethyl-3-oxopentanedinitrile (4 g), which was used for the next step reaction without further purification.

A solution of 2,2-dimethyl-3-oxopentanedinitrile (4.0 g, 29 mmol) and phenyl-hydrazine HCl salt (4.6 g, 31 mmol) in EtOH (50 mL) was treated with 2 N HCl solution (10 mL, 20 mmol). The reaction mixture was heated at reflux for 4 h. After cooling down, the mixture was neutralized with NaHCO$_3$ to pH 7-8 and then extracted with EtOAc (3×100 mL). The organics were concentrated and the residue was purified by chromatography to give 2-(5-amino-1-phenyl-1 H-pyrazol-3-yl)-2-methylpropanenitrile (3.5 g, 33% yield, 2 steps). $^1$HNMR (300 MHz, DMSO-d$_6$): δ 7.56-7.31 (m, 5 H), 5.52 (s, 1 H), 5.45 (br s, 2 H), 1.61 (s, 6 H); MS (ESI) m/z: 227.1(M+H$^+$).

A solution of 2-(5-amino-1-phenyl-1 H-pyrazol-3-yl)-2-methyl-propionitrile (1.0 g, 7.4 mmol) and aq NaOH (2 M, 11 mL, 22 mmol) in EtOH (10 mL) was heated to 70° C. for 12 h. The reaction mixture was partitioned between ether and water and the aqueous solution was acidified with HCl to pH 4-5. The aqueous was extracted with EtOAc (3×50 mL) and the extracts were concentrated in vacuo to give crude 2-(5-amino-1-phenyl-1 H-pyrazol-3-yl)-2-methylpropanoic acid (0.7 g, 39% yield) which was used without further purification.

Cone. H$_2$SO$_4$ (0.5 mL) was added to a solution of 2-(5-amino-1-phenyl-1 H-pyrazol-3-yl)-2-methylpropanoic acid (0.7 g, 28.5 mmol) in EtOH (10 mL) and the reaction was heated at 45° C. for 2 h. The reaction solution was neutralized with aq NaHCO$_3$ and then extracted with EtOAc (3×20 mL). The combined extracts were washed with aq NaHCO$_3$ solution, dried (Na$_2$SO$_4$), and concentrated in vacuo to give ethyl 2-(5-amino-1-phenyl-1 H-pyrazol-3-yl)-2-methylpropanoate (710 mg, 91% yield). $^1$H NMR (400 MHz, DMSO-d$_6$): δ 7.62 (d, δ 7.6 Hz, 2 H), 7.52 (t, J=7.6 Hz, 2 H), 7.35 (t, J=7.6 Hz, 1 H), 5.47 (s, 1 H), 5.35 (br s, 2 H), 4.12 (q, J=7.2 Hz, 2 H), 1.50 (s, 6 H), 1.22 (t, J=7.2 Hz, 3 H); MS (ESI) m/z: 274.1(M+H$^+$).

EXAMPLE B36

A solution of 2,2-dimethyl-3-oxo-pentanedinitrile (9 g, 66 mmol) and methyl-hydrazine (3 g, 66 mmol) in EtOH (100 mL) was treated with cone HCl (16.5 mL, 198 mmol) and the resulting mixture was refluxed overnight. The solvent was removed under reduced pressure and the residue was purified by chromatography to give 2-(5-amino-1-methyl-1 H-pyrazol-3-yl)-2-methylpropanenitrile (2.7 g, 25% yield), $^1$H NMR (300 MHz, CDCl$_3$): δ 5.56 (s, 1 H), 3.63 (s, 3 H), 1.67 (s, 6 H); MS (ESI) m/z: 165.2 [M+H]$^+$.

A mixture of 2-(5-amino-1-methyl-1 H-pyrazol-3-yl)-2-methylpropanenitrile (1.4 g, 8.5 mmol) in EtOH (30 mL) was treated with cone. H$_2$SO$_4$ (3 mL) and the resulting mixture was refluxed for 10 days. The reaction mixture was neutralized with saturated aq NaHCO$_3$ solution, and the mixture was extracted with EtOAc. The organics were washed with brine, dried (MgSO$_4$) and concentrated in vacuo. Recrystallization (EtOAc/petroleum ether) provided ethyl 2-(5-amino-1-methyl-1 H-pyrazol-3-yl)-2-methylpropanoate (0.8 g, 44% yield). $^1$H NMR (300 MHz, DMSO-d$_6$): δ5.13 (s, 1 H), 5.04 (s, 2 H), 4.00 (q, J=6.9 Hz, 2 H), 3.41 (s, 3 H), 1.11 (t, J=6.9 Hz, 6 H); MS (ESI) m/z: 212.0 [M+H]$^+$.

EXAMPLE B37

Sodium metal (13.8 g, 0.5 mol) was added portionwise to ice-cold anhydrous EtOH (700 mL). After complete dissolution of the Na, a mixture of 3,3-dimethylbutan-2-one (50 g, 0.5 mol) and oxalic acid diethyl ester (77 ml, 0.5 mol) was added drop-wise. The reaction mixture was stirred in ice-salt bath and until TLC indicated completion of the reaction. Acetic acid (38.1 ml, 0.5 mol) was added and the mixture was stirred at RT for 30 min. The reaction mixture was cooled in an ice-salt bath and treated with hydrazine hydrate (29.4 g, 0.5 mol). After complete addition, the mixture was warmed to RT and stirred until judged complete by TLC. The reaction mixture was concentrated under reduced pressure and re-dissolved in EtOAc. The EtOAc solution was washed with NaHCO$_3$, brine and water, dried (MgSO$_4$) and concentrated in vacuo. The resultant solid was washed with cold petroleum ether to give ethyl 3-tert-butyl-1 H-pyrazole-5-carboxylate (49 g, 50% yield over two steps) as a white solid. $^1$H NMR (400 MHz, CDCl$_3$): δ 6.65 (s, 1 H), 4.38 (q, J=6.8 Hz, 2 H), 1.39 (t, J=6.8 Hz, 3 H), 1.35 (s, 1H); MS (ESI) m/z: 197.2 (M+H$^+$).

EXAMPLE B38

Using a procedure analogous to Example B37, 3-methylbutan-2-one (100 g, 1.16 mol) was converted to ethyl 3-isopropyl-1 H-pyrazole-5-carboxylate (90 g, 42% yield, two steps) as an off-white solid. $^1$H NMR (300 MHz, CDCl$_3$): δ 12.00 (s, 1 H), 6.57 (s, 1 H), 4.30 (q, J=7.2 Hz, 2 H), 3.00 (m, 1 H), 1.46 (t, J=7.2 Hz, 3 H), 1.28 (d, J=6.8 Hz, 6 H); MS (ESI) m/z: 183.3 (M+H$^+$).

EXAMPLE B39

Nitric acid (2 mL) was added to a stirred solution of indazole (5.0 g, 42 mmol) in acetic acid (40 mL) at 0° C. The resulting mixture was stirred at RT for 30 min. Acetic anhydride (6 mL) was added in one portion and the mixture was stirred at RT overnight. The solvent was removed under reduced pressure and the residue was purified by chromatography to give 3-nitro-1 H-indazole (3.4 g, 49% yield). $^1$H NMR (400 MHz, DMSO-d$_4$): δ 14.46 (s, 1 H), 8.12 (m, 1 H), 7.76 (m, 1 H), 7.57 (m, 1 H), 7.48 (m, 1 H).

Cone. H$_2$SO$_4$ (2 mL) was added to a suspension of 3-nitro-1 H-indazole (3.4 g, 21 mmol) in 2-methyl-propan-2-ol (30 mL) and the resulting mixture was heated to 180° C. in a steel bomb. The reaction mixture was cooled to RT and diluted with EtOAc. The organic phase was washed with brine, dried (MgSO$_4$) and concentrated to give 1-tert-butyl-3-nitro-1 H-indazole (3.4 g, 76%). $^1$H NMR (400 MHz, DMSO-d$_6$): δ 8.18-8.15 (m, 2 H), 7.59-7.49 (m, 2 H), 1.76 (s, 9 H).

A mixture of 1-tert-butyl-3-nitro-1 H-indazole (3.0 g, 14 mmol) and Pd/C (1 g) in MeOH (50 mL) was hydrogenated (1 atm) at RT for 2 h. The reaction mixture was filtered and the filtrate was concentrated and purified by chromatography to give 1-tert-butyl-1 H-indazol-3-ylamine (1.7 g, 68% yield). $^1$H NMR (400 MHz, DMSO-d$_4$): δ 7.67 (m, 1 H), 7.52 (m, 1 H), 7.19 (m, 1 H), 6.89 (m, 1 H), 5.32 (s, 2 H), 1.58 (s, 9 H); MS (ESI) m/z: 190.1 [M+H$^+$].

EXAMPLE B40

In ethanol (40 mL) was placed t-butylcarbamidine hydrochloride (3.71 g, 27.2 mmol). This was treated with 21% sodium ethoxide in ethanol (8.80 g, 27.2 mmol) and stirred at RT for 15 min. To this was added the diethyl ethoxymethyl-enemalonate (5.87 g, 27.2 mmol) and the reaction mixture was stirred overnight at RT. The reaction mixture was refluxed for 1 hour and then cooled to RT. The solution was evaporated and the residue was dissolved in water (100 mL) and the pH adjusted to 3-4 (wet litmus) with acetic acid. The mixture formed a precipitate. The solid collected by filtration, washed with water (50 mL) and dried under vacuum to obtain ethyl 2-tert-butyl-4-hydroxypyrimidine-5-carboxylate (2.18 g, 36% yield). $^1$H NMR (400 MHz, DMSO-d$_6$): δ 12.6 (brs, 1 H), 8.44 (s, 1 H), 4.20 (q, J=7.2 Hz, 2 H), 1.25 (s, 9 H), 1.23 (t, J=12 Hz, 3 H); MS (ESI) m/z: 225.0 (M+H$^+$).

In cold (~0° C.) POCl$_3$ (20 mL) was dropped triethylamine (0.55 mL) with stirring. To this was added in parts of ethyl 2-tert-butyl-4-hydroxypyrimidine-5-carboxylate (2.18 g, 9.72 mmol). The mixture then warmed to 40° C. and stirred under Argon for 1 hour. The mixture was evaporated until free of POCl$_3$, diluted with CHCl$_3$ (100 mL) and poured carefully into ice (300 mL). The solution was stirred at RT to melt. The organic phase was separated, washed with sodium bicarbonate (100 mL), water (100 mL) and dried (Na$_2$SO$_4$). The solvents evaporated to give ethyl 2-tert-butyl-4-chloropyrimidine-5-carboxylate (2.0 g, 85% yield). $^1$H NMR (400 MHz, DMSO-d$_6$): δ 9.12 (s, 1 H), 4.34 (q, J=6.8 Hz, 2 H), 1.33 (s, 9 H), 1.27 (t, J=6.8 Hz, 3 H); MS (ESI) m/z: 243.0 (M+H$^+$).

To a solution of ethyl 2-tert-butyl-4-chloropyrimidine-5-carboxylate (0.30 g, 1.24 mmol) in NMP (3 mL) was added morpholine (0.54 g, 6.16 mmol) and it was heated at 80° C. for 1.5 hour. The reaction was checked by LC-MS, water was added and the solution was extracted with ethyl acetate (3×). The organic layer was washed with brine, dried (Na$_2$SO$_4$) and solvent was removed to obtain tert-butyl 4-(5-(3-tert-butyl-5-(ethoxycarbonyl)-1 H-pyrazol-1-yl)pyridin-2-yl)piperazine-1-carboxylate. MS (ESI) m/z: 294.0 (M+H$^+$).

To a stirring suspension of ethyl 2-tert-butyl-4-morpholinopyrimidine-5-carboxylate (0.36 g, 1.24 mmol) in 1:1:1 THF/EtOH/H$_2$O (9 ml) at RT was added LiOH—H$_2$O (130 mg, 4.95 mmol) and the mixture was stirred overnight at RT. The reaction mixture was checked by LC-MS and the completed reaction was concentrated to an aqueous residue, acidified (pH 3-4) with 3M HCl and the solution was extracted with EtOAc (3×). The combined organics were washed with brine (1×), dried (MgSO$_4$), filtered and concentration. The crude was dissolved in isopropanol and the solid (LiCl and NaCl) was filtered and washed with isopropanol. The filtrate was concentrated to obtain the desired product 2-tert-butyl-4-morpholinopyrimidine-5-carboxylic acid (0.15 g, 46% yield). MS (ESI) m/z: 266.0 (M+H$^+$).

EXAMPLE B41

In a mix of sat'd NaHCO$_3$:toluene:ethanol (1:2:1) (8 mL) was dissolved ethyl 2-tert-butyl-4-chloropyrimidine-5-carboxylate from Example B40 (300 mg, 1.24 mmol), 3-fluorophenylboronic acid (350 mg, 2.47 mmol) and to this was added tetrakis(triphenylphosphine)palladium(0) (29 mg). The mixture was heated overnight at 75° C. under Ar. The mixture was diluted with EtOAc (25 mL) and water (25 mL). The mixture was filtered to remove insolubles and the organic phase separated, washed with 5% citric acid (25 mL), then saturated sodium bicarbonate (25 mL) and brine (25 mL). The solvents evaporated at reduced pressure and the residue purified by silica gel column chromatography (Biotage: 25M, 5-50% EtOAc/Hex—550 mL) to give ethyl 2-tert-butyl-4-(3-fluorophenyl)pyrimidine-5-carboxylate (0.27 g, 72% yield).

Using a procedure to Example B40, 2-tert-butyl-4-(3-fluorophenyl)pyrimidine-5-carboxylate (0.27 g, 0.89 mmol) was treated with LiOH—H$_2$O (86 mg, 3.57 mmol) to afford 2-tert-butyl-4-morpholinopyrimidine-5-carboxylic acid (0.23 g, 92% yield). MS (ESI) m/z: 275.0 (M+H$^+$).

EXAMPLE B42

Using a procedure analogous to Example B41, ethyl 2-tert-butyl-4-chloropyrimidine-5-carboxylate from Example B40 (0.30 g, 1.24 mmol) and pyridin-3-ylboronic acid (1.8 g, 1.48 mmol) in presence of tetrakis(triphenylphosphine)palladium (0) (71 mg, 0.062 mmol) were combined to afford ethyl 2-tert-butyl-4-(pyridin-3-yl)pyrimidine-5-carboxylate (0.10 g, 28% yield).

Using a procedure analogous to Example B39, ethyl 2-tert-butyl-4-(pyridin-3-yl)pyrimidine-5-carboxylate (0.17 g, 0.60 mmol) was treated with LiOH.H$_2$O (57 mg, 2.38 mmol) to afford 2-tert-butyl-4-(pyridin-3-yl)pyrimidine-5-carboxylic acid (0.11 g, 72% yield). MS (ESI) m/z: 258.0 (M+H$^+$).

EXAMPLE B43

Using a procedure analogous to Example B40, ethyl 2-tert-butyl-4-chloropyrimidine-5-carboxylate from Example B40 (0.30 g, 1.24 mmol) and 1-methylpiperazine (0.62 g, 6.18 mmol) in presence of NMP (catalytic amount) were combined to afford 2-tert-butyl-4-(4-methylpiperazin-1-yl)pyrimidine-5-carboxylic acid (0.11 g, 32% yield). MS (ESI) m/z: 279.0 (M+H$^+$).

EXAMPLE B44

Using a procedure analogous to Example B40, 2-tert-butyl-4-chloropyrimidine-5-carboxylate from Example B40 (0.30 g, 1.24 mmol) and tert-butyl piperazine-1-carboxylate (1.15 g, 6.18 mmol) in presence of NMP (catalytic amount) were combined to afford 4-(4-(tert-butoxycarbonyl)piperazin-1-yl)-2-tert-butylpyrimidine-5-carboxylic acid (0.36 g, 80% yield). MS (ESI) m/z: 365.0 (M+H$^+$).

EXAMPLE B45

In ethanol (10 mL) was placed the tert-butylhydrazine hydrochloride (1.35 g, 10.8 mmol) and ethyl 2-((dimethylamino)methylene)-3-oxobutanoate (2.00 g, 10.8 mmol). The mixture warmed to reflux and stirred for 2 hrs, cooled to RT and stirred overnight. The mixture was evaporated at reduced pressure to give an oil which was dissolved in ether (25 mL) and washed successively with water (25 mL), saturated sodium bicarbonate (25 mL) and brine (25 mL), dried (Na$_2$SO$_4$), evaporated at reduced pressure and purified by chromatography (Biotage S1-25 column, 10-40% ethyl acetate/Hex) to give ethyl 1-tert-butyl-5-methyl-1 H-pyrazole-4-carboxylate (1.48 g, 65% yield) as an oil. MS (ESI) m/z: 211.0 (M+H$^+$).

In a mixture of ethanol:water:dioxane (1:1:1, 21 mL) was placed ethyl 1-tert-butyl-5-methyl-1 H-pyrazole-4-carboxylate (1.48 g, 7.04 mmol) and lithium hydroxide hydrate (886 mg, 21.12 mmol). The reaction was stirred at 40° C. for 3 hrs and then at RT overnight. The reaction was diluted with water (25 mL) and ether (25 mL). The ether layer was discarded and the aqueous phase made acidic (pH~=4) with 1N HCl. The acidic phase was then extracted with ethyl acetate (2×25 mL) and the combined ethyl acetate layers were washed with brine, dried (Na$_2$SO$_4$), evaporated at reduced pressure to give 1-tert-butyl-5-methyl-1 H-pyrazole-4-carboxylic acid as a white solid (1.12 g, 87% yield). $^1$H NMR (300 MHz, DMSO-d$_6$): δ 1.56 (s, 9 H), 2.67 (s, 3 H), 7.65 (s, 1 H), 12.13 (s, 1 H); MS (ESI) m/z: 183.0 (M+H$^+$).

EXAMPLE B46

Using a procedure analogous to Example B45, ethyl 1-tert-butyl-5-(trifluoromethyl)-1 H-pyrazole-4-carboxylate (750 mg, 2.84 mmol) was converted to 1-tert-butyl-5-(trifluoromethyl)-1 H-pyrazole-4-carboxylic acid (646 mg, 94% yield) using lithium hydroxide hydrate (357 mg, 8.51 mmol). $^1$H NMR (300 MHz, DMSO-d$_6$), δ 1.63 (s, 9 H), 7.92 (s, 1 H); MS (ESI) m/z: 259.0 (M+Na$^+$).

EXAMPLE B47

Using a procedure analogous to Example B17, 1-(2-(dimethylamino)-2-oxoethyl)-5-isopropyl-1 H-pyrazole-3-carboxylic acid was synthesized from ethyl 3-isopropyl-1 H-pyrazole-5-carboxylate as a white solid (0.35 g). $^1$H NMR (400 MHz, DMSO-d$_6$): δ 6.56 (s, 1 H), 5.21 (s, 2 H), 3.10 (s, 3 H), 2.92-2.88 (m, 4 H), 1.31 (t, J 7.2 Hz, 3 H), 1.20 (d, J=6.8 Hz, 6 H); MS (ESI) m/z: 240.0 (M+H$^+$).

EXAMPLE B48

NaH (6.8 g, 0.17 mol) was added portionwise to a 0° C. solution of 1 H-pyrazole (10 g, 0.15 mol) in DMF (150 mL) and the resulting mixture was stirred at room temperature for 30 min. 2-Iodopropane (30 mL, 0.3 mol) was added dropwise to the above mixture at 0° C., then the reaction mixture was stirred at room temperature for 10 h. H$_2$O was added and the mixture was extracted with ethyl ether (3×100 mL). The combined organic layers were washed with brine, dried over Na$_2$SO$_4$, and concentrated in vacuo. The residue was distilled under reduced pressure to afford 1-isopropyl-1 H-pyrazole (6.6 g, 40% yield). $^1$H NMR (400 MHz, DMSO-d$_6$): δ 7.68 (d, J=1.6 Hz, 1 H), 7.38 (d, J=1.2 Hz, 1 H), 6.17 (t, J=2.0 Hz, 1 H), 4.46 (m, 1 H), 1.37 (d, J=6.8 Hz, 6 H).

To a solution of 1-isopropyl-1 H-pyrazole (5 g, 45.5 mmol) in conc.$H_2SO_4$ (50 mL) was added $KNO_3$ (5.0 g, 50 mmol) portion wise at 0° C. After the addition, the resulting mixture was heated to 50 0° C. for 8 h. The reaction mixture was cooled to room temperature and poured into ice water, and the mixture was extracted with EtOAc. The combined organics were washed with saturated $Na_2CO_3$ solution, brine, and were dried over $Na_2SO_4$, and concentrated in vacuo. Chromatography on silica gel provided 1-isopropyl-4-nitro-1 H-pyrazole (3.2 g, 46% yield). $^1$H NMR (400 MHz, DMSO-$d_6$): δ 8.99 (s, 1 H), 8.32 (s, 1 H), 4.65 (m, 1 H), 1.51 (d, J=6.8 Hz, 6H).

A solution of 1-isopropyl-4-nitro-1 H-pyrazole (3 g, 19 mmol) in EtOH (30 mL) was stirred under a hydrogen atmosphere for 2 h in the presence of 10% Pd/C (300 mg). The catalyst was removed by filtration and the filtrate was concentrated under reduced pressure to afford 1-isopropyl-1 H-pyrazol-4-ylamine (1.8 g, 75.0% yield). $^1$H NMR (400 MHz, DMSO-$d_6$): δ 6.99 (s, 1 H), 6.84 (s, 1 H), 4.23 (m, 1 H), 3.70 (s, 2 H), 1.28 (d, J=6.8 Hz, 6 H); MS (ESI) m/z: 126.2 [M+H]$^+$.

EXAMPLE B49

In cold (~0° C.) phosphorous oxychloride (40 mL) was carefully added triethylamine (1.87 mL) with stirring. To this was added, in parts, ethyl 4-hydroxy-2-methylpyrimidine-5-carboxylate (5.00 g, 27.4 mmol). The mixture then warmed to 40° C. and stirred under Argon for 2 hours. The mixture was evaporated free of phosphorous oxychloride, diluted with chloroform (150 mL) and poured carefully into ice (400 mL) and allowed to warm to RT. The organic phase was separated, washed with saturated sodium bicarbonate (75 mL), then brine (100 mL) and dried over sodium sulfate. The solvents evaporated to give a thick oil which was purified by chromatography (Biotage Si-40 column, 15-40% ethyl acetate/hexane) to give ethyl 4-chloro-2-methylpyrimidine-5-carboxylate as a clear oil (2.96 g, 53% yield). $^1$H NMR (400 MHz, DMSO-$d_6$): δ 1.31 (t, 3 H), 2.66 (s, 3 H), 4.34 (q, 2 H), 9.06 (s, 1 H); MS (ESI) m/z: 201.0 (M+H$^+$).

In a mixture of saturated $NaHCO_3$:toluene:ethanol (1:2:1) (12 mL) was dissolved ethyl 4-chloro-2-methylpyrimidine-5-carboxylate (500 mg, 2.49 mmol), N-methylindole-5-boronic acid (872 mg, 4.98 mmol) and to this was added tetrakis(triphenylphosphine)-palladium(0) (58 mg). The reaction stirred at 75° C., under Ar, overnight. The reaction was allowed to cooled to RT, diluted with ethyl acetate (25 mL) and water (25 mL) and filtered free of insolubles. The organic phase was washed with 5% citric acid (25 mL), saturated sodium bicarbonate (25 mL) and brine (25 mL), evaporated at reduced pressure to give a reddish thick foam, and purified by chromatography (Biotage Si-25 column, 15-40% ethyl acetate/hexane) to give ethyl 2-methyl-4-(1-methyl-1 H-indol-5-yl)pyrimidine-5-carboxylate as a thick clear oil. The oil solidified overnight (391 mg, 53% yield). MS (ESI) m/z: 296.0 (M+H$^+$).

In a mix of ethanol:water:dioxane (1:1:1, 9 mL) was placed ethyl 2-methyl-4-(1-methyl-1 H-indol-5-yl)pyrimidine-5-carboxylate (391 mg, 1.324 mmol) and lithium hydroxide hydrate (222 mg, 5.30 mmol). The mix stirred at RT overnight. The mix was diluted with ethyl acetate (25 mL) and 5% citric acid (20 mL). The organic phase was separated, washed with brine (20 mL) and dried over sodium sulfate. The solvent was evaporated at reduced pressure to give 2-methyl-4-(1-methyl-1 H-indol-5-yl)pyrimidine-5-carboxylic acid as a tan solid (132 mg, 37% yield). MS (ESI) m/z: 268.0 (M+H$^+$).

EXAMPLE B50

A mixture of 1,1,3,3-tetramethoxypropane (13.6 g, 83 mmol) and N2-cyclopentyl-N1-(tert-butoxycarbonyl)hydrazine (16.6 g, 83 mmol, see Ranatunge et al., *J. Med. Chem.* (2004), 47, p2180-2193) in water (150 mL) was treated with conc. HCl (21 mL, 252 mmol). The resulting mixture was heated at reflux overnight. The completed reaction mixture was extracted with ether and the extracts were washed with brine, dried over anhydrous $MgSO_4$, and concentrated in vacuo to give 1-cyclopentyl-1 H-pyrazole (8.0 g, 71% yield. $^1$H NMR (400 MHz, CDCl$_3$): δ 7.52 (s, 1 H), 7.43 (s, 1 H), 6.24 (s, 1 H), 4.68 (m, 1 H), 2.20-1.71 (m, 8 H). MS (ESI) m/z; 137.1 [M+H$^+$].

To a suspension of $Na_2CO_3$ (13 g, 124 mmol) in $CH_2OH_2$ (100 mL) was added 1-cyclopentyl-1 H-pyrazole (8.35 g, 62 mmol) and $Br_2$ (3.2 mL). The resulting mixture was stirred at RT overnight. The solid was removed by filtration and the filter cake was washed with DCM. The combined filtrates were washed with water, brine and dried over anhydrous $MgSO_4$. The solvent was concentrated to dryness to give 4-bromo-1-cyclopentyl-1 H-pyrazole (14 g, 93%). $^1$H NMR (300 MHz, CDCl$_3$): δ7.46 (s, 1 H), 7.44 (s, 1 H), 4.64 (m, 1 H), 2.18-1.67(m, 8 H); MS (ESI) m/z: 215.0 [M+H]$^+$.

Using the procedure of Example B30, 4-bromo-1-cyclopentyl-1 H-pyrazole (9.0 g, 42 mmol), n-BuLi (2.5 M, 18.5 mL, 46.2 mmol) and $CO_2$ were combined to provide 1-cyclopentyl-1 H-pyrazole-4-carboxylic acid (3.5 g, 47% yield). $^1$H NMR (400 MHz, DMSO-$d_6$): δ 8.31 (s, 1H), 7.85 (s, 1 H), 4.78 (m, 1 H), 1.70-2.56 (m, 8 H); MS (ESI) m/z: 181.1 [M+H]$^+$.

EXAMPLE C1

A solution of ethyl 4-chloro-2-(methylthio)pyrimidine-5-carboxylate (42 g, 181 mmol) in EtOH (400 mL) was treated with a solution of methylamine (12.3 g, 397 mmol) in EtOH (100 mL) at 0° C. and the mixture was stirred for 3 h. The mixture was concentrated and then partitioned between $H_2O$ (200 mL) and $CH_2Cl_2$ (500 mL). The organic layer was washed with brine, dried ($Na_2SO_4$) and concentrated in vacuo to give ethyl 4-(methylamino)-2-(methylthio)pyrimidine-5-carboxylate as a white solid (36.0 g, 88% yield). $^1$H NMR (300 MHz, CDCl$_3$): 8.59 (s, 1 H), 8.18 (br s, 1 H), 4.31 (q, J=7.2 Hz, 2 H), 3.05 (d, J=4.8 Hz, 3 H), 2.52 (s, 3 H), 1.34 (t, J=7.2 Hz, 3 H); MS (ESI) m/z: 228.1 (M+H$^+$).

To a solution of ethyl 4-(methylamino)-2-(methylthio)pyrimidine-5-carboxylate (30 g, 132 mmol) in THF (300 mL) was added LiAlH$_4$ (7.5 g, 198 mmol). The reaction mixture was stirred for 1 h at RT. The reaction was carefully quenched with 10 mL water and 7 mL of 10% aq NaOH. The mixture was stirred for 1 h, filtered and the filtrate was concentrated to give (4-(methylamino)-2-(methylthio)pyrimidin-5-yl)methanol (22.0 g, 90% yield). $^1$H NMR (300 MHz, DMSO-$d_6$): 7.79 (s, 1 H), 6.79 (m, 1 H), 5.04 (t, J=5.4 Hz, 1 H), 4.27 (d, J=5.4 Hz, 2H), 2.83 (d, J=4.8 Hz, 3 H), 2.40 (s, 3 H). MS (ESI) m/z: 186.1 (M+H$^+$).

A mixture of (4-(methylamino)-2-(methylthio)pyrimidin-5-yl)methanol (22.0 g, 119 mmol) and $MnO_2$ (44 g, 506 mmol) in CHCl$_3$ (300 mL) was stirred at RT for 3 h. The reaction was filtered and the filtrate was concentrated to give 4-(methylamino)-2-(methylthio)pyrimidine-5-carbaldehyde as a pale solid (20 g, 92% yield). $^1$H NMR (400 MHz, DMSO-d₆): 9.71 (s, 1 H), 8.60 (br s, 1 H), 8.49 (s, 1 H), 2.96 (d, J=4.8 Hz, 3 H), 2.48 (s, 3 H) MS (ESI) m/z: 184.0 (M+H⁺).

EXAMPLE C2

To a 0° C. solution of ethyl 4-chloro-2-(methylthio)pyrimidine-5-carboxylate (19 g, 82 mmol) in CH₃CN (100 mL) was added a solution of aqueous ethylamine (70%, 8.1 g, 126 mmol). The resulting mixture was stirred at RT for 8 h. The organic solution was removed under reduced pressure, and the residue was partitioned between EtOAc and H₂O. The aqueous layer was extracted with ethyl acetate (3×30 mL) and the combined organics were washed with brine, dried (MgSO₄) and concentrated to give ethyl 4-(ethylamino)-2-(methylthio)pyrimidine-5-carboxylate (19.5 g, 99.1% yield). ¹H NMR (400 MHz, DMSO-d₆): δ 8.49 (s, 1 H), 8.26 (t, J=4.8 Hz, 1 H), 4.23 (q, J=7.2 Hz, 2 H), 3.48 (q, J=7.2 Hz, 2 H), 2.44 (s, 3 H), 1.26 (t, J=7.2 Hz, 3 H), 1.13 (t, J=7.2 Hz, 3 H).

To a solution of ethyl 4-(ethylamino)-2-(methylthio)pyrimidine-5-carboxylate (19.5 g, 81.9 mmol) in anhydrous THF (100 mL) was added LiAlH₄ (12.3 g, 327.6 mmol) in portions at 0° C. under N2 atmosphere. After stirring for 30 min, the reaction was quenched with water and then 2N aqueous NaOH as added. The suspension was filtered and the filtrate was concentrated to afford (4-(ethylamino)-2-(methylthio) pyrimidin-5-yl)methanol (15 g, 92.0% yield). ¹H NMR (400 MHz, DMSO-d₆): δ 7.78 (s, 1 H), 6.74 (t, J=4.8 Hz, 1 H), 5.05 (t, J=5.2 Hz, 1 H), 4.26 (d, J=5.2 Hz, 2 H), 3.36 (m, 2 H), 2.37 (s, 3 H), 1.10 (m, 3 H).

Activated MnO₂ (52 g, 0.6 mol) was added to a solution of (4-(ethylamino)-2-(methylamino)pyrimidin-5-yl)methanol (15 g, 0.075 mol) in CH₂CL₂ (300 mL) and the reaction mixture was stirred overnight at RT. The reaction solution was filtered and the filtrate was concentrated to give 4-(ethylamino)-2-(methylthio)pyrimidine-5-carbaldehyde (14 g, 93% yield). ¹H NMR (300 MHz, DMSO-d₆): δ 9.71 (s, 1 H), 8.67 (br s, 1 H), 8.49 (s, 1 H), 3.51 (m, 2 H), 2.48 (s, 3 H), 1.17 (t, J=7.2 Hz, 3 H).

EXAMPLE C3

To a solution of ethyl 4,6-dichloronicotinate (5 g, 22.8 mmol) in CH₃CN (30 mL) was added dropwise aqueous methylamine (65%, 5.2 g, 45.6 mmol) at 0° C. The resulting mixture was stirred at RT for 8 h. The organic solution was removed under reduced pressure to give the crude product, which was suspended in H₂O and extracted with EtOAc (3×20 mL). The combined extracts were washed with brine, dried (MgSO₄) and concentrated to give ethyl 6-chloro-4-(methylamino)nicotinate (4 g, 82% yield), which was used in the next step without further purification. ¹HNMR (300 MHz, DMSO-d₆): δ 8.48 (s, 1 H), 8.04 (d, J=4.5 Hz, 1 H), 6.71 (s, 1 H), 4.27 (q, J=6.9 Hz, 2 H), 2.85 (d, J=5.1 Hz, 1 H), 1.29 (t, J=6.9 Hz, 3 H).

To a 0° C. solution of ethyl 6-chloro-4-(methylamino)nicotinate (4 g, 18.7 mmol) in THF (40 mL) was added LiAlH₄ (1.4 g, 37.4 mmol) portionwise under N2 atmosphere. After stirring for 20 min, the reaction was quenched by cautious addition of water followed by aqueous solution of 2 N NaOH. The suspension was filtered and the filtrate was concentrated to afford (6-chloro-4-(methylamino)pyridin-3-yl)methanol (2.9 g, 90.6% yield), which was used in next step without purification. ¹HNMR (400 MHz, DMSO-d₆): δ 7.96 (s, 1 H), 6.63 (s, 1 H), 6.46 (s, 1 H), 5.04 (s, 1 H), 4.39 (m, 2 H), 2.81-2.68 (m, 3 H).

A mixture of (6-chloro-4-(methylamino)pyridin-3-yl) methanol (2.9 g, 16.7 mmol) and MnO₂ (11.7 g, 133.6 mmol) in anhydrous DCM (25 mL) was stirred at 30° C. for 6 h. The reaction mixture was cooled to RT, and filtered. The filtrate was concentrated in vacuo to give 6-chloro-4-(methylamino) nicotinaldehyde (2.5 g, 87% yield). ¹HNMR (400 MHz, DMSO-d₆): δ 9.83 (s, 1 H), 8.52 (br s, 1 H), 8.40 (s, 1 H), 6.75 (s, 1 H), 2.87 (d, J=5.8 Hz, 3 H); MS (ESI) m/z: 171.0 [M+H]⁺.

EXAMPLE C4

Ethyl 4-chloro-2-(methylthio)pyrimidine-5-carboxylate (17 g, 73 mmol) and cyclopentylamine (12.4 g, 146 mmol) were combined by the 3-step procedure of Example C1 to provide 4-cyclopentylamino-2-methylsulfanyl-pyrimidine-5-carbaldehyde (8.5 g, 49% yield over 3 steps). ¹H NMR (400 MHz, DMSO-d₆): δ 9.73 (s, 1 H), 8.55 (d, J=6.4 Hz, 1 H), 8.51 (s, 1 H), 4.43 (m, 1 H), 2.50 (s, 3 H, obscured by DMSO), 2.03-1.98 (m, 2 H), 1.69-1.48 (m, 6 H); MS (ESI) m/z: 238.3 [M+H]⁺.

EXAMPLE C5

To a solution of ethyl 4,6-dichloronicotinate (4.4 g, 20 mmol) in CH₃CN (50 mL) was added dropwise a solution of ethylamine in water (65%, 2.7 g, 39 mmol) at 0° C., then the resulting mixture was stirred at RT overnight. The reaction was concentrated and the residue was washed with water to give ethyl 6-chloro-4-(ethylamino)nicotinate (3.9 g, 91% yield). ¹H NMR (400 MHz, DMSO-d₆): δ 8.51 (s, 1 H), 8.08 (s, 1 H), 6.53 (m, 1 H), 4.19 (q, J=7.2 Hz, 2H), 2.78 (q, J=7.2 Hz, 2 H), 1.28 (t, J=7.2 Hz, 3 H), 1.13 (t, J=7.2 Hz, 3 H); MS (ESI) m/z: 229.1[M+H]⁺.

To a solution of ethyl 6-chloro-4-(ethylamino)nicotinate (3.9 g, 17 mmol) in anhydrous THF (50 mL) was added LiAlH₄ (3.6 g, 95 mmol) at −50° C., then the resulting mixture was allowed to warm to 0° C. and stirred for 1 h. Then the mixture was quenched by the addition of 10% aq NaOH solution (3.6 mL). The mixture was filtered and the filtrate was partitioned between water and EtOAc. The aqueous layer was extracted with EtOAc (3×100 mL). The combined organics were washed with brine, dried (MgSO₄) and concentrated in vacuo to provide to (6-chloro-4-(ethylamino)pyridin-3-yl) methanol (2.5 g, 79% yield). ¹H NMR (400 MHz, DMSO-d₆): δ 7.84 (s, 1 H), 76.55 (s, 1 H), 6.17 (m, 1 H), 5.25 (t, J=5.2 Hz, 1 H), 4.44 (q, J=7.2 Hz, 2 H), 3.23 (m, 2H), 1.23 (t, J=7.2 Hz, 3H).

To a solution of (6-chloro-4-(ethylamino)pyridin-3-yl) methanol (2.5 g, 13.4 mmol) in DCM (30 mL) was added MnO₂ (5.8 g, 67 mmol), then the reaction mixture was stirred at RT overnight. The reaction mixture was filtered and the filtrate was concentrated in vacuo to give 6-chloro-4-(ethylamino)nicotinaldehyde (2.2 g, 89% yield). ¹H-NMR (400 MHz, CDCl₃): δ δ 9.82 (s, 1 H), 8.51 (br s, 1 H), 8.27 (s, 1 H), 6.56 (s, 1 H), 3.28 (m, 2 H), 1.31 (t, J=7.2 Hz, 3H); MS (ESI) m/z: 185.0 [M+H]⁺.

EXAMPLE C6

To a solution of ethyl 4-chloro-2-(methylthio)pyrimidine-5-carboxylate (15 g, 64.7 mmol) in CH₃CN (100 mL) was added dropwise a solution of isopropylamine in water (7.6 g, 0.13 mol) at 0° C. The resulting mixture was stirred at RT for 8 h. The organic solution was removed under reduced pressure and the residue was partitioned between water and EtOAc, and the aqueous layer was extracted with EtOAc (3×50 mL). The combined organic layers were washed with brine, dried (MgSO₄) and concentrated to give ethyl 4-(isopropylamino)-2-(methylthio)pyrimidine-5-carboxylate (16.4 g, 99.6% yield), which was used in the next step without further purification. $^1$H NMR (400 MHz, DMSO-d$_6$): δ 8.51 (s, 1 H), 8.05 (d, J=7.6 Hz, 1 H), 4.31-4.22 (m, 3 H), 2.46 (s, 3 H), 1.27 (t, J=7.2 Hz, 3 H), 1.20 (d, J=6.4 Hz, 6 H).

To a solution of ethyl 4-(isopropylamino)-2-(methylthio) pyrimidine-5-carboxylate (16.4 g, 64.4 mmol) in anhydrous THF (100 mL) was added LAH (6.1 g, 0.16 mol) in portions at 0° C. under N$_2$ atmosphere, then the reaction mixture was stirred at r.t. for 30 min. The reaction was quenched by the addition of water (6 mL) followed by aqueous solution of 2N NaOH (6 mL). The suspension was filtered and the filtrate was concentrated to give (4-(isopropylamino)-2-(methylthio) pyrimidin-5-yl)methanol (13.5 g, 98.4% yield), which was used in next step without further purification. $^1$HNMR (400 MHz, DMSO-d$_6$): δ 7.79 (s, 1 H), 6.37 (d, J=7.6 Hz, 1 H), 5.10 (t, J=5.6 Hz, 1 H), 4.28-4.20 (m, 3 H), 2.38 (s, 3 H), 1.13 (d, J=6.4 Hz, 6 H).

To a solution of (4-(isopropylamino)-2-(methylthio)pyrimidin-5-yl)methanol (13.5 g, 63.4 mmol) in DCM (100 mL) was added manganese(IV) oxide (45 g, 0.5 mol), and the mixture was stirred at RT overnight. The reaction mixture was filtered and the filtrate was concentrated to give the 4-(isopropylamino)-2-(methylthio)pyrimidine-5-carbaldehyde (12.2 g, 91% yield), which was used in the next step without further purification. $^1$HNMR (400 MHz, DMSO-d$_6$): δ 9.71 (s, 1 H), 8.50 (s, 1 H), 8.41 (d, J=7.2 Hz, 1 H), 4.33 (m, 1 H), 2.47 (s, 3 H), 1.21 (d, J=6.4 Hz, 6 H).

EXAMPLE C7

Using the three-step procedure of Example C5, ethyl 4,6-dichloronicotinate (20 g, 91 mmol) and isopropylamine (60% in water, 18 g, 182 mmol) were converted to 6-chloro-4-(isopropylamino)nicotinaldehyde (16 g, 81% yield). $^1$H NMR (400 MHz, DMSO-d$_6$): δ 9.82 (s, 1 H), 8.43-8.39 (m, 2 H), 6.83 (s, 1 H), 3.84 (m, 1 H), 1.17 (d, J=6.4 Hz, 6 H).

EXAMPLE D1

To stirring fuming HNO$_3$ (90.00 wt %, 30.0 ml, 45 g, 643 mmol, 7.21 eq) at −15° C. was added 4-fluoro-2-methylphenylacetic acid (15.00 g, 89.2 mmol, 1.00 eq) in portions such that the internal temperature remained below −10° C. After completing the addition the reaction was stirred with warming to +5° C. over 15 min. The mixture was poured onto ice (400 g). Product separated as a slightly sticky solid which on manipulation with a spatula became powdery. The suspension was stirred vigorously until the ice had completely melted. While still very cold, the solids were collected by filtration, rinsed very well with H$_2$O and dried on the filter to afford crude 2-(4-fluoro-2-methyl-5-nitrophenyl)acetic acid (18.43 g, 97% yield) as a pale yellow solid which was used as is in the next reaction. $^1$H NMR (400 MHz, acetone-d$_6$): δ 8.06 (d, J=7.6 Hz, 1H), 7.36 (d, J=12.0 Hz), 3.84 (s, 2H), 2.44 (s, 3H)

2-(4-Fluoro-2-methyl-5-nitrophenyl)acetic acid (18.43 g, 86.5 mmol, 1.00 eq) and conc. H$_2$SO$_4$ (4.00 ml) were combined in EtOH (300 ml) and stirred with heating at 85° C. After 2.5 h, the completed reaction was cooled to RT and concentrated as completely as possible. The residue was dissolved in MTBE (250 ml) and washed with H$_2$O (2×) and brine (2×), dried (MgSO$_4$), filtered and evaporated to afford ethyl 2-(4-fluoro-2-methyl-5-nitrophenyl)acetate (16.79 g, 81% yield) as a dark orange oil which was used as is in the next reaction. MS (ESI) m/z: 242.0 (M+H)$^+$.

Ethyl 2-(4-fluoro-2-methyl-5-nitrophenyl)acetate (16.79 g, 69.6 mmol, 1.00) in EtOH (60 ml) was shaken with 10% Pd/C (50% H$_2$O) (7.41 g, 3.48 mmol, 0.050 eq) under H$_2$ (3.5 atm) at RT for 2 h until H$_2$ uptake was complete. The completed reaction was filtered on Celite, rinsing forward with EtOH. The cake was washed well with EtOH and the combined filtrates were concentrated and pumped on to afford ethyl 2-(5-amino-4-fluoro-2-methylphenyl)acetate (13.18 g, 90% yield) as a brown oil. $^1$H NMR (400 MHz, DMSO-d$_6$): δ 6.80 (d, J=12.4 Hz, 1 H), 6.59 (d, J=9.6 Hz, 1 H), 4.86 (s, 2 H), 4.05 (q, J=7.2 Hz, 2 H), 3.46 (s, 2 H), 2.05 (s, 3 H), 1.17 (t, J=7.2 Hz, 3 H); MS (ESI) m/z: 212.2 (M+H)$^+$.

EXAMPLE D2

To a solution of (2,4-difluoro-phenyl)acetic acid (14.5 g, 0.084 mol) in H$_2$SO$_4$ (60 mL) at 0° C. was added dropwise 69% HNO$_3$ (6 mL). After stirring at 0° C. for 35 min, the reaction mixture was poured into ice water. The aqueous layer was extracted with EtOAc, and the organic extracts were washed with brine, dried (Na$_2$SO$_4$), and concentrated in vacuo. The residue was purified by chromatography to give (2,4-difluoro-5-nitro-phenyl)acetic acid (16 g, 87.5% yield), $^1$H NMR (400 MHz, DMSO-d$_6$): δ 8.30 (t, J=8.0 Hz, 1 H), 7.68 (m, 1 H), 3.75 (s, 2 H).

A solution of (2,4-difluoro-5-nitro-phenyl)acetic acid (16 g, 74 mmol) in EtOH (200 mL) and 98% H$_2$SO$_4$ (14 mL) was refluxed at 80° C. for 2.5 h under a N$_2$ atmosphere. The reaction mixture was poured into ice-water, and the resultant solution was extracted with ether. The combined organic extracts were washed with brine, dried (Na$_2$SO$_4$) and concentrated in vacuo. The residue was purified by column chromatography to give ethyl 2-(2,4-difluoro-5-nitrophenyl)acetate (16 g, 89% yield). $^1$H NMR (300 MHz, DMSO-d$_6$): δ 8.22 (t, J=8.1 Hz, 1H), 7.55 (t, J=11.1 Hz, 1 H), 4.06 (m, 2 H), 3.77 (s, 2 H), 1.13 (t, J=6.9 Hz, 3 H).

A mixture of ethyl 2-(2,4-difluoro-5-nitrophenyl)acetate (16 g, 130 mmol) and 10% Pd/C (1.6 g, 1.5 mmol) in EtOAc was hydrogenated at 30 psi at RT for 12 h. The catalyst was filtered off and the filtrate was evaporated. Then the residue was purified by column chromatography to give ethyl 2-(5-amino-2,4-difluorophenyl)acetate (14 g, 99% yield). $^1$H NMR (300 MHz, DMSO-d$_6$): δ 6.98 (t, J=9.9 Hz, 1 H), 6.70 (t, J=7.8 Hz, 1 H), 4.50 (s, 2 H), 4.06 (m, 2 H), 3.53 (s, 2 H), 1.16 (t, 0.7=6.9 Hz, 3 H); MS (ESI) m/z: 216.2 [M+H]$^+$.

EXAMPLE D3

HNO$_3$ (10.35 g, 98.6 mmol) was added dropwise to a stirred solution of 2-(2-chloro-4-fluorophenyl)acetic acid (16.9 g, 89.6 mmol) in conc. H$_2$SO$_4$ (60 mL) at −10° C. After complete addition, the resulting mixture was stirred at 0° C. for 10 min, and was carefully poured into ice water. The off-white solid was collected by filtration and dried to give 2-(2-chloro-4-fluoro-5-nitrophenyl)acetic acid (20.5 g, 98.2% yield). $^1$HNMR (400 Hz, DMSO-d$_6$): δ 12.71 (br s, 1 H), 8.33 (d, J=8.0 Hz, 1 H), 7.92 (d, J=11.2 Hz, 1 H), 3.85 (s, 2 H).

A solution of 2-(2-chloro-4-fluoro-5-nitrophenyl)acetic acid (20.5 g, 88 mmol) in ethanol (150 mL) was treated with sulfuryl dichloride (21 g, 0.17 mol) at 0° C., then the mixture was heated to reflux for 1 h. The reaction mixture was concentrated under reduced pressure and the pH was adjusted to between pH 7-8 by addition of saturated Na$_2$CO$_3$ solution. Then resultant mixture was extracted with EtOAc (3×100 mL) and the combined organic layers were washed with brine, dried (MgSO$_4$) and concentrated to give ethyl 2-(2- chloro-4-fluoro-5-nitrophenyl)acetate (22.5 g, 97.8%). $^1$HNMR (400 Hz, DMSO-d$_6$): δ 8.32 (d, J=8.0 Hz, 1 H), 7.91 (d, J=11.2 Hz, 1 H), 4.09 (q, J=7.2 Hz, 2 H), 3.92 (s, 2 H), 1.17 (t, J=7.2 Hz, 3 H).

A solution of ethyl 2-(2-chloro-4-fluoro-5-nitrophenyl)acetate (22.5 g, 86.2 mmol) in ethanol (200 mL) was stirred with Raney Ni (20% slurry in water, ~5.0 g, 17 mmol) under a hydrogen atmosphere (30 psi) for 5 h. The catalyst was removed by filtration and the filtrate was concentrated to give ethyl 2-(5-amino-2-chloro-4-fluorophenyl)acetate (19 g, 95% yield). $^1$H NMR (400 MHz, DMSO-d$_6$): δ 7.10 (d, J=11.2 Hz, 1 H), 6.71 (d, J=9.2 Hz, 1 H), 5.27 (s, 2H), 4.05 (q, J=6.8 Hz, 2 H), 3.57 (s, 2 H), 1.14 (t, J=6.8 Hz, 3 H); MS (ESI) m/z: 232.0 [M+H]$^+$.

EXAMPLE D4

To a stirred solution of 1-bromo-4-fluoro-2-methylbenzene (30 g, 0.16 mol) in conc. H$_2$SO$_4$ (200 mL) was added KNO$_3$ (16.1 g, 0.16 mol) at 0° C. portion wise. After the resulting mixture was stirred at 0° C. for 30 min, the reaction was poured into ice water and extracted with EtOAc (3×100 mL). The combined organic layers were washed with saturated Na$_2$CO$_3$ solution and brine, dried, filtered and concentrated to give 1-bromo-4-fluoro-2-methyl-5-nitrobenzene (20 g, 53.6% yield). $^1$HNMR (300 Hz, DMSO-d$_6$): δ 8.15 (d, J=7.2 Hz, 1 H), 7.52 (d, J=12 Hz, 1 H), 2.35 (s, 3 H).

To a solution of 1-bromo-4-fluoro-2-methyl-5-nitrobenzene (20 g, 85.8 mmol) in methanol (300 mL) was added Raney Ni (20%/w, ~2.0 g, suspension in water, washed with acetone for several times), then the resulting mixture was hydrogenated under hydrogen atmosphere for 2 h. The catalyst was filtered, concentrated, and tire residue was recrystallized (petroleum ether) to afford 5-bromo-2-fluoro-4-methylphenylamine (10 g, 57.5% yield). $^1$HNMR (400 MHz, DMSO-d$_6$): δ 7.12 (d, J=10.2 Hz, 1 H), 6.78 (d, J=10.9 Hz, 1 H), 4.85 (s, 2 H), 2.29 (s, 3 H), 1.26 (s, 12 H).

Nitrogen was bubbled though a solution of 5-bromo-2-fluoro-4-methylphenylamine (3.5 g, 17.2 mmol), bis(pinacolato)diboron (3.9 g, 15.5 mmol), and KOAc (4.2 g, 51.6 mmol) in DMF (10 mL) for 20 min. To the above mixture was added dppf (954 mg, 1.7 mmol) and PdCL; (151 mg, 0.86 mmol), then nitrogen was continued to bubble for 30 min., and the resulting mixture was heated to 80° C. under nitrogen for 16 h. The excess DMF was removed under reduced pressure, and the residue was partitioned between water and EtOAc. The organic layer was wash with brine, dried, filtered and concentrated and purified by silica gel column chromatography to give 2-fluoro-4-methyl-5-(4,4,5,5-tetramethyl-1,3,2-dioxaborolan-2-yl)phenylamine (2 g, 47% yield). $^1$H NMR (400 MHz, DMSO-d$_6$): δ 7.10 (d, J=10.4 hz, 1 H), 6.76 (d, J=12.8 Hz, 1 H), 4.85 (s, 2 H), 2.27 (s, 3 H), 1.24 (s, 12 H); MS (ESI) m/z: 252.1[M+H]$^+$.

EXAMPLE D5

3-Oxo-pentanedioic acid (101 g, 0.5 mmol), diethyl ester, triethyl orthoformate (81.4 g, 0.55 mol) and acetic anhydride (102 g, 1 mol) were combined and heated to 120° C. for 2 h. The resulting mixture was cooled to RT and dissolved in DCM (1000 mL). After further cooling to 0° C., ammonia (30%, 80 mL) was added and the reaction mixture was allowed to warm to RT overnight. The product was extracted with water (2×1000 mL). Then the aqueous layer was acidified to pH 5 with conc HCl. The precipitate was collected by filtration to afford ethyl 4,6-dihydroxynicotinate (60.0 g, 60% yield). $^1$H NMR (400 MHz, DMSO-d$_6$): δ 7.99 (s, 1H), 5.58 (s, 1 H), 4.23 (q, J=6.8, 14.0 Hz, 2 H), 1.25 (t, J=7.2 Hz, 3 H). MS (ESI) m/z: 184.1 (M+H$^+$).

Ethyl 4,6-dihydroxynicotinate (60 g, 0.328 mol) was added slowly to a 2 L flask containing POCl$_3$ (500 mL). After complete addition, the reaction mixture was heated to reflux for 2 hours. The resulting mixture was distilled to remove POCl$_3$ under reduced pressure. The residue was poured into ice-water and stirred for 30 minutes before extracting with EtOAc (3×500 mL). The combined extracts were washed with brine (300 mL), dried (MgSO$_4$) and concentrated in vacuo to give ethyl 4,6-dichloronicotinate (65 g, 90.1%, yield). $^1$H NMR (300 MHz, DMSO-d$_6$); δ 8.80 (s, 1 H), 7.95 (s, 1 H), 4.34 (q, J=6.9 Hz, 2 H), 1.31 (t, J=6.9 Hz, 3H). MS (ESI) m/z: 220.1 (M+H$^+$).

EXAMPLE D6

A mixture of (2-chlorophenyl)acetic acid (15 g, 88 mmol) in conc. H$_2$SO$_4$ (100 mL) was cooled to −20° C. and treated (drop wise) with conc. HNO$_3$ (9.4 g, 97 mmol). The resulting mixture was stirred at −20° C. for an additional 30 min. The reaction mixture was poured into the ice-water, and the mixture was extracted with EtOAc (3×200 mL), the combined organics were washed with brine, dried over Na$_2$SO$_4$ and concentrated in vacuo to give (2-chloro-5-nitrophenyl)acetic acid (15 g, 79% yield). $^1$H NMR (400 MHz, DMSO-d$_6$): δ 8.58 (s, 1 H), 8.35 (m, 1 H), 7.96 (m, 1 H), 4.12 (s, 2 H).

Thionyl chloride (16.7 g, 0.14 mol) was added dropwise to a 0° C. solution of (2-chloro-5-nitro-phenyl)acetic acid (15 g, 0.07 mol) in EtOH (300 mL) and the resultant mixture was heated at reflux overnight. The reaction mixture was concentrated under reduced pressure and the residue was poured into ice water, and extracted with EtOAc (2×300 mL). The combined organics were washed with brine and saturated NaHCO$_3$ solution, were dried over Na$_2$SO$_4$, and were concentrated in vacuo to give ethyl 2-(2-chloro-5-nitrophenyl)acetate (17 g, 99% yield). $^1$H NMR (400 MHz, DMSO-d$_6$): δ 8.35 (d, J=2.8 Hz, 1 H), 8.12 (dd, J=8.4, 2.8 Hz, 1 H), 7.72 (d, J=8.4 Hz, 1 H), 4.10 (q, J=7.2 Hz, 2 H), 3.96 (s, 2 H), 1.15 (t, J=7.2 Hz, 3 H).

Iron powder (2.5 g, 44.7 mmol) was added portion wise to a solution of ethyl 2-(2-chloro-5-nitrophenyl)acetate (8 g, 4.68 mmol) and conc. HCl (12 M, 3.9 mL, 46.8 mmol) in EtOH (100 mL). The resultant mixture was heated at 50° C. for 2 hour. The mixture was filtered and the filtrate cake was washed with saturated aqueous Na$_2$CO$_3$ until pH 8. The filter cake was further washed with EtOAc and the combined filtrates were partitioned between EtOAc and water. The organics were dried over Na$_2$SO$_4$ and concentrated in vacuo to provide ethyl 2-(5-amino-2-chlorophenyl)acetate (5.6 g, 56% yield). $^1$H NMR (400 MHz, DMSO-d$_6$): δ 7.00 (d, J=8.4 Hz, 1 H), 6.50 (s, J=2.8 Hz, 1 H), 6.44 (dd, J=8.4 Hz, 2.8 Hz, 1H), 5.20 (s, 2 H), 4.05 (q, J=7.2 Hz, 2 H), 3.56 (s, 2 H), 1.15 (t, J=7.2 Hz, 3 H).

EXAMPLE 1

Using general method A, Example B1 (0.16 g, 0.42 mmol) and Example A1 (0.12 g, 0.42 mmol) were combined to afford 1-(5-(2-amino-8-methyl-7-oxo-7,8-dihydropyrido[2,3-d]pyrimidin-6-yl)-2-fluorophenyl)-3-(3-tert-butyl-1-phenyl-1H-pyrazol-5-yl)urea as the amine hydrochloride salt (85 mg, 38% yield). $^1$H NMR (400 MHz, DMSO-d$_6$): δ 9.03 (s, 1H), 8.94 (s, 1H), 8.71 (s, 1H), 8.42 (d, J=7.6 Hz, 1H), 7.89 (s, 1H), 7.58-7.52 (m, 4H), 7.45-7.42 (m, 1H), 7.28 (d, J=8.8 Hz, 1H), 6.41 (s, 1H), 3.73 (s, 3H), 1.28 (s, 9H); MS (ESI) m/z: 527.2 (M+H$^+$).

EXAMPLE 2

Using general method A, Example B2 (0.15 g, 0.46 mmol) and Example A1 (0.13 g, 0.46 mmol) were combined to afford 1-(5-(2-amino-8-methyl-7-oxo-7,8-dihydropyrido[2,3-d]pyrimidin-6-yl)-2-fluorophenyl)-3-(3-tert-butyl-1-methyl-1H-pyrazol-5-yl)urea as the amine hydrochloride salt (80 mg, 37% yield). $^1$H NMR (400 MHz, DMSO-$d_6$): δ 8.99 (brs, 1H), 8.87 (s, 1H), 8.68 (s, 1H), 8.43 (d, J=8.4 Hz, 1H), 7.88 (s, 1H), 7.41-7.38 (m, 2H), 7.31-7.29 (m, 2H), 6.12 (s, 1H), 3.63 (s, 3H), 3.57 (s, 3H), 1.21 (s, 9H); MS (ESI) m/z: 465.2 (M+H$^+$).

EXAMPLE 3

Using general method A, Example B3 (0.075 g, 0.17 mmol) and Example A1 (0.05 g, 0.17 mmol) were combined to afford 1-(1-(3-(2-amino-2-oxoethyl)phenyl)-3-tert-butyl-1H-pyrazol-5-yl)-3-(5-(2-amino-8-methyl-7-oxo-7,8-dihydropyrido[2,3-d]pyrimidin-6-yl)-2-fluorophenyl)urea as amine hydrochloride salt (41 mg, 42% yield). $^1$H NMR (400 MHz, DMSO-$d_6$): δ 9.03 (s, 1H), 8.95 (s, 1H), 8.72 (s, 1H), 8.44-8.42 (m, 1H), 7.90 (s, 1H), 7.54 (brs, 1H), 7.49-7.42 (m, 2H), 7.38-7.26 (m, 4H), 6.94 (brs, 1H), 6.41 (s, 1H), 3.58 (s, 3H), 3.48 (s, 2H), 1.28 (s, 9H); MS (ESI) m/z: 584.2 (M+H$^+$).

EXAMPLE 4

Using general method A, Example B4 (0.075 g, 0.14 mmol) and Example A1 (0.04 g, 0.14 mmol) were combined and then deprotected with HCl in dioxane solution to afford 1-(5-(2-amino-8-methyl-7-oxo-7,8-dihydropyrido[2,3-d]pyrimidin-6-yl)-2-fluorophenyl)-3-(3-tert-butyl-1-(1H-indazol-5-yl)-1H-pyrazol-5-yl)urea as the amine hydrochloride salt. $^1$H NMR (400 MHz, DMSO-$d_6$): δ 9.01 (s, 1H), 8.90 (s, 1H), 8.74 (s, 1H), 8.45-8.42 (m, 1H), 8.20 (s, 1H), 7.90 (s, 2H), 7.70 (d, J=8.8 Hz, 1H), 7.45 (dd, J=8.8 Hz, 2.0 Hz, 1H), 7.28-7.25 (m, 2H), 6.42 (s, 1H), 3.58 (s, 3H), 1.28 (s, 9H); MS (ESI) m/z: 567.3 (M+H$^+$).

EXAMPLE 5

Using general method B, 3-isopropyl-1-phenyl-1H-pyrazol-5-amine (0.071 g, 0.19 mmol) and Example A1 (0.054 g, 0.19 mmol) were combined to afford 1-(5-(2-amino-8-methyl-7-oxo-7,8-dihydropyrido[2,3-d]pyrimidin-6-yl)-2-fluorophenyl)-3-(3-isopropyl-1-phenyl-1H-pyrazol-5-yl)urea as the amine hydrochloride salt (36 mg, 38% yield). $^1$H NMR (400 MHz, DMSO-$d_6$): δ 9.05 (s, 1H), 8.97 (s, 1H), 8.74 (s, 1H), 8.42 (d, J=7.2 Hz, 1H), 7.91 (s, 1H), 7.57-7.44 (m, 5H), 7.28 (d, J=8.0 Hz, 1H), 6.37 (s, 1H), 3.62 (s, 3H), 2.89-2.86 (m, 1H), 1.23 (s, J=7.2 Hz, 1H); MS (ESI) m/z: 513.3 (M+H$^+$).

EXAMPLE 6

To a solution of ethyl 3-tert-butyl-1-(2-(dimethylamino)-2-oxoethyl)-1H-pyrazole-5-carboxylate from example B17 (0.48 g, 1.7 mmol) in THF (10 mL) was added a solution of lithium hydroxide (0.21 g, 5.1 mmol) in water (5 mL) and the mixture was stirred for 16 h at RT. Solvents were removed and the residue was acidified with 3M HCl and the product was extracted with EtOAc (2×30 ml). The combined organic extracts were washed with brine, dried (Na$_2$SO$_4$) and concentrated to afford 3-tert-butyl-1-(2-(dimethylamino)-2-oxoethyl)-1H-pyrazole-5-carboxylic acid (0.4, 93% yield) as a pasty mass. $^1$H NMR (400 MHz, DMSO-$d_6$): δ 6.69 (s, 1H), 5.30 (s, 2H), 3.02 (s, 3H), 2.82 (s, 3H), 1.24 (m, 9H); MS (ESI) m/z: 254.0 (M+H$^+$).

Using general method D, 3-tert-butyl-1-(2-(dimethylamino)-2-oxoethyl)-1H-pyrazole-5-carboxylic acid (0.055 g, 0.22 mmol) and Example A1 (0.23 g, 0.88 mmol) were combined to afford 1-(5-(2-amino-8-methyl-7-oxo-7,8-dihydropyrido[2,3-d]pyrimidin-6-yl)-2-fluorophenyl)-3-(3-tert-butyl-1-(2-(dimethylamino)-2-oxoethyl)-1H-pyrazol-5-yl)urea as the amine hydrochloride salt (81 mg, 70% yield). $^1$H NMR (400 MHz, DMSO-$d_6$): δ 9.55 (brs, 1H), 9.16 (s, 1H), 8.78 (s, 1H), 8.47-8.42 (m, 1H), 7.32-7.30 (m, 2H), 6.28 (s, 1H), 5.10 (s, 2H), 3.58 (s, 3H), 3.07 (s, 3H), 2.88 (s, 3H), 1.24 (m, 9H); MS (ESI) m/z: 536.2 (M+H$^+$).

EXAMPLE 7

Using general method B, the carbamate of Example B21 (0.055 g, 0.18 mmol) and Example A1 (0.05 g, 0.18 mmol) were combined to afford 1-(5-(2-amino-8-methyl-7-oxo-7,8-dihydropyrido[2,3-d]pyrimidin-6-yl)-2-fluorophenyl)-3-(1-phenyl-3-(trifluoromethyl)-1H-pyrazol-5-yl)urea as the amine hydrochloride salt (55 mg, 58% yield). $^1$H NMR (400 MHz, DMSO-$d_6$): δ 9.24 (s, 1H), 9.16 (s, 1H), 8.71 (s, 1H), 8.41-8.39 (m, 1H), 7.89 (s, 1H), 7.65-7.56 (m, 5H), 7.31-7.28 (m, 2H), 6.90 (s, 1H), 3.65 (s, 3H); MS (ESI) m/z: 539.0 (M+H$^+$).

EXAMPLE 8

Using general method A, Example B2 (0.075 g, 0.23 mmol) and Example A2 (0.07 g, 0.23 mmol) were combined to afford 1-(5-(2-amino-8-ethyl-7-oxo-7,8-dihydropyrido[2,3-d]pyrimidin-6-yl)-2-fluorophenyl)-3-(3-tert-butyl-1-methyl-1H-pyrazol-5-yl)urea as the amine hydrochloride salt (32 mg, 29% yield). $^1$H NMR (400 MHz, DMSO-$d_6$): δ 9.31 (s, 1H), 9.01 (s, 1H), 8.73 (s, 1H), 8.41 (d, J=8.4 Hz, 1H), 7.91 (s, 1H), 7.31 (d, J=8.4 Hz, 1H), 6.17 (s, 1H), 4.32 (q, J=6.8 Hz, 1H), 3.67 (s, 3H), 1.24-1.20 (m, 12H); MS (ESI) m/z: 479.2 (M+H$^+$).

EXAMPLE 9

Using general method C, Example B5 (400 mg, 0.96 mmol) and Example A1 (288 mg, 2.88 mmol) were combined to afford 1-(5-(2-amino-8-methyl-7-oxo-7,8-dihydropyrido[2,3-d]pyrimidin-6-yl)-2-fluorophenyl)-3-(1-phenyl-3-(thiophen-2-yl)-1H-pyrazol-5-yl)urea (208 mg, 39% yield) as the HCl salt. $^1$H-NMR (DMSO-$d_6$) δ 3.58 (s, 3H), 6.87 (s, 1H), 7.10-7.12 (m, 1H), 7.28-7.31 (m, 2H), 7.47-7.61 (m, 7H), 7.91 (s, 1H), 7.70-8.30 (br s, 2H), 8.43 (d, 1H), 8.80 (s, 1H), 9.19 (s, 2H); MS (ESI) m/z: 553.0 (M+H$^+$).

EXAMPLE 10

Using general method A, Example B6 (0.071 g, 0.2 mmol) and Example A1 (0.057 g, 0.2 mmol) were combined to afford 1-(5-(2-amino-8-methyl-7-oxo-7,8-dihydropyrido[2,3-d]pyrimidin-6-yl)-2-fluorophenyl)-3-(1-methyl-3-(thiophen-2-yl)-1H-pyrazol-5-yl)urea as the amine hydrochloride salt (25 mg, 25% yield). $^1$H NMR (400 MHz, DMSO-$d_6$): δ 9.39 (s, 1H), 9.06 (s, 1H), 8.74 (s, 1H), 8.45-8.43 (m, 1H), 7.93 (s, 1H), 7.42 (d, J=4.8 Hz, 1H), 7.34-7.31 (m, 3H), 7.06 (dd, 7-4.8 Hz, 3.6 Hz, 1H), 6.60 (s, 1H), 3.58 (s, 3H); MS (ESI) m/z: 491.0 (M+H$^+$).

EXAMPLE 11

Using general method A, Example B1 (0.075 g, 0.25 mmol) and Example A2 (0.075 g) were combined to afford 1-(5-(2-amino-8-ethyl-7-oxo-7,8-dihydropyrido[2,3-d]pyrimidin-6-yl)-2-fluorophenyl)-3-(3-tert-butyl-1-phenyl-1H-pyrazol-5-yl)urea as the amine hydrochloride salt (56 mg, 41% yield). $^1$H NMR (400 MHz, DMSO-d$_6$): δ 9.04 (s, 1H), 8.94 (s, 1H), 8.73 (s, 1H), 8.42-8.40 (m, 1H), 7.89 (s, 1H), 7.58-7.52 (m, 4H), 7.46-7.42 (m, 1H), 7.29-7.27 (m 2H), 6.41 (s, 1H), 4.32 (q, J=6.8 Hz, 1H), 1.28 (s, 9H), 1.22 (t, J=6.8 Hz, 3H); MS (ESI) m/z: 541.3 (M+H$^+$).

EXAMPLE 12

Using general method A, Example B2 (0.500 g, 3.3 mmol) and Example A3 (0.382 g, 1.21 mmol) were combined and purified by flash column chromatography (12-100% EtOAc/hexanes) to afford 1-(3-t-butyl-1-methyl-1H-pyrazol-5-yl)-3-(2-fluoro-5-(8-methyl-2-(methylthio)-7-oxo-7,8-dihydropyrido[2,3-d]pyrimidin-6-yl)phenyl)urea (0.180 g, 30% yield) as a foam. MS (ESI) m/z: 496.0 (M+H$^+$).

Using a procedure analogous to Example A1, 1-(3-t-butyl-1-methyl-1H-pyrazol-5-yl)-3-(2-fluoro-5-(8-methyl-2-(methylthio)-7-oxo-7,8-dihydropyrido[2,3-d]pyrimidin-6-yl)phenyl)urea (0.180 g, 0.363 mmol) and MeNH$_2$.HCl (0.0502 g, 0.743 mmol, 2.00 eq) were combined to afford 1-(3-t-butyl-1-methyl-1H-pyrazol-5-yl)-3-(2-fluoro-5-(8-methyl-2-(methylamino)-7-oxo-7,8-dihydropyrido[2,3-d]pyrimidin-6-yl)phenyl)urea (0.0451 g, 24% yield) as the HCl salt. $^1$H NMR (400 MHz, DMSO-d$_6$): δ 9.49 (brs, 1H), 9.07 (s, 1H), 8.44-8.41 (m, 1H), 7.97 (brs, 1H), 7.92 (s, 1H), 7.33-7.27 (m, 2H), 6.23 (s, 1H), 3.71 (s, 3H), 3.63 (brs, 3H), 2.94 (s, 3H), 1.24 (s, 9H); MS (ESI) m/z: 479.2 (M+H$^+$).

EXAMPLE 13

Using general method A, Example B7 (0.180 g, 0.444 mmol) and Example A1 (0.138 g, 0.484 mmol) were combined to afford 1-(5-(2-amino-8-methyl-7-oxo-7,8-dihydropyrido[2,3-d]pyrimidin-6-yl)-2-fluorophenyl)-3-(3-tert-butyl-1-(3-fluorophenyl)-1H-pyrazol-5-yl)urea (0.08 g, 33% yield) as a white foam. This was converted to corresponding HCl salt by reacting with HCl. $^1$H NMR (DMSO-d$_6$): δ 9.15 (s, 2H), 8.81 (s, 1H), 8.39 (d, J=7.8 Hz, 1H), 7.94 (s, 1H), 7.59-7.56 (m, 1H), 7.45-7.41 (m, 2H), 7.30-7.26 (m, 3H), 6.42 (s, 1H), 3.57 (s, 3H), 1.28 (s, 9H); MS (ESI) m/z: 545 (M+H$^+$).

EXAMPLE 14

Using general method A, Example B8 (0.10 g, 0.23 mmol) and Example A1 (65 mg, 0.23 mmol) were combined to afford 1-(5-(2-amino-8-methyl-7-oxo-7,8-dihydropyrido[2,3-d]pyrimidin-6-yl)-2-fluorophenyl)-3-(3-tert-butyl-1-(quinolin-6-yl)-1H-pyrazol-5-yl)urea as the HCl salt (43 mg, 32% yield). $^1$H NMR (400 MHz, DMSO-d$_6$): δ 9.08 (brs, 1H), 9.02 (dd, J=1.2, 3.6 Hz, 1H), 8.97 (m, 1H), 8.69 (s, 1H), 8.60 (m, 1H), 8.40 (dd, J=1.6, 8.0 Hz, 1H), 8.21 (m, 2H), 8.02 (dd, J=2.4, 8.4 Hz, 1H), 7.86 (s, 1H), 7.69 (dd, J=4.0, 8.4 Hz, 1H), 7.39 (brm, 1H), 7.27 (m, 2H), 6.49 (s, 1H), 3.58 (s, 3H), 1.32 (s, 9H); LC-MS (EI) m/z: 578.3 (M+H$^+$).

EXAMPLE 15

Using general method B, Example B9 (0.071 g, 0.26 mmol) and Example A1 (0.074 g, 0.26 mmol) were combined to afford 1-(5-(2-amino-8-methyl-7-oxo-7,8-dihydropyrido[2,3-d]pyrimidin-6-yl)-2-fluorophenyl)-1-methyl-1H-pyrazol-5-yl)urea (49 mg, 38% yield). This solid was converted to the amine hydrochloride salt by treating with 0.1 N HCl solution. $^1$H NMR (400 MHz, DMSO-d$_6$): δ 9.32 (brs, 1H), 9.01 (s, 1H), 8.72 (s, 1H), 8.43 (d, J=8.0 Hz, 1H), 7.94-7.90 (m, 2H), 7.35-7.21 (m, 5H), 6.67 (d, J=4.8 Hz 1H), 3.80 (s, 3H), 3.57 (s, 3H); MS (ESI) m/z: 503.3 (M+H$^+$).

EXAMPLE 16

Using general method A, Example B10 (85 m g, 0.21 mmol) and Example A2 (63 mg, 0.21 mmol) were combined to obtain 1-(5-(2-amino-8-ethyl-7-oxo-7,8-dihydropyrido[2,3-d]pyrimidin-6-yl)-2-fluorophenyl)-3-(3-tert-butyl-1-(6-methylpyridin-3-yl)-1H-pyrazol-5-yl)urea as the HCl salt (68 mg, 54% yield). $^1$H NMR (400 MHz, DMSO-d$_6$): δ 9.35 (brs, 1H), 9.13 (brs, 1H), 8.85 (d, J=2.0 Hz, 1H), 8.74 (s, 1H), 8.35 (dd, J=1.6, 8.4 Hz, 1H), 8.25 (m, 1H), 7.90 (s, 1H), 7.74 (d, J=8.4 Hz, 1H), 7.71 (brs, 1H), 7.29 (m, 2H), 6.46 (s, 1H), 4.31 (q, J=7.2 Hz, 2H), 2.66 (s, 3H), 1.29 (s, 9H), 1.22 (t, J=7.2 Hz, 3H); LC-MS (EI) m/z: 556.3 (M+H$^+$).

EXAMPLE 17

Using general method A, the TROC carbamate of Example B2 (0.071 g, 0.23 mmol) and Example A4 (0.071 g, 0.23 mmol) were combined to afford 1-(3-tert-butyl-1-methyl-1H-pyrazol-5-yl)-3-(5-(8-ethyl-2-(methylamino)-7-oxo-7,8-dihydropyrido[2,3-d]pyrimidin-6-yl)-2-fluorophenyl)urea (45 mg, 40% yield). $^1$H NMR (400 MHz, DMSO-d$_6$): δ 9.60 (s, 1H), 9.12 (s, 1H), 8.72 (brs, 1H), 8.40 (d, J=8.4 Hz, 1H), 7.98 (brs, 1H), 7.91 (s, 1H), 7.33-7.27 (m, 2H), 6.24 (s, 1H), 4.36 (brs, 2H), 3.79 (s, 3H), 2.93 (s, 3H), 1.24 (s, 12H); MS (ESI) m/z: 493.2 (M+H$^+$).

EXAMPLE 18

Using a procedure analogous to Example 12, Example B10 (0.051 g, 0.23 mmol), Example A3 (0.072 g, 0,23 mmol) and methylamine were combined to afford 1-(3-tert-butyl-1-(6-methylpyridin-3-yl)-1H-pyrazol-5-yl)-3-(2-fluoro-5-(8-methyl-2-(methylamino)-7-oxo-7,8-dihydropyrido[2,3-d]pyrimidin-6-yl)phenyl)urea (57 mg, 46% yield). $^1$H NMR (400 MHz, DMSO-d$_6$): δ 9.17 (s, 1H), 9.04 (s, 1H), 8.79 (d, J=2.0 Hz, 1H), 8.69 (brs, 1H), 8.38 (dd, J=2.0, and 5.6 Hz, 1H), 8.15 (m, 1H), 7.88 (s, 1H), 7.67 (d, J=8.8 Hz, 1H), 7.29 (m, 2H), 6.46 (s, 1H), 3.60 (brm, 3H), 2.93 (brs, 3H), 2.64 (s, 3H), 1.29 (s, 9H); LC-MS (EI) m/z: 556.3 (M+H$^+$).

EXAMPLE 19

Using general method B, the carbamate of 3-isopropyl-1-methyl-1H-pyrazol-5-amine (0.051 g, 0.23 mmol) and Example A4 (0.072 g, 0.23 mmol) were combined to afford 1-(5-(8-ethyl-2-(methylamino)-7-oxo-7,8-dihydropyrido[2,3-d]pyrimidin-6-yl)-2-fluorophenyl)-3-(3-isopropyl-1-methyl-1H-pyrazol-5-yl)urea (78 mg, 71% yield) as a white solid. $^1$H NMR (400 MHz, DMSO-d$_6$): δ 9.10 (s, 1H), 9.06 (s, 1H), 8.71 (brs, 1H), 8.40 (d, J=8.8 Hz, 1H), 7.96-7.87 (m, 2H), 7.35-7.27 (m, 2H), 6.19 (d, 7-7.6 Hz, 1H), 4.37 (brs, 2H), 3.69 (d, J=5.2 Hz, 3H), 2.92 (s, 3H), 2.85-2.81 (m, 1H), 1.25-1.17 (m, 9H); MS (ESI) m/z: 479.2 (M+H$^+$).

EXAMPLE 20

To a solution of 2-(3-tert-butyl-5-(ethoxycarbonyl)-1H-pyrazol-1-yl)acetic acid from Example B17 (0.77 g, 3.02 mmol) in DMF (5 mL) were added EDC (0.75 g, 3.93 mmol), HOBt (0.55 g, 3.62 mmol) and morpholine (0.39 g, 4.53 mmol). After stirring the mixture for 4 h at RT, water (50 mL)

and 3M HCl (5 mL) were added and the product was extracted with EtOAc (3×30 mL). The combined organic layers were washed with aq. LiCl, dried (Na$_2$SO$_4$), concentrated and purified by chromatography (EtOAc/CH$_2$Cl$_2$) to afford ethyl 3-tert-butyl-1-(2-morpholino-2-oxoethyl)-1H-pyrazole-5-carboxylate (0.67 g, 69% yield) as a solid. $^1$H NMR (400 MHz, Acetone-d$_6$): δ 6.74 (s, 1H), 5.40 (s, 2H), 4.27 (q, J=7.2 Hz, 2H), 3.73 (brs, 2H), 3.65-3.62 (m, 4H), 3.51 (brs, 2H), 1.32 (t, J=7.2 Hz, 3H), 1.29 (s, 9H); MS (ESI) m/z: 324.2 (M+H$^+$).

To a solution of ethyl 3-tert-butyl-1-(2-morpholino-2-oxoethyl)-1H-pyrazole-5-carboxylate (0.34 g, 1 mmol) in THF (10 mL) was added borane in THF (4 ml of 1M solution, 4 mmol) at 0° C. under an Ar atmosphere and the mixture was stirred at 60° C. for 12 h. The mixture was cooled to 0° C. and quenched with 3M HQ solution and heated to 60° C. for 30 min. The mixture was basified with solid NaHCO$_3$ to pH 8 and the product was extracted with CHCl$_3$ (2×30 ml) and the combined organic layers were washed with brine, dried (Na$_2$SO$_4$) and concentrated to afford ethyl 3-tert-butyl-1-(2-morpholinoethyl)-1H-pyrazole-5-carboxylate amine (0.25 g, 76% yield) as a pasty mass. $^1$H NMR (400 MHz, Acetone-d$_6$): δ 6.69 (s, 1H), 4.60 (t, J=6.4 Hz, 2H), 4.33 (q, J=7.2 Hz, 2H), 3.59-3.53 (m, 4H), 2.69 (t, J=6.4 Hz, 2H), 2.43-2.38 (m, 4H), 1.36 (t, J=7.2 Hz, 3H), 1.29 (s, 9H); MS (ESI) m/z: 310.3 (M+H$^+$).

To a solution of ethyl 3-tert-butyl-1-(2-morpholinoethyl)-1H-pyrazole-5-carboxylate amine (0.43 g, 1.4 mmol) in THF (5 mL) was added a solution of LiOH (0.17 g, 4.2 mmol) in water (2 mL) and the mixture was stirred for 16 h at RT. Solvents were removed, and then the thick liquid was diluted with water (5 mL) and the pH was adjusted to 4-5 with 50% aq.acetic acid. The product was extracted with EtOAc (3×25 ml) and the combined organic layers were washed with brine, dried (Na$_2$SO$_4$) and concentrated to afford 3-tert-butyl-1-(2-morpholinoethyl)-1H-pyrazole-5-carboxylic acid (0.16 g, 41% yield) as a pasty mass. $^1$H NMR (400 MHz, DMSO-d$_6$): δ 6.65 (s, 1H), 4.54 (t, J=6.4 Hz, 2H), 3.58-3.52 (m, 4H), 2.69 (t, J=6.4 Hz, 2H), 2.44 (brs, 4H), 1.28 (s, 9H); MS (ESI) m/z: 282.3 (M+H$^+$).

Using general method D, 3-tert-butyl-1-(2-morpholinoethyl)-1H-pyrazole-5-carboxylic acid (0.048 g, 0.17 mmol), Example A1 (0.097 g, 0.34 mmol), triethylamine (0.035 g, 0.34 mmol) and diphenylphospharyl azide (0.07 g, 0.26 mmol) were combined to afford 1-(5-(2-amino-8-methyl-7-oxo-7,8-dihydropyrido[2,3-d]pyrimidin-6-yl)-2-fluorophenyl)-3-(3-tert-butyl-1-(2-morpholinoethyl)-1H-pyrazol-5-yl)urea (38 mg, 40% yield) as the amine hydrochloride salt. $^1$H NMR (400 MHz, DMSO-d$_6$): δ 9.90 (s, 1H), 9.20 (s, 1H), 8.73 (s, 1H), 8.41 (d, J=8.8 Hz, 1H), 7.92 (s, 1H), 7.30 (d, J=8.4 Hz, 2H), 6.18 (s, 1H), 4.50-4.48 (m, 2H), 3.89-3.80 (m, 4H), 3.57 (s, 3H), 3.33-3.30 (m, 4H), 1.24 (m, 9H); MS (ESI) m/z: 564.3 (M+H$^+$).

EXAMPLE 21

Using a procedure analogous to Example 20, 2-(3-tert-butyl-5-(ethoxycarbonyl)-1H-pyrazol-1-yl)acetic acid from Example B17, benzyl piperazine-1-carboxylate and Example A1 were combined to afford benzyl 4-(2-(5-(3-(5-(2-amino-8-methyl-7-oxo-7,8-dihydropyrido[2,3-d]pyrimidin-6-yl)-2-fluorophenyl)ureido)-3-tert-butyl-1H-pyrazol-1-yl)ethyl)piperazine-1-carboxylate (117 mg) as a solid. $^1$H NMR (400 MHz, DMSO-d$_6$): δ 8.88 (s, 1H), 8.82 (s, 1H), 8.67 (s, 1H), 8.42-8.40 (m, 1H), 7.86 (s, 1H), 7.38-7.28 (m, 9H), 6.11 (s, 1H), 5.05 (s, 2H), 4.04 (t, J=6.8 Hz, 2H), 3.57 (s, 3H), 3.36 (brs, 4H), 2.68 (t, J=6.8 Hz, 2H), 2.40 (brs, 2H), 1.18 (s, 9H); MS (ESI) m/z: 697.0 (M+H$^+$).

To a solution of benzyl 4-(2-(5-(3-(5-(2-amino-8-methyl-7-oxo-7,8-dihydropyrido[2,3-d]pyrimidin-6-yl)-2-fluorophenyl)ureido)-3-tert-butyl-1H-pyrazol-1-yl)ethyl)piperazine-1-carboxylate (0.11 g, 0.16 mmol) in EtOAc (10 mL) was added palladium hydroxide (10% of 10 mg) and the mixture was stirred under a H$_2$ atmosphere for 18 h at RT. Then the mixture was filtered through a Celite pad, the pad was washed with EtOAc (2×5 ml). The filtrate was concentrated to afford a solid which was purified by chromatography using acetonitrile and water as eluents to afford 1-(5-(2-amino-8-methyl-7-oxo-7,8-dihydropyrido[2,3-d]pyrimidin-6-yl)-2-fluorophenyl)-3-(3-tert-butyl-1-(2-(piperazin-1-yl)ethyl)-1H-pyrazol-5-yl)urea as the amine hydrochloride salt (62 mg, 70% yield). $^1$H NMR (400 MHz, DMSO-d$_6$): δ 9.20 (brs, 1H), 9.16 (s, 1H), 8.71 (s, 1H), 8.41-8.39 (m, 1H), 7.91 (s, 1H), 7.31-7.29 (m, 2H), 6.18 (s, 1H), 4.44 (brs, 2H), 3.57 (s, 3H), 3.52-3.39 (m, 8H), 1.23 (s, 9H); MS (ESI) m/z: 562.8 (M+H$^+$).

EXAMPLE 22

Using general method E, 1-(3-t-butyl-1-methyl-1H-pyrazol-5-yl)-3-(2-fluoro-5-(8-methyl-2-(methylsulfinyl)-7-oxo-7,8-dihydropyrido[2,3-d]pyrimidin-6-yl)phenyl)urea from Example 12 (0.199 g, 0.389 mmol) and N$^1$,N$^1$-dimethylethane-1,2-diamine (0.214 ml, 1.94 mmol, 5.00 eq) were combined to afford 1-(3-t-butyl-1-methyl-1H-pyrazol-5-yl)-3-(5-(2-(2-(dimethylamino)ethylamino)-8-methyl-7-oxo-7,8-dihydropyrido[2,3-d]pyrimidin-6-yl)-2-fluorophenyl)urea which was subsequently treated with HCl to afford hydrochloride salt (20.8 mg, 10% yield) as a white solid. $^1$H NMR (400 MHz, DMSO-d$_4$): δ 9.07 (s, 1H), 8.91 (brs, 1H), 8.80-8.75 (brs, 1H), 8.47-8.44 (m, 1H), 8.01 (brs, 1H), 7.97 (s, 1H), 7.33-7.27 (m, 2H), 6.10 (s, 1H), 3.77-3.72 (m, 2H), 3.63 (s, 3H), 3.51 (brs, 3H), 3.37-3.33 (brm, 2H), 2.86 (m, 6H), 1.21 (s, 9H); MS (ESI) m/z: 536.2 (M+H$^+$).

EXAMPLE 23

Using general method F, Example A1 (76 mg, 0.27 mmol) and 1-isocyanato-3-(trifluoromethyl)benzene (80 mg, 0.43 mmol) were combined to provide 1-(5-(2-amino-8-methyl-7-oxo-7,8-dihydropyrido[2,3-d]pyrimidin-6-yl)-2-fluorophenyl)-3-(3-(trifluoromethyl)phenyl)urea (67 mg, 53% yield). $^1$H NMR (400 MHz, DMSO-d$_6$): δ 9.43 (s, 1H), 8.69 (s, 2 H), 8.41 (m, 1 H), 8.07 (s, 1 H), 7.90 (s, 1 H), 7.53 (m, 2 H), 7.35-7.25 (m, 5 H), 3.59 (s, 3 H); MS (ESI) m/z: 473.0 (M+H$^+$).

EXAMPLE 24

Using general method D, Example B17 (0.051 g, 0.21 mmol) and Example A1 (0.12 g, 0.43 mmol) in presence of tri ethyl amine (0.032 g, 0.32 mmol) and diphenylphospharyl azide (0.07 g, 0.26 mmol) were combined to afford 1-(5-(2-amino-8-methyl-7-oxo-7,8-dihydropyrido[2,3-d]pyrimidin-6-yl)-2-fluorophenyl)-3-(3-tert-butyl-1-(2-(dimethylamino)ethyl)-1H-pyrazol-5-yl)urea as the amine hydrochloride salt (0.036 g, 32% yield). $^1$H NMR (400 MHz, DMSO-d$_6$): δ 9.63 (brs, 1H), 9.44 (s, 1H), 9.02 (s, 1H), 8.67 (s, 1H), 8.41-8.38 (m, 1H), 7.88 (s, 1H), 7.36-7.27 (m, 3H), 7.18-7.15 (m, 1H), 6.18 (s, 1H), 4.37 (t, J=6.4 Hz, 2H), 3.55-3.51 (m, 2H), 2.84 (s, 3H), 2.82 (s, 3H), 1.23 (s, 9H); MS (ESI) m/z: 522.2 (M+H$^+$).

EXAMPLE 25

Using general method A, Example B2 (0.071 g, 0.22 mmol) and Example A8 (0.067 g, 0.22 mmol) were combined to afford 1-(5-(2-amino-8-cyclopropyl-7-oxo-7,8-dihydropyrido[2,3-d]pyrimidin-6-yl)-2-fluorophenyl)-3-(3-tert-butyl-1-methyl-1H-pyrazol-5-yl)urea as the hydrochloride salt (0.062 g, 59% yield). $^1$H NMR (400 MHz, DMSO-$d_6$): δ 9.12 (s, 1H), 8.92 (s, 1H), 8.66 (s, 1H), 8.38-8.36 (m, 1H), 7.30-7.28 (m, 2H), 6.13 (s, 1H), 3.64 (s, 3H), 2.89-2.84 (m, 1H), 1.21 (s, 9H), 1.19-1.14 (m, 2H), 0.85-0.81 (m, 2H); MS (ESI) m/z: 491.2 (M+H$^+$).

EXAMPLE 26

Using general method F, Example A1 (75 mg, 0.26 mmol) and 1-fluoro-2-isocyanato-4-methylbenzene (0.050 mL, 0.39 mmol) were combined to provide 1-(5-(2-amino-8-methyl-7-oxo-7,8-dihydropyrido[2,3-d]pyrimidin-6-yl)-2-fluorophenyl)-3-(2-fluoro-5-methylphenyl)urea (46 mg, 40% yield). $^1$H NMR (400 MHz, DMSO-$d_6$): δ 9.08 (d, J=1.8 Hz, 1H), 9.00 (d, J=2.2 Hz, 1 H), 8.69 (s, 1 H), 8.48 (m, 1 H), 8.03 (dd, J=7.9, 1.6 Hz, 1 H), 7.89 (s, 1 H), 7.34-7.25 (m, 4 H), 7.12 (dd, J=11.4, 8.6 Hz, 1 H), 6.81 (m, 1 H), 3.58 (s, 3 H), 2.27 (s, 3H); MS (ESI) m/z: 437.3 (M+H$^+$).

EXAMPLE 27

Using general method C, Example B13 (0.081 g, 0.21 mmol) and Example A2 (0.063 g, 0.21 mmol) were combined to afford 1-(5-(2-amino-8-ethyl-7-oxo-7,8-dihydropyrido[2,3-d]pyrimidin-6-yl)-2-fluorophenyl)-3-(1-isopropyl-3-(thiophen-2-yl)-1H-pyrazol-5-yl)urea as the hydrochloride salt (0.059 g, 52% yield). $^1$H NMR (400 MHz, DMSO-$d_6$): δ 9.13 (s, 1H), 8.94 (s, 1H), 8.70 (s, 1H), 8.42-8.40 (m, 1H), 7.89 (s, 1H), 7.41 (dd, J=5.2 Hz, 1.2 Hz, 1H), 7.34-7.30 (m, 3H), 7.06 (dd, J=5.2 Hz, 3.2 Hz, 1H), 6.57 (s, 1H), 4.54-4.49 (m, 1H), 4.32 (q, J=7.2 Hz, 2H), 1.42 (d, J=6.4 Hz, 6H), 1.22 (t, J=7.2 Hz, 3H); MS (ESI) m/z: 533.3 (M+H$^+$).

EXAMPLE 28

Using general method A, Example B13 (0.081 g, 0.21 mmol) and Example A1 (0.060 g, 0.21 mmol) were combined to afford 1-(5-(2-amino-8-methyl-7-oxo-7,8-dihydropyrido[2,3-d]pyrimidin-6-yl)-2-fluorophenyl)-3-(1-isopropyl-3-(thiophen-2-yl)-1H-pyrazol-5-yl)urea as the hydrochloride salt (0.049 g, 45% yield). $^1$H NMR (400 MHz, DMSO-$d_6$): δ 9.23 (s, 1H), 8.99 (s, 1H), 8.72 (s, 1H), 8.44-8.41 (m, 1H), 7.91 (s, 1H), 7.41 (dd, 0.7=5.2 Hz, 1.2 Hz, 1H), 7.34-7.30 (m, 3H), 7.06 (dd, J=5.2 Hz, 4.0 Hz, 1H), 6.57 (s, 1H), 4.52 (q, J=6.0 Hz, 1H), 3.58 (s, 3H), 1.42 (d, J=6.0 Hz, 6H); MS (ESI) m/z: 519.0 (M+H$^+$).

EXAMPLE 29

Using general method B, Example B9 (0.61 g, 0.22 mmol) and Example A2 (0.066 g, 0.22 mmol) were combined to afford 1-(5-(2-amino-8-ethyl-7-oxo-7,8-dihydropyrido[2,3-d]pyrimidin-6-yl)-2-fluorophenyl)-3-(3-(2-fluorophenyl)-1-methyl-1H-pyrazol-5-yl)urea as the hydrochloride salt (0.071 g, 62%, yield). $^1$H NMR (400 MHz, DMSO-$d_6$): δ 9.46 (s, 1H), 9.09 (s, 1H), 8.76 (s, 1H), 8.41 (d, J=8.0 Hz, 1H), 7.94-7.88 (m, 2H), 7.35-7.21 (m, 5H), 6.66 (d, J=4.0 Hz, 1H), 4.32 (q, J=7.2 Hz, 2H), 3.81 (s, 3H), 1.23 (t, J=7.2 Hz, 3H); MS (ESI) m/z: 517.3 (M+H$^+$).

EXAMPLE 30

Using general method F, 4-chloro-2-isocyanato-1-methylbenzene (0.112 g, 0.668 mmol) and Example A2 (0.100 g, 0.334 mmol) were combined in ethyl acetate to provide 1-(5-(2-amino-8-ethyl-7-oxo-7,8-dihydropyrido[2,3-d]pyrimidin-6-yl)-2-fluorophenyl)-3-(5-chloro-2-methylphenyl)urea, which was converted to the hydrochloride salt (120 mg, 77% yield)*H NMR (400 MHz, DMSO-$d_6$): δ 9.38 (s, 1H), 8.78 (brs, 1H), 8.66 (s, 1H), 8.45 (d, J=8.0 Hz, 1H), 8.07 (m, 1H), 7.94 (m, 1H), 7.31 (d, J=8.0 Hz, 1H), 7.20 (d, J=8.0 Hz, 1H), 6.98 (d, J=8.0 Hz, 1H), 4.30 (q, J=6.0 Hz, 2H), 2.26 (s, 3H), 1.22 (t, J=6.0 Hz, 3H); MS (ESL m/z: 467.0, M+H$^+$).

EXAMPLE 31

Using general method F, 4-chloro-1-isocyanato-2-methylbenzene (0.112 g, 0.668 mmol) and Example A2 (0.100 g, 0.334 mmol) were combined in ethyl acetate to provide 1-(5-(2-amino-8-ethyl-7-oxo-7,8-dihydropyrido[2,3-d]pyrimidin-6-yl)-2-fluorophenyl)-3-(4-chloro-2-methylphenyl)urea, which was converted to the hydrochloride salt (125 mg, 80% yield)*H NMR (400 MHz, DMSO-$d_6$): δ 9.16 (m, 1H), 8.74 (s, 1H), 8.54 (s, 1H), 8.46-8.43 (m, 2H), 7.93 (s, 1H), 7.91 (m, 1H), 7.31-7.27 (m, 3H), 7.20 (dd, J=8.0, 2.5 Hz, 1H), 4.32 (q, J=6.0 Hz, 2H), 2.26 (s, 3H), 1.22 (t, J=6.0 Hz, 3H); MS (ESI, m/z: 467.0, M+H$^+$).

EXAMPLE 32

Using general method F, 1-isocyanatonaphthalene (0.112 g, 0.668 mmol) and Example A2 (0.100 g, 0.334 mmol) were combined in ethyl acetate to provide 1-(5-(2-amino-8-ethyl-7-oxo-7,8-dihydropyrido[2,3-d]pyrimidin-6-yl)-2-fluorophenyl)-3-(naphthalen-1-yl)urea, which was converted to the hydrochloride salt (130 mg, 83% yield)*H NMR (400 MHz, DMSO-$d_6$): δ 9.36 (s, 1H), 9.26 (s, 1H), 8.77 (m, 1H), 8.50 (d, J=8 Hz, 1H), 8.23 (d, J=8 Hz, 1H), 8.06 (d, J=8 Hz, 1H), 7.94 (m, 1H), 7.66-7.46 (m, 4H), 7.31 (m, 4H), 4.32 (q, J=6.0 Hz, 2H), 2.26 (s, 3H), 1.22 (t, J=6.0 Hz, 3H); MS (ESI, m/z: 469.0, M+H$^+$).

EXAMPLE 33

Using general method F, 1-chloro-3-isocyanato-2-methylbenzene (0.112 g, 0.668 mmol) and Example A2 (0.100 g, 0.334 mmol) were combined in ethyl acetate to provide 1-(5-(2-amino-8-ethyl-7-oxo-7,8-dihydropyrido[2,3-d]pyrimidin-6-yl)-2-fluorophenyl)-3-(3-chloro-2-methylphenyl)urea, which was converted to the hydrochloride salt (128 mg, 82% yield). $^1$H NMR (400 MHz, DMSO-$d_6$): δ 9.12 (s, 1H), 8.74 (m, 1H), 8.66 (s, 1H), 8.43 (d, J=8 Hz, 1H), 7.90 (m, 1H), 7.78 (m, 1H), 0.29 (m, 2H), 7.17 (m, 1H), 4.32 (q, J=6.0 Hz, 2H), 2.26 (s, 3H), 1.22 (t, J=6.0 Hz, 3H); MS (ESI, m/z: 467.0, M+H$^+$).

EXAMPLE 34

A solution of 4-(1,3,4-oxadiazol-2-yl)phenol (1.05 g, 6.48 mmol) and triethylamine (1.82 mL, 13.0 mmol) in $CH_2Cl_2$ (12 mL) was cooled to 0° C. and treated with triflic chloride (0.83 mL, 7.77 mmol). The resultant orange-colored reaction was stirred 30 min at 0° C. and 30 min at RT. The reaction was poured into EtOAc (50 mL), washed with water (20 mL), satd aq $NaHCO_3$ (20 mL) and brine (20 mL), dried ($Na_2SO_4$) and concentrated in vacuo to provide 4-(1,3,4-Oxadiazol-2-yl) phenyl trifluoromethanesulfonate (1.94 g, 102% yield) as a beige-colored solid. $^1$H NMR (400 MHz, DMSO-d$_6$): δ 9.43 (s, 1 H), 8.22 (d, J=8.6 Hz, 2 H), 7.78 (d, J=8.6 Hz, 2 H).

4-(1,3,4-Oxadiazol-2-yl)phenyl trifluoromethane-sulfonate (0.645 g, 2.19 mmol), bis(pinacolato)diboron (0.72 g, 2.85 mol), and potassium acetate (0.645 g, 6.58 mmol) were combined in DMF (4 mL). The resultant mixture was de-gassed under vacuum, backfilling with argon (repeated 4×). Pd(dppf)Cl$_2$ (96 mg, 0.12 mmol) was added and the reaction warmed to 95° C. overnight. The reaction was diluted with EtOAc (50 mL), washed with water (2×15 mL) and brine (2×10 mL), dried (MgSO$_4$) and concentrated in vacuo. Silica gel chromatography provided 2-(4-(4,4,5,5-tetramethyl-1,3,2-dioxaborolan-2-yl)phenyl)-1,3,4-oxadiazole (504 mg, 86% yield) as a white solid. $^1$H NMR (400 MHz, DMSO-d$_6$): δ 8.50 (s, 1 H), 8.10 (d, J=8.0 Hz, 2 H), 7.97 (d, J=8.0 Hz, 2 H), 1.39 (s, 12 H).

A solution of 2-(4-(4,4,5,5-tetramethyl-1,3,2-dioxaborolan-2-yl)phenyl)-1,3,4-oxadiazole (0.504 g, 1.85 mmol) in THF (10 mL) and water (5 mL) was treated with sodium periodate (1.19 g, 5.56 mmol). The resultant slurry was stirred at RT for 5 h. Glacial acetic acid (0.21 mL, 3.7 mmol) was added and the mixture was stirred for 1 h and filtered. The filtered solid was washed with ethyl acetate (75 mL) and THF-methanol (1:1, 100 mL) and the filtrates were concentrated in vacuo to a white solid. The solid was suspended in THF (75 mL) and 10 mL of 0.1 M aq HCl and was sonicated to promote dissolution. The trace of insolubles were filtered and the organic layer was diluted with ethyl acetate (25 mL), washed with 0.1 M Na$_2$S$_2$O$_3$ (2×20 mL), water (2×20 mL) and brine (20 mL), dried (Na$_2$SO$_4$) and concentrated in vacuo to provide 4-(1,3,4-oxadiazol-2-yl)phenylboronic acid (304 mg, 86% yield) as a white powder. $^1$H NMR (400 MHz, DMSO-d$_6$): δ 9.37 (s, 1 H), 8.32 (s, 2 H), 7.99 (s, 4 H).

A mixture of 4-(1,3,4-oxadiazol-2-yl)phenylboronic acid (303 mg, 1.60 mmol) and powdered 4A molecular sieves (300 mg) in CH$_2$Cl$_2$ (6 mL) was heated to reflux for 2 h. Ethyl 3-tert-butyl-1H-pyrazole-5-carboxylate (310 mg, 1.6 mmol), pyridine (0.13 mL, 1.6 mmol) and copper (II) acetate (290 mg, 1.6 mmol) were added and the reaction mixture was refluxed for 24 h. The reaction was filtered and the solid was washed with EtOAc (40 mL) and MeOH (40 mL). The combined filtrate and washings were concentrated in vacuo and partitioned between EtOAc (40 mL) and water (20 mL). The organics were washed with water (20 mL), satd aq NaHCO$_3$ (20 mL), water (20 mL), and brine (20 mL), dried (Na$_2$SO$_4$) and concentrated in vacuo. The oily residue was chromatographed to provide ethyl 1-(4-(1,3,4-oxadiazol-2-yl)phenyl)-3-tert-butyl-1H-pyrazole-5-carboxylate (440 mg, > 100% yield) as a visocus oil contaminated with the starting ester. The mixture was used without further purification.

A solution of ethyl 1-(4-(1,3,4-oxadiazol-2-yl)phenyl)-3-tert-butyl-1H-pyrazole-5-carboxylate (440 mg, 1.29 mmol) in a mixture comprised of THF (3 mL), methanol (1 mL) and water (1 mL) was cooled to 0° C. and treated with lithium hydroxide (62 mg, 2.59 mmol). The reaction mixture was stirred 3 h at 0° C. and was then allowed to warm to RT over 4 h. Water (15 mL) was added and the mixture was extracted with ether (2×10 mL). The aqueous portion was acidified by addition of 1 M aq HCl (2.5 mL, 2.5 mmol) and was extracted with EtOAc (3×20 mL). The organics were dried (Na$_2$SO$_4$) and concentrated in vacuo to provide 1-(4-(1,3,4-oxadiazol-2-yl)phenyl)-3-tert-butyl-1H-pyrazole-5-carboxylic acid (355 mg, 88% yield). $^1$H NMR (400 MHz, DMSO-d$_6$): δ 13.35 (br s, 1 H), 9.40 (d, J=3.4 Hz, 1 H), 8.11 (m, 2 H), 7.69 (m, 2 H), 7.01 (d, J=3.2 Hz, 1 H), 1.32 (s, 9 H); MS (ESI) m/z: 313.0 (M+H$^+$).

Using general method D, 1-(4-(1,3,4-oxadiazol-2-yl)phenyl)-3-tert-butyl-1H-pyrazole-5-carboxylic acid (95 mg, 0.30 mmol), Example A1 (87 mg, 0.30 mmol) and pyridine (0.015 mL, 0.19 mmol) were combined to afford crude product. The product was chromatographed on silica gel (100% EtOAc) and further crystallized from EtOAc to provide 1-(1-(4-(1,3,4-oxadiazol-2-yl)phenyl)-3-tert-butyl-1H-pyrazol-5-yl)-3-(5-(2-amino-8-methyl-7-oxo-7,8-dihydropyrido[2,3-d]pyrimidin-6-yl)-2-fluorophenyl)urea. $^1$H NMR (400 MHz, DMSO-d$_6$): δ 9.39 (s, 1 H), 9.03 (br s, 1 H), 8.99 (br s, 1 H), 8.67 (s, 1 H), 8.39 (dd, J=8.0, 2.0 Hz, 1 H), 8.19 (d, J=8.6 Hz, 2 H), 7.86 (s, 1 H), 7.83 (s, 1 H), 7.82 (d, J=8.6 Hz, 2 H), 7.33-7.24 (m, 4 H), 6.47 (s, 1 H), 3.57 (s, 3 H), 1.30 (s, 9 H); MS (ESI) m/z: 595.2 (M+H$^+$).

EXAMPLE 35

Using general method A, the troc carbamate of pyrazole amine of Example 37 (0.2 g, 0.53 mmol) and Example A2 (0.160 g, 0.53 mmol) were combined to provide 1-(5-(2-amino-8-ethyl-7-oxo-7,8-dihydropyrido[2,3-d]pyrimidin-6-yl)-2-fluorophenyl)-3-(3-isopropyl-1-phenyl-1H-pyrazol-5-yl)urea which was converted to the hydrochloride salt (140 mg, 50% yield). $^1$H NMR (400 MHz, DMSO-d$_6$): δ9.10 (s, 1H), 9.05 (s, 1H), 8.79 (s, 1H), 8.40 (d, J=8 Hz, 1H), 7.90 (s, 1H), 7.54 (m, 4H), 7.43 (m, 1H), 7.27 (d, J=8 Hz, 1H), 6.36 (s, 1H), 4.32 (q, J= 6.0 Hz, 2H), 2.89 (m, 1H), 1.22 (m, 9H); MS (ESI, m/z: 527.2, M+H$^+$).

EXAMPLE 36

Using general method C, Example B14 (420 mg, 1.50 mmol) was converted to 73% mono-Troc, 2,2,2-trichloroethyl 3-tert-butyl-1-(2-methylquinolin-6-yl)-1H-pyrazol-5-yl-carbamate and 16% bis-Troc, based on LC analysis, and which was used without further purification in the next reaction (667 mg). MS (ESI) m/z: 456.5 (M+H$^+$). Example A1 (136 mg, 0.475 mmol) and the above Troc mixture (200 mg, 0.453 mmol) were combined to afford 1-(5-(2-amino-8-methyl-7-oxo-7,8-dihydropyrido[2,3-d]pyrimidin-6-yl)-2-fluorophenyl)-3-(3-tert-butyl-1-(2-methylquinolin-6-yl)-1H-pyrazol-5-yl)urea as the hydrochloride salt (22 mg, 8% yield). $^1$H NMR (300 MHz, DMSO-d$_6$), δ 1.32 (s, 9 H), 2.96 (s, 3H), 3.56 (s, 3 H), 6.49 (s, 1 H), 7.26-7.28 (m, 2 H), 7.70 (br. s, 2 H), 7.88 (s, 1 H), 7.95 (d, J=8.7, 1 H), 8.31-8.35 (m, 2 H), 8.42-8.44 (m, 1 H), 8.50 (m, 1 H), 8.74 (s, 1 H), 9.01 (m, 1 H), 9.17 (s, 1 H), 9.46 (s, 1 H); MS (ESI) m/z: 592.3 (M+H$^+$).

EXAMPLE 37

Using general method B, the carbamate of 3-isopropyl-1-phenyl-1H-pyrazol-5-amine (1.01 g, 5.02 mmol) and Example A12 (0.69 g, 2.3 mmol) were combined to afford 1-(2-fluoro-5-(8-methyl-2-(methylamino)-7-oxo-7,8-dihydropyrido[2,3-d]pyrimidin-6-yl)phenyl)-3-(3-isopropyl-1-phenyl-1H-pyrazol-5-yl)urea as an off-white solid (0.75 g, 62%, yield). $^1$H NMR (400 MHz, DMSO-d$_6$): δ 8.99 (s, 1H), 8.90 (s, 1H), 8.75-8.66 (m, 1H), 8.42 (dd, J=8.0 Hz, 1.6 Hz, 1H), 7.87 (s, 1H), 7.83-7.81 (m, 1H), 7.58-7.51 (m, 4H), 7.46-7.41 (m, 1H), 7.32-7.23 (m, 2H), 6.37 (s, 1H), 3.63-3.56 (m, 3H), 2.93-2.87 (m, 4H), 1.23 (d, J=6.8 Hz, 6H); MS (ESI) m/z: 527.2 (M+H$^+$).

EXAMPLE 38

Using general method B, Example B1 (1.01 g, 4.69 mmol) and Example A12 (1.25 g, 4.18 mmol) were combined to afford 1-(3-tert-butyl-1-phenyl-1H-pyrazol-5-yl)-3-(2-fluoro-5-(8-methyl-2-(methylamino)-7-oxo-7,8-dihydropyrido[2,3-d]pyrimidin-6-yl)phenyl)urea as off-white solid (1.39 g, 62%, yield). $^1$H NMR (400 MHz, DMSO-d$_6$): δ 9.00 (s, 1H), 8.89 (s, 1H), 8.75-8.67 (m, 1H), 8.42 (dd, J=8.0 Hz, 1.6 Hz, 1H), 7.88 (s, 1H), 7.83-7.81 (m, 1H), 7.58-7.51 (m, 4H), 7.46-7.41 (m, 1H), 7.32-7.23 (m, 2H), 6.41 (s, 1H), 3.63-3.56 (m, 3H), 2.92 (d, J=4.0 Hz, 3H), 1.28 (s, 9H); MS (ESI) m/z: 541.3 (M+H$^+$).

EXAMPLE 39

Using general method B, Example B9 (0.61 g, 0.22 mmol), and Example A12 (0.066 g, 0.22 mmol) were combined to afford 1-(2-fluoro-5-(8-methyl-2-(methylamino)-7-oxo-7,8-dihydropyrido[2,3-d]pyrimidin-6-yl)phenyl)-3-(3-(2-fluorophenyl)-1-methyl-1H-pyrazol-5-yl)urea as the hydrochloride salt (0.071 g, 62%, yield). $^1$H NMR (400 MHz, DMSO-d$_4$): δ 9.33 (s, 1H), 9.01 (s, 1H), 8.70 (s, 1H), 8.44-8.41 (m, 1H), 7.94-7.90 (m, 2H), 7.35-7.21 (m, 5H), 6.67 (d, J=4.4 Hz, 1H), 3.80 (s, 3H), 3.62 (s, 3H), 2.93 (s, 3H); MS (ESI) m/z: 517.3 (M+H$^+$).

EXAMPLE 40

Using general method F, 4-biphenylyl isocyanate (0.100 g, 0.512 mmol, 1.00 eq) and Example A3 (0.162 g, 0.512 mmol, 1.00 eq) were combined to afford 1-(2-fluoro-5-(8-methyl-2-(methylthio)-7-oxo-7,8-dihydropyrido[2,3-d]pyrimidin-6-yl)phenyl)-3-(4-biphenyl)urea (0.1884 g, 72% yield) as a peach-colored solid which was used as is in the next step. $^1$H NMR (400 MHz, DMSO-d$_6$): δ 9.22 (s, 1H), 8.98 (s, 1H), 8.68 (brs, 1H), 8.54-8.51 (m, 1H), 8.10 (s, 1H), 7.66-7.56 (m, 7H), 7.46-7.42 (m, 2H), 7.36-7.30 (m, 3H), 3.69 (s, 3H), 2.63 (s, 3H); MS (ESI) m/z: 512.3 (M+H$^+$), 534.0 (M+Na$^+$).

Using a procedure analogous to Example A1, 1-(2-fluoro-5-(8-methyl-2-(methylthio)-7-oxo-7,8-dihydropyrido[2,3-d]pyrimidin-6-yl)phenyl)-3-(4-biphenyl)urea and MeNH$_2$.HCl were combined to afford 1-(2-fluoro-5-(8-methyl-2-(methylamino)-7-oxo-7,8-dihydropyrido[2,3-d]pyrimidin-6-yl)phenyl)-3-(4-biphenyl)urea (59.9 mg) as a pale yellow solid which was subsequentually converted to the HCl salt (56.7 mg). $^1$H NMR (400 MHz, DMSO-d$_6$): δ 9.30 (s, 1H), 8.71 (brs, 1H), 8.67 (brs, 1H), 8.48 (dd, 1H, J=2.0 and 8.0 Hz), 7.92 (s, 1H), 7.65-7.56 (m, 7H), 7.46-7.41 (m, 2H), 7.34-7.26 (m, 3H), 3.64 (brs, 3H), 2.94 (brs, 3H); MS (ESI) m/z: 495.0 (M+H$^+$).

EXAMPLE 41

Using general method D, Example B17 (0.061 g, 0.25 mmol) and Example A37 (0.14 g, 0.51 mmol) in presence of tri ethyl amine (0.077 g, 0.76 mmol) and diphenylphospharyl azide (0.077 g, 0.28 mmol) were combined to afford 1-(3-(2-amino-8-methyl-7-oxo-7,8-dihydropyrido[2,3-d]pyrimidin-6-yl)phenyl)-3-(3-tert-butyl-1-(2-(dimethylamino)ethyl)-1H-pyrazol-5-yl)urea as the hydrochloride salt (0.063 g, 49% yield). $^1$H NMR (400 MHz, DMSO-d$_6$): δ 9.62 (brs, 1H), 9.46 (s, 1H), 9.24 (s, 1H), 8.67 (s, 1H), 7.89 (s, 1H), 7.45 (d, J=8.0 Hz, 1H), 7.36-7.31 (m, 4H), 7.17-7.12 (m, 1H), 6.15 (s, 1H), 4.38 (t, J=6.4 Hz, 2H), 3.58 (s, 3H), 3.55-3.51 (m, 2H), 2.84 (s, 3H), 2.83 (s, 3H), 1.24 (s, 9H); MS (ESI) m/z: 504.2 (M+H$^+$).

EXAMPLE 42

Using general method F, Example A1 (72 mg, 0.25 mmol) and 1-isocyanato-3-methylbenzene (0.049 mL, 0.38 mmol) were combined to provide 1-(5-(2-amino-8-methyl-7-oxo-7,8-dihydropyrido[2,3-d]pyrimidin-6-yl)-2-fluorophenyl)-3-m-tolylurea (57 mg, 52% yield). $^1$H NMR (400 MHz, DMSO-d$_6$): δ 9.01 (br s, 1 H), 8.69 (s, 1 H), 8.57 (d, J=2.5 Hz, 1H), 8.45 (m, 1 H), 7.89 (s, 1 H), 7.34-7.27 (m, 4 H), 7.22-7.14 (m, 3 H), 6.81 (d, J=7.1 Hz, 1H), 3.58 (s, 3 H), 2.29 (s, 3 H); MS (ESI) m/z: 419.2 (M+H$^+$).

EXAMPLE 43

Using general method C, Example B18 (0.250 g, 1.78 mmol, 1.00 eq) as the TROC carbamate and Example A3 (0.211 g, 0.665 mmol, 1.00 eq) were combined to afford 1-(3-t-butylisoxazol-5-yl)-3-(2-fluoro-5-(8-methyl-2-(methylthio)-7-oxo-7,8-dihydropyrido[2,3-d]pyrimidin-6-yl)phenyl)urea (0.180 g, 56% yield) as an oil. $^1$H NMR (400 MHz, acetone-d$_6$): δ 9.64 (brs, 1H), 8.91 (s, 1H), 8.62 (m, 1H), 8.35 (brs, 1H), 8.06 (s, 1H), 7.49 (m, 1H), 7.26 (m, 1H), 6.17 (s, 1H), 3.77 (s, 3H), 2.69 (s, 3H), 1.32 (s, 9H); MS (ESI) m/z: 483.3 (M+H$^+$).

Using a procedure analogous to Example A1, 1-(3-t-butylisoxazol-5-yl)-3-(2-fluoro-5-(8-methyl-2-(methylthio)-7-oxo-7,8-dihydropyrido[2,3-d]pyrimidin-6-yl)phenyl)urea (0.180 g, 0.373 mmol, 1.00 eq) was oxidized with MCPBA (70.00 wt %, 0.276 g, 1.12 mmol, 3.00 eq) and then subjected to MeNH$_2$.HCl (0.019 g, 0.28 mmol, 2.00 eq) to afford 1-(3-t-butylisoxazol-5-yl)-3-(2-fluoro-5-(8-methyl-2-(methylamino)-7-oxo-7,8-dihydropyrido[2,3-d]pyrimidin-6-yl)phenyl)urea (0.0346 g, 53% yield) as an off-white solid. The free base thus obtained converted to the hydrochloride (32.3 mg) as a pale yellow solid. $^1$H NMR (400 MHz, DMSO-d$_6$): δ 10.45 (s, 1H), 8.840 (s, 1H), 8.69 (brs, 1H), 8.42 (dd, J=8.0, 2.0 Hz, 1H), 7.92 (s, 1H), 7.90 (brs, 1H), 7.39-7.29 (m, 2H), 6.09 (s, 1H), 3.64 (brs, 3H), 2.93 (brs, 3H), 1.26 (s, 9H); MS (ESI) m/z: 466.2 (M+H$^+$).

EXAMPLE 44

Using general method D, Example B25 (0.1 g, 0.39 mmol) and Example A2 (0.234 g, 0.78 mmol) were combined to provide 1-(5-(2-amino-8-ethyl-7-oxo-7,8-dihydropyrido[2,3-d]pyrimidin-6-yl)-2-fluorophenyl)-3-(1-(3-cyanophenyl)-3-isopropyl-1H-pyrazol-5-yl)urea, which was converted to the hydrochloride salt (52 mg, 24% yield). $^1$H NMR (400 MHz, DMSO-d$_6$) δ9.18 (s, 1H), 9.10 (brs, 1H), 8.79 (s, 1H), 8.34 (d, J=8.0 Hz, 1H), 8.05 (m, 1H), 7.90 (m, 3H), 7.73 (t, J=8.5 Hz, 1H), 7.30 (d, J=8.5 Hz, 1H), 6.40 (s, 1H), 4.31 (q, J=8 Hz, 2H), 2.90 (m, 1H), 1.22 (m, 9H); MS (ESI, m/z: 552.2, M+H$^+$).

EXAMPLE 45

Using general procedure D, biphenyl-3-carboxylic acid (0.100 g, 0.504 mmol, 1.00 eq) and Example A3 (0.239 g, 0.757 mmol, 1.50 eq) were combined to afford 1-(2-fluoro-5-(8-methyl-2-(methylthio)-7-oxo-7,8-dihydropyrido[2,3-d]pyrimidin-6-yl)phenyl)-3-(3-biphenyl)urea (0.110 g, 43% yield) as a foam. $^1$H NMR (400 MHz, acetone-d$_6$): δ 9.23 (s, 1H), 8.97 (s, 1H), 8.69 (dd, J=8.0, 2.4 Hz), 8.64 (brs, 1H), 8.09 (s, 1H), 7.93 (m, 1H), 7.68-7.65 (m, 2H), 7.50-7.46 (m, 3H), 7.43-7.36 (m, 3H), 7.30-7.24 (m, 2H), 3.76 (s, 3H), 2.67 (s, 3H); MS (ESI) m/z: 512.0 (M+H$^+$).

Using a procedure analogous to example A1, 1-(2-fluoro-5-(8-methyl-2-(methylthio)-7-oxo-7,8-dihydropyrido[2,3-d]pyrimidin-6-yl)phenyl)-3-(3-biphenyl)urea (0.110 g, 0.215 mmol, 1.00 eq) was oxidized with MCPBA (70.00 wt %, 0.159 g, 0.645 mmol, 3.00 eq) and then subjected to MeNH$_2$.HCl (0.00870 g, 0.129 mmol, 2.00 eq) to afford 1-(2-fluoro-5-(8-methyl-2-(methylamino)-7-oxo-7,8-dihydropyrido[2,3-d]pyrimidin-6-yl)phenyl)-3-(3-biphenyl)urea (0.0227 g, 71% yield). This was converted to the HCl salt (0.021 g) as an off-white solid. $^1$H NMR (400 MHz, DMSO-d$_6$): δ 9.29 (brs, 1H), 8.71 (brs, 1H), 8.69 (brs, 1H), 8.44 (m, 1H), 7.92 (s, 1H), 7.84 (s, 1H), 7.64-7.61 (m, 2H), 7.50-7.46 (m, 2H), 7.40-7.36 (m, 3H), 7.31-7.26 (m, 3H), 3.64 (brs, 3H), 2.93 (brs, 3H); MS (ESI) m/z: 495.2 (M+H$^+$).

EXAMPLE 46

Using general method F, Example A1 (80 mg, 0.28 mmol) and 4-chloro-3-(trifluoromethyl)phenyl isocyanate (93 mg, 0.42 mmol) were combined to provide 1-(5-(2-amino-8-methyl-7-oxo-7,8-dihydropyrido[2,3-d]pyrimidin-6-yl)-2-fluorophenyl)-3-(4-chloro-3-(trifluoromethyl)phenyl)urea (62 mg, 44% yield). $^1$H NMR (400 MHz, DMSO-d$_6$): δ 9.52 (s, 1H), 8.71 (d, J=2.3 Hz, 1 H), 8.68 (s, 1 H), 8.37 (dd, J=8.2, 1.9 Hz, 1 H), 8.14 (d, J=2.2 Hz, 1H), 7.90 (s, 1 H), 7.65-7.58 (m, 2 H), 7.36-7.26 (m, 4 H), 3.58 (s, 3 H); MS (ESI) m/z: 507.0 (M+H$^+$).

EXAMPLE 47

6-t-Butyl-1H-thieno[3,2-d][1,3]oxazine-2,4-dione (0.075 g, 0.33 mmol, 1.0 eq; prepared according to the method disclosed in WO 99/32111) and Example A12 (0.100 g, 0.33 mmol, 1.0 eq) were combined in DMSO (3.3 ml) and stirred with heating at 70° C. for 16 h and at 110° C. for 24 h. The completed reaction was cooled to RT, diluted with brine and extracted with EtOAc (3×). The combined organics were washed with brine (2×), dried (Na$_2$SO$_4$), filtered, concentrated in vacuo and purified by flash column chromatography (10% EtOAc/hexanes-100% EtOAc) to afford 1-(5-t-butylthiophen-3-yl)-3-(2-fluoro-5-(8-methyl-2-(methylamino)-7-oxo-7,8-dihydropyrido[2,3-d]pyrimidin-6-yl)phenyl)urea (0.060 g, 38% yield) as a creamy yellow solid. $^1$H NMR (400 MHz, DMSO-d$_6$): δ 9.18 (s, 1H), 8.67 (brs, 1H), 8.49 (m, 1H), 8.42 (m, 1H), 7.89 (s, 1H), 7.82 (brs, 1H), 7.28-7.25 (m, 2H), 7.02 (d, J=1.6 Hz, 1H), 6.82 (d, J=1.6 Hz, 1H), 3.639 (brs, 3H), 2.93 (d, J=4.1 Hz, 3H); MS (ESI) m/z: 481.2 (M+H$^+$).

EXAMPLE 48

Using general method B, the carbamate of 1-phenyl-3-(trifluoromethyl)-1H-pyrazol-5-amine (1.01 g, 3.24 mmol) and Example A12 (0.97 g, 3.24 mmol) were combined to afford 1-(2-fluoro-5-(8-methyl-2-(methylamino)-7-oxo-7,8-dihydropyrido[2,3-d]pyrimidin-6-yl)phenyl)-3-(1-phenyl-3-(trifluoromethyl)-1H-pyrazol-5-yl)urea as an off-white solid (1.41 g, 79%, yield). $^1$H NMR (400 MHz, DMSO-d$_6$): δ 9.16 (s, 1H), 9.08 (s, 1H), 8.72 (s, 1H), 8.37 (dd, J=8.0 Hz, 1.6 Hz, 1H), 7.92 (s, 1H), 7.85 (brs, 1H), 7.64-7.54 (m, 5H), 7.32-7.20 (m, 2H), 6.87 (s, 1H), 3.60-3.57 (m, 3H), 2.89 (d, J=4.8 Hz, 3H); MS (ESI) m/z: 556.3 (M+H$^+$).

EXAMPLE 49

Using general method D, 3-tert-butyl-1-methyl-1H-pyrazole-5-carboxylic acid (0.041 g, 0.24 mmol) and Example A52 (0.085 g, 0.27 mmol) were combined in presence of tri ethyl amine (0.046 g, 0.45 mmol) and diphenylphospharyl azide (0.093 g, 0.34 mmol) to afford 1-(5-(2-amino-8-isopropyl-7-oxo-7,8-dihydropyrido[2,3-d]pyrimidin-6-yl)-2-fluorophenyl)-3-(3-tert-butyl-1-methyl-1H-pyrazol-5-yl)urea as a white solid (0.068 g, 61% yield). $^1$H NMR (400 MHz, DMSO-d$_6$): δ 8.92 (s, 1H), 8.82 (s, 1H), 8.64 (s, 1H), 8.37-8.35 (m, 1H), 7.80 (s, 1H), 7.29-7.26 (m, 4H), 6.01 (s, 1H), 5.80-5.76 (m, 1H), 3.62 (s, 3H), 1.54 (d, J=6.8 Hz, 6H), 1.21 (s, 9H); MS (ESI) m/z: 493.2 (M+H$^+$).

EXAMPLE 50

Using general method D, Example B24 (0.150 g, 0.403 mmol) and Example A2 (0.271 g, 0.906 mmol) were combined to provide 1-(5-(2-amino-8-ethyl-7-oxo-7,8-dihydropyrido[2,3-d]pyrimidin-6-yl)-2-fluorophenyl)-3-(1-(4-fluorophenyl)-3-isopropyl-1H-pyrazol-5-yl)urea, which was converted to the mesylate salt (184 mg, 63% yield). $^1$H NMR (400 MHz, DMSO-d$_6$): δ 9.06 (brs, 1H), 8.96 (s, 1H), 8.78 (s, 1H), 8.39 (d, j=9 Hz, 1H), 7.92 (s, 1H), 7.59 (m, 1H), 7.42 (m, 2H), 7.29 (m, 2H), 6.39 (s, 1H), 4.31 (q, J=7 Hz, 2H), 2.90 (m, 1H), 2.37 (s, 6H), 1.24 (m, 9H); MS (ESI, m/z: 545.3, M+H$^+$).

EXAMPLE 51

Using general method D, example B25 (0.150 g, 0.588 mmol) and Example A1 (0.2 g, 0.705 mmol) were combined to provide 1-(5-(2-amino-8-methyl-7-oxo-7,8-dihydropyrido[2,3-d]pyrimidin-6-yl)-2-fluorophenyl)-3-(1-(3-cyanophenyl)-3-isopropyl-1H-pyrazol-5-yl)urea which was converted to the mesylate salt (78 mg, 51% yield). $^1$H NMR (400 MHz, DMSO-d$_6$) δ9.00 (brs, 1H), 8.96 (s, 1H), 8.75 (s, 1H), 8.39 (d, J=8 Hz, 1H), 8.05 (s, 1H), 7.93-7.85 (m, 3H), 7.75 (m, 1H), 7.29 (d, J=8 Hz, 2H), 6.41 (s, 1H), 3.50 (s, 3H), 2.90 (m, 1H), 2.37 (s, 6H), 1.24 (d, J=7 Hz, 6H); MS (ESI, m/z: 538.3, M+H$^+$).

EXAMPLE 52

Using general method D, 1-(3-fluorophenyl)-3-isopropyl-1H-pyrazole-5-carboxylic acid (0.10 g, 0.403 mmol) and Example A2 (0.241 g, 0.806 mmol) were combined to provide 1-(5-(2-amino-8-ethyl-7-oxo-7,8-dihydropyrido[2,3-d]pyrimidin-6-yl)-2-fluorophenyl)-3-(1-(3-fluorophenyl)-3-isopropyl-1H-pyrazol-5-yl)urea, which was converted to the mesylate salt (70 mg, 63% yield). $^1$H NMR (400 MHz, DMSO-d$_6$): δ9.06 (brs, 1H), 8.96 (s, 1H), 8.78 (s, 1H), 8.39 (d, J=9 Hz, 1H), 7.92 (s, 1H), 7.59 (m, 1H), 7.42 (m, 2H), 7.29 (m, 2H), 6.39 (s, 1H), 4.31 (q, J=7 Hz, 2H), 2.90 (m, 1H), 2.37 (s, 6H), 1.24 (m, 9H); MS (ESI, m/z: 545.3, M+H$^+$).

EXAMPLE 53

To a stirring solution of Example A45 (0.460 g, 1.5 mmol, 1.0 eq) and (Boc)$_2$O (0.70 g, 3.2 mmol, 2.200 eq) in THF (15 ml) at 22° C. was added DMAP (0.040 g, 0.30 mmol, 0.20 eq). The mixture was heated at reflux for 1 h. The completed reaction was cooled to RT, concentrated to a residue and purified by flash column chromatography (0-35% EtOAc in hexanes) to afford bis-tert-butyl 3-(8-ethyl-2-(methylthio)-7-oxo-7,8-dihydropyrido[2,3-d]pyrimidin-6-yl)phenylcarbamate (0.54 g, 70% yield) as an oil that solidified under high vacuum. $^1$H NMR (400 MHz, acetone-d$_6$): δ 8.89 (s, 1H), 8.11 (s, 1H), 7.74 (ddd, J=1.2, 1.6, and 8.0 Hz, 1H), 7.68 (t, J=2.4 Hz, 1H), 7.48 (t, J=7.6 Hz, 1H), 7.26 (ddd, J=1.2, 2.0 and 8.0 Hz, 1H), 4.54 (q, J=6.8 Hz, 2H), 2.67 (s, 3H), 1.48 (s, 18H), 1.35 (t, J=6.8 Hz, 3H); MS (ESI) m/z: 513.3 (M+H$^+$), 535.2 (M+Na$^+$).

Using a procedure analogous to Example A1, bis-tert-butyl 3-(8-ethyl-2-(methylthio)-7-oxo-7,8-dihydropyrido[2,3-d]pyrimidin-6-yl)phenylcarbamate (0.540 g, 1.1 mmol) in CH$_2$Cl$_2$ (11 ml), MCPBA (70.00 wt %, 0.31 g, 1.3 mmol) and 0.5M NH₃ in 1,4-dioxane (11 ml, 5.3 mmol) were combined to afford desired product (0.50 g, 99% yield) as a brittle foam which was used as is in the next reaction. ¹H NMR (400 MHz, acetone-d₆): δ 8.66 (s, 1H), 7.94 (s, 1H), 7.70 (m, 1H), 7.65 (m, 1H), 7.44 (m, 1H), 7.19 (m, 1H), 6.65 (brs, 2H), 4.42 (q, J=6.8 Hz), 1.47 (s, 18H), 1.27 (t, J=6.8 Hz, 3H); MS (ESI) m/z: 482.2 (M+H⁺).

To a stirring solution of bis-t-butyl 3-(2-amino-8-ethyl-7-oxo-7,8-dihydropyrido[2,3-d]pyrimidin-6-yl)phenylcarbamate (0.500 g, 1.04 mmol, 1.00 eq) in MeOH (5.00 ml) at 22° C. was added 3M HCl (5.00 ml, 15.0 mmol, 14.4 eq). After 3 d, the completed reaction was concentrated to remove the MeOH and excess HCl. The aqueous residue was diluted with MeCN/H₂O, frozen and lyophilized to afford 2-amino-6-(3-aminophenyl)-8-ethylpyrido[2,3-d]pyrimidin-7(8H)-one hydrochloride (0.330 g, 100% yield) which was used as is in the next reaction. ¹H NMR (400 MHz, DMSO-d₆): δ 8.79 (s, 1H), 8.02 (s, 1H), 7.52 (t, J=2.0 Hz, 1H), 7.64 (dt, J=1.2 and 8.0 Hz, 1H), 7.56 (t, J=7.6 Hz, 1H), 7.39 (ddd, J=1.2, 2.0, and 8.0 Hz, 1H), 4.33 (q, J=7.2 Hz, 2H), 1.23 (t, J=7.2 Hz, 3H); MS (ESI) m/z: 282.3 (M+H⁺).

Using general method C, the TROC carbamate of Example B26 (0.304 g, 0.711 mmol) and 2-amino-6-(3-aminophenyl)-8-ethylpyrido[2,3-d]pyrimidin-7(8H)-one hydrochloride (0.226 g, 0.711 mmol) were combined to afford impure product (0.300 g) as a yellowish solid. This was triturated with CH₂Cl₂ at 0° C. The solids were collected by filtration, rinsed with ice-cold CH₂Cl₂ and dried on the filter to afford desired product (0.1584, 40% yield) as an off-white solid. The solid was treated with MsOH to afford 1-(3-(2-amino-8-ethyl-7-oxo-7,8-dihydropyrido[2,3-d]pyrimidin-6-yl)phenyl)-3-(3-isopropyl-1-(quinolin-6-yl)-1H-pyrazol-5-yl)urea (0.1793 g) as the bis-mesylate salt. ¹H NMR (400 MHz, DMSO-d₆): δ 9.19 (s, 1H), 9.15 (dd, J=1.2 and 4.40 Hz, 1H), 8.87 (d, J=8.8 Hz, 1H), 8.73-8.71 (m, 2H), 8.38 (d, J=2.0 Hz, 1H), 8.27 (d, J=8.8 Hz, 1H), 8.19 (dd, J=2.0 and 8.8 Hz, 1H), 7.91 (s, 1H), 7.88 (dd, J=4.4 and 8.4 Hz, 1H), 7.74 (dd, J=2.0 and 4.0 Hz, 1H), 7.41 (m, 1H), 7.31 (t, J=8.0 Hz, 1H), 7.22 (m, 1H), 6.44 (s, 1H), 4.31 (q, J=6.8 Hz, 2H), 2.96 (septet, J=6.8 Hz, 1H), 2.36 (s, 6H), 1.28 (d, J=6.8 Hz, 6H), 1.21 (t, J=6.8 Hz, 3H); MS (ESI) m/z: 560.2 (M+H⁺).

EXAMPLE 54

Using General Method A, Example A22 (197 mg, 0.697 mmol) and the 2,2,2-trichloroethyl carbamate of Example B18 (200 mg, 0.634 mmol) were combined to afford 1-(3-tert-butylisoxazol-5-yl)-3-(5-(1-ethyl-2-oxo-1,2-dihydro-1,6-naphthyridin-3-yl)-2-fluorophenyl)urea (98 mg, 34% yield) as the hydrochloride salt. ¹H NMR (300 MHz, DMSO-d₆) δ 1.25 (s, 9 H), 1.26-1.30 (d, 3 H), 4.39 (q, 2 H), 6.06 (s, 1 H), 7.40-7.43 (m, 2 H), 7.98-8.00 (m, 1 H), 8.34 (s, 1 H), 8.49-8.51 (m, 1 H), 8.78-8.80 (m, 1 H), 9.07 (s, 1 H), 9.28 (s, 1 H), 10.6 (s, 1H); MS (ESI) m/z: 450.2 (M+H⁺).

EXAMPLE 55

Using general method A, the TROC carbamate of Example B18 (0.083 g, 0.26 mmol) and Example A52 (0.082 g, 0.26 mmol) were combined to afford 1-(5-(2-amino-8-isopropyl-7-oxo-7,8-dihydropyrido[2,3-d]pyrimidin-6-yl)-2-fluorophenyl)-3-(3-tert-butylisoxazol-5-yl)urea as an off-white solid (0.051 mg, 40% yield). ¹H NMR (400 MHz, DMSO-d₆): δ 10.37 (s, 1H), 8.75 (s, 1H), 8.64 (s, 1H), 8.34 (dd, J=7.6 Hz, 1.6 Hz, 1H), 7.82 (s, 1H), 7.35-7.27 (m, 4H), 6.09 (s, 1H), 5.82-5.76 (m, 1H), 1.55 (d, J=7.2 Hz, 6H), 1.25 (s, 9H); MS (ESI) m/z: 480.2 (M+H⁺).

EXAMPLE 56

Using general method B, prop-1-en-2-yl 3-tert-butylphenylcarbamate (0.18 g, 0.75 mmol) and Example A12 (0.090 g, 0.30 mmol) were combined to afford 1-(3-tert-butylphenyl)-3-(2-fluoro-5-(8-methyl-2-(methylamino)-7-oxo-7,8-dihydropyrido[2,3-d]pyrimidin-6-yl)phenyl)urea (0.057 g, 40% yield) as a yellow solid. ¹H NMR (400 MHz, DMSO-d₆): δ 9.07 (s, 1H), 8.68 (s, 1H), 8.52 (s, 1H), 8.42 (dd, J=7.6, 2.4 Hz, 1H), 7.90 (s, 1H), 7.83 (s, 1H), 7.45 (s, 1H), 7.32-7.19 (m, 4H), 7.03 (d, J=4.4 Hz, 1H), 3.67 (m, 3H), 3.32 (s, 3H), 1.28 (s, 9H); MS (ESI) m/z: 475.2 (M+H⁺).

EXAMPLE 57

To a stirring solution of 1-(3-t-butylisoxazol-5-yl)-3-(2-fluoro-5-(8-methyl-2-(methylsulfinyl)-7-oxo-7,8-dihydropyrido[2,3-d]pyrimidin-6-yl)phenyl)urea from Example 43 (0.125 g, 0.251 mmol, 1.00 eq) in DMF (2.50 ml) at 0° C. was added unsym-dimethylethylenediamine (0.138 ml, 1.25 mmol, 5.00 eq). After 1 h, the completed reaction was diluted with brine (5 ml) and left to stir overnight. The solids were collected by filtration, rinsed well with H₂O and dried on the filter to afford crude desired product (76 mg) as a pale pink solid. The crude product was purified by reverse phase chromatography (5-40% MeCN (w/0.1% TFA)/H₂O (w/0.1% TFA)) to afford 1-(3-t-butylisoxazol-5-yl)-3-(5-(2-(2-(dimethylamino)ethylamino)-8-methyl-7-oxo-7,8-dihydropyrido[2,3-d]pyrimidin-6-yl)-2-fluorophenyl)urea (37.3 mg, 0.059 mmol) as the TFA salt following lyophilization. The TFA salt thus obtained was treated with MP-Carbonate resin and certified 0.1N HCl (1.0 eq), frozen and lyophilized to afford the HCl salt. ¹H NMR (400 MHz, DMSO-d₆): δ 10.44 (s, 1H), 9.56 (brs, 1H), 8.85 (brs, 1H), 8.76 (brs, 1H), 8.41 (dd, J=2.0 and 7.6 Hz, 1H), 8.01 (brs, 1H), 7.95 (s, 1H), 7.37-7.28 (m, 2H), 6.05 (s, 1H), 3.73 (m, 2H), 3.58 (brs, 3H), 3.41 (brs, 2H), 2.85 (brs, 6H), 1.24 (s, 9H); MS (ESI) m/z: 523.2 (M+H⁺).

EXAMPLE 58

Using General Method A, Example A24 (400 mg, 1.28 mmol) and the TROC carbamate of Example B18 (421 mg, 1.28 mmol) were combined to afford 1-(3-tert-butylisoxazol-5-yl)-3-(5-(1-ethyl-7-(methylamino)-2-oxo-1,2-dihydro-1,6-naphthyridin-3-yl)-2-fluorophenyl)urea (242 mg) as a foam. The foam was treated with methanesulfonic acid (47 mg, 0.492 mmol) and isolated as the methanesulfonic acid salt (248 mg, 87% yield). ¹H NMR (300 MHz, DMSO-d₆): δ 1.20-1.28 (m, 3 H), 1.22 (s, 9 H), 2.28 (s, 3 H), 2.94 (s, 3 H), 4.15-4.18 (q, 2 H), 6.04 (s, 1 H), 6.51 (s, 1 H), 7.31-7.33 (m, 2 H), 7.98 (s, 1 H), 8.37-8.39 (m, 1 H), 8.55 (s, 1H), 8.77 (s, 1 H), 10.3 (s, 1 H), acid proton missing; MS (ESI) m/z: 479.2 (M+H⁺).

EXAMPLE 59

Using general method A, Example A14 (54 mg, 0.18 mmol) and the TROC carbamate of Example B18 (57 mg, 0.18 mmol) were combined to provide 1-(5-(2-amino-8-methyl-7-oxo-7,8-dihydropyrido[2,3-d]pyrimidin-6-yl)-2-fluoro-4-methylphenyl)-3-(3-tert-butylisoxazol-5-yl)urea (45 mg, 54% yield). ¹H NMR (400 MHz, DMSO-d₆): δ 10.30 (s, 1 H), 8.68 (s, 1 H), 8.63 (s, 1 H), 7.90 (d, J=8.6 Hz, 1 H), 7.69 (s, 1 H), 7.32 (s, 2 H), 7.19 (d, J=12.2 Hz, 1 H), 6.03 (s, 1 H), 3.56 (s, 3 H), 2.10 (s, 3 H), 1.24 (s, 9 H); MS (ESI) m/z: 466.2 (M+H⁺).

EXAMPLE 60

Using general method A, Example A1 (54 mg, 0.18 mmol) and the TROC carbamate of Example B18 (57 mg, 0.18 mmol) were combined to provide 1-(5-(2-amino-8-methyl-7-oxo-7,8-dihydropyrido[2,3-d]pyrimidin-6-yl)-2-fluorophenyl)-3-(3-tert-butylisoxazol-5-yl)urea. $^1$H NMR (400 MHz, DMSO-d$_6$): δ 10.37 (s, 1 H), 8.77 (d, J=2.0 Hz, 1 H), 8.68 (s, 1H), 8.42 (dd, J=8.0, 2.0 Hz, 1 H), 7.90 (s, 1 H), 7.38-7.28 (m, 4 H), 6.09 (s, 1 H), 3.58 (s, 3 H), 1.27 (s, 9 H); MS (ESI) m/z: 452.2 (M+H$^+$).

EXAMPLE 61

Using a procedure analogous to Example A1, Example A3 (1.00 g, 3.16 mmol) and unsym-dimethylethylenediamine (1.74 ml, 15.8 mmol) were combined to afford 6-(3-amino-4-fluorophenyl)-2-(2-(dimethylamino)ethylamino)-8-methylpyrido[2,3-d]pyrimidin-7(8H)-one (0.8640 g, 77% yield) as a tan solid which was used as is in the next reaction. $^1$H NMR (400 MHz, DMSO-d$_6$): δ 8.62 (s, 1H), 7.80 (s, 1H), 7.71 (brt, 1H), 7.10 (dd, J=2.0 and 9.2 Hz, 1H), 7.00 (dd, J=8.4 and 11.2 Hz, 1H), 6.76 (ddd, J=2.0, 4.40, and 8.40 Hz, 1H), 5.14 (brs, 2H), 3.58 (brs, 3H), 3.47 (q, J=6.4 Hz, 2H), 2.47 (brm, 2H), 2.20 (s, 6H); MS (ESI) m/z: 357.2 (M+H$^+$).

Using general method F, 6-(3-amino-4-fluorophenyl)-2-(2-(dimethylamino)ethylamino)-8-methylpyrido[2,3-d]pyrimidin-7(8H)-one (0.1000 g, 0.281 mmol, 1.00 eq) and α,α,α-trifluoro-m-tolyl isocyanate (0.0589 ml, 0.421 mmol, 1.50 eq) were combined to afford crude product. The crude residue was purified by reverse phase chromatography and isolated as the HCl salt of 1-(5-(2-(2-(dimethylamino)ethylamino)-8-methyl-7-oxo-7,8-dihydropyrido[2,3-d]pyrimidin-6-yl)-2-fluorophenyl)-3-(3-(trifluoromethyl)phenyl)urea (63 mg). $^1$H NMR (400 MHz, DMSO-d$_6$): δ 9.62 (brs, 1H), 9.59 (s, 1H), 8.78 (brs, 1H), 8.75 (s, 1H), 8.40 (m, 1H), 8.05 (s, 1H), 7.99 (brs, 1H), 7.95 (s, 1H), 7.51-7.49 (m, 2H), 7.33-7.25 (m, 3H), 3.75-3.70 (m, 2H), 3.62 (brs, 3H), 3.32 (brs, 2H), 2.83 (brs, 6H), MS (ESI) m/z: 544.2 (M+H$^+$).

EXAMPLE 62

Using general procedure A, Example B3 (0.3000 g, 1.1 mmol, 1.0 eq) and 6-(3-amino-4-fluorophenyl)-2-(2-(dimethylamino)ethylamino)-8-methylpyrido[2,3-d]pyrimidin-7(8H)-one from Example 61 (0.0796 g, 0.223 mmol, 1.00 eq) were combined to give the target crude product. The crude product was purified by reverse phase chromatography to afford the TFA salt (34.2 mg) following lyophilization. The TFA salt thus obtained was converted to the HCl of desired product, 1-(1-(3-(2-amino-2-oxoethyl)phenyl)-3-t-butyl-1H-pyrazol-5-yl)-3-(5-(2-(2-(dimethylamino)ethylamino)-8-methyl-7-oxo-7,8-dihydropyrido[2,3-d]pyrimidin-6-yl)-2-fluorophenyl)urea (30 mg). $^1$H NMR (400 MHz, DMSO-d$_6$): δ 9.87 (brs, 1H), 9.05 (s, 1H), 8.97 (s, 1H), 8.77 (brs, 1H), 8.45 (m, 1H), 8.05 (brs, 1H), 7.95 (s, 1H), 7.55 (brs, 1H), 7.50-7.44 (m, 2H), 7.39-7.25 (m, 4H), 6.94 (brs, 1H), 6.40 (s, 1H), 3.76 (brm, 2H), 3.66 (brs, 3H), 3.48 (s, 2H), 3.34 (brm, 2H), 2.85 (brs, 6H), 1.28 (s, 9H); MS (ESI) m/z: 655.2 (M+H$^+$).

EXAMPLE 63

Using general method C, Example B27 (400 mg, 1.7 mmol) was converted to the bis(2,2,2-trichloroethyl)carbamate of 1-(6-methylpyridin-3-yl)-3-(trifluoromethyl)-1H-pyrazol-5-amine (435 mg, 43% yield). MS (ESI) m/z: 592.7/594.8 (M+H$^+$).

A solution of the bis(2,2,2-trichloroethyl)carbamate of 1-(6-methylpyridin-3-yl)-3-(trifluoromethyl)-1H-pyrazol-5-amine (433 mg, 0.7 mmol) and trichloroethanol (1 mL, 10 mmol) in acetonitrile (5 mL) was treated with K$_2$CO$_3$ (9 mg, 0.07 mmol). The resultant reaction mixture was stirred at RT for 7 h. The reaction mixture was diluted with ethyl acetate (30 mL), washed with water and brine, dried (MgSO$_4$) and concentrated in vacuo. Chromatography provided 2,2,2-trichloroethyl 1-(6-methylpyridin-3-yl)-3-(trifluoromethyl)-1H-pyrazol-5-ylcarbamate (270 mg, 89% yield) as a white foam. $^1$H NMR (400 MHz, DMSO-d$_6$): δ 10.56 (br s, 1 H), 8.61 (d, J=2.5 Hz, 1 H), 7.87 (dd, J=8.3, 2.8 Hz, 1 H), 7.47 (d, J=8.3 Hz, 1 H), 6.95 (s, 1 H), 4.89 (s, 2 H), 2.56 (s, 3 H); MS (ESI) m/z: 417.0/419.0 (M+H$^+$).

Using general method A, Example A1 (69 mg, 0.24 mmol) and 2,2,2-trichloroethyl 1-(6-methylpyridin-3-yl)-3-(trifluoromethyl)-1H-pyrazol-5-ylcarbamate (98 mg, 0.23 mmol) were combined to provide impure desired product. The residue was chromatographed and triturated with boiling CH$_2$Cl$_2$ to provide 1-(5-(2-amino-8-methyl-7-oxo-7,8-dihydropyrido[2,3-d]pyrimidin-6-yl)-2-fluorophenyl)3-(1-(6-methylpyridin-3-yl)-3-(trifluoromethyl)-1H 5-yl)urea (35 mg, 27% yield). $^1$H NMR (400 MHz, DMSO-d$_6$): δ 9.21 (br s, 1 H), 9.02 (m, 1H), 8.70 (d, J=2.4 Hz, 1 H), 8.65 (s, 1 H), 8.37 (dd, J=8.0, 1.2 Hz, 1 H), 7.96 (dd, J=8.0, 2.6 Hz, 1 H), 7.84 (s, 1 H), 7.51 (d, J=8.0 Hz, 1 H), 7.31-7.22 (m, 4 H), 6.89 (s, 1 H), 3.55 (s, 3 H), 2.58 (s, 3 H); MS (ESI) m/z: 554.0 (M+H$^+$).

EXAMPLE 64

Using general method A, 1-(5-(2-(2-(dimethylamino)ethylamino)-8-methyl-7-oxo-7,8-dihydropyrido[2,3-d]pyrimidin-6-yl)-2-fluorophenyl)-3-(3-isopropylisoxazol-5-yl)urea hydrochloride (210 mg, 45% yield) was prepared from the Troc carbamate of Example B20 (0.300 g, 0.995 mmol, 1.00 eq) and 6-(3-amino-4-fluorophenyl)-2-(2-(dimethylamino) ethylamino)-8-methylpyrido[2,3-d]pyrimidin-7(8H)-one from Example 61 (0.355 g, 0.995 mmol, 1.00 eq). $^1$H NMR (400 MHz, DMSO-fife): δ 10.40 (s, 1H), 9.43 (brs, 1H), 8.82 (d, J=2.4 Hz, 1H), 8.75 (brs, 1H), 8.39 (dd, J=2.0 and 7.6 Hz, 1H), 7.99 (brs, 1H), 7.95 (s, 1H), 7.37-7.28 (m, 2H), 6.01 (s, 1H), 3.73 (brm, 2H), 3.63 (brs, 3H), 3.32 (brm, 2H), 2.89 (septet, J=6.8 Hz, 1H), 2.85 (brs, 6H), 1.18 (d, J=6.8 Hz, 6H); MS (ESI) m/z: 509.2 (M+H$^+$).

EXAMPLE 65

Using a modified general method B, the carbamate of Example B19 (0.3 g, 1.36 mmol) and Example A3 (0.43 g, 1.36 mmol) in presence of 1-methylpyrrolidine (catalytic amount) were heated at 120° C. for 1.5 h under microwave irradiation to afford 1-(1-tert-butyl-1H-pyrazol-4-yl)-3-(2-fluoro-5-(8-methyl-2-(methylthio)-7-oxo-7,8-dihydropyrido[2,3-d]pyrimidin-6-yl)phenyl)urea (0.3 g, 47% yield). $^1$H NMR (400 MHz, DMSO-d$_6$): δ 8.95 (s, 1H), 8.72 (brs, 1H), 8.54 (d, J=2.0 Hz, 1H), 8.48-8.46 (m, 1H), 8.05 (s, 1H), 7.81 (s, 1H), 7.39 (s, 1H), 7.29-7.26 (m, 2H), 3.66 (s, 3H), 2.60 (s, 3H), 1.47 (s, 9H); (ESI) m/z: 482.2 (M+H$^+$).

Using a procedure analogous to Example A1, 1-(1-tert-butyl-1H-pyrazol-4-yl)-3-(2-fluoro-5-(8-methyl-2-(methylthio)-7-oxo-7,8-dihydropyrido[2,3-d]pyrimidin-6-yl)phenyl)urea (0.3 g, 0.63 mmol) and methyl amine (1.3 ml of 1M solution, 1.3 mmol) were combined to afford 1-(1-tert-butyl-1H-pyrazol-4-yl)-3-(2-fluoro-5-(8-methyl-2-(methylamino)-7-oxo-7,8-dihydropyrido[2,3-d]pyrimidin-6-yl)phenyl)urea as a white solid (0.135 g, 66% yield). ¹H NMR (400 MHz, DMSO-d₆): δ 8.73-8.70 (m, 1H), 8.65 (s, 1H), 8.48 (d, J=2.0 Hz, 1H), 8.41-8.39 (m, 1H), 7.85 (s, 1H), 7.81 (brs, 2H), 7.38 (s, 1H), 7.24-7.22 (m, 2H), 3.61-3.57 (m, 3H), 2.90 (d, J=4.0 Hz, 1H), 2.60 (s, 3H), 1.46 (s, 9H); (ESI) m/z: 465.2 (M+H*).

EXAMPLE 66

Using general method B, the carbamate of B2 (0.045 g, 0.19 mmol) and Example A14 (0.057 g, 0.19 mmol) were combined to afford 1-(5-(2-amino-8-methyl-7-oxo-7,8-dihydropyrido[2,3-d]pyrimidin-6-yl)-2-fluoro-4-methylphenyl)-3-(3-tert-butyl-1-methyl-1H-pyrazol-5-yl)urea (0.076 g, 84% yield). ¹H NMR (400 MHz, DMSO-d₆): δ 8.85 (s, 1H), 8.71 (m, 1H), 8.60 (s, 1H), 7.92 (d, J=8.8 Hz, 1H), 7.65 (s, 1H), 7.28 (s, 2H), 7.14 (d, J=12.4 Hz, 1H), 6.04 (s, 1H), 3.58 (s, 3H), 3.54 (s, 3H), 2.05 (s, 3H), 1.16 (s, 9H); MS (ESI) m/z: 479.2 (M+H⁺).

EXAMPLE 67

Using general method F, Example A3 (500 mg, 1.58 mmol) and 1-isocyanato-3-(trifluoromethyl)benzene (311 mg, 1.66 mmol) were combined in the presence of pyridine (500 mg, 6.32 mmol) to afford 1-(2-fluoro-5-(8-methyl-2-(methylthio)-7-oxo-7,8-dihydropyrido[2,3-d]pyrimidin-6-yl)phenyl)-3-(3-(trifluoromethyl)phenyl)urea (440 mg, 55% yield). ¹H NMR (300 MHz, DMSO-d₆): δ 2.60 (s, 3 H), 3.65 (s, 3 H), 7.29-7.34 (m, 3 H), 7.50-7.51 (m, 2 H), 8.04-8.08 (m, 2 H), 8.43-8.46 (m, 1 H), 8.69 (s, 1 H), 8.95 (s, 1 H), 9.42 (s, 1 H); MS (ESI) m/z: 504.0 (M+H⁺).

Using a procedure analogous to Example A1, 1-(2-fluoro-5-(8-methyl-2-(methylthio)-7-oxo-7,8-dihydropyrido[2,3-d]pyrimidin-6-yl)phenyl)-3-(3-(trifluoromethyl)phenyl)urea (436 mg, 0.866 mmol) and 2.00N methylamine in THF (1.93 mL, 3.85 mmol) were combined to provide 1-(2-fluoro-5-(8-methyl-2-(methylamino)-7-oxo-7,8-dihydropyrido[2,3-d]pyrimidin-6-yl)phenyl)-3-(3-(trifluoromethyl)phenyl)urea (141 mg, 75% yield). ¹H NMR (300 MHz, DMSO-d₆): δ 2.89 (s, 3 H), 3.53-3.61 (m, 3 H), 7.24-7.31 (m, 3 H), 7.49-7.51 (m, 2 H), 7.65-7.75 (br. m, 1 H), 7.79 (m, 1 H), 8.03 (s, 1 H), 8.37-8.39 (m, 1 H), 8.65-8.73 (m, 2 H), 9.40 (s, 1H); MS (ESI) m/z: 487.0 (M+H⁺).

EXAMPLE 68

Using general method C, 2,2,2-trichloroethyl-(2-phenyl)phenylcarbamate (0.10 g, 0.29 mmol) and Example A38 (87 mg, 0.29 mmol) were combined to afford 1-(2-fluoro-5-(1-methyl-7-(methylamino)-2-oxo-1,2-dihydro-1,6-naphthyridin-3-yl)phenyl)-3-(2-phenyl)phenylurea The product was treated with MsOH to obtain 1-(2-fluoro-5-(1-methyl-7-(methylamino)-2-oxo-1,2-dihydro-1,6-naphthyridin-3-yl)phenyl)-3-(2-phenyl)phenylurea mesylate salt (33 mg, 19% yield). ¹H NMR (400 MHz, DMSO-d₆): □ 8.90 (m, 1H), 8.48 (s, 1H), 8.41 (m, 1H), 8.18 (s, 1H), 7.89 (s, 1H), 7.84 (m, 1H), 7.1-7.5 (m, 11H), 6.29 (brs, 1H), 2.89 (brs, 3H), 2.27 (s, 3H), 2.05 (s, 3H); MS (ESI) m/z: 494.3 (M+H⁺).

EXAMPLE 69

Using general method B, the carbamate of Example B1 (0.081 g, 0.27 mmol) and Example A38 (0.081 g, 0.27 mmol) were combined to afford 1-(3-tert-butyl-1-phenyl-1H-pyrazol-5-yl)-3-(2-fluoro-5-(1-methyl-7-(methylamino)-2-oxo-1,2-dihydro-1,6-naphthyridin-3-yl)phenyl)urea as the methane sulfonic acid salt (0.105 g, 72% yield). ¹H NMR (400 MHz, DMSO-d₆): δ 9.00 (s, 1H), 8.87 (s, 1H), 8.52 (s, 1H), 8.40 (d, J=8.8 Hz, 1H), 7.93 (s, 1H), 7.55-7.48 (m, 4H), 7.43-7.39 (m, 1H), 7.27-7.25 (m, 2H), 6.40 (brs, 1H), 6.38 (s, 1H), 3.53 (s, 3H), 2.98 (s, 3H), 2.27 (s, 3H), 1.25 (s, 9H); MS (ESI) m/z: 540.3 (M+H⁺).

EXAMPLE 70

Using general method B, the carbamate of 3-isopropyl-1-phenyl-1H-pyrazol-5-amine (0.081 g, 0.28 mmol), and Example A38 (0.085 g, 0.28 mmol) were combined to afford 1-(2-fluoro-5-(1-methyl-7-(methylamino)-2-oxo-1,2-dihydro-1,6-naphthyridin-3-yl)phenyl)-3-(3-isopropyl-1-phenyl-1H-pyrazol-5-yl)urea as methane sulfonic acid salt (0.095 g, 64% yield). ¹H NMR (400 MHz, DMSO-d₆): δ 9.00 (s, 1H), 8.89 (s, 1H), 8.53 (s, 1H), 8.40 (d, J=8.8 Hz, 1H), 7.93 (s, 1H), 7.55-7.49 (m, 4H), 7.43-7.40 (m, 1H), 7.27-7.25 (m, 2H), 6.40 (brs, 1H), 6.34 (s, 1H), 3.54 (s, 3H), 2.93 (s, 3H), 2.90-2.83 (m, 1H), 2.28 (s, 3H), 1.20 (d, J=6.8 Hz, 6H); MS (ESI) m/z: 526.2 (M+H⁺).

EXAMPLE 71

Using general method B, prop-1-en-2-yl 3-tert-butylphenylcarbamate (0.18 g, 0.75 mmol) and Example A38 (0.090 g, 0.30 mmol) were combined to afford 1-(3-tert-butylphenyl)-3-(2-fluoro-5-(1-methyl-7-(methylamino)-2-oxo-1,2-dihydro-1,6-naphthyridin-3-yl)phenyl)urea (0.103 g, 72% yield) as a light yellow solid. ¹H NMR (400 MHz, DMSO-d₆): δ 9.05 (s, 1H), 8.50 (d, 0.7=2.0 Hz, 1H), 8.45 (s, 1H), 8.40 (dd, 0.7=6.8, 2.0 Hz, 1H), 7.86 (s, 1H), 7.44 (t, 0.7=2.0 Hz, 1H), 7.28-7.24 (m, 3H), 7.20 (t, J=8.0 Hz, 1H), 7.03-7.00 (m, 2H), 6.16 (s, 1H), 3.53 (s, 3H), 2.86 (d, J=5.2 Hz, 3H), 1.26 (s, 9H); MS (ESI) m/z: 474.2 (M+H⁺).

EXAMPLE 72

Using general method A, the TROC carbamate of Example B20 (0.250 g, 0.83 mmol) and Example A12 (0.248 g, 0.83 mmol) were combined to provide 1-(2-fluoro-5-(8-methyl-2-(methylamino)-7-oxo-7,8-dihydropyrido[2,3-d]pyrimidin-6-yl)phenyl)-3-(3-isopropylisoxazol-5-yl)urea (180 mg, 48% yield). ¹H NMR (400 MHz, DMSO-d₆): δ10.33 (s, 1H), 8.75 (brs, 1H), 8.64 (brs, 1H), 8.38 (brd, J=8 Hz, 1H), 7.90 (s, 1H), 7.80 (brs, 1H), 7.36-7.25 (m, 2H), 6.04 (s, 1H), 3.61 (brs, 3H), 2.89 (brs, 3H), 1.23 (s, 6H); MS (ESI, m/z: 452.2, M+H⁺).

EXAMPLE 73

Using general method A, the TROC carbamate of Example B18 (0.170 g, 0,54 mmol) and Example A38 (0.160 g, 0.54 mmol) were combined to provide 1-(3-tert-butylisoxazol-5-yl)-3-(2-fluoro-5(1-methyl-7-(methylamino)-2-oxo-1,2-dihydro-1,6-naphthyridin-3-yl)phenyl)urea (81 mg, 32% yield). % NMR (400 MHz, DMSO-d₆): δ10.32 (s, 1H), 8.72 (brs, 1H), 8.43 (s, 1H), 8.38 (dd, J=8.0, 2.0 Hz, 1H), 7.85 (s, 1H), 7.35-7.23 (m, 2H), 7.03 (m, 1H), 6.15 (brs, 1H), 6.06 (s, 1H), 3.51 (s, 3H), 2.85 (d, J=5 Hz, 3H), 1.22 (s, 9H); MS (ESI, m/z: 465.2, M+H⁺).

EXAMPLE 74

Using general method B, the carbamate of 3-isopropyl-phenyl-1H-pyrazol-5-amine (0.100 g, 0.35 mmol) and Example A4 (0.110 g, 0.35 mmol) were combined to provide 1-(5-(8-ethyl-2-(methylamino)-7-oxo-7,8-dihydropyrido[2,3-d]pyrimidin-6-yl)-2-fluorophenyl)-3-(3-isopropyl-1-phenyl-1H-pyrazol-5-yl)urea (130 mg, 68% yield). $^1$H NMR (400 MHz, DMSO-d$_6$): δ 8.95 (s, 1H), 8.86 (s, 1H), 8.66 (brs, 1H), 8.38 (brd, J=8.0 Hz, 1H), 7.83 (brs, 1H), 7.78 (brs, 1H), 7.50 (m, 4H), 7.40 (m, 1H), 7.30-7.20 (m, 2H), 6.34 (brs, 1H), 4.40 (brs, 2H), 2.85 (m, 4H), 1.22 (m, 9H); MS (ESI, m/z: 541.3, M+H$^+$).

EXAMPLE 75

Using general method F, 1-isocyanato-3-(trifluoromethyl)benzene (0.125 g, 0.668 mmol) and Example A2 (0.2 g, 0.668 mmol) were combined in ethyl acetate to provide 1-(5-(2-amino-8-ethyl-7-oxo-7,8-dihydropyrido[2,3-d]pyrimidin-6-yl)-2-fluorophenyl)-3-(3-(trifluoromethyl)phenyl)urea (188 mg, 58% yield) $^1$H NMR (400 MHz, DMSO-d$_6$: δ 9.46 (s, 1H), 8.72 (s, 1H), 8.70 (brd, J=8 Hz, 1H), 8.42 (dd, J=8.0, 2.0 Hz, 1H), 8.08 (s, 1H), 7.57 (m, 2H), 7.35 (m, 5H), 4.37 (q, J=6 Hz, 2H), 1.25 (t, J=6 Hz, 3H); MS (ESI, m/z: 487.2, M+H$^+$).

EXAMPLE 76

Using general method B, prop-1-en-2-yl 3-tert-butylphenylcarbamate (0.100 g, 0.43 mmol) and Example A4 (0.134 g, 0.43 mmol) were combined to provide 1-(3-tert-butylphenyl)-3-(5-(8-ethyl-2-(methylamino)-7-oxo-7,8-dihydropyrido[2,3-d]pyrimidin-6-yl)-2-fluorophenyl)urea (50 mg, 24% yield). $^1$H NMR (400 MHz, DMSO-d$_6$): δ9.04 (s, 1H), 8.65 (brs, 1H), 8.50 (d, J=2.4 Hz, 1H), 8.35 (brd, J=8.0 Hz, 1H), 7.86 (s, 1H), 7.78 (brs, 1H), 7.41 (m, 1H), 7.30-7.20 (m, 3H), 7.07 (brd, J=8 Hz, 1H), 4.37 (brs, 2H), 2.89 (d, J=5 Hz, 3H), 1.25 (s, 12H); MS (ESI, m/z: 489.2, M+H$^+$).

EXAMPLE 77

Using general method A, the TROC carbamate of Example B21 (0.100 g, 0.25 mmol) and Example A4 (0.078 g, 0.25 mmol) were combined to provide 1-(5-(8-ethyl-2-(methylamino)-7-oxo-7,8-dihydropyrido[2,3-d]pyrimidin-6-yl)-2-fluorophenyl)-3-(1-phenyl-3-(trifluoromethyl)-1H-pyrazol-5-yl)urea (98 mg, 70% yield). $^1$H NMR (400 MHz, DMSO-d$_6$): δ9.16 (s, 1H), 9.08 (s, 1H), 8.68 (brs, 1H), 8.35 (brd, J=8.0 Hz, 1H), 7.83 (s, 1H), 7.78 (brs, 1H), 7.63-7.50 (m, 5H), 7.30-7.20 (m, 2H), 6.87 (brs, 1H), 4.33 (brs, 2H), 3.54 (s, 3H), 2.88 (d, J=5 Hz, 3H); MS (ESI, m/z: 567.3, M+H$^+$).

EXAMPLE 78

Using general method D, Example B36 (0.050 g, 0.25 mmol) and Example A12 (0.099 g, 0.33 mmol) were combined to afford 1-(3-tert-butyl-1-ethyl-1H-pyrazol-5-yl)-3-(2-fluoro-5-(8-methyl-2-(methylamino)-7-oxo-7,8-dihydropyrido[2,3-d]pyrimidin-6-yl)phenyl)urea (33 mg, 26% yield). $^1$H NMR (400 MHz, DMSO-d$_6$, major rotomer): δ 8.83 (s, 1H), 8.79 (d, J=2.0 Hz, 1H), 8.64 (s, 1H), 8.41 (dd, J= 2.0, and 8.4 Hz, 1H), 7.86 (s, 1H), 7.79 (m, 1H), 7.27 (m, 2H), 6.08 (s, 1H), 3.93 (q, J=7.2 Hz, 2H), 3.61 (s, 3H), 2.89 (brd, J=4.0 Hz, 3H), 1.26 (t, J=7.2 Hz, 3H), 1.18 (s, 9H); MS (ESI) m/z: 493.2 (M+H$^+$).

EXAMPLE 79

Using General Method F, Example A3 (150 mg, 0.474 mmol) and 1-chloro-4-isocyanato-2-(trifluoromethyl)benzene (110 mg, 0.498 mmol) were combined in the presence of pyridine (150 mg, 1.90 mmol) to provide 1-(4-chloro-3-(trifluoromethyl)phenyl)-3-(2-fluoro-5-(8-methyl-2-(methylthio)-7-oxo-7,8-dihydropyrido[2,3-d]pyrimidin-6-yl)phenyl)urea (0.055 g, 22% yield). MS (ESI) m/z: 538.0 (M+H$^+$).

Using a procedure analogous to Example A1, 1-(4-chloro-3-(trifluoromethyl)phenyl)-3-(2-fluoro-5-(8-methyl-2-(methylthio)-7-oxo-7,8-dihydropyrido[2,3-d]pyrimidin-6-yl)phenyl)urea (55 mg, 0.100 mmol) and 2.00N methylamine in THF (4.00 mL, 8.0 mmol) were combined to provide 1-(4-chloro-3-(trifluoromethyl)phenyl)-3-(2-fluoro-5-(8-methyl-2-(methylamino)-7-oxo-7,8-dihydropyrido[2,3-d]pyrimidin-6-yl)phenyl)urea (36 mg, 67% yield). $^1$H NMR (300 MHz, DMSO-d$_6$): δ 2.90 (s, 3 H), 3.53-3.61 (m, 3 H), 7.26-7.31 (m, 2 H), 7.58-7.59 (m, 2 H), 7.60-7.75 (br. m, 1 H), 7.88 (s, 1 H), 8.10 (s, 1 H), 8.33-8.35 (m, 1 H), 8.64-8.77 (m, 2 H), 9.49 (s, 1H); MS (ESI) m/z: 521.0 (M+H$^+$).

EXAMPLE 80

Using the procedure in Example 57, 1-(3-t-butylisoxazol-5-yl)-3-(2-fluoro-5-(8-methyl-2-(methylsulfinyl)-7-oxo-7,8-dihydropyrido[2,3-d]pyrimidin-6-yl)phenyl)urea from Example 43 (0.150 g, 0.311 mmol, 1.00 eq) and L-alaninol (48.4 μL, 0.622 mmol, 2.00 eq) were combined to afford (S)-1-(3-t-butylisoxazol-5-yl)-3-(2-fluoro-5-(2-(1-hydroxypropan-2-ylamino)-8-methyl-7-oxo-7,8-dihydropyrido[2,3-d]pyrimidin-6-yl)phenyl)urea (72 mg, 46% yield) as an off-white solid. $^1$H NMR (400 MHz, DMSO-d$_4$): δ 10.34 (s, 1H), 8.73 (brs, 1H), 8.65 (brs, 1H), 8.39 (dd, J=2.4 and 8.0 Hz, 1H), 7.87 (s, 1H), 7.60-7.57 (m, 1H), 7.35-7.25 (m, 2H), 6.06 (s, 1H), 4.70 (t, J=6.0 Hz, 1H), 4.09 (brs, 1H), 3.58-3.49 (m, 4H), 3.35 (brs, 1H), 1.23 (s, 9H), 1.17-1.15 (m, 3H); MS (ESI) m/z: 510.2 (M+H$^+$).

EXAMPLE 81

Using general method B, the carbamate of Example B21 (0.071 g, 0.23 mmol) and Example A38 (0.068 g, 0.23 mmol) were combined to afford 1-(2-fluoro-5-(1-methyl-7-(methylamino)-2-oxo-1,2-dihydro-1,6-naphthyridin-3-yl)phenyl)-3-(1-phenyl-3-(trifluoromethyl)-1H-pyrazol-5-yl)urea as the methane sulfonic acid salt (0.076 g, 60% yield), $^1$H NMR (400 MHz, DMSO-d$_6$): δ 9.18 (s, 1H), 9.11 (s, 1H), 8.50 (s, 1H), 8.38-8.36 (m, 1H), 7.92 (s, 1H), 7.64-7.56 (m, 6H), 7.29-7.26 (m, 2H), 6.88 (s, 1H), 6.35 (brs, 1H), 3.53 (s, 3H), 2.91 (s, 3H), 2.27 (s, 3H); (ESI) m/z: 552.2 (M+H$^+$).

EXAMPLE 82

Using general method D, 3-tert-butyl-1-methyl-1H-pyrazole-5-carboxylic acid (0.051 g, 0.28 mmol) and Example A38 (0.1 g, 0.34 mmol) were combined to afford 1-(3-tert-butyl-1-methyl-1H-pyrazol-5-yl)-3-(2-fluoro-5-(1-methyl-7-(methylamino)-2-oxo-1,2-dihydro-1,6-naphthyridin-3-yl)phenyl)urea as the methane sulfonic acid salt (0.089 g, 67% yield). $^1$H NMR (400 MHz, DMSO-d$_6$): δ 8.94 (s, 1H), 8.85 (d, J=2.4 Hz, 1H), 8.53 (s, 1H), 8.41 (dd, J=8.0 Hz, 2.0 Hz, 1H), 7.95 (s, 1H), 7.30-7.27 (m, 2H), 6.42 (brs, 1H), 6.08 (s, 1H), 3.60 (s, 3H), 3.54 (s, 3H), 2.93 (s, 3H), 2.28 (s, 3H), 1.18 (s, 9H); (ESI) m/z: 478.3 (M+H$^+$).

EXAMPLE 83

Using general method C, the carbamate of Example B20 (2.70 g, 21.4 mmol, 1.00 eq) and Example A3 (0.525 g, 1.66 mmol, 1.00 eq) were combined to afford 1-(2-fluoro-5-(8-methyl-2-(methylthio)-7-oxo-7,8-dihydropyrido[2,3-d]pyrimidin-6-yl)phenyl)-3-(3-isopropylisoxazol-5-yl)urea (0.344 g, 44% yield) as a pale yellow foam. $^1$H NMR (400 MHz, DMSO-d$_6$): δ 10.35 (s, 1H), 8.93 (s, 1H), 8.79 (d, J=2.0 Hz, 1H), 8.44 (dd, J=2.00 and 8.0 Hz, 1H), 8.07 (s, 1H), 7.40-7.31 (m, 2H), 6.02 (s, 1H), 3.66 (s, 3H), 2.89 (septet, J=6.8 Hz, 1H), 2.60 (s, 3H), 1.18 (d, J=6.8 Hz, 6H); MS (ESI) m/z: 469.0 (M+H$^+$).

Using a procedure analogous to Example A1, 1-(2-fluoro-5-(8-methyl-2-(methylthio)-7-oxo-7,8-dihydropyrido[2,3-d]pyrimidin-6-yl)phenyl)-3-(3-isopropylisoxazol-5-yl)urea (0.150 g, 0.322 mmol, 1.00 eq) was oxidized and reacted with L-alaninol (41.4 μL, 0.533 mmol, 2.00 eq) to afford (S)-1-(2-fluoro-5-(2-(1-hydroxypropan-2-ylamino)-8-methyl-7-oxo-7,8-dihydropyrido[2,3-d]pyrimidin-6-yl)phenyl)-3-(3-isopropylisoxazol-5-yl)urea (67 mg, 51% yield) as an off-white solid. $^1$H NMR (400 MHz, DMSO-d$_6$): δ 10.34 (s, 1H), 8.73 (brs, 1H), 8.65 (brs, 1H), 8.39 (dd, J=2.4 and 8.0 Hz, 1H), 7.87 (s, 1H), 7.60-7.57 (m, 1H), 7.35-7.25 (m, 2H), 6.06 (s, 1H), 4.70 (t, J=6.0 Hz, 1H), 4.09 (brs, 1H), 3.58-3.49 (m, 4H), 3.35 (brs, 1H), 2.89 (m, 1H), 1.23 (s, 9H), 1.17-1.15 (m, 9H); MS (ESI) m/z: 496.3 (M+H$^+$).

EXAMPLE 84

Pivalonitrile (2.75 g, 33.1 mmol), water (20 mL), dioxane (20 mL), sodium hydrogensulfide hydrate (14.7 g, 198 mmol) and diethyl amine hydrochloride (21.8 g, 198 mmol) were combined and mixture was stirred at 55° C. for 48 h. Water (150 mL) and EtOAc (60 mL) were added, the organic layer was separated and the aqueous layer was extracted with EtOAC (1×60 mL). The combined organics were washed with brine, dried (Na$_2$SO$_4$) and concentrated in vacuo to afford 2,2-dimethylpropanethioamide as off-white solid (3.00 g, 89% yield).

Ethyl 3-bromo-2-oxopropanoate (1.95 g, 10 mmol) and 2,2-dimethylpropanethioamide (1.17 g, 10 mmol) were combined in ethanol (20 mL) and solution was stirred at RT for 48 h. Solvent was removed and to the residue Sat. NaHCO$_3$ solution was added and product was extracted with EtOAc (2×30 mL). The combined organics were washed with brine, dried (Na$_2$SO$_4$), concentrated in vacuo and purification by silica gel chromatography afforded ethyl 2-tert-butylthiazole-5-carboxylate (1.16 g, 55%) as a colorless liquid (1.16 g, 55% yield). MS (ESI) m/z: 214.0 (M+H$^+$).

To a solution of ethyl 2-tert-butylthiazole-5-carboxylate (1.16 g, 5.44 mmol) in THF (10 mL) was added lithium hydroxide (0.45 g, 10.9 mmol) in water (5 mL) and the mixture was stirred for 16 h at RT. Solvents were removed under vacuum, and the thick liquid was diluted with water (5 mL) and acidified with 2M HCl solution to pH 4 to 5. The product precipitated, was filtered, washed with water (2×5 mL) and dried to provide 2-tert-butylthiazole-5-carboxylic acid as white solid (0.55 g, 55% yield). $^1$H NMR (400 MHz, DMSO-d$_6$): δ 8.32 (s, 1H), 1.39 (s, 9H); MS (ESI) m/z: 186.0 (M+H$^+$).

To a solution of 2-tert-butylthiazole-5-carboxylic acid (0.46 g, 2.52 mmol) in dioxane (10 mL) was added with triethylamine (0.76 g, 7.55 mmol), Diphenylphosphorylazide (1.04 g, 3.77 mmol) and trichloroethanol (1.13 g, 7.55 mmol) and mixture was heated to 90° C. for 3 h. Sat. NaHCO$_3$ solution (30 mL) was added and the product was extracted with EtOAc (2×30 mL). The combined organics were washed with brine, dried (Na$_2$SO$_4$), concentrated in vacuo and puri- ficatied by silicagel chromatography provided 2,2,2-trichloroethyl 2-tert-butylthiazol-5-ylcarbamate as a pasty mass (0.55 g, 66% yield). $^1$H NMR (400 MHz, Acetone-d$_6$); δ 8.44 (s, 1H), 4.94 (s, 2H), 1.38 (s, 9H); MS (ESI) m/z: 333.0 (M+H$^+$).

Using general method C, 2,2,2-trichloroethyl 2-tert-butylthiazol-5-ylcarbamate (0.081 g, 0.24 mmol) and Example A12 (0.73 g, 0.24 mmol) were combined to afford 1-(2-tert-butylthiazol-5-yl)-3-(2-fluoro-5-(8-methyl-2-(methylamino)-7-oxo-7,8-dihydropyrido[2,3-d]pyrimidin-6-yl) phenyl)urea as an off-white solid (0.025 g, 21% yield). $^1$H NMR (400 MHz, DMSO-d$_6$): δ 9.88 (s, 1H), 8.64 (s, 1H), 8.44 (d, J=8.4 Hz, 1H), 7.87 (s, 1H), 7.88 (brs, 1H), 7.26-7.22 (m, 2H), 7.04 (s, 1H), 3.60 (s, 3H), 2.89 (d, J=4.4 Hz, 3H), 1.35 (s, 9H); MS (ESI) m/z: 482.2 (M+H$^+$).

EXAMPLE 85

Using general method B, the carbamate of Example B22 (0.10 g, 0.40 mmol) and Example A4 (0.10 g, 0.32 mmol) were combined to afford 1-(5-(8-ethyl-2-(methylamino)-7-oxo-7,8-dihydropyrido[2,3-d]pyrimidin-6-yl)-2-fluorophenyl)-3-(1-methyl-3-(trifluoromethyl)-1H-pyrazol-5-yl)urea (0.12 g, 61% yield). $^1$H NMR (400 MHz, DMSO-d$_6$, major rotomer): δ 9.27 (s, 1H), 8.94 (brs, 1H), 8.64 (s, 1H), 8.36 (dd, J=2.0, 8.0 Hz, 1H), 7.85 (s, 1H), 7.79 (m, 1H), 7.2-7.4 (m, 2H), 6.61 (s, 1H), 4.35 (q, J=5.6 Hz, 2H), 3.77 (s, 3H), 2.88 (d, J=4.4 Hz, 3H), 1.23 (t, J=6.8 Hz, 3H); MS (ESI) m/z: 505.2 (M+H$^+$).

EXAMPLE 86

Using general method B, the carbamate of B15 (0.05 g, 0.21 mmol) and Example A12 (0.063 g, 0.21 mmol) were combined to afford 1-(5-(8-ethyl-2-(methylamino)-7-oxo-7, 8-dihydropyrido[2,3-d]pyrimidin-6-yl)-2-fluorophenyl)-3-(1-methyl-3-(trifluoromethyl)-1H-pyrazol-5-yl)urea (55 mg, 55% yield). $^1$H NMR (400 MHz, DMSO-d$_6$, major rotomer): δ 11.0 (s, 1H), 8.91 (brs, 1H), 8.64 (s, 1H), 8.33 (dd, J=1.6, and 6.4 Hz, 1H), 7.90 (s, 1H), 7.83 (m, 1H), 7.2-7.4 (m, 2H), 6.52 (s, 1H), 3.61 (brs, 3H), 2.90 (brd, J=4.8 Hz, 3H); MS (ESI) m/z: 478.0 (M+H$^+$).

EXAMPLE 87

Using general method B, prop-1-en-2-yl 3-tert-butyl-1-methyl-1H-pyrazol-5-ylcarbamate (0.12 g, 0.51 mmol) and Example A24 (0.16 g, 0.51 mmol) were combined to afford 1-(3-tert-butyl-1-methyl-1H-pyrazol-5-yl)-3-(5-(1-ethyl-7-(methylamino)-2-oxo-1,2-dihydro-1,6-naphthyridin-3-yl)-2-fluorophenyl)urea as the mesylate salt (130 mg, 47% yield). $^1$H NMR (400 MHz, DMSO-d$_6$): δ 8.98 (s, 1H), 8.87 (brs, 1H), 8.57 (dd, y=2.0, and 8.0 Hz, 1H), 7.88 (s, 1H), 7.2-7.4 (m, 2H), 6.55 (brs, 1H), 6.09 (s, 1H), 4.18 (m, 2H), 3.61 (s, 3H), 2.96 (brs, 3H), 2.30 (s, 3H), 1.22 (t, J=6.4 Hz, 3H), 1.18 (s, 9H); MS (ESI) m/z: 492.3 (M+H$^+$).

EXAMPLE 88

Using general method B, prop-1-en-2-yl 3-tert-butylphenylcarbamate (0.545 g, 2.34 mmol) and Example A3 (0.592 g, 01.87 mmol) were combined to afford 1-(3-tert-butylphenyl)-3-(2-fluoro-5-(8-methyl-2-(methylthio)-7-oxo-7,8-dihydropyrido[2,3-d]pyrimidin-6-yl)phenyl)urea (0.574 g, 62% yield) as a light yellow solid. MS (ESI) m/z: 475.2 (M+H$^+$).

Using a procedure analogous to Example A1, 1-(3-tert-butylphenyl)-3-(2-fluoro-5-(8-methyl-2-(methylthio)-7- oxo-7,8-dihydropyrido[2,3-d]pyrimidin-6-yl)phenyl)urea (0.200 g, 0.407 mmol) and N,N-dimethylethylenediamine (0.181 mL, 1.65 mmol) were combined to afford 1-(3-tert-butylphenyl)-3-(5-(2-(2-(dimethylamino)ethylamino)-8-methyl-7-oxo-7,8-dihydropyrido[2,3-d]pyrimidin-6-yl)-2-fluorophenyl)urea (0.150 g, 86% yield) as a light yellow solid. It was converted to corresponding HCl salt by reacting with HCl (4.0 M HCl in dioxane, 1.0 eq.). $^1$H NMR (400 MHz, DMSO-$d_6$): δ 9.28 (s, 1H), 8.73 (s, 1H), 8.64 (d, J=1.6 Hz, 1H), 8.39 (d, J=7.6 Hz, 1H), 8.04 (s, 1H), 7.93 (s, 1H), 7.43 (s, 1H), 7.28-7.24 (m, 3H), 7.18 (t, J=8.0 Hz, 1H), 6.99 (tt, J=7.6, 0.8 Hz, 1H), 3.74 (broad, 2H), 3.63 (s, 3H), 3.30 (broad, 2H), 2.81 (d, J=4.8 Hz, 6H), 1.25 (s, 9H); MS (ESI) m/z: 532.3 (M+H$^+$).

EXAMPLE 89

Using a procedure analogous to Example A1, 1-(4-chloro-3-(trifluoromethyl)phenyl)-3-(2-fluoro-5-(8-methyl-2-(methylthio)-7-oxo-7,8-dihydropyrido[2,3-d]pyrimidin-6-yl)phenyl)urea from Example 67 (55 mg, 0.100 mmol) and 2-amino-1-propanol (249 mg, 3.31 mmol) were combined to provide 1-(2-fluoro-5-(2-(1-hydroxypropan-2-ylamino)-8-methyl-7-oxo-7,8-dihydropyrido[2,3-d]pyrimidin-6-yl)phenyl)-3-(3-(trifluoromethyl)phenyl)urea (489 mg, 22% yield). $^1$H NMR (300 MHz, DMSO-$d_4$), δ 1.15 (s, 3H), 3.37-3.56 (m, 4 H), 3.90-4.15 (m, 1 H), 4.69 (s, 1 H), 7.22-7.55 (m, 6 H), 7.84 (s, 1 H), 8.02 (s, 1 H), 8.36-8.38 (m, 1 H), 8.63 (br. s, 2 H), 9.38 (s, 1 H), OH missing; MS (ESI) m/z: 531.2 (M+H$^+$).

EXAMPLE 90

Using general method C, the TROC carbamate of Example B23 (150 mg, 0.421 mmol) and Example A12 (132 mg, 0.442 mmol) were combined to afford 1-(3-tert-butyl-1-isopropyl-1H-pyrazol-5-yl)-3-(2-fluoro-5-(8-methyl-2-(methylamino)-7-oxo-7,8-dihydropyrido[2,3-d]pyrimidin-6-yl)phenyl)urea (13 mg, 6% yield). $^1$H NMR (300 MHz, DMSO-$d_6$): δ 1.18 (s, 9 H), 1.31 (d, J=6.5, 6 H), 2.89 (s, 3 H), 3.50-3.61 (m, 3 H), 4.33 (hep, J=6.3, 1 H), 6.03 (s, 1 H), 7.24-7.26 (m, 2 H), 7.65-7.84 (m, 2 H), 8.37-8.39 (m, 1 H), 8.62-8.76 (m, 3 H); MS (ESI) m/z: 507.2 (M+H$^+$).

EXAMPLE 91

Using general method D, Example B16 (0.060 g, 0.31 mmol) and Example A4 (0.096 g, 0.31 mmol) were combined to afford 1-(3-tert-butyl-1-ethyl-1H-pyrazol-5-yl)-3-(5-(8-ethyl-2-(methylamino)-7-oxo-7,8-dihydropyrido[2,3-d]pyrimidin-6-yl)-2-fluorophenyl)urea (57 mg, 37% yield). $^1$H NMR (400 MHz, DMSO-$d_6$, major rotomer): δ 8.82 (s, 1H), 8.78 (m, 1H), 8.64 (s, 1H), 8.39 (dd, J=2.0, and 8.4 Hz, 1H), 7.85 (s, 1H), 7.78 (m, 1H), 7.27 (m, 2H), 6.08 (s, 1H), 4.30 (m, 2H), 3.93 (q, J=7.2 Hz, 2H), 2.89 (brd, J=4.0 Hz, 3H), 1.25 (m, 6H), 1.19 (s, 9H); MS (ESI) m/z: 507.2 (M+H$^+$).

EXAMPLE 92

Using general method F, Example A38 (88 mg, 0.29 mmol) and 1-isocyanato-3-(trifluoromethyl)benzene (63 mg, 0.34 mmol) were combined to provide 1-(2-fluoro-5-(1-methyl-7-(methylamino)-2-oxo-1,2-dihydro-1,6-naphthyridin-3-yl)phenyl)-3-(3-(trifluoromethyl)phenyl)urea (123 mg, 87% yield). $^1$H NMR (400 MHz, DMSO-$d_6$): δ 9.40 (s, 1H), 8.63 (s, 1 H), 8.44 (s, 1 H), 8.37 (dd, J=8.2, 2.2 Hz, 1 H), 8.03 (s, 1 H), 7.87 (s, 1 H), 7.51 (m, 2 H), 7.32-7.22 (m, 3 H), 7.03 (q, J=4.8 Hz, 1 H), 6.15 (s, 1 H), 3.52 (s, 3 H), 2.85 (d, J=5.0 Hz, 3 H); MS (ESI) m/z: 486.2 (M+H$^+$).

EXAMPLE 93

Using general procedure B, Example B11 (0.125 g, 0.362 mmol) and Example A12 (0.104 g, 0.347 mmol) were combined to form crude 1-(3-(1-(tert-butyldimethylsilyloxy)-2-methylpropan-2-yl)-1-phenyl-1H-pyrazol-5-yl)-3-(2-fluoro-5-(8-methyl-2-(methylamino)-7-oxo-7,8-dihydropyrido[2,3-d]pyrimidin-6-yl)phenyl)urea. TBAF (1.0 M in THF, 1.0 mL, 1.0 mmol) was added to the above filtrate, and the mixture was stirred at 30° C. for 2 d. Solvent was removed under reduced pressure. The residue was quenched with H$_2$O (15 mL) and extracted with EtOAc (2×25 mL). The combined organic layers were washed with brine (15 mL), dried (MgSO$_4$), concentrated in vacuo and purified by chromatography to afford 1-(2-fluoro-5-(8-methyl-2-(methylamino)-7-oxo-7,8-dihydropyrido[2,3-d]pyrimidin-6-yl)phenyl)-3-(3-(1-hydroxy-2-methylpropan-2-yl)-1-phenyl-1H-pyrazol-5-yl)urea (0.096 g, 52% yield) as a white solid. $^1$H NMR (400 MHz, DMSO-$d_6$), δ 8.98 (d, J=1.2 Hz, 1H), 8.88 (s, 1H), 8.655 (s, 1H), 8.40 (dd, J=8.0, 1.2 Hz, 1H), 7.86 (s, 1H), 7.82 (d, J=4.4 Hz, 1H), 7.56-7.49 (m, 4H), 7.44-7.39 (m, 1H), 7.28-7.21 (m, 2H), 6.39 (s, 1H), 4.59 (t, J=5.2 Hz, 1H), 3.61 (s, 2H), 3.54 (s, 1H), 3.41 (d, J=5.2 Hz, 2H), 2.90 (d, J=4.4 Hz, 3H), 1.19 (s, 6H); MS (ESI) m/z: 557.3 (M+H$^+$).

EXAMPLE 94

Using general method D, 3-tert-butyl-1-methyl-1H-pyrazole-5-carboxylic acid (0.041 g, 0.23 mmol) and Example A49 (0.081 g, 0.25 mmol) in presence of triethylamine (0.07 g, 0.68 mmol) and diphenylphospharyl azide (0.12 g, 0.45 mmol) were combined to afford 1-(3-tert-butyl-1-methyl-1H-pyrazol-5-yl)-3-(2-fluoro-5-(8-isopropyl-2-(methylamino)-7-oxo-7,8-dihydropyrido[2,3-d]pyrimidin-6-yl)phenyl)urea as white solid (0.86 g, 75% yield). $^1$H NMR (400 MHz, DMSO-$d_6$): δ 8.91 (s, 1H), 8.81 (d, J=2.4 Hz, 1H), 8.62 (s, 1H), 8.36-8.34 (m, 1H), 7.79-7.76 (m, 2H), 7.26-7.23 (m, 2H), 6.08 (s, 1H), 5.77-5.74 (m, 1H), 3.60 (s, 3H), 2.88 (d, J=4.4 Hz, 3H), 1.58-1.51 (m, 6H), 1.18 (s, 9H); MS (ESI) m/z: 507.2 (M+H$^+$).

EXAMPLE 95

Using general method D, 4-methylpyrimidine-5-carboxylic acid (300 mg, 2.17 mmol) and Example A3 (687 mg, 2.17 mmol) were combined to afford 1-(2-fluoro-5-(8-methyl-2-(methylthio)-7-oxo-7,8-dihydropyrido[2,3-d]pyrimidin-6-yl)phenyl)-3-(4-methylpyrimidin-5-yl)urea (305 mg, 31% yield). MS (ESI) m/z: 452.0 (M+H$^+$).

Using a procedure analogous to Example A1, 1-(2-fluoro-5-(8-methyl-2-(methylthio)-7-oxo-7,8-dihydropyrido[2,3-d]pyrimidin-6-yl)phenyl)-3-(4-methylpyrimidin-5-yl)urea (300 mg, 0.664 mmol) and 2.0 N methylamine in THF (2.3 mL, 4.53 mmol) were combined to afford 1-(2-fluoro-5-(8-methyl-2-(methylamino)-7-oxo-7,8-dihydropyrido[2,3-d]pyrimidin-6-yl)phenyl)-3-(4-methylpyrimidin-5-yl)urea (75 mg, 38% yield). $^1$H NMR (300 MHz, DMSO-$d_6$), δ 2.45 (s, 3H), 2.88 (s, 3 H), 3.50-3.57 (m, 3 H), 7.23-7.29 (m, 2 H), 7.67-7.79 (m, 1 H), 7.82 (s, 1 H), 8.39-8.42 (m, 1 H), 8.60 (s, 3 H), 8.68 (s, 2 H), 9.13 (m, 1 H); MS (ESI) m/z: 435.2 (M+H$^+$).

EXAMPLE 96

Using general method A, the TROC carbamate of Example B18 (0.5 g, 1.58 mmol) and Example A10 (0.523 g, 1.58 mmol) were combined to provide 1-(3-tert-butylisoxazol-5-yl)-3-(2-fluoro-4-methyl-5-(8-methyl-2-(methylthio)-7-oxo-7,8-dihydropyrido[2,3-d]pyrimidin-6-yl)phenyl)urea (440 mg, 56% yield). $^1$H NMR (400 MHz, DMSO-d$_6$): δ 10.3 (brs, 1H), 8.9 (s, 1H)), 8.70 (brs, 1H), 7.94 (d, J=9 Hz, 1H), 7.88 (s, 1H), 7.20 (d, J=12 Hz, 1H), 6.00 (s, 1H), 3.64 (s, 3H), 2.61 (s, 3H), 2.07 (s, 3H), 1.21 (s, 9H); MS (ESI) m/z: 497.2 (M+H$^+$).

Using a procedure analogous to Example A1, 1-(3-tert-butylisoxazol-5-yl)-3-(2-fluoro-4-methyl-5-(8-methyl-2-(methylthio)-7-oxo-7,8-dihydropyrido[2,3-d]pyrimidin-6-yl)phenyl)urea (1.70 g, 3.426 mmol) and methylamine (2 ml, 4 mmol, 2.0M in THF) were combined to provide 1-(3-tert-butylisoxazol-5-yl)-3-(2-fluoro-4-methyl-5-(8-methyl-2-(methylamino)-7-oxo-7,8-dihydropyrido[2,3-d]pyrimidin-6-yl)phenyl)urea (92 mg, 42% yield). $^1$H NMR (400 MHz, DMSO-d$_6$): δ 10.28 (brs, 1H), 8.67 (brs, 1H), 8.61 (s, 1H), 7.89 (d, J=9 Hz, 1H), 7.82 (brs, 1H), 7.68 (s, 1H), 7.17 (d, J=12 Hz, 1H), 6.00 (s, 1H), 3.58 (s, 3H), 2.90 (d, J=5 Hz, 3H), 2.08 (s, 3H), 1.21 (s, 9H); MS (ESI) m/z: 480.2(M+H$^+$).

EXAMPLE 97

Using general method A, the TROC carbamate of Example B21 (0.2 g, 0.5 mmol) and Example A39 (0.156 g, 0.5 mmol) were combined to provide 1-(2-fluoro-4-methyl-5-(8-methyl-2-(methylamino)-7-oxo-7,8-dihydropyrido[2,3-d]pyrimidin-6-yl)phenyl)-3-(1-phenyl-3-(trifluoromethyl)-1H-pyrazol-5-yl)urea (210 mg, 75% yield). $^1$H NMR (400 MHz, DMSO-d$_6$): δ9.12 (s, 1H), 9.02 (s, 1H), 8.60 (s, 1H), 7.90 (d, J=9.5 Hz, 1H), 7.6 (m, 6H), 7.13 (d, J=12 Hz, 1H), 6.83 (s, 1H), 3.54 (s, 3H), 2.90 (d, J=5 Hz, 3H), 2.07 (s, 3H); MS (ESI, m/z: 567.3, M+H$^+$).

EXAMPLE 98

Using a modified general method B, the carbamate of Example B21 (0.071 g, 0.23 mmol), and Example A38 (0.068 g, 0.23) were heated at 130° C. for 1 h under microwave irradiation to afford 1-(1-tert-butyl-1H-pyrazol-4-yl)-3-(2-fluoro-5-(1-methyl-7-(methylamino)-2-oxo-1,2-dihydro-1,6-naphthyridin-3-yl)phenyl)urea as the methane sulfonic acid salt (0.048 g, 45% yield). $^1$H NMR (400 MHz, DMSO-d$_6$): δ 8.72 (s, 1H), 8.54 (brs, 2H), 8.41 (dd, J=8.4 Hz, 2.4 Hz, 1H), 7.95 (s, 1H), 7.80 (s, 1H), 7.40 (s, 1H), 7.29-7.19 (m, 2H), 6.42 (brs, 1H), 3.54 (s, 3H), 2.94 (s, 3H), 2.27 (s, 3H), 1.47 (s, 9H); (ESI) m/z: 464.2 (M+H$^+$).

EXAMPLE 99

Using general method A, the carbamate of Example B1 (0.45 g, 1.5 mmol) and Example A10 (0.4 g, 1.21 mmol) were combined to provide 1-(3-tert-butyl-1-phenyl-1H-pyrazol-5-yl)-3-(2-fluoro-4-methyl-5-(8-methyl-2-(methylthio)-7-oxo-7,8-dihydropyrido[2,3-d]pyrimidin-6-yl)phenyl)urea as white solid (0.25 g, 36% yield). $^1$H NMR (400 MHz, DMSO-d$_6$): δ 8.94 (d, J=2.0 Hz, 1H), 8.90 (s, 1H), 8.83 (s, 1H), 7.98 (d, J=8.4 Hz, 1H), 7.87 (s, 1H), 7.54-7.47 (m, 4H), 7.43-7.39 (m, 1H), 7.15 (d, J=12.0 Hz, 1H), 6.34 (s, 1H), 3.64 (s, 3H), 2.61 (s, 3H), 2.06 (s, 3H), 1.22 (s, 9H); MS (ESI) m/z: 482.2 (M+H$^+$).

Using a procedure analogous to Example A1, 1-(3-tert-butyl-1-phenyl-1H-pyrazol-5-yl)-3-(2-fluoro-4-methyl-5-(8-methyl-2-(methylthio)-7-oxo-7,8-dihydropyrido[2,3-d]pyrimidin-6-yl)phenyl)urea (0.25, 0.43 mmol), MCPBA (0.081 g, 0.47 mmol) and 2 M methylamine in THF (1 mL) were combined to provide 1-(3-tert-butyl-1-phenyl-1H-pyrazol-5-yl)-3-(2-fluoro-4-methyl-5-(8-methyl-2-(methylamino)-7-oxo-7,8-dihydropyrido[2,3-d]pyrimidin-6-yl)phenyl)urea as white solid (0.17 g, 72% yield). $^1$H NMR (400 MHz, DMSO-d$_6$): δ 8.90 (d, J=2.0 Hz, 1H), 8.81 (s, 1H), 8.60 (s, 1H), 7.93 (d, J=8.4 Hz, 1H), 7.83-7.78 (m, 1H), 7.65 (s, 1H), 7.54-7.47 (m, 4H), 7.43-7.38 (m, 1H), 7.11 (d, J=12.0 Hz, 1H), 6.34 (s, 1H), 3.59 (s, 3H), 2.90 (d, J=4.4 Hz, 1H), 2.05 (s, 3H), 1.23 (s, 9H); MS (ESI) m/z; 555.2 (M+H$^+$).

EXAMPLE 100

Using general method B, Example B15 (0.15 g, 0.64 mmol) and Example A39 (0.20 g, 0.64 mmol) were combined to afford 1-(2-fluoro-4-methyl-5-(8-methyl-2-(methylamino)-7-oxo-7,8-dihydropyrido[2,3-d]pyrimidin-6-yl)phenyl)-3-(3-(trifluoromethyl)isoxazol-5-yl)urea (0.19 g, 60% yield). $^1$H NMR (400 MHz, DMSO-d$_6$, major rotomer): δ 11.0 (s, 1H), 8.82 (s, 1H), 8.60 (s, 1H), 7.81 (d, J=8.0 Hz, 1H), 7.68 (s, 1H), 7.20 (s, 1H), 6.46 (s, 1H), 3.59 (brs, 3H), 2.90 (brd, 7-4.4 Hz, 3H), 2.09 (s, 3H); MS (ESI) m/z: 492.3 (M+H$^+$).

EXAMPLE 101

Using general method F, 1-chloro-4-isocyanato-2-(trifluoromethyl)benzene (0.16 g, 0.55 mmol) and Example A39 (0.113 g, 0.51 mmoll) were combined in ethyl acetate to provide 1-(4-chloro-3-(trifluoromethyl)phenyl)-3-(2-fluoro-4-methyl-5-(8-methyl-2-(methylamino)-7-oxo-7,8-dihydropyrido[2,3-d]pyrimidin-6-yl)phenyl)urea (150 mg, 55% yield) $^1$H NMR (400 MHz, DMSO-d$_6$) δ 9.44 (s, 1H), 8.6 (s, 1H), 8.1 (d, J=2.5 Hz), 7.87 (d, J=9 Hz, 1H), 7.67 (s, 1H), 7.59 (d, J=9.0 Hz, 1H), 7.53 (dd, J=9.0, 2.5 Hz, 1H), 7.15 (d, J=12 Hz, 1H), 3.54 (s, 3H), 2.90 (d, J=5 Hz, 3H), 2.07 (s, 3H); MS (ESI, m/z: 535.0, M+H$^+$).

EXAMPLE 102

Using general procedure C, the TROC carbamate of Example B18 (0.212 g, 0.672 mmol, 1.00 eq) and Example A26 (0.2100 g, 0.672 mmol, 1.00 eq) were combined to provide crude desired product. The product was purified by reverse phase chromatography 5-42% MeCN (w/0.1% TFA)/H$_2$O (w/0.1% TFA) to obtain the TFA salt. The TFA salt thus obtained was treated with MP-Carbonate resin to obtain the free base and then 2 wt % MsOH/THF to afford 1-(3-tert-butylisoxazol-5-yl)-3-(2-fluoro-4-methyl-5-(1-methyl-7-(methylamino)-2-oxo-1,2-dihydro-1,6-naphthyridin-3-yl)phenyl)urea (60 mg, 16% yield) as the MsOH salt, $^1$H NMR (400 MHz, DMSO-d$_6$): δ 10.32 (s, 1H), 8.71 (d, J=2.00 Hz, 1H), 8.50 (s, 1H), J=8.8 Hz, 1H), 7.81 (s, 1H), 7.20 (d, J=12.4 Hz, 1H), 6.51 (s, 1H), 6.00 (s, 1H), 3.54 (s, 3H), 2.96 (brs, 3H), 2.31 (s, 3H), 2.09 (s, 3H), 1.21 (s, 9H); MS (ESI) m/z: 479.2 (M+H$^+$).

EXAMPLE 103

Using general procedure D, 3-(t-butyl)1-methyl-1H-pyrazole-5-carboxylic acid (0.111 g, 0.611 mmol, 1.00 eq) and Example A26 (0.210 g, 0.672 mmol, 1.10 eq) were combined to give desired product. The free base was slurried in THF and treated with 2% MsOH/THF solution (1.44 g, 1.00 eq) and the thick suspension was stirred overnight at RT. The solids were collected by filtration, rinsed with THF and EtOAc and dried under high vacuum to afford 1-(3-tert-butyl-1-methyl-1H-pyrazol-5-yl)-3-(2-fluoro-4-methyl-5-(1-methyl-7-(methylamino)-2-oxo-1,2-dihydro-1,6-naphthyridin-3-yl)phenyl)

urea (150 mg, 42% yield) as the MsOH salt. ¹H NMR (400 MHz, DMSO-d₆): δ 8.93 (s, 1H), 8.79 (brs, 1H), 8.50 (s, 1H), 7.97 (d, J=8.4 Hz), 7.80 (s, 1H), 7.18 (d, J=12.0 Hz, 1H), 6.50 (s, 1H), 6.05 (s, 1H), 3.59 (s, 3H), 3.53 (s, 3H), 2.96 (s, 3H), 2.30 (s, 3H), 2.07 (s, 3H), 1.17 (s, 9H); MS (ESI) m/z: 492.3 (M+H⁺).

EXAMPLE 104

Using general method B, the carbamate of Example B2 (0.171 g, 0.720 mmol) and Example A39 (0.150 g, 0.48 mmol) were combined to afford 1-(3-tert-butyl-1-methyl-1H-pyrazol-5-yl)-3-(2-fluoro-4-methyl-5-(8-methyl-2-(methylamino)-7-oxo-7,8-dihydropyrido[2,3-d]pyrimidin-6-yl)phenyl)urea (0.105 g, 44% yield) as a white solid. ¹H NMR (400 MHz, DMSO-d₆): δ 8.87 (s, 1H), 8.73 (d, J=2.0 Hz, 1H), 8.60 (s, 1H), 7.93 (d, J=8.4 Hz, 1H), 7.80 (m, 1H), 7.66 (s, 1H), 7.14 (d, J=12.4, 1H), 6.04 (s, 1H), 3.59-3.57 (m, 6H), 2.90 (d, J=4.4 Hz, 3H), 2.06 (s, 3H), 1.16 (s, 9H); MS (ESI) m/z: 493.2 (M+H⁺).

EXAMPLE 105

Using a modified method B, the carbamate of Example B19 (0.061 g, 0.27 mmol) and 6-(3-amino-4-fluorophenyl)-8-isopropyl-2-(methylthio)pyrido[2,3-d]pyrimidin-7(8H)-one from Example A59 (0.094 g, 0.27 mmol) in THF were stirred at 130° C. for 1 h under microwave irradiation. Solvents were removed and the crude residue was purified by silica gel chromatography to afford 1-(1-tert-butyl-1H-pyrazol-4-yl)-3-(2-fluoro-5-(8-isopropyl-2-(methylthio)-7-oxo-7,8-dihydropyrido[2,3-d]pyrimidin-6-yl)phenyl)urea as off-white solid (68 mg, 49% yield). ¹H NMR (400 MHz, Acetone-d₆): δ 8.89 (s, 1H), 8.58 (dd, J=8.0 Hz, 2.4 Hz, 1H), 8.21 (brs, 1H), 7.99 (brs, 1H), 7.96 (s, 1H), 7.89 (s, 3H), 7.39-7.35 (m, 2H), 7.17 (dd, J=11.2 Hz, 8.4 Hz, 1H), 5.94-5.89 (m, 1H), 2.65 (s, 3H), 1.66 (d, J=6.8 Hz, 6H), 1.54 (m, 9H); MS (ESI) m/z: 507.2 (M+H⁺).

Using a procedure analogous to Example A1, 1-(1-tert-butyl-1H-pyrazol-4-yl)-3-(2-fluoro-5-(8-isopropyl-2-(methylthio)-7-oxo-7,8-dihydropyrido[2,3-d]pyrimidin-6-yl)phenyl)urea (0.065 g, 0.13 mmol) and 2 M methylamine in THF (1 mL) were combined to afford 1-(1-tert-butyl-1H-pyrazol-4-yl)-3-(2-fluoro-5-(8-isopropyl-2-(methylamino)-7-oxo-7,8-dihydropyrido[2,3-d]pyrimidin-6-yl)phenyl)urea as white solid (39 mg, 62%). ¹H NMR (400 MHz, DMSO-d₆): δ 8.68 (s, 1H), 8.62 (s, 1H), 8.48 (d, J=2.0 Hz, 1H), 8.34 (d, J=7.6 Hz, 1H), 7.80 (s, 1H), 7.79 (s, 1H), 7.78-7.74 (m, 1H), 7.38 (s, 1H), 7.22-7.20 (m, 2H), 5.77-5.74 (m, 1H), 2.89 (d, J=4.4 Hz, 3H), 1.59-1.55 (m, 6H), 1.46 (m, 9H); MS (ESI) m/z: 493.2 (M+H⁺).

EXAMPLE 106

Using general method D, 6-phenylpyrimidine-4-carboxylic acid (250 mg, 1.25 mmol) and Example A3 were combined to afford 1-(2-fluoro-5-(8-methyl-2-(methylthio)-7-oxo-7,8-dihydropyrido[2,3-d]pyrimidin-6-yl)phenyl)-3-(6-phenylpyrimidin-4-yl)urea (265 mg, 41% yield) which was used without purification. ¹H NMR (300 MHz, DMSO-d₆) δ 2.59 (s, 3H), 3.66 (s, 3H), 7.36-7.38 (m, 2H), 7.53-7.55 (m, 3H), 8.03-8.12 (m, 4H), 8.50-8.52 (m, 1H), 8.88 (s, 1H), 8.95 (s, 1H), 10.2 (br. s, 2H); MS (ESI) m/z: 514.0 (M+H⁺).

Using a procedure analogous to Example A1, 1-(2-fluoro-5-(8-methyl-2-(methylthio)-7-oxo-7,8-dihydropyrido[2,3-d]pyrimidin-6-yl)phenyl)-3-(6-phenylpyrimidin-4-yl)urea (265 mg, 0.516 mmol) and 2.00 N methylamine in THF (3.87 mL, 7.73 mmol) were combined to afford 1-(2-fluoro-5-(8-methyl-2-(methylamino)-7-oxo-7,8-dihydropyrido[2,3-d]pyrimidin-6-yl)phenyl)-3-(6-phenylpyrimidin-4-yl)urea (139 mg, 54% yield). ¹H NMR (300 MHz, DMSO-d₆) δ 2.89 (m, 3H), 3.54-3.62 (m, 3H), 7.29-7.35 (m, 2H), 7.53-7.55 (m, 3H), 7.70-7.82 (m, 1H), 7.91 (s, 1H), 8.03-8.06 (m, 2H), 8.13 (s, 1H), 8.44-8.46 (s, 1H), 8.60-8.75 (m, 1H), 8.98 (s, 1H), 10.1 (br. s, 1H), 10.2 (s, 1H); MS (ESI) m/z: 497.2 (M+H⁺).

EXAMPLE 107

To a solution of 1-(1-tert-butyl-1H-pyrazol-4-yl)-3-(2-fluoro-5-(8-methyl-2-(methylsulfinyl)-7-oxo-7,8-dihydropyrido[2,3-d]pyrimidin-6-yl)phenyl)urea from Example 65 (0.1 g, 0.2 mmol) in DMF (1 mL) was added N1,N1-dimethylethane-1,2-diamine (0.054 g, 0.61 mmol) and the solution was stirred for 2 h at RT. The reaction mixture was purified by reverse phase chromatography to furnish product as the TFA salt. The TFA salt (0.2 g) thus obtained was suspended in THF (5 ml), MP-carbonate resin (0.2 g) was added and the slurry was orbitally shaken for a few hours. The solution was separated and concentrated to provide 1-(1-tert-butyl-1H-pyrazol-4-yl)-3-(5-(2-(2-(dimethylamino)ethylamino)-8-methyl-7-oxo-7,8-dihydropyrido[2,3-d]pyrimidin-6-yl)-2-fluorophenyl)urea as the hydrochloride salt (45 mg, 42% yield). ¹H NMR (400 MHz, DMSO-d₆): δ 8.70-8.69 (m, 2H), 8.49 (d, J=2.0 Hz, 1H), 8.38-8.36 (m, 1H), 7.95-7.93 (brs, 1H), 7.87 (s, 1H), 7.75 (s, 1H), 7.35 (s, 1H), 7.21-7.18 (m, 2H), 3.67-3.52 (m, 7H), 2.79 (s, 3H), 2.78 (s, 3H), 1.42 (s, 9H); (ESI) m/z: 522.2 (M+H⁺).

EXAMPLE 108

Using general method B, Example B15 (0.060 g, 0.25 mmol) and Example A30 (0.083 g, 0.25 mmol) were combined to afford 1-(5-(1-ethyl-7-(methylamino)-2-oxo-1,2-dihydro-1,6-naphthyridin-3-yl)-2-fluoro-4-methylphenyl)-3-(3-(trifluoromethyl)isoxazol-5-yl)urea (0.060 g, 47% yield). ¹H NMR (400 MHz, DMSO-d₆): δ 11.0 (s, 1H), 8.80 (s, 1H), 8.39 (s, 1H), 7.80 (d, J=8.4 Hz, 1H), 7.66 (s, 1H), 7.18 (d, J=12.0 Hz, 1H), 6.99 (q, J=5.2 Hz, 2H), 6.45 (s, 1H), 6.23 (s, 1H), 4.14 (q, J=6.8 Hz, 1H), 2.85 (d, J=4.8 Hz, 1H), 2.08 (s, 3H), 1.20 (t, J=7.2 Hz, 3H); MS (ESI) m/z: 505.2 (M+H⁺).

EXAMPLE 109

Using a modified general method B, the carbamate of Example B19 (0.17 g, 0.76 mmol), Example A10 (0.25 g, 0.76 mmol) and N-methylpyrrolidine (catalytic amount) were stirred at 120° C. in THF for 1 h under microwave irradiation. Solvents were removed and crude residue was purified by silica gel chromatography to afford 1-(1-tert-butyl-1H-pyrazol-4-yl)-3-(2-fluoro-4-methyl-5-(8-methyl-2-(methylthio)-7-oxo-7,8-dihydropyrido[2,3-d]pyrimidin-6-yl)phenyl)urea as an off-white solid (0.192 g, 51% yield). ¹H NMR (400 MHz, DMSO-d₆): δ 8.90 (s, 1H), 8.65 (s, 1H), 8.44 (d, J=1.6 Hz, 1H), 8.00 (d, J=8.4 Hz, 1H), 7.87 (s, 1H), 7.77 (s, 1H), 7.36 (s, 1H), 7.14 (d, J=8.4 Hz, 1H), 3.64 (s, 3H), 2.61 (s, 3H), 2.06 (s, 3H), 1.45 (s, 9H); (ESI) m/z: 496.3 (M+H⁺).

Using a procedure analogous to Example A1, 1-(1-tert-butyl-1H-pyrazol-4-yl)-3-(2-fluoro-4-methyl-5-(8-methyl-2-(methylthio)-7-oxo-7,8-dihydropyrido[2,3-d]pyrimidin-6-yl)phenyl)urea (0.192 g, 0.39 mmol) and 2M methylamine in THF (1 mL; 5 eq) were combined to afford 1-(1-tert-butyl-1H-pyrazol-4-yl)-3-(2-fluoro-4-methyl-5-(8-methyl-2-(methylamino)-7-oxo-7,8-dihydropyrido[2,3-d]pyrimidin-6-yl)

phenyl)urea as an off-white solid (0.174 g, 94% yield). $^1$H NMR (400 MHz, DMSO-d$_6$): δ 8.63 (s, 1H), 8.60 (s, 1H), 8.40 (d, J=1.6 Hz, 1H), 7.94 (d, J=8.8 Hz, 1H), 7.80-7.77 (m, 2H), 7.66 (s, 1H), 7.36 (s, 1H), 7.10 (d, J=8.4 Hz, 1H), 3.59-3.51 (m, 3H), 2.90 (d, J=4.4 Hz, 1H), 2.05 (s, 3H), 1.45 (s, 9H); (ESI) m/z: 479.2 (M+H$^+$).

EXAMPLE 110

Using general method B, Example B15 and Example A30 (0.083 g, 0.25 mmol) were combined to afford 1-(5-(1-ethyl-7-(methylamino)-2-oxo-1,2-dihydro-1,6-naphthyridin-3-yl)-2-fluoro-4-methylphenyl)-3-(3-(trifluoromethyl)isoxazol-5-yl)urea (60 mg, 47% yield), $^1$H NMR (400 MHz, DMSO-d$_6$): δ 11.0 (s, 1H), 8.80 (s, 1H), 8.39 (s, 1H), 7.80 (d, J=8.4 Hz, 1H), 7.66 (s, 1H), 7.18 (d, J=12.0 Hz, 1H), 6.99 (q, J=5.2 Hz, 1H), 6.45 (s, 1H), 6.23 (s, 1H), 4.13 (q, J=7.2 Hz, 2H), 2.85 (d, J=4.8 Hz, 3H), 2.08 (s, 3H), 1.20 (t, J=7.2 Hz, 3H); MS (ESI) m/z: 505.2 (M+H$^+$).

EXAMPLE 111

Using a procedure analogous to Example 102, Example A34 (1.61 g, 4.85 mmol) was converted to 3-(5-amino-4-fluoro-2-methylphenyl)-1-ethyl-7-(methylamino)-1,6-naphthyridin-2(1H)-one (1.16 g, 73% yield for two steps). $^1$H NMR (400 MHz, DMSO-d$_6$): δ 8.36 (s, 1H), 7.58 (s, 1H), 6.94-6.92 (brm, 1H), 6.83 (d, J=12.0 Hz, 1H), 6.57 (d, J=9.6 Hz, 1H), 4.87 (brs, 2H), 4.12 (q, J=6.8 Hz, 2H), 2.84 (d, J=4.8 Hz, 3H), 1.94 (s, 3H), 1.185 (t, J=7.2 Hz, 3H); MS (ESI) m/z: 327.2(M+H).

Using general procedure C, the TROC carbamate of B18 (0.212 g, 0.672 mmol, 1.00 eq) and 3-(5-amino-4-fluoro-2-methylphenyl)-1-ethyl-7-(methylamino)-1,6-naphthyridin-2(1H)-one (0.210 g, 0.672 mmol, 1.00 eq) were combined to form desired product which was subsequently treated with MsOH to afford 1-(3-tert-butylisoxazol-5-yl)-3-(5-(1-ethyl-7-(methylamino)-2-oxo-1,2-dihydro-1,6-naphthyridin-3-yl)-2-fluoro-4-methylphenyl)urea (96 mg, 24% yield) as the mesylate salt. $^1$H NMR (400 MHz, DMSO-d$_6$): δ 10.31 (s, 1H), 8.70 (brs, 1H), 8.50 (s, 1H), 7.92 (d, J=8.4 Hz, 1H), 7.79 (s, 1H), 7.20 (d, J=11.6 Hz, 1H), 6.526 (s, 1H), 5.99 (s, 1H), 4.16 (q, J=7.6 Hz, 2H), 2.95 (s, 3H), 2.29 (s, 3H), 2.08 (s, 3H), 1.23-1.19 (m, 12H); MS (ESI) m/z: 493.2(M+H).

EXAMPLE 112

Using general method D, Example B17 (0.061 g, 0.25 mmol) and Example A39 (0.088 g, 0.28 mmol) were combined in presence of methylamine (0.077 g, 0.76 mmol) and diphenylphospharyl azide (0.11 g, 0.38 mmol) to afford 1-(3-tert-butyl-1-(2-(dimethylamino)ethyl)-1H-pyrazol-5-yl)-3-(2-fluoro-4-methyl-5-(8-methyl-2-(methylamino)-7-oxo-7,8-dihydropyrido[2,3-d]pyrimidin-6-yl)phenyl)urea as the hydrochloride salt (70 mg, 50% yield). $^1$H NMR (400 MHz, DMSO-d$_6$): δ 9.50 (s, 1H), 9.26 (s, 1H), 8.87 (s, 1H), 8.59 (s, 1H), 7.88 (d, J=8.4 Hz, 1H), 7.82-7.80 (m, 1H), 7.65 (s, 1H), 7.15 (d, J=12.0 Hz, 1H), 6.11 (s, 1H), 4.31 (t, J=6.4 Hz, 2H), 3.59 (s, 3H), 3.51-3.46 (m, 2H), 2.89 (s, 3H), 2.79 (s, 3H), 2.78 (s, 3H), 2.06 (s, 3H), 1.19 (s, 9H); MS (ESI) m/z: 550.2 (M+H$^+$).

EXAMPLE 113

Using a modified general method G, the carbamate of 5-/-butylisoxazol-3-amine (60 mg, 0.27 mmol), Example A39 (84 mg, 0.27 mmol) and N-methylpyrrolidine (2.3 mg, 0.027 mmol) were combined in THF (1 mL) and were heated to 60° C. overnight. The reaction mixture was diluted with acetonitrile and filtered. The filtered solid was washed with acetonitrile and dried in vacuo to provide 1-(5-tert-butylisoxazol-3-yl)-3-(2-fluoro-4-methyl-5-(8-methyl-2-(methylamino)-7-oxo-7,8-dihydropyrido[2,3-d]pyrimidin-6-yl)phenyl)urea (53 mg, 41% yield). $^1$H NMR (400 MHz, DMSO-d$_6$): δ 9.78 (s, 1H), 8.74 (br s, 1H), 8.60 (br s, 1H), 7.92 (d, J=8.4 Hz, 1H), 7.81 (m, 1H), 7.68 (s, 1H), 7.16 (d, J=12.3 Hz, 1H), 6.43 (s, 1H), 3.59-3.52 (m, 3H), 2.90 (d, J=4.5 Hz, 3H), 2.07 (s, 3H), 1.25 (s, 9H); MS (ESI) m/z: 480.2 (M+H$^+$).

EXAMPLE 114

Using general method B, Example B15 (0.065 g, 0.28 mmol) and Example A10 (0.091 g, 0.28 mmol) were combined to afford 1-(2-fluoro-4-methyl-5-(8-methyl-2-(methylthio)-7-oxo-7,8-dihydropyrido[2,3-d]pyrimidin-6-yl)phenyl)-3-(3-(trifluoromethyl)isoxazol-5-yl)urea (0.090 g, 64% yield). MS (ESI) m/z: 509.0 (M+H$^+$).

Using a procedure analogous to Example A1, 1-(2-fluoro-4-methyl-5-(8-methyl-2-(methylthio)-7-oxo-7,8-dihydropyrido[2,3-d]pyrimidin-6-yl)phenyl)-3-(3-(trifluoromethyl)isoxazol-5-yl)urea (0.090 g, 0.18 mmol) was treated with mCPBA (70% wt, 0.052 g, 0.21 mmol) and then N,N-dimethylethylenediamine (0.039 g, 0.44 mmol) to afford 1-(5-(2-(2-(dimethylamino)ethylamino)-8-methyl-7-oxo-7,8-dihydropyrido[2,3-d]pyrimidin-6-yl)-2-fluoro-4-methylphenyl)-3-(3-(trifluoromethyl)isoxazol-5-yl)urea (0.071 g, 73% yield). $^1$H NMR (400 MHz, DMSO-d$_6$, major rotomer): δ 8.69 (brs, 1H), 8.60 (brs, 1H), 7.83 (d, J=8.4 Hz, 1H), 7.76 (m, 1H), 7.67 (s, 1H), 7.17 (d, J=12.4 Hz, 1H), 6.41 (s, 1H), 5.74 (s, 1H), 3.58 (brs, 3H), 3.48 (q, J=6.4 Hz, 2H), 2.53 (m, 2H), 2.24 (s, 6H), 2.08 (s, 3H); MS (ESI) m/z: 523.2 (M+H$^+$).

EXAMPLE 115

Using a procedure analogous to Example A1, 1-(1-tert-butyl-1H-pyrazol-4-yl)-3-(2-fluoro-4-methyl-5-(8-methyl-2-(methylsulfinyl)-7-oxo-7,8-dihydropyrido[2,3-d]pyrimidin-6-yl)phenyl)urea from Example 109 (0.081 g, 0.16 mmol) and (R)-1-phenylethanamine (0.058 g, 0.48 mmol) were combined in THF (1 mL) to provide (R)-1-(1-tert-butyl-1H-pyrazol-4-yl)-3-(2-fluoro-4-methyl-5-(8-methyl-7-oxo-2-(1-phenylethylamino)-7,8-dihydropyrido[2,3-d]pyrimidin-6-yl)phenyl)urea as a white solid (0.048 g, 53% yield). $^1$H NMR (400 MHz, DMSO-d$_6$): δ 8.62 (s, 1H), 8.60 (s, 1H), 8.48 (d, J=7.2 Hz, 1H), 8.39 (brs, 1H), 7.90 (d, J=8.0 Hz, 1H), 7.76 (s, 1H), 7.62 (s, 1H), 7.43-7.35 (m, 3H), 7.31-7.27 (m, 2H), 7.18 (t, J=7.2 Hz, 1H), 7.08 (d, J=12.8 Hz, 1H), 5.12 (t, J=7.2 Hz, 1H), 3.54-3.46 (m, 3H), 2.01 (s, 3H), 1.44 (s, 9H); (ESI) m/z: 569.3 (M+H$^+$).

EXAMPLE 116

To a solution of 1-(1-tert-butyl-1H-pyrazol-4-yl)-3-(2-fluoro-4-methyl-5-(8-methyl-2-(methylsulfinyl)-7-oxo-7,8-dihydropyrido[2,3-d]pyrimidin-6-yl)phenyl)urea from Example 109 (0.075 g, 0.15 mmol) in THF (1 mL) was added, N$_1$-dimethylethane-1,2-diamine (0.04 g, 0.44 mmol) and stirring continued for 4 h at RT. Solvent was removed under vacuum and crude product was purified by silica gel chromatography to provide 1-(1-tert-butyl-1H-pyrazol-4-yl)-3-(5-(2-(2-(dimethylamino)ethylamino)-8-methyl-7-oxo-7,8-dihydropyrido[2,3-d]pyrimidin-6-yl)-2-fluoro-4-methylphenyl)urea as the hydrochloride salt (0.058, 74% yield). $^1$H NMR (400 MHz, DMSO-d$_6$): δ 9.61 (brs, 1H), 8.67-8.64 (m, 2H), 8.42 (s, 1H), 7.95-7.88 (m, 2H), 7.71 (s, 1H), 7.68 (s, 1H), 7.32 (s, 1H), 7.07 (d, J=12.4 Hz, 1H), 3.68-3.65 (m, 2H), 3.57 (s, 3H), 3.28-3.26 (m, 2H), 2.79 (s, 3H), 2.78 (s, 3H), 2.00 (s, 3H), 1.40 (s, 9H); MS (ESI) m/z: 536.2 (M+H$^+$).

EXAMPLE 117

Using general method B, the carbamate of 5-t-butylisoxazol-3-amine (0.10 g, 0.45 mmol) and Example A12 (0.13 g, 0.45 mmol) were combined to afford 1-(5-tert-butylisoxazol-3-yl)-3-(2-fluoro-5-(8-methyl-2-(methylamino)-7-oxo-7,8-dihydropyrido[2,3-d]pyrimidin-6-yl)phenyl)urea (36 mg, 17% yield). $^1$H NMR (400 MHz, DMSO-d$_6$, major rotamer): δ 9.84 (s, 1H), 8.81 (brs, 1H), 8.65 (s, 1H), 8.40 (d, J=8.0 Hz, 1H), 7.88 (s, 1H), 7.2-7.4 (m, 2H), 6.49 (s, 1H), 3.61 (brs, 3H), 2.90 (brd, J=4.8 Hz, 3H); MS (ESI) m/z: 466.2 (M+H$^+$).

EXAMPLE 118

Using a procedure analogous to Example A1, 1-(1-tert-butyl-1H-pyrazol-4-yl)-3-(2-fluoro-4-methyl-5-(8-methyl-2-(methylsulfinyl)-7-oxo-7,8-dihydropyrido[2,3-d]pyrimidin-6-yl)phenyl)urea from Example 109 (0.075 g, 0.15 mmol) and (S)-1-phenylethanamine (0.053 g, 0.44 mmol) were combined in THF (1 mL) to afford (S)-1-(1-tert-butyl-1H-pyrazol-4-yl)-3-(2-fluoro-4-methyl-5-(8-methyl-7-oxo-2-(1-phenylethylamino)-7,8-dihydropyrido[2,3-d]pyrimidin-6-yl)phenyl)urea as a white solid (0.048 g, 58% yield). $^1$H NMR (400 MHz, DMSO-d$_6$): δ 8.62 (s, 1H), 8.60 (s, 1H), 8.48 (d, J=8.0 Hz, 1H), 8.39 (brs, 1H), 7.90 (d, J=8.4 Hz, 1H), 7.76 (s, 1H), 7.62 (s, 1H), 7.44-7.35 (m, 3H), 7.31-7.27 (m, 2H), 7.18 (t, J=7.2 Hz, 1H), 7.09 (d, J=12.4 Hz, 1H), 5.12 (t, J=6.8 Hz, 1H), 3.55-3.46 (m, 3H), 2.01 (s, 3H), 1.44 (s, 9H); (ESI) m/z: 569.3 (M+H$^+$).

EXAMPLE 119

Using general method C, 5-(trifluoromethyl)pyridin-3-amine (250 mg, 1.54 mmol) and Example A12 (295 mg, 0.984 mmol) were combined to afford 1-(2-fluoro-5-(8-methyl-2-(methylamino)-7-oxo-7,8-dihydropyrido[2,3-d]pyrimidin-6-yl)phenyl)-3-(5-(trifluoromethyl)pyridin-3-yl)urea (15 mg, 2.3% yield). $^1$H NMR (300 MHz, DMSO-d$_6$) δ 2.89 (s, 3H), 3.54-3.61 (m, 3H), 7.26-7.32 (m, 2H), 7.70-7.85 (m, 1H), 7.89 (s, 1H), 8.33-8.35 (m, 1H), 8.46 (s, 1H), 8.56 (s, 1H), 8.65 (s, 1H), 8.71 (s, 1H), 8.91 (s, 1H), 9.71 (s, 1H); MS (ESI) m/z: 488.3 (M+H$^+$).

EXAMPLE 120

Using a procedure analogous to Example 57, 1-(3-t-butylisoxazol-5-yl)-3-(2-fluoro-5-(8-methyl-2-(methylsulfinyl)-7-oxo-7,8-dihydropyrido[2,3-d]pyrimidin-6-yl)phenyl)urea from Example 43 (0.150 g, 0.311 mmol, 1.00 eq) and L-(−)-alpha-methylbenzylamine (0.0846 ml, 0.656 mmol, 3.00 eq) were combined to afford (S)-1-(3-tert-butylisoxazol-5-yl)-3-(2-fluoro-5-(8-methyl-7-oxo-2-(1-phenylethylamino)-7,8-dihydropyrido[2,3-d]pyrimidin-6-yl)phenyl)urea (36 mg, 30% yield) as a white solid. $^1$H NMR (400 MHz, DMSO-d$_6$): δ 10.34 (s, 1H), 8.73 (brs, 1H), 8.65 (brs, 1H), 8.51 (d, J=7.6 Hz, 1H), 8.37 (d, J=7.6 Hz, 1H), 7.85 (s, 1H), 7.44-7.38 (m, 2H), 7.31-7.25 (m, 4H), 7.20-7.16 (m, 1H), 6.06 (s, 1H), 5.16-5.09 (m, 1H), 3.48 (s, 3H), 1.48 (d, J=7.2 Hz, 3H), 1.23 (s, 9H); MS (ESI) m/z: 556.3(M+H$^+$).

EXAMPLE 121

Using a procedure analogous to Example 57, 1-(3-t-butylisoxazol-5-yl)-3-(2-fluoro-5-(8-methyl-2-(methylsulfinyl)-7-oxo-7,8-dihydropyrido[2,3-d]pyrimidin-6-yl)phenyl)urea from Example 43 (0.150 g, 0.311 mmol, 1.00 eq) and (R)-(+)-alpha-methylbenzylamine (0.0846 ml, 0.656 mmol, 3.00 eq) were combined to afford (R)-1-(3-tert-butylisoxazol-5-yl)-3-(2-fluoro-5-(8-methyl-7-oxo-2-(1-phenylethylamino)-7,8-dihydropyrido[2,3-d]pyrimidin-6-yl)phenyl)urea (51 mg, 42% yield) as a white solid. $^1$H NMR (400 MHz, DMSO-d$_6$): δ 10.34 (s, 1H), 8.73 (brs, 1H), 8.65 (brs, 1H), 8.51 (d, J=7.6 Hz, 1H), 8.37 (d, J=7.6 Hz, 1H), 7.85 (s, 1H), 7.44 7.38 (m, 2H), 7.31-7.25 (m, 4H), 7.20-7.16 (m, 1H), 6.06 (s, 1H), 5.16-5.09 (m, 1H), 3.48 (s, 3H), 1.48 (d, J=7.2 Hz, 3H), 1.23 (s, 9H); MS (ESI) m/z: 556.3(M+H$^+$).

EXAMPLE 122

Using general procedure G, the carbamate of B31 (212 mg, 0.81 mmol) and Example A10 (260 mg, 0.79 mmol) were combined to provide 1-(3-cyclopentyl-1-methyl-1H-pyrazol-5-yl)-3-(2-fluoro-4-methyl-5-(8-methyl-2-(methylthio)-7-oxo-7,8-dihydropyrido[2,3-d]pyrimidin-6-yl)phenyl)urea (285 mg, 68% yield). $^1$H NMR (400 MHz, DMSO-d$_6$): δ 8.90 (s, 1H), 8.89 (s, 1H), 8.76 (d, J=2.2 Hz, 1H), 7.97 (d, J=8.4 Hz, 1H), 7.88 (s, 1H), 7.18 (d, J=12.4 Hz, 1H), 5.98 (s, 1H), 3.64 (s, 3H), 3.57 (s, 3H), 2.83 (m, 1H), 2.61 (s, 3H), 2.07 (s, 3H), 1.90-1.80 (m, 2H), 1.66-1.46 (m, 6H); MS (ESI) m/z: 522.2 (M+H$^+$).

Using a procedure analogous to Example A1, 1-(3-cyclopentyl-1-methyl-1H-pyrazol-5-yl)-3-(2-fluoro-4-methyl-5-(S-methyl-2-(methylthio)-7-oxo-7,8-dihydropyrido[2,3-d]pyrimidin-6-yl)phenyl)urea (283 mg, 0.54 mmol) and methylamine in THF (2.0 M, 1.0 mL, 2.0 mmol) were combined to provide 1-(3-cyclopentyl-1-methyl-1H-pyrazol-5-yl)-3-(2-fluoro-4-methyl-5-(8-methyl-2-(methylamino)-7-oxo-7,8-dihydropyrido[2,3-d]pyrimidin-6-yl)phenyl)urea (34 mg, 46%). $^1$H NMR (400 MHz, DMSO-d$_6$): δ 8.87 (s, 1H), 8.71 (d, J=2.0 Hz, 1H), 8.60 (br s, 1H), 7.92 (d, J=8.4 Hz, 1H), 7.81 (m, 1H), 7.66 (s, 1H), 7.14 (d, J=12.8 Hz, 1H), 5.98 (s, 1H), 3.59 (br s, 3H), 3.57 (s, 3H), 2.91-2.85 (m, 4H), 2.06 (s, 3H), 1.86 (m, 2H), 1.64-1.50 (m, 6H); MS (ESI) m/z: 505.2 (M+H$^+$).

EXAMPLE 123

Using general method B, the carbamate of 5-t-butylisoxazol-3-amine (0.15 g, 0.67 mmol) and Example A3 (0.21 g, 0.67 mmol) were combined to afford 1-(5-tert-butylisoxazol-3-yl)-3-(2-fluoro-5-(8-methyl-2-(methylthio)-7-oxo-7,8-dihydropyrido[2,3-d]pyrimidin-6-yl)phenyl)urea (0.15 g, 46% yield). MS (ESI) m/z: 483.2 (M+H$^+$).

Using a procedure analogous to Example A1, 1-(5-tert-butylisoxazol-3-yl)-3-(2-fluoro-5-(8-methyl-2-(methylthio)-7-oxo-7,8-dihydropyrido[2,3-d]pyrimidin-6-yl)phenyl)urea (0.15 g, 0.31 mmol) was treated with mCPBA (70% wt, 0.092 g, 0.37 mmol) and then N,N-dimethylethylenediamine (0.070 g, 0.78 mmol) to afford 1-(5-tert-butylisoxazol-3-yl)-3-(5-(2-(2-(dimethylamino)ethylamino)-8-methyl-7-oxo-7,8-dihydropyrido[2,3-d]pyrimidin-6-yl)-2-fluorophenyl)urea (0.15 g, 92% yield). $^1$H NMR (400 MHz, DMSO-d$_6$, major rotamer): δ 9.88 (brs, 1H), 8.85 (brs, 1H), 8.65 (s, 1H), 8.40 (dd, J=2.4, 8.0 Hz, 1H), 7.88 (s, 1H), 7.76 (m, 1H), 7.2-7.4 (m, 2H), 6.49 (s, 1H), 3.59 (brs, 3H), 3.46 (m, 4H), 2.19 (s, 6H), 1.27 (s, 9H); MS (ESI) m/z: 523.2 (M+H$^+$).

EXAMPLE 124

Using a procedure analogous to Example 136, 1-(1-tert-butyl-1H-pyrazol-4-yl)-3-(2-fluoro-4-methyl-5-(8-methyl-2-(methylsulfinyl)-7-oxo-7,8-dihydropyrido[2,3-d]pyrimidin-6-yl)phenyl)urea from Example 109 (0.071 g, 0.14 mmol) and (2,2-dimethyl-1,3-dioxolan-4-yl)methanamine (0.055 g, 0.42 mmol) were combined in THF (1 mL) to provide 1-(1-tert-butyl-1H-pyrazol-4-yl)-3-(5-(2-(2,3-dihydroxypropylamino)-8-methyl-7-oxo-7,8-dihydropyrido[2,3-d]pyrimidin-6-yl)-2-fluoro-4-methylphenyl)urea as a white solid (0.047 g, 63% yield; 2 steps).
$^1$H NMR (400 MHz, DMSO-d$_6$): δ 8.76 (s, 1H), 8.63 (s, 1H), 8.48 (s, 1H), 7.96 (d, J=8.4 Hz, 1H), 7.79 (s, 1H), 7.68 (s, 1H), 7.54 (brs, 1H), 7.33 (s, 1H), 7.12 (d, J=12.4 Hz, 1H), 4.82 (brs, 1H), 4.60 (t, J=6.8 Hz, 1H), 3.78-3.74 (m, 1H), 3.59-3.52 (m, 5H), 2.01 (s, 3H), 1.44 (s, 9H); (ESI) m/z: 539.2 (M+H$^+$).

EXAMPLE 125

Using general method B, Example B15 (0.070 g, 0.30 mmol) and Example A26 (0.093 g, 0.30 mmol) were combined to afford 1-(2-fluoro-4-methyl-5-(1-methyl-7-(methylamino)-2-oxo-1,2-dihydro-1,6-naphthyridin-3-yl)phenyl)-3-(3-(trifluoromethyl)isoxazol-5-yl)urea (80 mg, 55% yield).
$^1$H NMR (400 MHz, DMSO-d$_6$): δ 11.0 (s, 1H), 8.83 (s, 1H), 8.41 (s, 1H), 7.83 (d, J=8.4 Hz, 1H), 7.69 (s, 1H), 7.21 (d, J=12.0 Hz, 1H), 7.06 (q, J=4.8 Hz, 1H), 6.48 (s, 1H), 6.19 (s, 1H), 3.52 (s, 3H), 2.87 (d, J=4.4 Hz, 3H), 2.11 (s, 3H); MS (ESI) m/z: 491.2 (M+H$^+$).

EXAMPLE 126

Using general method B, Example B15 0.0378 g, 0.160 mmol) and Example A7 (0.0455 g, 0.123 mmol) were combined to afford 1-(5-(7-(2-(dimethylamino)ethylamino)-1-methyl-2-oxo-1,2-dihydro-1,6-naphthyridin-3-yl)-2-fluoro-4-methylphenyl)-3-(3-(trifluoromethyl)isoxazol-5-yl)urea (0.018 g, 27% yield) as a white solid. It was converted to corresponding mesylate salt by reacting with MsOH (1.0 eq.).
$^1$H NMR (400 MHz, DMSO-d$_6$), δ 10.9 (s, 1H), 9.31 (m, 1H), 8.81 (s, 1H), 8.41 (s, 1H), 7.77 (d, J=8.4 Hz, 1H), 7.70 (s, 1H), 7.29 (m, 1H), 7.16 (d, J=12.0 Hz, 1H), 6.39 (s, 1H), 6.31 (s, 1H), 3.65 (q, J=5.2 Hz, 2H), 3.47 (s, 3H), 3.23 (m, 2H), 2.79 (d, J=2.0 Hz, 6H), 2.24 (s, 3H), 2.04 (s, 3H); MS (ESI) m/z: 548.3 (M+H$^+$).

EXAMPLE 127

Using general method B, the carbamate of B2 (0.0463 g, 0.195 mmol) and Example A6 (0.0482 g, 0.130 mmol) were combined to afford 1-(3-tert-butyl-1-methyl-1H-pyrazol-5-yl)-3-(5-(2-(2-(dimethylamino)ethylamino)-8-methyl-7-oxo-7,8-dihydropyrido[2,3-d]pyrimidin-6-yl)-2-fluoro-4-methylphenyl)urea (0.046 g, 64% yield) as a white solid. It was converted to the corresponding HCl salt by reacting with HCl (4.0 M HCl in dioxane, 1.0 eq.).
$^1$H NMR (400 MHz, DMSO-d$_6$), δ 9.78 (s, 1H), 9.61 (s, 1H), 9.16 (s, 1H), 8.89 (s, 1H), 8.68 (s, 1H), 8.02 (s, 1H), 7.94 (d, J=8.0 Hz, 1H), 7.73 (s, 1H), 7.16 (d, J=12.4 Hz, 1H), 6.06 (m, 1H), 3.97 (m, 3H), 3.54 (m, 3H), 3.32 (m, 2H), 2.82 (d, J=4.4 Hz, 6H), 2.06 (s, 3H), 1.17 (s, 9H); MS (ESI) m/z: 550.2 (M+H$^+$).

EXAMPLE 128

Using general method A, the TROC carbamate of Example B18 (208 mg, 0.658 mmol) and Example A40 (120 mg, 0.470 mmol) were combined to afford 1-(3-tert-butylisoxazol-5-yl)-3-(2-fluoro-5-(2-oxo-1,2-dihydro-1,6-naphthyridin-3-yl)phenyl)urea (35 mg, 18% yield). $^1$H NMR (300 MHz, DMSO-d$_6$): δ 1.22 (s, 9H), 6.07 (s, 1H), 7.20-7.22 (m, 1H), 7.31-7.35 (m, 1H), 7.42-7.45 (m, 1H), 8.15 (s, 1H), 8.43-8.46 (m, 2H), 8.80 (br. s, 1H), 8.91 (br. s, 1H), 10.3 (br. s, 1H), 12.2 (br. s, 1H); MS (ESI) m/z: 422.2 (M+H$^+$).

EXAMPLE 129

Using general method A, the TROC carbamate of Example B18 (0.256 g, 0.81 mmol) and Example A6 (0.300 g, 0.81 mmol) were combined to provide 1-(3-tert-butylisoxazol-5-yl)-3-(5-(2-(2-(dimethylamino)ethylamino)-8-methyl-7-oxo-7,8-dihydropyrido[2,3-d]pyrimidin-6-yl)-2-fluoro-4-methylphenyl)urea, which was converted to the mesylate salt (27 mg, 6% yield). $^1$H NMR (400 MHz, DMSO-d$_6$): δ 10.36 (s, 1H), 9.62 (brs, 1H), 8.74 (s, 1H), 8.64 (s, 1H), 7.97 (brs, 1H), 7.85 (d, J=9 Hz), 7.70 (s, 1H), 7.34 (d, J=12 Hz, 1H), 5.94 (s, 1H), 3.68 (brs, 2H), 3.28 (brs, 2H), 2.90 (brs, 6H), 2.23 (s, 3H), 2.03 (s, 3H), 1.16 (s, 9H); MS (ESI, m/z: 537.3, M+H$^+$).

EXAMPLE 130

Using general method B, the carbamate of 5-t-butylisoxazol-3-amine (0.029 g, 0.130 mmol) and Example A6 (0.032 g, 0.086 mmol) were combined to afford 1-(5-tert-butylisoxazol-3-yl)-3-(5-(2-(2-(dimethylamino)ethylamino)-8-methyl-7-oxo-7,8-dihydropyrido[2,3-d]pyrimidin-6-yl)-2-fluoro-4-methylphenyl)urea (0.011 g, 24% yield) as a white solid. It was converted to the corresponding mesylate salt by reacting with MsOH (1.0 eq.). $^1$H NMR (400 MHz, DMSO-d$_6$): δ 9.80 (s, 1H), 9.34 (m, 1H), 8.77 (s, 1H), 8.69 (s, 1H), 7.99 (m, 1H), 7.92 (d, J=8.0 Hz, 1H), 7.74 (s, 1H), 7.18 (d, J=12.0 Hz, 1H), 6.42 (s, 1H), 3.70 (q, J=6.0 Hz, 2H), 3.61 (m, 2H), 2.84 (s, 6H), 2.31 (s, 3H), 2.07 (s, 3H), 1.33 (s, 3H), 1.25 (s, 9H); MS (ESI) m/z: 537.3 (M+H$^+$).

EXAMPLE 131

A solution 1-(3-cyclopentyl-1-methyl-1H-pyrazol-5-yl)-3-(2-fluoro-4-methyl-5-(8-methyl-2-(methylsulfinyl)-7-oxo-7,8-dihydropyrido[2,3-d]pyrimidin-6-yl)phenyl)urea from Example 122 (80 mg, 0.15 mmol) in THF (1 mL) was treated with N,N-dimethylethylenediamine (0.080 mL, 0.74 mmol). The reaction was stirred 1 h at RT, diluted with EtOAc (15 mL) and washed with 2 M aq Na$_2$CO$_3$ (2×10 mL), water (10 mL) and brine (10 mL). The organics were dried (Na$_2$SO$_4$), concentrated in vacuo and chromatographed on reverse phase silica gel to provide 1-(3-cyclopentyl-1-methyl-1H-pyrazol-5-yl)-3-(5-(2-(2-(dimethylamino)ethylamino)-8-methyl-7-oxo-7,8-dihydropyrido[2,3-d]pyrimidin-6-yl)-2-fluoro-4-methylphenyl)urea (33 mg, 39% yield). $^1$H NMR (400 MHz, DMSO-d$_6$): δ 8.87 (s, 1H), 8.72 (d, J=2.0 Hz, 1H), 8.65 and 8.60 (br s, 1H), 7.91 (d, J=8.6 Hz, 1H), 7.75 and 7.59 (m, 1H), 7.66 (s, 1H), 7.14 (d, J=8.4 Hz, 1H), 5.98 (s, 1H), 3.59-3.43 (m, 8H), 2.86 (m, 1H), 2.21 (br s, 6H), 2.49 (m, 2H obscured by solvent), 2.06 (s, 3H), 1.87 (m, 2H), 1.66-1.48 (m, 6H); MS (ESI) m/z: 562.3 (M+H$^+$).

EXAMPLE 132

Using general method F, 1-isocyanato-3-(trifluoromethyl)benzene (0.120 g, 0.648 mmol) and Example A6 (0.240 g, 0.648 mmol) were combined in ethyl acetate to provide 1-(5-(2-(2-(dimethylamino)ethylamino)-8-methyl-7-oxo-7,8-dihydropyrido[2,3-d]pyrimidin-6-yl)-2-fluoro-4-methylphenyl)-3-(3-(trifluoromethyl)phenyl)urea (106 mg, 28% yield) *H NMR (400 MHz, DMSO-$d_6$): δ9.34 (s, 1H), 8.65 (m, 1H), 8.65 (m, 1H), 8.59 (m, 1H)), 8.02 (s, 1H), 7.91 (d, J=9 Hz, 1H), 7.74 (m, 1H), 7.67 (s, 1H), 7.49 (m, 4H), 7.29 (d, J=6.5 Hz, 1H), 7.15 (d, J=12 Hz, 1H); 3.45-3.6 (m, 4H), 2.18 (s, 6H), 2.07 (s, 3H), 1.97 (s, 3H); MS (ESI, m/z: 558.3, M+H$^+$).

EXAMPLE 133

Using the general method E, 1-(1-tert-butyl-1H-pyrazol-4-yl)-3-(2-fluoro-4-methyl-5-(8-methyl-2-(methylsulfinyl)-7-oxo-7,8-dihydropyrido[2,3-d]pyrimidin-6-yl)phenyl)urea from Example 109 (0.081 g, 0.16 mmol) and propan-2-amine (0.029 g, 0.49 mmol) were combined in THF (1 mL) to provide 1-(1-tert-butyl-1H-pyrazol-4-yl)-3-(2-fluoro-5-(2-(isopropylamino)-8-methyl-7-oxo-7,8-dihydropyrido[2,3-d]pyrimidin-6-yl)-4-methylphenyl)urea as a white solid (0.042 g, 50% yield). $^1$H NMR (400 MHz, DMSO-$d_6$): δ 8.63 (s, 1H), 8.60 (s, 1H), 8.40 (d, J=2.0 Hz, 1H), 7.93 (d, J=8.4 Hz, 1H), 7.77 (s, 1H), 7.64 (s, 1H), 7.36 (s, 1H), 7.10 (d, J=12.4 Hz, 1H), 4.16-4.13 (m, 1H), 3.56-3.54 (m, 3H), 2.05 (s, 3H), 1.45 (s, 9H), 1.20 (d, J=6.0 Hz, 6H); (ESI) m/z: 507.2 (M+H$^+$).

EXAMPLE 134

Using general method B, the carbamate of 5-t-butylisoxazol-3-amine (0.050 g, 0.22 mmol) and Example A26 (0.070 g, 0.22 mmol) were combined to afford 1-(5-tert-butylisoxazol-3-yl)-3-(2-fluoro-4-methyl-5-(1-methyl-7-(methylamino)-2-oxo-1,2-dihydro-1,6-naphthyridin-3-yl)phenyl)urea (66 mg, 62% yield). $^1$H NMR (400 MHz, DMSO-$d_6$): δ 9.78 (s, 1H), 8.73 (s, 1H), 8.38 (s, 1H), 7.91 (d, J=8.4 Hz, 1H), 7.66 (s, 1H), 7.14 (d, J=12.0 Hz, 1H), 7.03 (q, J=4.8 Hz, 1H), 6.43 (s, 1H), 6.17 (s, 1H), 3.50 (s, 3H), 2.85 (d, J=4.4 Hz, 3H), 2.07 (s, 3H), 1.28 (s, 9H); MS (ESI) m/z: 479.2 (M+H$^+$).

EXAMPLE 135

Using a procedure analogous to Example 93, Example B12 (0.119 g) and Example A12 (0.086 g, 0.289 mmol) were combined to afford 1-(2-fluoro-5-(8-methyl-2-(methylamino)-7-oxo-7,8-dihydropyrido[2,3-d]pyrimidin-6-yl)phenyl)-3-(3-(1-hydroxy-2-methylpropan-2-yl)-1-methyl-1H-pyrazol-5-yl)urea (0.043 g, 32% yield) as a light yellow solid. $^1$H NMR (400 MHz, DMSO-$d_6$), δ 8.57 (s, 1H), 8.29 (dd, J=7.6, 2.0 Hz, 1H), 7.85 (s, 1H), 7.40-7.35 (m, 1H), 7.18 (dd, J=10.4, 8.4 Hz, 1H), 6.17 (s, 1H), 3.75-3.68 (m, 6H), 3.53 (s, 2H), 3.03 (s, 3H), 1.25 (s, 6H); MS (ESI) m/z: 495.2 (M+H$^+$).

EXAMPLE 136

To a solution of 1-(1-tert-butyl-1H-pyrazol-4-yl)-3-(2-fluoro-5-(8-methyl-2-(methylsulfinyl)-7-oxo-7,8-dihydropyrido[2,3-d]pyrimidin-6-yl)phenyl)urea from Example 65 (0.082 g, 0.16 mmol) in THF (1 mL) was added 2,2-dimethyl-1,3-dioxolan-4-yl)methanamine (0.065 g, 0.48 mmol). After stirring for 20 h at RT, the solvent was removed and crude residue was purified by silica gel chromatography to afford 1-(1-tert-butyl-1H-pyrazol-4-yl)-3-(5-(2-((2,2-dimethyl-1,3-dioxolan-4-yl)methylamino)-8-methyl-7-oxo-7,8-dihydropyrido[2,3-d]pyrimidin-6-yl)-2-fluorophenyl)urea (64 mg) as a white solid.

This intermediate was stirred in THF and 2M HCl (5 mL, 4:1) for 2 h at RT. The reaction mixture was concentrated to 1 mL, and 2N NaOH was added until the pH of the solution was around 8. The resultant solid was filtered, washed with water and dried to provide 1-(1-tert-butyl-1H-pyrazol-4-yl)-3-(5-(2-(2,3-dihydroxypropylamino)8-methyl-7-oxo-7,8-dihydropyrido[2,3-d]pyrimidin-6-yl)-2-fluorophenyl)urea as a white solid (53 mg, 61% yield, 2 steps). $^1$H NMR (400 MHz, DMSO-$d_6$): δ 8.70 (brs, 2H), 8.65 (s, 1H), 8.49 (d, J=2.0 Hz, 1H), 8.40 (d, J=8.0 Hz, 1H), 7.85 (s, 1H), 7.81 (s, 1H), 7.70-7.67 (m, 1H), 7.38 (s, 1H), 7.24 (s, 1H), 7.22 (s, 1H), 4.79 (d, 0.7=4.8 Hz, 1H), 4.58 (t, J=5.6 Hz, 1H), 3.73-3.48 (m, 5H), 3.38-3.33 (m, 3H), 1.47 (s, 9H); (ESI) m/z: 525.3 (M+H$^+$).

EXAMPLE 137

Using general method G, 2-amino-5-t-butyl-1,3,4-thiadiazole (0.5000 g, 3.2 mmol) and Example A10 (0.342 g, 1.04 mmol) were combined to afford 1-(5-t-butyl-1,3,4-thiadiazol-2-yl)-3-(2-fluoro-4-methyl-5-(8-methyl-2-(methylthio)-7-oxo-7,8-dihydropyrido[2,3-d]pyrimidin-6-yl)phenyl)urea (0.345 g, 65% yield) as a white solid which was used as is in the next reaction. $^1$H NMR (400 MHz, CDCl$_3$): δ 8.67 (s, 1H), 7.94 (d, J=7.6 Hz), 7.67 (s, 1H), 6.96 (d, J=11.2 Hz), 3.91 (s, 3H), 2.69 (s, 3H), 2.15 (s, 3H), 1.45 (s, 9H); MS (ESI) m/z: 514.2 (M+H).

Using a procedure analogous to Example A1, 1-(5-t-butyl-1,3,4-thiadiazol-2-yl)-3-(2-fluoro-4-methyl-5-(8-methyl-2-(methylthio)-7-oxo-7,8-dihydropyrido[2,3-d]pyrimidin-6-yl)phenyl)urea (0.345 g, 0.672 mmol) and 2.00M MeNH$_2$/THF (3.36 ml, 6.72 mmol) were combined to afford 1-(5-tert-butyl-1,3,4-thiadiazol-2-yl)-3-(2-fluoro-4-methyl-5-(8-methyl-2-(methylamino)-7-oxo-7,8-dihydropyrido[2,3-d]pyrimidin-6-yl)phenyl)urea (0.311 g, 93% yield) as a white solid. $^1$H NMR (400 MHz, DMSO-$d_6$): δ 7.822-7.75 (m, 3H), 7.69 (s, 1H), 7.39-7.37 (m, 1H), 7.34-7.30 (m, 1H), 7.16 (d, J=12.0 Hz, 1H), 2.90 (brd, J=4.8 Hz, 3H), 2.35 (s, 3H), 2.09 (s, 3H), 1.34 (s, 9H); MS (ESI) m/z: 497.0 (M+H).

EXAMPLE 138

Using general method B, the carbamate of Example B19 (0.080 g, 0.36 mmol) and Example A7 (0.088 g, 0.24 mmol) were combined to afford 1-(1-tert-butyl-1H-pyrazol-4-yl)-3-(5-(7-(2-(dimethylamino)ethylamino)-1-methyl-2-oxo-1,2-dihydro-1,6-naphthyridin-3-yl)-2-fluoro-4-methylphenyl)urea (0.0469 g, 37% yield) as a white solid. It was converted to corresponding mesyalte salt by reacting with MsOH (1.0 eq.). $^1$H NMR (400 MHz, DMSO-$d_6$): δ 9.38 (s, 1H), 8.66 (s, 1H), 8.44-8.43 (m, 2H), 7.94 (d, J= 8.4 Hz, 1H), 7.76 (s, 1H), 7.71 (s, 1H), 7.37 (s, 1H), 7.27 (t, J=5.6 Hz, 1H), 7.11 (d, J=12.0 Hz, 1H), 6.34 (s, 1H), 3.68 (q, J=5.6 Hz, 2H), 3.50 (s, 3H), 3.27 (t, J=5.6 Hz, 2H), 2.83 (s, 6H), 2.30 (s, 3H), 2.05 (s, 3H), 1.45 (s, 9H); MS (ESI) m/z: 535.2 (M+H$^+$).

EXAMPLE 139

Using General Method B, Example B15 (100 mg, 0.381 mmol) Example A16 (116 mg, 0.346 mmol) were combined to afford 1-(2,4-difluoro-5-(8-methyl-2-(methylthio)-7-oxo-7,8-dihydropyrido[2,3-d]pyrimidin-6-yl)phenyl)-3-(3-(trifluoromethyl)isoxazol-5-yl)urea (65 mg, 37% yield) as an oil, which was used without purification in the next reaction.

Using a procedure analogous to Example A1, 1-(2,4-difluoro-5-(8-methyl-2-(methylthio)-7-oxo-7,8-dihydropyrido[2,3-d]pyrimidin-6-yl)phenyl)-3-(3-(trifluoromethyl)isoxazol-5-yl)urea (65 mg, 0.130 mmol) and 2.0N methylamine in THF (0.63 mL, 1.3 mmol) were combined to afford 1-(2, 4-difluoro-5-(8-methyl-2-(methylamino)-7-oxo-7,8-dihydropyrido[2,3-d]pyrimidin-6-yl)phenyl)-3-(3-(trifluoromethyl)isoxazol-5-yl)urea (8 mg, 13% yield). MS (ESI) m/z: 496.0 (M+H$^+$).

EXAMPLE 140

Using General Method B, Example B15 (120 mg, 0.457 mmol) and Example A17 (100 mg, 0.286 mmol) were combined to afford 1-(4-chloro-2-fluoro-5-(8-methyl-2-(methylthio)-7-oxo-7,8-dihydropyrido[2,3-d]pyrimidin-6-yl)phenyl)-3-(3-(trifluoromethyl)isoxazol-5-yl)urea (75 mg, 50% yield) which was used without further purification. MS (ESI) m/z: 529.0 (M+H$^+$).

Using a procedure analogous to Example A1, 1-(4-chloro-2-fluoro-5-(8-methyl-2-(methylthio)-7-oxo-7,8-dihydropyrido[2,3-d]pyrimidin-6-yl)phenyl)-3-(3-(trifluoromethyl)isoxazol-5-yl)urea (75 mg, 0.140 mmol) and 2.0 N methylamine in THF (0.71 mL) were combined to afford 1-(4-chloro-2-fluoro-5-(8-methyl-2-(methylamino)-7-oxo-7,8-dihydropyrido[2,3-d]pyrimidin-6-yl)phenyl)-3-(3-(trifluoromethyl)isoxazol-5-yl)urea (15 mg, 21% yield). $^1$H NMR (300 MHz, DMSO-d$_6$) δ 2.89 (s, 3H), 3.51-3.58 (m, 3H), 6.48 (s, 1H), 7.61 (d, J=11 Hz, 1H), 7.77 (s, 1H), 7.88-7.90 (m, 1H), 8.04 (d, J=9.5 Hz, 1H), 8.61-8.69 (m, 1H), 9.01 (s, 1H), 11.0 (s, 1H); MS (ESI) m/z: 512.0 (M+H$^+$).

EXAMPLE 141

In a solution of ethanol:water:dioxane (1:1:1, 9 mL) was placed ethyl 1-tert-butyl-5-(trifluoromethyl)-1H-pyrazole-4-carboxylate (750 mg, 2.84 mmol) and lithium hydroxide hydrate (357 mg, 8.51 mmol). The mixture was stirred at 40° C. for 3 hrs and then at RT overnight. The mixture was diluted with water (25 mL) and 1N HCl (10 mL) and extracted with ethyl acetate (2×25 mL). The combined organic phases were washed with brine (20 mL), dried (Na$_2$SO$_4$) and evaporated at reduced pressure to afford 1-tert-butyl-5-(trifluoromethyl)-1H-pyrazole-4-carboxylic acid (646 mg, 94% yield) as a solid. $^1$H NMR (300 MHz, DMSO-d$_6$) δ 1.63 (s, 9H), 7.92 (s, 1H); MS (ESI) m/z: 259.0 (M+Na$^+$).

Using General Method D, 1-tert-butyl-5-(trifluoromethyl)-1H-pyrazole-4-carboxylic acid (200 mg, 0.847 mmol) and Example A3 (268 mg, 0.847 mmol) were combined to afford 1-(1-tert-butyl-5-(trifluoromethyl)-1H-pyrazol-4-yl)-3-(2-fluoro-5-(8-methyl-2-(methylthio)-7-oxo-7,8-dihydropyrido[2,3-d]pyrimidin-6-yl)phenyl)urea (247 mg, 53% yield).

Using a procedure analogous to Example A1, 1-(1-tert-butyl-5-(trifluoromethyl)-1H-pyrazol-4-yl)-3-(2-fluoro-5-(8-methyl-2-(methylthio)-7-oxo-7,8-dihydropyrido[2,3-d]pyrimidin-6-yl)phenyl)urea (247 mg, 0.449 mmol) and 2.0N methylamine in THF (2.25 mL, 4.49 mmol) were combined to afford 1-(1-tert-butyl-5-(trifluoromethyl)-1H-pyrazol-4-yl)-3-(2-fluoro-5-(8-methyl-2-(methylamino)-7-oxo-7,8-dihydropyrido[2,3-d]pyrimidin-6-yl)phenyl)urea (152 mg, 63% yield). $^1$H NMR (300 MHz, acetone-d$_6$) δ 1.64 (s, 9H), 2.82 (s, 3H), 3.06 (m, 3H), 6.80-6.95 (m, 1H), 7.14-7.19 (m, 1H), 7.38-7.42 (m, 1H), 7.85 (s, 1H), 8.06 (s, 1H), 8.11 (br. s, 1H), 8.50 (br. s, 1H), 8.57-8.59 (m, 1H), 8.60-8.63 (m, 1H); MS (ESI) m/z: 533.3 (M+H$^+$).

EXAMPLE 142

To a stirring solution of 4-chloro-3-(trifluoromethyl)phenyl isocyanate (0.0750 g, 0.401 mmol, 1.00 eq) in THF (5 ml) at 22° C. was added Example A25 (0.125 g, 0.401 mmol, 1.00 eq). The reaction became homogeneous and then solids precipitated. The suspension was stirred overnight at RT. The reaction was chilled thoroughly at 0-5° C. The solids were collected by filtration, rinsed well with ice-cold THF and dried on the filter. The free base thus obtained was treated with MsOH in THF (2 wt %, 1.64 g, 0.342 mmol, 1.0 eq) to afford 1-(2-fluoro-4-methyl-5-(1-methyl-7-(methylamino)-2-oxo-1,2-dihydro-1,6-naphthyridin-3-yl)phenyl)-3-(3-(trifluoromethyl)phenyl)urea (182 mg, 76% yield) as the mesylate salt as a nearly white solid. $^1$H NMR (400 MHz, DMSO-d$_6$): δ 9.34 (s, 1H), 8.65 (brs, 1H), 8.51 (s, 1H), 8.05 (s, 1H), 7.96 (d, J=8.4 Hz, 1H), 7.82 (s, 1H), 7.51-7.44 (m, 2H), 7.30 (d, J=7.6 Hz, 1H), 7.18 (d, J=12.4 Hz, 1H), 6.51 (s, 1H), 3.54 (s, 3H), 2.96 (s, 3H), 2.30 (s, 3H), 2.08 (s, 3H); MS (ESI) m/z: 500.3 (M+H).

EXAMPLE 143

Using a procedure analogous to Example 142, 4-chloro-3-(trifluoromethyl)phenyl isocyanate (0.1000 g, 0.451 mmol, 1.00 eq) and Example A26 (0.141 g, 0.451 mmol, 1.00 eq) were combined to afford 1-(4-chloro-3-(trifluoromethyl)phenyl)-3-(2-fluoro-4-methyl-5-(1-methyl-7-(methylamino)-2-oxo-1,2-dihydro-1,6-naphthyridin-3-yl)phenyl)urea mesylate (168 mg, 59% yield) as a nearly white solid. $^1$H NMR (400 MHz, DMSO-d$_6$) δ 9.47 (s, 1H), 8.65 (brs, 1H), 8.48 (s, 1H), 8.12 (d, J=2.4 Hz, 1H), 7.91 (d, J=8.8 Hz, 1H), 7.78 (s, 1H), 7.59 (d, J=8.8 Hz, 1H), 7.51 (dd, J=2.4 and 8.8 Hz, 1H), 7.18 (d, J=12.4 Hz, 1H), 6.43 (s, 1H), 3.53 (s, 3H), 2.94 (s, 3H), 2.28 (s, 3H), 2.08 (s, 3H); MS (ESI) m/z: 534.2 (M+H$^+$).

EXAMPLE 144

3-(Trifluoromethyl)phenyl isocyanate (0.075 g, 0.40 mmol, 1.0 eq) and Example A10 (0.13 g, 0.40 mmol, 1.0 eq) were combined in THF (5 ml) and stirred at RT overnight. The resulting suspension was chilled at 0-5° C. and the solids collected by filtration. The solids were washed sparingly with ice-cold THF and dried on the filter to afford 1-(2-fluoro-4-methyl-5-(8-methyl-2-(methylthio)-7-oxo-7,8-dihydropyrido[2,3-d]pyrimidin-6-yl)phenyl)-3-(3-(trifluoromethyl)phenyl)urea (92 mg, 44% yield) as a white solid which was used as is in the next reaction. $^1$H NMR (400 MHz, acetone-d$_6$) δ 8.89 (s, 1H), 8.78 (brs, 1H), 8.16-8.08 (m, 2H), 7.88 (s, 1H), 7.63 (brd, J=8.0 Hz, 1H), 7.51 (dd, J=8.0 and 16.4 Hz, 1H), 7.33-7.31 (m, 1H), 7.09 (d, J=12.4 Hz, 1H), 3.76 (s, 3H), 2.67 (s, 3H), 2.17 (s, 3H); MS (ESI) m/z: 518.0 (M+H$^+$).

Using a procedure analogous to Example A1, 1-(2-fluoro-4-methyl-5-(8-methyl-2-(methylthio)-7-oxo-7,8-dihydropyrido[2,3-d]pyrimidin-6-yl)phenyl)-3-(3-(trifluoromethyl)phenyl)urea (0.092 g, 0.18 mmol) and 2.00M MeNH$_2$/THF (0.89 ml, 1.8 mmol) were combined to afford 1-(2-fluoro-4-methyl-5-(8-methyl-2-(methylamino)-7-oxo-7,8-dihydropyrido[2,3-d]pyrimidin-6-yl)phenyl)-3-(3-(trifluoromethyl)phenyl)urea (28 mg, 31% yield) as a white solid. $^1$H NMR (400 MHz, DMSO-d$_6$) δ 8.78 (s, 1H), 8.61 (s, 1H), 8.12-8.09 (m, 2H), 8.04 (s, 1H), 7.68 s, 1H), 7.64 (brd, J=10.0 Hz, 1H), 7.50 (dd, J=7.6 and 16.0 Hz, 1H), 7.31 (brd, J=7.6 Hz, 1H), 7.06 (d, J=12.4 Hz, 1H), 6.82 (brs, 1H), 3.59 (s, 3H), 3.08 (brd, J=4.4 Hz, 3H), 2.16 (s, 3H); MS (ESI) m/z: 501.0 (M+H$^+$).

EXAMPLE 145

Using general method E, 1-(1-tert-butyl-1H-pyrazol-4-yl)-3-(2-fluoro-4-methyl-5-(8-methyl-2-(methylsulfinyl)-7-oxo-7,8-dihydropyrido[2,3-d]pyrimidin-6-yl)phenyl)urea from Example 109 (0.081 g, 0.16 mmol) and cyclopropanamine (0.027 g, 0.48 mmol) were combined in THF (1 mL) to provide 1-(1-tert-butyl-1H-pyrazol-4-yl)-3-(5-(2-(cyclopropylamino)-8-methyl-7-oxo-7,8-dihydropyrido[2,3-d]pyrimidin-6-yl)-2-fluoro-4-methylphenyl)urea as a white solid (0.051 g, 64% yield). $^1$H NMR (400 MHz, DMSO-$d_6$): δ 8.64 (s, 1H), 8.60 (brs, 1H), 8.40 (d, J=1.6 Hz, 1H), 8.06-8.04 (m, 1H), 7.94 (d, J=8.8 Hz, 1H), 7.77 (s, 1H), 7.66 (s, 1H), 7.36 (s, 1H), 7.10 (d, J=12.4 Hz, 1H), 3.61-3.54 (m, 3H), 2.78-2.83 (m, 1H), 2.05 (s, 3H), 1.45 (s, 9H), 0.725 (brs, 2H), 0.55-0.53 (m, 2H); (ESI) m/z: 505.2 (M+H$^+$).

EXAMPLE 146

Using general method E, 1-(1-tert-butyl-1H-pyrazol-4-yl)-3-(2-fluoro-4-methyl-5-(8-methyl-2-(methylsulfinyl)-7-oxo-7,8-dihydropyrido[2,3-d]pyrimidin-6-yl)phenyl)urea from Example 109 (0.081 g, 0.16 mmol) and (S)-2-aminopropan-1-ol (0.036 g, 0.48 mmol) were combined in THF (1 mL) to provide (S)-1-(1-tert-butyl-1H-pyrazol-4-yl)-3-(2-fluoro-5-(2-(1-hydroxypropan-2-ylamino)-8-methyl-7-oxo-7,8-dihydropyrido[2,3-d]pyrimidin-6-yl)-4-methylphenyl)urea as a white solid (0.062 g, 75% yield). $^1$H NMR (400 MHz, DMSO-$d_6$): δ 8.64 (s, 1H), 8.60 (s, 1H), 8.40 (d, J=1.6 Hz, 1H), 7.94 (d, J=8.4 Hz, 1H), 7.77 (s, 1H), 7.64 (s, 1H), 7.59 (d, J=8.0 Hz, 1H) 7.36 (s, 1H), 7.10 (d, J=12.4 Hz, 1H), 4.72 (t, J=5.6 Hz, 1H), 4.10-4.06 (m, 1H), 3.65-3.53 (m, 3H), 2.05 (s, 3H), 1.45 (s, 9H), 1.17 (d, J=6.4 Hz, 3H); (ESI) m/z: 523.2 (M+H$^+$).

EXAMPLE 147

Using general method E, 1-(1-tert-butyl-1H-pyrazol-4-yl)-3-(2-fluoro-4-methyl-5-(8-methyl-2-(methylsulfinyl)-7-oxo-7,8-dihydropyrido[2,3-d]pyrimidin-6-yl)phenyl)urea from Example 109 (0.085 g, 0.17 mmol) and (R)-2-aminopropan-1-ol (0.037 g, 0.50 mmol) were combined in THF (1 mL) to provide (R)-1-(1-tert-butyl-1H-pyrazol-4-yl)-3-(2-fluoro-5-(2-(1-hydroxypropan-2-ylamino)-8-methyl-7-oxo-7,8-dihydropyrido[2,3-d]pyrimidin-6-yl)-4-methylphenyl)urea as a white solid (0.055 g, 63% yield). $^1$H NMR (400 MHz, DMSO-$d_6$): δ 8.64 (s, 1H), 8.60 (s, 1H), 8.40 (d, J=2.0 Hz, 1H), 7.94 (d, J=8.8 Hz, 1H), 7.77 (s, 1H), 7.64 (s, 1H), 7.59 (d, J=8.0 Hz, 1H) 7.36 (s, 1H), 7.10 (d, J=12.4 Hz, 1H), 4.72 (t, J=5.6 Hz, 1H), 4.10-4.06 (m, 1H), 3.56-3.53 (m, 3H), 2.05 (s, 3H), 1.45 (s, 9H), 1.17 (d, J=6.4 Hz, 3H); (ESI) m/z: 523.2 (M+H$^+$).

EXAMPLE 148

Using general method B, the carbamate of 5-/-butylisoxazol-3-amine (0.07 g, 0.31 mmol) and Example A17 (0.11 g, 0.31 mmol) were combined to afford 1-(5-tert-butylisoxazol-3-yl)-3-(4-chloro-2-fluoro-5-(8-methyl-2-(methylthio)-7-oxo-7,8-dihydropyrido[2,3-d]pyrimidin-6-yl)phenyl)urea (48 mg, 30% yield). MS (ESI) m/z: 517.0 (M+H$^+$).

Using a procedure analogous to Example A1, 1-(5-tert-butylisoxazol-3-yl)-3-(4-chloro-2-fluoro-5-(8-methyl-2-(methylthio)-7-oxo-7,8-dihydropyrido[2,3-d]pyrimidin-6-yl)phenyl)urea (0.048 g, 0.093 mmol) was treated with mCPBA (70% wt, 0.027 g, 0.11 mmol) and then N-methylamine (2.0M in THF, 0.19 mL, 0.37 mmol) to afford 1-(5-tert-butylisoxazol-3-yl)-3-(4-chloro-2-fluoro-5-(8-methyl-2-(methylamino)-7-oxo-7,8-dihydropyrido[2,3-d]pyrimidin-6-yl)phenyl)urea (30 mg, 65% yield). $^1$H NMR (400 MHz, DMSO-$d_6$, major rotomer): δ 9.86 (brs, 1H), 8.92 (brs, 1H), 8.62 (s, 1H), 8.15 (d, J=8.8 Hz, 1H), 7.89 (m, 1H), 7.76 (s, 1H), 7.58 (d, J=10.8 Hz, 1H), 6.44 (s, 1H), 3.59 (brs, 3H), 2.90 (brd, J=4.8 Hz, 3H), 1.25 (s, 9H); MS (ESI) m/z: 500.0 (M+H$^+$).

EXAMPLE 149

Using general method B, the carbamate of 5-/-butylisoxazol-3-amine (0.07 g, 0.31 mmol) and Example A41 0.11 g, 0.31 mmol) were combined to afford 1-(5-tert-butylisoxazol-3-yl)-3-(5-(8-ethyl-2-(methylthio)-7-oxo-7,8-dihydropyrido[2,3-d]pyrimidin-6-yl)-2-fluoro-4-methylphenyl)urea (97 mg, 61% yield). MS (ESI) m/z: 511.2 (M+H$^+$).

Using a procedure analogous to Example A1, 1-(5-tert-butylisoxazol-3-yl)-3-(5-(8-ethyl-2-(methylthio)-7-oxo-7,8-dihydropyrido[2,3-d]pyrimidin-6-yl)-2-fluoro-4-methylphenyl)urea (0.097 g, 0.19 mmol) was treated with mCPBA (70% wt, 0.056 g, 0.23 mmol) and then N-methylamine (2.0M in THF, 0.38 mL, 0.76 mmol) to afford 1-(5-tert-butylisoxazol-3-yl)-3-(5-(8-ethyl-2-(methylamino)-7-oxo-7,8-dihydropyrido[2,3-d]pyrimidin-6-yl)-2-fluoro-4-methylphenyl)urea (59 mg, 63% yield). $^1$H NMR (400 MHz, DMSO-$d_6$, major rotomer): δ 9.79 (s, 1H), 8.74 (brs, 1H), 8.60 (s, 1H), 7.91 (d, J=8.4 Hz, 1H), 7.80 (m, 1H), 7.67 (s, 1H), 7.16 (d, J=12.0 Hz, 1H), 6.44 (s, 1H), 4.35 (m, 2H), 2.89 (brd, J=4.4 Hz, 3H), 2.06 (s, 3H), 1.25 (s, 9H), 1.19 (m, 3H); MS (ESI) m/z: 494.2 (M+H$^+$).

EXAMPLE 150

Using general method B, the carbamate of 3-isopropyl-1-phenyl-1H-pyrazol-5-amine (0.061 g, 0.21 mmol), and Example A50 (0.07 g, 0.21 mmol) were combined to afford 1-(5-(8-ethyl-2-(methylamino)-7-oxo-7,8-dihydropyrido[2,3-d]pyrimidin-6-yl)-2-fluoro-4-methylphenyl)-3-(3-isopropyl-1-phenyl-1H-pyrazol-5-yl)urea as an off-white solid (53 mg, 45%, yield). $^1$H NMR (400 MHz, DMSO-$d_6$): δ 8.90 (s, 1H), 8.82 (s, 1H), 8.67-8.60 (m, 1H), 7.91 (d, J=8.4 Hz, 1H), 7.81-7.79 (m, 1H), 7.64 (s, 1H), 7.54-7.47 (m, 4H), 7.43-7.38 (m, 1H), 7.11 (d, J=12.4 Hz, 1H), 6.30 (s, 1H), 4.36-4.32 (m, 2H), 2.89-2.80 (m, 4H), 2.04 (s, 3H), 1.23-1.17 (m, 9H); MS (ESI) m/z: 555.2 (M+H$^+$).

EXAMPLE 151

Using general method D, Example B30 (0.051 g, 0.3 mmol) and Example A50 (0.1 g, 0.3 mmol) were combined in presence of triethylamine (0.092 g, 0.91 mmol) and diphenylphospharyl azide (0.13 g, 0.45 mmol) to afford 1-(1-tert-butyl-1H-pyrazol-4-yl)-3-(5-(8-ethyl-2-(methylamino)-7-oxo-7,8-dihydropyrido[2,3-d]pyrimidin-6-yl)-2-fluoro-4-methylphenyl)urea (65 mg, 44% yield). $^1$H NMR (400 MHz, DMSO-$d_6$): δ 8.63 (s, 1H), 8.60 (s, 1H), 8.40 (d, J=2.0 Hz, 1H), 7.94 (d, J=8.8 Hz, 1H), 7.80-7.77 (m, 2H), 7.65 (s, 1H), 7.36 (s, 1H), 7.10 (d, J=12.0 Hz, 1H), 4.36-4.32 (m, 2H), 2.89 (d, J=4.4 Hz, 1H), 2.04 (s, 3H), 1.45 (s, 9H), 1.24-1.20 (m, 3H); MS (ESI) m/z: 493.2 (M+H$^+$).

EXAMPLE 152

Using general method A, the TROC carbamate of Example B18 (0.3 g, 0.95 mmol) and Example A17 (0.3 g, 0.86 mmol) were combined to provide 1-(3-tert-butylisoxazol-5-yl)-3-(4-chloro-2-fluoro-5-(8-methyl-2-(methylthio)-7-oxo-7,8-dihydropyrido[2,3-d]pyrimidin-6-yl)phenyl)urea (175 mg, 40% yield). $^1$H NMR (400 MHz, DMSO-$d_6$): δ10.38 (brs, 1H), 8.92 (s, 1H)), 8.90 (m, 1H), 8.17 (d, J=8.5 Hz, 1H), 8.00

(s, 1H), 7.63 (d, J=12 Hz, 1H), 6.03 (s, 1H), 3.54 (s, 3H), 2.50 (s, 3H), 2.61 (s, 3H), 1.21 (s, 9H); MS (ESI) m/z: 517.0 (M+H$^+$).

Using a procedure analogous to Example A1, 1-(3-tert-butylisoxazol-5-yl)-3-(4-chloro-2-fluoro-5-(8-methyl-2-(methylthio)-7-oxo-7,8-dihydropyrido[2,3-d]pyrimidin-6-yl)phenyl)urea and methylamine were combined to provide 1-(3-tert-butylisoxazol-5-yl)-3-(4-chloro-2-fluoro-5-(8-methyl-2-(methylamino)-7-oxo-7,8-dihydropyrido[2,3-d]pyrimidin-6-yl)phenyl)urea (88 mg, 50% yield). $^1$H NMR (400 MHz, DMSO-d$_6$): δ10.5 (brs, 1H), 9.00 (brs, 1H), 8.61 (s, 1H), 8.11 (d, J=9 Hz, 1H), 7.88 (brs, 1H), 7.76 (s, 1H), 7.57 (d, J=12 Hz, 1H), 6.00 (s, 1H), 3.58 (s, 3H), 2.89 (d, J=5 Hz, 3H), 1.21 (s, 9H); MS (ESI) m/z: 500.3 (M+H$^+$).

EXAMPLE 153

Using general method A, the TROC carbamate of Example B18 (0.3 g, 0.95 mmol) and Example A41 (0.3 g, 0.67 mmol) were combined in presence of N-methylpyrrolidine (0.080 g, 0.95 mmol), to provide 1-(3-tert-butylisoxazol-5-yl)-3-(5-(8-ethyl-2-(methylthio)-7-oxo-7,8-dihydropyrido[2,3-d]pyrimidin-6-yl)-2-fluoro-4-methylphenyl)urea (320 mg, 72% yield) $^1$H NMR (400 MHz, DMSO-d$_6$) δ10.3 (brs, 1H), 8.91 (s, 1H)), 8.71 (brs, 1H), 7.94 (d, J=9 Hz, 1H), 7.89 (s, 1H), 7.20 (d, J=12 Hz, 1H), 6.00 (s, 1H), 3.64 (s, 3H), 4.38 (q, J=6 Hz, 2H), 2.61 (s, 3H), 2.07 (s, 3H), 1.24 (t, J=6 Hz, 3H), 1.21 (s, 9H); MS (ESI) m/z: 511.2 (M+H$^+$).

Using a procedure analogous to Example A1, 1-(3-tert-butylisoxazol-5-yl)-3-(5-(8-ethyl-2-(methylthio)-7-oxo-7,8-dihydropyrido[2,3-d]pyrimidin-6-yl)-2-fluoro-4-methylphenyl)urea (0.16 g, 0.315 mmol) and methylamine were combined to provide 1-(3-tert-butylisoxazol-5-yl)-3-(5-(8-ethyl-2-(methylamino)-7-oxo-7,8-dihydropyrido[2,3-d]pyrimidin-6-yl)-2-fluoro-4-methylphenyl)urea (62 mg, 20% yield). $^1$H NMR (400 MHz, DMSO-d$_6$): δ 10.3 (brs, 1H), 8.67 (brs, 1H), 8.61 (brs, 1H), 7.88 (d, J=9 Hz, 1H), 7.80 (brs, 1H), 7.66 (s, 1H), 7.16 (d, J=12 Hz, 1H), 6.00 (s, 1H), 5.73 (s, 1H), 4.34 (br, 2H), 2.89 (d, J=6 Hz, 3H), 2.07 (s, 3H), 1.21 (br, 12H); MS (ESI) m/z: 494.2 (M+H$^+$).

EXAMPLE 154

Using general procedure C, the TROC carbamate of Example B20 (0.150 g, 0.497 mmol, 1.00 eq) and Example A10 (0.164 g, 0.497 mmol, 1.00 eq) were combined to afford 1-(2-fluoro-4-methyl-5-(8-methyl-2-(methylthio)-7-oxo-7,8-dihydropyrido[2,3-d]pyrimidin-6-yl)phenyl)-3-(3-isopropylisoxazol-5-yl)urea (0.203 g, 85% yield) as a pale yellow solid. $^1$H NMR (400 MHz, DMSO-d$_6$): δ 10.30 (s, 1H), 8.90 (s, 1H), 8.72 (brs, 1H), 7.93 (d, J=8.4 Hz, 1H), 7.89 (s, 1H), 7.21 (d, J=12.4 Hz, 1H), 5.96 (s, 1H), 3.64 (s, 3H), 2.87 (septet, J=7.2 Hz, 1H), 2.61 (s, 3H), 2.09 (s, 3H), 1.16 (d, J=6.8 Hz, 6H); MS (ESI) m/z: 483.0 (M+H$^+$).

Using a procedure analogous to Example A1, 1-(2-fluoro-4-methyl-5-(8-methyl-2-(methylthio)-7-oxo-7,8-dihydropyrido[2,3-d]pyrimidin-6-yl)phenyl)-3-(3-isopropylisoxazol-5-yl)urea (0.203 g, 0.421 mmol, 1.00 eq) and 2.00M MeNH$_2$/THF (2.10 ml, 4.21 mmol, 10.00 eq,) were combined to afford 1-(2-fluoro-4-methyl-5-(8-methyl-2-(methylamino)-7-oxo-7,8-dihydropyrido[2,3-d]pyrimidin-6-yl)phenyl)-3-(3-isopropylisoxazol-5-yl)urea (41 mg, 21% yield) as a pale yellow powder. $^1$H NMR (400 MHz, DMSO-d$_6$) δ 10.28 (s, 1H), 8.67 (brs, 1H), 8.60 (brs, 1H), 7.88 (d, J=8.0 Hz, 1H), 7.81 (brq, J=4.0 Hz, 1H), 7.67 9s, 1H), 7.17 (d, J=12.8 Hz, 1H), 5.96 (s, 1H), 3.59 (s, 3H), 2.90 (d, J=4.8 Hz, 3H), 2.89 (septet, J=7.2 Hz, 1H), 2.08 (s, 3H), 1.16 (d, J=7.2 Hz, 6H); MS (ESI) m/z: 466.0 (M+H$^+$).

EXAMPLE 155

Using general method B, the carbamate of 5-t-butylisoxazol-3-amine (0.07 g, 0.31 mmol) and Example A16 (0.10 g, 0.31 mmol were combined to afford 1-(5-tert-butylisoxazol-3-yl)-3-(2,4-difluoro-5-(8-methyl-2-(methylthio)-7-oxo-7,8-dihydropyrido[2,3-d]pyrimidin-6-yl)phenyl)urea (80 mg, 50% yield). MS (ESI) m/z: 501.0 (M+H$^+$).

Using a procedure analogous to Example A1, 1-(5-tert-butylisoxazol-3-yl)-3-(2,4-difluoro-5-(8-methyl-2-(methylthio)-7-oxo-7,8-dihydropyrido[2,3-d]pyrimidin-6-yl)phenyl)urea (0.080 g, 0.16 mmol) was treated with mCPBA (70% wt, 0.047 g, 0.19 mmol) and then N-methylamine (2.0M in THF, 0.32 mL, 0.64 mmol) to afford 1-(5-tert-butylisoxazol-3-yl)-3-(2,4-difluoro-5-(8-methyl-2-(methylamino)-7-oxo-7,8-dihydropyrido[2,3-d]pyrimidin-6-yl)phenyl)urea (58 mg, 75% yield). $^1$H NMR (400 MHz, DMSO-d$_6$, major rotomer): δ 9.81 (s, 1H), 8.78 (brs, 1H), 8.63 (s, 1H), 8.13 (t, J=8.4 Hz, 1H), 7.89 (m, 1H), 7.84 (s, 1H), 7.40 (dd, J= 10.0, and 11.2 Hz, 1H), 6.45 (s, 1H), 3.59 (s, 3H), 2.99 (brd, J=4.8 Hz, 3H), 1.28 (s, 9H); MS (ESI) m/z: 484.2 (M+H$^+$).

EXAMPLE 156

Using general method D, 3-tert-butyl-1-methyl-1H-pyrazole-5-carboxylic acid (0.061 g, 0.33 mmol) and Example A50 (0.1 g, 0.33 mmol) were combined in presence of triethylamine (0.1 g, 1 mmol) and diphenylphosphoryl azide (0.14 g, 0.5 mmol) to afford 1-(3-tert-butyl-1-methyl-1H-pyrazol-5-yl)-3-(5-(8-ethyl-2-(methylamino)-7-oxo-7,8-dihydropyrido[2,3-d]pyrimidin-6-yl)-2-fluoro-4-methylphenyl)urea as a white solid (140 mg, 83% yield). $^1$H NMR (400 MHz, DMSO-d$_6$): δ 8.86 (s, 1H), 8.73 (s, 1H), 8.59 (s, 1H), 7.93 (d, J= 8.4 Hz, 1H), 7.81-7.79 (m, 1H), 7.65 (s, 1H), 7.14 (d, J=12.4 Hz, 1H), 6.04 (s, 1H), 4.35-4.32 (m, 2H), 3.58 (s, 3H), 2.89 (d, J=4.4 Hz, 1H), 2.05 (s, 3H), 1.23-1.16 (m, 12H); MS (ESI) m/z: 507.2 (M+H$^+$).

EXAMPLE 157

Using general method D, 3-tert-butyl-1-methyl-1H-pyrazole-5-carboxylic acid (0.21 g, 1.2 mmol), Example A17 (0.4 g, 1.2 mmol) were combined in presence of triethylamine (0.35 g, 3.5 mmol) and diphenylphosphoryl azide (0.48 g, 1.7 mmol) to afford 1-(3-tert-butyl-1-methyl-1H-pyrazol-5-yl)-3-(4-chloro-2-fluoro-5-(8-methyl-2-(methylthio)-7-oxo-7,8-dihydropyrido[2,3-d]pyrimidin-6-yl)phenyl)urea as a white solid (0.49 g, 80% yield). $^1$H NMR (400 MHz, DMSO-d$_6$): δ 8.97 (brs, 2H), 8.92 (s, 1H), 8.22 (d, J=8.4 Hz, 1H), 7.98 (s, 1H), 7.60 (d, J=11.2 Hz, 1H), 6.04 (s, 1H), 3.64 (s, 3H), 3.58 (s, 3H), 2.61 (s, 3H), 1.16 (s, 9H); MS (ESI) m/z: 530.2 (M+H$^+$).

Using a procedure analogous to example A1, 1-(3-tert-butyl-1-methyl-1H-pyrazol-5-yl)-3-(4-chloro-2-fluoro-5-(8-methyl-2-(methylthio)-7-oxo-7,8-dihydropyrido[2,3-d]pyrimidin-6-yl)phenyl)urea (0.2, 0.38 mmol) and 2 M methylamine in THF (3 eq) were combined and purified via C-18 chromatography to provide 1-(3-tert-butyl-1-methyl-1H-pyrazol-5-yl)-3(4-chloro-2-fluoro-5-(8-methyl-2-(methylamino)-7-oxo-7,8-dihydropyrido[2,3-d]pyrimidin-6-yl) phenyl)urea as a white solid (0.045 g, 23% yield). $^1$H NMR (400 MHz, DMSO-d$_6$): δ 8.95 (brs, 2H), 8.61 (s, 1H), 8.17 (d, J=8.8 Hz, 1H), 7.87 (brs, 1H), 7.75 (s, 1H), 7.55 (d, J=10.8

EXAMPLE 158

Using general procedure B, the carbamate of 3-isopropyl-1-phenyl-1H-pyrazol-5-amine (0.075 g, 0.26 mmol, 1.0 eq) and Example A26 (0.082 g, 0.26 mmol, 1.0 eq) were combined to afford slightly impure desired product. This was slurried in MeCN/H$_2$O, cooled thoroughly at 0-5° C. and the solids collected by filtration, rising with cold H$_2$O. The solids were dried under high vacuum. The free base thus obtained was dissolved in a minimum volume of hot THF (70° C.) and treated with 2% MsOH/THF (0.82 g, 0.17 mmol, 1.00 eq) to afford 1-(2-fluoro-4-methyl-5-(1-methyl-7-(methylamino)-2-oxo-1,2-dihydro-1,6-naphthyridin-3-yl)phenyl)-3-(3-isopropyl-1-phenyl-1H-pyrazol-5-yl)urea mesylate (92 mg; 56% yield) as an off-white solid. $^1$H NMR (400 MHz, DMSO-d$_6$): δ 8.95 (brs, 1H), 8.85 (s, 1H), 8.49 (s, 1H), 7.96 (d, J=8.4 Hz, 1H), 7.78 (s, 1H), 7.56-7.48 (m, 4H), 7.44-7.40 (m, 1H), 7.15 (d, J=12.4 Hz, 1H), 6.45 (brs, 1H), 6.31 (s, 1H), 3.54 (s, 3H), 2.95 (s, 3H), 2.85 (septet, J=6.8 Hz, 1H), 2.29 (s, 3H), 2.07 (s, 3H), 1.19 (d, J=7.6 Hz, 6H); MS (ESI) m/z: 540.3 (M+H$^+$).

EXAMPLE 159

Using general procedure D, 3-(t-butyl)1-methyl-1H-pyrazole-5-carboxylic acid (0.125 g, 0.686 mmol, 1.00 eq) and Example A30 (0.210 g, 0.672 mmol, 1.10 eq) were combined to afford desired product which was subsequently treated with 2% MsOH/THF (0.67 g, 0.14 mmol, 1.00 eq) to afford 1-(3-tert-butyl-1-methyl-1H-pyrazol-5-yl)-3-(5-(1-ethyl-7-(methylamino)-2-oxo-1,2-dihydro-1,6-naphthyridin-3-yl)-2-fluoro-4-methylphenyl)urea mesylate (70 mg, 17% yield) as a white solid. $^1$H NMR (400 MHz, DMSO-d$_6$): δ 8.92 (s, 1H), 8.79 (brs, 1H), 8.50 (s, 1H), 7.97 (d, J=8.4 Hz, 1H), 7.78 (s, 1H), 7.18 (d, J=12.0 Hz, 1H), 6.53 (brs, 1H), 6.05 (s, 1H), 4.17 (q, J=7.2 Hz, 2H), 3.59 (s, 3H), 2.95 (s, 3H), 2.29 (s, 3H), 2.07 (s, 3H), 1.21 (t, J=7.2 Hz, 3H), 1.16 (s, 9H); MS (ESI) m/z: 506.2 (M+H$^+$).

EXAMPLE 160

Using general method A, the TROC carbamate of Example B18 (0.66 g, 1.9 mmol) and Example A42 (0.68 g, 2.09 mmol) were combined to provide 1-(3-tert-butylisoxazol-5-yl)-3-(2-fluoro-5-(8-isopropyl-2-(methylthio)-7-oxo-7,8-dihydropyrido[2,3-d]pyrimidin-6-yl)-4-methylphenyl)urea (440 mg, 44%)*H NMR (400 MHz, DMSO-d$_6$) δ 10.3 (s, 1H), 8.88 (s, 1H)), 8.70 (brs, 1H), 7.94 (d, J=9 Hz, 1H), 7.85 (s, 1H), 7.20 (d, J=12 Hz, 1H), 6.00 (s, 1H), 5.75 (m, 1H), 2.61 (s, 3H), 2.07 (s, 3H), 1.55 (d, J=6 Hz, 6H), 1.21 (s, 9H); MS (ESI) m/z: 525.3 (M+H$^+$).

In a procedure analogous to Example A1, 1-(3-tert-butylisoxazol-5-yl)-3-(2-fluoro-5-(8-isopropyl-2-(methylthio)-7-oxo-7,8-dihydropyrido[2,3-d]pyrimidin-6-yl)-4-methylphenyl)urea (0.1 g, 0.2 mmol) and methylamine were combined to provide 1-(3-tert-butylisoxazol-5-yl)-3-(2-fluoro-5-(8-isopropyl-2-(methylamino)-7-oxo-7,8-dihydropyrido[2,3-d]pyrimidin-6-yl)-4-methylphenyl)urea (45 mg, 50% yield). $^1$H NMR (400 MHz, DMSO-d$_6$): δ 8.78 (brs, 1H), 8.57 (brs, 1H), 7.85 (d, J=9 Hz, 1H), 7.75 (brs, 1H), 7.62 (s, 1H), 7.15 (d, J=12 Hz, 1H), 6.00 (s, 1H), 5.74 (m, 1H), 2.89 (d, J=5 Hz, 3H), 2.07 (s, 3H), 1.56 (d, J=6 Hz, 6H), 1.21 (s, 9H); MS (ESI) m/z: 508.3 (M+H$^+$).

EXAMPLE 161

Using general method D, 1-tert-butyl-1H-pyrazole-4-carboxylic acid (150 mg, 0.892 mmol) and Example A16 (298 mg, 0.892 mmol) were combined to afford 1-(1-tert-butyl-1H-pyrazol-4-yl)-3-(2,4-difluoro-5-(8-methyl-2-(methylthio)-7-oxo-7,8-dihydropyrido[2,3-d]pyrimidin-6-yl)phenyl)urea (80 mg, 95% yield).

Using a procedure analogous to Example A1, 1-(1-tert-butyl-1H-pyrazol-4-yl)-3-(2,4-difluoro-5-(8-methyl-2-(methylthio)-7-oxo-7,8-dihydropyrido[2,3-d]pyrimidin-6-yl) phenyl)urea (80 mg, 0.160 mmol) and 2.00N methylamine in THF (0.9 mL, 1.80 mmol) were combined to afford 1-(1-tert-butyl-1H-pyrazol-4-yl)-3-(2,4-difluoro-5-(8-methyl-2-(methylamino)-7-oxo-7,8-dihydropyrido[2,3-d]pyrimidin-6-yl) phenyl)urea (31 mg, 36% yield). $^1$H NMR (300 MHz, DMSO-d$_6$) δ 1.53 (s, 9H), 2.90 (s, 3H), 3.52-3.59 (m, 3H), 7.31-7.38 (m, 2H), 7.78-7.90 (m, 3H), 8.12-8.16 (m, 1H), 8.48 (s, 1H), 8.63-8.70 (m, 1H), 8.65 (s, 1H); MS (ESI) m/z: 483.3 (M+H$^+$).

EXAMPLE 162

Using a procedure analogous to Example 141, ethyl 1-tert-butyl-5-methyl-1H-pyrazole-4-carboxylate (500 mg, 2.38 mmol), Example A3 (260 mg, 0.823 mmol) and 2.0N methylamine in THF (2.0 mL, 3.96 mmol) were combined to afford 1-(1-tert-butyl-5-methyl-1H-pyrazol-4-yl)-3-(2-fluoro-5-(8-methyl-2-(methylamino)-7-oxo-7,8-dihydropyrido[2,3-d] pyrimidin-6-yl)phenyl)urea (106 mg). $^1$H NMR (300 MHz, DMSO-d$_6$) δ 1.50 (s, 9H), 2.30 (s, 3H), 2.90 (s, 3H), 3.53-3.60 (m, 3H), 7.20-7.24 (m, 2H), 7.44 (s, 1H), 7.60-7.81 (m, 1H), 7.84 (s, 1H), 8.16 (s, 1H), 8.39-8.41 (m, 1H), 8.54-8.72 (m, 1H), 8.63 (s, 1H); MS (ESI) m/z: 479.2 (M+H$^+$).

EXAMPLE 163

Using general method A, the TROC carbamate of 3-isopropyl-1-phenyl-1H-pyrazol-5-amine (0.25 g, 0.66 mmol) and Example A10 (0.22 g, 0.66 mmol) were combined to afford 1-(2-fluoro-4-methyl-5-(8-methyl-2-(methylthio)-7-oxo-7,8-dihydropyrido[2,3-d]pyrimidin-6-yl)phenyl)-3-(3-isopropyl-1-phenyl-1H-pyrazol-5-yl)urea as an off-white solid (0.24 g, 65% yield). $^1$H NMR (400 MHz, DMSO-d$_6$): δ 8.96 (s, 1H), 8.90 (s, 1H), 8.87 (s, 1H), 7.97 (d, J=8.4 Hz, 1H), 7.87 (s, 1H), 7.55-7.48 (m, 4H), 7.43-7.39 (m, 1H), 7.16 (d, J=12.4 Hz, 1H), 6.30 (s, 1H), 3.65 (s, 3H), 2.87-2.80 (m, 1H), 2.61 (s, 3H), 2.06 (s, 3H), 1.18 (d, J=7.2 Hz, 6H); MS (ESI) m/z: 558.3 (M+H$^+$).

Using a procedure analogous to Example A1, 1-(2-fluoro-4-methyl-5-(8-methyl-2-(methylthio)-7-oxo-7,8-dihydropyrido[2,3-d]pyrimidin-6-yl)phenyl)-3-(3-isopropyl-1-phenyl-1H-pyrazol-5-yl)urea (0.24, 0.43 mmol) and 2 M methylamine in THF (3 eq) were combined to provide 1-(2-fluoro-4-methyl-5-(8-methyl-2-(methylamino)-7-oxo-7,8-dihydropyrido[2,3-d]pyrimidin-6-yl)phenyl)-3-(3-isopropyl-1-phenyl-1H-pyrazol-5-yl)urea as a white solid (0.12 g, 52% yield). $^1$H NMR (400 MHz, DMSO-d$_6$): δ 8.90 (s, 1H), 8.82 (s, 1H), 8.68-8.60 (m, 1H), 7.92 (d, J=8.8 Hz, 1H), 7.82-7.79 (m, 1H), 7.66 (s, 1H), 7.55-7.47 (m, 4H), 7.43-7.39 (m, 1H), 7.12 (d, J=12.4 Hz, 1H), 6.30 (s, 1H), 3.59-3.52 (m, 3H), 2.91-2.80 (m, 4H), 2.05 (s, 3H), 1.18 (d, J=7.2 Hz, 6H); MS (ESI) m/z: 541.3 (M+H$^+$).

EXAMPLE 164

Using general procedure D, 5-isopropylisoxazole-3-carboxylic acid (0.0750 g, 0.483 mmol, 1.00 eq) and Example A10 (0.192 g, 0.580 mmol, 1.20 eq) were combined to afford 1-(2-fluoro-4-methyl-5-(8-methyl-2-(methylthio)-7-oxo-7,8-dihydropyrido[2,3-d]pyrimidin-6-yl)phenyl)-3-(5-isopropylisoxazol-3-yl)urea (63.5 mg, 27% yield) as an off-white solid which was used as is in the next reaction. $^1$H NMR (400 MHz, DMSO-$d_6$): δ 9.79 (s, 1H), 8.91 (s, 1H), 8.79 (brs, 1H), 7.97 (d, J=8.4 Hz, 1H), 7.90 (s, 1H), 7.20 (d, J=12.4 Hz, 1H), 6.44 (s, 1H), 3.65 (s, 3H), 2.99 (septet, J=7.2 Hz, 1H), 2.62 (s, 3H), 2.08 (s, 3H), 1.20 (d, J=6.8 Hz, 6H); MS (ESI) m/z: 483.3 (M+H$^+$).

Following a procedure analogous to Example A1, 1-(2-fluoro-4-methyl-5-(8-methyl-2-(methylthio)-7-oxo-7,8-dihydropyrido[2,3-d]pyrimidin-6-yl)phenyl)-3-(5-isopropylisoxazol-3-yl)urea (0.0635 g, 0.13 mmol) and 2.0M MeNH$_2$/THF (0.66 ml, 1.3 mmol) were combined to afford 1-(2-fluoro-4-methyl-5-(8-methyl-2-(methylamino)-7-oxo-7,8-dihydropyrido[2,3-d]pyrimidin-6-yl)phenyl)-3-(5-isopropylisoxazol-3-yl)urea (38 mg, 62% yield) as a pale yellow solid. $^1$H NMR (400 MHz, DMSO-$d_6$): δ 9.77 (s, 1H), 8.75 (brs, 1H), 8.60 (s, 1H), 7.92 (d, J=8.4 Hz, 1H), 7.80 (brq, J=4.4 Hz, 1H), 7.68 (s, 1H), 7.36 (d, J=12.4 Hz, 1H), 6.45 (s, 1H), 3.60 (s, 3H), 2.99 (septet, J=6.8 Hz, 1H), 2.90 (brd, J=4.4 Hz, 3H), 2.07 (s, 3H), 1.20 (d, J=6.8 Hz, 6H); MS (ESI) m/z: 466.2 (M+H$^+$).

EXAMPLE 165

Using general procedure D, 5-isopropylisoxazole-3-carboxylic acid (0.0750 g, 0.483 mmol, 1.00 eq) and Example A17 (0.203 g, 0.580 mmol, 1.20 eq) were combined to afford 1-(4-chloro-2-fluoro-5-(8-methyl-2-(methylthio)-7-oxo-7,8-dihydropyrido[2,3-d]pyrimidin-6-yl)phenyl)-3-(5-isopropylisoxazol-3-yl)urea (0.113 g, 47% yield) as an off-white solid. $^1$H NMR (400 MHz, DMSO-$d_6$): δ 9.87 (s, 1H), 8.97 (brs, 1H), 8.93 (s, 1H), 8.20 (d, J=8.8 Hz, 1H), 8.00 (s, 1H), 7.63 (d, J=10.8 Hz, 1H), 6.54 (s, 1H), 3.65 (s, 3H), 3.00 (septet, J=6.8 Hz, 1H), 2.62 (s, 3H), 1.20 (d, J=7.2 Hz, 6H); MS (ESI) m/z: 503.0 (M+H$^+$), 505.0 (M+2+H$^+$).

Using a procedure analogous to Example A1, 1-(4-chloro-2-fluoro-5-(8-methyl-2-(methylthio)-7-oxo-7,8-dihydropyrido[2,3-d]pyrimidin-6-yl)phenyl)-3-(5-isopropylisoxazol-3-yl)urea (0.113 g, 0.225 mmol) and 2.0M MeNH$_2$/THF (1.12 ml, 2.25 mmol) were combined to afford 1-(4-chloro-2-fluoro-5-(8-methyl-2-(methylamino)-7-oxo-7,8-dihydropyrido[2,3-d]pyrimidin-6-yl)phenyl)-3-(5-isopropylisoxazol-3-yl)urea (52 mg, 48% yield) as a faintly yellow solid. $^1$H NMR (400 MHz, DMSO-$d_6$): δ 9.85 (s, 1H), 8.94 (brs, 1H), 8.62 (s, 1H), 8.15 (d, J=8.8 Hz, 1H), 7.88 (brq, J=4.8 Hz, 1H), 7.77 (s, 1H), 7.58 (d, J=10.8 Hz, 1H), 6.46 (s, 1H), 3.59 (s, 3H), 3.00 (septet, J=6.8 Hz, 1H), 2.91 (d, J=4.8 Hz, 3H), 1.20 (d, J=6.8 Hz, 6H); MS (ESI) m/z: 486.2 (M+H$^+$), 488.3 (M+2+H$^+$).

EXAMPLE 166

Using general method A, the TROC carbamate of Example B18 (0.066 g, 0.21 mmol) and Example A43 (0.076 g, 0.20 mmol) were combined to afford 1-(3-tert-butylisoxazol-5-yl)-3-(5-(2-(3-(dimethylamino)propylamino)-8-methyl-7-oxo-7,8-dihydropyrido[2,3-d]pyrimidin-6-yl)-2-fluoro-4-methylphenyl)urea (0.022 g, 20% yield) as an off white solid. $^1$H NMR (400 MHz, DMSO-$d_6$): δ 10.3 (s, 1H), 9.21 (m, 1H), 8.68-8.64 (m, 2H), 7.98 (m, 1H), 7.90 (d, J=8.4 Hz, 1H), 7.70 (s, 1H), 7.18 (d, J=12.4 Hz, 1H), 6.00 (s, 1H), 3.63-3.51 (m, 3H), 3.44 (q, J=6.8 Hz, 2H), 3.14-2.98 (m, 2H), 2.77 (s, 6H), 2.28 (s, 3H), 2.08 (s, 3H), 1.99-1.86 (m, 2H), 1.21 (s, 9H); MS (ESI) m/z: 551.2 (M+H$^+$).

EXAMPLE 167

Example A11 (0.125 g, 0.394 mmol, 1.00 eq) and aniline (0.108 ml, 1.18 mmol, 3.00 eq) were combined in NMP (4 ml) and heated in a microwave for 7 h at 220° C. The roughly half-complete reaction was diluted with H$_2$O (40 ml) and extracted with EtOAc (3×20 ml). The combined organics were washed with H$_2$O (2×), brine (1×), dried (MgSO$_4$), concentrated in vacuo and purified by flash column chromatography (50:50 EtOAc/hexanes-100% EtOAc) to afford 3-(5-amino-4-fluoro-2-methylphenyl)-1-methyl-7-(phenylamino)-1,6-naphthyridin-2(1H)-one (51 mg, 17% yield) as an off-white solid. $^1$H NMR (400 MHz, DMSO-$d_6$): δ 9.40 (s, 1H), 8.52, s, 1H), 7.70-7.64 (m, 3H), 7.31-7.27 (m, 2H), 6.95-6.93 (m, 1H), 6.86 (d, J=12.0 Hz, 1H), 6.68 (s, 1H), 6.59 (d, J=9.2 Hz, 1H), 4.91 (brs, 2H), 3.52 (s, 3H), 1.96 (s, 3H); MS (ESI) m/z: 375.2 (M+H$^+$).

Using general procedure A, the TROC carbamate of Example B18 (0.0431 g, 0.136 mmol) and 3-(5-amino-4-fluoro-2-methylphenyl)-4-methyl-7-(phenylamino)-1,6-naphthyridin-2(1H)-one (0.0511 g, 0.136 mmol) were combined to afford desired product. The free base thus obtained was converted to the mesylate salt, 1-(3-tert-butylisoxazol-5-yl)-3-(2-fluoro-4-methyl-5-(1-methyl-2-oxo-7-(phenylamino)-1,2-dihydro-1,6-naphthyridin-3-yl)phenyl)urea mesylate (19 mg, 21% yield) as an off-white solid. $^1$H NMR (400 MHz, DMSO-$d_6$): δ 10.30 (s, 1H), 9.55 (s, 1H), 8.69 (brs, 1H), 8.56 (s, 1H), 7.92 (d, J=8.4 Hz, 1H), 7.79 (s, 1H), 7.63 (dd, J= 1.2 and 8.4 Hz, 2H), 7.34-7.29 (m, 2H), 7.19 (d, J=12.4 Hz, 1H), 6.98 9dd, J=7.2 and 13.6 Hz, 1H), 6.71 (s, 1H), 6.01 (s, 1H), 3.54 (s, 3H), 2.30 (s, 3H), 2.10 (s, 3H), 1.21 (s, 9H); MS (EST) m/z: 541.3 (M+H$^+$).

EXAMPLE 168

Example A11 (0.250 g, 0.787 mmol, 1.00 eq), phenylboronic acid (0.115 g, 0.944 mmol, 1.20 eq) and 2M K$_2$CO$_3$ (1.06 ml, 2.12 mmol, 2.70 eq) were combined in DME (0.90 ml) and degassed with Ar. Pd(PPh$_3$)$_4$ (0.0455 g, 0.0393 mmol, 0.05 eq) was then added and the mixture was stirred with heating at 90° C. After 16 h, the completed reaction cooled to RT, diluted generously with EtOAc and filtered on Celite, rinsing forward with more EtOAc. The combined filtrates were washed with brine (2×), dried (MgSO$_4$), filtered and evaporated to a dark orange solid. This was triturated with cold EtOAc. The solid product was collected by filtration, rinsed sparingly with ice-cold EtOAc and dried on the filter to afford desired product (0.112 g, 40% yield) as a gold-colored solid which was used as is in the next reaction. $^1$H NMR (400 MHz, DMSO-$d_6$): δ 8.96 (s, 1H), 8.26-8.23 (m, 2H), 7.93-7.91 (m, 2H), 7.55-7.45 (m, 3H), 6.89 (d, J=12.4 Hz, 1H), 6.63 (d, J=9.6 Hz, 1H), 4.96 (brs, 2H), 3.75 (s, 3H), 1.98 (s, 3H); MS (ESI) m/z: 360.0 (M+H$^+$).

Using general procedure A, the TROC carbamate of Example B18 (0.100 g, 0.317 mmol, 1.00 eq) and 3-(5-amino-4-fluoro-2-methylphenyl)-1-methyl-7-phenyl-1,6-naphthyridin-2(1H)-one (0.114 g, 0.317 mmol, 1.00 eq) were combined to afford desired product. The free base thus obtained was converted to the mesylate salt, 1-(3-tert-butylisoxazol-5-yl)-3-(2-fluoro-4-methyl-5-(1-methyl-2-oxo-7-phenyl-1,2-dihydro-1,6-naphthyridin-3-yl)phenyl)urea mesylate (53 mg, 27% yield) as a white solid. $^1$H NMR (400 MHz, DMSO-$d_6$): δ 10.32 (s, 1H), 9.04 (s, 1H), 8.72 (brs, 1H), 8.26-8.23 (m, 2H), 8.03-7.96 (m, 3H), 7.58-7.49 (m, 3H), 7.23 (d, J=12.0 Hz, 1H), 6.01 (s, 1H), 3.78 (s, 3H), 2.29 (s, 3H), 2.12 (s, 3H), 1.21 (s, 9H); MS (ESI) m/z: 526.2 (M+H$^+$).

EXAMPLE 169

Using general method D, 3-tert-butyl-1-methyl-1H-pyrazole-5-carboxylic acid (0.051 g, 0.28 mmol) and Example A51 (0.096 g, 0.28 mmol) were combined in presence of triethylamine (0.085 g, 0.84 mmol) and diphenylphospharyl azide (0.12 g, 0.42 mmol) to afford 1-(3-tert-butyl-1-methyl-1H-pyrazol-5-yl)-3-(2-fluoro-5-(8-isopropyl-2-(methylamino)-7-oxo-7,8-dihydropyrido[2,3-d]pyrimidin-6-yl)-4-methylphenyl)urea as white solid (0.095 g, 65% yield). $^1$H NMR (400 MHz, DMSO-d$_6$): δ 8.87 (s, 1H), 8.73 (s, 1H), 8.57 (s, 1H), 7.92 (d, J=8.4 Hz, 1H), 7.76-7.73 (m, 1H), 7.60 (s, 1H), 7.14 (d, J=12.4 Hz, 1H), 6.04 (s, 1H), 5.74 (brs, 1H), 3.58 (s, 3H), 2.88 (d, J=4.4 Hz, 3H), 2.05 (s, 3H), 1.57-1.49 (m, 6H), 1.16 (s, 9H); MS (ESI) m/z: 521.3 (M+H$^+$).

EXAMPLE 170

Using general method D, Example B30 (0.041 g, 0.24 mmol) and Example A51 (0.083 g, 0.24 mmol) were combined in presence of tri ethyl amine (0.074 g, 0.73 mmol) and diphenylphospharyl azide (0.1 g, 0.37 mmol) to afford 1-(1-tert-butyl-1H-pyrazol-4-yl)-3-(2-fluoro-5-(8-isopropyl-2-(methylamino)-7-oxo-7,8-dihydropyrido[2,3-d]pyrimidin-6-yl)-4-methylphenyl)urea as a white solid (0.055 g, 45% yield). $^1$H NMR (400 MHz, DMSO-d$_6$): δ 8.59 (s, 1H), 8.52 (s, 1H), 8.36 (s, 1H), 7.88 (d, J=8.0 Hz, 1H), 7.73 (s, 1H), 7.71-7.68 (m, 1H), 7.55 (s, 1H), 7.34 (s, 1H), 7.05 (d, J=12.4 Hz, 1H), 5.69-5.66 (m, 1H), 2.84 (d, J=4.4 Hz, 3H), 1.99 (s, 3H), 1.52-1.51 (m, 6H), 1.40 (s, 9H); MS (ESI) m/z: 507.2 (M+H$^+$).

EXAMPLE 171

Using general procedure B, the carbamate of Example B21 (0.100 g, 0.321 mmol, 1.00 eq) and Example A44 (0.100 g, 0.321 mmol, 1.00 eq) were combined to afford 1-(4-methyl-3-(8-methyl-2-(methylthio)-7-oxo-7,8-dihydropyrido[2,3-d]pyrimidin-6-yl)phenyl)-3-(1-phenyl-3-(trifluoromethyl)-1H-pyrazol-5-yl)urea (0.1231 g, 68% yield) as a pale yellow solid which was used as is in the next reaction. $^1$H NMR (400 MHz, DMSO-d$_6$): δ 9.12 (s, 1H), 8.91 (s, 1H), 8.72 (s, 1H), 7.89 (s, 1H), 7.65-7.55 (m, 5H), 7.38 (brs, 1H), 7.25 (brd, J=8.8 Hz, 1H), 7.18 (d, J=8.4 Hz, 1H), 6.86 (s, 1H), 3.67 (s, 3H), 2.63 (s, 3H), 2.08 (s, 3H); MS (ESI) m/z: 566.2 (M+H$^+$).

Using a procedure analogous to example A1, 1-(4-methyl-3-(8-methyl-2-(methylthio)-7-oxo-7,8-dihydropyrido[2,3-d]pyrimidin-6-yl)phenyl)-3-(1-phenyl-3-(trifluoromethyl)-1H-pyrazol-5-yl)urea (0.1231 g, 0.218 mmol) and 2.0M MeNH$_2$/THF (1.088 ml, 2.177 mmol) were combined to afford 1-(4-methyl-3-(8-methyl-2-(methylamino)-7-oxo-7,8-dihydropyrido[2,3-d]pyrimidin-6-yl)phenyl)-3-(1-phenyl-3-(trifluoromethyl)-1H-pyrazol-5-yl)urea (93 mg, 78% yield) as a white solid. $^1$H NMR (400 MHz, DMSO-d$_6$): δ 9.08 (s, 1H), 8.69 (s, 1H), 8.59 (s, 1H), 7.81 (brq, J=4.4 Hz, 1H), 7.66 (s, 1H), 7.63-7.52 (m, 5H), 7.30 (d, J=2.0 Hz, 1H) 7.21 (dd, J=2.0 and 8.4 Hz, 1H), 7.13 (d, J=8.4 Hz, 1H), 6.85 (s, 1H), 3.59 (s, 3H), 2.90 (brd, J=4.8 Hz, 3H), 2.05 (s, 3H); MS (ESI) m/z: 549.3 (M+H$^+$).

EXAMPLE 172

Using general method C, the TROC carbamate of Example B18 (150 mg, 0.475 mmol) and Example A27 (142 mg, 0.475 mmol) were combined to provide 1-(5-(7-amino-1-methyl-2-oxo-1,2-dihydro-1,6-naphthyridin-3-yl)-2-fluoro-4-methylphenyl)-3-(3-tert-butylisoxazol-5-yl)urea (105 mg, 48% yield). $^1$H NMR (400 MHz, DMSO-d$_6$): δ 10.31 (s, 1H), 8.67 (s, 1H), 8.33 (s, 1H), 7.88 (d, J=8.5 Hz, 1H), 7.66 (s, 1H), 7.16 (d, J=12.3 Hz, 1H), 6.54 (s, 2H), 6.26 (s, 1H), 6.01 (s, 1H), 3.47 (s, 3H), 2.08 (s, 3H), 1.21 (s, 9H); MS (ESI) m/z: 465.2 (M+H$^+$).

EXAMPLE 173

Using general method D, Example B30 (150 mg, 0.892 mmol), triethylamine (104 mg, 1.03 mmol) and Example A17 (313 mg, 0.892 mmol) were combined to afford 1-(1-tert-butyl-1H-pyrazol-4-yl)-3-(4-chloro-2-fluoro-5-(8-methyl-2-(methylthio)-7-oxo-7,8-dihydropyrido[2,3-d]pyrimidin-6-yl)phenyl)urea (143 mg, 31% yield). Using a procedure analogous to Example A1, 1-(1-tert-butyl-1H-pyrazol-4-yl)-3-(4-chloro-2-fluoro-5-(8-methyl-2-(methylthio)-7-oxo-7,8-dihydropyrido[2,3-d]pyrimidin-6-yl)phenyl)urea (143 mg, 0.277 mmol) and 2.0N were combined and purified by reverse phase chromatography (Biotage C18-25 column, 0-100% acetonitrile/water—750 mL), treated with 10% potassium carbonate solution (2 mL) and set aside to precipitate. The solid was collected by filtration, washed with water (2×5 mL) and dried on high vacuum line to give 1-(1-tert-butyl-1H-pyrazol-4-yl)-3-(4-chloro-2-fluoro-5-(8-methyl-2-(methylamino)-7-oxo-7,8-dihydropyrido[2,3-d]pyrimidin-6-yl) phenyl)urea (59 mg, 42% yield). $^1$H NMR (300 MHz, DMSO-d$_6$): δ 1.45 (s, 9H), 2.90 (s, 3H), 3.51-3.59 (m, 3H), 7.38 (s, 1H), 7.52 (d, J=10.9 Hz, 1H), 7.75 (s, 1H), 7.78 (s, 1H), 7.86 (br s, 1H), 8.20 (d, J=8.9 Hz, 1H), 8.62-8.69 (m, 2H), 8.70-8.72 (m, 1H); MS (ESI) m/z: 499.2 (M+H$^+$).

EXAMPLE 174

Using general method D, Example B30 (0.041 g, 0.24 mmol) and Example A26 (0.076 g, 0.24 mmol) in presence of triethylamine (0.074 g, 0.75 mmol) and diphenylphospharyl azide (0.1 g, 0.37 mmol) were combined to afford 1-(1-tert-butyl-1H-pyrazol-4-yl)-3-(2-fluoro-4-methyl-5-(1-methyl-7-(methylamino)-2-oxo-1,2-dihydro-1,6-naphthyridin-3-yl) phenyl)urea as a white solid (0.055 g, 47% yield). $^1$H NMR (400 MHz, DMSO-d$_6$): δ 8.63 (s, 1H), 8.38 (s, 2H), 7.94 (d, J=8.8 Hz, 1H), 7.78 (s, 1H), 7.65 (s, 1H), 7.36 (s, 1H), 7.10 (d, J=12.4 Hz, 1H), 7.04-7.00 (m, 1H), 6.17 (s, 1H), 3.50 (s, 3H), 2.85 (d, J=4.8 Hz, 3H), 2.05 (s, 3H), 1.45 (s, 9H); MS (ESI) m/z: 478.3 (M+H$^+$).

EXAMPLE 175

Using general method D, Example B30 (0.027 g, 0.161 mmol) and Example A53 (0.0925 g, 0.24 mmol) were combined to afford 1-(1-tert-butyl-1H-pyrazol-4-yl)-3-(5-(7-(3-(dimethylamino)propylamino)-1-methyl-2-oxo-1,2-dihydro-1,6-naphthyridin-3-yl)-2-fluoro-4-methylphenyl)urea (0.029 g, 33% yield). It was converted to corresponding bis-mesylate salt by reacting with MsOH (2.0 eq.). $^1$H NMR (400 MHz, DMSO-d$_6$): δ 8.49 (s, 1H), 8.00 (d, J=8.4 Hz, 1H), 7.76 (s, 2H), 7.38 (s, 1H), 7.33 (t, 0.7=8.4 Hz, 1H), 7.17-7.10 (m, 1H), 6.46 (s, 1H), 3.53 (s, 3H), 3.43 (m, 2H), 3.18-3.09 (m, 2H), 2.79 (s, 6H), 2.35 (s, 6H), 2.06 (s, 3H), 1.96-1.89 (m, 2H), 1.45 (s, 9H); MS (ESI) m/z: 549.3 (M+H$^+$).

EXAMPLE 176

Using general method C, the TROC carbamate of Example B18 (0.66 g, 1.9 mmol) and Example A42 (0.68 g, 2.09 mmol)

were combined to provide 1-(3-tert-butylisoxazol-5-yl)-3-(2-fluoro-5-(8-isopropyl-2-(methylthio)-7-oxo-7,8-dihydropyrido[2,3-d]pyrimidin-6-yl)-4-methylphenyl)urea (0.44 g, 44% yield). $^1$H NMR (400 MHz, DMSO-d$_6$): δ10.3 (s, 1H), 8.88(s, 1H), 8.70 (brs, 1H), 7.94 (d, J=9 Hz, 1H), 7.85 (s, 1H), 7.20 (d, J=12 Hz, 1H), 6.00 (s, 1H), 5.75 (m, 1H), 2.61 (s, 3H), 2.07 (s, 3H), 1.55 (d, J=6 Hz, 6H), 1.21 (s, 9H); MS (ESI) m/z: 525.3 (M+H$^+$).

Using a procedure analogous to Example A1, oxidation of the intermediate sulfide with MCPBA, followed by reaction with excess (S)-alaninol provided (S)-1-(3-tert-butylisoxazol-5-yl)-3-(2-fluoro-5-(2-(1-hydroxypropan-2-ylamino)-8-isopropyl-7-oxo-7,8-dihydropyrido[2,3-d]pyrimidin-6-yl)-4-methylphenyl)urea (33% yield). $^1$H NMR (400 MHz, DMSO-d$_6$): δ8.75(s, 1H), 8.58 (s, 1H), 7.86 (d, J=9 Hz, 1H), 7.61 (s, 1H), 7.55 (m, 1H), 7.15 (d, J=12 Hz, 1H), 6.00 (s, 1H), 5.71 (brs, 1H), 4.75 (brs, 1H), 4.03 (m, 1H), 3.50 (m, 1H), 3.35 (m, 1H), 2.07 (s, 3H), 1.55 (d, J=6 Hz, 6H), 1.21 (s, 9H), 1.16 (d, J=6 Hz, 3H); MS (ESI) m/z: 525.3 (M+H$^+$).

EXAMPLE 177

Using general method B, the carbamate of Example B2 (120 mg, 0.506 mmol) and Example A28 (168 mg, 0.506 mmol) were combined to afford 1-(3-tert-butyl-1-methyl-1H-pyrazol-5-yl)-3-(4-chloro-2-fluoro-5-(1-methyl-7-(methylamino)-2-oxo-1,2-dihydro-1,6-naphthyridin-3-yl)phenyl)urea (128 mg, 49% yield). $^1$H NMR (300 MHz, DMSO-d$_6$): δ 1.16 (s, 9H), 2.85 (s, 3H), 3.49 (s, 3H), 3.56 (s, 3H), 6.05 (s, 1H), 6.16 (s, 1H), 7.09-7.11 (m, 1H), 7.53-7.56 (m, 1H), 7.72 (s, 1H), 8.15-8.17 (m, 1H), 8.39 (s, 1H), 8.93-8.94 (m, 2H); MS (ESI) m/z: 512.3 (M+H$^+$).

EXAMPLE 178

Using general method C, the TROC carbamate of Example B18 (0.080 g, 0.25 mmol) and Example A28 (85 mg, 0.25 mmol) were combined to afford 1-(3-tert-butylisoxazol-5-yl)-3-(4-chloro-2-fluoro-5-(1-methyl-7-(methylamino)-2-oxo-1,2-dihydro-1,6-naphthyridin-3-yl)phenyl)urea (0.050 g, 40% yield). $^1$H NMR (400 MHz, DMSO-d$_6$): δ 10.4 (s, 1H), 8.86 (brs, 1H), 8.40 (s, 1H), 8.12 (d, J=8.4 Hz, 1H), 7.75 (s, 1H), 7.58 (d, J=10.4 Hz, 1H), 7.11 (q, J=4.8 Hz, 1H), 6.17 (s, 1H), 6.03 (s, 1H), 3.50 (s, 3H), 2.86 (d, J=4.8 Hz, 3H), 1.21 (s, 3H); MS (ESI) m/z: 499.2 (M+H$^+$).

EXAMPLE 179

Using general method B, the carbamate of 5-t-butylisoxazol-3-amine (70 mg, 0.31 mmol) and Example A29 (99 mg, 0.31 mmol) were combined to afford 1-(5-tert-butylisoxazol-3-yl)-3-(4-chloro-5-(1-ethyl-7-(methylamino)-2-oxo-1,2-dihydro-1,6-naphthyridin-3-yl)-2-fluorophenyl)urea (0.15 g, 100% yield). $^1$H NMR (400 MHz, DMSO-d$_6$): δ 9.91 (brs, 1H), 8.89 (brs, 1H), 8.42 (s, 1H), 8.11 (m, 1H), 7.83 (s, 1H), 7.38 (dd, J=9.6, and 10.8 Hz, 1H), 7.13 (q, J=4.8 Hz, 1H), 6.46 (s, 1H), 6.17 (brs, 1H), 3.50 (s, 3H), 2.85 (d, 7-4.8 Hz, 3H), 1.26 (s, 9H); MS (ESI) m/z: 483.3 (M+H$^+$).

EXAMPLE 180

Using general method D, 1-methyl-1H-pyrazole-5-carboxylic acid (150 mg, 1.19 mmol) and Example A3 (376 mg, 1.19 mmol) were converted to the intermediate 1-(2-fluoro-5-(8-methyl-2-(methylthio)-7-oxo-7,8-dihydropyrido[2,3-d]pyrimidin-6-yl)phenyl)-3-(1-methyl-1H-pyrazol-5-yl)urea (487 mg, 93% yield). This was then further converted using a procedure analogous to Example A1 with 2.0N methylamine in THF (5.5 mL, 11.1 mmol) to afford 1-(2-fluoro-5-(8-methyl-2-(methylamino)-7-oxo-7,8-dihydropyrido[2,3-d]pyrimidin-6-yl)phenyl)-3-(1-methyl-1H-pyrazol-5-yl)urea (48 mg, 9% yield). $^1$H NMR (300 MHz, DMSO-d$_6$): δ 2.93 (s, 3H), 3.59 (m, 3H), 3.74 (s, 3H), 6.27 (s, 1H), 7.27-7.30 (m, 2H), 7.41 (s, 1H), 7.92 (s, 1H), 8.20 (br s, 1H), 8.36-8.38 (m, 1H), 8.75 (s, 1H), 9.20 (s, 1H), 9.73 (s, 1H); MS (ESI) m/z: 423.3 (M+H$^+$).

EXAMPLE 181

Using general method D, Example B32 (150 mg, 0.585 mmol) and Example A57 (165 mg, 0.585 mmol) were combined and purified by chromatography (Biotage Si-25 column, 50-100% ethyl acetate) to give 1-(2-tert-butyl-4-phenylpyrimidin-5-yl)-3-(3-(8-methyl-2-(methylamino)-7-oxo-7,8-dihydropyrido[2,3-d]pyrimidin-6-yl)phenyl)urea as an off white foam (81 mg, 25% yield). $^1$H NMR (300 MHz, DMSO-d$_6$): δ 1.37 (s, 9H), 2.90 (s, 3H), 3.52-3.59 (m, 3H), 7.21-7.31 (m, 2H), 7.43-7.57 (m, 4H), 7.70-7.88 (m, 5H), 8.11 (s, 1H), 8.62-8.70 (m, 1H), 9.07 (s, 1H), 9.19 (s, 1H); MS (ESI) m/z: 535.2 (M+H$^+$).

EXAMPLE 182

Using general method G, Example B32 (150 mg, 0.585 mmol) and Example A10 (193 mg, 0.585 mmol) were combined to give the intermediate sulfide (224 mg, 65% yield). Using a procedure analogous to Example A1, The sulfide and 2.0N methylamine in THF (1.917 ml, 3.83 mmol) were combined to afford 1-(2-tert-butyl-4-phenylpyrimidin-5-yl)-3-(2-fluoro-4-methyl-5-(8-methyl-2-(methylthio)-7-oxo-7,8-dihydropyrido[2,3-d]pyrimidin-6-yl)phenyl)urea (150 mg, 69% yield). $^1$H NMR (300 MHz, DMSO-d$_6$): δ 1.35 (s, 9H), 2.05 (s, 3H), 2.90 (s, 3H), 3.52-3.59 (m, 3H), 7.11 (d, J=12.4 Hz, 1H), 7.51-7.91 (m, 8H), 8.54 (s, 1H), 8.59-8.64 (m, 1H), 8.93 (s, 1H), 9.02 (s, 1H); MS (ESI) m/z: 567.3 (M+H$^+$).

EXAMPLE 183

Using general method D, Example B32 (61 mg, 0.237 mmol) and Example A26 (74 mg, 0.237 mmol) were combined to afford 1-(2-tert-butyl-4-phenylpyrimidin-5-yl)-3-(2-fluoro-4-methyl-5-(1-methyl-7-(methylamino)-2-oxo-1,2-dihydro-1,6-naphthyridin-3-yl)phenyl)urea (69 mg, 51% yield). $^1$H NMR (300 MHz, DMSO-d$_6$); δ 1.35 (s, 9H), 2.05 (s, 3H), 2.84 (s, 3H), 3.49 (s, 3H), 6.16 (s, 1H), 7.03-7.04 (m, 1H), 7.09-7.12 (m, 1H), 7.51-7.57 (m, 3H), 7.64 (s, 1H), 7.71-7.74 (m, 2H), 7.89 (d, J=8.5 Hz, 1H), 8.38 (s, 1H), 8.53 (s, 1H), 8.92 (s, 1H), 9.02 (s, 1H); MS (ESI) m/z: 566.2 (M+Na$^+$).

EXAMPLE 184

Using general method F, Example A39 (0.100 g, 0.319 mmol) was reacted with 1-isocyanatonaphthalene (0.054 g, 0.319 mmol) in ethyl acetae at room temperature for 14 hours to provide 1-(2-fluoro-4-methyl-5-(8-methyl-2-(methylamino)-7-oxo-7,8-dihydropyrido[2,3-d]pyrimidin-6-yl)phenyl)-3-(naphthalen-1-yl)urea (0.052 g, 33% yield). $^1$H NMR (400 MHz, DMSO-d$_6$): □ 9.12 (s, 1H), 9.00 (brs, 1H), 8.60 (s, 1H), 8.15 (d, J=8 Hz, 1H), 8.03 (d, J=9 Hz, 1H), 8.00 (d, J=8 Hz, 1H), 7.91 (d, J=9 Hz, 1H), 7.80 (m, 1H), 7.69 (s, 1H), 7.63-7.4 (m, 4H), 7.16 (d, J=12 Hz, 1H), 5.75 (s, 1H), 3.60 (brs, 3H), 2.90 (d, J=5 Hz, 3H), 2.08 (s, 3H); MS (ESI) m/z: 483.3 (M+H$^+$).

EXAMPLE 185

Using a procedure analogous to Example 186, (R)-1-(3-tert-butylisoxazol-5-yl)-3-(2-fluoro-5-(2-(1-hydroxy-3-methylbutan-2-ylamino)-8-methyl-7-oxo-7,8-dihydropyrido[2,3-d]pyrimidin-6-yl)-4-methylphenyl)urea was prepared from the carbamate of B18, Example A10 and R(−)-2-amino-3-methyl-1-butanol. $^1$H NMR (400 MHz, DMSO-d$_6$): δ8.67 (s, 1H), 8.61 (m, 1H), 7.88 (d, J=9 Hz, 1H), 7.64 (m, 1H), 7.57 (d, J=9 Hz, 1H), 7.16 (d, J=12 Hz, 1H), 6.10 (s, 1H), 4.59 (m, 1H), 3.97 (m, 1H), 3.56 (s, 3H), 3.52 (m, 2H), 2.08 (s, 3H), 1.98 (m, 1H), 1.22 (s, 9H), 0.91 (m. 6H); MS (ESI) m/z: 552.2 (M+H$^+$).

EXAMPLE 186

Using general method C, the TROC carbamate of Example B18 (0.5 g, 1.58 mmol) and Example A10 (0.52 g, 1.58 mmol) were combined to provide 1-(3-tert-butylisoxazol-5-yl)-3-(2-fluoro-4-methyl-5-(8-methyl-2-(methylthio)-7-oxo-7,8-dihydropyrido[2,3-d]pyrimidin-6-yl)phenyl)urea (0.44 g, 56% yield). $^1$H NMR (400 MHz, DMSO-d$_6$): δ10.3(brs, 1H), 8.9 (s, 1H), 8.70 (brs, 1H), 7.94 (d, J=9 Hz, 1H), 7.88 (s, 1H), 7.20 (d, J=12 Hz, 1H), 6.00 (s, 1H), 3.64 (s, 3H), 2.61 (s, 3H), 2.07 (s, 3H), 1.21 (s, 9H); LC-MS (ES, m/z, M+H) 497.2.

Using a procedure analogius to Example A1, the sulfide was oxidatized with MCPBA and subjected to excess S(+)-2-amino-3-methyl-1-butanol to provide (S)-1-(3-tert-butylisoxazol-5-yl)-3-(2-fluoro-5-(2-(1-hydroxy-3-methylbutan-2-ylamino)-8-methyl-7-oxo-7,8-dihydropyrido[2,3-d]pyrimidin-6-yl)-4-methylphenyl)urea (47% yield). $^1$H NMR (400 MHz, DMSO-d$_6$): δ 8.67 (s, 1H), 8.61 (m, 1H), 7.88 (d, J=9 Hz, 1H), 7.64 (m, 1H), 7.57 (d, J=9 Hz, 1H), 7.16 (d, J=12 Hz, 1H), 6.10 (s, 1H), 4.59 (m, 1H), 3.97 (m, 1H), 3.56 (s, 3H), 3.52 (m, 2H), 2.08 (s, 3H), 1.98 (m, 1H), 1.22 (s, 9H), 0.91 (m. 6H); MS (ESI) m/z: 552.2 (M+H$^+$).

EXAMPLE 187

Using general method C, the TROC carbamate of Example B18 (0.091 g, 0.29 mmol) and Example A33 (0.1 g, 0.29 mmol) were combined to afford 1-(3-tert-butylisoxazol-5-yl)-3-(4-chloro-5-(1-ethyl-7-(methylamino)-2-oxo-1,2-dihydro-1,6-naphthyridin-3-yl)-2-fluorophenyl)urea as a white solid (0.051 g, 35% yield). $^1$H NMR (400 MHz, DMSO-d$_6$): δ 8.56 (s, 1H), 8.41 (s, 1H), 8.11 (d, J=8.8 Hz, 1H), 7.74 (s, 1H), 7.57 (d, J=10.8 Hz, 1H), 7.07-7.04 (m, 1H), 6.23 (s, 1H), 6.02 (s, 1H), 4.13 (q, J=7.2 Hz, 1H), 2.86 (d, J=4.8 Hz, 3H), 1.21-1.17 (m, 12H); MS (ESI) m/z: 513.3 (M+H$^+$).

EXAMPLE 188

Using general method C, the TROC carbamate of Example B18 (0.091 g, 0.29 mmol) and Example A31 (0.09 g, 0.28 mmol) were combined to afford 1-(5-(7-amino-1-ethyl-2-oxo-1,2-dihydro-1,6-naphthyridin-3-yl)-2-fluoro-4-methylphenyl)-3-(3-tert-butylisoxazol-5-yl)urea as a white solid (0.12 g, 87% yield). $^1$H NMR (400 MHz, DMSO-d$_6$): δ 10.3 (s, 1H), 8.66 (s, 1H), 8.34 (s, 1H), 7.87 (d, J=8.4 Hz, 1H), 7.65 (s, 1H), 7.16 (d, J=12.0 Hz, 1H), 6.49 (s, 1H), 6.33 (s, 1H), 6.01 (s, 1H), 4.09 (q, J=7.2 Hz, 1H), 2.07 (s, 3H), 1.21-1.18 (m, 12H); MS (ESI) m/z: 479.2 (M+H$^+$).

EXAMPLE 189

Using general method B, the caramate of 5-t-butylisoxazol-3-amine (70 mg, 0.31 mmol) and Example A47 (108 mg, 0.31 mmol) were combined to afford 1-(5-tert-butylisoxazol-3-yl)-3-(4-ethyl-2-fluoro-5-(8-methyl-2-(methylthio)-7-oxo-7,8-dihydropyrido[2,3-d]pyrimidin-6-yl)phenyl)urea (0.085 g, 53% yield). MS (ESI) m/z: 511.2 (M+H$^+$).

Using a procedure analogous to Example A1, 1-(5-tert-butylisoxazol-3-yl)-3-(4-ethyl-2-fluoro-5-(8-methyl-2-(methylthio)-7-oxo-7,8-dihydropyrido[2,3-d]pyrimidin-6-yl)phenyl)urea (0.085 g, 0.17 mmol) was treated with mCPBA (70% wt, 0.049 g, 0.20 mmol) and then N-methylamine (2.0M in THF, 0.34 mL, 0.67 mmol) to afford 1-(5-tert-butylisoxazol-3-yl)-3-(4-ethyl-2-fluoro-5-(8-methyl-2-(methylamino)-7-oxo-7,8-dihydropyrido[2,3-d]pyrimidin-6-yl)phenyl)urea (72 mg, 88% yield). $^1$H NMR (400 MHz, DMSO-d$_6$, major rotomer): δ 9.79 (s, 1H), 8.76 (brs, 1H), 8.60 (s, 1H), 7.88 (d, J=8.4 Hz, 1H), 7.81 (q, J=4.4 Hz, 1H), 7.67 (s, 1H), 7.18 (d, 12.4 Hz, 1H), 6.43 (s, 1H), 3.59 (s, 3H), 2.91 (d, J=4.4 Hz, 3H), 2.38 (q, J=7.6 Hz, 2H), 1.25 (s, 9H), 1.02 (t, J=7.6 Hz, 3H); MS (ESI) m/z: 494.0 (M+H$^+$).

EXAMPLE 190

Using general method C, the TROC carbamate of Example B18 (212 mg, 0.672 mmol) and Example A44 (150 mg, 0.480 mmol) were combined and purified by reverse phase chromatography (Biotage Si-25 column, 25-85% ethyl acetate/Hex) to give the intermediate sulfide 1-(3-tert-butylisoxazol-5-yl)-3-(4-methyl-3-(8-methyl-2-(methylthio)-7-oxo-7,8-dihydropyrido[2,3-d]pyrimidin-6-yl)phenyl)urea (68 mg, 29% yield).

Using a procedure analogous to Example A1, 1-(3-tert-butylisoxazol-5-yl)-3-(4-methyl-3-(8-methyl-2-(methylthio)-7-oxo-7,8-dihydropyrido[2,3-d]pyrimidin-6-yl)phenyl)urea (56 mg, 0.117 mmol) and 2.0N methylamine in THF (0.71 mL, 1.421 mmol) were combined to afford 1-(3-tert-butylisoxazol-5-yl)-3-(4-methyl-3-(8-methyl-2-(methylamino)-7-oxo-7,8-dihydropyrido[2,3-d]pyrimidin-6-yl)phenyl)urea (29 mg, 44% yield). $^1$H NMR (300 MHz, DMSO-d$_6$), δ 1.46 (s, 9H), 2.04 (s, 3H), 2.89 (s, 3H), 3.52-3.60 (m, 3H), 5.74 (s, 1H), 7.08-7.10 (m, 1H), 7.22-7.25 (m, 1H), 7.33-7.36 (m, 2H), 7.65 (s, 1H), 7.78 (s, 1H), 7.68-7.82 (m, 1H), 8.25 (s, 1H), 8.53 (s, 1H), 8.60-8.65 (m, 1H); MS (ESI) m/z: 462.3 (M+H$^+$).

EXAMPLE 191

Using general method D, Example B30 (150 mg, 0.585 mmol) and Example A44 (165 mg, 0.585 mmol) were combined to give the intermediate sulfide, 1-(1-tert-butyl-1H-pyrazol-4-yl)-3-(4-methyl-3-(8-methyl-2-(methylthio)-7-oxo-7,8-dihydropyrido[2,3-d]pyrimidin-6-yl)phenyl)urea (56 mg, 24% yield). Using a procedure analogous to Example A1, the sulfide (56 mg, 0.117 mmol) was combined with 2.0N methylamine in THF (0.59 mL, 1.173 mmol) to afford the desired product, 1-(1-tert-butyl-1H-pyrazol-4-yl)-3-(4-methyl-3-(8-methyl-2-(methylamino)-7-oxo-7,8-dihydropyrido[2,3-d]pyrimidin-6-yl)phenyl)urea (43 mg, 80% yield). $^1$H NMR (300 MHz, DMSO-d$_6$), δ 1.22 (s, 9H), 2.06 (s, 3H), 2.90 (s, 3H), 3.53-3.60 (m, 3H), 6.01 (s, 1H), 7.14-7.16 (d, 1H), 7.27-7.29 (d, 1H), 7.34 (s, 1H), 7.67 (s, 1H), 7.68-7.81 (m, 1H), 8.60-8.65 (m, 1H), 8.74 (s, 1H), 10.06 (s, 1H); MS (ESI) m/z: 461.2 (M+H$^+$).

EXAMPLE 192

Using general method F, 1-isocyanato-3-methylbenzene (42 mg, 0.32 mmol) and Example A39 (100 mg, 0.32 mmol) in presence of pyridine (52 µL, 0.64 mmol) were combined to afford 1-(2-fluoro-4-methyl-5-(8-methyl-2-(methylamino)-7-oxo-7,8-dihydropyrido[2,3-d]pyrimidin-6-yl)phenyl)-3-m-tolylurea (91 mg, 64% yield). $^1$H NMR (400 MHz, DMSO-d$_6$, major rotamer): δ 8.94 (s, 1H), 8.61 (s, 1H), 8.47 (d, J=2.0 Hz, 1H), 7.96 (d, J=8.8 Hz, 1H), 7.81 (q, J=4.8 Hz, 1H), 7.68 (s, 1H), 7.28 (brs, 1H), 7.14 (m, 2H), 6.77 (d, J=7.2 Hz, 1H), 3.60 (s, 3H), 2.91 (d, 7-4.8 Hz, 3H), 2.24 (s, 3H), 2.06 (s, 3H); MS (ESI) m/z: 447.0 (M+H$^+$).

EXAMPLE 193

Using general method F, 1-chloro-3-isocyanatobenzene (49 mg, 0.32 mmol) and Example A39 (100 mg, 0.32 mmol) in presence of pyridine (52 μL, 0.64 mmol) were combined to afford 1-(3-chlorophenyl)-3-(2-fluoro-4-methyl-5-(8-methyl-2-(methylamino)-7-oxo-7,8-dihydropyrido[2,3-d]pyrimidin-6-yl)phenyl)urea (123 mg, 83% yield). $^1$H NMR (400 MHz, DMSO-d$_6$, major rotamer): δ 9.20 (s, 1H), 8.61 (s, 1H), 8.55 (d, J=1.6 Hz, 1H), 7.91 (d, J=8.4 Hz, 1H), 7.81 (q, J=4.4 Hz, 1H), 7.71 (t, J=2.0 Hz, 1H), 7.68 (s, 1H), 7.28 (t, J=8.0 Hz, 1H), 7.17 (m, 2H), 7.00 (m, 1H), 3.60 (s, 3H), 2.91 (d, J=4.4 Hz, 3H), 2.07 (s, 3H); MS (ESI) m/z: 467.0 (M+H$^+$).

EXAMPLE 194

Using general method F, 1-bromo-3-isocyanatobenzene (63 mg, 0.32 mmol) and Example A39 (100 mg, 0.32 mmol) in presence of pyridine (52 μL, 0.64 mmol) were combined to afford 1-(3-bromophenyl)-3-(2-fluoro-4-methyl-5-(8-methyl-2-(methylamino)-7-oxo-7,8-dihydropyrido[2,3-d]pyrimidin-6-yl)phenyl)urea (115 mg, 71% yield). $^1$H NMR (400 MHz, DMSO-d$_6$, major rotamer): δ 9.19 (s, 1H), 8.61 (s, 1H), 8.55 (d, J=2.0 Hz, 1H), 7.91 (d, J=8.8 Hz, 1H), 7.86 (m, 1H), 7.81 (q, J=4.4 Hz, 1H), 7.68 (s, 1H), 7.1-7.3 (m, 4H), 3.60 (s, 3H), 2.91 (d, J=4.4 Hz, 3H), 2.07 (s, 3H); MS (ESI) m/z: 511.0 (M+H$^+$).

EXAMPLE 195

Using general method F, 1-fluoro-3-isocyanatobenzene (44 mg, 0.32 mmol) and Example A39 (100 mg, 0.32 mmol) in the presence of pyridine (52 mL, 0.64 mmol) were combined to afford 1-(3-fluorophenyl)-3-(2-fluoro-4-methyl-5-(8-methyl-2-(methylamino)-7-oxo-7,8-dihydropyrido[2,3-d]pyrimidin-6-yl)phenyl)urea (92 mg, 64% yield). $^1$H NMR (400 MHz, DMSO-d$_6$, major rotamer): δ 9.23 (s, 1H), 8.61 (s, 1H), 8.55 (d, J=2.0 Hz, 1H), 7.91 (d, J=8.4 Hz, 1H), 7.81 (q, J=4.4 Hz, 1H), 7.68 (s, 1H), 7.46 (dt, J=2.0, and 11.6 Hz, 1H), 7.28 (m, 1H), 7.15 (d, J=12.4 Hz, 1H), 7.04 (m, 1H), 6.77 (dt, J=2.4, and 8.4 Hz, 1H), 3.60 (s, 3H), 2.91 (d, J= 4.4 Hz, 3H), 2.07 (s, 3H); MS (ESI) m/z: 451.0 (M+H$^+$).

EXAMPLE 196

Using general method F, 1-chloro-3-isocyanato-2-methylbenzene (43 mg, 0.26 mmol) and Example A39 (80 mg, 0.32 mmol) in the presence of pyridine (41 μL, 0.51 mmol) were combined to afford 1-(3-chloro-2-methylphenyl)-3-(2-fluoro-4-methyl-5(8-methyl-2-(methylamino)-7-oxo-7,8-dihydropyrido[2,3-d]pyrimidin-6-yl)phenyl)urea (98 mg, 80% yield). $^1$H NMR (400 MHz, DMSO-d$_6$, major rotamer): δ 8.95 (d, J=1.6 Hz, 1H), 8.60 (s, 1H), 8.48 (s, 1H), 7.96 (d, J=8.8 Hz, 1H), 7.81 (q, J=4.4 Hz, 1H), 7.74 (m, 1H), 7.67 (s, 1H), 7.12 (m, 3H), 3.59 (s, 3H), 2.90 (d, J=4.4 Hz, 3H), 2.28 (s, 3H), 2.07 (s, 3H); MS (ESI) m/z: 481.0 (M+H$^+$).

EXAMPLE 197

Using general method F, 1,2-dichloro-3-isocyanatobenzene (48 mg, 0.26 mmol) and Example A39 (80 mg, 0.32 mmol) in the presence of pyridine (41 μL, 0.51 mmol) were combined to afford 1-(2,3-dichlorophenyl)-3-(2-fluoro-4-methyl-5-(8-methyl-2-(methylamino)-7-oxo-7,8-dihydropyrido[2,3-d]pyrimidin-6-yl)phenyl)urea (100 mg, 78% yield). $^1$H NMR (400 MHz, DMSO-d$_6$, major rotamer): δ 9.39 (brs, 1H), 8.89 (s, 1H), 8.60 (s, 1H), 8.10 (dd, J=3.2, and 6.8 Hz, 1H), 7.94 (d, J=8.4 Hz, 1H), 7.81 (q, J=4.4 Hz, 1H), 7.68 (s, 1H), 7.27 (m, 2H), 7.16 (d, J=12.0 Hz, 1H), 3.60 (s, 3H), 2.90 (d, J=4.4 Hz, 3H), 2.07 (s, 3H); MS (ESI) m/z: 501.0 (M+H$^+$).

EXAMPLE 198

Using general method F, 1-chloro-2-isocyanato-4-(trifluoromethyl)benzene (49 mg, 0.22 mmol) and Example A39 (70 mg, 0.22 mmol) in the presence of pyridine (36 μL, 0.48 mmol) were combined to afford 1-(2-chloro-5-(trifluoromethyl)phenyl)-3-(2-fluoro-4-methyl-5-(8-methyl-2-(methylamino)-7-oxo-7,8-dihydropyrido[2,3-d]pyrimidin-6-yl)phenyl)urea (100 mg, 84% yield). $^1$H NMR (400 MHz, DMSO-d$_6$, major rotamer): δ 9.49 (brs, 1H), 9.04 (s, 1H), 8.61 (brs, 1H), 8.57 (d, J=2.0 Hz, 1H), 7.96 (d, J=8.4 Hz, 1H), 7.81(q, J=4.8 Hz, 1H), 7.70 (m, 2H), 7.35 (dd, J=1.6, and 8.4 Hz, 1H), 7.17 (d, J=12.4 Hz, 1H), 3.60 (s, 3H), 2.90 (d, J=4.8 Hz, 3H), 2.08 (s, 3H); MS (ESI) m/z: 535.0 (M+H$^+$).

EXAMPLE 199

Using general method B, the carbamate of 5-t-butylisoxazol-3-amine (0.075 g, 0.334 mmol) and Example A28 (0.111 g, 0.334 mmol) were combined to afford 1-(5-tert-butylisoxazol-3-yl)-3-(4-chloro-2-fluoro-5-(1-methyl-7-(methylamino)-2-oxo-1,2-dihydro-1,6-naphthyridin-3-yl)phenyl)urea (0.042 g, 25%) as a white solid. $^1$H NMR (400 MHz, DMSO-d$_6$): δ 9.86 (s, 1H), 8.91 (s, 1H), 8.40 (s, 1H), 8.15 (d, J=8.4 Hz, 1H), 7.75 (s, 1H), 7.57 (d, J=10.8 Hz, 1H), 7.11 (m, 1H), 6.45 (s, 1H), 3.50 (s, 3H), 2.86 (d, J=5.2 Hz, 3H), 1.25 (s, 9H); MS (ESI) m/z: 499.0 (M+H$^+$).

EXAMPLE 200

Using general method D, 2-methyl-5-(trifluoromentyl)benzoic acid (50 mg, 0.25 mmol) and Example A39 (92 mg, 0.29 mmol) in presence of DPPA (58 μL, 0.27 mmol) and Et$_3$N (38 μL, 0.27 mmol) were combined to afford 1-(2-fluoro-4-methyl-5-(8-methyl-2-(methylamino)-7-oxo-7,8-dihydropyrido[2,3-d]pyrimidin-6-yl)phenyl)-3-(2-methyl-5-(trifluoromethyl)phenyl)urea (83 mg, 66% yield). $^1$H NMR (400 MHz, DMSO-d$_6$, major rotamer): δ 9.15 (d, J=1.6 Hz, 1H), 8.61 (brs, 1H), 8.54 (s, 1H), 8.35 (d, J=1.6 Hz, 1H), 7.99 (d, J=8.4 Hz, 1H), 7.81 (q, J=4.4 Hz, 1H), 7.68 (s, 1H), 7.38 (d, J=8.4 Hz, 1H), 7.24 (m, 1H), 7.16 (d, J=12.4 Hz, 1H), 3.60 (s, 3H), 2.90 (d, J=4.4 Hz, 3H), 2.32 (s, 3H), 2.07 (s, 3H); MS (ESI) m/z: 515.0 (M+H$^+$).

EXAMPLE 201

Using general method F, 3-(trifluoromethyl)phenylisocyanate. (45 mg, 0.24 mmol) and Example A28 (80 mg, 0.24 mmol) in the presence of pyridine (39 μL, 0.48 mmol) were combined to afford 1-(4-chloro-2-fluoro-5-(1-methyl-7-(methylamino)-2-oxo-1,2-dihydro-1,6-naphthyridin-3-yl)phenyl)-3-(3-(trifluoromethyl)phenyl)urea (55 mg, 44% yield). $^1$H NMR (400 MHz, DMSO-d$_6$): δ 9.53 (brs, 1H), 8.85 (s, 1H), 8.41 (s, 1H), 8.14 (d, J=8.8 Hz, 1H), 8.02 (brs, 1H), 7.75 (s, 1H), 7.55 (d, J=10.8 Hz, 1H), 7.50 (m, 2H), 7.31 (m, 1H), 7.11 (q, J=4.4 Hz, 1H), 6.17 (s, 1H), 3.50 (s, 3H), 2.86 (d, J=4.4 Hz, 3H); MS (ESI) m/z: 520.0 (M+H$^+$).

EXAMPLE 202

Using general method D, 3-bromo-2-methylbenzoic acid (50 mg, 0.23 mmol) and Example A39 (87 mg, 0.28 mmol) in presence of DPPA (55 µL, 0.25 mmol) and Et$_3$N (36 µL, 0.25 mmol) were combined to afford 1-(3-bromo-2-methylphenyl)-3-(2-fluoro-4-methyl-5-(8-methyl-2-(methylamino)-7-oxo-7,8-dihydropyrido[2,3-d]pyrimidin-6-yl)phenyl)urea (105 mg, 86% yield). $^1$H NMR (400 MHz, DMSO-d$_6$, major rotomer): δ 8.94 (d, J=2.0 Hz, 1H), 8.60 (brs, 1H), 8.49 (s, 1H), 7.95 (d, J=8.8 Hz, 1H), 7.81 (q, J=4.4 Hz, 1H), 7.76 (brd, 7.2 Hz, 1H), 7.67 (s, 1H), 7.29 (m, 1H), 7.15 (d, J=12.4 Hz, 1H), 7.06 (t, J=8.4 Hz, 1H), 3.59 (s, 3H), 2.90 (d, J=4.4 Hz, 3H), 2.32 (s, 3H), 2.07 (s, 3H); MS (ESI) m/z: 525.0 (M+H$^+$).

EXAMPLE 203

Using general method F, 3-chloro-2-methylphenylisocyanate (39 mg, 0.23 mmol) and Example A12 (70 mg, 0.23 mmol) in the presence of pyridine (38 µL, 0.47 mmol) were combined to afford 1-(2-chloro-5-(trifluoromethyl)phenyl)-3-(2-fluoro-4-methyl-5-(8-methyl-2-(methylamino)-7-oxo-7,8-dihydropyrido[2,3-d]pyrimidin-6-yl)phenyl)urea (75 mg, 69% yield). $^1$H NMR (400 MHz, DMSO-d$_6$, major rotomer): δ 9.03 (d, J=2.0 Hz, 1H), 8.65 (brs, 1H), 8.55 (s, 1H), 8.43 (m, 1H), 7.86 (s, 1H), 7.82 (m, 1H), 7.78 (dd, J=2.8, and 6.8 Hz, 1H), 7.27 (m, 2H), 7.15 (m, 2H), 3.61 (s, 3H), 2.90 (d, J=4.4 Hz, 3H), 2.30 (s, 3H); MS (ESI) m/z: 467.0 (M+H$^+$).

EXAMPLE 204

Using general method B, the carbamate of 4-bromonaphthalen-1-amine (0.061 g, 0.2 mmol) and Example A14 (0.06 g, 0.2 mmol) were combined to afford 1-(5-(2-amino-8-methyl-7-oxo-7,8-dihydropyrido[2,3-d]pyrimidin-6-yl)-2-fluoro-4-methylphenyl)-3-(4-bromonaphthalen-1-yl)urea as off-white solid (35 mg, 32%, yield). $^1$H NMR (400 MHz, DMSO-d$_6$): δ 9.24 (s, 1H), 9.06 (s, 1H), 8.61 (s, 1H), 8.24-8.21 (m, 1H), 8.15-8.13 (m, 1H), 8.01 (d, J=8.4 Hz, 1H), 7.98 (d, J=8.4 Hz, 1H), 7.81 (d, J=8.4 Hz, 1H), 7.74-7.68 (m, 3H), 7.31 (brs, 2H), 7.18 (d, J=12.4 Hz, 1H), 3.54 (s, 3H), 2.08 (s, 3H); MS (ESI) m/z: 547.0 (M+H$^+$).

EXAMPLE 205

To a degassed solution of 2-bromo-4-methylbenzenamine (0.301 g, 1.618 mmol), phenyl boronic acid (0.296 g, 2.427 mmol), and tetrakistriphenylphosphine palladium(0) (0.187 g, 0.162 mmol) in DME (8 mL) was added 2M sodium carbonate solution (3 ml, 6 mmol) and the mixture was stirred for 16 h at 80° C. Water (30 ml) was added and the product was extracted with EtOAc (2×30 mL). The combined organics were washed with brine, dried (Na$_2$SO$_4$), concentrated and purified by silica gel chromatography to provide 2-phenyl-4-methylbenzenamine as a thick syrup (0.22 g, 75% yield). $^1$H NMR (400 MHz, CDCl$_3$): δ 7.47-7.41 (m, 4H), 7.36-7.32 (m, 1H), 6.99-6.96 (m, 2H), 6.71 (d, J=8.0 Hz, 1H), 2.28 (s, 3H); MS (ESI) m/z: 184.2 (M+H$^+$).

To a biphasic solution of 2-phenyl-4-methylbenzenamine (0.29 g, 1.583 mmol) in EtOAc (10 mL) and NaHCO$_3$ (10 ml) was added prop-1-en-2-yl carbonochloridate (0.259 ml, 2.374 mmol) and mixture was stirred for 16 h at RT. The layers were separated and the aqueous layer was extracted with EtOAc (1×30 mL). The combined organics were washed with brine, dried (Na$_2$SO$_4$) and concentrated to provide prop-1-en-2-yl 2-phenyl-4-methylphenylcarbamate as an off-white solid (0.33 g, 78% yield). $^1$H NMR (400 MHz, CDCl$_3$): δ 8.00 (brs, 1H), 7.50-7.46 (m, 2H), 7.42-7.35 (m, 3H), 7.18 (dd, J=8.4 Hz, 1.6 Hz, 1H), 7.05 (s, 1H), 6.67 (brs, 1H), 4.72 (s, 1H), 4.68 (s, 1H), 2.34 (s, 3H), 1.94 (s, 3H); MS (ESI) m/z: 290.0 (M+Na$^+$).

Using general method C, prop-1-en-2-yl 2-Phenyl-4-methylphenylcarbamate (0.061 g, 0.23 mmol) and Example A26 (0.071 g, 0.23 mmol) were combined to afford 1-(2-phenyl-4-methylphenyl)-3-(2-fluoro-4-methyl-5-(1-methyl-7-(methylamino)-2-oxo-1,2-dihydro-1,6-naphthyridin-3-yl)phenyl)urea as a white solid (0.034 g, 28% yield). $^1$H NMR (400 MHz, MeOH-d$_4$): δ 8.35 (s, 1H), 7.79 (d, J=8.0 Hz, 1H), 7.68 (s, 1H), 7.57 (d, J=8.0 Hz, 1H), 7.45-7.41 (m, 2H), 7.37-7.33 (m, 3H), 7.14 (dd, J=8.0 Hz, 2.0 Hz, 1H), 7.06 (d, J=2.0 Hz, 1H), 6.99 (d, J=11.6 Hz, 1H), 6.29 (s, 1H), 3.63 (s, 3H), 2.97 (s, 3H), 2.33 (s, 3H), 2.12 (s, 3H); MS (ESI) m/z: 522.2 (M+H$^+$).

EXAMPLE 206

Using general method D, [1,1'-biphenyl]-2-carboxylic acid, 2'-methyl (0.051 g, 0.24 mmol) and Example A26 (0.075 g, 0.24 mmol) in presence of triethylamine (0.073 g, 0.72 mmol) and diphenylphospharyl azide (0.13 g, 0.48 mmol) were combined to afford 1-[2-(2-methylphenyl)]-3-(2-fluoro-4-methyl-5-(1-methyl-7-(methylamino)-2-oxo-1,2-dihydro-1,6-naphthyridin-3-yl)phenyl)urea as a white solid (83 mg, 66%). $^1$H NMR (400 MHz, DMSO-d$_6$): δ 8.87 (s, 1H), 8.38 (s, 1H), 7.91 (d, J=8.4 Hz, 1H), 7.89 (d, J=8.4 Hz, 1H), 7.76 (s, 1H), 7.65 (s, 1H), 7.34-7.26 (m, 4H), 7.14-7.02 (m, 5H), 6.16 (s, 1H), 3.50 (s, 3H), 2.84 (d, J=4.8 Hz, 3H), 2.04 (s, 3H), 2.01 (s, 3H); MS (ESI) m/z: 522.2 (M+H$^+$).

EXAMPLE 207

Using general method B, the carbamate of 2-aminobiphenyl (0.071 g, 0.28 mmol) and Example A26 (0.088 g, 0.28 mmol) were combined to afford 1-(2-phenylphenyl)-3-(2-fluoro-4-methyl-5-(1-methyl-7-(methylamino)-2-oxo-1,2-dihydro-1,6-naphthyridin-3-yl)phenyl)urea as a white solid (0.107 g, 75% yield). $^1$H NMR (400 MHz, DMSO-d$_6$): δ 8.82 (s, 1H), 8.39 (s, 1H), 8.11 (s, 1H), 7.34 (d, J=8.4 Hz, 1H), 7.81 (d, J=8.0 Hz, 1H), 7.65 (s, 1H), 7.51-7.47 (m, 2H), 7.42-7.37 (m, 3H), 7.30-7.26 (m, 1H), 7.19 (dd, J=8.0 Hz, 1.6 Hz, 1H), 7.13-7.02 (m, 3H), 6.16 (s, 1H), 3.50 (s, 3H), 2.84 (d, J=4.8 Hz, 3H), 2.05 (s, 3H); MS (ESI) m/z: 508.0 (M+H$^+$).

EXAMPLE 208

A degassed mixture of ethyl 5-chloro-2-iodobenzoate (0.621 g, 2.00 mmol), Pd(PPh$_3$)$_4$ (0.116 mg, 0.1 mmol), dimethoxyethane (20 mL), phenylboronic acid (0.268 g, 2.2 mmol), K2CO3 (0.829 g, 6.0 mmol), and water (5 mL) was heated under reflux for 6 h. Solvent was removed under reduced pressure. The residue was diluted with sat. NH$_4$Cl (15 mL) and extracted with EtOAc (2×30 mL). The combined organic layers were dried (MgSO4) and concentrated. The crude product was purified by chromatography to afford ethyl 5-chloro-2-phenylbenzoate (0.473 g, 91%) as colorless oil. MS (ESI) m/z: 261.0 (M+H$^+$).

Ethyl 5-chloro-2-phenylbenzoate (0.473 g, 1.81 mmol) was hydrolyzed with lithium hydroxide monohydrate to provide 5-chloro-2-phenylbenzoic acid (0.336 g, 80% yield). MS (ESI) m/z: 233.0 (M+H$^+$)

Using general method D, 3-chloro-6-phenyl benzoic acid (0.084 g, 0.36 mmol) and Example A27 were combined to afford 1-(3-chloro-6-phenylphenyl)-3-(2-fluoro-4-methyl-5-(1-methyl-7-(methylamino)-2-oxo-1,2-dihydro-1,6-naphthyridin-3-yl)phenyl)urea (0.117 g, 60%) as a white solid. $^1$H NMR (400 MHz, DMSO-d$_6$): δ 9.00 (s, 1H), 8.40 (s, 1H), 8.24 (s, 1H), 8.03 (s, 1H), 7.94 (d, J=8.4 Hz, 1H), 7.66 (s, 1H), 7.53-7.50 (m, 2H), 7.45-7.37 (m, 3H), 7.20-7.03 (m, 4H), 6.17 (s, 1H), 3.51 (s, 3H), 2.86 (d, J=4.8 Hz, 3H), 2.06 (s, 3H); MS (ESI) m/z: 542.0 (M+H$^+$).

EXAMPLE 209

Using general method B, the carbamate of 4-chloronaphthalen-1-amine (0.061 g, 0.23 mmol) and Example A14 (0.07 g, 0.23 mmol) were combined to afford 1-(5-(2-amino-8-methyl-7-oxo-7,8-dihydropyrido[2,3-d]pyrimidin-6-yl)-2-fluoro-4-methylphenyl)-3-(4-chloronaphthalen-1-yl)urea as off-white solid (25 mg, 21%, yield). $^1$H NMR (400 MHz, DMSO-d$_6$): δ 9.25 (s, 1H), 9.17 (s, 1H), 8.56 (s, 1H), 8.27-8.24 (m, 1H), 8.18-8.16 (m, 1H), 8.01 (d, J=8.4 Hz, 1H), 7.97 (d, J=8.4 Hz, 1H), 7.72-7.63 (m, 3H), 7.58 (d, J=8.4 Hz, 1H), 7.26 (brs, 2H), 7.13 (d, J=12.4 Hz, 1H), 3.49 (s, 3H), 2.03 (s, 3H); MS (ESI) m/z: 503.0 (M+H$^+$).

EXAMPLE 210

Using general method B, the carbamate of 5-t-butylisoxazol-3-amine (60 mg, 0.27 mmol) and Example A33 (93 mg, 0.27 mmol) were combined to afford 1-(5-tert-butylisoxazol-3-yl)-3-(4-chloro-5-(1-ethyl-7-(methylamino)-2-oxo-1,2-dihydro-1,6-naphthyridin-3-yl)-2-fluorophenyl)urea (0.045 g, 33% yield). $^1$H NMR (400 MHz, DMSO-d$_6$): δ 9.86 (s, 1H), 8.91 (brs, 1H), 8.41 (s, 1H), 8.15 (d, J=8.8 Hz, 1H), 7.74 (s, 1H), 7.56 (d, J=11.2 Hz, 1H), 7.06 (q, J=4.8 Hz, 1H), 6.45 (s, 1H), 6.24 (brs, 1H), 4.14 (q, J=6.8 Hz, 2H), 2.86 (d, J=4.8 Hz, 3H), 1.26 (s, 9H), 1.20 (t, J=6.8 Hz, 3H); MS (ESI) m/z: 513.3 (M+H$^+$).

EXAMPLE 211

Using general method D, Example B33 (200 mg, 0.806 mmol) and Example A3 (255 mg, 0.806 mmol) were combined to give the intermediate sulfide (132 mg, 29% yield). Using a procedure analogous to Example A1, The sulfide and 2.0N methylamine in THF (1.2 mL, 2.35 mmol) were combined to give 1-(2-tert-butyl-4-(trifluoromethyl)pyrimidin-5-yl)-3-(2-fluoro-5-(8-methyl-2-(methylthio)-7-oxo-7,8-dihydropyrido[2,3-d]pyrimidin-6-yl)phenyl)urea (79 mg, 61% yield). $^1$H NMR (300 MHz, DMSO-d$_4$): δ 1.35 (s, 9H), 2.90 (s, 3H), 3.53-3.60 (m, 3H), 7.29-7.33 (m, 2H), 7.70-7.80 (br m, 1H), 7.87 (s, 1H), 8.37-8.39 (m, 1H), 8.63-8.70 (m, 1H), 8.89 (s, 1H), 9.33 (s, 1H), 9.38 (s, 1H); MS (ESI) m/z: 545.3 (M+H$^+$).

EXAMPLE 212

Using general method F, Example A3 (0.173 g, 0.547 mmol) and 1-naphthyl isocyate (0.086 ml, 0.602 mmol) were combined to provide 1-(2-fluoro-5-(8-methyl-2-(methylthio)-7-oxo-7,8-dihydropyrido[2,3-d]pyrimidin-6-yl)phenyl)-3-(naphthalene-1-yl)urea (246 mg, 94% yield). $^1$H NMR (400 MHz, DMSO-d$_6$): δ 9.20 (s, 1H), 9.16 (s, 1H), 8.96 (s, 1H), 8.57 (m, 1H), 8.17 (d, J=8.3 Hz, 1H), 8.09 (m, 1H), 8.05 (d, J=6.8 Hz, 1H), 7.93 (d, J=7.8 Hz, 1H), 7.65-7.52 (m, 3H), 7.46 (t, J=7.8 Hz, 1H), 7.38-7.32 (m, 2H), 3.67 (s, 3H), 2.61 (s, 3H).

Using a procedure analogous to Example A1, 1-(2-fluoro-5-(8-methyl-2-(methylthio)-7-oxo-7,8-dihydropyrido[2,3-d]pyrimidin-6-yl)phenyl)-3-(□aphthalene-1-yl)urea (244 mg, 0.503 mmol), mCPBA (136 mg, 0.553 mmol) and N,N-dimethylethylenediamine (0.11 mL, 1.01 mmol) were combined to provide 1-(5-(2-(2-(dimethylamino)ethylamino)-8-methyl-7-oxo-7,8-dihydropyrido[2,3-d]pyrimidin-6-yl)-2-fluorophenyl)-3-(□aphthalene-1-yl)urea (110 mg, 100% yield). $^1$H NMR (400 MHz, DMSO-d$_4$): δ 9.13 (s, 1H), 9.05 (d, J=1.9 Hz, 1H), 8.67 and 8.61 (s, 1H), 8.45 (d, J=8.5 Hz, 1H), 8.12 (d, J=8.0 Hz, 1H), 8.00 (d, J=8.2 Hz, 1H), 7.88 (d, J=7.7 Hz, 1H), 7.83 (s, 1H), 7.71 (t, J=5.6 Hz, 1H), 7.60-7.47 (m, 3H), 7.41 (t, J=7.9 Hz, 1H), 7.25 (d, J=8.2 Hz, 2H), 3.55 and 3.50 (s, 3H), 3.41 (q, J=6.5 Hz, 2H), 2.41 (m, 2H), 2.14 and 2.11 (s, 6H); MS (ESI) m/z: 526.2 (M+H$^+$).

EXAMPLE 213

Using general method G, the carbamate of 5–/–butylisoxazol-3-amine (1.340 g, 5.97 mmol), and Example A30 (1.50 g, 4.60 mmol) were combined to furnish 1-(5-tert-butylisoxazol-3-yl)-3-(5-(1-ethyl-7-(methylamino)-2-oxo-1,2-dihydro-1,6-naphthyridin-3-yl)-2-fluoro-4-methylphenyl)urea (1.99 g, 88% yield). $^1$H NMR (400 MHz, DMSO-d$_6$): δ 9.79 (s, 1H), 8.74 (s, 1H)), 8.40 (s, 1H), 7.91 (d, J=8 Hz, 1H), 7.66 (s, 1H), 7.15 (d, J=13 Hz, 1H), 7.00 (m, 1H), 6.44 (s, 1H), 6.23 (s, 1H), 4.15 (m, 2H), 2.86 (d, J=5 Hz, 3H), 2.07 (s, 3H), 1.26 (s, 9H), 1.20 (t, J=6 Hz, 3H): MS (ESI) m/z: 493.2 (M+H$^+$).

EXAMPLE 214

Using general method B, the carbamate of 2-phenylaniline (0.089 g, 0.353 mmol) and Example A54 (0.100 g, 0.353 mmol) were combined to afford 1-(2-phenylphenyl)-3-(2-fluoro-4-methyl-5-(1-methyl-2-oxo-1,2-dihydro-1,6-naphthyridin-3-yl)phenyl)urea (0.128 g, 76% yield) as a white solid. $^1$H NMR (400 MHz, DMSO-d$_6$): δ 8.92 (s, 1H), 8.87 (s, 1H), 8.60 (d, J=5.6 Hz, 1H), 8.14 (s, 1H), 8.03-7.97 (m, 2H), 7.81 (d, J=8.4 Hz, 1H), 7.53-7.48 (m, 3H), 7.43-7.37 (m, 3H), 7.29 (t, J=8.8 Hz, 1H), 7.21-7.12 (m, 3H), 3.65 (s, 3H), 2.07 (s, 3H); MS (ESI) m/z: 479.2 (M+H$^+$).

EXAMPLE 215

Using general method B, the carbamate of 5-t-butylisoxazol-3-amine (80 mg, 0.36 mmol) and Example A48 (122 mg, 0.36 mmol) were combined to afford 1-(5-tert-butylisoxazol-3-yl)-3-(4-cyano-2-fluoro-5-(8-methyl-2-(methylthio)-7-oxo-7,8-dihydropyrido[2,3-d]pyrimidin-6-yl)phenyl)urea (0.046 g, 25% yield). MS (ESI) m/z: 508.2 (M+H$^+$).

Using a procedure analogous to Example A1, 1-(5-tert-butylisoxazol-3-yl)-3-(4-cyano-2-fluoro-5-(8-methyl-2-(methylthio)-7-oxo-7,8-dihydropyrido[2,3-d]pyrimidin-6-yl)phenyl)urea (0.046 g, 0.091 mmol) was treated with mCPBA (70% wt, 0.027 g, 0.11 mmol) and then N-methylamine (2.0M in THF, 0.18 mL, 0.36 mmol) to afford 1-(5-tert-butylisoxazol-3-yl)-3-(4-cyano-2-fluoro-5-(8-methyl-2-(methylamino)-7-oxo-7,8-dihydropyrido[2,3-d]pyrimidin-6-yl)phenyl)urea (15 mg, 34% yield). $^1$H NMR (400 MHz, DMSO-d$_6$): δ 10.0 (s, 1H), 9.24 (brs, 1H), 8.67 (s, 1H), 8.41 (d, J=7.6 Hz, 1H), 7.98 (d, J=11.2 Hz, 1H), 7.94 (s, 1H), 7.88 (m, 1H), 6.49 (s, 1H), 3.61 (s, 3H), 2.92 (d, 0.7=4.8 Hz, 3H), 1.26 (s, 9H); MS (ESI) m/z: 491.2 (M+H$^+$).

EXAMPLE 216

Using general method D, Example B34 (200 mg, 0.646 mmol) and Example A3 (205 mg, 0.646 mmol) were combined to give the intermediate sulfide (215 mg, 53% yield). Using a procedure analogous to Example A1, the sulfide and 2.00N methylamine in THF (1.35 mL, 2.70 mmol) were combined to afford 1-(2-tert-butyl-4-(1-methyl-1H-indol-5-yl)pyrimidin-5-yl)-3-(2-fluoro-5-(8-methyl-2-(methylamino)-7-oxo-7,8-dihydropyrido[2,3-d]pyrimidin-6-yl)phenyl)urea (22 mg, 13% yield). $^1$H NMR (300 MHz, DMSO-$d_6$): δ 1.38 (s, 9H), 2.90 (s, 3H), 3.53-3.60 (m, 3H), 3.83 (s, 3H), 6.55 (s, 1H), 7.23-7.29 (m, 3H), 7.41 (m, 1H), 7.56-7.61 (m, 2H), 7.85 (s, 1H), 7.98 (s, 1H), 8.38-8.40 (m, 1H), 8.63-8.70 (m, 2H), 9.01-9.05 (br. s, 2H); MS (ESI) m/z: 606.2 (M+H$^+$).

EXAMPLE 217

Using general method F, Example A30 (70 mg, 0.21 mmol) and 1-isocyanato-3-(trifluoromethyl)benzene (0.035 mL, 0.25 mmol) were combined to provide 1-(5-(1-ethyl-7-(methylamino)-2-oxo-1,2-dihydro-1,6-naphthyridin-3-yl)-2-fluoro-4-methylphenyl)-3-(3-(trifluoromethyl)phenyl)urea (43 mg, 39% yield). $^1$H NMR (400 MHz, DMSO-$d_6$): δ 9.37 (s, 1H), 8.58 (d, J=1.5 Hz, 1H), 8.41 (s, 1H), 8.02 (s, 1H), 7.90 (d, J=8.4 Hz, 1H), 7.67 (s, 1H), 7.52-7.45 (m, 2H), 7.30 (br d, J=6.2 Hz, 1H), 7.14 (d, J=12.2 Hz, 1H), 7.00 (q, J=4.8 Hz, 1H), 6.24 (s, 1H), 4.15 (q, J=7.0 Hz, 2H), 2.86 (d, J=4.8 Hz, 3H), 2.07 (s, 3H), 1.21 (t, J=7.0 Hz, 3H); MS (ESI) m/z: 514.2 (M+H$^+$).

EXAMPLE 218

Using general method B, the carbamate of 2-phenylaniline (0.107 g, 0.422 mmol) and Example A56 (0.100 g, 0.281 mmol) were combined to afford 1-(5-(7-(2-(dimethylamino)ethylamino)-1-methyl-2-oxo-1,2-dihydro-1,6-naphthyridin-3-yl)-2-fluorophenyl)-3-(2-phenylphenyl)urea (0.276 g, 18%) as a white solid. It was converted to the corresponding bis-methylate salt by reacting with MsOH (2.0 eq.). $^1$H NMR (400 MHz, DMSO-$d_6$): δ 8.54 (s, 1H), 8.36 (dd, J=7.6, 2.0 Hz, 1H), 7.94 (s, 1H), 7.82 (dd, J= 8.4, 0.8 Hz, 1H), 7.50-7.46 (m, 2H), 7.41-7.32 (m, 5H), 7.27 (dd, J=7.6, 1.6 Hz, 1H), 7.22-7.13 (m, 2H), 6.72 (s, 1H), 3.90 (t, J=6.0 Hz, 2H), 3.70 (s, 3H), 3.50 (t, J=6.0 Hz, 2H), 3.01 (s, 6H), 2.72 (s, 6H); MS (ESI) m/z: 551.2 (M+H$^+$).

EXAMPLE 219

Using general method B, the carbamate of 3-isopropyl-1-phenyl-1H-pyrazol-5-amine (0.100 g, 0.350 mmol) and Example A28 (0.111 g, 0.334 mmol) were combined to afford 1-(4-chloro-2-fluoro-5-(1-methyl-7-(methylamino)-2-oxo-1,2-dihydro-1,6-naphthyridin-3-yl)phenyl)-3-(3-isopropyl-1-phenyl-1H-pyrazol-5-yl)urea (0.075 g, 40% yield) as a white solid. $^1$H NMR (400 MHz, DMSO-$d_6$): δ 8.36 (s, 1H), 8.13 (d, J=8.4 Hz, 1H), 7.74 (s, 1H), 7.57-7.52 (m, 2H), 7.49-7.45 (m, 3H), 7.29 (d, J=10.8 Hz, 1H), 6.39 (s, 1H), 6.29 (s, 1H), 3.62 (s, 3H), 2.97-2.91 (m, 4H), 1.27 (d, J=6.8 Hz, 6H); MS (ESI) m/z: 560.2 (M+H$^+$).

EXAMPLE 220

Using general method D, 2-fluoro-5-(trifluoromethyl)benzoic acid (50 mg, 0.24 mmol) and Example A39 (75 mg, 0.24 mmol) in presence of DPPA (57 μL, 0.26 mmol) and Et$_3$N (37 μL, 0.26 mmol) were combined to afford 1-(2-fluoro-4-methyl-5-(8-methyl-2-(methylamino)-7-oxo-7,8-dihydropyrido[2,3-d]pyrimidin-6-yl)phenyl)-3-(2-fluoro-5-(trifluoromethyl)phenyl)urea (90 mg, 76% yield). $^1$H NMR (400 MHz, DMSO-$d_6$, major rotomer): δ 9.33 (d, J=2.4 Hz, 1H), 9.12 (brs, 1H), 8.61 (s, 1H), 8.59 (dd, J= 2.4, and 7.6 Hz, 1H), 7.97 (d, J=8.4 Hz, 1H), 7.81 (q, J=4.4 Hz, 1H), 7.69 (s, 1H), 7.48 (m, 1H), 7.37 (m, 1H), 7.16 (d, J=12.4 Hz, 1H), 3.60 (s, 3H), 3.54 (s, 3H), 2.91 (d, J=4.4 Hz, 3H), 2.08 (s, 3H); MS (ESI) m/z: 519.0 (M+H$^+$).

EXAMPLE 221

In a manner analogous to that described for the preparation of Example 137, prop-1-en-2-yl 5-t-butyl-1,3,4-thiadiazol-2-ylcarbamate (100 mg, 0.414 mmol, 1.00 eq) and Example A17 (145 mg, 0.414 mmol, 1.00 eq) were reacted in the presence of N-methylpyrrolidine (0.043 ml, 0.041 mmol, 0.10 eq) in THF (4 ml). Subsequent oxidation with mCPBA (44.3 mg, 0.180 mmol, 1.20 eq) and displacement with 2.0M methylamine in THF (0.749 ml, 1.498 mmol, 10.00 eq) afforded 1-(5-tert-butyl-1,3,4-thiadiazol-2-yl)-3-(4-chloro-2-fluoro-5-(8-methyl-2-(methylamino)-7-oxo-7,8-dihydropyrido[2,3-d]pyrimidin-6-yl)phenyl)urea (14 mg, 6.5% overall yield) as a white solid. $^1$H NMR (400 MHz, DMSO-$d_6$): δ 8.98 (brs, 1H), 8.66 (brs, 1H), 8.58 (brs, 1H), 8.05 (d, 1H, J=8.0 Hz), 7.85 (brq, 1H), 7.73 (s, 1H), 7.56 (d, 1H, J=10.8 Hz), 3.55 (brs, 3H), 2.86 (brd, 3H), 1.30 (s, 9H); MS (ESI) m/z: 517.0 (M+H).

EXAMPLE 222

Using general method B, the carbamate of Example B19 (3.00 g, 13.44 mmol) and Example A28 (3.00 g, 9.02 mmol) were combined to provide 1-(1-tert-butyl-1H-pyrazol-4-yl)-3-(4-chloro-2-fluoro-5-(1-methyl-7-(methylamino)-2-oxo-1,2-dihydro-1,6-naphthyridin-3-yl)phenyl)urea (1.85 g, 41% yield). $^1$H NMR (400 MHz, DMSO-$d_6$): □ 8.72 (s, 1H), 8.63 (brs, 1H), 8.40 (s, 1H), 8.18 (d, J=9 Hz, 1H), 7.79 (s, 1H), 7.73 (s, 1H), 7.50 (d, J=11Hz, 1H), 7.39 (s, 1H), 7.10 (m, 1H), 6.17 (s, 1H), 3.50 (s, 3H), 2.85 (d, J=5 Hz, 3H), 1.46 (s, 9H); MS (ESI) m/z: 498.0 (M+H$^+$).

EXAMPLE 223

Using general method B, the carbamate of 5-t-butylisoxazol-3-amine (50 mg, 0.223 mmol) and Example A46 (72 mg, 0.223 mmol) were combined to afford 1-(5-tert-butylisoxazol-3-yl)-3-(4-ethynyl-2-fluoro-5-(8-methyl-2-(methylamino)-7-oxo-7,8-dihydropyrido[2,3-d]pyrimidin-6-yl)phenyl)urea (0.058 g, 53% yield). $^1$H NMR (400 MHz, DMSO-$d_6$, major isomers): δ 9.90 (s, 1H), 8.99 (s, 1H), 8.62 (s, 1H), 8.22 (d, J=8.4 Hz, 1H), 7.87 (q, J=4.8 Hz, 1H), 7.80 (s, 1H), 7.48 (d, J=11.6 Hz, 1H), 6.47 (s, 1H), 4.08 (s, 1H), 3.60 (s, 3H), 2.91 (d, J=4.8 Hz, 3H), 1.26 (s, 9H); MS (ESI) m/z: 490.2 (M+H$^+$).

EXAMPLE 224

To a stirring suspension of 3-t-butyl-1-(3-nitrophenyl)-1H-pyrazol-5-amine hydrochloride (0.500 g, 1.685 mmol, 1.00 eq) and pyridine (0.412 ml, 5.05 mmol, 3.00 eq) in CH$_2$Cl$_2$ (17 ml) at 22° C. was added Troc-Cl (0.244 ml, 1.769 mmol, 1.05 eq). The reaction was stirred overnight at RT. The completed reaction was diluted with CH$_2$Cl$_2$ and washed with 3M HCl (2×). The combined aqueous were extracted with CH$_2$Cl$_2$ (1×). The combined organics were washed with H$_2$O (2×), brine (1×), dried (Na$_2$SO$_4$), filtered ad evaporated. The crude product was purified by flash column chromatography (100% hexanes to 30% EtOAc/hexanes) to afford 2,2,2- trichloroethyl 3-t-butyl-1-(3-nitrophenyl)-1H-pyrazol-5-yl-carbamate (0.67 g, 91% yield) as an oil.

2,2,2-Trichloroethyl 3-t-butyl-1-(3-nitrophenyl)-1H-pyrazol-5-ylcarbamate (0.67 g, 1.538 mmol, 1.00 eq) in EtOAc (30 ml) was shaken under $H_2$ (3.5 arm) at 22° C. over 10% Pd/C (0.327 g, 0.154 mmol, 0.10 eq, 50% $H_2O$) overnight. The completed hydrogenation was treated with $Ac_2O$ (3 ml) and stirred at RT. After 45 min, the mixture was filtered through Celite, rinsing forward with EtOAc. The filtrate was treated with a roughly equal volume of satd. $NaHCO_3$ and stirred briskly at RT for 3 h. The layers were separated and the organic layer washed with satd. $NaHCO_3$ (2×). The combined aqueous layers were extracted with EtOAc (1×). The combined organics were washed with brine (1×), dried ($MgSO_4$), filtered and evaporated to afford 2,2,2-trichloroethyl 1-(3-acetamidophenyl)-3-t-butyl-1H-pyrazol-5-ylcarbamate (0.50 g, 73% yield) as a white solid which was used as is in the next reaction. $^1$H NMR (400 MHz, DMSO-$d_6$): δ 10.10 (s, 1H), 9.95 (brs, 1H), 7.74 (brs, 1H), 7.54-7.51 (m, 1H), 7.37-7.31 (m, 1H), 7.08 (d, J=7.6 Hz, 1H), 6.26 (s, 1H), 4.84 (s, 2H), 2.03 (s, 3H), 1.26 (s, 9H); MS (ESI) m/z: 447.0 (M+H), 449.0 ((M+2+H).

Using general method C, 2,2,2-trichloroethyl 1-(3-acetamidophenyl)-3-t-butyl-1H-pyrazol-5-ylcarbamate (0.100 g, 0.223 mmol, 1.00 eq) and Example A39 (0.070 g, 0.223 mmol, 1.00 eq) were combined to afford 1-(1-(3-acetamidophenyl)-3-tert-butyl-1H-pyrazol-5-yl)-3-(2-fluoro-4-methyl-5-(8-methyl-2-(methylamino)-7-oxo-7,8-dihydropyrido[2,3-d]pyrimidin-6-yl)phenyl)urea (20 mg, 15% yield) as an off-white solid. $^1$H NMR (400 MHz, DMSO-$d_6$): δ 10.17 (s, 2H), 8.92 (s, 1H), 8.85 (s, 1H), 8.61 (brs, 1H), 7.95 (d, J=8.4 Hz, 1H), 7.82 (brq, 1H), 7.68 (d, J=8.0 Hz, 2H), 7.44 (dd, J=7.6 and 16.4 Hz, 1H), 7.16-7.11 (m, 2H), 6.35 (s, 1H), 3.60 (s, 3H), 2.90 (brd, 3H), 2.05 (brs, 3H), 1.23 (s, 9H); MS (ESI) m/z: 612.3 (M+H).

EXAMPLE 225

Using general method D, Example B30 (0.051 g, 0.3 mmol) and Example A30 (0.1 g, 0.3 mmol) in presence of triethylamine (0.12 g, 1.2 mmol) and diphenylphospharyl azide (0.25 g, 0.91 mmol) were combined to afford 1-(1-tert-butyl-1H-pyrazol-4-yl)-3-(5-(1-ethyl-7-(methylamino)-2-oxo-1,2-dihydro-1,6-naphthyridin-3-yl)-2-fluoro-4-methylphenyl)urea as a white solid (41 mg. 27% yield). $^1$H NMR (400 MHz, DMSO-$d_6$): δ 8.64 (s, 1H), 8.41 (s, 1H), 8.40 (s, 1H), 7.94 (d, J=8.8 Hz, 1H), 7.78 (s, 1H), 7.64 (s, 1H), 7.36 (s, 1H), 7.10 (d, J=12.0 Hz, 1H), 7.01-6.97 (m, 1H), 6.23 (s, 1H), 4.14 (q, J=6.8 Hz, 2H), 2.85 (d, J=4.8 Hz, 3H), 2.05 (s, 3H), 1.45 (s, 9H), 1.20 (t, J=6.8 Hz, 3H); MS (ESI) m/z: 492.3 (M+H$^+$).

EXAMPLE 226

Using general method F, Example A22 (0.060 g, 0.21 mmol) and 1-naphthyl isocyate (0.033 mL, 0.23 mmol) were combined to provide 1-(5-(1-ethyl-2-oxo-1,2-dihydro-1,6-naphthyridin-3-yl)-2-fluorophenyl)-3-(naphthalen-1-yl)urea (72 mg, 75% yield). $^1$H NMR (400 MHz, DMSO-$d_6$): δ 9.14 (s, 1H), 9.08 (d, J=2.0 Hz, 1H), 8.92 (s, 1H), 8.54-8.51 (m, 2H), 8.13-8.11 (m, 2H), 7.99 (d, J=7.8 Hz, 1H), 7.88 (d, J=7.4 Hz, 1H), 7.60-7.47 (m, 4H), 7.42 (t, J=7.8 Hz, 1H), 7.31 (d, J=9.0 Hz, 2H), 4.26 (q, J=7.0 Hz, 2H), 1.19 (t, J=7.0 Hz, 3H); MS (ESI) m/z: 453.3 (M+H$^+$).

EXAMPLE 227

Using general method D, 2,3-difluorobenzoic acid (40 mg, 0.25 mmol) and Example A39 (80 mg, 0.25 mmol) in presence of DPPA (60 μL, 0.28 mmol) and $Et_3N$ (40 μL, 0.28 mmol) were combined to afford 1-(2,3-difluorophenyl)-3-(2-fluoro-4-methyl-5-(8-methyl-2-(methylamino)-7-oxo-7,8-dihydropyrido[2,3-d]pyrimidin-6-yl)phenyl)urea (90 mg, 76% yield). $^1$H NMR (400 MHz, DMSO-$d_6$, major rotomer): δ 9.16 (brs, 1H), 9.02 (brs, 1H), 8.61 (brs, 1H), 7.9-8.0 (m, 2H), 7.80 (m, 1H), 7.69 (s, 1H), 7.16 (d, J=12.4 Hz, 1H), 7.10 (m, 1H), 7.00 (m, 1H), 3.60 (s, 3H), 2.91 (d, J=4.4 Hz, 3H), 2.07 (s, 3H); MS (ESI) m/z: 469.0 (M+H$^+$).

EXAMPLE 228

Using general method C, the TROC carbamate of 4-bromo-3-(trifluoromethyl)aniline (0.10 g, 0.24 mmol), and Example A12 (72 mg, 0.24 mmol) (0.10 mL, 0.54 mmol) were combined to afford 1-(4-bromo-3-(trifluoromethyl)phenyl)-3-(2-fluoro-5-(8-methyl-2-(methylamino)-7-oxo-7,8-dihydropyrido[2,3-d]pyrimidin-6-yl)phenyl)urea (0.027 g, 20% yield). $^1$H NMR (400 MHz, DMSO-$d_6$, major rotomer): δ 9.52 (s, 1H), 8.70 (d, J=2.0 Hz, 1H), 8.66 (s, 1H), 8.35 (dd, J=1.6, and 7.6 Hz, 1H), 8.11 (d, J=2.4 Hz, 1H), 7.90 (s, 1H), 7.73, m, 1H), 7.76 (d, J=9.2 Hz, 1H), 7.51 (dd, J=2.8, and 8.8 Hz, 1H), 7.30 (m, 2H), 3.62 (s, 3H), 2.91 (d, J=4.8 Hz, 3H); MS (ESI) m/z: 566.0 (M+H$^+$).

EXAMPLE 229

Using general method C, Example A1 (127 mg, 0.444 mmol), and 2,2,2-trichloroethyl quinolin-8-ylcarbamate (142 mg, 0.444 mmol), at 120° C., were combined to afford 1-(5-(2-amino-8-methyl-7-oxo-7,8-dihydropyrido[2,3-d]pyrimidin-6-yl)-2-fluorophenyl)-3-(quinolin-8-yl)urea (18 mg, 8% yield). $^1$H NMR (300 MHz, DMSO-$d_6$): δ 3.55 (s, 3H), 7.29-7.31 (m, 2H), 7.51-7.64 (m, 3H), 7.50-8.00 (br. s, 2H), 7.94 (s, 1H), 8.37-8.40 (m, 1H), 8.45-8.48 (m, 1H), 8.54-8.56 (m, 1H), 8.75 (s, 1H), 8.92-8.93 (m, 1H), 9.82 (s, 1H), 10.20 (s, 1H); MS (ESI) m/z: 456.0 (M+H$^+$).

EXAMPLE 230

Using general method C, the TROC carbamate of Example B20 (0.10 g, 0.33 mmol) and Example A17 (116 mg, 0.33 mmol) were combined to afford 1-(4-chloro-2-fluoro-5-(8-methyl-2-(methylthio)-7-oxo-7,8-dihydropyrido[2,3-d]pyrimidin-6-yl)phenyl)-3-(3-isopropylisoxazol-5-yl)urea (0.087 g, 52% yield). MS (ESI) m/z: 503.0 (M+H$^+$).

Using a procedure analogous to Example A1, 1-(4-chloro-2-fluoro-5-(8-methyl-2-(methylthio)-7-oxo-7,8-dihydropyrido[2,3-d]pyrimidin-6-yl)phenyl)-3-(3-isopropylisoxazol-5-yl)urea (0.087 g, 0.17 mmol) was treated with mCPBA (70% wt, 0.051 g, 0.21 mmol) and then N-methylamine (2.0M in THF, 0.35 mL, 0.69 mmol) to afford 1-(4-chloro-2-fluoro-5-(8-methyl-2-(methylamino)-7-oxo-7,8-dihydropyrido[2,3-d]pyrimidin-6-yl)phenyl)-3-(3-isopropylisoxazol-5-yl)urea (65 mg, 77% yield). $^1$H NMR (400 MHz, DMSO-$d_6$, major rotomer): δ 10.4 (brs, 1H), 8.93 (brs, 1H), 8.62 (s, 1H), 8.11 (d, J=8.8 Hz, 1H), 7.88 (m, 1H), 7.77 (s, 1H), 7.59 (d, J=10.8 Hz, 1H), 5.99 (s, 1H), 3.59 (s, 3H), 2.90 (m, 4H), 1.16 (d, J=7.2 Hz, 6H); MS (ESI) m/z: 486.0 (M+H$^+$).

EXAMPLE 231

Using general method F, Example A1 (0.150 g, 0.526 mmol) and 1-isocyanatonaphthalene (0.100 g, 0.591 mmol) were combined to provide 1-(5-(2-amino-8-methyl-7-oxo-7,8-dihydropyrido[2,3-d]pyrimidin-6-yl)-2-fluorophenyl)-3-(naphthalen-1-yl)urea (0.11 g, 40% yield). $^1$H NMR (400

MHz, DMSO-d$_6$): δ 9.16 (s, 1H), 9.10 (brs, 1H), 8.66 (s, 1H), 8.51 (m, 1H), 8.18 (d, J=9 Hz, 1H), 8.05 (brd, J=8 Hz, 1H), 7.93 (brd, J=8 Hz, 1H), 7.89 (s, 1H), 7.65-7.45 (m, 4H), 7.31 (m, 4H), 3.56 (s, 3H); MS (ESI) m/z: 455.0 (M+H$^+$).

EXAMPLE 232

Using general method B, the carbamate of 3-isopropyl-1-phenyl-1H-pyrazol-5-amine (0.100 g, 0.350 mmol), and Example A30 (0.100 g, 0.306 mmol) were combined to provide 1-(5-(1-ethyl-7-(methylamino)-2-oxo-1,2-dihydro-1,6-naphthyridin-3-yl)-2-fluoro-4-methylphenyl)-3-(3-isopropyl-1-phenyl-1H-pyrazol-5-yl)urea (0.14 g, 72% yield). $^1$H NMR (400 MHz, DMSO-d$_6$): δ 8.89 (s, 1H), 8.82 (s, 1H), 8.40 (s, 1H), 7.91 (d, J=9 Hz, 1H), 7.64 (s, 1H), 7.50 (m, 4H), 7.41 (m, 1H), 7.10 (d, J=12 Hz, 1H), 7.00 (m, 1H), 6.31 (s, 1H), 6.24 (s, 1H), 4.14 (q, J=6 Hz, 2H), 2.85 (m 4H), 2.06 (s, 3H), 1.20 (t, J=6 Hz, 3H), 1.18 (d, J=6 Hz, 6H); MS (ESI) m/z: 554.2 (M+H$^+$).

EXAMPLE 233

To a stirring solution of Example B28 (0.200 g, 1.314 mmol, 1.00 eq) and pyridine (0.213 ml, 2.63 mmol, 2.00 eq) in CH$_2$Cl$_2$ (13 ml) at 0° C. was added isopropenyl chloroformate (0.158 ml, 1.446 mmol, 1.10 eq). After 45 min at 0° C., the completed reaction was diluted with CH$_2$Cl$_2$ and washed with 3M HCl (2×). The combined aqueous layers were extracted with CH$_2$Cl$_2$ (1×). The combined organics were washed with H$_2$O (1×), and brine (1×), dried (Na$_2$SO$_4$), filtered and evaporated to afford crude prop-1-en-2-yl 3-cyclopentylisoxazol-5-ylcarbamate (0.41 g, 132% yield) as an oil which was used as is in the next reaction. MS (ESI) m/z: 237.0 (M+H)$^+$.

Prop-1-en-2-yl 3-cyclopentylisoxazol-5-ylcarbamate (0.310 g, 1.312 mmol), Example A39 (0.411 g, 1.312 mmol) and 1-methylpyrrolidine (0.027 ml, 0.262 mmol) were combined in THF (13 ml) and stirred with heating at 60° C. overnight. The completed reaction was cooled to RT, applied to a samplet and allowed to dry. The crude product was purified by flash column chromatography (10-75% EtOAc/hexanes) and then by reverse phase chromatography (10-60% MeCN (w/0.1% TFA)/H$_2$O (w/0.1% TFA)) to afford 1-(3-cyclopentylisoxazol-5-yl)-3-(2-fluoro-4-methyl-5(8-methyl-2-(methylamino)-7-oxo-7,8-dihydropyrido[2,3-d]pyrimidin-6-yl)phenyl)urea (75 mg, 12% yield) as an off-white solid following lyophilization. $^1$H NMR (400 MHz, DMSO-d$_6$): δ 10.30 (s, 1H), 8.68 (brs, 1H), 8.61 (brs, 1H), 7.88 (d, J=8.4 Hz, 1H), 7.83 (brq, 1H), 7.68 (s, 1H), 7.17 (d, J=12.0 Hz, 1H), 5.93 (s, 1H), 3.60 (brs, 3H), 3.03-2.95 (m, 1H), 2.90 (brs, 3H), 2.08 (s, 3H), 1.96-1.90 (m, 2H), 1.69-1.54 (m, 6H); MS (ESI) m/z: 492.3 (M+H).

EXAMPLE 234

In a manner analogous to that described for the preparation of Example 233, Example B29 (0.200 g, 1.203 mmol, 1.00 eq) and Example A39 (0.377 g, 1.203 mmol) were reacted to afford 1-(2-fluoro-4-methyl-5-(8-methyl-2-(methylamino)-7-oxo-7,8-dihydropyrido[2,3-d]pyrimidin-6-yl)phenyl)-3-(3-(1-methylcyclopentyl)isoxazol-5-yl)urea (107 mg, 18% yield) as an off-white solid. $^1$H NMR (400 MHz, DMSO-d$_6$): δ 10.30 (s, 1H), 8.68 (brs, 1H), 8.61 (s, 1H), 7.89 (d, J=8.4 Hz, 1H), 7.85 (brq, 1H), 7.68 (s, 1H), 7.17 (d, J=12.4 Hz, 1H), 5.97 (s, 1H), 3.60 (brs, 3H), 2.95 (brs, 3H) 2.08 (s, 3H), 1.95-1.91 (m, 2H), 1.70-1.52 (m, 6H), 1.23 (s, 3H); MS (ESI) m/z: 506.2 (M+H).

EXAMPLE 235

The carbamate of 5-t-butylisoxazol-3-amine (100 mg, 0.446 mmol), Example A31 (139 mg, 0.446 mmol) and 1-methylpyrrolidine (9.27 µl, 0.089 mmol) were combined in THF (5 ml) and stirred with heating at 60° C. in a sealed screw-cap vial for 24 h. The completed reaction was cooled to RT and concentrated to dryness. The crude product was purified by reverse phase chromatography (5-45% MeCN (w/0.1% TFA)/H$_2$O (w/0.1% TFA)). Fractions containing pure product were pooled and neutralized with satd. NaHCO$_3$. This was extracted with EtOAc (2×). The combined organics were washed with brine (2×), dried (MgSO$_4$), filtered and evaporated to a solid residue. This was dissolved/suspended in MeCN/H$_2$O, frozen and lyophilized to afford 1-(5-(7-amino-1-ethyl-2-oxo-1,2-dihydro-1,6-naphthyridin-3-yl)-2-fluoro-4-methylphenyl)-3-(5-tert-butylisoxazol-3-yl)urea (108 mg, 50.6% yield) as a beige solid. $^1$H NMR (400 MHz, DMSO-d$_6$): δ 9.79 (s, 1H), 8.74 (s, 1H), 8.35 (s, 1H), 7.91 (d, J=8.4 Hz, 1H), 7.65 (s, 1H), 7.15 (d, J=12.0 Hz, 1H), 6.49 (brs, 2H), 6.44 (s, 1H), 6.34 (s, 1H), 4.09 (q, J=6.8 Hz, 2H), 2.07 (s, 3H), 1.25 (s, 9H), 1.20 (t, J=6.8 Hz, 3H); MS (ESI) m/z: 479.2 (M+H).

EXAMPLE 236

Using general method B, the carbamate of 5-t-butylisoxazol-3-amine (108 mg, 0.480 mmol) and Example A44 (150 mg, 0.480 mmol) were combined to give the intermediate sulfide, 1-(5-tert-butylisoxazol-3-yl)-3-(4-methyl-3-(8-methyl-2-(methylthio)-7-oxo-7,8-dihydropyrido[2,3-d]pyrimidin-6-yl)phenyl)urea (35 mg, 15% yield). Using a procedure analogous to Example A1, 1-(5-tert-butylisoxazol-3-yl)-3-(4-methyl-3-(8-methyl-2-(methylthio)-7-oxo-7,8-dihydropyrido[2,3-d]pyrimidin-6-yl)phenyl)urea (158 mg, 0.330 mmol) and 2.0N solution of methylamine in THF (1.7 mL) were combined and purified by chromatography (Biotage Si-25 column, 60-100% ethyl acetate/Hex) to afford 1-(5-tert-butylisoxazol-3-yl)-3-(4-methyl-3-(8-methyl-2-(methylamino)-7-oxo-7,8-dihydropyrido[2,3-d]pyrimidin-6-yl)phenyl)urea (49 mg, 32% yield). $^1$H NMR (300 MHz, DMSO-d$_6$): δ 1.26 (s, 9H), 2.06 (s, 3H), 2.90 (s, 3H), 3.53-3.60 (m, 3H), 6.46 (s, 1H), 7.14-7.16 (m, 1H), 7.26-7.28 (m, 1H), 7.32 (s, 1H), 7.67 (s, 1H), 7.65-7.80 (br m, 1H), 8.60-8.65 (m, 1H), 8.72 (s, 1H), 9.47 (s, 1H); MS (ESI) m/z: 462.0 (M+H$^+$).

EXAMPLE 237

Using general method D, Example B40 (50 mg, 0.19 mmol) and Example A12 (56 mg, 0.19 mmol) in presence of DPPA (46 µL, 0.21 mmol) and Et$_3$N (30 µL, 0.21 mmol) were combined to afford 1-(2-tert-butyl-4-morpholinopyrimidin-5-yl)-3-(2-fluoro-5-(8-methyl-2-(methylamino)-7-oxo-7,8-dihydropyrido[2,3-d]pyrimidin-6-yl)phenyl)urea. This was treated with aqueous HCl (0.100 M) to afford 1-(2-tert-butyl-4-morpholinopyrimidin-5-yl)-3-(2-fluoro-5-(8-methyl-2-(methylamino)-7-oxo-7,8-dihydropyrido[2,3-d]pyrimidin-6-yl)phenyl)urea HCl salt (14 mg, 13% yield). $^1$H NMR (400 MHz, DMSO-d$_6$, major isomers): δ 9.17 (s, 1H), 8.90 (brs, 1H), 8.65 (brs, 1H), 8.32 (s, 1H), 8.30 (dd, J= 2.0, and 8.0 Hz, 1H), 7.88 (brs 1H), 7.86 (s, 1H), 7.27 (m, 2H), 4.00 (m, 4H), 3.73 (m, 4H), 3.60 (s, 3H), 2.90 (s, 3H), 1.36 (s, 9H); MS (ESI) m/z: 562.3 (M+H$^+$).

EXAMPLE 238

Using general method D, 3-tert-butyl-1-methyl-1H-pyrazole-5-carboxylic acid (0.061 g, 0.33 mmol) and Example A63 (0.116 g, 0.33 mmol) in presence of triethylamine (0.1 g, 0.97 mmol) and diphenylphospharyl azide (0.14 g, 0.5 mmol) were combined to afford 1-(3-tert-butyl-1-methyl-1H-pyrazol-5-yl)-3-(4-chloro-5-(8-ethyl-2-(methylamino)-7-oxo-7,8-dihydropyrido[2,3-d]pyrimidin-6-yl)-2-fluorophenyl)urea as a white solid (0.045 g, 25% yield). $^1$H NMR (400 MHz, DMSO-d$_6$): δ 8.96-8.95 (m, 2H), 8.61 (s, 1H), 8.17 (d, J= 8.8 Hz, 1H), 7.88-7.86 (m, 1H), 7.74 (s, 1H), 7.56 (d, J= 7.2 Hz, 1H), 6.05 (s, 1H), 4.36-4.31 (m, 2H), 3.59 (s, 3H), 2.89 (d, J=4.4 Hz, 3H), 1.24-1.17 (m, 12H); MS (ESI) m/z: 527.2 (M+H$^+$).

EXAMPLE 239

Using general method D, 3-isopropyl-1-methyl-1H-pyrazole-5-carboxylic acid (0.055 g, 0.33 mmol) and Example A63 (0.114 g, 0.33 mmol) in presence of triethylamine (0.1 g, 0.97 mmol) and diphenylphospharyl azide (0.14 g, 0.5 mmol) were combined to afford 1-(4-chloro-5-(8-ethyl-2-(methylamino)-7-oxo-7,8-dihydropyrido[2,3-d]pyrimidin-6-yl)-2-fluorophenyl)-3-(3-isopropyl-1-methyl-1H-pyrazol-5-yl) urea as a white solid (0.037 g, 22% yield). $^1$H NMR (400 MHz, DMSO-d$_6$): δ 8.98 (s, 1H), 8.96 (s, 1H), 8.61 (s, 1H), 8.16 (d, J=8.4 Hz, 1H), 7.88-7.86 (m, 1H), 7.74 (s, 1H), 7.57 (d, J=10.8 Hz, 1H), 6.01 (s, 1H), 4.36-4.31 (m, 2H), 3.58 (s, 3H), 2.90 (d, J=4.4 Hz, 3H), 2.77-2.70 (m, 1H), 1.22 (t, J=6.8 Hz, 3H), 1.12 (d, J= 6.0 Hz, 6H); MS (ESI) m/z: 513.0 (M+H$^+$).

EXAMPLE 240

Using general method D, Example B45 (100 mg, 0.549 mmol), triethylamine (64 mg, 0.631 mmol), Example A38 (164 mg, 0.549 mmol) and diphenylphosphorylazide (174 mg, 0.631 mmol) were combined to afford 1-(1-tert-butyl-5-methyl-1H-pyrazol-4-yl)-3-(2-fluoro-5-(1-methyl-7-(methylamino)-2-oxo-1,2-dihydro-1,6-naphthyridin-3-yl)phenyl)urea (81 mg, 30% yield). This was converted to the mono mesylate salt (91 mg). $^1$H NMR (300 MHz, DMSO-d$_6$): δ 1.53 (s, 9H), 2.31 (s, 3H), 2.33 (s, 3H), 2.97 (s, 3H), 3.54 (s, 3H), 6.53 (s, 1H), 7.20-7.29 (m, 2H), 7.45 (s, 1H), 7.98 (s, 1H), 8.18-8.35 (br. s, 1H), 8.21 (s, 1H), 8.42 (d, 1H), 8.58 (s, 1H), 8.63 (br. s, 1H); MS (ESI) m/z: 478.3 (M+H$^+$).

EXAMPLE 241

Using general method D, Example B46 (124 mg, 0.525 mmol), triethylamine (61 mg, 0.604 mmol), Example A38 (157 mg, 0.525 mmol) and diphenylphosphorylazide (166 mg, 0.604 mmol) were combined to afford 1-(1-tert-butyl-5-(trifluoromethyl)-1H-pyrazol-4-yl)-3-(2-fluoro-5-(1-methyl-7-(methylamino)-2-oxo-1,2-dihydro-1,6-naphthyridin-3-yl)phenyl)urea (62 mg, 22% yield). This was converted to the mono mesylate salt (55 mg). $^1$H NMR (300 MHz, DMSO-d$_6$): δ 1.57 (m, 9H), 2.29 (s, 3H), 2.95 (s, 3H), 3.54 (s, 3H), 6.46 (s, 1H), 7.24-7.30 (m, 2H), 7.94 (s, 1H), 7.97 (s, 1H), 8.05 (br. s, 1H), 8.39-8.41 (m, 1H), 8.56 (d, 2H), 9.15 (s, 1H); MS (ESI) m/z: 532.0 (M+H$^+$).

EXAMPLE 242

Using general method F, Example A39 (75 mg, 0.239 mmol) and cyclopentyl isocyanate (0.270 ml, 2.396 mmol) were combined to afford 1-cyclopentyl-3-(2-fluoro-4-methyl-5-(8-methyl-2-(methylamino)-7-oxo-7,8-dihydropyrido[2,3-d]pyrimidin-6-yl)phenyl)urea (81 mg, 80% yield) as a white solid. $^1$H NMR (400 MHz, DMSO-d$_6$): δ 8.59 (brs, 1H), 8.05 (d, J=2.4 Hz, 1H), 7.94 (d, J=8.81 Hz, 1H), 7.80 (brq, 1H), 7.64 (s, 1H), 7.05 (d, J=12.8 Hz, 1H), 6.60 (d, J=7.21 Hz, 1H), 3.87 (m, J=6.8 Hz, 1H), 3.59 (brs, 3H), 2.90 (brs, 3H), 2.03 (s, 3H), 1.84-1.75 (m, 2H), 1.64-1.46 (m, 4H), 1.36-1.28 (m, 2H); MS (ESI) m/z: 425.2 (M+H$^+$).

EXAMPLE 243

Using general method B, the carbamate of Example B2 (114 mg, 0.480 mmol) and Example A44 (150 mg, 0.480 mmol) were combined to afford 1-(3-tert-butyl-1-methyl-1H-pyrazol-5-yl)-3-(4-methyl-3-(8-methyl-2-(methylthio)-7-oxo-7,8-dihydropyrido[2,3-d]pyrimidin-6-yl)phenyl)urea as a light yellow solid (217 mg, 92% yield). MS (ESI) m/z: 492.3 (M+H$^+$).

Using a procedure analogous to Example A1, 1-(3-tert-butyl-1-methyl-1H-pyrazol-5-yl)-3-(4-methyl-3-(8-methyl-2-(methylthio)-7-oxo-7,8-dihydropyrido[2,3-d]pyrimidin-6-yl)phenyl)urea (217 mg, 0.441 mmol) and 2.0N methylamine in THF (2.2 mL, 4.41 mmol) were combined and purified by reverse phase chromatography (Biotage C18-25 column, 10-100% acetonitrile/water) and neutralized with 10% sodium carbonate to give 1-(3-tert-butyl-1-methyl-1H-pyrazol-5-yl)-3-(4-methyl-3-(8-methyl-2-(methylamino)-7-oxo-7,8-dihydropyrido[2,3-d]pyrimidin-6-yl)phenyl)urea (60 mg, 28% yield). $^1$H NMR (300 MHz, DMSO-d$_6$): δ 1.15 (s, 9H), 2.06 (s, 3H), 2.90 (s, 3H), 3.53-3.63 (m, 6H), 6.02 (s, 1H), 7.12-7.14 (m, 1H), 7.23-7.26 (m, 1H), 7.34 (s, 1H), 7.66-7.80 (m, 2H), 8.42 (s, 1H), 8.58-8.68 (m, 1H), 8.79 (s, 1H); MS (ESI) m/z: 475.2 (M+H$^+$).

EXAMPLE 244

Using general method C, the TROC carbamate of Example B18 (0.150 g, 0.475 mmol) and Example A64 (0.100 g, 0.317 mmol) were combined to afford 1-(3-tert-butylisoxazol-5-yl)-3-(4-chloro-3-(8-methyl-2-(methylamino)-7-oxo-7,8-dihydropyrido[2,3-d]pyrimidin-6-yl)phenyl)urea (0.055 g, 36%) as a white solid. $^1$H NMR (400 MHz, DMSO-d$_6$): δ 10.20 (s, 1H), 8.99 (s, 1H), 8.62 (s, 1H), 7.88 (m, 1H), 7.77 (s, 1H), 7.56 (t, J=1.4 Hz, 1H), 7.44-7.42 (m, 2H), 6.04 (s, 1H), 3.60 (s, 3H), 2.91 (m, 3H), 1.23 (s, 9H); MS (ESI) m/z: 482.0 (M+H$^+$).

EXAMPLE 245

Using general method D, Example B41 (60 mg, 0.22 mmol) and Example A12 (65 mg, 0.22 mmol) in presence of DPPA (52 μL, 0.26 mmol) and Et$_3$N (34 μL, 0.26 mmol) were combined to afford 1-(2-tert-butyl-4-(3-fluorophenyl)pyrimidin-5-yl)-3-(2-fluoro-5-(8-methyl-2-(methylamino)-7-oxo-7,8-dihydropyrido[2,3-d]pyrimidin-6-yl)phenyl)urea (68 mg, 55% yield). $^1$H NMR (400 MHz, DMSO-d$_6$, major isomer): δ 9.08 (s, 1H), 9.01 (brs, 1H), 8.64 (brs, 1H), 8.62 (brs, 1H), 8.34 (dd, J=2.0, and 8.0 Hz, 1H), 7.85 (s, 1H), 7.81 (m, 1H), 7.59 (m, 3H), 7.38 (m, 1H), 7.28 (m, 2H), 3.61 (s, 3H), 2.90 (d, J=4.8 Hz, 3H), 1.37 (s, 9H); MS (ESI) m/z: 571.3 (M+H$^+$).

EXAMPLE 246

Using general method F, Example A12 (50 mg, 0.167 mmol) and 3,5-dimethylphenyl isocyanate (0.025 ml, 0.175 mmol) were combined and purified by reverse phase chromatography (MeCN (w/0.1% TFA)/H$_2$O (w/0.1% TFA)) to afford 1-(3,5-dimethylphenyl)-3-(2-fluoro-5-(8-methyl-2-(methylamino)-7-oxo-7,8-dihydropyrido[2,3-d]pyrimidin- 6-yl)phenyl)urea (34 mg, 46% yield) as a white solid. $^1$H NMR (400 MHz, DMSO-d$_6$): δ 8.95 (brs, 1H), 8.69 (brs, 1H), 8.57 (brs, 1H), 8.48-8.45 (m, 1H), 7.90 (s, 1H), 7.83 (brq, 1H), 7.29-7.27 (m, 2H), 7.09-7.05 (m, 2H), 6.64-6.61 (m, 1H), 3.60 (brs, 3H), 2.93 (brs, 3H), 2.24 (s, 3H), 2.22 (s, 3H); MS (ESI) m/z: 447.0

EXAMPLE 247

Using general method F, Example A12 (50 mg, 0.167 mmol) and 3,5-dichlorophenyl isocyanate (0.024 ml, 0.175 mmol) were combined to afford 1-(3,5-dichlorophenyl)-3-(2-fluoro-5-(8-methyl-2-(methylamino)-7-oxo-7,8-dihydropyrido[2,3-d]pyrimidin-6-yl)phenyl)urea (70 mg, 86% yield) as a solid. $^1$H NMR (400 MHz, DMSO-d$_6$): δ 9.42 (brs, 1H), 8.75-8.68 (m, 2H), 8.39-8.37 (m, 1H), 7.92 (s, 1H), 7.84 (brq, 1H), 7.54-7.53 (m, 2H), 7.35-7.27 (m, 2H), 7.21-7.19 (m, 1H), 3.64 (brs, 3H), 2.93 (brs, 3H); MS (ESI) m/z: 487.0 (M+H$^+$), 489.0 (M+2+H$^+$).

EXAMPLE 248

Using general method D, Example B45 (69 mg, 0.378 mmol), triethylamine (44 mg, 0.435 mmol), Example A10 (125 mg, 0.378 mmol) and diphenylphosphorylazide (120 mg, 0.435 mmol) were combined and purified by chromatography (Biotage Si-25 column, 50-100% ethyl acetate/hexane—1200 mL) to give 1-(1-tert-butyl-5-methyl-1H-pyrazol-4-yl)-3-(2-fluoro-4-methyl-5-(8-methyl-2-(methylthio)-7-oxo-7,8-dihydropyrido[2,3-d]pyrimidin-6-yl)phenyl)urea as a tan solid (31 mg, 16% yield). MS (ESI) m/z: 510.0 (M+H$^+$).

Using a procedure analogous to Example A1, 1-(1-tert-butyl-5-methyl-1H-pyrazol-4-yl)-3-(2-fluoro-4-methyl-5-(8-methyl-2-(methylthio)-7-oxo-7,8-dihydropyrido[2,3-d]pyrimidin-6-yl)phenyl)urea (31 mg, 0.061 mmol), MCPBA (19 mg, 0.079 mmol) and 2.0N methylamine in THF (0.4 mL) were converted to 1-(1-tert-butyl-5-methyl-1H-pyrazol-4-yl)-3-(2-fluoro-4-methyl-5-(8-methyl-2-(methylamino)-7-oxo-7,8-dihydropyrido[2,3-d]pyrimidin-6-yl)phenyl)urea (15 mg, 50% yield). $^1$H NMR (300 MHz, DMSO-d$_6$), δ 1.60 (s, 9H), 2.20 (s, 3H), 2.35 (s, 3H), 2.95 (s, 3H), 3.60-3.70 (m, 3H), 7.20-7.25 (m, 1H), 7.50 (s, 1H), 7.70 (s, 1H), 7.70-7.90 (m, 1H), 8.05 (m, 1H), 8.20 (s, 1H), 8.55 (m, 1H), 8.70-8.80 (m, 1H); MS (ESI) m/z: 493.0 (M+H$^+$).

EXAMPLE 249

Using general method D, quinoline-5-carboxylic acid (92 mg, 0.529 mmol), triethylamine (64 mg, 0.635 mmol), Example A22 (150 mg, 0.529 mmol) and diphenylphosphorylazide (175 mg, 0.635 mmol) were combined to afford 1-(5-(1-ethyl-2-oxo-1,2-dihydro-1,6-naphthyridin-3-yl)-2-fluorophenyl)-3-(quinolin-5-yl)urea. This was converted to the dichloride salt using 4N HCl/dioxane, 1-(5-(1-ethyl-2-oxo-1,2-dihydro-1,6-naphthyridin-3-yl)-2-fluorophenyl)-3-(quinolin-5-yl)urea dihydrochloride (139 mg, 49% yield). $^1$H NMR (300 MHz, DMSO-d$_6$): δ 1.29 (t, 3H), 4.37 (q, 2H), 7.40-7.43 (m, 2H), 7.86-8.00 (m, 4H), 8.29-8.35 (m, 2H), 8.57 (d, 1H), 8.75-8.80 (m, 1H), 9.14-9.19 (m, 2H), 9.29 (s, 1H), 9.53 (s, 1H), 10.01 (s, 1H); MS (ESI) m/z: 454.0 (M+H$^+$).

EXAMPLE 250

Using general method D, Example B46 (101 mg, 0.428 mmol), triethylamine (52 mg, 0.513 mmol), Example A17 (150 mg, 0.428 mmol) and diphenylphosphorylazide (141 mg, 0.513 mmol) were combined to afford 1-(1-tert-butyl-5-(trifluoromethyl)-1H-pyrazol-4-yl)-3-(4-chloro-2-fluoro-5-(8-methyl-2-(methylthio)-7-oxo-7,8-dihydropyrido[2,3-d]pyrimidin-6-yl)phenyl)urea (230 mg, 92% yield). MS (ESI) m/z: 584.0 (M+Na$^+$).

Using a procedure analogous to Example A1, 1-(1-tert-butyl-5-(trifluoromethyl)-1H-pyrazol-4-yl)-3-(4-chloro-2-fluoro-5-(8-methyl-2-(methylthio)-7-oxo-7,8-dihydropyrido[2,3-d]pyrimidin-6-yl)phenyl)urea (230 mg, 0.394 mmol), MCPBA (126 mg, 0.512 mmol) and 2.0N methylamine in THF (1.97 mL, 3.94 mmol) were combined to afford 1-(1-tert-butyl-5-(trifluoromethyl)-1H-pyrazol-4-yl)-3-(4-chloro-2-fluoro-5-(8-methyl-2-(methylamino)-7-oxo-7,8-dihydropyrido[2,3-d]pyrimidin-6-yl)phenyl)urea (127 mg, 56% yield). $^1$H NMR (300 MHz, DMSO-d$_6$), δ 1.59 (s, 9H), 2.92 (s, 3H), 3.53-3.62 (m, 3H), 7.55-7.65 (m, 1H), 7.78 (s, 1H), 7.80-7.90 (m, 1H), 7.93 (s, 1H), 8.15-8.25 (m, 1H), 8.45-8.70 (m, 2H), 9.25 (s, 1H); MS (ESI) m/z: 567.0 (M+H$^+$).

EXAMPLE 251

Using general method D, Example B42 (60 mg, 0.23 mmol) and Example A12 (70 mg, 0.23 mmol) in presence of DPPA (55 μL, 0.26 mmol) and Et$_3$N (36 μL, 0.26 mmol) were combined to afford 1-(2-tert-butyl-4-(pyridin-3-yl)pyrimidin-5-yl)-3-(2-fluoro-5-(8-methyl-2-(methylamino)-7-oxo-7,8-dihydropyrido[2,3-d]pyrimidin-6-yl)phenyl)urea (78 mg, 60% yield). $^1$H NMR (400 MHz, DMSO-d$_6$, major isomer): δ 9.10 (s, 1H), 9.02 (brs, 1H), 8.96 (m, 1H), 8.75 (brs, 1H), 8.72 (dd, J=2.0, and 5.2 Hz, 1H), 8.65 (brs, 1H), 8.35 (dd, J=2.0, and 7.6 Hz, 1H), 8.19 (dt, J=1.6, and 7.6 Hz, 1H), 7.86 (s, 1H), 7.83 (m, 1H), 7.61 (m, 1H), 7.29 (m, 2H), 3.62 (s, 3H), 2.92 (d, J=4.0 Hz, 3H), 1.40 (s, 9H); MS (ESI) m/z: 554.2 (M+H$^+$).

EXAMPLE 252

Using general method D, B46 (89 mg, 0.378 mmol), triethylamine (44 mg, 0.435 mmol), Example A10 (125 mg, 0.378 mmol) and diphenylphosphorylazide (120 mg, 0.435 mmol) were combined to afford 1-(1-tert-butyl-5-(trifluoromethyl)-1H-pyrazol-4-yl)-3-(2-fluoro-4-methyl-5-(8-methyl-2-(methylthio)-7-oxo-7,8-dihydropyrido[2,3-d]pyrimidin-6-yl)phenyl)urea (124 mg, 58% yield). MS (ESI) m/z: 564.0 (M+H$^+$).

Using a procedure analogous to Example A1, 1-(1-tert-butyl-5-(trifluoromethyl)-1H-pyrazol-4-yl)-3-(2-fluoro-4-methyl-5-(8-methyl-2-(methylthio)-7-oxo-7,8-dihydropyrido[2,3-d]pyrimidin-6-yl)phenyl)urea (148 mg, 0.263 mmol), MCPBA (81 mg, 0.328 mmol) and 2.0N methylamine in THF (1.3 mL) were combined to afford 1-(1-tert-butyl-5-(trifluoromethyl)-1H-pyrazol-4-yl)-3-(2-fluoro-4-methyl-5-(8-methyl-2-(methylamino)-7-oxo-7,8-dihydropyrido[2,3-d]pyrimidin-6-yl)phenyl)urea (103 mg, 71% yield). $^1$H NMR (300 MHz, DMSO-d$_6$): δ 1.59 (s, 9H), 2.08 (s, 3H), 2.92 (s, 3H), 3.55-3.62 (m, 3H), 7.25-7.30 (m, 1H), 7.69 (s, 1H), 7.70-7.80 (m, 1H), 7.93 (s, 1H), 7.95-8.05 (m, 1H), 8.51 (s, 1H), 8.20-8.25 (m, 1H), 9.04 (s, 1H); MS (ESI) m/z: 547.2 (M+H$^+$).

EXAMPLE 253

Using general method D, Example B43 (50 mg, 0.18 mmol) and Example A12 (54 mg, 0.18 mmol) in presence of DPPA (43 μL, 0.20 mmol) and Et$_3$N (28 μL, 0.20 mmol) were combined to afford 1-(2-tert-butyl-4-(4-methylpiperazin-1-yl)pyrimidin-5-yl)-3-(2-fluoro-5-(8-methyl-2-(methylamino)-7-oxo-7,8-dihydropyrido[2,3-d]pyrimidin-6-yl)phenyl)urea (78 mg, 60% yield). This was then treated with aqueous HCl (0.100 M) to afford 1-(2-tert-butyl-4-(4-methylpiperazin-1-yl)pyrimidin-5-yl)-3-(2-fluoro-5-(8-methyl-2-(methylamino)-7-oxo-7,8-dihydropyrido[2,3-d]pyrimidin-6-yl)phenyl)urea HCl salt (27 mg, 37% yield). $^1$H NMR (400 MHz, DMSO-$d_6$, major isomer): δ 9.92 (s, 1H), 8.64 (brs, 1H), 8.36 (dd, J=1.2, and 8.0 Hz, 1H), 8.33 (s, 1H), 7.20 (s, 1H), 7.85 (s, 1H), 7.81 (m, 1H), 7.28 (m, 2H),

EXAMPLE 254

Using general method F, Example A39 (50 mg, 0.160 mmol) and 1-isocyanato-1,2,3,4-tetrahydronaphthalene (0.0275 mL, 0.175 mmol) were combined to afford 1-(2-fluoro-4-methyl-5-(8-methyl-2-(methylamino)-7-oxo-7,8-dihydropyrido[2,3-d]pyrimidin-6-yl)phenyl)-3-(1,2,3,4-tetrahydronaphthalen-1-yl)urea (73 mg, 94% yield) as a white solid. $^1$H NMR (400 MHz, DMSO-$d_6$): δ 8.69-8.61 (m, 1H), 8.15 (brs, 1H), 8.01 (d, J=8.8 Hz, 1H), 7.82 (brq, 1H), 7.68 (s, 1H), 7.27-7.24 (m, 1H), 7.17-7.14 (m, 2H), 7.13-7.06 (m, 2H), 6.95 (d, J=8.41 Hz, 1H), 4.81 (m, 1H), 3.59 (brs, 3H), 2.92 (brs, 3H), 2.80-2.65 (m, 2H), 2.05 (s, 3H), 1.91-1.87 (m, 1H), 1.81-1.71 (m, 3H); MS (ESI) m/z: 487.3 (M+H$^+$).

EXAMPLE 255

Using general method D, Example B45 (78 mg, 0.428 mmol), triethylamine (52 mg, 0.513 mmol), Example A17 (150 mg, 0.428 mmol) and diphenylphosphorylazide (141 mg, 0.513 mmol) were combined to afford 1-(1-tert-butyl-5-methyl-1H-pyrazol-4-yl)-3-(4-chloro-2-fluoro-5-(8-methyl-2-(methylthio)-7-oxo-7,8-dihydropyrido[2,3-d]pyrimidin-6-yl)phenyl)urea (80 mg, 35% yield). MS (ESI) m/z: 530.02 (M$^+$).

Using a procedure analogous to Example A1, 1-(1-tert-butyl-5-methyl-1H-pyrazol-4-yl)-3-(4-chloro-2-fluoro-5-(8-methyl-2-(methylthio)-7-oxo-7,8-dihydropyrido[2,3-d]pyrimidin-6-yl)phenyl)urea (80 mg, 0.151 mmol), MCPBA (47 mg, 0.189 mmol) and 2.0N methylamine in THF (0.8 mL) were combined to afford 1-(1-tert-butyl-5-methyl-1H-pyrazol-4-yl)-3-(4-chloro-2-fluoro-5-(8-methyl-2-(methylamino)-7-oxo-7,8-dihydropyrido[2,3-d]pyrimidin-6-yl)phenyl)urea (48 mg, 62% yield). $^1$H NMR (300 MHz, DMSO-$d_6$): δ 1.49 (s, 9H), 2.27 (s, 3H), 2.89 (s, 3H), 3.49-3.56 (m, 3H), 7.39 (s, 1H), 7.49 (d, 1H), 7.74 (s, 1H), 7.94 (br. s, 1H), 8.17 (d, 1H), 8.29 (s, 1H), 8.62-8.74 (m, 2H); MS (ESI) m/z: 513.0 (M+H$^+$).

EXAMPLE 256

Using general method D, Example B45 (84 mg, 0.460 mmol), triethylamine (56 mg, 0.552 mmol), Example A30 (150 mg, 0.460 mmol) and DPPA (152 mg, 0.552 mmol) were combined to afford 1-(1-tert-butyl-5-methyl-1H-pyrazol-4-yl)-3-(5-(1-ethyl-7-(methylamino)-2-oxo-1,2-dihydro-1,6-naphthyridin-3-yl)-2-fluoro-4-methylphenyl)urea (52 mg, 22% yield). $^1$H NMR (300 MHz, DMSO-$d_6$): δ 1.17 (t, 3H), 1.49 (s, 9H), 2.03 (s, 3H), 2.26 (s, 3H), 2.83 (s, 3H), 4.11 (q, 2H), 6.23 (s, 1H), 7.05 (br. s, 1H), 7.08 (d, 1H), 7.38 (s, 1H), 7.63 (s, 1H), 7.92 (d, 1H), 8.08 (s, 1H), 8.38 (s, 1H), 8.40 (br. s, 1H); MS (ESI) m/z: 506.2 (M+H$^+$).

EXAMPLE 257

((R)-Aminoindan hydrochloride (81 mg, 0.475 mmol) and triphosgene (56.4 mg, 0.19 mmol) were combined in toluene (5 ml) and stirred with heating at 110° C. After 3 h, Example A39 (100 mg, 0.319 mmol) was added and the reaction was heated overnight at 110° C. The reaction was cooled to RT, diluted with H$_2$O and extracted with EtOAc (2×). The combined organics were washed with satd. NaHCO$_3$ (2×), H$_2$O (1×), and brine (1×), dried (MgSO$_4$), filtered and evaporated. The crude residue was triturated with CH$_2$Cl$_2$/hexanes. The solids were collected by filtration, rinsed well with hexanes and dried on the filter to afford (R)-1-(2,3-dihydro-1H-inden-1-yl)-3-(2-fluoro-4-methyl-5-(8-methyl-2-(methylamino)-7-oxo-7,8-dihydropyrido[2,3-d]pyrimidin-6-yl)phenyl)urea (92 mg, 62% yield) as a pale tan solid. $^1$H NMR (400 MHz, DMSO-$d_6$): δ 8.61 (s, 1H), 8.19 (brs, 1H), 7.99 (d, J=8.4 Hz, 1H), 7.80 (brq, 1H), 7.67 (s, 1H), 7.29-7.16 (m, 4H), 7.07 (d, J=12.4 Hz, 1H), 6.93 (d, J=8 Hz, 1H), 5.17-5.07 (m, 1H), 3.58 (brs, 3H), 2.90 (brs, 3H), 2.87-2.74 (m, 1H), 2.48-2.39 (m, 1H), 2.04 (s, 3H), 1.77-1.67 (m, 2H); MS (ESI) m/z: 473.0 (M+H$^+$).

EXAMPLE 258

Using a procedure analogous to Example 257, (S)-aminoindan HCl (81 mg, 0.477 mmol), triphosgene (71.0 mg, 0.239 mmol) and Example A39 (100 mg, 0.319 mmol) were combined and purified by flash column chromatography (EtOAc/hexanes) to afford (S)-1-(2,3-dihydro-1H-inden-1-yl)-3-(2-fluoro-4-methyl-5-(8-methyl-2-(methylamino)-7-oxo-7,8-dihydropyrido[2,3-d]pyrimidin-6-yl)phenyl)urea (41 mg, 27% yield) as an off-white solid. $^1$H NMR (400 MHz, DMSO-$d_6$): δ 8.61 (s, 1H), 8.19 (brs, 1H), 7.99 (d, J=8.4 Hz, 1H), 7.80 (brq, 1H), 7.67 (s, 1H), 7.29-7.16 (m, 4H), 7.07 (d, J=12.4 Hz, 1H), 6.93 (d, J=8 Hz, 1H), 5.17-5.07 (m, 1H), 3.58 (brs, 3H), 2.90 (brs, 3H), 2.87-2.74 (m, 1H), 2.48-2.39 (m, 1H), 2.04 (s, 3H), 1.77-1.67 (m, 2H); MS (ESI) m/z: 473.0 (M+H$^+$).

EXAMPLE 259

Using general method C, the TROC carbamate of Example B18 (80 mg, 0.25 mmol) and Example A36 (91 mg, 0.25 mmol) were combined to afford 1-(3-tert-butylisoxazol-5-yl)-3-(2-fluoro-5-(7-(methylamino)-2-oxo-1-phenyl-1,2-dihydro-1,6-naphthyridin-3-yl)phenyl)urea (31 mg, 25% yield), $^1$H NMR (400 MHz, DMSO-$d_6$): δ 10.4 (s, 1H), 8.75 (brs, 1H), 8.52 (s, 1H), 8.45 (dd, J=2.0, and 8.0 Hz, 1H), 8.04 (s, 1H), 7.2-7.7 (m, 7H), 7.01 (q, J=4.4 Hz, 1H), 6.08 (s, 1H), 5.32 (s, 1H), 2.69 (d, J=4.4 Hz, 2H), 1.25 (s, 9H); MS (ESI) m/z: 527.0 (M+H$^+$).

EXAMPLE 260

Using general method C, the TROC carbamate of Example B18 (100 mg, 0.32 mmol) and Example A21 (122 mg, 0.32 mmol) were combined to afford 1-(3-tert-butylisoxazol-5-yl)-3-(5-(8-cyclopentyl-2-(methylthio)-7-oxo-7,8-dihydropyrido[2,3-d]pyrimidin-6-yl)-2-fluoro-4-methylphenyl)urea (115 mg, 66% yield). MS (ESI) m/z: 551.0 (M+H$^+$).

Using a procedure analogous to Example A1, 1-(3-tert-butylisoxazol-5-yl)-3-(5-(8-cyclopentyl-2-(methylthio)-7-oxo-7,8-dihydropyrido[2,3-d]pyrimidin-6-yl)-2-fluoro-4-methylphenyl)urea (115 mg, 0.21 mmol) was treated with mCPBA (70% wt, 62 mg, 0.25 mmol) and then 2 M methylamine (0.42 mL, 0.84 mmol) to afford 1-(3-tert-butylisoxazol-5-yl)-3-(5-(8-cyclopentyl-2-(methylamino)-7-oxo-7,8-dihydropyrido[2,3-d]pyrimidin-6-yl)-2-fluoro-4-methylphenyl)urea (91 mg, 82% yield). $^1$H NMR (400 MHz, DMSO-$d_6$, major isomer): δ 10.3 (s, 1H), 8.69 (d, J=2.0 Hz, 1H), 8.61 (brs, 1H), 7.89 (d, J=8.4 Hz, 1H), 7.79 (brs, 1H), 7.65 (s, 1H), 7.18 (d, J=12.4 Hz, 1H), 6.03 (s, 1H), 5.94 (m, 1H), 2.91 (d, J=4.8 Hz, 3H), 2.33 (m, 2H), 2.09 (s, 3H), 1.98 (m, 2H), 1.81 (m, 2H), 1.63 (m, 2H), 1.24 (s, 9H); MS (ESI) m/z: 534.2 (M+H$^+$).

EXAMPLE 261

Using general method C, the TROC carbamate of Example B18 (100 mg, 0.32 mmol), and Example A19 (120 mg, 0.32 mmol) were combined to afford 1-(3-tert-butylisoxazol-5-yl)-3-(5-(8-cyclopentyl-2-(methylthio)-7-oxo-7,8-dihydropyrido[2,3-d]pyrimidin-6-yl)-2-fluorophenyl)urea (105 mg, 62% yield); MS (ESI) m/z: 537. (M+H$^+$).

Using a procedure analogous to Example A1, 1-(3-tert-butylisoxazol-5-yl)-3-(5-(8-cyclopentyl-2-(methylthio)-7-oxo-7,8-dihydropyrido[2,3-d]pyrimidin-6-yl)-2-fluorophenyl)urea (105 mg, 0.20 mmol) was treated with mCPBA (70% wt, 58 mg, 0.24 mmol) and then 2 M methylamine (0.39 mL, 0.78 mmol) to afford 1-(3-tert-butylisoxazol-5-yl)-3-(5-(8-cyclopentyl-2-(methylamino)-7-oxo-7,8-dihydropyrido[2,3-d]pyrimidin (61 mg, 60% yield). $^1$H NMR (400 MHz, DMSO-d$_6$, major isomer): δ 10.4 (s, 1H), 8.80 (d, J=2.0 Hz, 1H), 8.68 (s, 1H), 8.36 (m, 1H), 7.88 (s, 1H), 7.85 (m, 1H), 7.35 (m, 2H), 6.11 (s, 1H), 5.97 (m, 1H), 2.93 (d, J=4.8 Hz, 3H), 2.42 (m, 2H), 2.03 (s, 3H), 1.98 (m, 2H), 1.81 (m, 2H), 1.65 (m, 2H), 1.28 (s, 9H); MS (ESI) m/z: 520.2 (M+H$^+$).

EXAMPLE 262

Using general method D, Example B50 (0.061 g, 0.34 mmol) and Example A38 (0.1 g, 0.34 mmol) in presence of triethylamine (0.1 g, 1 mmol) and DPPA (0.18 g, 0.67 mmol) were combined to afford 1-(1-cyclopentyl-1H-pyrazol-4-yl)-3-(2-fluoro-5-(1-methyl-7-(methylamino)-2-oxo-1,2-dihydro-1,6-naphthyridin-3-yl)phenyl)urea as a white solid (0.061 g, 38% yield). $^1$H NMR (400 MHz, DMSO-d$_4$): δ 8.66 (s, 1H), 8.42 (s, 1H), 8.39 (s, 1H), 8.35-8.33 (m, 1H), 7.79 (s, 1H), 7.73 (s, 1H), 7.32 (s, 1H), 7.18-7.16 (m, 2H), 7.03-7.00 (m, 1H), 6.11 (s, 1H), 4.58-4.51 (m, 1H), 3.47 (s, 3H), 2.80 (d, J=4.8 Hz, 3H), 2.00-1.93 (m, 2H), 1.85-1.64 (m, 4H), 1.59-1.50 (m, 2H); MS (ESI) m/z: 476.2 (M+H$^+$).

EXAMPLE 263

Using general method F, 1-isocyanatonaphthalene (0.051 g, 0.3 mmol) and Example A30 (0.1 g, 0.3 mmol) were combined to afford 1-(5-(1-ethyl-7-(methylamino)-2-oxo-1,2-dihydro-1,6-naphthyridin-3-yl)-2-fluoro-4-methylphenyl)-3-(naphthalen-1-yl)urea as a white solid (0.115 g, 77% yield). $^1$H NMR (400 MHz, DMSO-d$_6$): δ 9.16 (s, 1H), 9.05 (s, 1H), 8.45 (s, 1H), 8.19 (d, J=8.4 Hz, 1H), 8.08-8.04 (m, 2H), 7.96 (d, J=7.6 Hz, 1H), 7.72 (s, 1H), 7.67-7.58 (m, 3H), 7.47 (t, J=8.0 Hz, 1H), 7.21 (d, J=12.4 Hz, 1H), 7.05-7.02 (m, 1H), 6.28 (s, 1H), 4.21-4.16 (m, 2H), 2.89 (d, J=4.8 Hz, 3H), 2.12 (s, 3H), 1.25 (t, J=6.8 Hz, 3H); MS (ESI) m/z: 496.3 (M+H$^+$).

EXAMPLE 264

Using general method C, the TROC carbamate of Example B18 (100 mg, 0.32 mmol) and Example A59 (110 mg, 0.32 mmol) were combined to afford 1-(3-tert-butylisoxazol-5-yl)-3-(2-fluoro-5-(8-isopropyl-2-(methylthio)-7-oxo-7,8-dihydropyrido[2,3-d]pyrimidin-6-yl)phenyl)urea (90 mg, 56% yield). MS (ESI) m/z: 511.0 (M+H$^+$).

Using a procedure analogous to Example A1, 1-(3-tert-butylisoxazol-5-yl)-3-(2-fluoro-5-(8-isopropyl-2-(methylthio)-7-oxo-7,8-dihydropyrido[2,3-d]pyrimidin-6-yl)phenyl)urea (87 mg, 0.17 mmol) was treated with mCPBA (70% wt, 50 mg, 0.20 mmol) and then 2 M methylamine (0.34 mL, 0.68 mmol) to afford 1-(3-tert-butylisoxazol-5-yl)-3-(2-fluoro-5-(8-isopropyl-2-(methylamino)-7-oxo-7,8-dihydropyrido[2,3-d]pyrimidin-6-yl)phenyl)urea (48 mg, 57% yield). $^1$H NMR (400 MHz, DMSO-d$_6$, major isomer): δ 10.4 (s, 1H), 8.82 (d, J=2.0 Hz, 1H), 8.69 (s, 1H), 8.42 (brd, J=8.0 Hz, 1H), 7.89 (s, 1H), 7.85 (q, J=4A Hz, 1H), 7.36 (m, 2H), 6.14 (s, 1H), 5.83 (brs, 1H), 2.97 (d, J=4A Hz, 3H), 1.66 (d, J=6.4 Hz, 6H), 1.30 (s, 9H); MS (ESI) m/z: 494.2 (M+H$^+$).

EXAMPLE 265

To a stirring solution of Example A39 (0.100 g, 0.319 mmol) in CH$_2$Cl$_2$ (5 ml) at 0° C. was rapidly added 20 wt % COCl$_2$ in PhMe (0.185 ml, 0.351 mmol). After 10 min at 0° C., Et$_3$N (0.200 ml, 1.436 mmol) was then added. The reaction was stirred at 0° C. for another 10 min and then treated with 8-methyl-8-azabicyclo[3.2.1]octan-3-amine dihydrochloride (0.068 g, 0.319 mmol). The reaction was stirred at RT overnight. The reaction was diluted generously with CH$_2$Cl$_2$ and washed with brine (2×). The combined aqueous were back-extracted with CH$_2$Cl$_2$ (2×). The combined organics were washed with brine (1×), dried (Na$_2$SO$_4$), filtered, evaporated and purified by reverse phase chromatography (MeCN (w/0.1% TFA)/H2O (w/0.1% TFA)). The TFA salt thus obtained was converted to the free base in the presence of MP-Carbonate resin to afford 1-(2-fluoro-4-methyl-5-(8-methyl-2-(methylamino)-7-oxo-7,8-dihydropyrido[2,3-d]pyrimidin-6-yl)phenyl)-3-(8-methyl-8-aza-bicyclo[3.2.1]octan-3-yl)urea (43 mg, 28% yield) as a white solid. $^1$H NMR (400 MHz, DMSO-d$_6$): δ 9.37 (brs, 1H), 8.60 (brs, 1H), 8.40 (brs, 1H), 7.94 (d, J=8.8 Hz, 1H), 7.78 (brq, 1H), 7.64 (s, 1H), 7.09 (d, J=12.4 Hz, 1H), 6.86-6.84 (m, 1H), 3.85-3.78 (m, 1H), 3.63-3.51 (brs, 3H), 2.91 (brs, 3H), 2.69 (brs, 3H), 2.32-2.30 (m, 6H), 2.05 (s, 3H), 1.95-1.91 (m, 2H); MS (ESI) m/z: 480.2 (M+H$^+$).

EXAMPLE 266

Using general method F, 1-isocyanato-3-(trifluoromethyl) benzene (0.055 ml, 0.401 mmol) and Example A58 (0.131 g, 0.401 mmol) were combined and purified by flash column chromatography (EtOAc/hexanes) and then by reverse phase chromatography (MeCN (w/0.1% TFA)/H$_2$O (w/0.1% TFA)). The TFA salt thus obtained was converted to the free base with MP-Carbonate resin to afford 1-(2-fluoro-5-(1-isopropyl-7-(methylamino)-2-oxo-1,2-dihydro-1,6-naphthyridin-3-yl)phenyl)-3-(3-(trifluoromethyl)phenyl)urea (70 mg, 34% yield) as a pale yellow solid, $^1$H NMR (400 MHz, DMSO-d$_6$): δ 9.46 (s, 1H), 8.71 (s, 1H), 8.49 (s, 1H), 8.32 (d, J=8.4 Hz, 1H), 8.05 (s, 1H), 7.88 (s, 1H), 7.53-7.49 (m, 3H), 7.33-7.27 (m, 3H), 6.80 (s, 1H), 6.58 (brs, 1H), 2.91 (brs, 3H), 1.53 (d, J=6.8 Hz, 6H); MS (ESI) m/z: 514.0 (M+H$^+$).

EXAMPLE 267

Using general method F, cyclohexyl isocyanate (0.051 ml, 0.399 mmol) and Example A58 (0.130 g, 0.399 mmol) were combined and purified directly by reverse phase chromatography (MeCN (w/0.1% TFA)/H$_2$O (w/0.1% TFA)) to give impure product after basification (2M Na2CO3) and extraction into EtOAc. The impure product was re-purified by flash column chromatography (EtOAc/hexanes) to afford 1-cyclohexyl-3-(2-fluoro-5-(1-isopropyl-7-(methylamino)-2-oxo-1,2-dihydro-1,6-naphthyridin-3-yl)phenyl)urea (40 mg, 22% yield) as a fluffy white solid. $^1$H NMR (400 MHz, DMSO-d$_6$): δ 8.41 (s, 1H), 8.34 (d, J=8.4 Hz, 1H), 8.18 (brs, 1H), 7.74 (s, 1H), 7.17-7.15 (m, 2H), 6.95 (m, 1H), 6.86 (s, 1H), 6.59 (d, J=7.6 Hz, 1H), 6.43 (brs, 1H), 3.47-3.45 (m, 1H), 2.85 (d, J=4.80 Hz, 3H), 1.80-1.77 (m, 2H), 1.66-1.63 (m, 2H)< 1.52 (d, J=6.8 Hz, 6H), 1.34-1.14 (m, 6H); MS (ESI) m/z: 452.2 (M+H$^+$).

EXAMPLE 268

Using a procedure analogous to Example 265, Example A39 (0.100 g, 0.319 mmol), 20 wt % COCl$_2$ in PhMe (0.185 ml, 0.351 mmol) and 1-methylpiperidin-4-amine (0.036 g, 0.319 mmol) were combined to afford 1-(2-fluoro-4-methyl-5-(8-methyl-2-(methylamino)-7-oxo-7,8-dihydropyrido[2,3-d]pyrimidin-6-yl)phenyl)-3-(1-methylpiperidin-4-yl)urea (63 mg, 44% yield) as a white solid. $^1$H NMR (400 MHz, DMSO-d$_6$): δ 9.37 (brs, 1H), 8.60 (brs, 1H), 8.40 (brs, 1H), 7.94 (d, J=8.8 Hz, 1H), 7.78 (brq, 1H), 7.64 (s, 1H), 7.09 (d, J=12.4 Hz, 1H), 6.86-6.84 (m, 1H), 3.69 (brs, 3H), 3.52-3.42 (m, 1H), 3.22-3.08 (m, 4H), 2.91 (brs, 3H), 2.81 (brs, 3H), 2.040 (s, 3H), 2.02-1.79 (m, 4H); MS (ESI) m/z: 454.2 (M+H$^+$).

EXAMPLE 269

Using general method F, 1-isocyanatonaphthalene (0.045 g, 0.26 mmol) and Example A24 (0.1 g, 0.3 mmol) were combined to afford 1-(5-(1-ethyl-7-(methylamino)-2-oxo-1,2-dihydro-1,6-naphthyridin-3-yl)-2-fluorophenyl)-3-(naphthalen-1-yl)urea as a white solid (0.062 g, 48% yield). $^1$H NMR (400 MHz, DMSO-d$_4$): δ 9.23 (s, 1H), 9.14 (s, 1H), 8.56-8.54 (m, 1H), 8.52 (s, 1H), 8.23 (d, J=8.4 Hz, 1H), 8.11 (d, J=7.6 Hz, 1H), 8.09 (d, J=7.6 Hz, 1H), 7.93 (s, 1H), 7.71-7.59 (m, 3H), 7.53 (t, J=8.0 Hz, 1H), 7.36-7.34 (m, 2H), 7.10-7.07 (m 1H), 6.29 (s, 1H), 4.23 (q, J=6.8 Hz, 2H), 2.92 (d, J=4.8 Hz, 3H), 1.28 (t, J=7.2 Hz, 3H); MS (ESI) m/z: 482.0 (M+H$^+$).

EXAMPLE 270

Using general method D, Example B47 (0.071 g, 0.3 mmol) and Example A12 (0.1 g, 0.33 mmol; DP-2201) in presence of triethylamine (0.09 g, 0.89 mmol) and DPPA (0.16 g, 0.59 mmol) were combined to afford 1-(1-(2-(dimethylamino)-2-oxoethyl)-5-isopropyl-1H-pyrazol-3-yl)-3-(2-fluoro-5-(8-methyl-2-(methylamino)-7-oxo-7,8-dihydropyrido[2,3-d]pyrimidin-6-yl)phenyl)urea as a white solid (0.075 g, 47% yield). $^1$H NMR (400 MHz, DMSO-d$_6$): δ 9.29 (s, 1H), 8.73 (s, 1H), 8.53 (d, J=8.4 Hz, 1H), 7.95 (s, 1H), 7.90-7.87 (m, 1H), 7.34-7.29 (m, 2H), 6.15-6.10 (m, 1H), 4.98 (s, 2H), 3.69 (s, 3H), 3.10 (s, 3H), 2.97 (d, J=4.8 Hz, 3H), 2.90-2.85 (m, 4H), 1.20 (d, J=6.4 Hz, 6H); MS (ESI) m/z: 536.2 (M+H$^+$).

EXAMPLE 271

Using general method D, Example B44 (70 mg, 0.19 mmol) and Example A4 (60 mg, 0.19 mmol) in presence of DPPA (55 μL, 0.21 mmol) and Et$_3$N (30 μL, 0.21 mmol) were combined to afford tert-butyl 4-(2-tert-butyl-5-(3-(5-(8-ethyl-2-(methylamino)-7-oxo-7,8-dihydropyrido[2,3-d]pyrimidin-6-yl)-2-fluorophenyl)ureido)pyrimidin-4-yl)piperazine-1-carboxylate (50 mg, 39% yield). This was then treated with HCl (4.0 M, in dioxane) to afford 1-(2-tert-butyl-4-(piperazin-1-yl)pyrimidin-5-yl)-3-(5-(8-ethyl-2-(methylamino)-7-oxo-7,8-dihydropyrido[2,3-d]pyrimidin-6-yl)-2-fluorophenyl)urea HCl salt (40 mg, 94% yield). $^1$H NMR (400 MHz, DMSO-d$_6$, major isomer): δ 9.72 (brs, 1H), 9.66 (brs, 1H), 8.82 (brs, 1H), 8.58 (s, 1H), 8.38 (dd, J=1.6, and 7.6 Hz, 1H), 8.11 (brs, 1H), 7.98 (s, 1H), 7.38 (m, 2H), 4.44 (brs, 2H), 4.29 (brm, 4H), 3.35 (brm, 4H), 1.47 (s, 9H), 1.31 (brm, 3H); MS (ESI) m/z: 575.2 (M+H$^+$).

EXAMPLE 272

Using general method B, the carbamate of Example B31 (0.123 g, 0.493 mmol) and Example A3 (0.130 g, 0.411 mmol) were combined to afford 1-(3-cyclopentyl-1-methyl-1H-pyrazol-5-yl)-3-(2-fluoro-5-(8-methyl-2-(methylthio)-7-oxo-7,8-dihydropyrido[2,3-d]pyrimidin-6-yl)phenyl)urea (0.068 g, 33%) as a white solid. MS (ESI) m/z: 508.0 (M+H$^+$).

Using a procedure analogous to Example A1, 1-(3-cyclopentyl-1-methyl-1H-pyrazol-5-yl)-3-(2-fluoro-5-(8-methyl-2-(methylthio)-7-oxo-7,8-dihydropyrido[2,3-d]pyrimidin-6-yl)phenyl)urea (0.068 g, 0.134 mmol) and MeNH$_2$ (2.0 M in THF, 1.4 mL) were combined to afford 1-(3-cyclopentyl-1-methyl-1H-pyrazol-5-yl)-3-(2-fluoro-5-(8-methyl-2-(methylamino)-7-oxo-7,8-dihydropyrido[2,3-d]pyrimidin-6-yl)phenyl)urea (0.013 g, 20%) as white solid. $^1$H NMR (400 MHz, DMSO-d$_6$): δ 9.02 (s, 1H), 8.89 (d, J=2.0 Hz, 1H), 8.73 (s, 1H), 8.49 (d, J=7.6 Hz, 1H), 7.95 (m, 1H), 7.92 (m, 1H), 7.38-7.34 (m, 2H), 6.11 (s, 1H), 3.70-3.68 (m, 6H), 2.99-2.94 (m, 4H), 1.99-1.94 (m, 2H), 1.73-1.68 (m, 2H), 1.67-1.60 (m, 4H); MS (ESI) m/z: 491.2 (M+H$^+$).

EXAMPLE 273

Using general method D, 2-fluoro-5-(trifluoromethyl)benzoic acid (75 mg, 0.360 mmol), DPPA (0.116 ml, 0.541 mmol) and Example A58 (129 mg, 0.396 mmol) were combined and purified by flash column chromatography (10% EtOAc/hexanes to 100% EtOAc) to afford 1-(2-fluoro-5-(1-isopropyl-7-(methylamino)-2-oxo-1,2-dihydro-1,6-naphthyridin-3-yl)phenyl)-3-(2-fluoro-5-(trifluoromethyl)phenyl)urea (111 mg, 58% yield) as a white solid. $^1$H NMR (400 MHz, DMSO-d$_6$): δ 9.37 (s, 1H), 9.17 (s, 1H), 8.63-8.61(m, 1H), 8.44 (s, 1H), 8.37-8.35 (m, 1H), 7.82 (s, 1H), 7.53-7.48 (m, 1H), 7.41-7.38 (1, 1H), 7.29-7.24 (m, 2H), 6.96 (brm, 1H), 6.44 (brs, 1H), 2.86 (d, J=4.4 Hz, 3H), 1.53 (d, J=6.8 Hz, 6H); MS (ESI) m/z: 532.0 (M+H$^+$).

EXAMPLE 274

Using general method F, 1-isocyanato-3-(trifluoromethyl)benzene (0.1 mg, 0.534 mmol) and Example A33 (0.093 mg, 0.267 mmol) were combined to provide 1-(4-chloro-5-(1-ethyl-7-(methylamino)-2-oxo-1,2-dihydro-1,6-naphthyridin-3-yl)-2-fluorophenyl)-3-(3-(trifluoromethyl)phenyl)urea (0.115 mg, 81% yield). $^1$H NMR (400 MHz, DMSO-d$_6$): δ 8.45 (s, 1H), 8.17 (d, J=9 Hz, 1H), 8.05 (s, 1H), 7.78 (s, 1H), 7.58 (d, J=10.5 Hz, 1H), 7.52 (m, 2H), 7.35 (m, 1H), 7.08 (brs, 1H), 6.27 (s, 1H), 4.18 (q, J=6 Hz, 2H), 2.89 (brs, 3H), 1.24 (t, J=6 Hz, 3H); MS (ESI) m/z: 534.0 (M+H$^+$).

EXAMPLE 275

Using general method F, 1-chloro-4-isocyanato-2-(trifluoromethyl)benzene (0.100 g, 0.451 mmol) and Example A24 (0.141 g, 0.451 mmol) were combined to provide 1-(4-chloro-3-(trifluoromethyl)phenyl)-3-(5-(1-ethyl-7-(methylamino)-2-oxo-1,2-dihydro-1,6-naphthyridin-3-yl)-2-fluorophenyl)urea (0.172 g, 7% yield). $^1$H NMR (400 MHz, DMSO-d$_6$): δ 9.54 (s, 1H), 8.72 (brs, 1H), 8.49 (s, 1H), 8.36 (m, 1H), 8.14 (brs, 1H), 7.91 (s, 1H), 7.64 (m, 2H), 7.38-7.26 (m, 2H), 7.05 (m, 1H), 6.27 (s, 1H), 4.18 (q, J=6 Hz, 2H), 2.89 (d, J=5.5 Hz, 3H), 1.25 (t, J=6 Hz, 3H; MS (ESI) m/z: 534.0 (M+H$^+$).

EXAMPLE 276

Using general method F, 1-isocyanatobenzene (0.05 g, 0.420 mmol) and Example A33 (0.146 g, 0.420 mmol) were combined to provide 1-(4-chloro-5-(1-ethyl-7-(methylamino)-2-oxo-1,2-dihydro-1,6-naphthyridin-3-yl)-2-fluorophenyl)-3-phenylurea (0.180 g, 92% yield). $^1$H NMR (400 MHz, DMSO-d$_6$): δ 9.16 (s, 1H), 8.75 (s, 1H), 8.45 (s, 1H), 8.22 (d, J=9 Hz, 1H), 7.78 (s, 1H), 7.58 (d, J=10.5 Hz, 1H), 7.46 (s, 1H), 7.44 (s, 1H), 7.30 (m, 2H), 7.08 (m, 1H), 7.00 (s, 1H), 6.27 (s, 1H), 4.18 (q, J=5 Hz, 2H), 2.89 (d, J=5 Hz, 3H), 1.24 (t, J=6 Hz, 3H); MS (ESI) m/z: 466.0 (M+H$^+$).

EXAMPLE 277

Using general method D, 2,3-difluorobenzoic acid (0.100 g, 0.633 mmol) and Example A33 (0.219 g, 0.633 mmol) were combined to provide 1-(4-chloro-5-(1-ethyl-7-(methylamino)-2-oxo-1,2-dihydro-1,6-naphthyridin-3-yl)-2-fluorophenyl)-3-(2,3-difluorophenyl)urea (0.172 g, 54% yield). $^1$H NMR (400 MHz, DMSO-d$_6$): δ 9.27 (s, 1H), 9.24 (s, 1H), 8.45 (s, 1H)), 8.22 (d, J=10 Hz, 1H), 7.96 (m, 1H), 7.77 (s, 1H), 7.58 (d, J=12 Hz, 1H), 7.18-7.00 (m, 3H), 6.27 (s, 1H), 4.17 (q, J=6 Hz, 2H), 2.90 (d, J=5.5 Hz, 3H), 1.24 (t, J=6 Hz, 3H; MS (ESI) m/z: 502.0 (M+H$^+$).

EXAMPLE 278

Using a procedure analogous to Example 265, Example A39 (100 mg, 0.319 mmol), 20% COCl$_2$ in PhMe (0.185 ml, 0.351 mmol) and 4-aminotetrahydropyran (32.3 mg, 0.319 mmol) were combined and purified directly by reverse phase chromatography (MeCN(w/0.1% TFA)/H$_2$O(w/0.1% TFA)) to afford 1-(2-fluoro-4-methyl-5-(8-methyl-2-(methylamino)-7-oxo-7,8-dihydropyrido[2,3-d]pyrimidin-6-yl)phenyl)-3-(tetrahydro-2H-pyran-4-yl)urea (46 mg, 33% yield) as a nearly white solid. $^1$H NMR (400 MHz, DMSO-d$_6$): δ 8.60 (brs, 1H), 8.13 (brs, 1H), 7.92 (d, J=8.4 Hz, 1H), 7.83 (brq, 1H), 7.65 (s, 1H), 7.06 (d, J=12.4 Hz, 1H), 6.64 (d, J=7.2 Hz, 1H), 3.81-3.76 (m, 2H), 3.68-3.57 (m, 1H), 3.59 (brs, 3H), 3.39-3.33 (m, 2H), 2.90 (brs, 3H), 2.04 (s, 3H), 1.79-1.76 (m, 2H), 1.38-1.30 (m, 2H); MS (ESI) m/z: 441.2 (M+H$^+$).

EXAMPLE 279

Using a procedure analogous to Example 265, Example A39 (0.100 g, 0.319 mmol), 20 wt % COCl$_2$ in PhMe (0.185 ml, 0.351 mmol) and 1-Cbz-4-aminopiperidine (0.075 g, 0.319 mmol) were combined and purified by flash column chromatography (EtOAc/hexanes) to afford benzyl 4-(3-(2-fluoro-4-methyl-5-(8-methyl-2-(methylamino)-7-oxo-7,8-dihydropyrido[2,3-d]pyrimidin-6-yl)phenyl)ureido) piperidine-1-carboxylate (80 mg, 44% yield) as a white solid. MS (ESI) m/z: 574.2 (M+H$^+$).

Benzyl 4-(3-(2-fluoro-4-methyl-5-(8-methyl-2-(methylamino)-7-oxo-7,8-dihydropyrido[2,3-d]pyrimidin-6-yl)phenyl)ureido)piperidine-1-carboxylate (80 mg, 0.139 mmol) was hydrogenated (1 atm) in MeOH (5 ml) over 10% Pd/C (50% H$_2$O) (98 mg, 0.046 mmol) After 3 h, the reaction mixture was filtered through Celite, rinsing forward generously with MeOH. The combined filtrates were concentrated to dryness. The crude product was purified by reverse phase chromatography (MeCN (w/0.1% TFA)/H$_2$O (w/0.1% TFA)) to afford 1-(2-fluoro-4-methyl-5-(8-methyl-2-(methylamino)-7-oxo-7,8-dihydropyrido[2,3-d]pyrimidin-6-yl)phenyl)-3-(piperidin-4-yl)urea trifluoroacetic acid salt (12 mg 15% yield) as a white solid. $^1$H NMR (400 MHz, DMSO-d$_6$): δ 8.54 (brs, 1H), 8.38 (brm, 1H), 8.14 (brm, 1H), 8.03 (brs, 1H), 7.84-7.74 (m, 2H), 7.58 (s, 1H), 7.02 (d, J=12.4 Hz, 1H), 6.70 (d, J=7.2 Hz, 1H), 3.63 (m, 1H), 3.59 (brs, 3H), 3.15-3.13 (m, 2H), 2.97-2.92 (m, 2H), 2.90 (brs, 3H), 1.99 (s, 3H), 1.93-1.89 (m, 2H), 1.50-1.40 (m, 2H); MS (ESI) m/z: 440.2 (M+H$^+$).

EXAMPLE 280

Using general method C, the TROC carbamate of B18 (80 mg, 0.25 mmol) and Example A58 (83 mg, 0.254 mmol) were combined to afford 1-(3-tert-butylisoxazol-5-yl)-3-(2-fluoro-5-(1-isopropyl-7-(methylamino)-2-oxo-1,2-dihydro-1,6-naphthyridin-3-yl)phenyl)urea (43 mg, 34% yield). $^1$H NMR (400 MHz, DMSO-d$_6$): δ 10.4 (s, 1H), 8.82 (d, J=1.6 Hz, 1H), 8.51 (brs, 1H), 8.42 (dd, J=1.6, and 7.6 Hz, 1H), 7.90 (s, 1H), 7.38 (m, 1H), 7.06 (q, J=4.8 Hz, 1H), 6.52 (brs, 1H), 6.16 (s, 1H), 2.94 (d, J=4.8 Hz, 3H), 1.62 (d, J=7.2 Hz, 6H), 1.32 (s, 9H); MS (ESI) m/z: 493.2 (M+H$^+$).

EXAMPLE 281

Using general method F, Example A24 (100 mg, 0.320 mmol) and alpha,alpha,alpha-trifluoro-m-tolyl isocyanate (0.066 ml, 0.480 mmol) were combined and purified by flash column chromatography (5% EtOAc/hexanes to 100% EtOAc) to afford 1-(5-(1-ethyl-7-(methylamino)-2-oxo-1,2-dihydro-1,6-naphthyridin-3-yl)-2-fluorophenyl)-3-(3-(trifluoromethyl)phenyl)urea (8 mg, 5% yield) as a white solid. $^1$H NMR (400 MHz, DMSO-d$_6$): δ 9.47 (s, 1H), 8.68 (brs, 1H), 8.46 (s, 1H), 8.40-8.37 (m, 1H), 7.88 (s, 1H), 7.67-7.62 (m, 3H), 7.34-7.24 (m, 2H), 7.01 (brq, 1H), 6.23 (s, 1H), 4.16 (q, J=6.4 Hz, 2H), 2.86 (d, J=4.4 Hz, 3H), 1.23 (t, J=6.4 Hz, 3H); MS (ESI) m/z: 500.3 (M+H$^+$).

EXAMPLE 282

Using general method F, 1-isocyanatobenzene (0.036 g, 0.302 mmol) and Example A58 (0.1 g, 0.302 mmol) were combined to provide 1-(2-fluoro-5-(1-isopropyl-7-(methylamino)-2-oxo-1,2-dihydro-1,6-naphthyridin-3-yl)phenyl)-3-phenylurea (0.94 g, 70% yield). $^1$H NMR (400 MHz, DMSO-d$_6$): δ 9.03 (s, 1H), 8.62 (s, 1H)), 8.49 (s, 1H), 8.42 (d, J=8 Hz, 1H), 7.86 (s, 1H), 7.52 (s, 1H), 7.50 (s, 1H), 7.32 (m, 4H), 7.03 (m, 2H), 6.50 (brs, 1H), 3.40 (s, 1H), 2.91 (d, J=6 Hz, 3H), 1.60 (d, J=6 Hz, 6H); MS (ESI) m/z: 446.3 (M+H$^+$).

EXAMPLE 283

Using general method B, the carbamate of Example B48 (0.084 g, 0.401 mmol) and Example A12 (0.060 g, 0.20 mmol) were combined to afford 1-(2-fluoro-5-(8-methyl-2-(methylamino)-7-oxo-7,8-dihydropyrido[2,3-d]pyrimidin-6-yl)phenyl)-3-(1-isopropyl-1H-pyrazol-4-yl)urea (0.074 g, 82%) as white solid. $^1$H NMR (400 MHz, DMSO-d$_6$): δ 8.82 (s, 1H), 8.74 (s, 1H), 8.58 (d, J=1.6 Hz, 1H), 8.50 (d, J=8.0 Hz, 1H), 7.96-7.79 (m, 3H), 7.46 (s, 1H), 7.34-7.31 (m, 2H), 4.50

(m, 1H), 3.71 (s, 3H), 2.99 (m, 3H), 1.45 (d, J=6.8 Hz, 1H); MS (ESI) m/z: 451.2 (M+H$^+$).

EXAMPLE 284

Using general method F, 1-isocyanatonaphthalene (0.05 g, 0.29 mmol) and Example A33 (0.1 g, 0.29 mmol) were combined to afford 1-(4-chloro-5-(1-ethyl-7-(methylamino)-2-oxo-1,2-dihydro-1,6-naphthyridin-3-yl)-2-fluorophenyl)-3-(naphthalen-1-yl)urea as a white solid (0.121 g, 79% yield). $^1$H NMR (400 MHz, DMSO-d$_6$): δ 9.26 (brs, 2H), 8.48 (s, 1H), 8.32 (d, J=8.8 Hz, 1H), 8.21 (d, J=8.8 Hz, 1H), 8.05 (dd, J=7.6 Hz, 0.8 Hz, 1H), 7.98 (d, J=8.4 Hz, 1H), 7.81 (s, 1H), 7.71-7.58 (m, 4H), 7.51 (t, J=8.0 Hz, 1H), 7.11 (q, J=4.8 Hz, 1H), 6.30 (s, 1H), 4.20 (q, J=6.8 Hz, 2H), 2.92 (d, J=4.8 Hz, 3H), 1.27 (t, 0.7=6.8 Hz, 3H); MS (ESI) m/z: 516.0 (M+H$^+$).

EXAMPLE 285

Using general method D, 2-fluoro-5-(trifluoromethyl)benzoic acid (75 mg, 0.360 mmol), DPPA (0.116 ml, 0.541 mmol) and Example A24 (124 mg, 0.396 mmol) were combined and purified by flash column chromatography (5% EtOAc/hexanes to 100% EtOAc) to afford 1-(5-(1-ethyl-7-(methylamino)-2-oxo-1,2-dihydro-1,6-naphthyridin-3-yl)-2-fluorophenyl)-3-(2-fluoro-5-(trifluoromethyl)phenyl)urea (66 mg, 35% yield) as a white solid. $^1$H NMR (400 MHz, DMSO-d$_6$): δ 9.38 (brs, 1H), 9.18 (brs, 1H), 8.64-8.62 (m, 1H), 8.47 (s, 1H), 8.44-8.41 (m, 1H), 7.89 (s, 1H), 7.53-7.48 (m, 1H), 7.41-7.38 (m, 1H), 7.33-7.26 (m, 2H), 7.01 (brq, 1H), 6.23 (s, 1H), 4.17 (q, J=7.6 Hz, 2H), 2.86 (d, J=4.4 Hz, 3H), 1.23 (t, J=7.6 Hz, 3H); MS (ESI) m/z: 518.2 (M+H$^+$).

EXAMPLE 286

Using general method B, prop-1-en-2-yl 5-tert-butyl-1,3,4-thiadiazol-2-ylcarbamate (0.06 g, 0.25 mmol) and Example A24 (0.08 g, 0.25 mmol) were combined to afford 1-(5-tert-butyl-1,3,4-thiadiazol-2-yl)-3-(5-(1-ethyl-7-(methylamino)-2-oxo-1,2-dihydro-1,6-naphthyridin-3-yl)-2-fluorophenyl)urea as a white solid (0.08 g, 64% yield). $^1$H NMR (400 MHz, DMSO-d$_6$); δ 11.16 (s, 1H), 9.00 (s, 1H), 8.54 (s, 1H), 8.45 (d, J=6.4 Hz, 1H), 7.98 (s, 1H), 7.47-7.36 (m, 2H), 7.13-7.10 (m, 1H), 6.31 (s, 1H), 4.28-4.22 (m, 2H), 2.94 (d, J=4.8 Hz, 3H), 1.46 (s, 9H), 1.31 (t, J=6.8 Hz, 3H); MS (ESI) m/z: 496.3 (M+H$^+$).

EXAMPLE 287

Using general method B, prop-1-en-2-yl 5-tert-butyl-1,3,4-thiadiazol-2-ylcarbamate (0.07 g, 0.3 mmol), and Example A30 (0.096 g, 0.29 mmol) were combined to afford 1-(5-tert-butyl-1,3,4-thiadiazol-2-yl)-3-(5-(1-ethyl-7-(methylamino)-2-oxo-1,2-dihydro-1,6-naphthyridin-3-yl)-2-fluoro-4-methylphenyl)urea as a white solid (0.09 g, 60% yield). $^1$H NMR (400 MHz, DMSO-d$_6$): δ11.12 (s, 1H), 8.95 (s, 1H), 8.51 (s, 1H), 7.96 (d, J=8.8 Hz, 1H), 7.78 (s, 1H), 7.28 (d, J=7.6 Hz, 1H), 7.10 (d, J=4.8 Hz, 1H), 6.34 (s, 1H), 4.25 (q, J=6.8 Hz, 2H), 2.96 (d, J=4.8 Hz, 3H), 2.18 (s, 3H), 1.45 (s, 9H), 1.31 (t, J=6.8 Hz, 3H); MS (ESI) m/z: 510.2 (M+H$^+$).

EXAMPLE 288

Using general method D 3-tert-butyl-1-methyl-1H-pyrazole-5-carboxylic acid (0.051 g, 0.28 mmol) and Example A58 (0.09 g, 0.28 mmol) in presence of triethylamine (0.06 g, 0.56 mmol) and DPPA (0.15 g, 0.56 mmol) were combined to afford 1-(3-tert-butyl-1-methyl-1H-pyrazol-5-yl)-3-(2-fluoro-5-(1-isopropyl-7-(methylamino)-2-oxo-1,2-dihydro-1,6-naphthyridin-3-yl)phenyl)urea as a white solid (0.085 g, 60% yield). $^1$H NMR (400 MHz, DMSO-d$_6$): δ 9.00 (s, 1H), 8.89 (s, 1H), 8.51 (s, 1H), 8.44-8.42 (m, 1H), 7.87 (s, 1H), 7.35-7.33 (m, 2H), 7.07-7.04 (m 1H), 6.52 (brs, 1H), 6.17 (s, 1H), 3.69 (s, 3H), 2.94 (d, J=4.8 Hz, 3H), 1.61 (d, J=7.2 Hz, 3H), 1.28 (s, 9H); MS (ESI) m/z: 506.2 (M+H$^+$).

EXAMPLE 289

Using general method D, Example B50 (0.041 g, 0.23 mmol) and Example A12 (0.069 g, 0.23 mmol) were combined to afford 1-(1-cyclopentyl-1H-pyrazol-4-yl)-3-(2-fluoro-5-(8-methyl-2-(methylamino)-7-oxo-7,8-dihydropyrido[2,3-d]pyrimidin-6-yl)phenyl)urea (0.033 g, 30%) as a brown solid. $^1$H NMR (400 MHz, DMSO-d$_6$): δ 8.82 (s, 1H), 8.75 (s, 1H), 8.58 (d, J=1.6 Hz, 1H), 8.50 (d, J=8.0 Hz, 1H), 7.96-7.79 (m, 3H), 7.47 (s, 1H), 7.35-7.32 (m, 2H), 4.70 (m, 1H), 3.71 (s, 3H), 2.99 (m, 3H), 2.14-2.09 (m, 2H), 1.98-1.92 (m, 2H), 1.86-1.82 (m, 2H), 1.71-1.97 (m, 2H); MS (ESI) m/z: 477.2 (M+H$^+$).

EXAMPLE 290

Using general method B, prop-1-en-2-yl 5-tert-butyl-1,3,4-thiadiazol-2-ylcarbamate (0.081 g, 0.33 mmol) and Example A49 (0.11 g, 0.33 mmol) were combined to afford 1-(5-tert-butyl-1,3,4-thiadiazol-2-yl)-3-(2-fluoro-5-(8-isopropyl-2-(methylamino)-7-oxo-7,8-dihydropyrido[2,3-d]pyrimidin-6-yl)phenyl)urea as a white solid (0.09 g, 52% yield). $^1$H NMR (400 MHz, DMSO-d$_6$): δ 11.17 (s, 1H), 9.02 (s, 1H), 8.73 (s, 1H), 8.42 (brs, 1H), 7.93 (s, 1H), 7.90-7.87 (m, 1H), 7.45-7.37 (m, 2H), 5.89 (brs, 1H), 3.00 (d, J=4.4 Hz, 3H), 1.69 (d, J=6.4 Hz, 6H), 1.47 (s, 9H); MS (ESI) m/z: 511.2 (M+H$^+$).

EXAMPLE 291

Using general method B, the carbamate of Example B19 (70 mg, 0.31 mmol) and Example A36 (80 mg, 0.28 mmol) were combined to afford 1-(1-tert-butyl-1H-pyrazol-4-yl)-3-(2-fluoro-5-(7-(methylamino)-2-oxo-1-phenyl-1,2-dihydro-1,6-naphthyridin-3-yl)phenyl)urea (55 mg, 33% yield). $^1$H NMR (400 MHz, DMSO-d$_6$): δ 8.80 (s, 1H), 8.61 (s, 1H), 8.58 (brs, 1H), 8.53 (dd, J=1.6, and 7.6 Hz, 1H), 8.09 (s, 1H), 7.91 (s, 1H), 7.71 (m, 2H), 7.64 (m, 1H), 7.49 (s, 1H), 7.45 (m, 2H), 7.33 (m, 2H), 7.08 (q, J=4.0 Hz, 1H), 2.78 (d, J=4.0 Hz, 3H), 1.57 (s, 9H); MS (ESI) m/z: 526.2 (M+H$^+$).

EXAMPLE 292

Using general method C, the TROC carbamate of Example B20 (80 mg, 0.27 mmol) and Example A36 (96 mg, 0.27 mmol) were combined to afford 1-(2-fluoro-5-(7-(methylamino)-2-oxo-1-phenyl-1,2-dihydro-1,6-naphthyridin-3-yl)phenyl)-3-(3-isopropylisoxazol-5-yl)urea (55 mg, 33% yield). $^1$H NMR (400 MHz, DMSO-d$_6$): δ 10.4 (s, 1H), 8.84 (s, 1H), 8.60 (s, 1H), 8.52 (dd, J=1.6, and 7.6 Hz, 1H), 8.12 (s, 1H), 7.67 (m, 3H), 7.41 (m, 4H), 7.09 (q, J=4.0 Hz, 1H), 6.12 (s, 1H), 5.40 (s, 1H), 2.98 (m, 1H), 2.77 (d, J=4.0 Hz, 1H), 1.28 (d, J=6.8 Hz, 3H); MS (ESI) m/z: 513.0 (M+H$^+$).

EXAMPLE 293

Using general method F, 3-(trifluoromethyl)phenylisocyanate (50 mg, 0.274 mmol) and Example A40 (70 mg, 0.274 mmol) were combined to afford 1-(2-fluoro-5-(2-oxo-1,2-dihydro-1,6-naphthyridin-3-yl)phenyl)-3-(3-(trifluoromethyl)phenyl)urea (69 mg, 57% yield $^1$H NMR (400 MHz, DMSO-d$_6$): δ 12.2 (s, 1H), 9.44 (s, 1H), 8.93 (s, 1H), 8.72 (brs, 1H), 8.44 (m, 2H), 8.16 (s, 1H), 8.05 (brs, 1H), 7.52 (m, 2H), 7.41 (m, 1H), 7.32 (m, 2H), 7.22 (d, J=5.6 Hz, 1H); MS (ESI) m/z: 443.0 (M+H$^+$).

EXAMPLE 294

Using general method C, the TROC carbamate of Example B20 (0.145 g, 0.482 mmol) and Example A26 (0.075 g, 0.0241 mmol) were combined to afford 1-(2-fluoro-4-methyl-5-(1-methyl-7-(methylamino)-2-oxo-1,2-dihydro-1,6-naphthyridin-3-yl)phenyl)-3-(3-isopropylisoxazol-5-yl)urea (0.0612 g, 55%) as white solid. $^1$H NMR (400 MHz, DMSO-d$_6$): δ 10.44 (s, 1H), 8.82 (s, 1H), 8.53 (s, 1H), 8.01 (d, J=8.4 Hz, 1H), 7.81 (s, 1H), 7.31 (d, J=12.4 Hz, 1H), 7.19 (m, 1H), 6.31 (s, 1H), 6.11 (s, 1H), 3.65 (s, 3H), 3.04-2.99 (m, 4H), 2.23 (s, 3H), 1.30 (d, J=12 Hz, 6H); MS (ESI) m/z: 465.2 (M+H$^+$).

EXAMPLE 295

Using general method C, the TROC carbamate of Example B20 (0.145 g, 0.482 mmol) and Example A30, 0.079 g, 0.0241 mmol) were combined to afford 1-(5-(1-ethyl-7-(methylamino)-2-oxo-1,2-dihydro-1,6-naphthyridin-3-yl)-2-fluoro-4-methylphenyl)-3-(3-isopropylisoxazol-5-yl)urea (0.017 g, 15%) as white solid. $^1$H NMR (400 MHz, DMSO-d$_6$): δ 10.31 (s, 1H), 8.68 (s, 1H), 8.41 (s, 1H), 7.88 (d, J=8.4 Hz, 1H), 7.68 (s, 1H), 7.17 (d, J=12.4 Hz, 1H), 7.01 (m, 1H), 6.25 (s, 1H), 5.98 (s, 1H), 4.15 (m, 1H), 2.91-2.86 (m, 4H), 2.09 (s, 3H), 1.24-1.16 (m, 9H); MS (ESI) m/z: 479.2 (M+H$^+$).

EXAMPLE 296

Using general method C, the TROC carbamate of Example B18 (0.152 g, 0.483 mmol) and Example A62, 0.079 g, 0.241 mmol) were combined to afford 1-(3-tert-butylisoxazol-5-yl)-3-(4-chloro-3-(1-ethyl-7-(methylamino)-2-oxo-1,2-dihydro-1,6-naphthyridin-3-yl)phenyl)urea (0.0423 g, 36%) as a white solid. $^1$H NMR (400 MHz, DMSO-d$_6$): δ 10.25 (s, 1H), 9.02 (s, 1H), 8.45 (s, 1H), 7.78 (s, 1H), 7.58 (d, J=1.6 Hz, 1H), 7.50-7.41 (m, 2H), 7.10 (m, 1H), 6.28 (s, 1H), 6.08 (s, 1H), 4.18 (m, 2H), 2.90 (d, J=4.8 Hz, 3H), 1.27-1.19 (m, 12H); MS (ESI) m/z: 495.2 (M+H$^+$).

EXAMPLE 297

A suspension of 1-(3-tert-butylisoxazol-5-yl)-3-(2-fluoro-4-methyl-5-(8-methyl-2-(methylthio)-7-oxo-7,8-dihydropyrido[2,3-d]pyrimidin-6-yl)phenyl)urea from Example 96 (15 mg, 0.030 mmol) in CH$_2$Cl$_2$ (1 mL) was treated with mCPBA (70%, 8.94 mg, 0.036 mmol). After 30 min, methanol (0.050 mL 1.2 mmol) and triethylamine (0.020 mL, 0.14 mmol) were added and the resultant mixture was heated to 40° C. overnight. The reaction was concentrated in vacuo and purified by chromatography to provide 1-(3-tert-butylisoxazol-5-yl)-3-(2-fluoro-5-(2-methoxy-8-methyl-7-oxo-7,8-dihydropyrido[2,3-d]pyrimidin-6-yl)-4-methylphenyl)urea. (8.6 mg, 59% yield). $^1$H NMR (400 MHz, DMSO-d$_6$): δ 10.32 (s, 1H), 8.93 (s, 1H), 8.72 (s, 1H), 7.93 (d, J=8.3 Hz, 1H), 7.90 (s, 1H), 7.20 (d, J=12.3 Hz, 1H), 6.00 (s, 1H), 4.02 (s, 3H), 3.63 (s, 3H), 2.09 (s, 3H), 1.21 (s, 9H); MS (ESI) m/z: 481.2 (M+H$^+$).

EXAMPLE 298

Using General Method F, Example A33 (100 mg, 0.288 mmol) and cyclohexyl isocyanate (0.074 ml, 0.577 mmol) were reacted to afford 1-(4-chloro-5-(1-ethyl-7-(methylamino)-2-oxo-1,2-dihydro-1,6-naphthyridin-3-yl)-2-fluorophenyl)-3-cyclohexylurea (37 mg, 27% yield) as a white solid. $^1$H NMR (400 MHz, DMSO-d$_6$): δ 8.39 (s, 1H), 8.29 (d, J=2.0 Hz, 1H), 8.14 (d, J=8.8 Hz, 1H), 7.70 (s, 1H), 7.41 (D, J=11.2 Hz, 1H), 7.30 (brs, 1H), 6.80 (s, 1H), 6.61-6.58 (m, 2H), 6.28 (s, 1H), 4.08 (q, J=6.81 Hz, 2H), 3.40 (brm, 1H), 2.83 (s, 3H), 1.75-1.68 (m, 2H), 1.61-1.55 (m, 2H), 1.46-1.40 (m, 1H), 1.25-1.05 (m, 5H), 1.15 (t, J=7.2 Hz, 3H); MS (ESI) m/z: 472.2 (M+H$^+$), 474.2 (M+2+H$^+$).

EXAMPLE 299

By analogy to Example A11, Example A41 125 mg, 0.363 mmol), mCPBA (107 mg, 0.436 mmol) and 2M MeNH$_2$ in THF were reacted to afford 6-(5-amino-4-fluoro-2-methylphenyl)-8-ethyl-2-(methylamino)pyrido[2,3-d]pyrimidin-7(8H)-one (67 mg, 0.205 mmol) which, in turn, was reacted according to General Method F with cyclohexyl isocyanate (0.105 mL, 0.822 mmol) to afford 1-cyclohexyl-3-(5-(8-ethyl-2-(methylamino)-7-oxo-7,8-dihydropyrido[2,3-d]pyrimidin-6-yl)-2-fluoro-4-methylphenyl)urea (11 mg, 12% yield) as a white solid. $^1$H NMR (400 MHz, DMSO-d$_6$): δ 8.60 (brs, 1H), 8.11-8.09 (m, 1H), 7.94-7.92 (m, 1H), 7.79 (brm, 1H), 7.62 (s, 1H), 7.05 (d, J=12.4 Hz, 1H), 6.54 (d, J=8.0 Hz, 1H), 4.33 (brq, 2H), 3.43-3.37 (m, 1H), 2.88 (d, J=4.0 Hz, 3H), 2.02 (s, 3H), 1.77-1.73 (m, 2H), 1.65-1.60 (m, 2H), 1.52-1.46 (m, 1H), 1.34-1.05 (m, 5H), 1.22 (brt, 3H); MS (ESI) m/z: 453.3 (M+H$^+$).

EXAMPLE 300

Using General Method F, Example A26 (0.100 g, 0.320 mmol) and cyclohexyl isocyanate (0.041 ml, 0.320 mmol) were reacted to afford 1-cyclohexyl-3-(2-fluoro-4-methyl-5-(1-methyl-7-(methylamino)-2-oxo-1,2-dihydro-1,6-naphthyridin-3-yl)phenyl)urea (77 mg, 55% yield) as an off-white solid. $^1$H NMR (400 MHz, DMSO-d$_6$): δ 8.38 (s, 1H), 8.10 (d, J=2.0 Hz, 1H), 7.93 (d, J=8.4 Hz, 1H), 7.63 (s, 1H), 7.06-7.02 (m, 2H), 6.54 (d, J=7.6 Hz, 1H), 6.17 (s, 1H), 3.50 (s, 3H), 3.46-3.36 (m, 1H), 2.85 (d, J=5.2 Hz, 3H), 2.03 (s, 3H), 1.81-1.75 (m, 2H), 1.73-1.56 (m, 2H), 1.48-1.45 (m, 1H), 1.38-1.09 (m, 5H); MS (ESI) m/z: 438.3 (M+H$^+$).

EXAMPLE 301

Using General Method B, Example B39 (125 mg, 0.66 mmol) and Example A26 (114 mg, 0.366 mmol) were reacted to afford 1-(1-tert-butyl-1H-indazol-3-yl)-3-(2-fluoro-4-methyl-5-(1-methyl-7-(methylamino)-2-oxo-1,2-dihydro-1,6-naphthyridin-3-yl)phenyl)urea (77 mg, 40% yield) as a white solid. $^1$H NMR (400 MHz, DMSO-d$_6$): δ 10.04 (brs, 1H), 8.41 (s, 1H), 8.09 (dd, J=8.4 and 14.0 Hz, 1H), 7.77 (d, J=8.4 Hz, 1H), 7.70 (s, 1H), 7.37 (dd, J=7.6 and 15.6 Hz, 1H), 7.20 (d, J=12.0 Hz, 1H), 7.09-7.05 (m, 2H), 6.19 (s, 1H), 3.52 (s, 3H), 2.86 (d, J=5.2 Hz, 3H), 2.09 (s, 3H), 1.72 (s, 9H); MS (ESI) m/z: 528.3 (M+H$^+$).

EXAMPLE 302

Using General Method B, Example B39 (125 mg, 0.66 mmol) Example A28 (138 mg, 0.415 mmol) were reacted to afford 1-(1-tert-butyl-1H-indazol-3-yl)-3-(4-chloro-2- fluoro-5-(1-methyl-7-(methylamino)-2-oxo-1,2-dihydro-1,6-naphthyridin-3-yl)phenyl)urea (47 mg, 21% yield) as a white solid. $^1$H NMR (400 MHz, DMSO-$d_6$): δ 10.15 (brs, 1H), 8.42 (s, 1H), 8.33 (d, J=8.8 Hz, 1H), 8.06 (d, J=7.6 Hz, 1H), 7.78 (dd, J=4.4 and 8.8 Hz, 1H), 7.62 (d, J=10.4 vHz, 1H), 7.40-7.36 (m, 1H), 7.13-7.06 (m, 2H), 6.18 (s, 1H), 3.51 (s, 3H), 2.86 (d, J=4.8 Hz, 3H), 1.72 (s, 9H); MS (ESI) m/z: 548.3 (M+H$^+$), 550.3 (M+2+H$^+$).

EXAMPLE 303

Using general method D, 3-tert-butyl-1-methyl-1H-pyrazole-5-carboxylic acid (50 mg, 0.27 mmol) and Example A19 (0.10 g, 0.27 mmol) in presence of DPPA (65 μL, 0.30 mmol) and Et$_3$N (42 μL, 0.30 mmol) were combined to afford 1-(3-tert-butyl-1-methyl-1H-pyrazol-5-yl)-3-(5-(8-cyclopentyl-2-(methylthio)-7-oxo-7,8-dihydropyrido[2,3-d]pyrimidin-6-yl)-2-fluorophenyl)urea.

Using a procedure analogous to Example A1, 1-(3-tert-butyl-1-methyl-1H-pyrazol-5-yl)-3-(5-(8-cyclopentyl-2-(methylthio)-7-oxo-7,8-dihydropyrido[2,3-d]pyrimidin-6-yl)-2-fluorophenyl)urea (150 mg, 0.27 mmol) was treated with mCPBA (70% wt, 74 mg, 0.30 mmol) and then 2 M methylamine (1.4 mL) to afford 1-(3-tert-butyl-1-methyl-1H-pyrazol-5-yl)-3-(5-(8-cyclopentyl-2-(methylamino)-7-oxo-7,8-dihydropyrido[2,3-d]pyrimidin-6-yl)-2-fluorophenyl) urea (67 mg, 46% yield). $^1$H NMR (400 MHz, DMSO-$d_6$, major isomer): δ 9.04 (s, 1H), 8.94 (d, J=2.4 Hz, 1H), 8.76 (brs, 1H), 8.46 (brd, J=7.6 Hz, 1H), 7.93 (s, 1H), 7.74 (brq, J=4.8 Hz, 1H), 7.38 (m, 2H), 6.21 (s, 1H), 6.04 (m, 1H), 3.73 (s, 3H), 3.01 (d, J=4.8 Hz, 3H), 2.49 (brs, 1H), 2.33 (brs, 1H), 2.11 (s, 3H), 2.11 (brs, 2H), 1.90 (brs, 2H), 1.74 (brs, 2H), 1.31 (s, 9H); MS (ESI) m/z: 533.3 (M+H$^+$).

EXAMPLE 304

Using general method D, Example B45 (100 mg, 0.549 mmol), triethylamine (64 mg, 0.631 mmol), Example A58 (179 mg, 0.549 mmol) and DPPA (174 mg, 0.631 mmol) were combined to provide 1-(1-tert-butyl-5-methyl-1H-pyrazol-4-yl)-3-(2-fluoro-5-(1-isopropyl-7-(methylamino)-2-oxo-1,2-dihydro-1,6-naphthyridin-3-yl)phenyl)urea (101 mg, 36% yield). $^1$H NMR (400 MHz, DMSO-$d_6$): δ 1.68 (d, 6H), 1.69 (s, 9H), 2.46 (s, 3H), 3.00 (d, 3H), 4.16-4.18 (hep, 1H), 6.58 (br. s, 1H), 7.11 (br. s, 1H), 7.35-7.38 (m, 2H), 7.59 (s, 1H), 7.92 (s, 1H), 8.30 (s, 1H), 8.49-8.51 (m, 1H), 8.57 (s, 1H), 8.69 (br. s, 1H); MS (ESI) m/z: 506.2 (M+H$^+$).

EXAMPLE 305

Using general method D, Example B49 (134 mg, 0.501 mmol), triethylamine (58 mg, 0.577 mmol), Example A13 (135 mg, 0.501 mmol) and DPPA (159 mg, 0.577 mmol) were combined and purified by reverse phase chromatography (Biotage C18-25 column, 30-100% acetonitrile/water) to afford 1-(2-fluoro-5-(8-methyl-7-oxo-7,8-dihydropyrido[2,3-d]pyrimidin-6-yl)phenyl)-3-(2-methyl-4-(1-methyl-1H-indol-5-yl)pyrimidin-5-yl)urea (34 mg, 12% yield). $^1$H NMR (400 MHz, DMSO-$d_6$): δ 2.60 (s, 3H), 3.69 (s, 3H), 3.83 (s, 3H), 6.55 (s, 1H), 7.30-7.32 (m, 2H), 7.41-7.42 (m, 1H), 7.48 (d, 1H), 7.60 (d, 1H), 7.91 (s, 1H), 8.13 (s, 1H), 8.47-8.49 (m, 1H), 8.58 (s, 1H), 9.05 (br. s, 1H), 9.10-9.25 (m, 2H), 9.11 (s, 1H); MS (ESI) m/z: 535.2 (M+H$^+$).

EXAMPLE 306

Using general method D, 2,3-difluorobenzoic acid (0.030 g, 0.190 mmol) was reacted with DPPA (0.0104 g, 0.380 mmol) in presence of triethylamine (0.058 g, 0.569 mmol) in Dioxane (2 ml) at room temp for 1 hour followed by treatment with Example A49 (0.062 g, 0.190 mmol) at 80° C. for 2 hours to provide 1-(2,3-difluorophenyl)-3-(2-fluoro-5-(8-isopropyl-2-(methylamino)-7-oxo-7,8-dihydropyrido[2,3-d]pyrimidin-6-yl)phenyl)urea (0.065 g, 71% yield). $^1$HNMR (400 MHz, DMSO-$d_6$): δ 9.31 (brs, 1H), 9.18 (s, 1H)), 8.72 s, 1H), 8.47 (d, J=7 Hz, 1H), 8.07 (m, 1H), 7.90 (s, 1H), 7.86 (m, 1H), 7.36 (d, J=8.5 Hz, 1H), 7.21 (m, 1H), 7.12 (m, 1H), 5.85 (brs, 1H), 2.90 (d, J=5 Hz, 3H), 1.67 (d, J=6 Hz, 6H); MS (ESI) m/z: 483.3 (M+H$^+$).

EXAMPLE 307

Using general method G, 2,2,2-trichloroethyl pyridin-3-ylcarbamate (0.060 g, 0.223 mmol) was reacted with Example A49 (0.073 g, 0.223 mmol) in presence of N-methylpyrrolidine (0.019 g, 0.223 mmol) in dioxane (3 ml) at 90° C. for 15 hours to provide 1-(2-fluoro-5-(8-isopropyl-2-(methylamino)-7-oxo-7,8-dihydropyrido[2,3-d]pyrimidin-6-yl)phenyl)-3-(pyridin-3-yl)urea (0.025 g, 25% yield). $^1$H NMR (400 MHz, DMSO-$d_6$): δ 9.34 (s, 1H), 8.79 (s, 1H), 8.72 (s, 1H), 8.68 (d, J=2.5 Hz, 1H), 8.43 (d, J=8 Hz, 1H), 8.27 (m, 1H), 8.05 (m, 1H), 7.92 (s, 1H), 7.86 (m, 1H), 7.40 (dd, J=9, 5 Hz, 1H), 7.37 (m, 2H), 5.85 (brs, 1H), 2.90 (d, J=5 Hz, 3H), 1.67 (d, J=6 Hz, 6H): MS (ESI) m/z: 448.2 (M+H$^+$).

EXAMPLE 308

Using general method F, 1-isocyanato-3-(trifluoromethyl) benzene (0.060 g, 0.321 mmol) was reacted Example A49 (0.060 g, 0.183 mmol) in methylene chloride (2 ml) for 6 hours to provide 1-(2-fluoro-5-(8-isopropyl-2-(methylamino)-7-oxo-7,8-dihydropyrido[2,3-d]pyrimidin-6-yl)phenyl)-3-(3-(trifluoromethyl)phenyl)urea (0.090 g, 95% yield). $^1$H NMR (400 MHz, DMSO-$d_6$): δ 9.52 (s, 1H), 8.79 (brs, 1H), 8.75 (s, 1H), 8.43 (d, J=8 Hz, 1H), 8.17 (s, 1H), 7.92 (s, 1H), 7.86 (m, 1H), 7.62 (m, 2H), 7.37 (m, 2H), 5.85 (brs, 1H), 2.90 (d, J=5 Hz, 3H), 1.67 (d, J=6 Hz, 6H); MS (ESI) m/z: 515.2 (M+H$^+$).

EXAMPLE 309

Using general method F, 1-isocyanatobenzene (0.050 g, 0.420 mmol) was reacted with Example A49 (0.060 g, 0.183 mmol) in methylene chloride (2 ml) for 6 hours to provide 1-(2-fluoro-5-(8-isopropyl-2-(methylamino)-7-oxo-7,8-dihydropyrido[2,3-d]pyrimidin-6-yl)phenyl)-3-phenylurea (0.065 g, 79% yield). $^1$HNMR (400 MHz, DMSO-$d_6$): δ 9.18 (s, 1H), 8.75 (s, 1H), 8.68 (brs, 1H), 8.48 (d, J=8 Hz, 1H), 7.93 (s, 1H), 7.89 (m, 1H), 7.56 (m, 2H), 7.38 (m, 4H), 7.10 (m, 1H), 5.85 (brs, 1H), 2.90 (d, J=5 Hz, 3H), 1.67 (d, J=6 Hz, 6H); MS (ESI) m/z: 447.3 (M+H$^+$).

EXAMPLE 310

Using general method F, 1-isocyanatonaphthalene (0.060 g, 0.355 mmol) was reacted with Example A49 (0.060 g, 0.183 mmol) in methylene chloride (2 ml) for 6 hours to provide 1-(2-fluoro-5-(8-isopropyl-2-(methylamino)-7-oxo-7,8-dihydropyrido[2,3-d]pyrimidin-6-yl)phenyl)-3-(naphthalen-1-yl)urea, (0.070 g, 42% yield). $^1$H NMR (400 MHz, DMSO-$d_6$): δ 9.28 (s, 1H), 9.20 (s, 1H), 8.74 (s, 1H), 8.57 (d, J=8 Hz, 1H), 8.27 (d, J=9 Hz, 1H), 8.17 (m, 1H), 8.04 (m, 1H), 7.93 (s, 1H), 7.77-7.55 (m, 4H), 7.37 (m, 2H), 5.85 (brs, 1H), 2.90 (d, J=5 Hz, 3H), 1.67 (d, J=6 Hz, 6H); MS (ESI) m/z: 497.2.2 (M+H$^+$).

EXAMPLE 311

Using general method F, 1-chloro-4-isocyanato-2-(trifluoromethyl)benzene (0.06 g, 0.271 mmol) was reacted with Example A49 (0.06 g, 0.183 mmol) in methylene chloride (2 ml) for 6 hours to provide 1-(4-chloro-3-(trifluoromethyl)phenyl)-3-(2-fluoro-5-(8-isopropyl-2-(methylamino)-7-oxo-7,8-dihydropyrido[2,3-d]pyrimidin-6-yl)phenyl)urea (0.080 g, 80% yield) $^1$H NMR (400 MHz, DMSO-$d_6$); δ 9.62 (s, 1H), 8.79 (s, 1H), 8.74 (s, 1H), 8.40 (d, J=8 Hz, 1H), 8.21 (s, 1H), 7.93 (s, 1H), 7.89 (m, 1H), 7.71 (s, 2H), 7.40 (m, 2H), 5.85 (brs, 1H), 2.90 (d, J=5 Hz, 3H), 1.67 (d, J=6 Hz, 6H): MS (ESI) m/z: 549.0 (M+H$^+$).

EXAMPLE 312

Using general method F, 1-fluoro-2-isocyanato-4-(trifluoromethyl)benzene (0.060 g, 0.293 mmol) was reacted with Example A49 (0.06 g, 0.183 mmol) in methylene chloride (2 ml) for 6 hours to provide 1-(2-fluoro-5-(8-isopropyl-2-(methylamino)-7-oxo-7,8-dihydropyrido[2,3-d]pyrimidin-6-yl)phenyl)-3-(2-fluoro-5-(trifluoromethyl)phenyl)urea (0.075 g, 48.2% yield). $^1$H NMR (400 MHz, DMSO-$d_6$): δ 9.51 (s, 1H), 9.31 (s, 1H), 8.76 (m, 2H), 8.50 (d, J=8 Hz, 1H), 7.95 (s, 1H), 7.90 (m, 1H), 7.63 (m, 1H), 7.52 (m, 1H), 7.42 (s, 1H), 7.40 (s, 1H), 5.85 (brs, 1H), 2.90 (d, J=5 Hz, 3H), 1.67 (d, J=6 Hz, 6H; MS (ESI) m/z: 533.0 (M+H$^+$).

EXAMPLE 313

Using general method F, 3-isocyanatobenzonitrile (0.06 g, 0.416 mmol) was reacted with Example A49 (0.06 g, 0.183 mmol) in methylene chloride (2 ml) for 6 hours to provide 1-(3-cyanophenyl)-3-(2-fluoro-5-(8-isopropyl-2-(methylamino)-7-oxo-7,8-dihydropyrido[2,3-d]pyrimidin-6-yl)phenyl)urea (0.068 g, 79% yield). $^1$H NMR (400 MHz, DMSO-$d_6$): δ 9.51 (s, 1H), 8.83 (s, 1H), 8.75 (s, 1H), 8.43 (d, J=8 Hz, 1H), 8.11 (m, 1H), 7.93 (s, 1H), 7.89 (m, 1H), 7.75 (m, 1H), 7.60 (t, J=8 Hz, 1H), 7.54 (m, 1H), 7.37 (m, 2H), 5.85 (brs, 1H), 2.90 (d, J=5 Hz, 3H), 1.67 (d, J=6 Hz, 6H); MS (ESI) m/z: 472.2 (M+H$^+$).

EXAMPLE 314

Using general method F, isocyanatocyclohexane (0.050 g, 0.399 mmol) was reacted with Example A49 (0.070 g, 0.214 mmol) in pyridine (2 ml) at 50° C. for 3 hours to provide 1-cyclohexyl-3-(2-fluoro-5-(8-isopropyl-2-(methylamino)-7-oxo-7,8-dihydropyrido[2,3-d]pyrimidin-6-yl)phenyl)urea (0.03 g, 31% yield). $^1$H NMR (400 MHz, DMSO-$d_6$): δ 8.74 (s, 1H), 8.47 d, J=9 Hz, 1H), 8.31 (brs, 1H), 7.88 (s, 2H), 7.27 (m, 2H), 6.72 (d, J=9 Hz, 1H), 5.87 (brs, 1H), 3.58 (m, 1H), 3.00 (d, J=5 Hz, 3H), 1.95-1.20 (m, 10H), 1.70 (d, J=6 Hz, 6H); MS (ESI) m/z: 453.3 (M+H$^+$).

EXAMPLE 315

Using general method F, isocyanatocyclohexane (0.050 g, 0.399 mmol) was reacted with Example A12 (0.070 g, 0.234 mmol) in pyridine (2 ml) at 50° C. for 3 hours provide 1-cyclohexyl-3-(2-fluoro-5-(8-methyl-2-(methylamino)-7-oxo-7,8-dihydropyrido[2,3-d]pyrimidin-6-yl)phenyl)urea (0.045 g, 45% yield). $^1$H NMR (400 MHz, DMSO-$d_6$) δ 8.76 (s, 1H), 8.50 (d, J=9 Hz, 1H), 8.31 (brs, 1H), 7.88 (s, 2H), 7.29 (m, 2H), 6.72 (d, J=9 Hz, 1H), 3.71 (s, 3H), 3.58 (m, 1H), 3.00 (d, J=5 Hz, 3H), 1.95-1.20 (m, 10H); MS (ESI) m/z: 425.2 (M+H$^+$).

EXAMPLE 316

Using general Method F, isocyanatocyclohexane (0.100 g, 0.799 mmol) was reacted with Example A28 (0.100 g, 0.301 mmol) in pyridine (2 ml) at 50° C. for 2 hours to provide 1-(4-chloro-2-fluoro-5-(1-methyl-7-(methylamino)-2-oxo-1,2-dihydro-1,6-naphthyridin-3-yl)phenyl)-3-cyclohexylurea (0.082 g, 60% yield). $^1$H NMR (400 MHz, DMSO-$d_6$): δ 8.39 (s, 1H), 8.32 (brs, 1H)), 8.17 (d, J=9 Hz, 1H), 7.70 (s, 1H), 7.43 (d, J=11.5 Hz, 1H), 7.08 (m, 1H), 6.62 (d, J=8 Hz, 1H), 6.15 (s, 1H), 3.49 (s, 3H), 3.41 (m, 1H), 2.86 (d, J=5 Hz, 3H), 1.85-1.45 (m, 5H), 1.35-1.20 (m, 5H); MS (ESI) m/z: 458.1 (M+H$^+$).

EXAMPLE 317

Using general method F, 1-isocyanatobenzene (0.050 g, 0.420 mmol) was reacted with Example A28 (0.070 g, 0.210 mmol) in ethylacetate (2 ml) for 13 hours to provide 1-(4-chloro-2-fluoro-5-(1-methyl-7-(methylamino)-2-oxo-1,2-dihydro-1,6-naphthyridin-3-yl)phenyl)-3-phenylurea (0.080 g, 84% yield). $^1$H NMR (400 MHz, DMSO-$d_6$): δ 9.08 (s, 1H), 8.68 (brs, 1H)), 8.40 (s, 1H), 8.17 (d, J=9 Hz, 1H), 7.74 (s, 1H), 7.53 (d, J=11.5 Hz, 1H), 7.41 (m, 1H), 7.26 (m, 1H), 7.10 (m, 1H), 6.96 (m, 1H), 6.15 (s, 1H), 3.49 (s, 3H), 2.86 (d, J=5 Hz, 3H); MS (ESI) m/z: 452.0 (M+H$^+$).

EXAMPLE 318

Using general method F, 1-isocyanatonaphthalene (0.050 g, 0.296 mmol) was reacted with Example A28 (0.070 g, 0.210 mmol) in ethylacetate (2 ml) at RT for 13 hours to provide 1-(4-chloro-2-fluoro-5-(1-methyl-7-(methylamino)-2-oxo-1,2-dihydro-1,6-naphthyridin-3-yl)phenyl)-3-(naphthalen-1-yl)urea, (0.07 g, 67% yield). $^1$H NMR (400 MHz, DMSO-$d_6$): δ 9.18 (s, 2H), 8.40 (s, 1H), 8.26 (d, J=9 Hz, 1H), 8.14 (d, J=9 Hz, 1H), 7.98 (d, J=7 Hz, 1H), 7.90 (d, J=8 Hz, 1H), 7.74 (s, 1H), 7.60 (m, 3H), 7.43 (t, J=8 Hz, 1H), 7.11 (m, 1H), 7.26 (m, 1H), 6.16 (s, 1H), 3.49 (s, 3H), 2.86 (d, J=5 Hz, 3H); MS (ESI) m/z: 502.0 (M+H$^+$).

EXAMPLE 319

Using general method F, 1-chloro-4-isocyanato-2-(trifluoromethyl)benzene (0.070 g, 0.316 mmol) was reacted with Example A28 (0.070 g, 0.210 mmol) in ethyl acetate (2 ml) for 13 hours to provide 1-(4-chloro-2-fluoro-5-(1-methyl-7-(methylamino)-2-oxo-1,2-dihydro-1,6-naphthyridin-3-yl)phenyl)-3-(4-chloro-3-(trifluoromethyl)phenyl)urea (0.104 g, 89% yield). $^1$H NMR (400 MHz, DMSO-$d_6$): δ 9.54 (s, 1H), 8.83 (brs, 1H)), 8.43 (s, 1H), 8.12 (m, 2H), 7.77 (s, 1H), 7.65-7.50 (m, 3H), 7.12 (m, 1H), 6.15 (s, 1H), 3.52 (s, 3H), 2.86 (d, J=5 Hz, 3H); MS (ESI) m/z: 555.0 (M+H$^+$).

EXAMPLE 320

Using general method F, 1-fluoro-2-isocyanato-4-(trifluoromethyl)benzene (0.070 g, 0.341 mmol) was reacted with Example A28 (0.070 g, 0.210 mmol) in ethyl acetae (2 ml) for 13 hours to provide 1-(4-chloro-2-fluoro-5-(1-methyl-7-(methylamino)-2-oxo-1,2-dihydro-1,6-naphthyridin-3-yl)phenyl)-3-(2-fluoro-5-(trifluoromethyl)phenyl)urea (0.095 g, 84% yield). $^1$H NMR (400 MHz, DMSO-$d_6$): δ 9.41 (brs, 1H), 9.31 (brs, 1H)), 8.57 (dd, J=7, 2 Hz, 1H), 8.42 (s, 1H), 8.22 (d, J=9 Hz, 1H), 7.77 (s, 1H), 7.58 (d, J=11.5 Hz, 1H), 7.51 (m, 1H), 7.40 (m, 1H), 7.10 (m, 1H), 6.15 (s, 1H), 3.51 (s, 3H), 2.86 (d, J=5 Hz, 3H); MS (ESI) m/z:538.0 (M+H$^+$).

EXAMPLE 321

Using general method F, 3-isocyanatobenzonitrile (0.050 g, 0.347 mmol) was reacted with Example A28 (0.070 g, 0.210 mmol) in ethyl acetate (2 ml) for 13 hours to provide 1-(4-chloro-2-fluoro-5-(1-methyl-7-(methylamino)-2-oxo-1,2-dihydro-1,6-naphthyridin-3-yl)phenyl)-3-(3-cyanophenyl)urea (0.090 g, 90% yield). $^1$H NMR (400 MHz, DMSO-d$_6$): δ 9.42 (s, 1H), 8.86 (brs, 1H), 8.44 (s, 1H), 8.17 (d, J=9 Hz, 1H), 7.99 (m, 1H), 7.77 (s, 1H), 7.63 (m, 1H), 7.58 (d, J=11.5 Hz, 1H), 7.51 (t, J=7 Hz, 1H), 7.45 (m, 1H), 7.14 (m, 1H), 6.19 (s, 1H), 3.52 (s, 3H), 2.86 (d, J=5 Hz, 3H); MS (ESI) m/z: 477.0 (M+H$^+$).

EXAMPLE 322

Using general method D, 2,3-difluorobenzoic acid (0.071 g, 0.449 mmol), triethylamine (0.091 g, 0.898 mmol), DPPA (0.124 g, 0.449 mmol) and Example A28 (0.100 g, 0.299 mmol) were combined to provide 1-(4-chloro-2-fluoro-5-(1-methyl-7-(methylamino)-2-oxo-1,2-dihydro-1,6-naphthyridin-3-yl)phenyl)-3-(2,3-difluorophenyl)urea (0.070 g, 48% yield). $^1$H NMR (400 MHz, DMSO-d$_6$): δ 9.26 (brs, 1H), 9.22 (brs, 1H)), 8.42 (s, 1H), 8.20 (d, J=10 Hz, 1H), 7.94 (m, 1H), 7.77 (s, 1H), 7.57 (d, J=12 Hz, 1H), 7.12 (m, 2H), 7.04 (m, 1H), 6.18 (s, 1H), 3.51 (s, 3H), 2.86 (d, J=5 Hz, 3H); MS (ESI) m/z: 488.0 (M+H$^+$).

EXAMPLE 323

Using general method F, isocyanatocyclohexane (0.100 g, 0.799 mmol) was reacted with Example A62 (0.100 g, 0.304 mmol) in pyridine (2 ml) for 3 hours at 50° C. to provide 1-(4-chloro-3-(1-ethyl-7-(methylamino)-2-oxo-1,2-dihydro-1,6-naphthyridin-3-yl)phenyl)-3-cyclohexylurea (0.075 g, 54% yield). $^1$H NMR (400 MHz, DMSO-d$_6$): δ 8.46 (s, 1H), 8.40 (s, 1H)), 7.71 (s, 1H), 7.45 (s, 1H), 7.32 (brs, 2H), 7.04 (m, 1H), 6.24 (s, 1H), 6.11 (d, J=8 Hz, 1H), 6.25 (s, 1H), 6.00 (s, 1H), 4.15 (q, J=6 Hz, 2H), 3.43 (m, 1H), 2.86 (d, J=5 Hz, 3H), 1.85-1.50 (m, 5H), 1.35-1.20 (m, 5H), 1.20 (t, J=6 Hz, 3H); MS (ESI) m/z: 454.1 (M+H$^+$).

EXAMPLE 324

Using general method C, 2,2,2-trichloroethyl 3-isopropylisoxazol-5-ylcarbamate (0.077 g, 0.255 mmol) was reacted with Example A62 (0.070 g, 0.213 mmol) in dioxane (2 ml) in presence of N-methylpyrrolidine (0.018 g, 0.213 mmol) at 80° C. for 4 hours to provide 1-(4-chloro-3-(1-ethyl-7-(methylamino)-2-oxo-1,2-dihydro-1,6-naphthyridin-3-yl)phenyl)-3-(3-isopropylisoxazol-5-yl)urea (0.080 g, 78% yield). $^1$H NMR (400 MHz, DMSO-d$_6$): δ 10.2 (s, 1H), 9.00 (s, 1H)), 8.43 (s, 1H), 7.75 (s, 1H), 7.54 (d, J=2.5 Hz, 1H), 7.44 (m, 2H), 7.06 (m, 1H), 6.25 (s, 1H), 6.00 (s, 1H), 4.15 (q, J=6 Hz, 2H), 2.90 (m, 1H), 2.87 (d, J=6 Hz, 3H), 1.20 (m, 9H); MS (ESI) m/z: 481.2 (M+H$^+$).

EXAMPLE 325

Using general method D, 3-tert-butyl-1-methyl-1H-pyrazole-5-carboxylic acid (50 mg, 0.27 mmol) and Example A21 (0.102 g, 0.27 mmol) in presence of DPPA (65 μL, 0.30 mmol) and Et$_3$N (42 μL, 0.30 mmol) were combined to afford 1-(3-tert-butyl-1-methyl-1H-pyrazol-5-yl)-3-(5-(8-cyclopentyl-2-(methylthio)-7-oxo-7,8-dihydropyrido[2,3-d]pyrimidin-6-yl)-2-fluoro-4-methylphenyl)urea.

Using a procedure analogous to Example A1, 1-(3-tert-butyl-1-methyl-1H-pyrazol-5-yl)-3-(5-(8-cyclopentyl-2-(methylthio)-7-oxo-7,8-dihydropyrido[2,3-d]pyrimidin-6-yl)-2-fluoro-4-methylphenyl)urea (150 mg, 0.27 mmol) was treated with mCPBA (70% wt, 74 mg, 0.30 mmol) and then 2 M methylamine (1.4 mL) to afford 1-(3-tert-butyl-1-methyl-1H-pyrazol-5-yl)-3-(5-(8-cyclopentyl-2-(methylamino)-7-oxo-7,8-dihydropyrido[2,3-d]pyrimidin-6-yl)-2-fluoro-4-methylphenyl)urea (85 mg, 58% yield). $^1$H NMR (400 MHz, DMSO-d$_6$, major isomer): 9.00 (s, 1H), 8.86 (d, J=2.0 Hz, 1H), 8.71 (brs, 1H), 8.04 (d, J=8.8 Hz, 1H), 7.90 (q, J=4.4 Hz, 1H), 7.75 (s, 1H), 7.26 (d, J=12.4 Hz, 1H), 6.17 (s, 1H), 6.06 (brm, 1H), 3.71 (s, 3H), 3.01 (d, J=4.4 Hz, 3H), 2.42 (brs, 2H), 2.18 (s, 3H), 2.07 brs, 2H), 1.90 (brs, 2H), 1.72 brs, 2H), 1.29 (s, 9H); MS (ESI) m/z: 547.2 (M+H$^+$).

The following examples are prepared by the methods described in Schemes 1-12, General Methods A-G, the above Examples and the methods described in WO 2006/071940.

1-(3-tert-butyl-1-methyl-1H-pyrazol-5-yl)-3-(2-fluoro-5-(1-isopropyl-7-(methylamino)-2-oxo-1,2-dihydro-1,6-naphthyridin-3-yl)-4-methylphenyl)urea, 1-(1-(2-(dimethylamino)ethyl)-5-isopropyl-1H-pyrazol-3-yl)-3-(2-fluoro-4-methyl-5-(8-methyl-2-(methylamino)-7-oxo-7,8-dihydropyrido[2,3-d]pyrimidin-6-yl)phenyl)urea, 1-(2-tert-butyloxazol-5-yl)-3-(2-fluoro-4-methyl-5-(8-methyl-2-(methylamino)-7-oxo-7,8-dihydropyrido[2,3-d]pyrimidin-6-yl)phenyl)urea, 1-(2-tert-butyloxazol-5-yl)-3-(4-chloro-2-fluoro-5-(8-methyl-2-(methylamino)-7-oxo-7,8-dihydropyrido[2,3-d]pyrimidin-6-yl)phenyl)urea, 1-(2-tert-butyloxazol-5-yl)-3-(5-(8-ethyl-2-(methylamino)-7-oxo-7,8-dihydropyrido[2,3-d]pyrimidin-6-yl)-2-fluorophenyl)urea, 1-(5-tert-butyl-4-methylisoxazol-3-yl)-3-(5-(8-ethyl-2-(methylamino)-7-oxo-7,8-dihydropyrido[2,3-d]pyrimidin-6-yl)-2-fluoro-4-methylphenyl)urea, 1-(bicyclo[2.2.1]-hept-5-en-2-yl)-3-(2-fluoro-4-methyl-5-(8-methyl-2-(methylamino)-7-oxo-7,8-dihydropyrido[2,3-d]pyrimidin-6-yl)phenyl)urea, 1-(bicyclo[2.2.1]heptan-2-yl)-3-(2-fluoro-4-methyl-5-(8-methyl-2-(methylamino)-7-oxo-7,8-dihydropyrido[2,3-d]pyrimidin-6-yl)phenyl)urea, 1-(2-fluoro-4-methyl-5-(8-methyl-2-(methylamino)-7-oxo-7,8-dihydropyrido[2,3-d]pyrimidin-6-yl)phenyl)-3-isopropylurea, (R)-1-(2-fluoro-4-methyl-5-(8-methyl-2-(methylamino)-7-oxo-7,8-dihydropyrido[2,3-d]pyrimidin-6-yl)phenyl)-3-(1-phenylethyl)urea, 1-(2-fluoro-4-methyl-5-(8-methyl-2-(methylamino)-7-oxo-7,8-dihydropyrido[2,3-d]pyrimidin-6-yl)phenyl)-3-(1-(pyridin-3-yl)ethyl)urea, 1-(2-fluoro-5-(1-(2-hydroxyethyl)-7-(methylamino)-2-oxo-1,2-dihydro-1,6-naphthyridin-3-yl)-4-methylphenyl)-3-isopropylurea, 1-(5-(8-ethyl-2-(methylamino)-7-oxo-7,8-dihydropyrido[2,3-d]pyrimidin-6-yl)-2-fluorophenyl)-3-(5-(trifluoromethyl)pyridin-3-yl)urea, 1-(2-fluoro-5-(8-methyl-2-(methylamino)-7-oxo-7,8-dihydropyrido[2,3-d]pyrimidin-6-yl)phenyl)-3-(2-fluoro-5-(trifluoromethyl)phenyl)urea, 1-(2-fluoro-5-(8-(2-hydroxyethyl)-2-(methylamino)-7-oxo-7,8-dihydropyrido[2,3-d]pyrimidin-6-yl)phenyl)-3-(2-fluoro-5-(trifluoromethyl)phenyl)urea, 1-(4-chloro-2-fluoro-5-(8-methyl-2-(methylamino)-7-oxo-7,8-dihydropyrido[2,3-d]pyrimidin-6-yl)phenyl)-3-cyclohexylurea, 1-cyclohexyl-3-(2,4-difluoro-5-(8-methyl-2-(methylamino)-7-oxo-7,8-dihydropyrido[2,3-d]pyrimidin-6-yl)phenyl)urea, 1-(4-cyano-2-fluoro-5-(8-methyl-2-(methylamino)-7-oxo-7,8-dihydropyrido[2,3-d]pyrimidin-6-yl)phenyl)-3-cyclohexylurea, 1-cyclohexyl-3-(5-(8-ethyl-2-(methylamino)-7-oxo-7,8-dihydropyrido[2,3-d]pyrimidin-6-yl)-2-fluorophenyl)urea, 1-cyclohexyl-3-(2- fluoro-4-methyl-5-(8-methyl-2-(methylamino)-7-oxo-7,8-dihydropyrido[2,3-d]pyrimidin-6-yl)phenyl)urea, 1-cyclohexyl-3-(2-fluoro-5-(8-(2-hydroxyethyl)-2-(methylamino)-7-oxo-7,8-dihydropyrido[2,3-d]pyrimidin-6-yl)phenyl)urea, 1-(2-fluoro-4-methyl-5-(8-methyl-2-(methylamino)-7-oxo-7,8-dihydropyrido[2,3-d]pyrimidin-6-yl)phenyl)-3-((1R,2R)-2-methylcyclohexyl)urea, 1-(2-fluoro-4-methyl-5-(8-methyl-2-(methylamino)-7-oxo-7,8-dihydropyrido[2,3-d]pyrimidin-6-yl)phenyl)-3-((1S,2S)-2-methylcyclohexyl)urea, and 1-(2-fluoro-4-methyl-5-(8-methyl-2-(methylamino)-7-oxo-7,8-dihydropyrido[2,3-d]pyrimidin-6-yl)phenyl)-3-((1r,4r)-4-methylcyclohexyl)urea.

The following examples are prepared by the methods described in Schemes 1-12, General Methods A-G, the above Examples and the methods described in WO 2006/071940.

1-(4-tert-butylthiophen-2-yl)-3-(2-fluoro-4-methyl-5-(1-methyl-7-(methylamino)-2-oxo-1,2-dihydro-1,6-naphthyridin-3-yl)phenyl)urea, 1-(4-tert-butyl-3-methylthiophen-2-yl)-3-(2-fluoro-4-methyl-5-(1-methyl-7-(methylamino)-2-oxo-1,2-dihydro-1,6-naphthyridin-3-yl)phenyl)urea, 1-(4-tert-butyl-3-chlorothiophen-2-yl)-3-(2-fluoro-4-methyl-5-(1-methyl-7-(methylamino)-2-oxo-1,2-dihydro-1,6-naphthyridin-3-yl)phenyl)urea, 1-(4-tert-butyl-3-fluorothiophen-2-yl)-3-(2-fluoro-4-methyl-5-(1-methyl-7-(methylamino)-2-oxo-1,2-dihydro-1,6-naphthyridin-3-yl)phenyl)urea, 1-(4-tert-butyl-3-methylthiophen-2-yl)-3-(2-fluoro-5-(1-(2-hydroxyethyl)-7-(methylamino)-2-oxo-1,2-dihydro-1,6-naphthyridin-3-yl)-4-methylphenyl)urea, 1-(1-tert-butyl-2-methyl-1H-pyrrol-3-yl)-3-(2-fluoro-4-methyl-5-(1-methyl-7-(methylamino)-2-oxo-1,2-dihydro-1,6-naphthyridin-3-yl)phenyl)urea, 1-(1-tert-butyl-2-methyl-1H-pyrrol-3-yl)-3-(4-chloro-2-fluoro-5-(1-methyl-7-(methylamino)-2-oxo-1,2-dihydro-1,6-naphthyridin-3-yl)phenyl)urea, 1-(1-tert-butyl-2-methyl-1H-pyrrol-3-yl)-3-(2,4-difluoro-5-(1-methyl-7-(methylamino)-2-oxo-1,2-dihydro-1,6-naphthyridin-3-yl)phenyl)urea, 1-(1-tert-butyl-2-methyl-1H-pyrrol-3-yl)-3-(5-(1-ethyl-7-(methylamino)-2-oxo-1,2-dihydro-1,6-naphthyridin-3-yl)-2-fluoro-4-methylphenyl)urea, 1-(1-tert-butyl-2-methyl-1H-pyrrol-3-yl)-3-(5-(1-ethyl-7-(methylamino)-2-oxo-1,2-dihydro-1,6-naphthyridin-3-yl)-2-fluorophenyl)urea, 1-(1-tert-butyl-1H-pyrrol-3-yl)-3-(2-fluoro-4-methyl-5-(1-methyl-7-(methylamino)-2-oxo-1,2-dihydro-1,6-naphthyridin-3-yl)phenyl)urea, 1-(1-tert-butyl-4-chloro-1H-pyrrol-3-yl)-3-(2-fluoro-4-methyl-5-(1-methyl-7-(methylamino)-2-oxo-1,2-dihydro-1,6-naphthyridin-3-yl)phenyl)urea, 1-(4-tert-butyl-1-methyl-1H-pyrrol-2-yl)-3-(2-fluoro-4-methyl-5-(1-methyl-7-(methylamino)-2-oxo-1,2-dihydro-1,6-naphthyridin-3-yl)phenyl)urea, 1-(4-tert-butyl-1-methyl-1H-pyrrol-2-yl)-3-(5-(1-ethyl-7-(methylamino)-2-oxo-1,2-dihydro-1,6-naphthyridin-3-yl)-2-fluorophenyl)urea, 1-(4-tert-butyl-3-chloro-1-methyl-1H-pyrrol-2-yl)-3-(2-fluoro-4-methyl-5-(1-methyl-7-(methylamino)-2-oxo-1,2-dihydro-1,6-naphthyridin-3-yl)phenyl)urea, 1-(3-tert-butyl-1-methyl-1H-pyrazol-5-yl)-3-(2-fluoro-5-(1-isopropyl-7-(methylamino)-2-oxo-1,2-dihydro-1,6-naphthyridin-3-yl)-4-methylphenyl)urea, 1-(2-tert-butyloxazol-5-yl)-3-(2-fluoro-4-methyl-5-(1-methyl-7-(methylamino)-2-oxo-1,2-dihydro-1,6-naphthyridin-3-yl)phenyl)urea, 1-(2-tert-butyloxazol-5-yl)-3-(4-chloro-2-fluoro-5-(1-methyl-7-(methylamino)-2-oxo-1,2-dihydro-1,6-naphthyridin-3-yl)phenyl)urea, 1-(2-tert-butyloxazol-5-yl)-3-(5-(1-ethyl-7-(methylamino)-2-oxo-1,2-dihydro-1,6-naphthyridin-3-yl)-2-fluorophenyl)urea, 1-(2-tert-butyloxazol-5-yl)-3-(2-fluoro-5-(1-(2-hydroxyethyl)-7-(methylamino)-2-oxo-1,2-dihydro-1,6-naphthyridin-3-yl)-4-methylphenyl)urea, 1-(2-tert-butyloxazol-5-yl)-3-(4-chloro-2-fluoro-5-(1-(2-hydroxyethyl)-7-(methylamino)-2-oxo-1,2-dihydro-1,6-naphthyridin-3-yl)phenyl)urea, 1-(5-tert-butylisoxazol-3-yl)-3-(2-fluoro-5-(1-(2-hydroxyethyl)-7-(methylamino)-2-oxo-1,2-dihydro-1,6-naphthyridin-3-yl)-4-methylphenyl)urea, 1-(5-tert-butyl-4-methylisoxazol-3-yl)-3-(5-(1-ethyl-7-(methylamino)-2-oxo-1,2-dihydro-1,6-naphthyridin-3-yl)-2-fluoro-4-methylphenyl)urea, 1-(4-tert-butylfuran-2-yl)-3-(2-fluoro-4-methyl-5-(1-methyl-7-(methylamino)-2-oxo-1,2-dihydro-1,6-naphthyridin-3-yl)phenyl)urea, 1-(4-tert-butyl-3-chlorofuran-2-yl)-3-(2-fluoro-4-methyl-5-(1-methyl-7-(methylamino)-2-oxo-1,2-dihydro-1,6-naphthyridin-3-yl)phenyl)urea, 1-(4-tert-butyl-3-fluorofuran-2-yl)-3-(2-fluoro-4-methyl-5-(1-methyl-7-(methylamino)-2-oxo-1,2-dihydro-1,6-naphthyridin-3-yl)phenyl)urea, 1-(4-tert-butyl-3-methylfuran-2-yl)-3-(2-fluoro-5-(1-(2-hydroxyethyl)-7-(methylamino)-2-oxo-1,2-dihydro-1,6-naphthyridin-3-yl)-4-methylphenyl)urea, 1-cyclopropyl-3-(2-fluoro-4-methyl-5-(1-methyl-7-(methylamino)-2-oxo-1,2-dihydro-1,6-naphthyridin-3-yl)phenyl)urea, 1-(2-fluoro-4-methyl-5-(1-methyl-7-(methylamino)-2-oxo-1,2-dihydro-1,6-naphthyridin-3-yl)phenyl)-3-isopropylurea, (R)-1-(2-fluoro-4-methyl-5-(1-methyl-7-(methylamino)-2-oxo-1,2-dihydro-1,6-naphthyridin-3-yl)phenyl)-3-(1-phenylethyl)urea, 1-(2-fluoro-4-methyl-5-(1-methyl-7-(methylamino)-2-oxo-1,2-dihydro-1,6-naphthyridin-3-yl)phenyl)-3-(1-(pyridin-3-yl)ethyl)urea, 1-(5-(1-cyclopentyl-7-(methylamino)-2-oxo-1,2-dihydro-1,6-naphthyridin-3-yl)-2-fluoro-4-methylphenyl)-3-isopropylurea, 1-(2-fluoro-5-(1-((3R)-3-hydroxycyclopentyl)-7-(methylamino)-2-oxo-1,2-dihydro-1,6-naphthyridin-3-yl)-4-methylphenyl)-3-isopropylurea, 1-(2-fluoro-4-methyl-5-(1-methyl-7-(methylamino)-2-oxo-1,2-dihydro-1,6-naphthyridin-3-yl)phenyl)-3-(5-(trifluoromethyl)pyridin-3-yl)urea, 1-(2-fluoro-4-methyl-5-(1-methyl-7-(methylamino)-2-oxo-1,2-dihydro-1,6-naphthyridin-3-yl)phenyl)-3-(4-methyl-5-(trifluoromethyl)pyridin-3-yl)urea, 1-(2,4-difluoro-5-(1-methyl-7-(methylamino)-2-oxo-1,2-dihydro-1,6-naphthyridin-3-yl)phenyl)-3-(5-(trifluoromethyl)pyridin-3-yl)urea, 1-(5-(1-ethyl-7-(methylamino)-2-oxo-1,2-dihydro-1,6-naphthyridin-3-yl)-2-fluorophenyl)-3-(5-(trifluoromethyl)pyridin-3-yl)urea, 1-(2-fluoro-4-methyl-5-(1-methyl-7-(methylamino)-2-oxo-1,2-dihydro-1,6-naphthyridin-3-yl)phenyl)-3-(4-fluoro-5-(trifluoromethyl)pyridin-3-yl)urea, 1-(4-chloro-2-fluoro-5-(1-methyl-7-(methylamino)-2-oxo-1,2-dihydro-1,6-naphthyridin-3-yl)phenyl)-3-(5-(trifluoromethyl)pyridin-3-yl)urea, 1-(2-fluoro-5-(1-(2-hydroxyethyl)-7-(methylamino)-2-oxo-1,2-dihydro-1,6-naphthyridin-3-yl)phenyl)-3-(5-(trifluoromethyl)pyridin-3-yl)urea, 1-(5-(7-amino-1-methyl-2-oxo-1,2-dihydro-1,6-naphthyridin-3-yl)-2-fluoro-4-methylphenyl)-3-(3-(trifluoromethyl)phenyl)urea, 1-(2-fluoro-5-(1-(2-hydroxyethyl)-7-(methylamino)-2-oxo-1,2-dihydro-1,6-naphthyridin-3-yl)-4-methylphenyl)-3-(3-(trifluoromethyl)phenyl)urea, 1-(2-fluoro-4-methyl-5-(1-methyl-7-(methylamino)-2-oxo-1,2-dihydro-1,6-naphthyridin-3-yl)phenyl)-3-(2-fluoro-5-(trifluoromethyl)phenyl)urea, 1-(2-fluoro-5-(1-(2-hydroxyethyl)-7-(methylamino)-2-oxo-1,2-dihydro-1,6-naphthyridin-3-yl)-4-methylphenyl)-3-(2-fluoro-5-(trifluoromethyl)phenyl)urea, 1-(2-fluoro-5-(1-(2-hydroxyethyl)-7-(methylamino)-2-oxo-1,2-dihydro-1,6-naphthyridin-3-yl)phenyl)-3-(2-fluoro-5-(trifluoromethyl)phenyl)urea, 1-(1-tert-butyl-5-(hydroxymethyl)-1H-pyrazol-4-yl)-3-(4-chloro-2-fluoro-5-(1-methyl-7-(methylamino)-2-oxo-1,2-dihydro-1,6-naphthyridin-3-yl)phenyl)urea, 1-(1-tert-butyl-5-(hydroxymethyl)-1H-pyrazol-4-yl)-3-(2-fluoro-4-methyl-5-(1-methyl-7-(methylamino)-2-oxo-1,2-dihydro-1,6- naphthyridin-3-yl)phenyl)urea, 1-(1-tert-butyl-5-(hydroxymethyl)-1H-pyrazol-4-yl)-3-(2,4-difluoro-5-(1-methyl-7-(methylamino)-2-oxo-1,2-dihydro-1,6-naphthyridin-3-yl)phenyl)urea, 1-(1-tert-butyl-5-(1-hydroxyethyl)-1H-pyrazol-4-yl)-3-(4-chloro-2-fluoro-5-(1-methyl-7-(methylamino)-2-oxo-1,2-dihydro-1,6-naphthyridin-3-yl)phenyl)urea, 1-(1-tert-butyl-5-(1-hydroxyethyl)-1H-pyrazol-4-yl)-3-(2-fluoro-4-methyl-5-(1-methyl-7-(methylamino)-2-oxo-1,2-dihydro-1,6-naphthyridin-3-yl)phenyl)urea, 1-(1-tert-butyl-5-(1-hydroxyethyl)-1H-pyrazol-4-yl)-3-(2,4-difluoro-5-(1-methyl-7-(methylamino)-2-oxo-1,2-dihydro-1,6-naphthyridin-3-yl)phenyl)urea, 1-(1-tert-butyl-5-ethyl-1H-pyrazol-4-yl)-3-(4-chloro-2-fluoro-5-(1-methyl-7-(methylamino)-2-oxo-1,2-dihydro-1,6-naphthyridin-3-yl)phenyl)urea, 1-(1-tert-butyl-5-ethyl-1H-pyrazol-4-yl)-3-(2-fluoro-4-methyl-5-(1-methyl-7-(methylamino)-2-oxo-1,2-dihydro-1,6-naphthyridin-3-yl)phenyl)urea, 1-(1-tert-butyl-5-ethyl-1H-pyrazol-4-yl)-3-(2,4-difluoro-5-(1-methyl-7-(methylamino)-2-oxo-1,2-dihydro-1,6-naphthyridin-3-yl)phenyl)urea, 1-(1-tert-butyl-5-methyl-1H-pyrazol-4-yl)-3-(2-fluoro-4-methyl-5-(1-methyl-7-(methylamino)-2-oxo-1,2-dihydro-1,6-naphthyridin-3-yl)phenyl)urea, 1-(1-tert-butyl-5-methyl-1H-pyrazol-4-yl)-3-(4-chloro-2-fluoro-5-(1-methyl-7-(methylamino)-2-oxo-1,2-dihydro-1,6-naphthyridin-3-yl)phenyl)urea, 1-(1-tert-butyl-5-methyl-1H-pyrazol-4-yl)-3-(2,4-difluoro-5-(1-methyl-7-(methylamino)-2-oxo-1,2-dihydro-1,6-naphthyridin-3-yl)phenyl)urea, 1-cyclohexyl-3-(2-fluoro-4-methyl-5-(1-methyl-7-(methylamino)-2-oxo-1,2-dihydro-1,6-naphthyridin-3-yl)phenyl)urea, 1-cyclohexyl-3-(5-(1-ethyl-7-(methylamino)-2-oxo-1,2-dihydro-1,6-naphthyridin-3-yl)-2-fluoro-4-methylphenyl)urea, 1-cyclohexyl-3-(2-fluoro-5-(1-isopropyl-7-(methylamino)-2-oxo-1,2-dihydro-1,6-naphthyridin-3-yl)-4-methylphenyl)urea, 1-cyclohexyl-3-(2-fluoro-5-(1-isopropyl-7-(methylamino)-2-oxo-1,2-dihydro-1,6-naphthyridin-3-yl)phenyl)urea, 1-cyclohexyl-3-(5-(1-cyclopentyl-7-(methylamino)-2-oxo-1,2-dihydro-1,6-naphthyridin-3-yl)-2-fluorophenyl)urea, 1-cyclohexyl-3-(5-(1-ethyl-7-(methylamino)-2-oxo-1,2-dihydro-1,6-naphthyridin-3-yl)-2-fluorophenyl)urea, 1-cyclohexyl-3-(2-fluoro-5-(1-((3R)-3-hydroxycyclopentyl)-7-(methylamino)-2-oxo-1,2-dihydro-1,6-naphthyridin-3-yl)phenyl)urea, 1-cyclohexyl-3-(2-fluoro-5-(1-((3R)-3-hydroxycyclopentyl)-7-(methylamino)-2-oxo-1,2-dihydro-1,6-naphthyridin-3-yl)-4-methylphenyl)urea, 1-cyclohexyl-3-(2-fluoro-5-(1-(1-hydroxypropan-2-yl)-7-(methylamino)-2-oxo-1,2-dihydro-1,6-naphthyridin-3-yl)phenyl)urea, 1-(4-chloro-2-fluoro-5-(1-methyl-7-(methylamino)-2-oxo-1,2-dihydro-1,6-naphthyridin-3-yl)phenyl)-3-cyclohexylurea, 1-cyclohexyl-3-(2,4-difluoro-5-(1-methyl-7-(methylamino)-2-oxo-1,2-dihydro-1,6-naphthyridin-3-yl)phenyl)urea, 1-(4-cyano-2-fluoro-5-(1-methyl-7-(methylamino)-2-oxo-1,2-dihydro-1,6-naphthyridin-3-yl)phenyl)-3-cyclohexylurea, 1-(2-fluoro-4-methyl-5-(1-methyl-7-(methylamino)-2-oxo-1,2-dihydro-1,6-naphthyridin-3-yl)phenyl)-3-((1R,2R)-2-methylcyclohexyl)urea, 1-(2-fluoro-4-methyl-5-(1-methyl-7-(methylamino)-2-oxo-1,2-dihydro-1,6-naphthyridin-3-yl)phenyl)-3-((1S,2S)-2-methylcyclohexyl)urea, 1-(2-fluoro-4-methyl-5-(1-methyl-7-(methylamino)-2-oxo-1,2-dihydro-1,6-naphthyridin-3-yl)phenyl)-3-((1r,4r)-4-methylcyclohexyl)urea, 1-(3-tert-butylisoxazol-5-yl)-3-(5-(1-cyclopentyl-7-(methylamino)-2-oxo-1,2-dihydro-1,6-naphthyridin-3-yl)-2-fluorophenyl)urea, 1-(3-cyclopentylisoxazol-5-yl)-3-(2-fluoro-4-methyl-5-(1-methyl-7-(methylamino)-2-oxo-1,2-dihydro-1,6-naphthyridin-3-yl)phenyl)urea, 1-(5-(7-amino-1-ethyl-2-oxo-1,2-dihydro-1,6-naphthyridin-3-yl)-2-fluorophenyl)-3-(3-tert-butylisoxazol-5-yl)urea, 1-(5-(7-amino-1-ethyl-2-oxo-1,2-dihydro-1,6-naphthyridin-3-yl)-2-fluoro-4-methylphenyl)-3-(3-tert-butylisoxazol-5-yl)urea, 1-(3-tert-butylisoxazol-5-yl)-3-(4-chloro-2-fluoro-5-(1-(2-hydroxyethyl)-7-(methylamino)-2-oxo-1,2-dihydro-1,6-naphthyridin-3-yl)phenyl)urea, 1-(3-tert-butylisoxazol-5-yl)-3-(2-fluoro-5-(1-(2-hydroxyethyl)-7-(methylamino)-2-oxo-1,2-dihydro-1,6-naphthyridin-3-yl)-4-methylphenyl)urea, 1-(2-fluoro-4-methyl-5-(1-methyl-7-(methylamino)-2-oxo-1,2-dihydro-1,6-naphthyridin-3-yl)phenyl)-3-(3-isopropylisoxazol-5-yl)urea, 1-(3-tert-butylisoxazol-5-yl)-3-(2-fluoro-5-(1-isopropyl-7-(methylamino)-2-oxo-1,2-dihydro-1,6-naphthyridin-3-yl)-4-methylphenyl)urea, 1-(3-tert-butylisoxazol-5-yl)-3-(2-fluoro-5-(1-(2-hydroxyethyl)-7-(methylamino)-2-oxo-1,2-dihydro-1,6-naphthyridin-3-yl)phenyl)urea, 1-(5-(7-amino-1-methyl-2-oxo-1,2-dihydro-1,6-naphthyridin-3-yl)-2-fluoro-4-methylphenyl)-3-(3-tert-butylisoxazol-5-yl)urea, 1-(3-cyclopentylisoxazol-5-yl)-3-(2-fluoro-5-(1-(2-hydroxyethyl)-7-(methylamino)-2-oxo-1,2-dihydro-1,6-naphthyridin-3-yl)-4-methylphenyl)urea, 1-(3-tert-butylisoxazol-5-yl)-3-(2-fluoro-5-(1-(2-hydroxyethyl)-7-(methylamino)-2-oxo-1,2-dihydro-1,6-naphthyridin-3-yl)-4-methylphenyl)urea, 1-(3-tert-butylisoxazol-5-yl)-3-(2-fluoro-5-(1-(2-hydroxyethyl)-7-(methylamino)-2-oxo-1,2-dihydro-1,6-naphthyridin-3-yl)phenyl)urea, 1-(3-tert-butylisoxazol-5-yl)-3-(2-fluoro-5-(1-((3R)-3-hydroxycyclopentyl)-7-(methylamino)-2-oxo-1,2-dihydro-1,6-naphthyridin-3-yl)-4-methylphenyl)urea, 1-(3-tert-butylisoxazol-5-yl)-3-(2-fluoro-5-(1-((3R)-3-hydroxycyclopentyl)-7-(methylamino)-2-oxo-1,2-dihydro-1,6-naphthyridin-3-yl)phenyl)urea, 1-(3-tert-butyl-4-methylisoxazol-5-yl)-3-(2-fluoro-4-methyl-5-(1-methyl-7-(methylamino)-2-oxo-1,2-dihydro-1,6-naphthyridin-3-yl)phenyl)urea, 1-(3-tert-butyl-4-chloroisoxazol-5-yl)-3-(2-fluoro-4-methyl-5-(1-methyl-7-(methylamino)-2-oxo-1,2-dihydro-1,6-naphthyridin-3-yl)phenyl)urea, 1-(3-tert-butyl-4-fluoroisoxazol-5-yl)-3-(2-fluoro-4-methyl-5-(1-methyl-7-(methylamino)-2-oxo-1,2-dihydro-1,6-naphthyridin-3-yl)phenyl)urea, 1-(3-tert-butyl-4-methylisoxazol-5-yl)-3-(2-fluoro-5-(1-(2-hydroxyethyl)-7-(methylamino)-2-oxo-1,2-dihydro-1,6-naphthyridin-3-yl)-4-methylphenyl)urea, 1-(3-tert-butyl-4-chloroisoxazol-5-yl)-3-(2-fluoro-5-(1-(2-hydroxyethyl)-7-(methylamino)-2-oxo-1,2-dihydro-1,6-naphthyridin-3-yl)-4-methylphenyl)urea, 1-(3-tert-butyl-4-fluoroisoxazol-5-yl)-3-(2-fluoro-5-(1-(2-hydroxyethyl)-7-(methylamino)-2-oxo-1,2-dihydro-1,6-naphthyridin-3-yl)-4-methylphenyl)urea, 1-(5-tert-butyl-1,3,4-thiadiazol-2-yl)-3-(4-chloro-2-fluoro-5-(1-methyl-7-(methylamino)-2-oxo-1,2-dihydro-1,6-naphthyridin-3-yl)phenyl)urea, 1-(5-tert-butyl-1,3,4-thiadiazol-2-yl)-3-(5-(1-ethyl-7-(methylamino)-2-oxo-1,2-dihydro-1,6-naphthyridin-3-yl)-2-fluorophenyl)urea, 1-(5-tert-butyl-1,3,4-thiadiazol-2-yl)-3-(2-fluoro-5-(1-(2-hydroxyethyl)-7-methylamino)-2-oxo-1,2-dihydro-1,6-naphthyridin-3-yl)phenyl)urea, 1-(5-tert-butyl-1,3,4-thiadiazol-2-yl)-3-(2-fluoro-5-(1-(2-hydroxyethyl)-7-(methylamino)-2-oxo-1,2-dihydro-1,6-naphthyridin-3-yl)-4-methylphenyl)urea, 1-(5-tert-butyl-1,3,4-thiadiazol-2-yl)-3-(2,4-difluoro-5-(1-(2-hydroxyethyl)-7-(methylamino)-2-oxo-1,2-dihydro-1,6-naphthyridin-3-yl)phenyl)urea, 1-(1-tert-butyl-5-methyl-1H-imidazol-4-yl)-3-(2-fluoro-4-methyl-5-(1-methyl-7-(methylamino)-2-oxo-1,2-dihydro-1,6-naphthyridin-3-yl)phenyl)urea, 1-(1-tert-butyl-5-chloro-1H-imidazol-4-yl)-3-(2-fluoro-4-methyl-5-(1-methyl-7-(methylamino)-2-oxo-1,2-dihydro-1,6-naphthyridin-3-yl)phenyl)urea, 1-(1-tert-butyl-5-fluoro-1H-imidazol-4-yl)-3-(2-fluoro-4-methyl-5-(1-methyl-7-(methylamino)-2-oxo-1, 2-dihydro-1,6-naphthyridin-3-yl)phenyl)urea, 1-(1-tert-butyl-5-methyl-1H-imidazol-4-yl)-3-(5-(1-ethyl-7-(methylamino)-2-oxo-1,2-dihydro-1,6-naphthyridin-3-yl)-2-fluoro-4-methylphenyl)urea, 1-(1-tert-butyl-5-methyl-1H-imidazol-4-yl)-3-(5-(1-ethyl-7-(methylamino)-2-oxo-1,2-dihydro-1,6-naphthyridin-3-yl)-2-fluorophenyl)urea, and 1-(1-tert-butyl-5-methyl-1H-imidazol-4-yl)-3-(2-fluoro-5-(1-(2-hydroxyethyl)-7-(methylamino)-2-oxo-1,2-dihydro-1,6-naphthyridin-3-yl)phenyl)urea.

B-Raf(V600E) Kinase Assay: The activity of B-Raf (V600E) kinase was determined by following the formation of ADP from the reaction through coupling with the pyruvate kinase/lactate dehydrogenase system (e.g., Schindler, et al. Science (2000)289, 1938-1942). In this assay, the oxidation of NADH (thus the decrease at $A_{340nm}$) was continuously monitored spectrophotometrically. The reaction mixture (100 μl) contained B-Raf(V600E) kinase (2.1 nM nominal concentration), unphosphorylated, full-length MEK1 (45 nM), $MgCl_2$ (13 mM), pyruvate kinase (3.5 units), lactate dehydrogenase (5.5 units), phosphoenolpyruvate (1 mM), and NADH (0.28 mM), in 60 mM Tris buffer, containing 0.13% octyl-glucoside and 3.5% DMSO concentration at pH 7.5. The test compounds were incubated with the reaction mixture at 30° C. for 2 h or 4 h. The reaction was initiated by adding ATP (0.2 mM, final concentration). The absorption at 340 ran was continuously monitored for 3 h at 30° C. on a Polarstar Optima plate reader (BMG). The reaction rate was calculated using the 1.5 h to 2.5 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

```
B-Raf(V600E) protein sequence used for screening:
                                       (SEQ. ID NO. 1)
EDRNRMKTLGRRDSSDDWEIPDGQITVGQRIGSGSFGTVYKGKWHGDVAV

KMLNVTAPTPQQLQAFKNEVGVLRKTRHVNILLFMGYSTKPQLAIVTQWC

EGSSLYHHLHIIETKFEMIKLIDIARQTAQGMDYLHAKSIIHRDLKSNNI

FLHEDLTVKIGDFGLATEKSRWSGSHQFEQLSGSILWMAPEVIRMQDKNP

YSFQSDVYAFGIVLYELMTGQLPYSNINNRDQIIFMVGRGYLSPDLSKVR

SNCPKAMKRLMAECLKKKRDERPLFPQILASIELLARSLPKIHR

MEK1 protein sequence used for screening:
                                       (SEQ. ID NO. 2)
MELKDDDFEKISELGAGNGGVVFKVSHKPSGLVMARKLIHLEIKPAIRNQ

IIRELQVLHECNSPYIVGFYGAFYSDGEISICMEHMDGGSLDQVLKKAGR

IPEQILGKVSIAVIKGLTYLREKHKIMHRDVKPSNILVNSRGEIKLCDFG

VSGQLIDSMANSFVGTRSYMSPERLQGTHYSVQSDIWSMGLSLVEMAVGR

YPIPPPDAKELELMFGCQVEGDAAETPPRPRTPGRPLSSYGMDSRPPMAI

FELLDYIVNEPPPKLPSGVFSLEFQDFVNKCLIKNPAERADLKQLMVHAF

IKRSDAEEVDFAGWLCSTIGLNQPSTPTHAAGV
```

C-Raf Kinase Assay: The activity of C-Raf kinase was determined by following the formation of ADP from the reaction through coupling with the pyruvate kinase/lactate dehydrogenase system (e.g., Schindler, et al. Science (2000) 289, 1938-1942). In this assay, the oxidation of NADH (thus the decrease at A340 nm) was continuously monitored spectrophotometrically. The reaction mixture (100 μl) contained C-Raf kinase (0.28 nM nominal concentration, available from Upstate, catalogue #14-352), unphosphorylated, full-length MEK1 (27 nM), $MgCl_2$ (13 mM), pyruvate kinase (3.5 units), lactate dehydrogenase (5.5 units), phosphoenolpyruvate (1 mM), and NADH (0.28 mM), in 60 mM Tris buffer, containing 0.13% octyl-glucoside and 3.5% DMSO concentration at pH 7.5. The test compounds were incubated with the reaction mixture at 30° C. for 2 h or 4 h. The reaction was initiated by adding ATP (0.2 mM, final concentration). The absorption at 340 ran was continuously monitored for 3 h at 30° C. on a Polarstar Optima plate reader (BMG). Tire reaction rate was calculated using the 1.0 h to 2.0 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

In general, compounds 1-325 disclosed herein had >50% inhibition activity at 0.2-2 uM concentration against V600E BRaf and CRaf kinases utilizing the above assay conditions.

Cell Culture: A-375 cells were obtained from American Type Culture Collection (Rockville, Md.). Briefly, cells were grown in Dulbecco's Modified Eagle Medium with 4.5 g/L glucose, 6 mM L-glutamine, and 10% certified fetal bovine serum (Invitrogen, Carlsbad, Calif.) at 37 degrees Celsius, 5% $CO_2$, 95% humidity. Cells were allowed to expand until reaching 80% confluency at which point they were subcultured or harvested for assay use.

Cell Proliferation Assay: A serial dilution of test compound was dispensed into a 96 well black clear bottom plate (Corning, Corning, N.Y.). Five thousand cells (A375) were then added to each well in growth medium. Plates were incubated for 72 hours at 37 degrees Celsius, 5% $CO_2$, 95% humidity. At the end of the incubation period Cell Titer Blue (Promega, Madison, Wis.) was added to each well and an additional 4.5 hour incubation at 37 degrees Celsius, 5% $CO_2$, 95% humidity was performed. Plates were then read on a BMG Fluostar Optima (BMG, Durham, N.C.) using an excitation of 544 nM and an emission of 612 nM. Data was analyzed using Prism software (Graphpad, San Diego, Calif.) to calculate $IC_{50}$ values.

In general, compounds 1-325 disclosed herein had >50% inhibition activity at 1-10 uM concentration against A375 cells utilizing the above assay conditions.

All references mentioned or referred to herein are incorporated by reference into this disclosure.

The invention claimed is:

1. A compound, or a salt thereof, of the formula IIa:

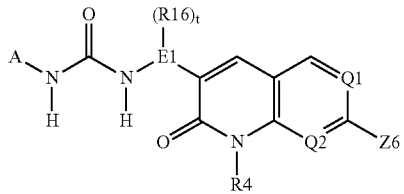

wherein Q1 is N and Q2 is CR3;
wherein E1 is phenyl;

wherein A is selected from the group consisting of phenyl, naphthyl, C3-C8carbocyclyl, —CHR4R8, pyridinyl, and benzothienyl;

when A has one or more substitutable sp2-hybridized carbon atom, each respective sp2 hybridized carbon atom may be optionally substituted with a Z3 substituent;

when A has one or more substitutable sp3-hybridized carbon atom, each respective sp3 hybridized carbon atom may be optionally substituted with a R3 substituent;

each Z3 is independently and individually selected from the group consisting of H, methyl, ethyl, isopropyl, C3-C4 carbocyclyl, halogen, fluoroalkyl wherein the alkyl moiety can be partially or fully fluorinated, and cyano Z6 is (R3)$_2$N—; wherein each R3 is independently and individually selected from the group consisting of H, C1-C6alkyl, branched C3-C7alkyl, and C3-C8carbocyclyl;

each R4 is independently and individually selected from the group consisting of C1-C4alkyl, branched C3-C5alkyl, and C3-C5carbocyclyl;

each R8 is independently and individually selected from the group consisting of C3-C8carbocyclyl, and Z3-substituted phenyl;

R16 is independently and individually selected from the group consisting of hydrogen, methyl, ethyl, halogen, fluoroalkyl wherein the alkyl moiety can be partially or fully fluorinated, cyano, and C2-C3alkynyl;

and t is 1-3.

2. A compound of claim 1 having the formula IIb:

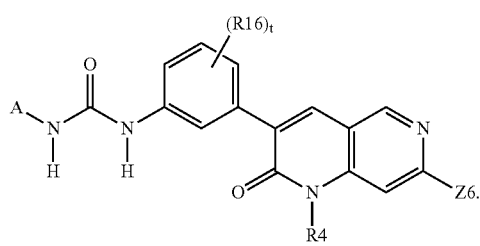

IIb

3. A compound of claim 2 having formula IIv:

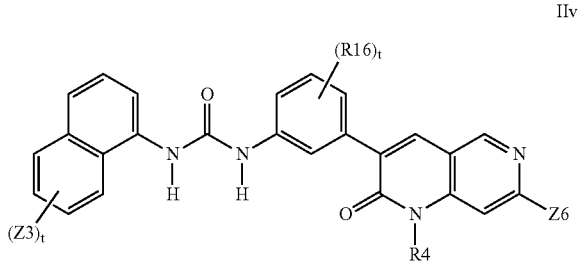

IIv wherein R16 is methyl, ethyl, cyano, -ethynyl, or halogen, and wherein the substituent Z3 can be in either of the fused phenyl rings comprising the naphthyl ring.

4. A compound of claim 3 having formula IIw:

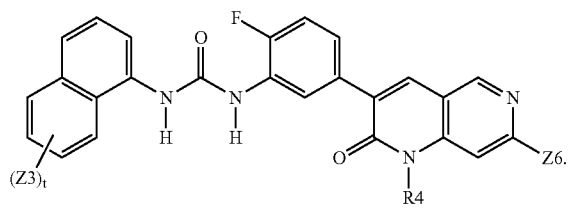

IIw

5. A compound of claim 3 having formula IIx:

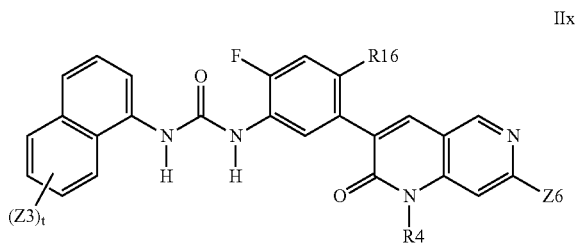

IIx and wherein R16 is methyl, ethyl, cyano, -ethynyl, or halogen.

6. A compound of claim 2 having formula IIy:

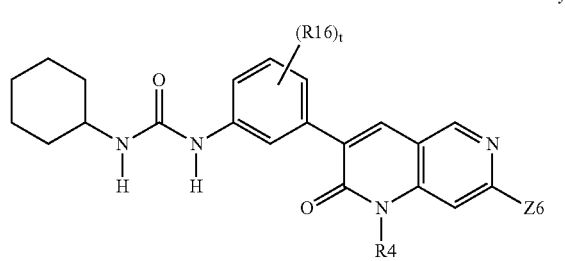

IIy and wherein R16 is methyl, ethyl, cyano, -ethynyl, or halogen.

7. A compound of claim 6 having formula IIz:

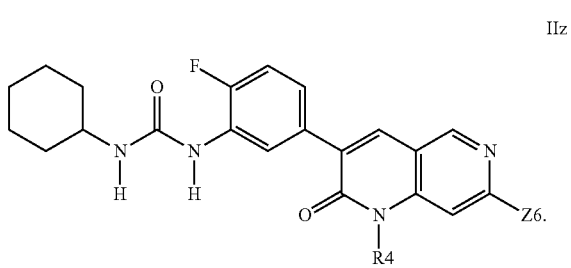

IIz

8. A compound of claim 6 having formula IIaa:

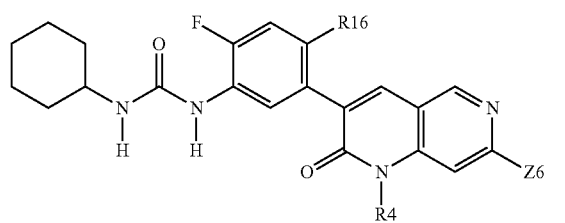

IIaa wherein R16 is methyl, cyano, -ethynyl, or halogen.

9. A compound of claim 2 having formula IIbb:

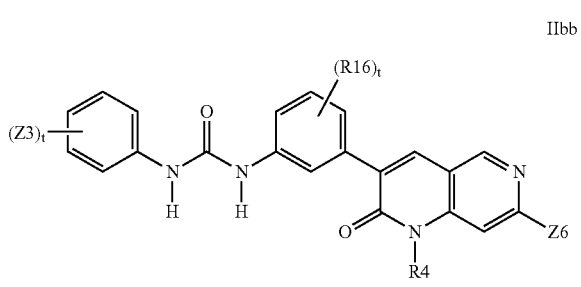

IIbb wherein R16 is methyl, ethyl, cyano, -ethynyl, or halogen.

10. A compound of claim 9 having formula IIcc:

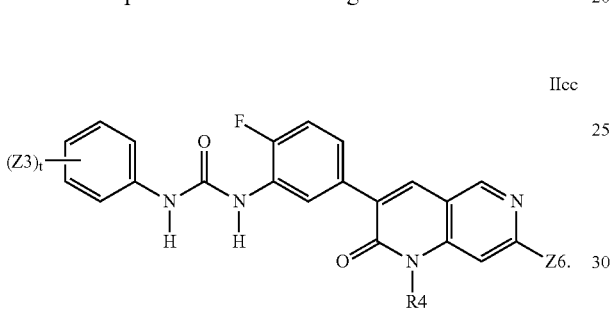

IIcc

11. A compound of claim 9 having formula IIdd:

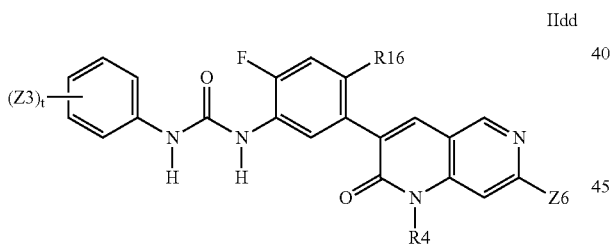

IIdd wherein R16 is methyl, ethyl, cyano, -ethynyl, or halogen.

12. A compound of claim 2 having formula IIee:

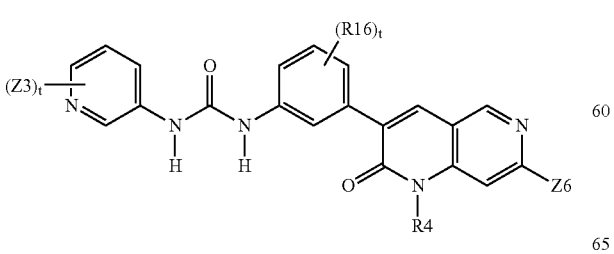

IIee wherein R16 is methyl, ethyl, cyano, -ethynyl, or halogen.

13. A compound of claim 12 having formula IIff:

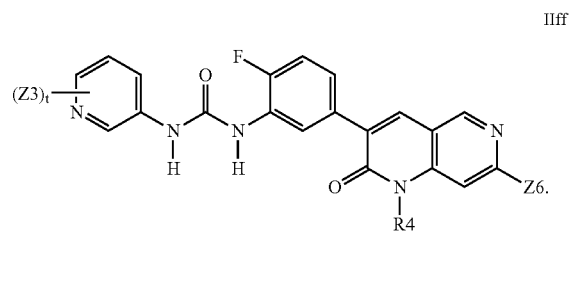

IIff

14. A compound of claim 12 having formula IIgg:

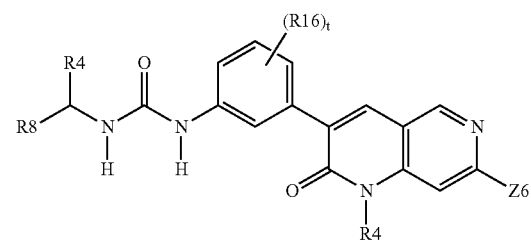

IIgg wherein R16 is methyl, ethyl, cyano, -ethynyl, or halogen.

15. A compound of claim 2 having formula IIhh:

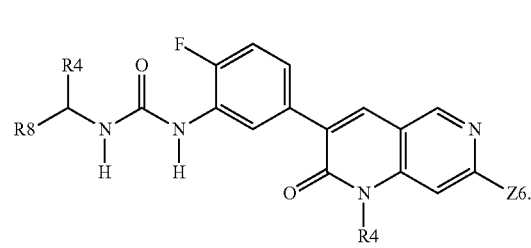

IIhh and wherein R16 is methyl, ethyl, cyano, -ethynyl, or halogen.

16. A compound of claim 15 having formula IIii:

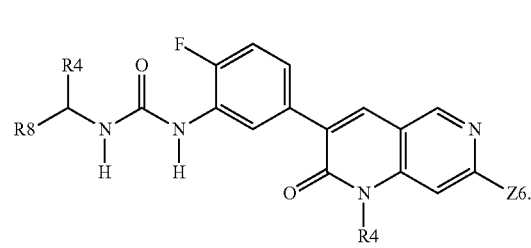

IIii

17. A compound of claim 15 having formula IIjj:

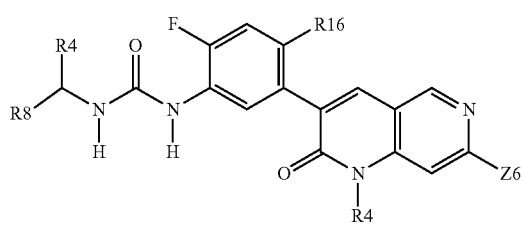

and wherein R16 is methyl, cyano, -ethynyl, or halogen.

18. A compound selected from the group consisting of 1-(2-fluoro-5-(1-methyl-7-(methylamino)-2-oxo-1,2-dihydro-1,6-naphthyridin-3-yl)phenyl)-3-(3-(trifluoromethyl)phenyl)urea, 1-(2-fluoro-4-methyl-5-(1-methyl-7-(methylamino)-2-oxo-1,2-dihydro-1,6-naphthyridin-3-yl)phenyl)-3-(3-(trifluoromethyl)phenyl)urea, 1-(4-chloro-3-(trifluoromethyl)phenyl)-3-(2-fluoro-4-methyl-5-(1-methyl-7-(methylamino)-2-oxo-1,2-dihydro-1,6-naphthyridin-3-yl)phenyl)urea, 1-(4-chloro-2-fluoro-5-(1-methyl-7-(methylamino)-2-oxo-1,2-dihydro-1,6-naphthyridin-3-yl)phenyl)-3-(3-(trifluoromethyl)phenyl)urea, 1-(5-(1-ethyl-7-(methylaimino)-2-oxo-1,2-dihydro-1,6-naphthyridin-3-yl)-2-fluoro-4-methylphenyl)-3-(3-(trifluoromethyl)phenyl)urea, 1-(5-(1-ethyl-7-(methylamino)-2-oxo-1,2-dihydro-1,6-naphthyridin-3-yl)-2-fluoro-4-methylphenyl)-3-(naphthalen-1-yl)urea, 1-(2-fluoro-5-(1-isopropyl-7-(methylamino)-2-oxo-1,2-dihydro-1,6-naphthyridin-3-yl)phenyl)-3-(3-(trifluoromethyl)phenyl)urea, 1-cyclohexyl-3-(2-fluoro-5-(1-isopropyl-7-(methylamino)-2-oxo-1,2-dihydro-1,6-naphthyridin-3-yl)phenyl)urea, 1-(5-(1-ethyl-7-(methylamino)-2-oxo-1,2-dihydro-1,6-naphthyridin-3-yl)-2- fluorophenyl)-3-(naphthalen-1-yl)urea, 1-(2-fluoro-5-(1-isopropyl-7-(methyl am ino)-2-oxo-1,2-dihydro-1,6-naphthyridin-3-yl)phenyl)-3-(2-flu oro-5-(trifluoromethyl)phenyl)urea, 1-(4-chloro-5-(1-ethyl-7-(methylamino)-2-oxo-1,2-dihydro-1,6-naphthyridin-3-yl)-2-fluorophenyl)-3-(3-(trifluoromethyl)phenyl)urea, 1-(4-chloro-3-(trifluoromethyl)phenyl)-3-(5-(1-ethyl-7-(methylamino)-2-oxo-1,2-dihydro-1,6-naphthyridin-3-y1)-2-fluorophenyl) urea, 1-(4-chloro-5-(1-ethyl-7-(methylamino)-2-oxo-1,2-dihydro-1,6-naphthyridin-3-yl)-2-fluorophenyl)-3-phenylurea, 1 (4-chloro-5-(1-ethyl-7-(methylamino)-2-oxo-1,2-dihydro-1,6-naphthyridin-3-yl)-2-fluorophenyl)-3-(2,3-difluorophenyl)urea, 1-(5-(1-ethyl-7-(methylamino)-2-oxo-1,2-dihydro-1,6-naphthyridin-3-yl)-2-fluorophenyl)-3-(3-(trifluoromethyl)phenyl)urea, 1-(2-fluoro-5-(1-isopropyl-7-(methylamino)-2-oxo-1,2-dihydro-1,6-naphthyridin-3-yl)phenyl)-3-phenylurea, 1-(4-chloro-5-(1-ethyl-7-(methylamino)-2-oxo-1,2-dihydro-1,6-naphthyridin-3-yl)-2-fluorophenyl)-3-(naphthalen-1-yl)urea, 1-(5-(1-ethyl-7-(methylamino)-2-oxo-1,2-dihydro-1,6-naphthyridin-3-yl)-2-fluorophenyl)-3-(2-fluoro-5-(trifluoromethyl)phenyl)urea, 1-(4-chloro-2-fluoro-5-(1-methyl-7-(methylamino)-2-oxo-1,2-dihydro-1,6-naphthyridin-3-yl)phenyl)-3-cyclohexylurea, 1-(4-chloro-2-fluoro-5-(1-methyl-7-(methylamino)-2-oxo-1,2-dihydro-1,6-naphthyridin-3-yl)phenyl)-3-phenylurea, 1-(4-chloro-2-fluoro-5-(1-methyl-7-(methylamino)-2-oxo-1,2-dihydro-1,6-naphthyridin-3-yl)phenyl)-3-(naphthalen-1-yl)urea, 1-(4-chloro-2-fluoro-5-(1-methyl-7-(methylamino)-2-oxo-1,2-dihydro-1,6-naphthyridin-3-yl)phenyl)-3-(4-chloro-3-(trifluoromethyl)phenyl)urea, 1-(4-chloro-2-fluoro-5-(1-methyl-7-(methylamino)-2-oxo-1,2-dihydro-1,6-naphthyridin-3-yl)phenyl)-3-(2-fluoro-5-(trifluoromethyl)phenyl)urea, 1-(4-chloro-2-fluoro-5-(1-methyl-7-(methylamino)-2-oxo-1,2-dihydro-1,6-naphthyridin-3-yl)phenyl)-3-(3-cyanophenyl)urea, 1-(4-chloro-2-fluoro-5-(1-methyl-7-(methylamino)-2-oxo-1,2-dihydro-1,6-naphthyridin-3-yl)phenyl)-3-(2,3-difluorophenyl)urea, 1-(4-chloro-3-(1-ethyl-7-(methylamino)-2-oxo-1,2-dihydro-1,6-naphthyridin-3-yl)phenyl)-3-cyclohexylurea, 1-cyclopropyl-3-(2-fluoro-4-methyl-5-(1-methyl-7-(methylamino)-2-oxo-1,2-dihydro-1,6-naphthyridin-3-yl)phenyl)urea, (R)-1-(2-fluoro-4-methyl-5-(1-methyl-7-(methylamino)-2-oxo-1,2-dihydro-1,6-naphthyridin-3-yl)phenyl)-3-(1-phenylethyl)urea, 1-(2-fluoro-4-methyl-5-(1-methyl-7-(methylamino)-2-oxo-1,2-dihydro-1,6-naphthyridin-3-yl)phenyl)-3-(5-(trifluoromethyl)pyridin-3-yl)urea, 1-(2-fluoro-4-methyl-5-(1-methyl-7-(methylamino)-2-oxo-1,2-dihydro-1,6-naphthyridin-3-yl)phenyl)-3-(4-methyl-5-(trifluoromethyppyridin-3-yl)urea, 1-(2,4-difluoro-5-(1-methyl-7-(methylamino)-2-oxo-1,2-dihydro-1,6-naphthyridin-3-yl)phenyl)-3-(5-(trifluoromethyppyridin-3-yl)urea, 1-(5-(1-ethyl-7-(methylamino)-2-oxo-1,2-dihydro-1,6-naphthyridin-3-yl)-2-fluorophenyl)-3-(5-(trifluoromethyl)pyridin-3-yl)urea, 1-(2-fluoro-4-methyl-5-(1-methyl-7-(methylamino)-2-oxo-1,2-dihydro-1,6-naphthyridin-3-yl)phenyl)-3-(4-fluoro-5-(trifluoromethyppyridin-3-yl)urea, 1-(4-chloro-2-fluoro-5-(1-methyl-7-(methylamino)-2-oxo-1,2-dihydro-1,6-naphthyridin-3-yl)phenyl)-3-(5-(trifluoromethyl)pyridin-3-yl)urea, 1-(5-(7-amino-1-methyl-2-oxo-1,2-dihydro-1,6-naphthyridin-3-yl)-2-fluoro-4-methylphenyl)-3-(3-(trifluoromethyl)phenyl)ureal -(2-fluoro-4-methyl-5-(1-methyl-7-(methylamino)-2-oxo-1,2-dihydro-1,6-naphthyridin-3-yl)phenyl)-3-(2-fluoro-5-(trifluoromethyl)phenyl)urea, 1-cyclohexyl-3-(5-(1-ethyl-7-(methylamino)-2-oxo-1,2-dihydro-1,6-naphthyridin-3-yl)-2-fluoro-4-methylphenyl)urea,-1-cyclohexyl-3-(2-fluoro-5-(1-isopropyl-7-(methylamino)-2-oxo-1,2-dihydro-1,6-naphthyridin-3-yl)-4-methylphenyl)urea,-1-cyclohexyl-3-(5-(1-cyclopentyl-7-(rnethylamino)-2-oxo-1,2-dihydro-1,6-naphthyridin-3-yl)-2-fluorophenyl)urea, 1-cyclohexyl-3-(5-(1-ethyl-7-(methylamino)-2-oxo-1,2-dihydro-1,6-naphthyridin-3-yl)-2-fluorophenyl)urea, 1-cyclohexyl-3-(2,4-difluoro-5-(1-methyl-7-(methylamino)-2-oxo-1,2-dihydro-1,6-naphthyridin-3-yl)phenyl)urea, 1-(4-cyano-2-fluoro-5-(1-methyl-7-(methylamino)-2-oxo-1,2-dihydro-1,6-naphthyridin-3-yl)phenyl)-3-cyclohexylurea, 1-(2-fluoro-4-methyl-5-(1-methyl-7-(methylamino)-2-oxo-1,2-dihydro-1,6-naphthyridin-3-yl)phenyl)-3-((1R,2R)-2-methylcyclohexyl)urea, 1-(2-fluoro-4-methyl-5-(1-methyl-7-(methylamino)-2-oxo-1,2-dihydro-1,6-naphthyridin-3-yl)phenyl)-3-((1S,2S)-2-methylcyclohexyl)urea, and 1-(2-fluoro-4-methyl-5-(1-methyl-7-(methylamino)-2-oxo-1,2-dihydro-1,6-naphthyridin-3-yl)phenyl)-3-((1 r,4r)-4-methylcyclohexyl)urea.

19. A pharmaceutical composition comprising a compound of claims 1 or 18 and salts thereof, together with a pharmaceutically acceptable carrier, said carrier including an additive selected from the group including adjuvants, excipients, diluents, and stablilizers.

* * * * *

SEQUENCE LISTING

<160> NUMBER OF SEQ ID NOS: 2

<210> SEQ ID NO 1
<211> LENGTH: 294
<212> TYPE: PRT
<213> ORGANISM: Homo sapiens -continued

```
<220> FEATURE:
<221> NAME/KEY: MISC_FEATURE
<223> OTHER INFORMATION: B-Raf(V600E)

<400> SEQUENCE: 1

Glu Asp Arg Asn Arg Met Lys Thr Leu Gly Arg Arg Asp Ser Ser Asp
1               5                   10                  15

Asp Trp Glu Ile Pro Asp Gly Gln Ile Thr Val Gly Gln Arg Ile Gly
            20                  25                  30

Ser Gly Ser Phe Gly Thr Val Tyr Lys Gly Lys Trp His Gly Asp Val
        35                  40                  45

Ala Val Lys Met Leu Asn Val Thr Ala Pro Thr Pro Gln Gln Leu Gln
50                  55                  60

Ala Phe Lys Asn Glu Val Gly Val Leu Arg Lys Thr Arg His Val Asn
65                  70                  75                  80

Ile Leu Leu Phe Met Gly Tyr Ser Thr Lys Pro Gln Leu Ala Ile Val
                85                  90                  95

Thr Gln Trp Cys Glu Gly Ser Ser Leu Tyr His His Leu His Ile Ile
            100                 105                 110

Glu Thr Lys Phe Glu Met Ile Lys Leu Ile Asp Ile Ala Arg Gln Thr
        115                 120                 125

Ala Gln Gly Met Asp Tyr Leu His Ala Lys Ser Ile Ile His Arg Asp
130                 135                 140

Leu Lys Ser Asn Asn Ile Phe Leu His Glu Asp Leu Thr Val Lys Ile
145                 150                 155                 160

Gly Asp Phe Gly Leu Ala Thr Glu Lys Ser Arg Trp Ser Gly Ser His
                165                 170                 175

Gln Phe Glu Gln Leu Ser Gly Ser Ile Leu Trp Met Ala Pro Glu Val
            180                 185                 190

Ile Arg Met Gln Asp Lys Asn Pro Tyr Ser Phe Gln Ser Asp Val Tyr
        195                 200                 205

Ala Phe Gly Ile Val Leu Tyr Glu Leu Met Thr Gly Gln Leu Pro Tyr
210                 215                 220

Ser Asn Ile Asn Asn Arg Asp Gln Ile Ile Phe Met Val Gly Arg Gly
225                 230                 235                 240

Tyr Leu Ser Pro Asp Leu Ser Lys Val Arg Ser Asn Cys Pro Lys Ala
                245                 250                 255

Met Lys Arg Leu Met Ala Glu Cys Leu Lys Lys Lys Arg Asp Glu Arg
            260                 265                 270

Pro Leu Phe Pro Gln Ile Leu Ala Ser Ile Glu Leu Leu Ala Arg Ser
        275                 280                 285

Leu Pro Lys Ile His Arg
    290

<210> SEQ ID NO 2
<211> LENGTH: 333
<212> TYPE: PRT
<213> ORGANISM: Homo sapiens
<220> FEATURE:
<221> NAME/KEY: MISC_FEATURE
<223> OTHER INFORMATION: MEK1

<400> SEQUENCE: 2

Met Glu Leu Lys Asp Asp Asp Phe Glu Lys Ile Ser Glu Leu Gly Ala
1               5                   10                  15

Gly Asn Gly Gly Val Val Phe Lys Val Ser His Lys Pro Ser Gly Leu
            20                  25                  30
```

```
Val Met Ala Arg Lys Leu Ile His Leu Glu Ile Lys Pro Ala Ile Arg
    35                  40                  45

Asn Gln Ile Ile Arg Glu Leu Gln Val Leu His Glu Cys Asn Ser Pro
    50                  55                  60

Tyr Ile Val Gly Phe Tyr Gly Ala Phe Tyr Ser Asp Gly Glu Ile Ser
65                  70                  75                  80

Ile Cys Met Glu His Met Asp Gly Ser Leu Asp Gln Val Leu Lys
                85                  90                  95

Lys Ala Gly Arg Ile Pro Glu Gln Ile Leu Gly Lys Val Ser Ile Ala
                100                 105                 110

Val Ile Lys Gly Leu Thr Tyr Leu Arg Glu Lys His Lys Ile Met His
            115                 120                 125

Arg Asp Val Lys Pro Ser Asn Ile Leu Val Asn Ser Arg Gly Glu Ile
    130                 135                 140

Lys Leu Cys Asp Phe Gly Val Ser Gly Gln Leu Ile Asp Ser Met Ala
145                 150                 155                 160

Asn Ser Phe Val Gly Thr Arg Ser Tyr Met Ser Pro Glu Arg Leu Gln
                165                 170                 175

Gly Thr His Tyr Ser Val Gln Ser Asp Ile Trp Ser Met Gly Leu Ser
            180                 185                 190

Leu Val Glu Met Ala Val Gly Arg Tyr Pro Ile Pro Pro Pro Asp Ala
        195                 200                 205

Lys Glu Leu Glu Leu Met Phe Gly Cys Gln Val Glu Gly Asp Ala Ala
    210                 215                 220

Glu Thr Pro Pro Arg Pro Arg Thr Pro Gly Arg Pro Leu Ser Ser Tyr
225                 230                 235                 240

Gly Met Asp Ser Arg Pro Pro Met Ala Ile Phe Glu Leu Leu Asp Tyr
                245                 250                 255

Ile Val Asn Glu Pro Pro Pro Lys Leu Pro Ser Gly Val Phe Ser Leu
                260                 265                 270

Glu Phe Gln Asp Phe Val Asn Lys Cys Leu Ile Lys Asn Pro Ala Glu
        275                 280                 285

Arg Ala Asp Leu Lys Gln Leu Met Val His Ala Phe Ile Lys Arg Ser
    290                 295                 300

Asp Ala Glu Glu Val Asp Phe Ala Gly Trp Leu Cys Ser Thr Ile Gly
305                 310                 315                 320

Leu Asn Gln Pro Ser Thr Pro Thr His Ala Ala Gly Val
                325                 330
```